US010639286B2

(12) United States Patent
Scott et al.

(10) Patent No.: US 10,639,286 B2
(45) Date of Patent: *May 5, 2020

(54) ALKOXY COMPOUNDS FOR DISEASE TREATMENT

(71) Applicant: Acucela Inc., Seattle, WA (US)

(72) Inventors: Ian L. Scott, Trabuco Canyon, CA (US); Vladimir A. Kuksa, Bothell, WA (US); Mark W. Orme, Seattle, WA (US); Thomas L. Little, Jr., Seattle, WA (US); Anna Gall, Woodinville, WA (US); Feng Hong, Bellevue, WA (US)

(73) Assignee: ACUCELA INC., Seattle, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/043,019

(22) Filed: Jul. 23, 2018

(65) Prior Publication Data

US 2019/0183816 A1    Jun. 20, 2019

Related U.S. Application Data

(63) Continuation of application No. 15/672,031, filed on Aug. 8, 2017, now Pat. No. 10,188,615, which is a
(Continued)

(51) Int. Cl.
| | | |
|---|---|---|
| *C07C 215/20* | (2006.01) | |
| *A61K 31/137* | (2006.01) | |
| *C07C 217/60* | (2006.01) | |
| *C07C 217/62* | (2006.01) | |
| *C07C 217/64* | (2006.01) | |
| *C07C 217/72* | (2006.01) | |
| *C07C 225/16* | (2006.01) | |
| *C07C 229/38* | (2006.01) | |
| *C07C 233/18* | (2006.01) | |
| *C07C 235/08* | (2006.01) | |

(Continued)

(52) U.S. Cl.
CPC .......... *A61K 31/137* (2013.01); *A61K 31/165* (2013.01); *A61K 31/222* (2013.01); *C07C 215/20* (2013.01); *C07C 217/20* (2013.01); *C07C 217/60* (2013.01); *C07C 217/62* (2013.01); *C07C 217/64* (2013.01); *C07C 217/72* (2013.01); *C07C 217/84* (2013.01); *C07C 225/16* (2013.01); *C07C 229/38* (2013.01); *C07C 233/18* (2013.01); *C07C 235/08* (2013.01); *C07C 251/86* (2013.01); *C07C 279/08* (2013.01); *C07C 309/06* (2013.01); *C07C 317/28* (2013.01); *C07C 323/25* (2013.01); *C07C 323/33* (2013.01); *C07D 277/24* (2013.01); *C07D 309/06* (2013.01); *C07C 2601/02* (2017.05); *C07C 2601/04* (2017.05); *C07C 2601/08* (2017.05); *C07C 2601/14* (2017.05); *C07C 2601/18* (2017.05); *C07C 2602/42* (2017.05)

(58) Field of Classification Search
CPC .. A61K 31/137; A61K 31/165; A61K 31/222; C07C 31/137; C07C 31/165; C07C 31/222; C07C 215/20; C07C 217/20; C07C 217/60; C07C 217/62; C07C 217/64; C07C 217/72; C07C 217/84; C07C 225/16; C07C 229/38; C07C 233/18; C07C 235/08; C07C 251/86; C07C 2601/02; C07C 2601/04; C07C 2601/08; C07C 2601/14; C07C 2601/18; C07C 2602/42; C07C 279/08; C07C 309/06; C07C 317/28; C07C 323/25; C07C 323/33; C07C 2101/02; C07C 2101/04; C07C 2101/08; C07C 2101/14; C07C 2101/18; C07C 2102/42; C07D 277/24; C07D 309/06
See application file for complete search history.

(56) References Cited

U.S. PATENT DOCUMENTS 3,105,854 A    10/1963  Druey et al.
3,644,353 A     2/1972  Lawrence et al.
(Continued)

FOREIGN PATENT DOCUMENTS

| CH | 396941 A | 8/1965 |
|---|---|---|
| EP | 0133259 A2 | 2/1985 |

(Continued)

OTHER PUBLICATIONS

Acucela to Present ACU-4429 Phase 1 Data at the 10th International Symposium on Ocular Pharmacology and Therapeutics. www.businesswire.com [online] Nov. 30, 2011 [retrieved on Feb. 17, 2012]. Retrieved from the Internet: www.businesswire.com/news/home/20111130005347/en (2 pgs.).

Acucela to Present Update on ACU-4429 at the Annual Retina International Scientific & Medical Advisory Board Meeting. www.drugs.com [online] May 2010 [retrieved on Feb. 17, 2012]. Retrieved from the Internet: www.drugs.com/clinical_trials/acucela-present-update-acu-4429-annual-retina-international-scientific-medical-advisory-board-9297.html (3 pgs.).

Chandler. Progress in the Development of ACU-4429 for the Treatment of Dry AMD. 10th Internatl Symp Ocular Pharmacol Therap, Final Program, Dec. 2011, [online] [retrieved on Feb. 17, 2012]. Retrieved the the Internet: http://www.isopt.net/isopt2011/images/abstracts/Chandler%20-%20ACU-4429%20for%20Dry%20AMD.pdf (2 pgs.).

(Continued)

*Primary Examiner* — Yevgeny Valenrod
*Assistant Examiner* — Blaine G Doletski
(74) *Attorney, Agent, or Firm* — Wilson Sonsini Goodrich & Rosati

(57) ABSTRACT

The present invention relates generally to compositions and methods for treating neurodegenerative diseases and disorders, particularly ophthalmic diseases and disorders. Provided herein are alkoxyl derivative compounds and pharmaceutical compositions comprising these compounds. The subject compositions are useful for treating and preventing ophthalmic diseases and disorders, including age-related macular degeneration (AMD) and Stargardt's Disease.

15 Claims, 11 Drawing Sheets

Related U.S. Application Data continuation of application No. 15/260,127, filed on Sep. 8, 2016, now Pat. No. 9,737,496, which is a continuation of application No. 14/631,763, filed on Feb. 25, 2015, now Pat. No. 9,458,088, which is a continuation of application No. 14/631,779, filed on Feb. 25, 2015, now abandoned, and a continuation of application No. 13/111,679, filed on May 19, 2011, now Pat. No. 8,981,153, and a continuation of application No. 13/111,679, filed on May 19, 2011, now Pat. No. 8,981,153, which is a continuation of application No. 12/287,039, filed on Oct. 3, 2008, now Pat. No. 7,982,071.

(60) Provisional application No. 60/977,957, filed on Oct. 5, 2007, provisional application No. 61/066,353, filed on Feb. 19, 2008, provisional application No. 61/051,657, filed on May 8, 2008, provisional application No. 61/043,127, filed on Apr. 7, 2008, provisional application No. 61/060,083, filed on Jun. 9, 2008.

(51) Int. Cl.

| | | |
|---|---|---|
| *C07C 251/86* | (2006.01) | |
| *C07C 279/08* | (2006.01) | |
| *C07C 317/28* | (2006.01) | |
| *C07C 323/25* | (2006.01) | |
| *C07D 277/24* | (2006.01) | |
| *C07D 309/06* | (2006.01) | |
| *C07C 217/20* | (2006.01) | |
| *C07C 309/06* | (2006.01) | |
| *C07C 217/84* | (2006.01) | |
| *C07C 323/33* | (2006.01) | |
| *A61K 31/165* | (2006.01) | |
| *A61K 31/222* | (2006.01) | |

(56) References Cited

U.S. PATENT DOCUMENTS

| | | | |
|---|---|---|---|
| 3,987,158 | A | 10/1976 | Hodson |
| 4,214,001 | A | 7/1980 | Englehardt et al. |
| 5,049,587 | A | 9/1991 | Okamoto et al. |
| 5,135,955 | A | 8/1992 | Campbell et al. |
| 5,314,879 | A | 5/1994 | Camaggi et al. |
| 5,475,034 | A | 12/1995 | Yanni et al. |
| 5,541,228 | A | 7/1996 | Takaki et al. |
| 5,541,343 | A | 7/1996 | Himmelsbach et al. |
| 5,661,185 | A | 8/1997 | Takaki et al. |
| 6,051,605 | A | 4/2000 | Capiris et al. |
| 6,162,943 | A | 12/2000 | Lui et al. |
| 6,271,385 | B1 | 8/2001 | Ito et al. |
| 6,713,458 | B1 | 3/2004 | Yerxa et al. |
| 7,220,780 | B2 | 5/2007 | Slusher et al. |
| 7,982,071 | B2 | 7/2011 | Scott et al. |
| 8,829,244 | B2 | 9/2014 | Scott et al. |
| 8,981,153 | B2 | 3/2015 | Scott et al. |
| 8,993,807 | B2 | 3/2015 | Scott et al. |
| 9,079,825 | B2 | 7/2015 | Scott et al. |
| 9,458,088 | B2 | 10/2016 | Scott et al. |
| 9,737,496 | B2 | 8/2017 | Scott et al. |
| 2002/0058685 | A1 | 5/2002 | Hamilton |
| 2003/0032078 | A1 | 2/2003 | Travis |
| 2003/0186961 | A1 | 10/2003 | Hamilton et al. |
| 2003/0186981 | A1 | 10/2003 | Duplantier et al. |
| 2004/0009968 | A1* | 1/2004 | Binch .............. C07D 231/56 514/217.05 |
| 2005/0101783 | A1 | 5/2005 | Ito et al. |
| 2006/0069078 | A1 | 3/2006 | Rando |
| 2006/0252107 | A1 | 11/2006 | Kubota et al. |
| 2006/0281821 | A1 | 12/2006 | Palczewski et al. |
| 2009/0221552 | A1* | 9/2009 | Teicher .............. A61K 31/00 514/211.11 |
| 2011/0003895 | A1 | 1/2011 | Kubota et al. |
| 2015/0239836 | A1 | 8/2015 | Scott et al. |
| 2018/0177746 | A1 | 6/2018 | Scott et al. |

FOREIGN PATENT DOCUMENTS

| | | |
|---|---|---|
| EP | 0525360 A2 | 2/1993 |
| EP | 0706994 A1 | 4/1996 |
| EP | 1661881 A2 | 5/2006 |
| GB | 884663 A | 12/1961 |
| JP | S50112386 A | 9/1975 |
| JP | H04264068 A | 9/1992 |
| JP | H0741468 A | 2/1995 |
| JP | H08510479 A | 11/1996 |
| JP | H10511098 A | 10/1998 |
| JP | H11503418 A | 3/1999 |
| JP | 2001031636 A | 2/2001 |
| JP | 2003535098 A | 11/2003 |
| JP | 2007008957 A | 1/2007 |
| WO | WO-9315045 A1 | 8/1993 |
| WO | WO-9519952 A1 | 7/1995 |
| WO | WO-9630014 A1 | 10/1996 |
| WO | WO-9746511 A1 | 12/1997 |
| WO | WO-9912902 A1 | 3/1999 |
| WO | WO-9916783 A1 | 4/1999 |
| WO | WO-0185684 A1 | 11/2001 |
| WO | WO-2004013082 A2 | 2/2004 |
| WO | WO-2006105215 A2 | 10/2006 |
| WO | WO-2006113837 A2 | 10/2006 |
| WO | WO-2007038372 A1 | 4/2007 |
| WO | WO-2007079593 A1 | 7/2007 |
| WO | WO-2007120528 A2 | 10/2007 |
| WO | WO-2009045479 A1 | 4/2009 |
| WO | WO-2011003103 A2 | 1/2011 |

OTHER PUBLICATIONS

Chemical Encyclopedia. GreatRussian Encyclopedia, Moscow. 4(752):380 (1985), 5 pages.

Dr. Ryo. Acucela's Focus on Diabetic Eye Disease. www.drryo.com [online] Nov. 24, 2009 [retrieved on Feb. 17, 2012]. Retrieved from the Internet: http://drryo.com/2009/11/24/acucela%e2%80%99s-focus-on-diabetic-eye-disease/ (1 pg.).

Dr. Ryo. Diabetic Retinopathy 101. www.drryo.com [online] Nov. 19, 2009 [retrieved on Feb. 17, 2012]. Retrieved from the Internet: http://drryo.com/2009/11/19/diabetic-retinopathy-101/ (1 pg.).

Dr. Ryo. On the FDA 'Fast Track': ACU-4429: On the FDA 'Fast Track'. wwwdrryo.com [online] May 12, 2010 [retrieved on Feb. 17, 2012]. Retrieved from the Internet: http://drryo.com/2010/05/12/acu-4429-on-the-fda-fast-track/ (1 pg.).

Dr. Ryo. A Great Opportunity to Tell the ACU-4429 Story. www.drryo.com [online] Jun. 1, 2010 [retrieved on Feb. 17, 2012]. Retrieved from the Internet: http://drryo.com/2010/06/01/a-great-opportunity-to-tell-the-acu-4429-story/ (1 pg.).

Dr. Ryo. A Week to Help Grow Awareness, Understanding of AMD. wwwdrryo.com [online] Sep. 17, 2010 [retrieved Feb. 17, 2012]. Retrieved from the Internet: http://drryo.com/2010/09/17/a-week-to-help-grow-awareness-understanding-of-amd/ (1 pg.).

Dr. Ryo. Blinding Eye Disease Treatments on the Horizon. www.drryo.com [online] Oct. 26, 2009 [retrieved on Feb. 17, 2012]. Retrieved from the Internet: http://drryo.com/2009/10/26/blinding-eye-disease-treatments-on-the-horizon/ (1 pg.).

Dr. Ryo. Charting a New Course . . . www.drryo.com [online] Aug. 28, 2009 [retrieved on Feb. 17, 2012]. Retrieved from the Internet: http://drryo.com/2009/08/28/new-course/ (1 pg.).

Dr. Ryo. ENVISION-ing the Future of Dry-AMD Treatment. www.drryo.com [online] Feb. 23, 2010 [retrieved on Feb. 17, 2012]. Retrieved from the internet: http://drryo.com/2010/02/23/envision-ing-the-future-of-dry-amd-treatment/ (1 pg.).

Dr. Ryo. New Paper Shares First Demonstrated Effect of VCM Treatment on Retinopathy. www.drryo.com [online] Aug. 12, 2010 [retrieved on Feb. 17, 2012]. Retrieved from the Internet: http://

(56) References Cited

OTHER PUBLICATIONS drryo.com/2010/08/12/new-paper-shares-first-demonstrated-effect-of-vcm-treatment-on-retinopathy/ (1 pg.).

Dr. Ryo. Retina Paper Highlights Progress in the Fight Against AMD. wwwdrryo.com [online] Apr. 26, 2011 [retrieved on Feb. 17, 2012]. Retrieved from the Internet: http://drryo.com/2011/04/26/retina-paper-highlights-progress-in-the-fight-against-amd/ (1 pg.).

Dr. Ryo. Thanks for Your Interest in our 'ENVISION Clarity' Clinical Trial. www.drryo.com [online] Mar. 11, 2010 [retrieved on Feb. 17, 2012]. Retrieved from the Internet: http://drryo.com/2010/03/11/thanks-for-your-interest-in-our-envision-clarity-clinical-trial/ (2 pgs.).

Dr. Ryo. Visual Cycle Modulation (VCM) 101. www.drryo.com [online] Sep. 4, 2009 [retrieved on Feb. 17, 2012]. Retrieved from the Internet: http://drryo.com/2009/09/04/vcm-101/ (1 pgs.).

Dr. Ryo. Why Chickens See Better Colors Than Us and What It Means for AMD? www.drryo.com [online] Jul. 20, 2010 [retrieved on Feb. 17, 2012]. Retrieved from the Internet: http://drryo.com/2010/07/20/why-chickens-see-better-colors-than-us-and-what-it-means-for-amd/ (2 pgs.).

Envision Clarity Trial 2010 [online] [retrieved on Feb. 16, 2012]. Retrieved from the Internet: http://www.envisiontrial.com, Acucela, Inc. (24 pgs.).

Epstein. Alkoxyphenyl N-Substituted Aminopropanols. J. Am. Chem. Soc. 81(23):6207-6209 (1959).

Ettmayer. Lessons Learned from Marketed and Investigational Prodrugs. Medicinal Chemistry 47(10):2394-2404 (2004).

Experimental Treatments for Macular Degeneration. [online] The New York Times: Consults, Experts on the Front Lines of Medicine, Sep. 21, 2011, [retrieved on Feb. 17, 2012], Retrieved from the Internet: http://consults.blogs.nytimes.com/2011/09/21/experimental-treatments-for- macular-degeneration/ (5 pgs.).

Golczak et al. Positively charged retinoids are potent and selective inhibitors of the trans-cis isomerization in the retinoid (visual) cycle. PNAS 102(23):8162-8167 (2005).

Kano et al. A synthesis of dibenz[b,f]azecines from 1-halogenobenzyl-1H-2-benzazepines. Chem. Pharm. Bull. 25(9):2401-2409 (1977).

Kano et al. Formation of dibenzo[b,f]azecines by the reaction of 1-halogeno-phenethyl-1H-2-benzazepines with dimsylsodium. Chemical & Pharmaceutical Bulletin 25(11):2875-2881 (1977).

Kucklaender et al. Investigations on the formation of 6-hydroxyindole in the nenitzescu reaction. II. Cyclization of N-(quinonylalkyl)enaminone derivatives. Chemische Berichte 122(8):1493-1498 (1989).

Maeda et al. Evaluation of the role of the retinal G protein-coupled receptor (RGR) in the vertebrate retina in vivo. J Neurochem. 85(4):944-56 (2003).

Maeda et al. Effects of potent inhibitors of the retinoid cycle on visual function and photoreceptor protection from light damage in mice. Mol Pharmacol 70(4):1220-1229 (Oct. 2006).

Mata et al. Isomerization and oxidation of vitamin A in cone-dominant retinas: a novel pathway for visual-pigment regeneration in daylight. Neuron 36(1):69-80 (2002).

Morisette et al. High-throughput crystallization: polymorphs, slats, co-crystals, and solvates of pharmaceutical solids. Advanced Drug Delivery Reviews 56:275-300 (2004).

National Eye Institute, Facts About Stargardt Disease, Apr. 2015, National Institute of Health, printed from (https://nei.nih.gov/health/stargardt/star_facts on Nov. 22, 2016 (6 pgs).

PCT/US2008/011421 International Preliminary Report on Patentability and Written Opinion dated Apr. 7, 2010.

PCT/US2008/011421 International Search Report dated Dec. 23, 2008.

PCT/US2010/40983 International Search Report and Written Opinion dated Mar. 31, 2011.

Prasad et al. Age-related macular degeneration: Current and novel therapies. Maturitas 66(1):46-50 (May 2012) retrieved on Apr. 15, 2010.

Radu et al. Treatment with isotretinoin inhibits lipofuscin accumulation in a mouse model of recessive Stargardt's macular degeneration PNAS USA 100(8):4742-4747 (2003).

Saari et al. Synthesis and Norepinephrine Depleting Activity of Some Metaralninol Ethers. J Med Chem 13(6):1057-1061 (1970).

Scott et al. U.S. Appl. No. 14/631,711, filed Feb. 25, 2015 U.S. File History downloaded from U.S. Patent Office PAIR (accessed Apr. 12, 2018) (600 pgs).

Sieving et al. Inhibition of the visual cycle in vivo by 13-cis retinoic acid protects from light damage and provides a mechanism for night blindness in isotretinoin therapy. PNAS 98(4):1835-1840 (Feb. 13, 2001).

Stella. Prodrugs as therapeutics. Expert Opinion of Therapeutic Patents 14(3):277-280 (2004).

STN RN 1025987-12-5 (1 pg.) (2008).

Testa. Prodrug Research: futile or fertile? Biochemical Pharmacology. 68:2097-2106 (2004).

Twitter entry for @DrRyo [online], posted Nov. 23, 2011, 9:00 am PST [retrieved on Feb. 17, 2012], Retrieved from the internet: www.twitter.com (1 pg.).

Tyukavina et al. Bio Organic Chemistry p. 83-85 (2005).

U.S. Appl. No. 12/287,039 Office Action dated Jan. 20, 2011.
U.S. Appl. No. 12/830,155 Office Action dated Aug. 18, 2017.
U.S. Appl. No. 12/830,155 Office Action dated Dec. 1, 2016.
U.S. Appl. No. 12/830,155 Office Action dated Jul. 28, 2015.
U.S. Appl. No. 12/830,155 Office Action dated Jun. 12, 2018.
U.S. Appl. No. 12/830,155 Office Action dated Mar. 3, 2016.
U.S. Appl. No. 12/830,155 Office Action dated May 30, 2013.
U.S. Appl. No. 12/830,155 Office Action dated Nov. 21, 2014.
U.S. Appl. No. 12/830,155 Office Action dated Oct. 18, 2012.
U.S. Appl. No. 13/111,679 Office Action dated Dec. 4, 2013.
U.S. Appl. No. 13/111,679 Office Action dated Mar. 21, 2014.
U.S. Appl. No. 13/111,679 Office Action dated May 9, 2012.
U.S. Appl. No. 13/111,679 Office Action dated Sep. 25, 2012.
U.S. Appl. No. 13/291,932 Office Action dated Aug. 15, 2012.
U.S. Appl. No. 13/291,932 Office Action dated Mar. 6, 2013.
U.S. Appl. No. 13/291,932 Office Action dated May 23, 2014.
U.S. Appl. No. 13/291,932 Office Action dated Oct. 23, 2013.
U.S. Appl. No. 13/291,948 Office Action dated Dec. 2, 2013.
U.S. Appl. No. 13/291,948 Office Action dated Mar. 14, 2013.
U.S. Appl. No. 13/291,948 Office Action dated May 19, 2014.
U.S. Appl. No. 13/291,948 Office Action dated Sep. 5, 2012.
U.S. Appl. No. 13/620,388 Office Action dated Dec. 5, 2013.
U.S. Appl. No. 14/631,763 Office Action dated Jan. 26, 2016.
U.S. Appl. No. 14/631,779 Office Action dated Jan. 8, 2016.

Vippagunta et al. Crystalline Solids. Advanced Drug Delivery Reviews 48:3-26 (2001).

Wittig et al. Dopamine/Serotonin Receptor Ligands. 9.1 Oxygen-Containing Midsized Heterocyclic Ring Systems and Nonrigidized Analogues. A Step toward Dopamine D5 Receptor Selectivity. Journal of Medicinal Chemistry 47:4155-8, Supporting Information p. S1-S8 (2004).

Wolff. Burger's Medicinal Chemistry and Drug Discovery. 5th Ed. Part 1, pp. 975-977 (1995).

* cited by examiner

ALKOXY COMPOUNDS FOR DISEASE TREATMENT

CROSS-REFERENCE

This application is a continuation of U.S. patent application Ser. No. 15/672,031, filed Aug. 8, 2017, which is a continuation of U.S. patent application Ser. No. 15/260,127, filed Sep. 8, 2016, which issued as U.S. Pat. No. 9,737,496 on Aug. 22, 2017, which is a continuation of U.S. patent application Ser. No. 14/631,763, filed Feb. 25, 2015, which issued as U.S. Pat. No. 9,458,088 on Oct. 4, 2016, and U.S. patent application Ser. No. 14/631,779, filed Feb. 25, 2015, now abandoned, both of which are a continuation of U.S. patent application Ser. No. 13/111,679, filed on May 19, 2011, which issued as U.S. Pat. No. 8,981,153 on Mar. 17, 2015, which is a continuation of U.S. patent application Ser. No. 12/287,039, filed on Oct. 3, 2008, which issued as U.S. Pat. No. 7,982,071 on Jul. 19, 2011, which claims the benefit of U.S. Provisional Application No. 60/977,957, filed Oct. 5, 2007; U.S. Provisional Application No. 61/066,353, filed Feb. 19, 2008; U.S. Provisional Application No. 61/043,127, filed Apr. 7, 2008; U.S. Provisional Application No. 61/051,657, filed May 8, 2008; and U.S. Provisional Application No. 61/060,083, filed Jun. 9, 2008, each of which is incorporated herein by reference in its entirety.

BACKGROUND

Neurodegenerative diseases, such as glaucoma, macular degeneration, and Alzheimer's disease, affect millions of patients throughout the world. Because the loss of quality of life associated with these diseases is considerable, drug research and development in this area is of great importance.

Age-related macular degeneration (AMD) affects between ten and fifteen million patients in the United States, and it is the leading cause of blindness in aging populations worldwide. AMD affects central vision and causes the loss of photoreceptor cells in the central part of retina called the macula. Macular degeneration can be classified into two types: dry-form and wet-form. The dry-form is more common than the wet; about 90% of age-related macular degeneration patients are diagnosed with the dry-form. The wet-form of the disease and geographic atrophy, which is the end-stage phenotype of dry-form AMD, causes the most serious vision loss. All patients who develop wet-form AMD are believed to previously have developed dry-form AMD for a prolonged period of time. The exact causes of AMD are still unknown. The dry-form of AMD may result from the senescence and thinning of macular tissues associated with the deposition of pigment in the macular retinal pigment epithelium. In wet-form AMD, new blood vessels grow beneath the retina, form scar tissue, bleed, and leak fluid. The overlying retina can be severely damaged, creating "blind" areas in the central vision.

For the vast majority of patients who have the dry-form of AMD, no effective treatment is yet available. Because the dry-form of AMD precedes development of the wet-form of AMD, therapeutic intervention to prevent or delay disease progression in the dry-form AMD would benefit patients with dry-form of AMD and might reduce the incidence of the wet-form of AMD.

Decline of vision noticed by the patient or characteristic features detected by an ophthalmologist during a routine eye exam may be the first indicator of AMD. The formation of "drusen," or membranous debris beneath the retinal pigment epithelium of the macula is often the first physical sign that AMD is developing. Late symptoms include the perceived distortion of straight lines and, in advanced cases, a dark, blurry area or area with absent vision appears in the center of vision; and/or there may be color perception changes.

Different forms of genetically-linked macular degenerations may also occur in younger patients. In other maculopathies, factors in the disease are heredity, nutritional, traumatic, infection, or other ecologic factors.

Glaucoma is a broad term used to describe a group of diseases that causes a slowly progressive visual field loss, usually asymptomatically. The lack of symptoms may lead to a delayed diagnosis of glaucoma until the terminal stages of the disease. The prevalence of glaucoma is estimated to be 2.2 million in the United States, with about 120,000 cases of blindness attributable to the condition. The disease is particularly prevalent in Japan, which has four million reported cases. In many parts of the world, treatment is less accessible than in the United States and Japan, thus glaucoma ranks as a leading cause of blindness worldwide. Even if subjects afflicted with glaucoma do not become blind, their vision is often severely impaired.

The progressive loss of peripheral visual field in glaucoma is caused by the death of ganglion cells in the retina. Ganglion cells are a specific type of projection neuron that connects the eye to the brain. Glaucoma is usually accompanied by an increase in intraocular pressure. Current treatment includes use of drugs that lower the intraocular pressure; however, contemporary methods to lower the intraocular pressure are often insufficient to completely stop disease progression. Ganglion cells are believed to be susceptible to pressure and may suffer permanent degeneration prior to the lowering of intraocular pressure. An increasing number of cases of normal-tension glaucoma are observed in which ganglion cells degenerate without an observed increase in the intraocular pressure. Current glaucoma drugs only treat intraocular pressure and are ineffective in preventing or reversing the degeneration of ganglion cells.

Recent reports suggest that glaucoma is a neurodegenerative disease, similar to Alzheimer's disease and Parkinson's disease in the brain, except that it specifically affects retinal neurons. The retinal neurons of the eye originate from diencephalon neurons of the brain. Though retinal neurons are often mistakenly thought not to be part of the brain, retinal cells are key components of the central nervous system, interpreting the signals from the light-sensing cells.

Alzheimer's disease (AD) is the most common form of dementia among the elderly. Dementia is a brain disorder that seriously affects a person's ability to carry out daily activities. Alzheimer's is a disease that affects four million people in the United States alone. It is characterized by a loss of nerve cells in areas of the brain that are vital to memory and other mental functions. Currently available drugs can ameliorate AD symptoms for a relatively finite period of time, but no drugs are available that treat the disease or completely stop the progressive decline in mental function. Recent research suggests that glial cells that support the neurons or nerve cells may have defects in AD sufferers, but the cause of AD remains unknown. Individuals with AD seem to have a higher incidence of glaucoma and age-related macular degeneration, indicating that similar pathogenesis may underlie these neurodegenerative diseases of the eye and brain. (See Giasson et al., *Free Radic. Biol. Med.* 32:1264-75 (2002); Johnson et al., *Proc. Natl. Acad. Sci. USA* 99:11830-35 (2002); Dentchev et al., *Mol. Vis.* 9:184-90 (2003)).

Neuronal cell death underlies the pathology of these diseases. Unfortunately, very few compositions and methods that enhance retinal neuronal cell survival, particularly photoreceptor cell survival, have been discovered. A need therefore exists to identify and develop compositions that can be used for treatment and prophylaxis of a number of retinal diseases and disorders that have neuronal cell death as a primary, or associated, element in their pathogenesis.

In vertebrate photoreceptor cells, the irradiance of a photon causes isomerization of 11-cis-retinylidene chromophore to all-trans-retinylidene and uncoupling from the visual opsin receptors. This photoisomerization triggers conformational changes of opsins, which, in turn, initiate the biochemical chain of reactions termed phototransduction (Filipek et al., *Annu. Rev. Physiol.* 65:851-79 (2003)). Regeneration of the visual pigments requires that the chromophore be converted back to the 11-cis-configuration in the processes collectively called the retinoid (visual) cycle (see, e.g., McBee et al., *Prog. Retin. Eye Res.* 20:469-52 (2001)). First, the chromophore is released from the opsin and reduced in the photoreceptor by retinol dehydrogenases. The product, all-trans-retinol, is trapped in the adjacent retinal pigment epithelium (RPE) in the form of insoluble fatty acid esters in subcellular structures known as retinosomes (Imanishi et al., *J. Cell Biol.* 164:373-87 (2004)).

In Stargardt's disease (Allikmets et al., *Nat. Genet.* 15:236-46 (1997)), a disease associated with mutations in the ABCR transporter that acts as a flippase, the accumulation of all-trans-retinal may be responsible for the formation of a lipofuscin pigment, A2E, which is toxic towards retinal pigment epithelial cells and causes progressive retinal degeneration and, consequently, loss of vision (Mata et al., *Proc. Natl. Acad. Sci. USA* 97:7154-59 (2000); Weng et al., *Cell* 98:13-23 (1999)). Treating patients with an inhibitor of retinol dehydrogenases, 13-cis-RA (Isotretinoin, Accutane®, Roche), has been considered as a therapy that might prevent or slow the formation of A2E and might have protective properties to maintain normal vision (Radu et al., *Proc. Natl. Acad. Sci. USA* 100:4742-47 (2003)). 13-cis-RA has been used to slow the synthesis of 11-cis-retinal by inhibiting 11-cis-RDH (Law et al., *Biochem. Biophys. Res. Commun.* 161:825-9 (1989)), but its use can also be associated with significant night blindness. Others have proposed that 13-cis-RA works to prevent chromophore regeneration by binding RPE65, a protein essential for the isomerization process in the eye (Gollapalli et al., *Proc. Natl. Acad. Sci. USA* 101:10030-35 (2004)). Gollapalli et al. reported that 13-cis-RA blocked the formation of A2E and suggested that this treatment may inhibit lipofuscin accumulation and, thus, delay either the onset of visual loss in Stargardt's disease or age-related macular degeneration, which are both associated with retinal pigment-associated lipofuscin accumulation. However, blocking the retinoid cycle and forming unliganded opsin may result in more severe consequences and worsening of the patient's prognosis (see, e.g., Van Hooser et al., *J. Biol. Chem.* 277:19173-82 (2002); Woodruff et al., *Nat. Genet.* 35:158-164 (2003)). Failure of the chromophore to form may lead to progressive retinal degeneration and may produce a phenotype similar to Leber Congenital Amaurosis (LCA), which is a very rare genetic condition affecting children shortly after birth.

BRIEF SUMMARY OF THE INVENTION

A need exists in the art for an effective treatment for treating ophthalmic diseases or disorders resulting in ophthalmic dysfunction including those described above. In particular, there exists a pressing need for compositions and methods for treating Stargardt's disease and age-related macular degeneration (AMD) without causing further unwanted side effects such as progressive retinal degeneration, LCA-like conditions, night blindness, or systemic vitamin A deficiency. A need also exists in the art for effective treatments for other ophthalmic diseases and disorders that adversely affect the retina.

In one embodiment is a compound of Formula (A) or tautomer, stereoisomer, geometric isomer or a pharmaceutically acceptable solvate, hydrate, salt, N-oxide or prodrug thereof:

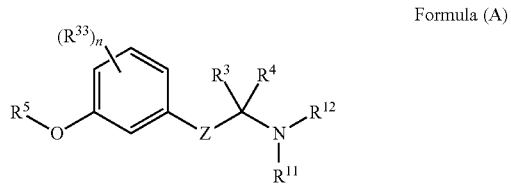

Formula (A)

wherein
Z is —C($R^9$)($R^{10}$)—C($R^1$)($R^2$)—, —X—C($R^{31}$)($R^{32}$)—, —C($R^9$)($R^{10}$)—C($R^1$)($R^2$)—C($R^{36}$)($R^{37}$)— or —X—C($R^{31}$)($R^{32}$)—C($R^1$)($R^2$)—;

$R^1$ and $R^2$ are each independently selected from hydrogen, halogen, $C_1$-$C_5$ alkyl, fluoroalkyl, —$OR^6$ or —$NR^7R^8$; or $R^1$ and $R^2$ together form an oxo;

$R^{31}$ and $R^{32}$ are each independently selected from hydrogen, $C_1$-$C_5$ alkyl, or fluoroalkyl;

$R^{36}$ and $R^{37}$ are each independently selected from hydrogen, halogen, $C_1$-$C_5$ alkyl, fluoroalkyl, —$OR^6$ or —$NR^7R^8$; or $R^{36}$ and $R^{37}$ together form an oxo; or optionally, $R^{36}$ and $R^1$ together form a direct bond to provide a double bond; or optionally, $R^{36}$ and $R^1$ together form a direct bond, and $R^{37}$ and $R^2$ together form a direct bond to provide a triple bond;

$R^3$ and $R^4$ are each independently selected from hydrogen, alkyl, alkenyl, fluoroalkyl, aryl, heteroaryl, carbocyclyl or C-attached heterocyclyl; or $R^3$ and $R^4$ together with the carbon atom to which they are attached, form a carbocyclyl or heterocyclyl; or $R^3$ and $R^4$ together form an imino;

$R^5$ is $C_5$-$C_{15}$ alkyl or carbocyclylalkyl;

$R^7$ and $R^8$ are each independently selected from hydrogen, alkyl, carbocyclyl, heterocyclyl, —C(=O)$R^{13}$, $SO_2R^{13}$, $CO_2R^{13}$ or $SO_2NR^{24}R^{25}$; or $R^7$ and $R^8$ together with the nitrogen atom to which they are attached, form an N-heterocyclyl;

X is —O—, —S—, —S(=O)—, —S(=O)$_2$—, —N($R^{30}$)—, —C(=O)—, —C(=$CH_2$)—, —C(=N—$NR^{35}$)—, or —C(=N—$OR^{35}$)—

$R^9$ and $R^{10}$ are each independently selected from hydrogen, halogen, alkyl, fluoroalkyl, —$OR^{19}$—, —$NR^{20}R^{21}$ or carbocyclyl; or $R^9$ and $R^{10}$ form an oxo; or optionally, $R^9$ and $R^1$ together form a direct bond to provide a double bond; or optionally, $R^9$ and $R^1$ together form a direct bond, and $R^{10}$ and $R^2$ together form a direct bond to provide a triple bond;

$R^{11}$ and $R^{12}$ are each independently selected from hydrogen, alkyl, carbocyclyl, —C(=O)$R^{23}$, —C(NH)$NH_2$, $SO_2R^{23}$, $CO_2R^{23}$ or $SO_2NR^{28}R^{29}$; or $R^{11}$ and $R^{12}$, together with the nitrogen atom to which they are attached, form an N-heterocyclyl;

each $R^{13}$, $R^{22}$ and $R^{23}$ is independently selected from alkyl, heteroalkyl, alkenyl, aryl, aralkyl, carbocyclyl, heteroaryl or heterocyclyl;

$R^6$, $R^{19}$, $R^{30}$, $R^{34}$ and $R^{35}$ are each independently hydrogen or alkyl;

$R^{20}$ and $R^{21}$ are each independently selected from hydrogen, alkyl, carbocyclyl, heterocyclyl, —C(=O)$R^{22}$, SO$_2R^{22}$, CO$_2R^{22}$ or SO$_2$NR$^{26}R^{27}$; or $R^{20}$ and $R^{21}$ together with the nitrogen atom to which they are attached, form an N-heterocyclyl; and each $R^{24}$, $R^{25}$, $R^{26}$, $R^{27}$, $R^{28}$ and $R^{29}$ is independently selected from hydrogen, alkyl, alkenyl, fluoroalkyl, aryl, heteroaryl, carbocyclyl or heterocyclyl;

each $R^{33}$ is independently selected from halogen, OR$^{34}$, alkyl, or fluoroalkyl; and n is 0, 1, 2, 3, or 4; with the provision that $R^5$ is not 2-(cyclopropyl)-1-ethyl or an unsubstituted normal alkyl.

In another embodiment is the compound of Formula (A), wherein

Z is —C(R$^9$)(R$^{10}$)—C(R$^1$)(R$^2$)—, —X—C(R$^{31}$)(R$^{32}$)—, —C(R$^9$)(R$^{10}$)—C(R$^1$)(R$^2$)—(R$^{36}$)(R$^{37}$)— or —X—C(R$^{31}$)(R$^{32}$)—C(R$^1$)(R$^2$)—;

$R^1$ and $R^2$ are each independently selected from hydrogen, halogen, C$_1$-C$_5$ alkyl, fluoroalkyl, —OR$^6$ or —NR$^7R^8$; or $R^1$ and $R^2$ together form an oxo;

$R^{31}$ and $R^{32}$ are each independently selected from hydrogen, C$_1$-C$_5$ alkyl, or fluoroalkyl;

$R^{36}$ and $R^{37}$ are each independently selected from hydrogen, halogen, C$_1$-C$_5$ alkyl, fluoroalkyl, —OR$^6$ or —NR$^7R^8$; or $R^{36}$ and $R^{37}$ together form an oxo;

$R^3$ and $R^4$ are each independently selected from hydrogen, alkyl, alkenyl, fluoroalkyl, aryl, heteroaryl, carbocyclyl or C-attached heterocyclyl; or $R^3$ and $R^4$ together with the carbon atom to which they are attached, form a carbocyclyl or heterocyclyl; or $R^3$ and $R^4$ together form an imino;

$R^5$ is C$_5$-C$_{15}$ alkyl or carbocyclyalkyl;

$R^7$ and $R^8$ are each independently selected from hydrogen, alkyl, carbocyclyl, heterocyclyl, —C(=O)R$^{13}$, SO$_2R^{13}$, CO$_2R^{13}$ or SO$_2$NR$^{24}R^{25}$; or $R^7$ and $R^8$ together with the nitrogen atom to which they are attached, form an N-heterocyclyl;

X is —O—, —S—, —S(=O)—, —S(=O)$_2$—, —N(R$^{30}$)—, —C(=O)—, —C(=CH$_2$)—, —C(=N—NR$^{35}$)—, or —C(=N—OR$^{35}$)—;

$R^9$ and $R^{10}$ are each independently selected from hydrogen, halogen, alkyl, fluoroalkyl, —OR$^{19}$—, —NR$^{20}R^{21}$ or carbocyclyl; or $R^9$ and $R^{10}$ form an oxo;

$R^{11}$ and $R^{12}$ are each independently selected from hydrogen, alkyl, carbocyclyl, —C(=O)R$^{23}$, SO$_2R^{23}$, CO$_2R^{23}$ or SO$_2$NR$^{28}R^{29}$; or $R^{11}$ and $R^{12}$, together with the nitrogen atom to which they are attached, form an N-heterocyclyl;

each $R^{13}$, $R^{22}$ and $R^{23}$ is independently selected from alkyl, heteroalkyl, alkenyl, aryl, aralkyl, carbocyclyl, heteroaryl or heterocyclyl;

$R^6$, $R^{19}$, $R^{30}$, $R^{34}$ and $R^{35}$ are each independently hydrogen or alkyl;

$R^{20}$ and $R^{21}$ are each independently selected from hydrogen, alkyl, carbocyclyl, heterocyclyl, —C(=O)R$^{22}$, SO$_2R^{22}$, CO$_2R^{22}$ or SO$_2$NR$^{26}R^{27}$; or $R^{20}$ and $R^{21}$ together with the nitrogen atom to which they are attached, form an N-heterocyclyl; and each $R^{24}$, $R^{25}$, $R^{26}$, $R^{27}$, $R^{28}$ and $R^{29}$ is independently selected from hydrogen, alkyl, alkenyl, fluoroalkyl, aryl, heteroaryl, carbocyclyl or heterocyclyl;

each $R^{33}$ is independently selected from halogen, OR$^{34}$, alkyl, or fluoroalkyl; and n is 0, 1, 2, 3, or 4.

In a further embodiment is the compound having the structure of Formula (B),

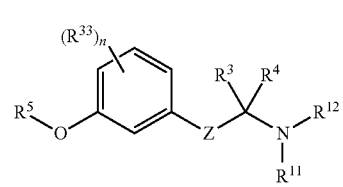

Formula (B)

wherein

Z is —C(R$^9$)(R$^{10}$)—C(R$^1$)(R$^2$)— or —O—C(R$^{31}$)(R$^{32}$)—;

$R^1$ and $R^2$ are each independently selected from hydrogen, halogen, C$_1$-C$_5$ alkyl, fluoroalkyl, —OR$^6$ or —NR$^7R^8$; or $R^1$ and $R^2$ together form an oxo;

$R^{31}$ and $R^{32}$ are each independently selected from hydrogen, C$_1$-C$_5$ alkyl, or fluoroalkyl;

$R^3$ and $R^4$ are each independently selected from hydrogen or alkyl; or $R^3$ and $R^4$ together form an imino;

$R^5$ is C$_5$-C$_{15}$ alkyl or carbocyclyalkyl;

$R^7$ and $R^8$ are each independently selected from hydrogen, alkyl, carbocyclyl or —C(=O)R$^{13}$; or $R^7$ and $R^8$, together with the nitrogen atom to which they are attached, form an N-heterocyclyl;

$R^9$ and $R^{10}$ are each independently selected from hydrogen, halogen, alkyl, fluoroalkyl, —OR$^{19}$—, —NR$^{20}R^{21}$ or carbocyclyl; or $R^9$ and $R^{10}$ together form an oxo;

$R^{11}$ and $R^{12}$ are each independently selected from hydrogen, alkyl, carbocyclyl or —C(=O)R$^{23}$; or $R^{11}$ and $R^{12}$, together with the nitrogen atom to which they are attached, form an N-heterocyclyl; and each $R^{13}$, $R^{22}$ and $R^{23}$ is independently selected from alkyl, alkenyl, aryl, aralkyl, carbocyclyl, heteroaryl or heterocyclyl;

$R^6$, $R^{19}$, and $R^{34}$ are each independently hydrogen or alkyl;

each $R^{33}$ is independently selected from halogen, OR$^{34}$, alkyl, or fluoroalkyl; and n is 0, 1, 2, 3, or 4;

$R^{20}$ and $R^{21}$ are each independently selected from hydrogen, alkyl, carbocyclyl, —C(=O)R$^{22}$; or $R^{20}$ and $R^{21}$, together with the nitrogen atom to which they are attached, form an N-heterocyclyl; and each $R^{24}$, $R^{25}$, $R^{26}$, $R^{27}$, $R^{28}$ and $R^{29}$ is independently selected from hydrogen, alkyl, alkenyl, fluoroalkyl, aryl, heteroaryl, carbocyclyl or heterocyclyl.

In a further embodiment is the compound having the structure of Formula (C),

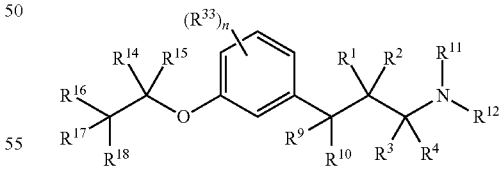

Formula (C)

wherein $R^1$ and $R^2$ are each independently selected from hydrogen, halogen, C$_1$-C$_5$ alkyl, fluoroalkyl, —OR$^6$ or —NR$^7R^8$; or $R^1$ and $R^2$ together form an oxo;

$R^3$ and $R^4$ are each independently selected from hydrogen or alkyl; or $R^3$ and $R^4$ together form an imino;

$R^7$ and $R^8$ are each independently selected from hydrogen, alkyl, carbocyclyl or —C(=O)R$^{13}$; or $R^7$ and $R^8$, together with the nitrogen atom to which they are attached, form an N-heterocyclyl;

$R^9$ and $R^{10}$ are each independently selected from hydrogen, halogen, alkyl, fluoroalkyl, —$OR^{19}$—, —$NR^{20}R^{21}$ or carbocyclyl; or $R^9$ and $R^{10}$ together form an oxo;

$R^{11}$ and $R^{12}$ are each independently selected from hydrogen, alkyl, carbocyclyl or —C(=O)$R^{23}$; or $R^{11}$ and $R^{12}$, together with the nitrogen atom to which they are attached, form an N-heterocyclyl;

each $R^{13}$, $R^{22}$ and $R^{23}$ is independently selected from alkyl, alkenyl, aryl, aralkyl, carbocyclyl, heteroaryl or heterocyclyl;

$R^6$, $R^{19}$ and $R^{34}$ are each independently hydrogen or alkyl;

$R^{20}$ and $R^{21}$ are each independently selected from hydrogen, alkyl, carbocyclyl, —C(=O)$R^{22}$; or $R^{20}$ and $R^{21}$, together with the nitrogen atom to which they are attached, form an N-heterocyclyl; and each $R^{24}$, $R^{25}$, $R^{26}$, $R^{27}$, $R^{28}$ and $R^{29}$ is independently selected from hydrogen, alkyl, alkenyl, fluoroalkyl, aryl, heteroaryl, carbocyclyl or heterocyclyl;

$R^{14}$ and $R^{15}$ are each independently selected from hydrogen or alkyl;

$R^{16}$ and $R^{17}$ are each independently selected from hydrogen, $C_1$-$C_{13}$ alkyl, halo or fluoroalkyl; or $R^{16}$ and $R^{17}$, together with the carbon to which they are attached form a carbocyclyl;

each $R^{33}$ is independently selected from halogen, $OR^{34}$, alkyl, or fluoroalkyl; and n is 0, 1, 2, 3, or 4; and $R^{18}$ is selected from a hydrogen, alkyl, alkoxy, hydroxy, halo or fluoroalkyl.

In a further embodiment is the compound of Formula (C), wherein n is 0 and each of $R^{11}$ and $R^{12}$ is hydrogen.

In a further embodiment is the compound of Formula (C), wherein each of $R^3$, $R^4$, $R^{14}$ and $R^{15}$ is hydrogen.

In a further embodiment is the compound of Formula (C), wherein, $R^1$ and $R^2$ are each independently selected from hydrogen, halogen, $C_1$-$C_5$ alkyl, or —$OR^6$;

$R^9$ and $R^{10}$ are each independently selected from hydrogen, halogen, alkyl, or —$OR^{19}$; or $R^9$ and $R^{10}$ together form an oxo;

$R^6$ and $R^{19}$ are each independently hydrogen or alkyl;

$R^{16}$ and $R^{17}$, together with the carbon to which they are attached form a carbocyclyl; and $R^{18}$ is selected from a hydrogen, alkoxy or hydroxy.

In a further embodiment is the compound of Formula (C), wherein $R^{16}$ and $R^{17}$, together with the carbon to which they are attached, form a cyclohexyl or cycloheptyl and $R^{18}$ is hydrogen or hydroxy.

In a further embodiment is the compound of Formula (C), wherein $R^{16}$ and $R^{17}$, together with the carbon to which they are attached, form a cyclobutyl, cyclopentyl, cyclohexyl, cycloheptyl, or cyclooctyl, and $R^{18}$ is hydrogen or hydroxy.

In a further embodiment is the compound of Formula (C), wherein $R^{11}$ is hydrogen and $R^{12}$ is —C(=O)$R^{23}$, wherein $R^{23}$ is alkyl.

In a further embodiment is the compound of Formula (C), wherein $R^1$ and $R^2$ are each independently selected from hydrogen, halogen, $C_1$-$C_5$ alkyl, or —$OR^6$;

$R^9$ and $R^{10}$ are each independently selected from hydrogen, halogen, alkyl, or —$OR^{19}$; or $R^9$ and $R^{10}$ together form an oxo;

$R^6$ and $R^{19}$ are each independently hydrogen or alkyl;

$R^{16}$ and $R^{17}$, together with the carbon atom to which they are attached, form a carbocyclyl; and $R^{18}$ is hydrogen, hydroxy or alkoxy.

In a further embodiment is the compound of Formula (C), wherein n is 0;

$R^{16}$ and $R^{17}$, together with the carbon atom to which they are attached, form a cyclopentyl, cyclohexyl or cyclohexyl; and $R^{18}$ is hydrogen or hydroxy.

In a further embodiment is the compound of Formula (C), wherein $R^1$ and $R^2$ are each independently selected from hydrogen, halogen, $C_1$-$C_5$ alkyl or —$OR^6$;

$R^9$ and $R^{10}$ are each independently selected from hydrogen, halogen, alkyl, or —$OR^{19}$; or $R^9$ and $R^{10}$ together form an oxo;

$R^6$ and $R^{19}$ are each independently hydrogen or alkyl;

$R^{16}$ and $R^{17}$ is independently selected from $C_1$-$C_{13}$ alkyl; and $R^{18}$ is hydrogen, hydroxy or alkoxy.

In an additional embodiment is the compound having the structure of Formula (D),

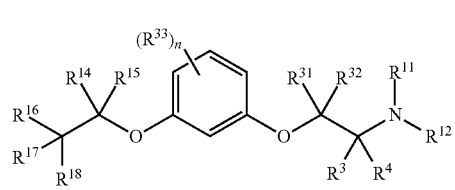

Formula (D)

wherein, $R^{31}$ and $R^{32}$ are each independently selected from hydrogen, $C_1$-$C_5$ alkyl, or fluoroalkyl;

$R^3$ and $R^4$ are each independently selected from hydrogen or alkyl; or $R^3$ and $R^4$ together form an imino;

$R^{11}$ and $R^{12}$ are each independently selected from hydrogen, alkyl, carbocyclyl, or —C(=O)$R^{23}$; or $R^{11}$ and $R^{12}$, together with the nitrogen atom to which they are attached, form an N-heterocyclyl;

$R^{23}$ is selected from alkyl, alkenyl, aryl, carbocyclyl, heteroaryl or heterocyclyl;

$R^{14}$ and $R^{15}$ are each independently selected from hydrogen or alkyl;

$R^{16}$ and $R^{17}$ are each independently selected from hydrogen, $C_1$-$C_{13}$ alkyl, halo or fluoroalkyl; or $R^{16}$ and $R^{17}$, together with the carbon atom to which they are attached, form a carbocyclyl;

$R^{18}$ is selected from a hydrogen, alkyl, alkoxy, hydroxy, halo or fluoroalkyl;

$R^{34}$ is hydrogen or alkyl; and each $R^{33}$ is independently selected from halogen, $OR^{34}$, alkyl, or fluoroalkyl; and n is 0, 1, 2, 3, or 4.

In a further embodiment is the compound of Formula (D), wherein n is 0 and each of $R^{11}$ and $R^{12}$ is hydrogen.

In a further embodiment is the compound of Formula (D), wherein each $R^3$, $R^4$, $R^{14}$ and $R^{15}$ is hydrogen.

In a further embodiment is the compound of Formula (D), wherein $R^{31}$ and $R^{32}$ are each independently hydrogen, or $C_1$-$C_5$ alkyl;

$R^{16}$ and $R^{17}$, together with the carbon atom to which they are attached, form a carbocyclyl; and $R^{18}$ is hydrogen, hydroxy, or alkoxy.

In a further embodiment is the compound of Formula (C), wherein $R^{16}$ and $R^{17}$, together with the carbon atom to which they are attached form cyclopentyl, cyclohexyl or cycloheptyl and $R^{18}$ is hydrogen or hydroxy.

In a further embodiment is the compound of Formula (D), wherein $R^{31}$ and $R^{32}$ are each independently selected from hydrogen, or $C_1$-$C_5$ alkyl; and $R^{18}$ is hydrogen, hydroxy or alkoxy.

In a further embodiment is the compound of Formula (E),

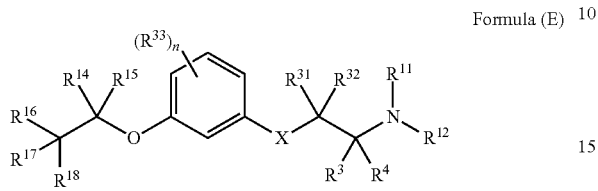

Formula (E)

wherein

X is —S—, —S(=O)—, —S(=O)$_2$—, —N($R^{30}$)—, —C(=O)—, —C(=CH$_2$)—, —C(=N—N$R^{35}$)—, or —C(=N—O$R^{35}$)—;

$R^{31}$ and $R^{32}$ are each independently selected from hydrogen, $C_1$-$C_5$ alkyl, or fluoroalkyl;

$R^3$ and $R^4$ are each independently selected from hydrogen or alkyl; or $R^3$ and $R^4$ together form an imino;

$R^{11}$ and $R^{12}$ are each independently selected from hydrogen, alkyl, carbocyclyl, or —C(=O)$R^{23}$; or $R^{11}$ and $R^{12}$, together with the nitrogen atom to which they are attached, form an N-heterocyclyl;

$R^{23}$ is selected from alkyl, alkenyl, aryl, carbocyclyl, heteroaryl or heterocyclyl;

$R^{14}$ and $R^{15}$ are each independently selected from hydrogen or alkyl;

$R^{16}$ and $R^{17}$ are each independently selected from hydrogen, $C_1$-$C_{13}$ alkyl, halo or fluoroalkyl; or $R^{16}$ and $R^{17}$, together with the carbon atom to which they are attached, form a carbocyclyl;

$R^{30}$, $R^{34}$ and $R^{35}$ are each independently hydrogen or alkyl;

$R^{18}$ is selected from a hydrogen, alkyl, alkoxy, hydroxy, halo or fluoroalkyl;

each $R^{33}$ is independently selected from halogen, O$R^{34}$, alkyl, or fluoroalkyl; and n is 0, 1, 2, 3, or 4.

In a further embodiment is the compound of Formula (E), wherein n is 0 and each $R^{11}$ and $R^{12}$ is hydrogen.

In a further embodiment is the compound of Formula (E), wherein each $R^3$, $R^4$, $R^{14}$ and $R^{15}$ is hydrogen.

In a further embodiment is the compound of Formula (E), wherein $R^{31}$ and $R^{32}$ are each independently hydrogen, or $C_1$-$C_5$ alkyl;

$R^{16}$ and $R^{17}$, together with the carbon atom to which they are attached, form a carbocyclyl; and $R^{18}$ is hydrogen, hydroxy, or alkoxy.

In a further embodiment is the compound of Formula (E), wherein $R^{16}$ and $R^{17}$, together with the carbon atom to which they are attached form cyclopentyl, cyclohexyl or cycloheptyl and $R^{18}$ is hydrogen or hydroxy.

In a further embodiment is the compound of Formula (E), wherein, $R^{31}$ and $R^{32}$ are each independently selected from hydrogen, or $C_1$-$C_5$ alkyl; and $R^{18}$ is hydrogen, hydroxy or alkoxy.

In an additional embodiment is the compound of Formula (A), selected from the group consisting of:

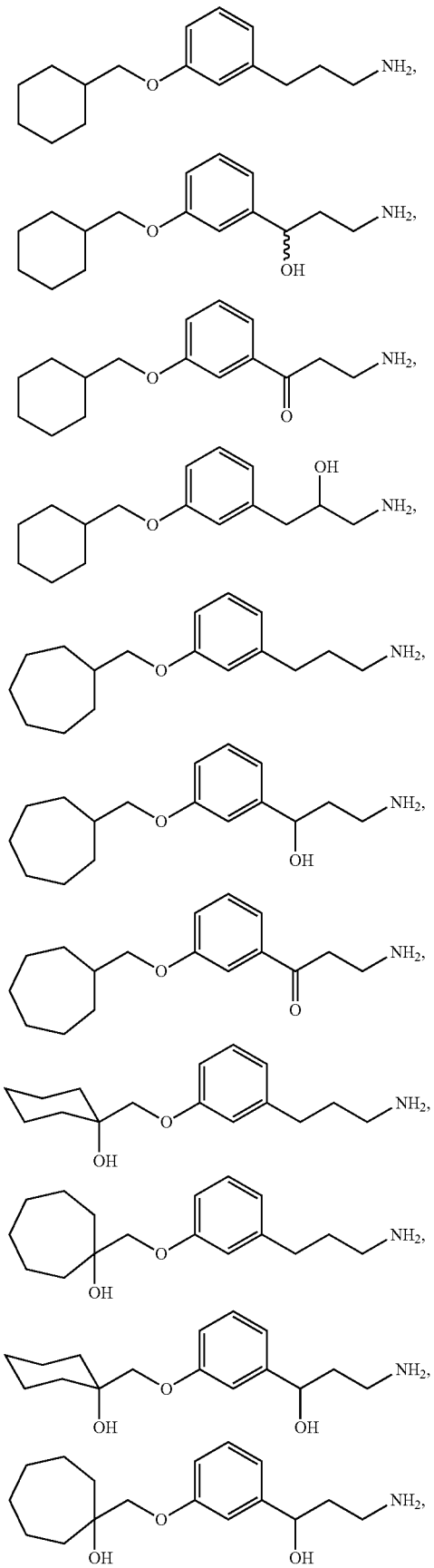

-continued
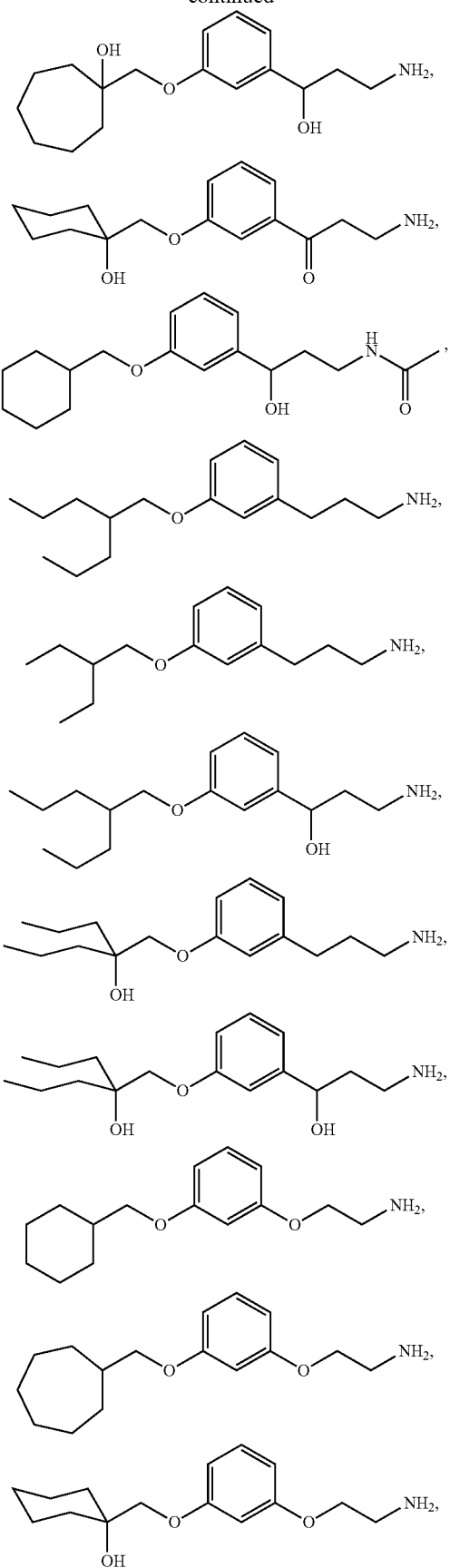
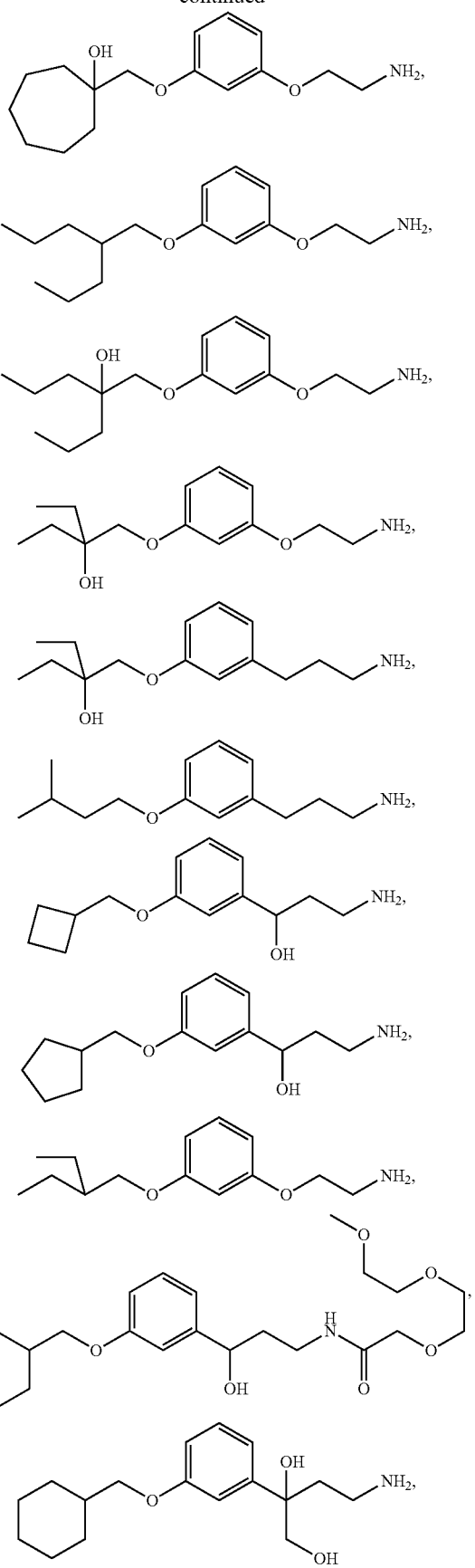

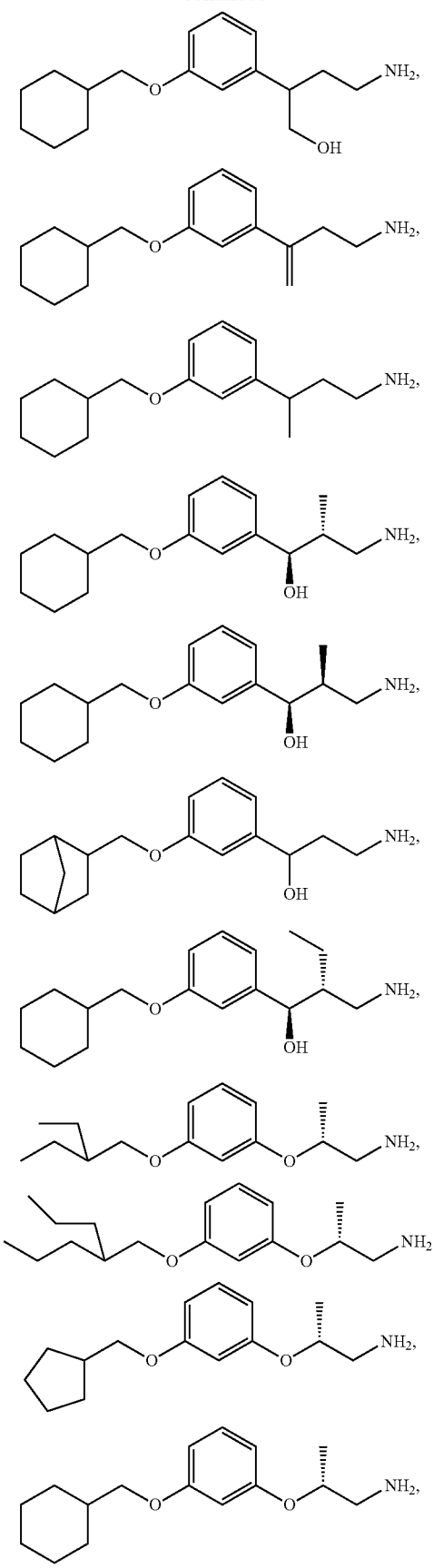
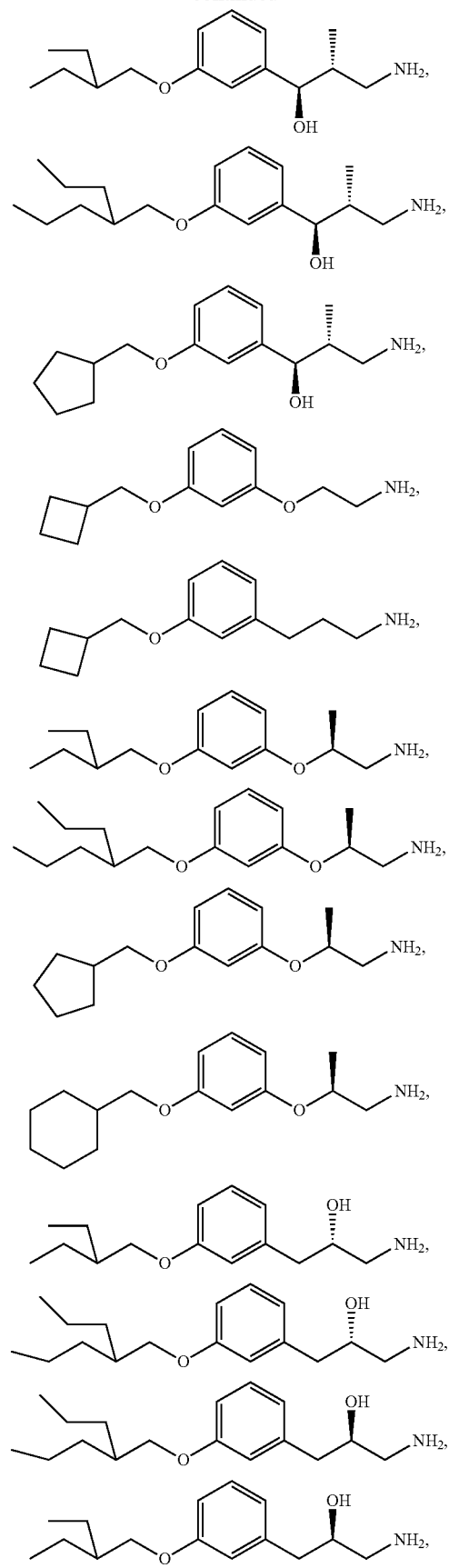

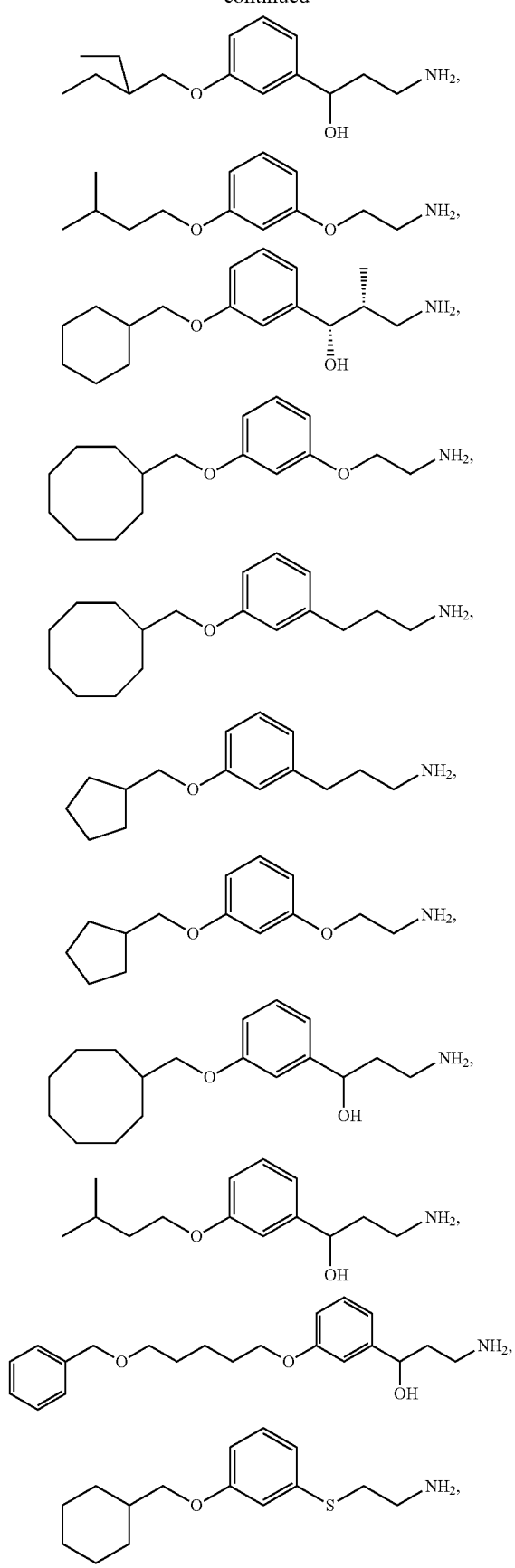
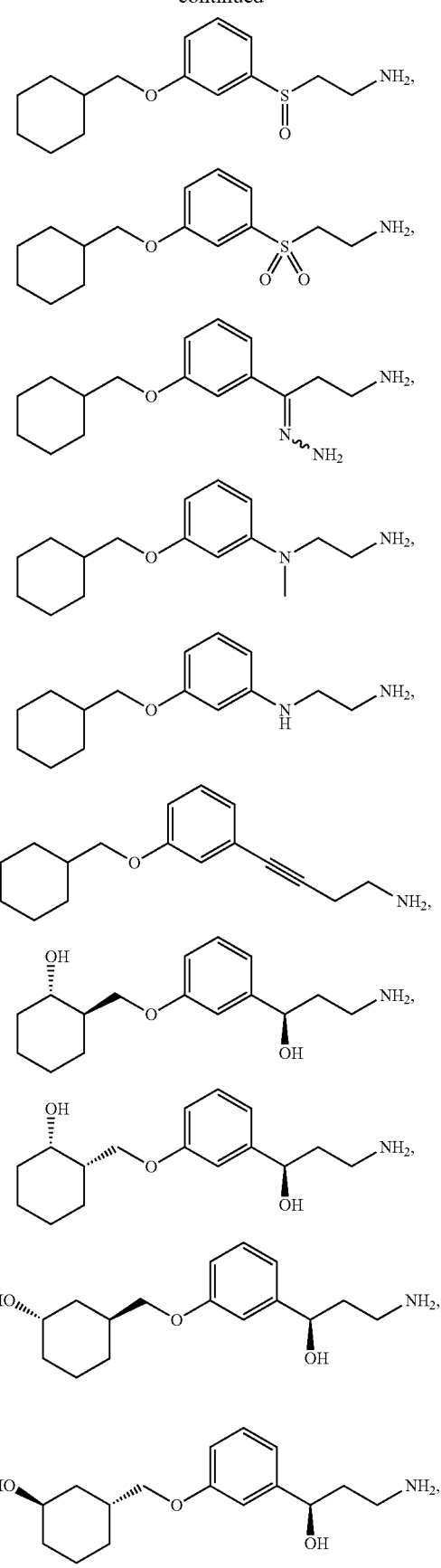

-continued

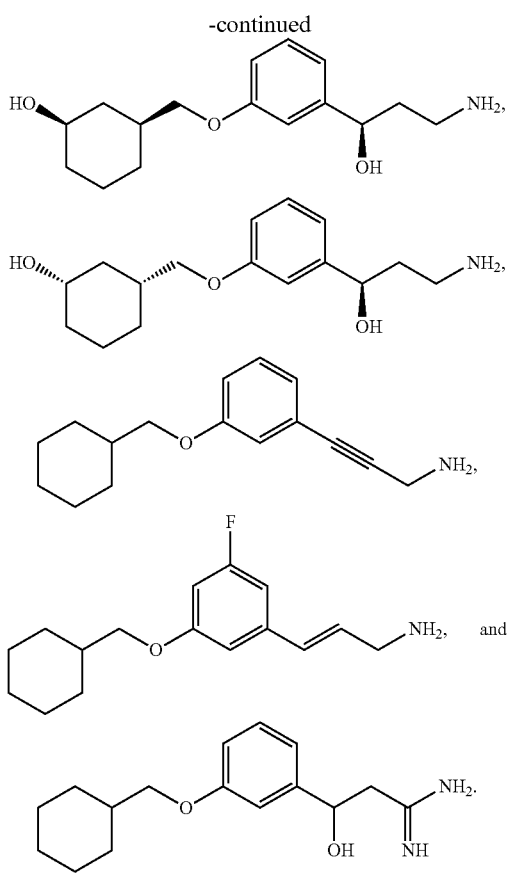

In yet other embodiments, a compound is provided that has a structure of Formula (I):

Formula (I)

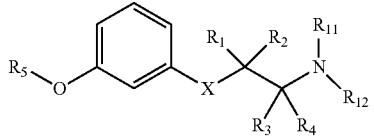

as a tautomer or a mixture of tautomers, or as a pharmaceutically acceptable salt, hydrate, solvate, N-oxide or prodrug thereof, wherein:

$R_1$ and $R_2$ are each the same or different and independently hydrogen, halogen, alkyl, fluoroalkyl, —$OR_6$, —$NR_7R_8$ or carbocyclyl; or $R_1$ and $R_2$ form an oxo;

$R_3$ and $R_4$ are each the same or different and independently hydrogen or alkyl;

$R_5$ is $C_5$-$C_{15}$ alkyl or carbocyclylalkyl;

$R_6$ is hydrogen or alkyl;

$R_7$ and $R_8$ are each the same or different and independently hydrogen, alkyl, carbocyclyl, or —C(=O)$R_{13}$; or $R_7$ and $R_8$, together with the nitrogen atom to which they are attached, form an N-heterocyclyl;

X is —C($R_9$)($R_{10}$)— or —O—;

$R_9$ and $R_{10}$ are each the same or different and independently hydrogen, halogen, alkyl, fluoroalkyl, —$OR_6$, —$NR_7R_8$ or carbocyclyl; or $R_9$ and $R_{10}$ form an oxo;

$R_{11}$ and $R_{12}$ are each the same or different and independently hydrogen, alkyl, or —C(=O)$R_{13}$; or $R_{11}$ and $R_{12}$, together with the nitrogen atom to which they are attached, form an N-heterocyclyl; and $R_{13}$ is alkyl, alkenyl, aryl, aralkyl, carbocyclyl, heteroaryl or heterocyclyl.

Also provided are compounds having structures of any of Formulae (II), (IIa), or (IIb):

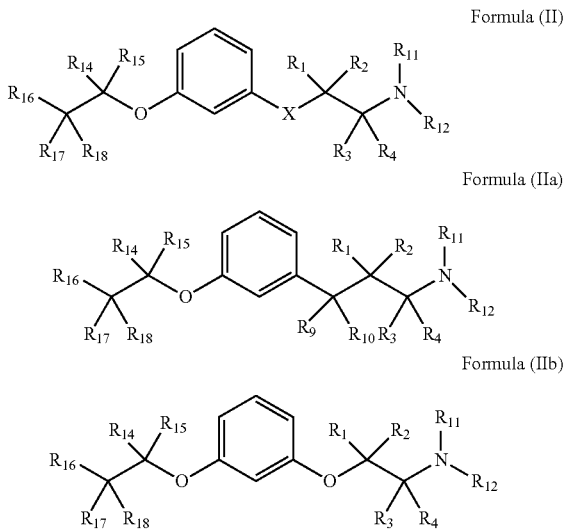

wherein, $R_1$, $R_2$, $R_3$, $R_4$, $R_5$, $R_9$, $R_{10}$, $R_{11}$, $R_{12}$, $R_{14}$, $R_{15}$, $R_{16}$, $R_{17}$ and $R_{18}$ are as defined above and herein (see Detailed Description).

In an additional embodiment is a pharmaceutical composition comprising a pharmaceutically acceptable carrier and a compound disclosed herein, including without limitation a compound of any one of Formulae (A)-(E), (I), (IIa), (IIb), and their respective substructures thereof.

In yet another embodiment is a compound that inhibits 11-cis-retinol production with an $IC_{50}$ of about 1 μM or less when assayed in vitro, utilizing extract of cells that express RPE65 and LRAT, wherein the extract further comprises CRALBP, wherein the compound is stable in solution for at least about 1 week at room temperature. In a specific embodiment, the compound inhibits 11-cis-retinol production with an $IC_{50}$ of about 100 nM or less when assayed in vitro, utilizing extract of cells that express RPE65 and LRAT, wherein the extract further comprises CRALBP, wherein the compound is stable in solution for at least about 1 week at room temperature. In a further embodiment, the compound inhibits 11-cis-retinol production with an $IC_{50}$ of about 10 nM or less when assayed in vitro, utilizing extract of cells that express RPE65 and LRAT, wherein the extract further comprises CRALBP, wherein the compound is stable in solution for at least about 1 week, 1 month, 2 months, 4 months, 6 months, 8 months, 10 months, 1 year, 2 years, 5 years or longer, at room temperature.

In an additional embodiment is a non-retinoid compound that inhibits an isomerase reaction resulting in production of 11-cis retinol, wherein said isomerase reaction occurs in RPE, and wherein said compound has an $ED_{50}$ value of 1 mg/kg or less when administered to a subject. In a further embodiment is a non-retinoid compound wherein the $ED_{50}$ value is measured after administering a single dose of the compound to said subject for about 2 hours or longer. In an additional embodiment the compound is an alkoxyphenyl-linked amine compound. In a further embodiment the compound is a non-retinoid compound.

In a further embodiment is a pharmaceutical composition comprising a pharmaceutically acceptable carrier and a compound that inhibits 11-cis-retinol production with an $IC_{50}$ of about 1 µM or less when assayed in vitro, utilizing extract of cells that express RPE65 and LRAT, wherein the extract further comprises CRALBP, wherein the compound is stable in solution for at least about 1 week at room temperature. In an additional embodiment is a pharmaceutical composition comprising a pharmaceutically acceptable carrier and a non-retinoid compound that inhibits an isomerase reaction resulting in production of 11-cis retinol, wherein said isomerase reaction occurs in RPE, and wherein said compound has an $ED_{50}$ value of 1 mg/kg or less when administered to a subject.

In another embodiment, the present invention provides a method of modulating chromophore flux in a retinoid cycle comprising introducing into a subject a compound disclosed herein, including a compound of any one of Formulae (A)-(E), (I), (IIa), (IIb), and their respective substructures thereof. In a further embodiment the method results in a reduction of lipofuscin pigment accumulated in an eye of the subject. In yet another embodiment the lipofuscin pigment is N-retinylidene-N-retinyl-ethanolamine (A2E).

In yet another embodiment is a method for treating an ophthalmic disease or disorder in a subject, comprising administering to the subject compounds or the pharmaceutical composition described herein. In a further embodiment, the ophthalmic disease or disorder is age-related macular degeneration or Stargardt's macular dystrophy. In yet another embodiment the method results in a reduction of lipofuscin pigment accumulated in an eye of the subject. In yet another embodiment the lipofuscin pigment is N-retinylidene-N-retinyl-ethanolamine (A2E).

In additional embodiments, the ophthalmic disease or disorder is selected from retinal detachment, hemorrhagic retinopathy, retinitis pigmentosa, cone-rod dystrophy, Sorsby's fundus dystrophy, optic neuropathy, inflammatory retinal disease, diabetic retinopathy, diabetic maculopathy, retinal blood vessel occlusion, retinopathy of prematurity, or ischemia reperfusion related retinal injury, proliferative vitreoretinopathy, retinal dystrophy, hereditary optic neuropathy, Sorsby's fundus dystrophy, uveitis, a retinal injury, a retinal disorder associated with Alzheimer's disease, a retinal disorder associated with multiple sclerosis, a retinal disorder associated with Parkinson's disease, a retinal disorder associated with viral infection, a retinal disorder related to light overexposure, myopia, and a retinal disorder associated with AIDS.

In a further embodiment is a method of inhibiting dark adaptation of a rod photoreceptor cell of the retina comprising contacting the retina with a compound disclosed herein, including a compound of any one of Formulae (A)-(E), (I), (IIa), (IIb), and their respective substructures thereof.

In an additional embodiment is a method of inhibiting regeneration of rhodopsin in a rod photoreceptor cell of the retina comprising contacting the retina with a compound of any one of Formulae (A)-(E), (I), (IIa), (IIb), and their respective substructures thereof, a compound that inhibits 11-cis-retinol production with an $IC_{50}$ of about 1 µM or less when assayed in vitro, utilizing extract of cells that express RPE65 and LRAT, wherein the extract further comprises CRALBP, wherein the compound is stable in solution for at least about 1 week at room temperature, or a non-retinoid compound that inhibits an isomerase reaction resulting in production of 11-cis retinol, wherein said isomerase reaction occurs in RPE, and wherein said compound has an $ED_{50}$ value of 1 mg/kg or less when administered to a subject.

In a further embodiment is a method of reducing ischemia in an eye of a subject comprising administering to the subject a pharmaceutical composition of a compound of any one of Formulae (A)-(E), (I), (IIa), (IIb), and their respective substructures thereof, a compound that inhibits 11-cis-retinol production with an $IC_{50}$ of about 1 µM or less when assayed in vitro, utilizing extract of cells that express RPE65 and LRAT, wherein the extract further comprises CRALBP, wherein the compound is stable in solution for at least about 1 week at room temperature, or a non-retinoid compound that inhibits an isomerase reaction resulting in production of 11-cis retinol, wherein said isomerase reaction occurs in RPE, and wherein said compound has an $ED_{50}$ value of 1 mg/kg or less when administered to a subject. In a further embodiment, the pharmaceutical composition is administered under conditions and at a time sufficient to inhibit dark adaptation of a rod photoreceptor cell, thereby reducing ischemia in the eye.

In a further embodiment is a method of inhibiting neovascularization in the retina of an eye of a subject comprising administering to the subject a pharmaceutical composition of a compound of any one of Formulae (A)-(E), (I), (IIa), (IIb), and their respective substructures thereof. In a specific embodiment, the pharmaceutical composition is administered under conditions and at a time sufficient to inhibit dark adaptation of a rod photoreceptor cell, thereby inhibiting neovascularization in the retina.

In a further embodiment is a method of inhibiting degeneration of a retinal cell in a retina comprising contacting the retina with a pharmaceutical composition comprising a compound of Formula (A), or a compound that inhibits 11-cis-retinol production with an $IC_{50}$ of about 1 µM or less when assayed in vitro, utilizing extract of cells that express RPE65 and LRAT, wherein the extract further comprises CRALBP, wherein the compound is stable in solution for at least about 1 week at room temperature, or a non-retinoid compound that inhibits an isomerase reaction resulting in production of 11-cis retinol, wherein said isomerase reaction occurs in RPE, and wherein said compound has an $ED_{50}$ value of 1 mg/kg or less when administered to a subject. In a further embodiment, the pharmaceutical composition is administered under conditions and at a time sufficient to inhibit dark adaptation of a rod photoreceptor cell, thereby reducing ischemia in the eye. In a specific embodiment is the method wherein the retinal cell is a retinal neuronal cell. In a certain embodiment, the retinal neuronal cell is a photoreceptor cell In another embodiment, a method is provided for treating an ophthalmic disease or disorder in a subject, comprising administering to the subject a pharmaceutical composition comprising a pharmaceutically acceptable carrier and a compound having a structure of any of Formulae (I), (II), (IIa), or (IIb) as described above and herein. In one embodiment, the ophthalmic disease or disorder is a retinal disease or disorder. In specific embodiments, the retinal disease or disorder is age-related macular degeneration or Stargardt's macular dystrophy. In another embodiment, the ophthalmic disease or disorder is selected from retinal detachment, hemorrhagic retinopathy, retinitis pigmentosa, optic neuropathy, inflammatory retinal disease, proliferative vitreoretinopathy, retinal dystrophy, hereditary optic neuropathy, Sorsby's fundus dystrophy, uveitis, a retinal injury, a retinal disorder associated with Alzheimer's disease, a retinal disorder associated with multiple sclerosis, a retinal disorder associated with Parkinson's disease, a retinal disorder associated with viral infection, a retinal disorder related to light overexposure, and a retinal disorder associated with AIDS. In yet another embodiment, the ophthalmic disease or disorder is selected from diabetic retinopathy, diabetic maculopathy, retinal blood vessel occlusion, retinopathy of prematurity, or ischemia reperfusion related retinal injury.

Further provided is a method of reducing lipofuscin pigment accumulated in a subject's retina comprising administering to the subject a pharmaceutical composition described here. In one embodiment the lipofuscin pigment is N-retinylidene-N-retinyl-ethanolamine (A2E).

In another embodiment, a method of inhibiting at least one visual cycle trans-cis isomerase in a cell is provided, wherein the method comprises contacting the cell with a compound having a structure of any of Formulae (I), (II), (IIa), or (IIb) as described herein, thereby inhibiting the at least one visual cycle trans-cis isomerase. In one certain embodiment, the cell is a retinal pigment epithelial (RPE) cell.

Also provided herein in another embodiment is a method of inhibiting at least one visual cycle trans-cis isomerase in a subject comprising administering to the subject a pharmaceutical composition comprising a pharmaceutically acceptable carrier and a compound having a structure of any of Formulae (I), (II), (IIa), or (IIb) as described herein. In certain embodiments, the subject is a human or is a non-human animal.

In particular embodiments of the methods described above and herein, accumulation of lipofuscin pigment is inhibited in an eye of the subject and in certain particular embodiments, the lipofuscin pigment is N-retinylidene-N-retinyl-ethanolamine (A2E). In other certain embodiments, degeneration of a retinal cell is inhibited. In a specific embodiment, the retinal cell is a retinal neuronal cell, wherein the retinal neuronal cell is a photoreceptor cell, an amacrine cell, a horizontal cell, a ganglion cell, or a bipolar cell. In another specific embodiment, the retinal cell is a retinal pigment epithelial (RPE) cell.

In an additional embodiment is a pharmaceutical composition comprising a pharmaceutically acceptable carrier and a compound of Formula (A) or tautomer, stereoisomer, geometric isomer, or pharmaceutically acceptable solvate, hydrate, salt, N-oxide or prodrug thereof:

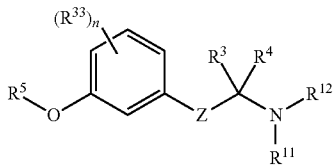

Formula (A)

wherein,

Z is —C($R^9$)($R^{10}$)—C($R^1$)($R^2$)—, —X—C($R^{31}$)($R^{32}$)—, —C($R^9$)($R^{10}$)—C($R^1$)($R^2$)—C($R^{36}$)($R^{37}$)— or —X—C($R^{31}$)($R^{32}$)—C($R^1$)($R^2$)—;

$R^1$ and $R^2$ are each independently selected from hydrogen, halogen, $C_1$-$C_5$ alkyl, fluoroalkyl, —$OR^6$ or —$NR^7R^8$; or $R^1$ and $R^2$ together form an oxo;

$R^{31}$ and $R^{32}$ are each independently selected from hydrogen, $C_1$-$C_5$ alkyl, or fluoroalkyl;

$R^{36}$ and $R^{37}$ are each independently selected from hydrogen, halogen, $C_1$-$C_5$ alkyl, fluoroalkyl, —$OR^6$ or —$NR^7R^8$; or $R^{36}$ and $R^{37}$ together form an oxo; or optionally, $R^{36}$ and $R^1$ together form a direct bond to provide a double bond;

or optionally, $R^{36}$ and $R^1$ together form a direct bond, and $R^{37}$ and $R^2$ together form a direct bond to provide a triple bond;

$R^3$ and $R^4$ are each independently selected from hydrogen, alkyl, alkenyl, fluoroalkyl, aryl, heteroaryl, carbocyclyl or C-attached heterocyclyl; or $R^3$ and $R^4$ together with the carbon atom to which they are attached, form a carbocyclyl or heterocyclyl; or $R^3$ and $R^4$ together form an imino;

$R^5$ is $C_5$-$C_{15}$ alkyl or carbocyclylalkyl;

$R^7$ and $R^8$ are each independently selected from hydrogen, alkyl, carbocyclyl, heterocyclyl, —C(=O)$R^{13}$, $SO_2R^{13}$, $CO_2R^{13}$ or $SO_2NR^{24}R^{25}$; or $R^7$ and $R^8$ together with the nitrogen atom to which they are attached, form an N-heterocyclyl;

X is —O—, —S—, —S(=O)—, —S(=O)$_2$—, —N($R^{30}$)—, —C(=O)—, —C(=CH$_2$)—, —C(=N—NR$^{35}$)—, or —C(=N—OR$^{35}$)—

$R^9$ and $R^{10}$ are each independently selected from hydrogen, halogen, alkyl, fluoroalkyl, —$OR^{19}$—, —$NR^{20}R^{21}$ or carbocyclyl; or $R^9$ and $R^{10}$ form an oxo; or optionally, $R^9$ and $R^1$ together form a direct bond to provide a double bond; or optionally, $R^9$ and $R^1$ together form a direct bond, and $R^{10}$ and $R^2$ together form a direct bond to provide a triple bond;

$R^{11}$ and $R^{12}$ are each independently selected from hydrogen, alkyl, carbocyclyl, —C(=O)$R^{23}$, —C(NH)NH$_2$, $SO_2R^{23}$, $CO_2R^{23}$ or $SO_2NR^{28}R^{29}$; or $R^{11}$ and $R^{12}$, together with the nitrogen atom to which they are attached, form an N-heterocyclyl;

each $R^{13}$, $R^{22}$ and $R^{23}$ is independently selected from alkyl, heteroalkyl, alkenyl, aryl, aralkyl, carbocyclyl, heteroaryl or heterocyclyl;

$R^6$, $R^{19}$, $R^{30}$, $R^{34}$ and $R^{35}$ are each independently hydrogen or alkyl;

$R^{20}$ and $R^{21}$ are each independently selected from hydrogen, alkyl, carbocyclyl, heterocyclyl, —C(=O)$R^{22}$, $SO_2R^{22}$, $CO_2R^{22}$ or $SO_2NR^{26}R^{27}$; or $R^{20}$ and $R^{21}$ together with the nitrogen atom to which they are attached, form an N-heterocyclyl;

each $R^{24}$, $R^{25}$, $R^{26}$, $R^{27}$, $R^{28}$ and $R^{29}$ is independently selected from hydrogen, alkyl, alkenyl, fluoroalkyl, aryl, heteroaryl, carbocyclyl or heterocyclyl;

each $R^{33}$ is independently selected from halogen, $OR^{34}$, alkyl, or fluoroalkyl; and n is 0, 1, 2, 3, or 4; with the provision that $R^5$ is not 2-(cyclopropyl)-1-ethyl or an unsubstituted normal alkyl.

In an additional embodiment is a non-retinoid compound that inhibits an isomerase reaction resulting in production of 11-cis retinol, wherein said isomerase reaction occurs in RPE, and wherein said compound has an ED$_{50}$ value of 1 mg/kg or less when administered to a subject. In a further embodiment is the non-retinoid compound wherein the ED$_{50}$ value is measured after administering a single dose of the compound to said subject for about 2 hours or longer. In a further embodiment is the non-retinoid compound, wherein the non-retinoid compound is an alkoxyl compound. In an additional embodiment is a pharmaceutical composition comprising a pharmaceutically acceptable carrier and a non-retinoid compound as described herein. In an additional embodiment is a method for treating an ophthalmic disease or disorder in a subject, comprising administering to the subject a pharmaceutical composition comprising a pharmaceutically acceptable carrier and a non-retinoid compound as described herein.

In an additional embodiment is a compound that inhibits 11-cis-retinol production with an IC$_{50}$ of about 1 μM or less when assayed in vitro, utilizing extract of cells that express RPE65 and LRAT, wherein the extract further comprises CRALBP, wherein the compound is stable in solution for at least about 1 week at room temperature. In a further embodiment, the compound inhibits 11-cis-retinol production with an IC$_{50}$ of about 0.1 µM or less. In a further embodiment, the compound inhibits 11-cis-retinol production with an IC$_{50}$ of about 0.01 µM or less. In a further embodiment, the compound that inhibits 11-cis-retinol production is a non-retinoid compound. In an additional embodiment is a pharmaceutical composition comprising a pharmaceutically acceptable carrier and a compound that inhibits 11-cis-retinol production as described herein. In an additional embodiment is a method for treating an ophthalmic disease or disorder in a subject, comprising administering to the subject a pharmaceutical composition comprising a pharmaceutically acceptable carrier and a compound that inhibits 11-cis-retinol production as described herein. In an additional embodiment is a method of modulating chromophore flux in a retinoid cycle comprising introducing into a subject a compound that inhibits 11-cis-retinol production as described herein.

In an additional embodiment is a method for treating an ophthalmic disease or disorder in a subject, comprising administering to the subject a compound of Formula (F) or tautomer, stereoisomer, geometric isomer or a pharmaceutically acceptable solvate, hydrate, salt, N-oxide or prodrug thereof:

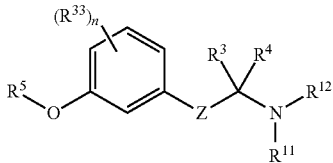

Formula (F)

wherein,

Z is a bond, —C(R$^1$)(R$^2$)—, —C(R$^9$)(R$^{10}$)—C(R$^1$)(R$^2$)—, —X—C(R$^{31}$)(R$^{32}$)—, —C(R$^9$)(R$^{10}$)—C(R$^1$)(R$^2$)—C(R$^{36}$)(R$^{37}$)— or —X—C(R$^{31}$)(R$^{32}$)—C(R$^1$)(R$^2$)—

R$^1$ and R$^2$ are each independently selected from hydrogen, halogen, C$_1$-C$_5$ alkyl, fluoroalkyl, —OR$^6$ or —NR$^7$R$^8$; or R$^1$ and R$^2$ together form an oxo;

R$^{31}$ and R$^{32}$ are each independently selected from hydrogen, C$_1$-C$_5$ alkyl, or fluoroalkyl;

R$^{36}$ and R$^{37}$ are each independently selected from hydrogen, halogen, C$_1$-C$_5$ alkyl, fluoroalkyl, —OR$^6$ or —NR$^7$R$^8$; or R$^{36}$ and R$^{37}$ together form an oxo; or optionally, R$^{36}$ and R$^1$ together form a direct bond to provide a double bond; or optionally, R$^{36}$ and R$^1$ together form a direct bond, and R$^{37}$ and R$^2$ together form a direct bond to provide a triple bond;

R$^3$ and R$^4$ are each independently selected from hydrogen, alkyl, alkenyl, fluoroalkyl, aryl, heteroaryl, carbocyclyl or C-attached heterocyclyl; or R$^3$ and R$^4$ together with the carbon atom to which they are attached, form a carbocyclyl or heterocyclyl; or R$^3$ and R$^4$ together form an imino;

R$^5$ is C$_1$-C$_{15}$ alkyl, carbocyclalkyl, arylalkyl, heteroarylalkyl or heterocyclylalkyl;

R$^7$ and R$^8$ are each independently selected from hydrogen, alkyl, carbocyclyl, heterocyclyl, —C(═O)R$^{13}$, SO$_2$R$^{13}$, CO$_2$R$^{13}$ or SO$_2$NR$^{24}$R$^{25}$; or R$^7$ and R$^8$ together with the nitrogen atom to which they are attached, form an N-heterocyclyl;

X is —O—, —S—, —S(═O)—, —S(═O)$_2$—, —N(R$^{30}$)—, —C(═O)—, —C(═CH$_2$)—, —C(═N—NR$^{35}$)—, or —C(═N—OR$^{35}$)—;

R$^9$ and R$^{10}$ are each independently selected from hydrogen, halogen, alkyl, fluoroalkyl, —OR$^{19}$—, —NR$^{20}$R$^{21}$ or carbocyclyl; or R$^9$ and R$^{10}$ form an oxo; or optionally, R$^9$ and R$^1$ together form a direct bond to provide a double bond; or optionally, R$^9$ and R$^1$ together form a direct bond, and R$^{10}$ and R$^2$ together form a direct bond to provide a triple bond;

R$^{11}$ and R$^{12}$ are each independently selected from hydrogen, alkyl, carbocyclyl, —C(═O)R$^{23}$, —C(NH)NH$_2$, SO$_2$R$^{23}$, CO$_2$R$^{23}$ or SO$_2$NR$^{28}$R$^{29}$; or R$^{11}$ and R$^{12}$, together with the nitrogen atom to which they are attached, form an N-heterocyclyl;

each R$^{13}$, R$^{22}$ and R$^{23}$ is independently selected from alkyl, heteroalkyl, alkenyl, aryl, aralkyl, carbocyclyl, heteroaryl or heterocyclyl;

R$^6$, R$^{19}$, R$^{30}$, R$^{34}$ and R$^{35}$ are each independently hydrogen or alkyl;

R$^{20}$ and R$^{21}$ are each independently selected from hydrogen, alkyl, carbocyclyl, heterocyclyl, —C(═O)R$^{22}$, SO$_2$R$^{22}$, CO$_2$R$^{22}$ or SO$_2$NR$^{26}$R$^{27}$; or R$^{20}$ and R$^{21}$ together with the nitrogen atom to which they are attached, form an N-heterocyclyl; and each R$^{24}$, R$^{25}$, R$^{26}$, R$^{27}$, R$^{28}$ and R$^{29}$ is independently selected from hydrogen, alkyl, alkenyl, fluoroalkyl, aryl, heteroaryl, carbocyclyl or heterocyclyl;

each R$^{33}$ is independently selected from halogen, OR$^{34}$, alkyl, or fluoroalkyl; and n is 0, 1, 2, 3, or 4.

In an additional embodiment is a method of modulating chromophore flux in a retinoid cycle comprising introducing into a subject a compound of Formula (F). In a further embodiment is the method resulting in a reduction of lipofuscin pigment accumulated in an eye of the subject. In a further embodiment is the method resulting in a reduction of lipofuscin pigment accumulated in an eye of the subject, wherein the lipofuscin pigment is N-retinylidene-N-retinylethanolamine (A2E).

In a further embodiment is the method of treating an ophthalmic disease or disorder in a subject as described herein resulting in a reduction of lipofuscin pigment accumulated in an eye of the subject. In a further embodiment is the method of treating an ophthalmic disease or disorder in a subject as described herein resulting in a reduction of lipofuscin pigment accumulated in an eye of the subject, wherein the lipofuscin pigment is N-retinylidene-N-retinylethanolamine (A2E).

In a further embodiment is the method of treating an ophthalmic disease or disorder in a subject as described herein, wherein the ophthalmic disease or disorder is age-related macular degeneration or Stargardt's macular dystrophy. In a further embodiment is the method of treating an ophthalmic disease or disorder in a subject as described herein, wherein the ophthalmic disease or disorder is selected from retinal detachment, hemorrhagic retinopathy, retinitis pigmentosa, cone-rod dystrophy, Sorsby's fundus dystrophy, optic neuropathy, inflammatory retinal disease, diabetic retinopathy, diabetic maculopathy, retinal blood vessel occlusion, retinopathy of prematurity, or ischemia reperfusion related retinal injury, proliferative vitreoretinopathy, retinal dystrophy, hereditary optic neuropathy, Sorsby's fundus dystrophy, uveitis, a retinal injury, a retinal disorder associated with Alzheimer's disease, a retinal disorder associated with multiple sclerosis, a retinal disorder associated with Parkinson's disease, a retinal disorder associated with viral infection, a retinal disorder related to light overexposure, myopia, and a retinal disorder associated with AIDS. In a further embodiment is the method of treating an ophthalmic disease or disorder in a subject as described herein resulting in a reduction of lipofuscin pigment accumulated in an eye of the subject. In a further embodiment is the method of treating an ophthalmic disease or disorder in a subject as described herein resulting in a reduction of lipofuscin pigment accumulated in an eye of the subject, wherein the lipofuscin pigment is N-retinylidene-N-retinyl-ethanolamine (A2E).

In another embodiment is a method of inhibiting dark adaptation of a rod photoreceptor cell of the retina comprising contacting the retina with a compound of Formula (F). In another embodiment is a method of inhibiting dark adaptation of a rod photoreceptor cell of the retina comprising contacting the retina with a non-retinoid compound as described herein. In another embodiment is a method of inhibiting dark adaptation of a rod photoreceptor cell of the retina comprising contacting the retina with a compound that inhibits 11-cis-retinol production as described herein.

In another embodiment is a method of inhibiting regeneration of rhodopsin in a rod photoreceptor cell of the retina comprising contacting the retina with a compound of Formula (F). In another embodiment is a method of inhibiting regeneration of rhodopsin in a rod photoreceptor cell of the retina comprising contacting the retina with a non-retinoid compound as described herein. In another embodiment is a method of inhibiting regeneration of rhodopsin in a rod photoreceptor cell of the retina comprising contacting the retina with a compound that inhibits 11-cis-retinol production as described herein.

In another embodiment is a method of reducing ischemia in an eye of a subject comprising administering to the subject a pharmaceutical composition comprising a pharmaceutically acceptable carrier and a compound of Formula (F).

In an additional embodiment is a method of reducing ischemia in an eye of a subject comprising administering to the subject a pharmaceutical composition comprising a pharmaceutically acceptable carrier and a non-retinoid compound as described herein. In an additional embodiment is a method of reducing ischemia in an eye of a subject comprising administering to the subject a pharmaceutical composition comprising a pharmaceutically acceptable carrier and a compound that inhibits 11-cis-retinol production as described herein. In a further embodiment is the method of reducing ischemia in an eye of a subject, wherein the pharmaceutical composition is administered under conditions and at a time sufficient to inhibit dark adaptation of a rod photoreceptor cell, thereby reducing ischemia in the eye.

In an additional embodiment is a method of inhibiting neovascularization in the retina of an eye of a subject comprising administering to the subject a pharmaceutical composition comprising a pharmaceutically acceptable carrier and a non-retinoid compound as described herein. In an additional embodiment is a method of inhibiting neovascularization in the retina of an eye of a subject comprising administering to the subject a pharmaceutical composition comprising a pharmaceutically acceptable carrier and a compound that inhibits 11-cis-retinol production as described herein. In a further embodiment is the method of inhibiting neovascularization in the retina of an eye of a subject, wherein the pharmaceutical composition is administered under conditions and at a time sufficient to inhibit dark adaptation of a rod photoreceptor cell, thereby inhibiting neovascularization in the retina.

In an additional embodiment is a method of inhibiting degeneration of a retinal cell in a retina comprising contacting the retina with a compound of Formula (F). In an additional embodiment is a method of inhibiting degeneration of a retinal cell in a retina comprising contacting the retina with a non-retinoid compound as described herein. In an additional embodiment is a method of inhibiting degeneration of a retinal cell in a retina comprising contacting the retina with a compound that inhibits 11-cis-retinol production as described herein.

In a further embodiment is the method of inhibiting degeneration of a retinal cell in a retina wherein the retinal cell is a retinal neuronal cell. In a further embodiment is the method of inhibiting degeneration of a retinal cell in a retina wherein the retinal neuronal cell is a photoreceptor cell.

In another embodiment is a method of reducing lipofuscin pigment accumulated in a subject's retina comprising administering to the subject a pharmaceutical composition comprising a pharmaceutically acceptable carrier and a compound of Formula (F). In an additional embodiment is a method of reducing lipofuscin pigment accumulated in a subject's retina wherein the lipofuscin is N-retinylidene-N-retinyl-ethanolamine (A2E).

In an additional embodiment is a method of reducing lipofuscin pigment accumulated in a subject's retina comprising administering to the subject a pharmaceutical composition comprising a pharmaceutically acceptable carrier and a non-retinoid compound as described herein. In an additional embodiment is a method of reducing lipofuscin pigment accumulated in a subject's retina comprising administering to the subject a pharmaceutical composition comprising a pharmaceutically acceptable carrier and a compound that inhibits 11-cis-retinol production as described herein. In an additional embodiment is a method of reducing lipofuscin pigment accumulated in a subject's retina wherein the lipofuscin is N-retinylidene-N-retinyl-ethanolamine (A2E).

In a further embodiment is the method for treating an ophthalmic disease or disorder in a subject, comprising administering to the subject a compound of Formula (F), wherein the compound of Formula (F) is selected from the group consisting of:

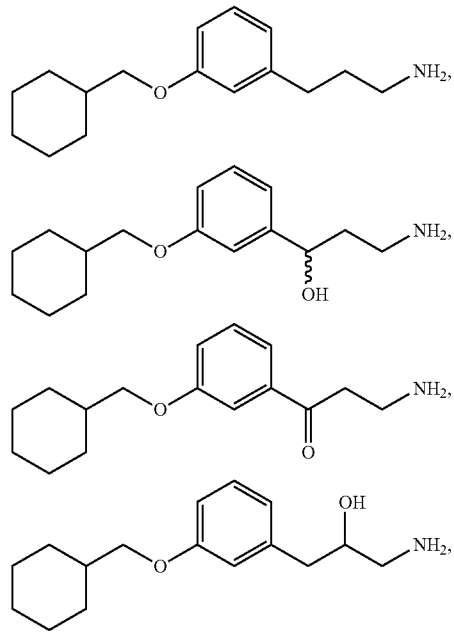

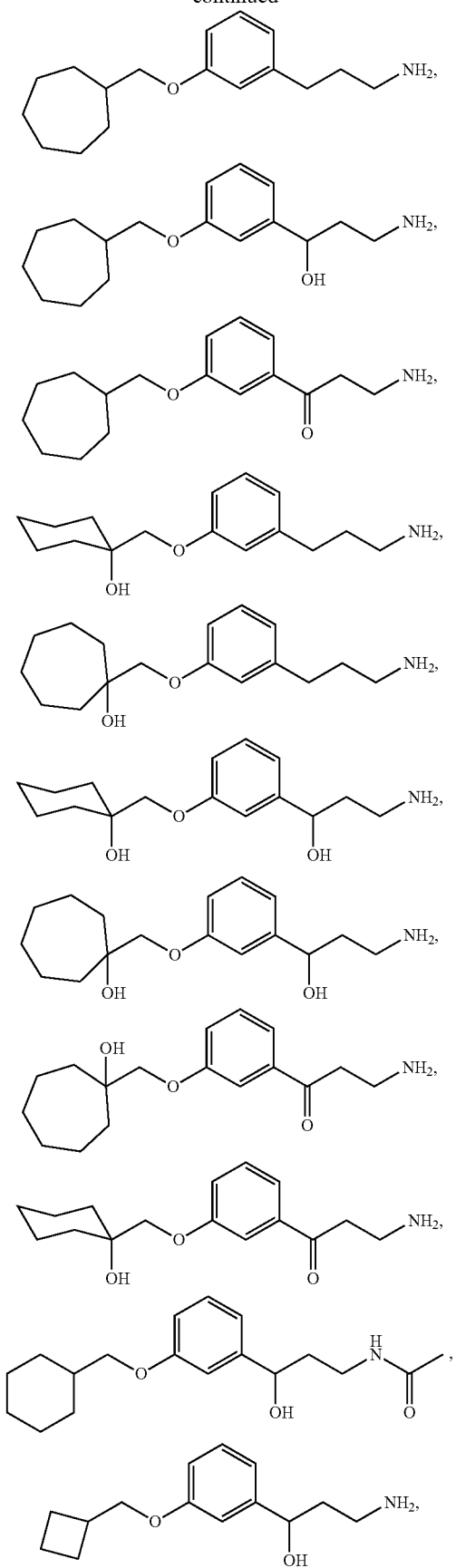

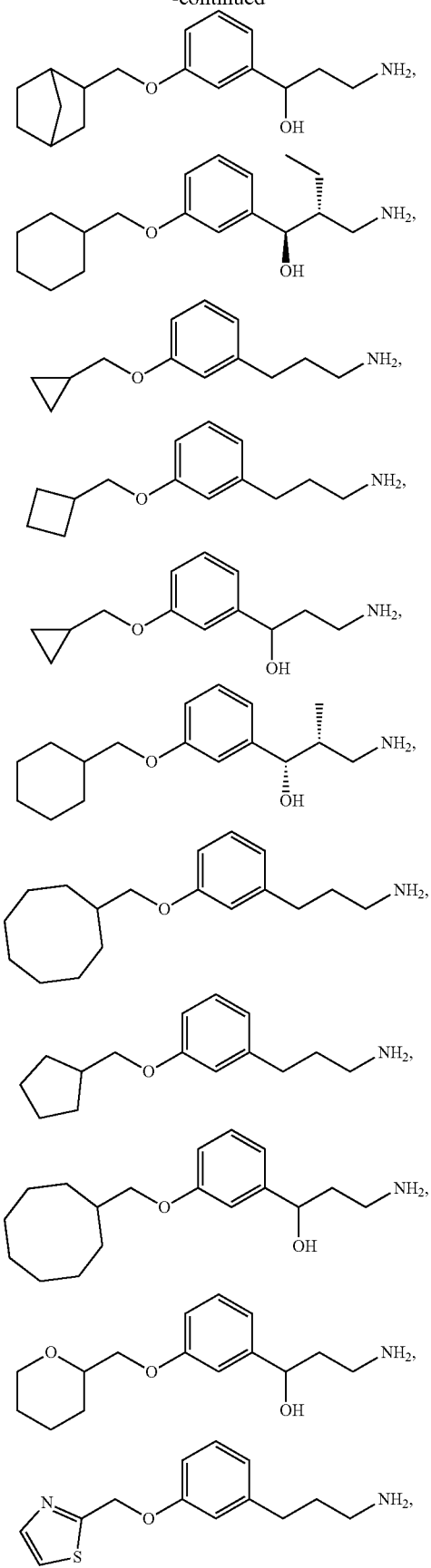
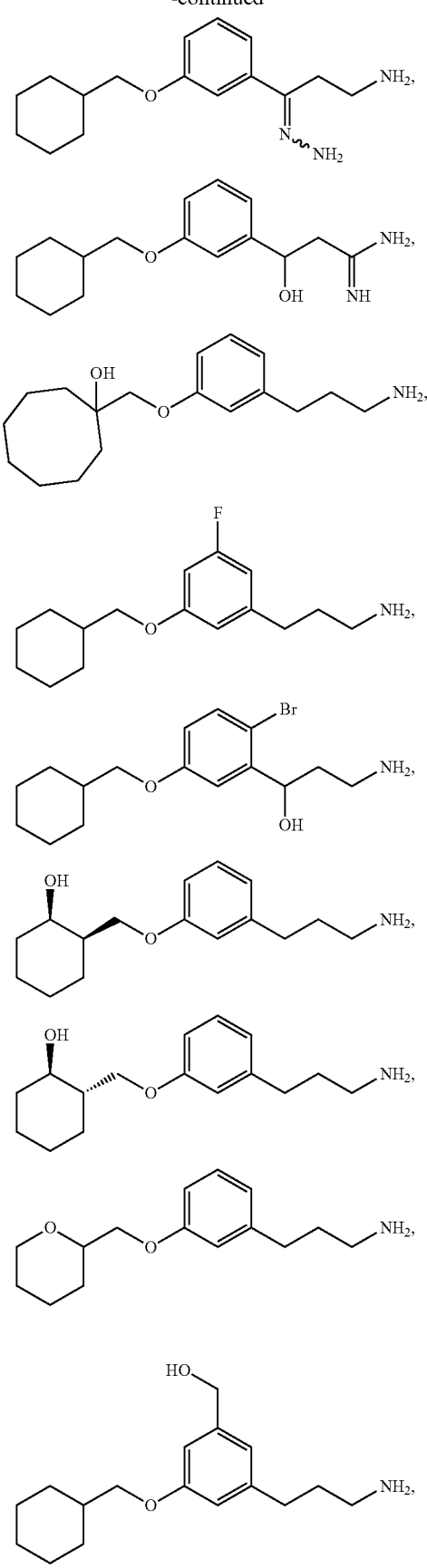

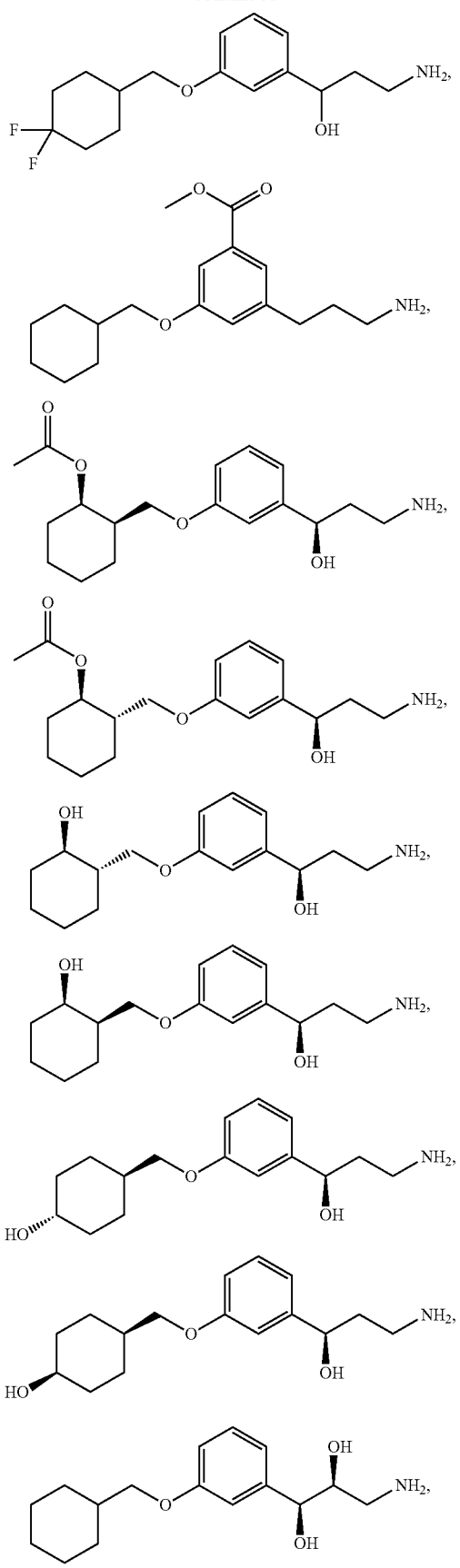

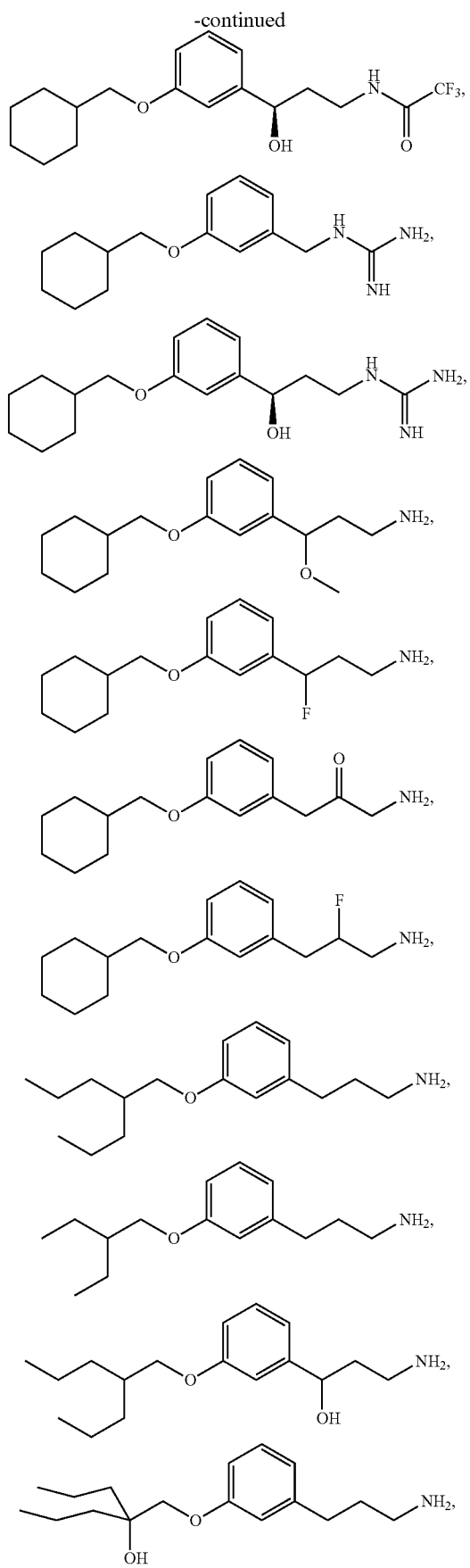
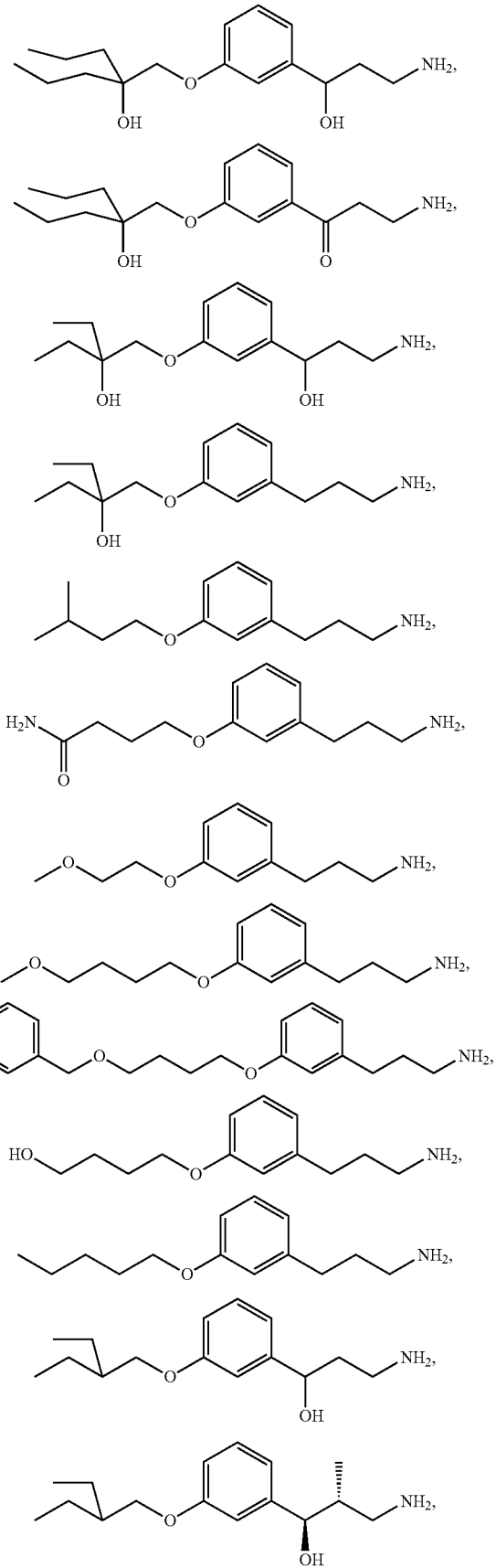

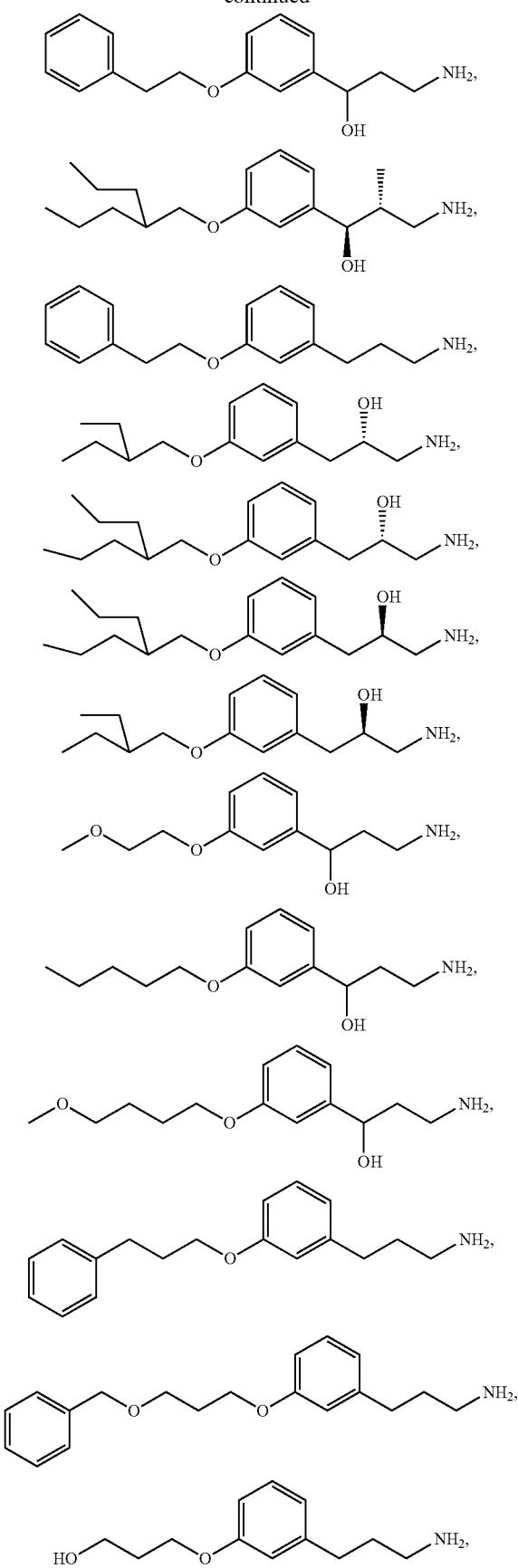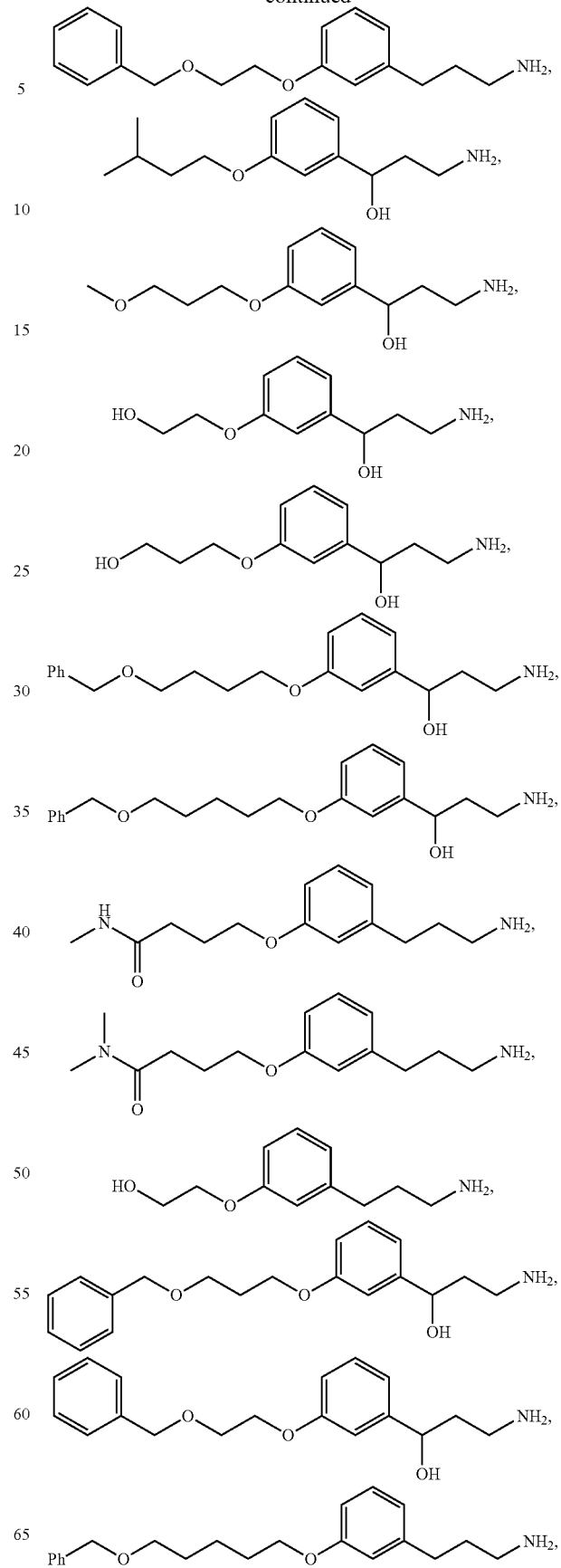

-continued
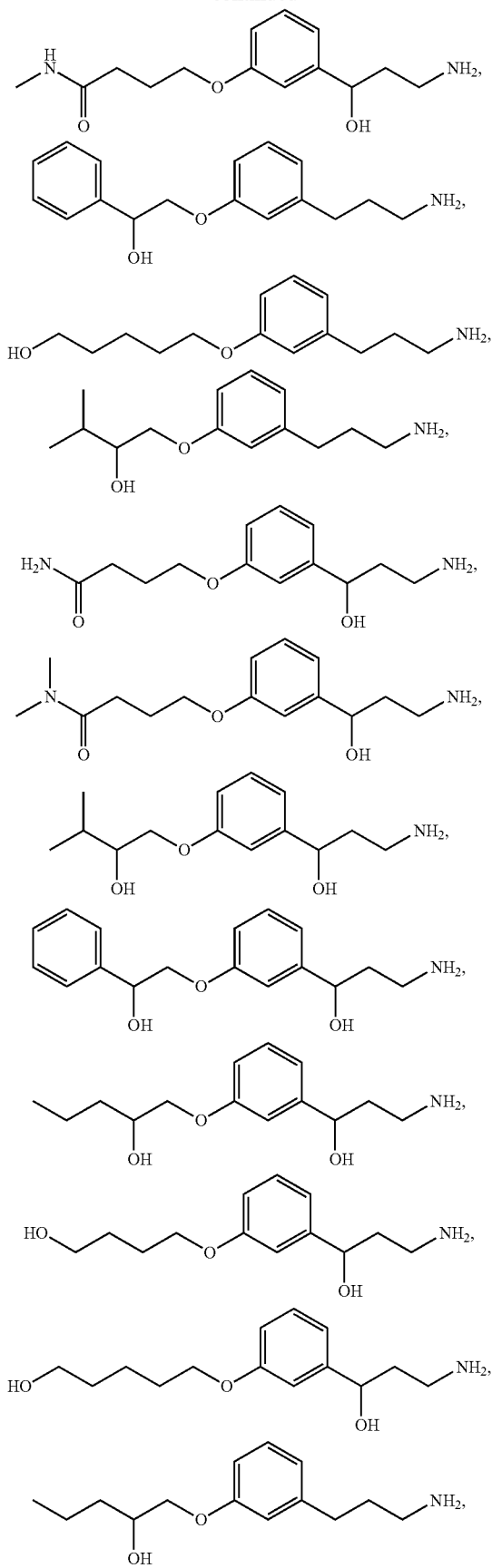
-continued
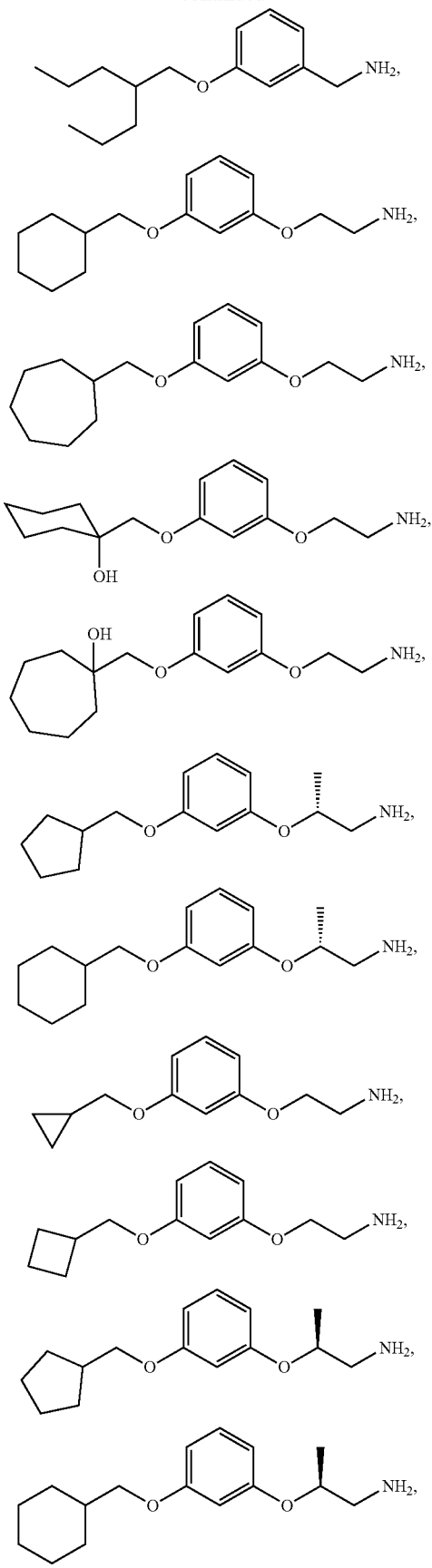

-continued
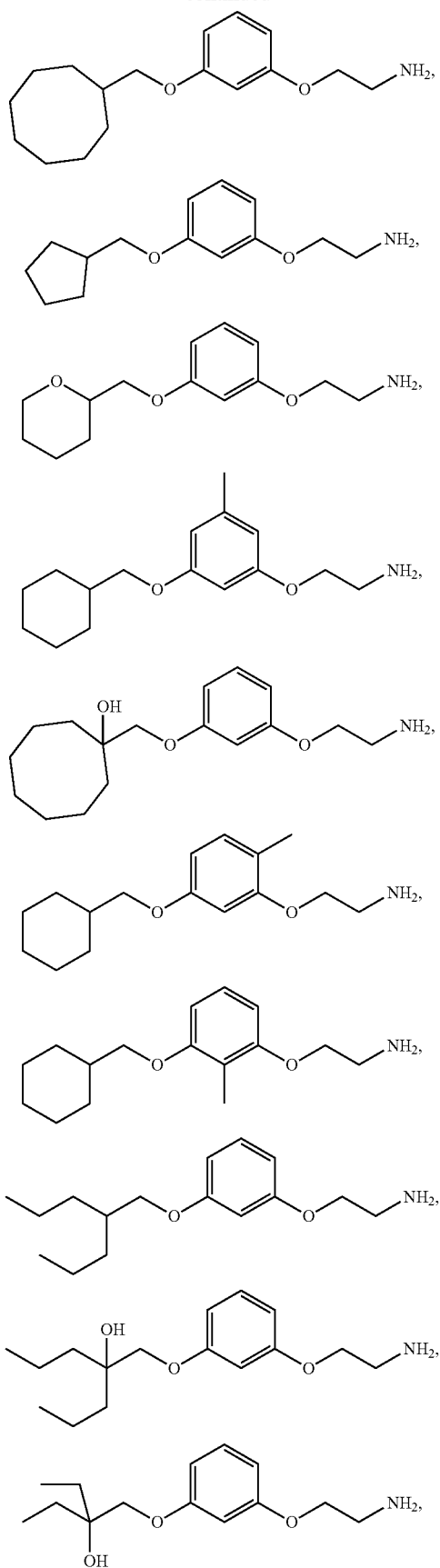
-continued
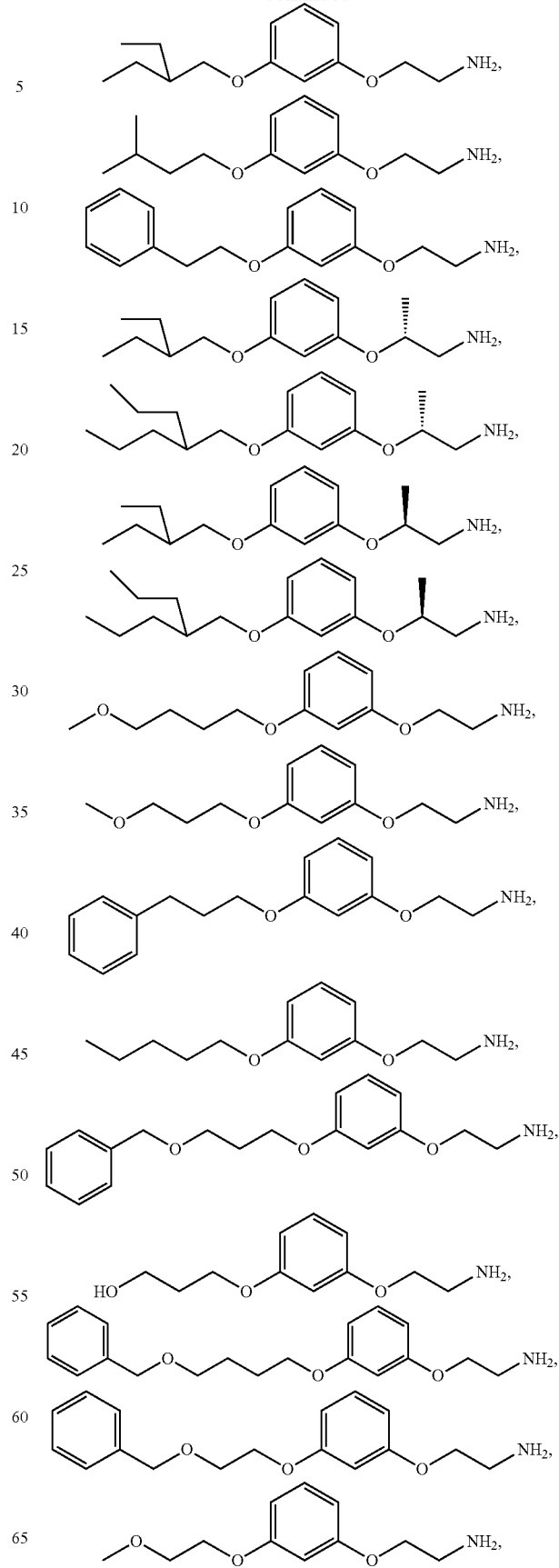

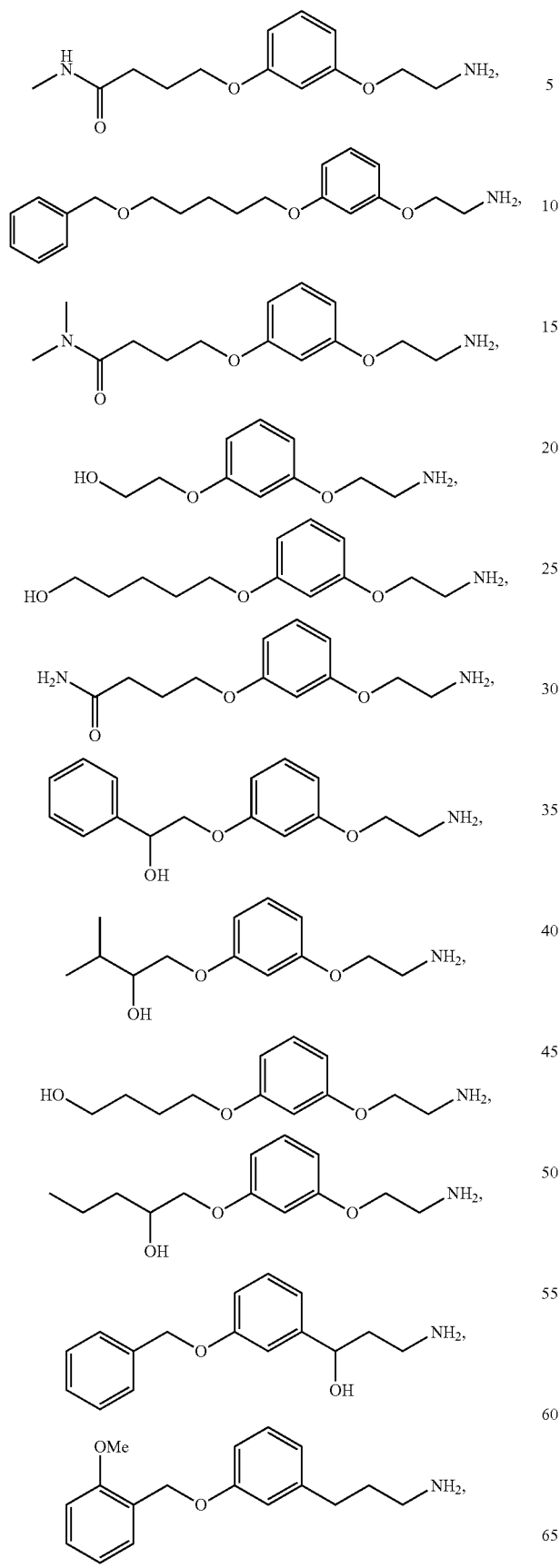
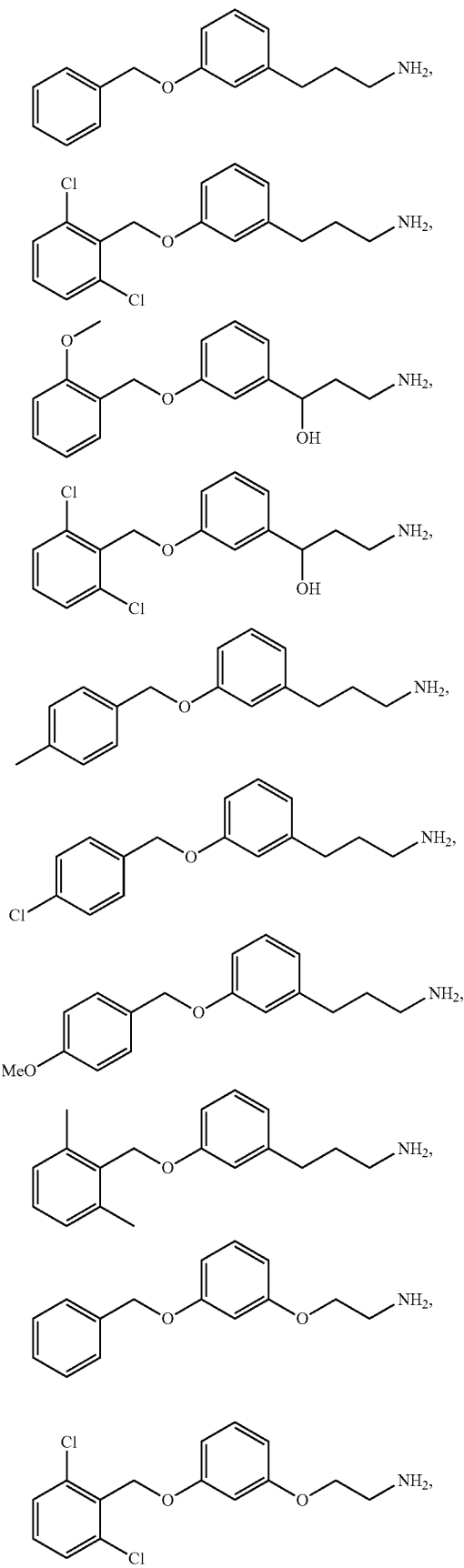

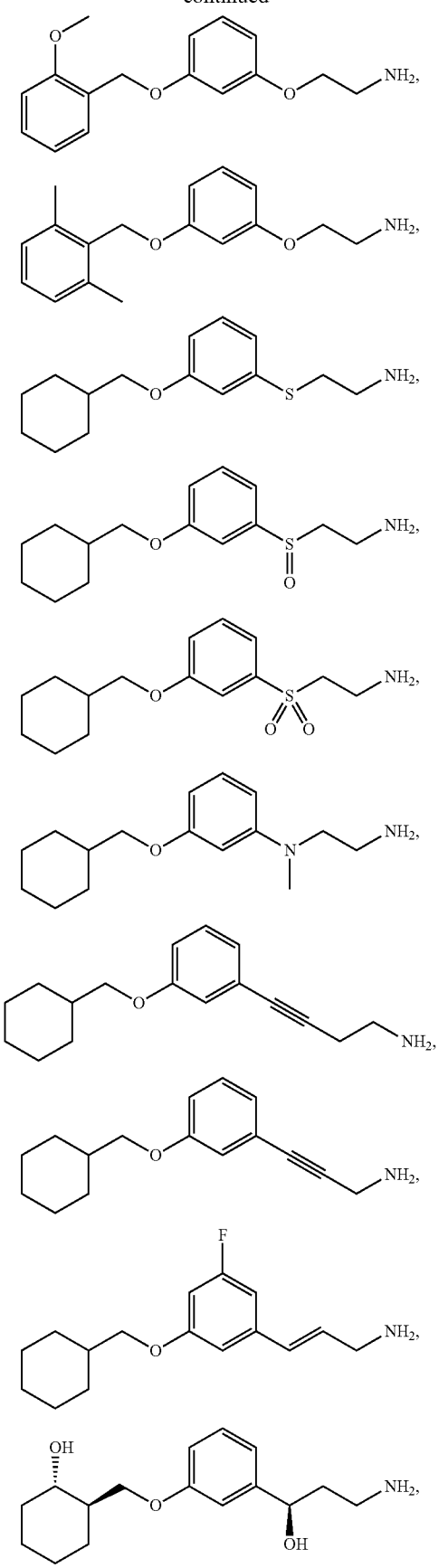
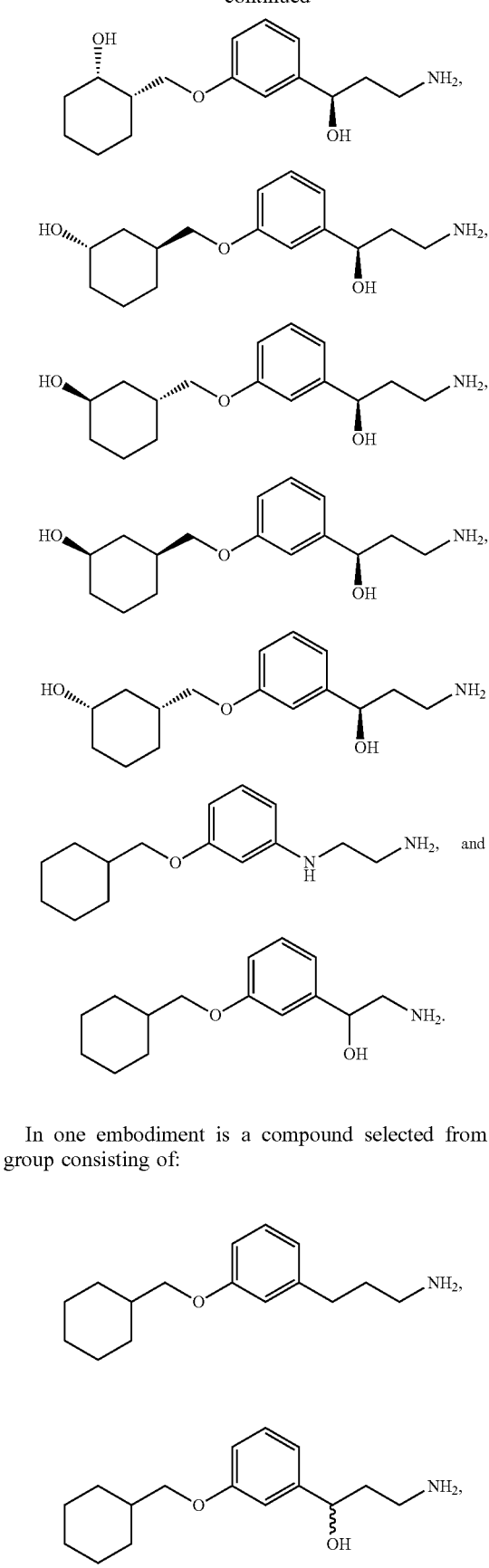
In one embodiment is a compound selected from the group consisting of:

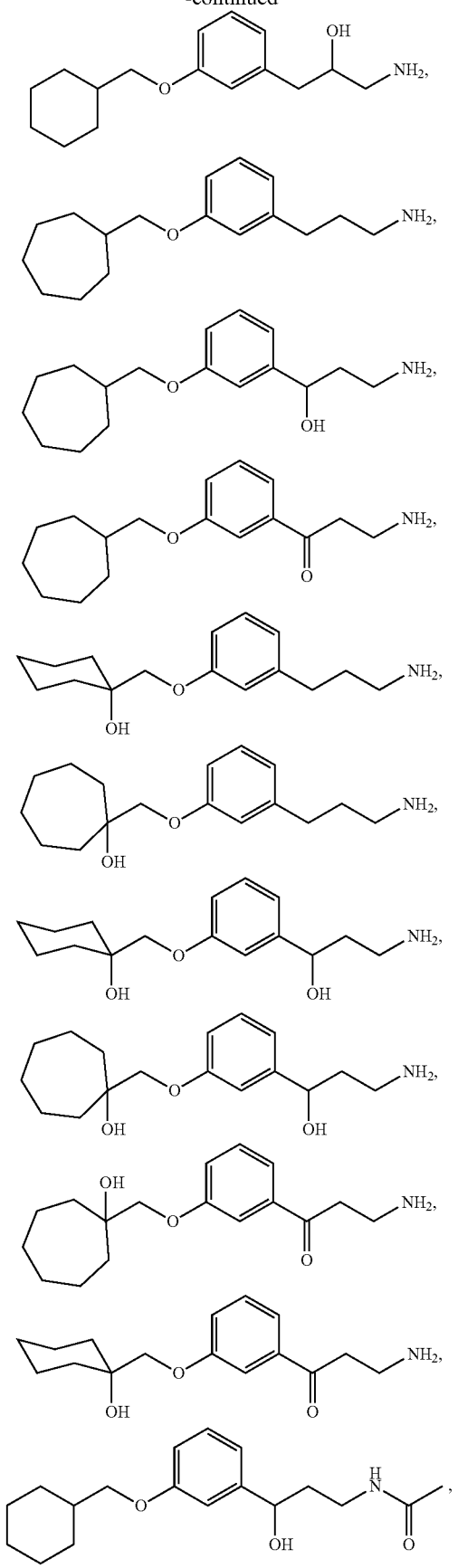
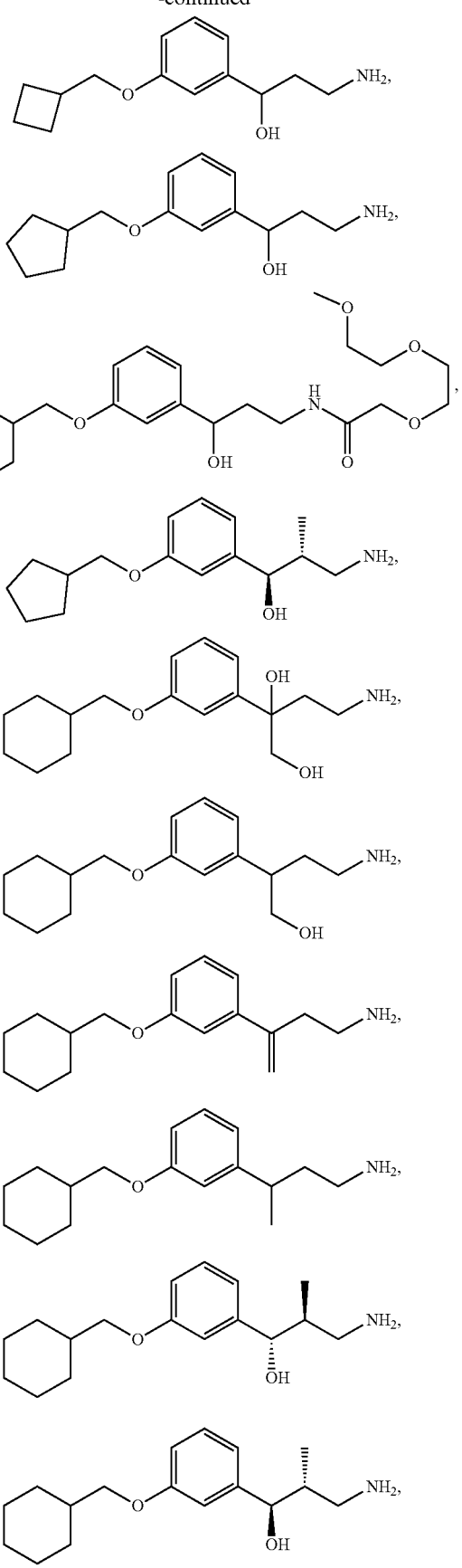

-continued
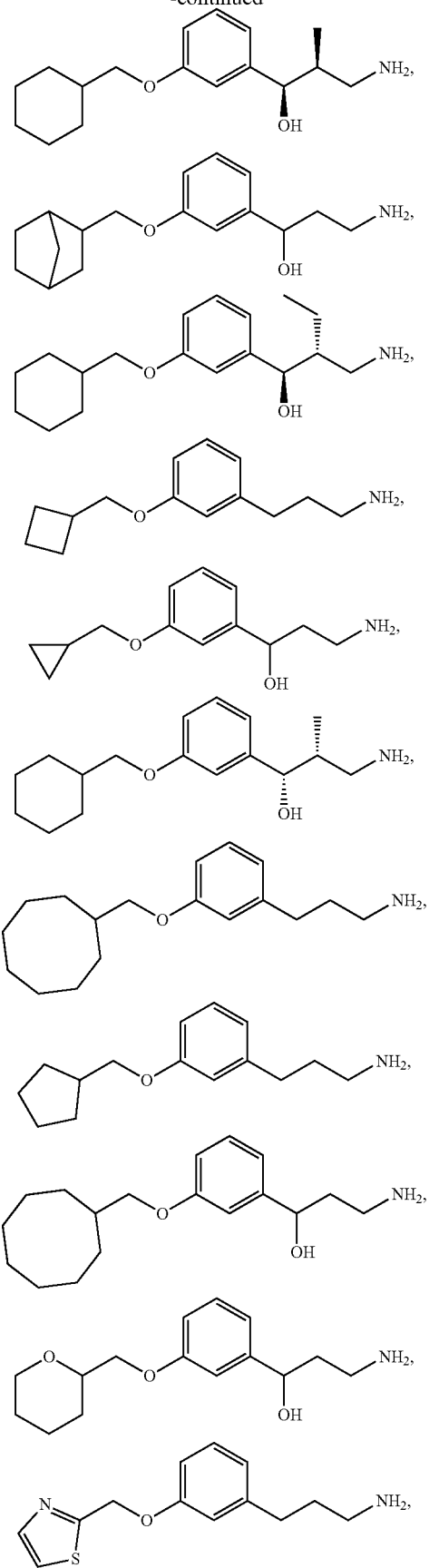
-continued
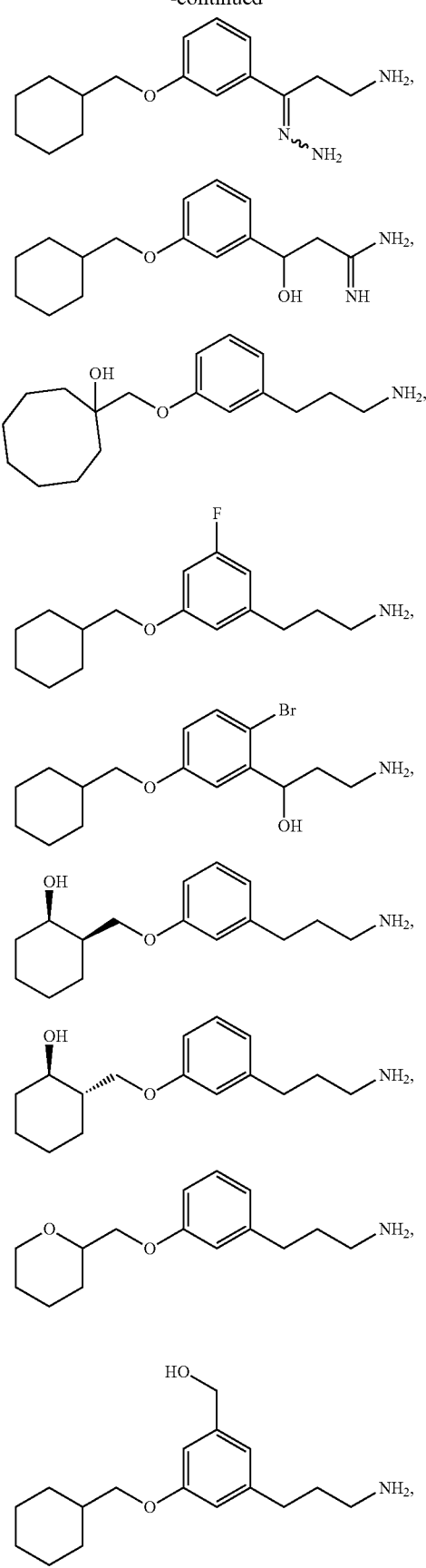

-continued
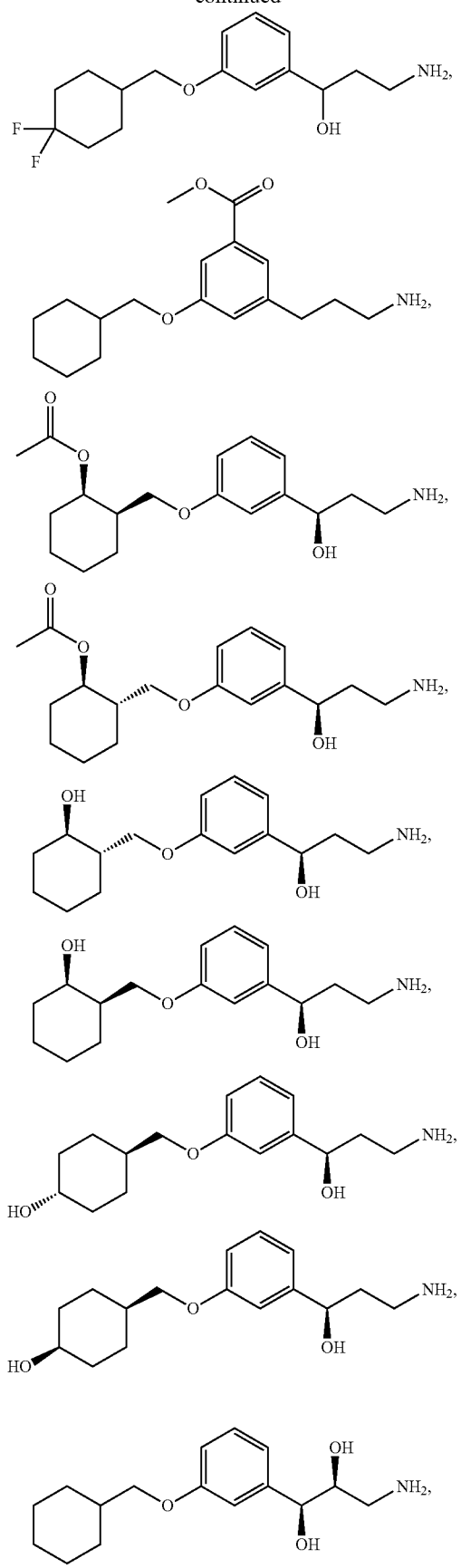
-continued
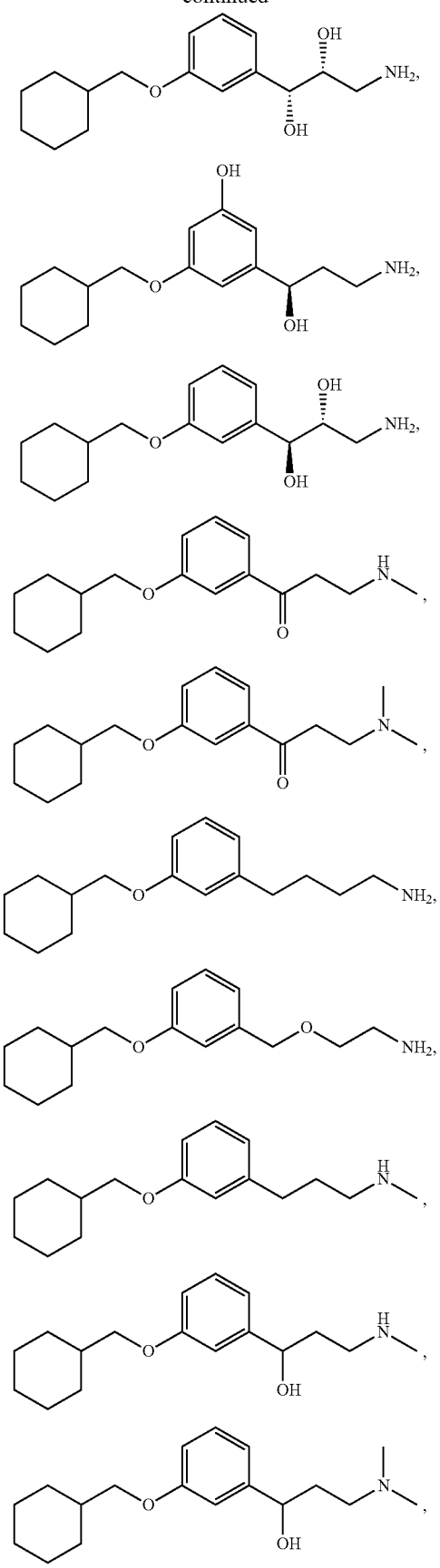

51
-continued
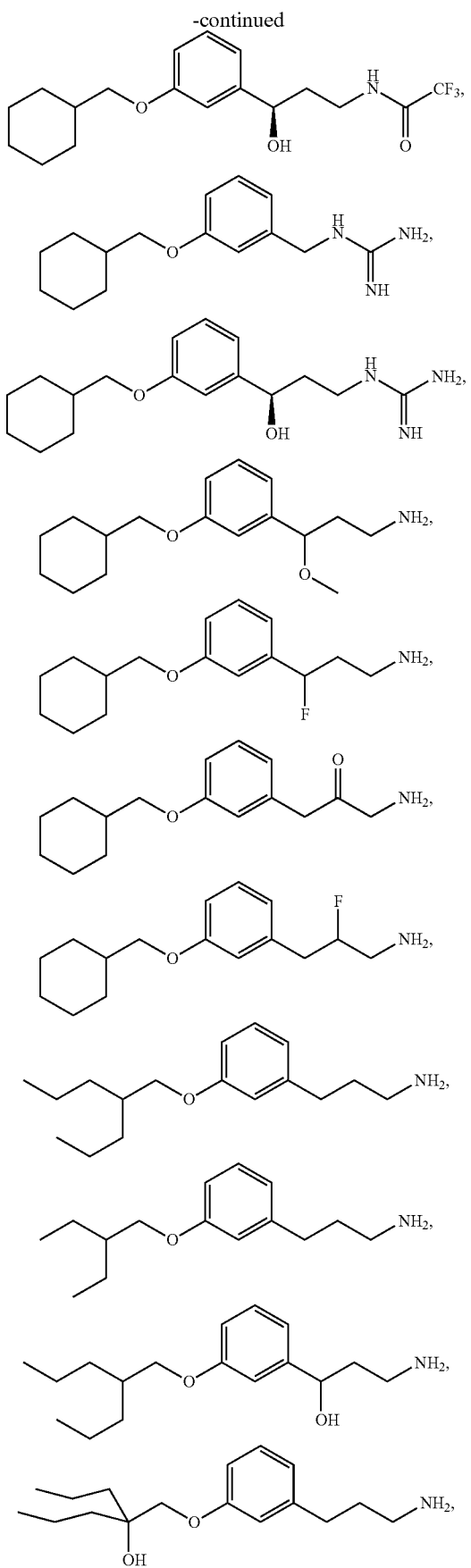
52
-continued
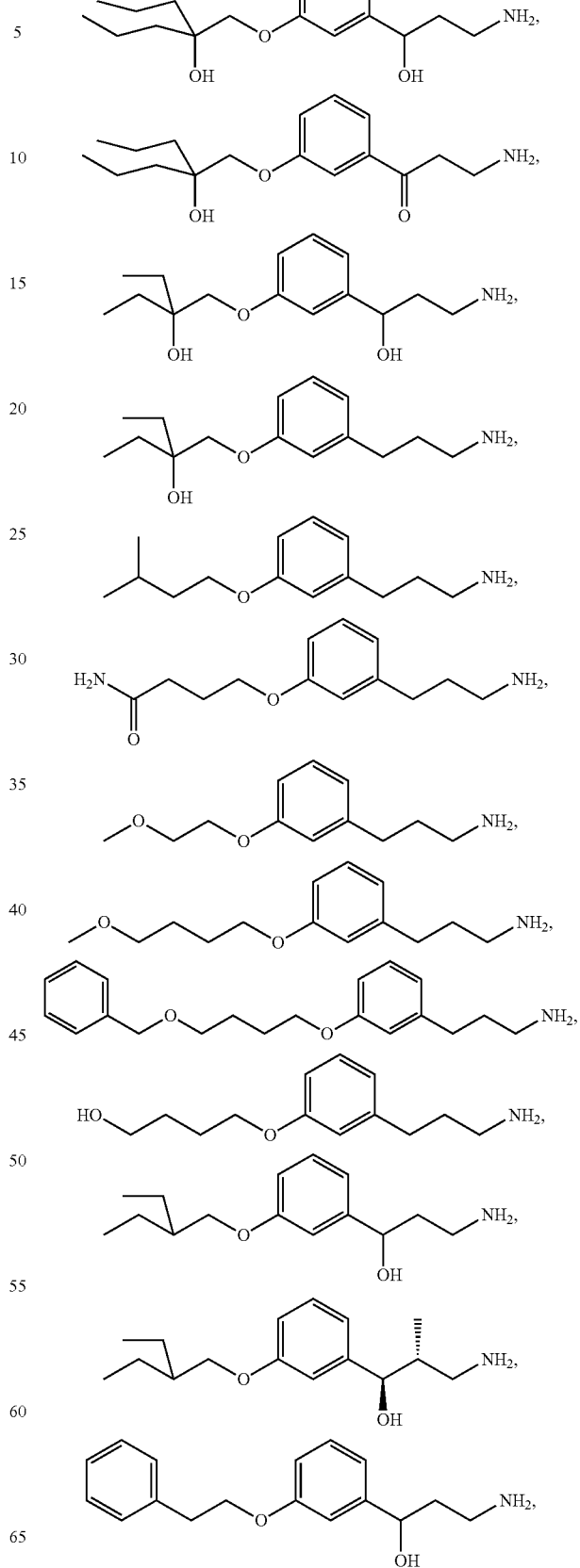

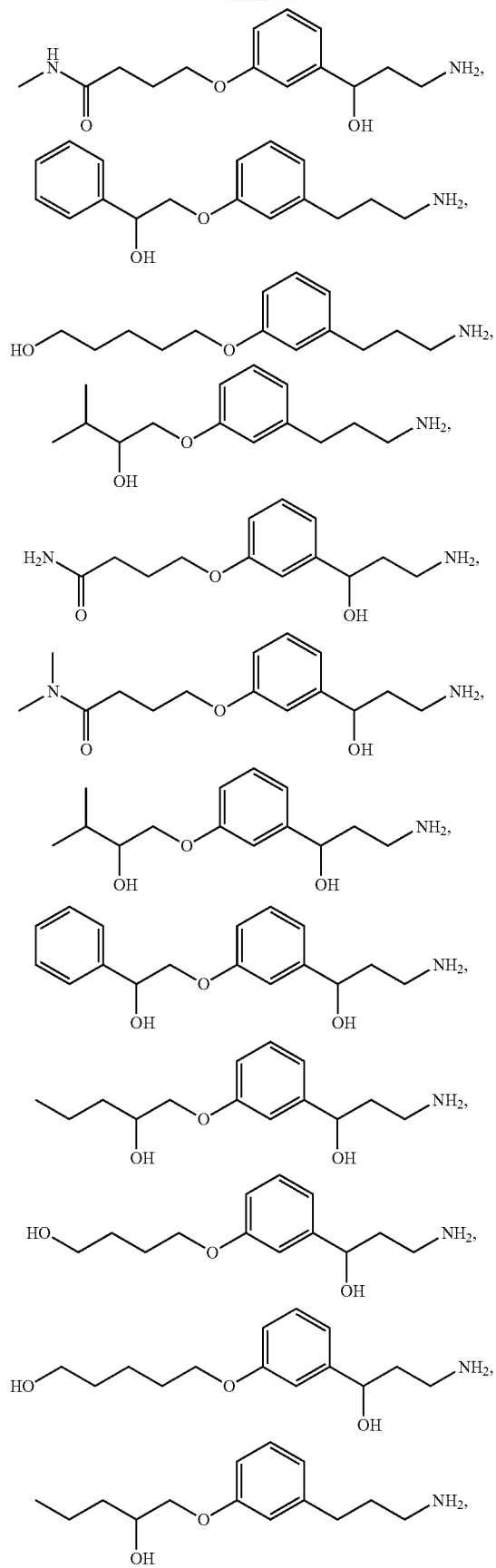
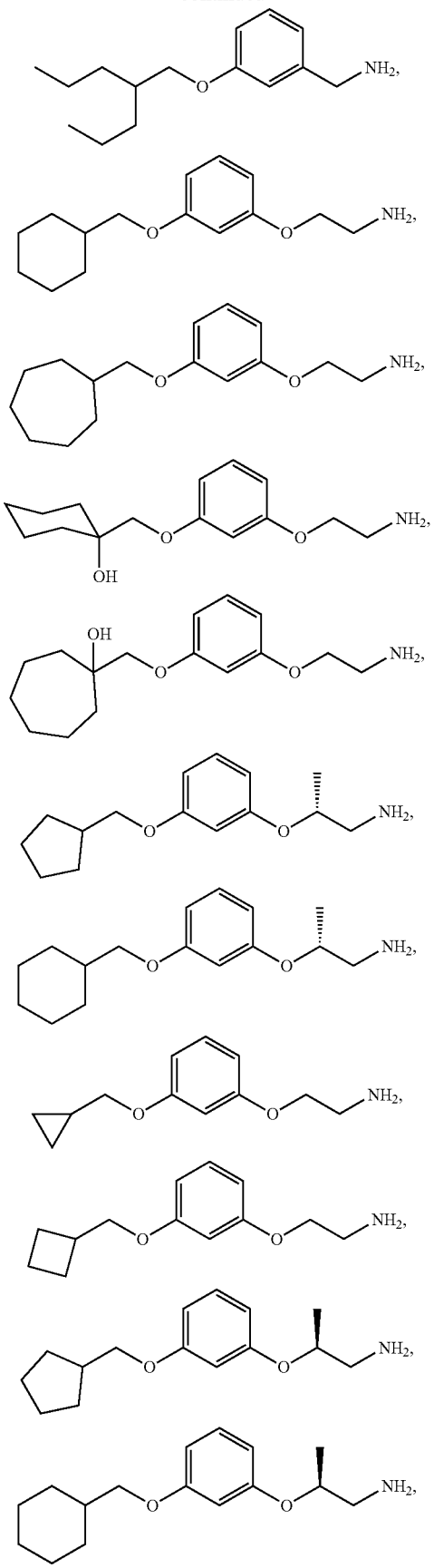

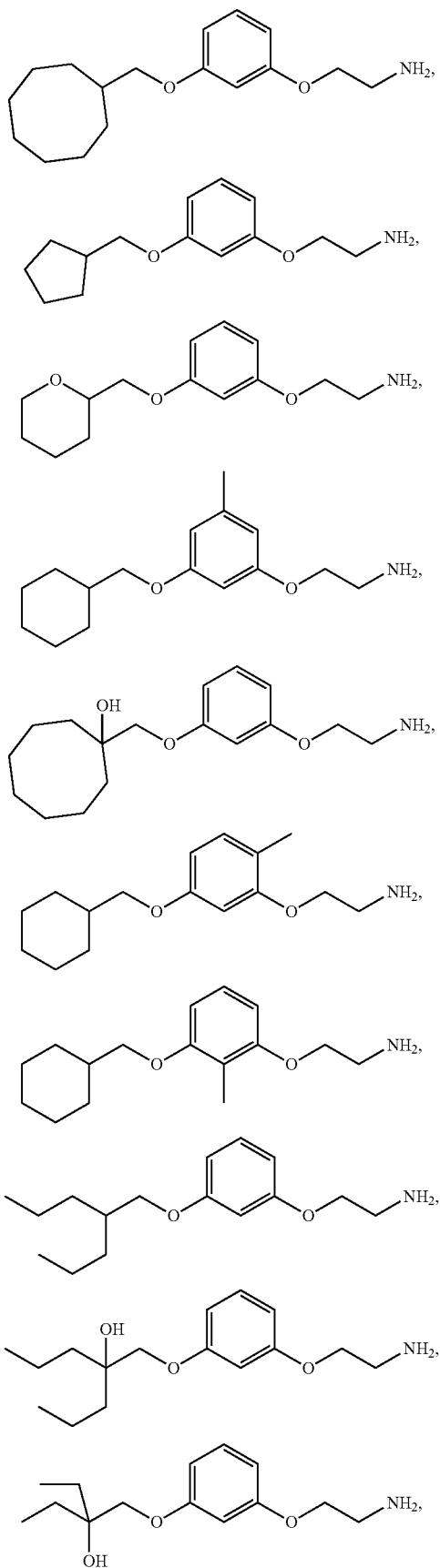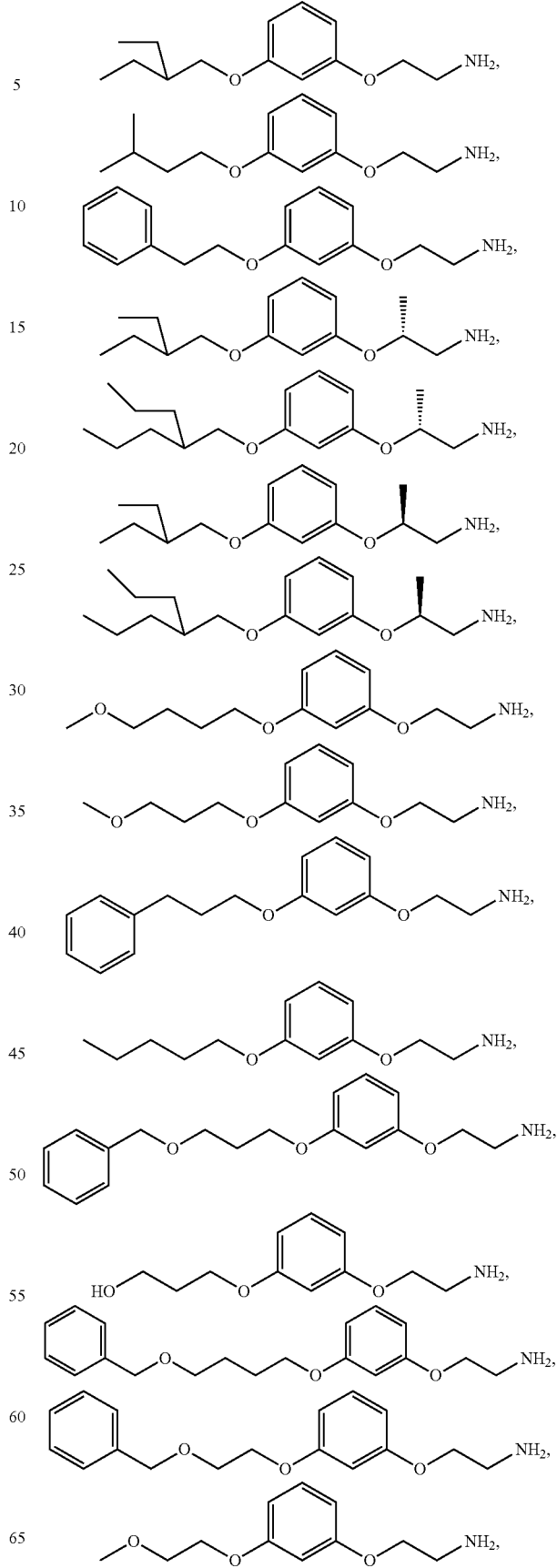

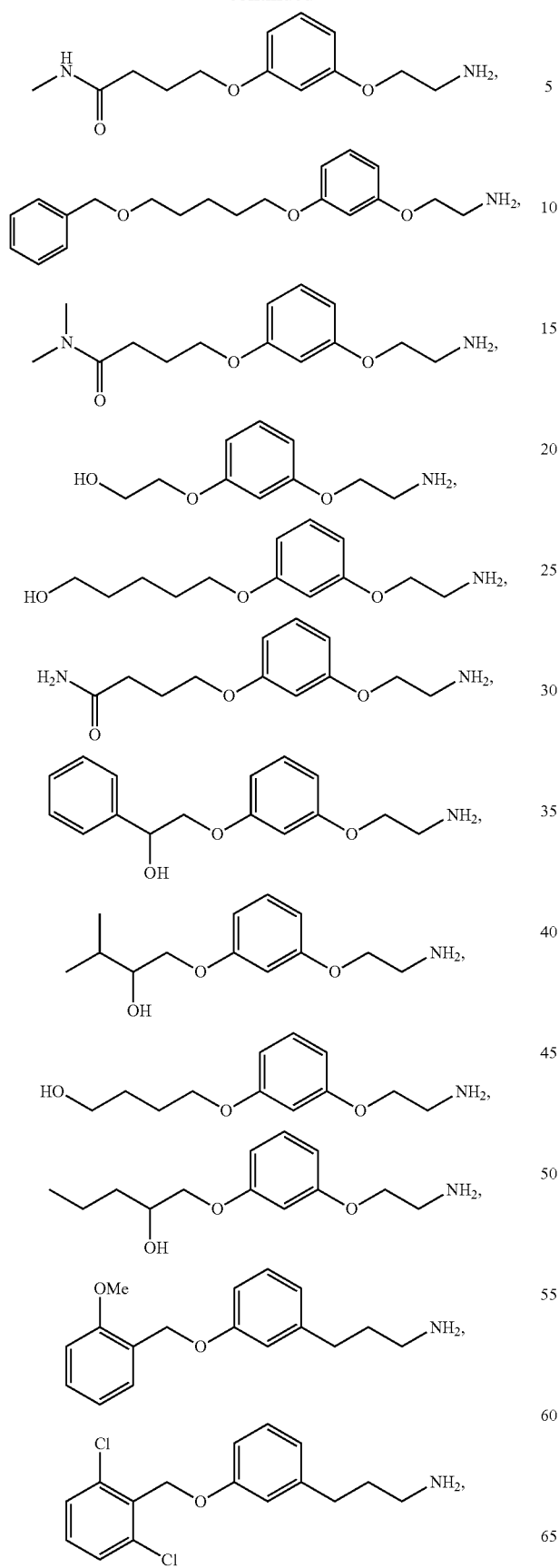
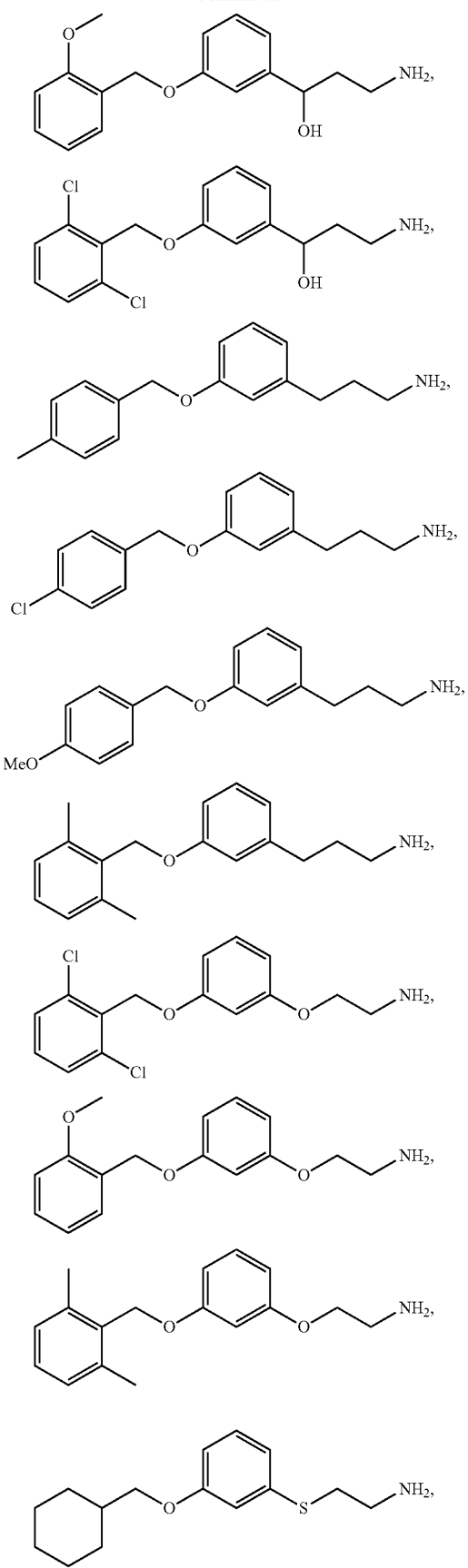

61

-continued

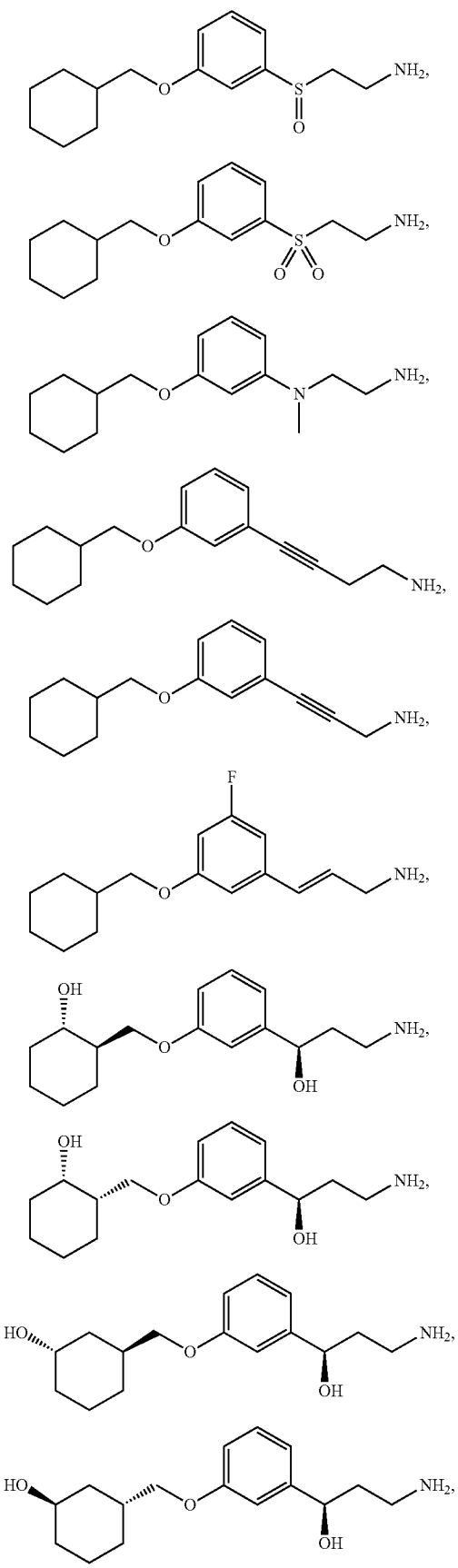

62

-continued

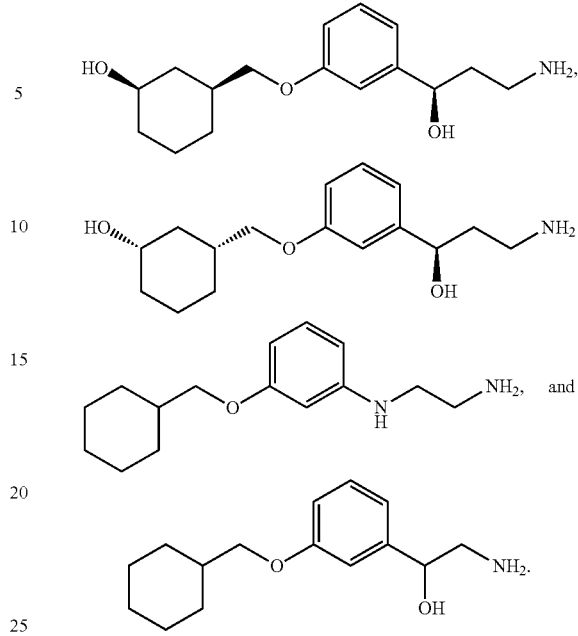

As used herein and in the appended claims, the singular forms "a," "and," and "the" include plural referents unless the context clearly dictates otherwise. Thus, for example, reference to "an agent" includes a plurality of such agents, and reference to "the cell" includes reference to one or more cells (or to a plurality of cells) and equivalents thereof known to those skilled in the art, and so forth. When ranges are used herein for physical properties, such as molecular weight, or chemical properties, such as chemical formulae, all combinations and subcombinations of ranges and specific embodiments therein are intended to be included. The term "about" when referring to a number or a numerical range means that the number or numerical range referred to is an approximation within experimental variability (or within statistical experimental error), and thus the number or numerical range may vary between 1% and 15% of the stated number or numerical range. The term "comprising" (and related terms such as "comprise" or "comprises" or "having" or "including") is not intended to exclude that in other certain embodiments, for example, an embodiment of any composition of matter, composition, method, or process, or the like, described herein, may "consist of" or "consist essentially of" the described features.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
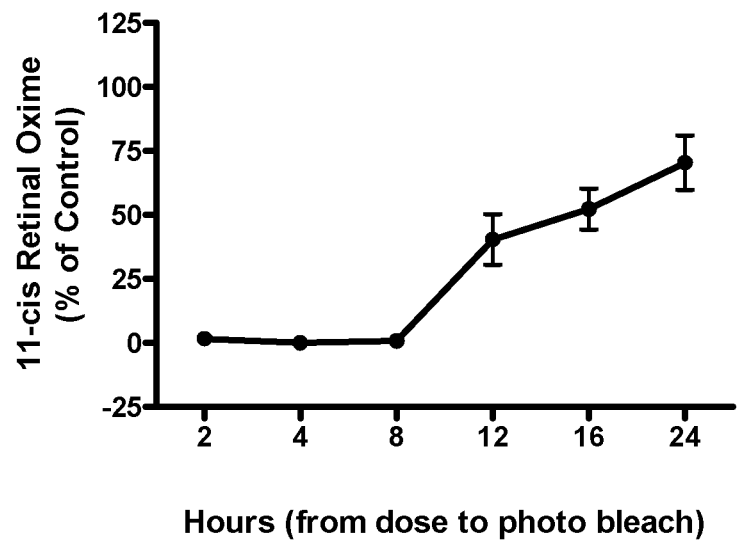
FIG. 1 illustrates time-dependent inhibition of isomerase activity by the compound of Example 4 (Compound 4) in a mouse model. Five animals were included in each treatment group. The error bars correspond to standard error.

Alkoxyphenyl-linked amine derivative compounds are described herein that inhibit an isomerization step of the retinoid cycle. These compounds and compositions comprising these compounds may be useful for inhibiting degeneration of retinal cells or for enhancing retinal cell survival. The compounds described herein may, therefore, be useful for treating ophthalmic diseases and disorders, including retinal diseases or disorders, such as age related macular degeneration and Stargardt's disease.

Alkoxyphenyl-Linked Amine Derivative Compounds

In one embodiment is a compound of Formula (A) or tautomer, stereoisomer, geometric isomer or a pharmaceutically acceptable solvate, hydrate, salt, N-oxide or prodrug thereof:

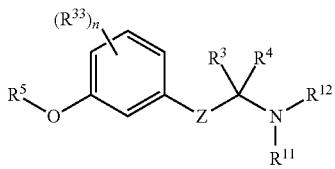

Formula (A)

wherein
Z is —C(R$^9$)(R$^{10}$)—C(R$^1$)(R$^2$)—, —X—C(R$^{31}$)(R$^{32}$)—, —C(R$^9$)(R$^{10}$)—C(R$^1$)(R$^2$)—C(R$^{36}$)(R$^{37}$)— or —X—C(R$^{31}$)(R$^{32}$)—C(R$^1$)(R$^2$)—;
R$^1$ and R$^2$ are each independently selected from hydrogen, halogen, C$_1$-C$_5$ alkyl, fluoroalkyl, —OR$^6$ or —NR$^7$R$^8$; or R$^1$ and R$^2$ together form an oxo;
R$^{31}$ and R$^{32}$ are each independently selected from hydrogen, C$_1$-C$_5$ alkyl, or fluoroalkyl;
R$^{36}$ and R$^{37}$ are each independently selected from hydrogen, halogen, C$_1$-C$_5$ alkyl, fluoroalkyl, —OR$^6$ or —NR$^7$R$^8$; or R$^{36}$ and R$^{37}$ together form an oxo; or optionally, R$^{36}$ and R$^1$ together form a direct bond to provide a double bond; or optionally, R$^{36}$ and R$^1$ together form a direct bond, and R$^{37}$ and R$^2$ together form a direct bond to provide a triple bond;
R$^3$ and R$^4$ are each independently selected from hydrogen, alkyl, alkenyl, fluoroalkyl, aryl, heteroaryl, carbocyclyl or C-attached heterocyclyl; or R$^3$ and R$^4$ together with the carbon atom to which they are attached, form a carbocyclyl or heterocyclyl; or R$^3$ and R$^4$ together form an imino;
R$^5$ is C$_5$-C$_{15}$ alkyl or carbocyclyalkyl;
R$^7$ and R$^8$ are each independently selected from hydrogen, alkyl, carbocyclyl, heterocyclyl, —C(=O)R$^{13}$, SO$_2$R$^{13}$, CO$_2$R$^{13}$ or SO$_2$NR$^{24}$R$^{25}$; or R$^7$ and R$^8$ together with the nitrogen atom to which they are attached, form an N-heterocyclyl;
X is —O—, —S—, —S(=O)—, —S(=O)$_2$—, —N(R$^{30}$)—, —C(=O)—, —C(=CH$_2$)—, —C(=N—NR$^{35}$)—, or —C(=N—OR$^{35}$)—;
R$^9$ and R$^{10}$ are each independently selected from hydrogen, halogen, alkyl, fluoroalkyl, —OR$^{19}$—, —NR$^{20}$R$^{21}$ or carbocyclyl; or R$^9$ and R$^{10}$ form an oxo; or optionally, R$^9$ and R$^1$ together form a direct bond to provide a double bond; or optionally, R$^9$ and R$^1$ together form a direct bond, and R$^{10}$ and R$^2$ together form a direct bond to provide a triple bond;
R$^{11}$ and R$^{12}$ are each independently selected from hydrogen, alkyl, carbocyclyl, —C(=O)R$^{23}$, —C(NH)NH$_2$, SO$_2$R$^{23}$, CO$_2$R$^{23}$ or SO$_2$NR$^{28}$R$^{29}$; or R$^{11}$ and R$^{12}$, together with the nitrogen atom to which they are attached, form an N-heterocyclyl;
each R$^{13}$, R$^{22}$ and R$^{23}$ is independently selected from alkyl, heteroalkyl, alkenyl, aryl, aralkyl, carbocyclyl, heteroaryl or heterocyclyl;
R$^6$, R$^{19}$, R$^{30}$, R$^{34}$ and R$^{35}$ are each independently hydrogen or alkyl;
R$^{20}$ and R$^{21}$ are each independently selected from hydrogen, alkyl, carbocyclyl, heterocyclyl, —C(=O)R$^{22}$, SO$_2$R$^{22}$, CO$_2$R$^{22}$ or SO$_2$NR$^{26}$R$^{27}$; or R$^{20}$ and R$^{21}$ together with the nitrogen atom to which they are attached, form an N-heterocyclyl; and
each R$^{24}$, R$^{25}$, R$^{26}$, R$^{27}$, R$^{28}$ and R$^{29}$ is independently selected from hydrogen, alkyl, alkenyl, fluoroalkyl, aryl, heteroaryl, carbocyclyl or heterocyclyl;
each R$^{33}$ is independently selected from halogen, OR$^{34}$, alkyl, or fluoroalkyl; and n is 0, 1, 2, 3, or 4; with the provision that R$^5$ is not 2-(cyclopropyl)-1-ethyl or an unsubstituted normal alkyl.

In another embodiment is the compound of Formula (A), wherein
Z is —C(R$^9$)(R$^{10}$)—C(R$^1$)(R$^2$)—, —X—C(R$^{31}$)(R$^{32}$)—, —C(R$^9$)(R$^{10}$)—C(R$^1$)(R$^2$)—C(R$^{36}$)(R$^7$)— or —X—C(R$^{31}$)(R$^{32}$)—C(R$^1$)(R$^2$)—;
R$^1$ and R$^2$ are each independently selected from hydrogen, halogen, C$_1$-C$_5$ alkyl, fluoroalkyl, —OR$^6$ or —NR$^7$R$^8$; or R$^1$ and R$^2$ together form an oxo;

$R^{31}$ and $R^{32}$ are each independently selected from hydrogen, $C_1$-$C_5$ alkyl, or fluoroalkyl;

$R^{36}$ and $R^{37}$ are each independently selected from hydrogen, halogen, $C_1$-$C_5$ alkyl, fluoroalkyl, —$OR^6$ or —$NR^7R^8$; or $R^{36}$ and $R^{37}$ together form an oxo;

$R^3$ and $R^4$ are each independently selected from hydrogen, alkyl, alkenyl, fluoroalkyl, aryl, heteroaryl, carbocyclyl or C-attached heterocyclyl; or $R^3$ and $R^4$ together with the carbon atom to which they are attached, form a carbocyclyl or heterocyclyl; or $R^3$ and $R^4$ together form an imino;

$R^5$ is $C_5$-$C_{15}$ alkyl or carbocyclyalkyl;

$R^7$ and $R^8$ are each independently selected from hydrogen, alkyl, carbocyclyl, heterocyclyl, —$C(=O)R^{13}$, $SO_2R^{13}$, $CO_2R^{13}$ or $SO_2NR^{24}R^{25}$; or $R^7$ and $R^8$ together with the nitrogen atom to which they are attached, form an N-heterocyclyl;

X is —O—, —S—, —S(=O)—, —S(=O)$_2$—, —N($R^{30}$)—, —C(=O)—, —C(=$CH_2$)—, —C(=N—$NR^{35}$)—, or —C(=N—$OR^{35}$)—;

$R^9$ and $R^{10}$ are each independently selected from hydrogen, halogen, alkyl, fluoroalkyl, —$OR^{19}$—, —$NR^{20}R^{21}$ or carbocyclyl; or $R^9$ and $R^{10}$ form an oxo;

$R^{11}$ and $R^{12}$ are each independently selected from hydrogen, alkyl, carbocyclyl, —$C(=O)R^{23}$, $SO_2R^{23}$, $CO_2R^{23}$ or $SO_2NR^{28}R^{29}$; or $R^{11}$ and $R^{12}$, together with the nitrogen atom to which they are attached, form an N-heterocyclyl;

each $R^{13}$, $R^{22}$ and $R^{23}$ is independently selected from alkyl, heteroalkyl, alkenyl, aryl, aralkyl, carbocyclyl, heteroaryl or heterocyclyl;

$R^6$, $R^{19}$, $R^{30}$, $R^{34}$ and $R^{35}$ are each independently hydrogen or alkyl;

$R^{20}$ and $R^{21}$ are each independently selected from hydrogen, alkyl, carbocyclyl, heterocyclyl, —$C(=O)R^{22}$, $SO_2R^{22}$, $CO_2R^{22}$ or $SO_2NR^{26}R^{27}$; or $R^{20}$ and $R^{21}$ together with the nitrogen atom to which they are attached, form an N-heterocyclyl; and each $R^{24}$, $R^{25}$, $R^{26}$, $R^{27}$, $R^{28}$ and $R^{29}$ is independently selected from hydrogen, alkyl, alkenyl, fluoroalkyl, aryl, heteroaryl, carbocyclyl or heterocyclyl;

each $R^{33}$ is independently selected from halogen, $OR^{34}$, alkyl, or fluoroalkyl; and n is 0, 1, 2, 3, or 4.

In a further embodiment is the compound having the structure of Formula (B),

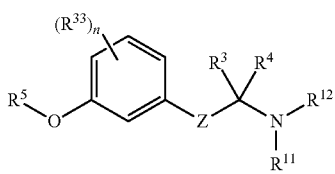

Formula (B)

wherein

Z is —C($R^9$)($R^{10}$)—C($R^1$)($R^2$)— or —O—C($R^{31}$)($R^{32}$);

$R^1$ and $R^2$ are each independently selected from hydrogen, halogen, $C_1$-$C_5$ alkyl, fluoroalkyl, —$OR^6$ or —$NR^7R^8$; or $R^1$ and $R^2$ together form an oxo;

$R^{31}$ and $R^{32}$ are each independently selected from hydrogen, $C_1$-$C_5$ alkyl, or fluoroalkyl;

$R^3$ and $R^4$ are each independently selected from hydrogen or alkyl; or $R^3$ and $R^4$ together form an imino;

$R^5$ is $C_5$-$C_{15}$ alkyl or carbocyclyalkyl;

$R^7$ and $R^8$ are each independently selected from hydrogen, alkyl, carbocyclyl or —C(=O)$R^{13}$; or $R^7$ and $R^8$, together with the nitrogen atom to which they are attached, form an N-heterocyclyl;

$R^9$ and $R^{10}$ are each independently selected from hydrogen, halogen, alkyl, fluoroalkyl, —$OR^{19}$—, —$NR^{20}R^{21}$ or carbocyclyl; or $R^9$ and $R^{10}$ together form an oxo;

$R^{11}$ and $R^{12}$ are each independently selected from hydrogen, alkyl, carbocyclyl or —C(=O)$R^{23}$; or $R^{11}$ and $R^{12}$, together with the nitrogen atom to which they are attached, form an N-heterocyclyl; and each $R^{13}$, $R^{22}$ and $R^{23}$ is independently selected from alkyl, alkenyl, aryl, aralkyl, carbocyclyl, heteroaryl or heterocyclyl;

$R^6$, $R^{19}$, and $R^{34}$ are each independently hydrogen or alkyl;

each $R^{33}$ is independently selected from halogen, $OR^{34}$, alkyl, or fluoroalkyl; and n is 0, 1, 2, 3, or 4;

$R^{20}$ and $R^{21}$ are each independently selected from hydrogen, alkyl, carbocyclyl, —C(=O)$R^{22}$; or $R^{20}$ and $R^{21}$, together with the nitrogen atom to which they are attached, form an N-heterocyclyl; and each $R^{24}$, $R^{25}$, $R^{26}$, $R^{27}$, $R^{28}$ and $R^{29}$ is independently selected from hydrogen, alkyl, alkenyl, fluoroalkyl, aryl, heteroaryl, carbocyclyl or heterocyclyl.

In a further embodiment is the compound having the structure of Formula (C),

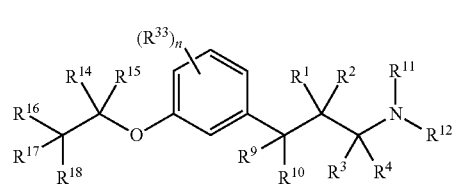

Formula (C)

wherein $R^1$ and $R^2$ are each independently selected from hydrogen, halogen, $C_1$-$C_5$ alkyl, fluoroalkyl, —$OR^6$ or —$NR^7R^8$; or $R^1$ and $R^2$ together form an oxo;

$R^3$ and $R^4$ are each independently selected from hydrogen or alkyl; or $R^3$ and $R^4$ together form an imino;

$R^7$ and $R^8$ are each independently selected from hydrogen, alkyl, carbocyclyl or —C(=O)$R^{13}$; or $R^7$ and $R^8$, together with the nitrogen atom to which they are attached, form an N-heterocyclyl;

$R^9$ and $R^{10}$ are each independently selected from hydrogen, halogen, alkyl, fluoroalkyl, —$OR^{19}$—, —$NR^{20}R^{21}$ or carbocyclyl; or $R^9$ and $R^{10}$ together form an oxo;

$R^{11}$ and $R^{12}$ are each independently selected from hydrogen, alkyl, carbocyclyl or —C(=O)$R^{23}$; or $R^{11}$ and $R^{12}$, together with the nitrogen atom to which they are attached, form an N-heterocyclyl;

each $R^{13}$, $R^{22}$ and $R^{23}$ is independently selected from alkyl, alkenyl, aryl, aralkyl, carbocyclyl, heteroaryl or heterocyclyl;

$R^6$, $R^{19}$ and $R^{34}$ are each independently hydrogen or alkyl;

$R^{20}$ and $R^{21}$ are each independently selected from hydrogen, alkyl, carbocyclyl, —C(=O)$R^{22}$; or $R^{20}$ and $R^{21}$, together with the nitrogen atom to which they are attached, form an N-heterocyclyl; and each $R^{24}$, $R^{25}$, $R^{26}$, $R^{27}$, $R^{28}$ and $R^{29}$ is independently selected from hydrogen, alkyl, alkenyl, fluoroalkyl, aryl, heteroaryl, carbocyclyl or heterocyclyl;

$R^{14}$ and $R^{15}$ are each independently selected from hydrogen or alkyl;

$R^{16}$ and $R^{17}$ are each independently selected from hydrogen, $C_1$-$C_{13}$ alkyl, halo or fluoroalkyl; or $R^{16}$ and $R^{17}$, together with the carbon to which they are attached form a carbocyclyl;

each $R^{33}$ is independently selected from halogen, $OR^{34}$, alkyl, or fluoroalkyl; and n is 0, 1, 2, 3, or 4; and $R^{18}$ is selected from a hydrogen, alkyl, alkoxy, hydroxy, halo or fluoroalkyl.

In a further embodiment is the compound of Formula (C), wherein n is 0 and each of $R^{11}$ and $R^{12}$ is hydrogen.

In a further embodiment is the compound of Formula (C), wherein each of $R^3$, $R^4$, $R^{14}$ and $R^{15}$ is hydrogen.

In a further embodiment is the compound of Formula (C), wherein, $R^1$ and $R^2$ are each independently selected from hydrogen, halogen, $C_1$-$C_5$ alkyl, —$OR^6$;

$R^9$ and $R^{10}$ are each independently selected from hydrogen, halogen, alkyl, —$OR^{19}$; or $R^9$ and $R^{10}$ together form an oxo;

$R^6$ and $R^{19}$ are each independently hydrogen or alkyl;

$R^{16}$ and $R^{17}$, together with the carbon to which they are attached form a carbocyclyl; and $R^{18}$ is selected from a hydrogen, alkoxy or hydroxy.

In a further embodiment is the compound of Formula (C), wherein $R^{16}$ and $R^{17}$, together with the carbon to which they are attached, form a cyclohexyl or cycloheptyl and $R^{18}$ is hydrogen or hydroxy.

In a further embodiment is the compound of Formula (C), wherein $R^{16}$ and $R^{17}$, together with the carbon to which they are attached, form a cyclobutyl, cyclopentyl, cyclohexyl, cycloheptyl, or cyclooctyl, and $R^{18}$ is hydrogen or hydroxy.

In a further embodiment is the compound of Formula (C), wherein $R^{11}$ is hydrogen and $R^{12}$ is —C(=O)$R^{23}$, wherein $R^{23}$ is alkyl.

In a further embodiment is the compound of Formula (C), wherein $R^1$ and $R^2$ are each independently selected from hydrogen, halogen, $C_1$-$C_5$ alkyl, or —$OR^6$;

$R^9$ and $R^{10}$ are each independently selected from hydrogen, halogen, alkyl, or —$OR^{19}$; or $R^9$ and $R^{10}$ together form an oxo;

$R^6$ and $R^{19}$ are each independently selected from hydrogen or alkyl;

$R^{16}$ and $R^{17}$, together with the carbon atom to which they are attached, form a carbocyclyl; and $R^{18}$ is hydrogen, hydroxy or alkoxy.

In a further embodiment is the compound of Formula (C), wherein n is 0;

$R^{16}$ and $R^{17}$, together with the carbon atom to which they are attached, form a cyclopentyl, cyclohexyl or cyclohexyl; and $R^{18}$ is hydrogen or hydroxy.

In a further embodiment is the compound of Formula (C), wherein $R^1$ and $R^2$ are each independently selected from hydrogen, halogen, $C_1$-$C_5$ alkyl or —$OR^6$;

$R^9$ and $R^{10}$ are each independently selected from hydrogen, halogen, alkyl, or —$OR^{19}$; or $R^9$ and $R^{10}$ together form an oxo;

$R^6$ and $R^{19}$ are each independently hydrogen or alkyl;

$R^{16}$ and $R^{17}$ is independently selected from $C_1$-$C_{13}$ alkyl; and $R^{18}$ is hydrogen, hydroxy or alkoxy.

In an additional embodiment is the compound having the structure of Formula (D),

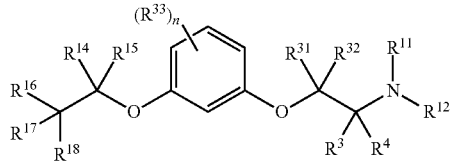

Formula (D)

wherein, $R^{31}$ and $R^{32}$ are each independently selected from hydrogen, $C_1$-$C_5$ alkyl, or fluoroalkyl;

$R^3$ and $R^4$ are each independently selected from hydrogen or alkyl; or $R^3$ and $R^4$ together form an imino;

$R^{11}$ and $R^{12}$ are each independently selected from hydrogen, alkyl, carbocyclyl, or —C(=O)$R^{23}$; or $R^{11}$ and $R^{12}$, together with the nitrogen atom to which they are attached, form an N-heterocyclyl;

$R^{23}$ is selected from alkyl, alkenyl, aryl, carbocyclyl, heteroaryl or heterocyclyl;

$R^{14}$ and $R^{15}$ are each independently selected from hydrogen or alkyl;

$R^{16}$ and $R^{17}$ are each independently selected from hydrogen, $C_1$-$C_{13}$ alkyl, halo or fluoroalkyl; or $R^{16}$ and $R^{17}$, together with the carbon atom to which they are attached, form a carbocyclyl;

$R^{18}$ is selected from a hydrogen, alkyl, alkoxy, hydroxy, halo or fluoroalkyl;

$R^{34}$ is hydrogen or alkyl; and each $R^{33}$ is independently selected from halogen, $OR^{34}$, alkyl, or fluoroalkyl; and n is 0, 1, 2, 3, or 4.

In a further embodiment is the compound of Formula (D), wherein n is 0 and each of $R^{11}$ and $R^{12}$ is hydrogen.

In a further embodiment is the compound of Formula (D), wherein each $R^3$, $R^4$, $R^{14}$ and $R^{15}$ is hydrogen.

In a further embodiment is the compound of Formula (D), wherein $R^{31}$ and $R^{32}$ are each independently hydrogen, or $C_1$-$C_5$ alkyl;

$R^{16}$ and $R^{17}$, together with the carbon atom to which they are attached, form a carbocyclyl; and $R^{18}$ is hydrogen, hydroxy, or alkoxy.

In a further embodiment is the compound of Formula (C), wherein $R^{16}$ and $R^{17}$, together with the carbon atom to which they are attached form cyclopentyl, cyclohexyl or cycloheptyl and $R^{18}$ is hydrogen or hydroxy.

In a further embodiment is the compound of Formula (D), wherein $R^{31}$ and $R^{32}$ are each independently selected from hydrogen, or $C_1$-$C_5$ alkyl; and $R^{18}$ is hydrogen, hydroxy or alkoxy.

In a further embodiment is the compound of Formula (E),

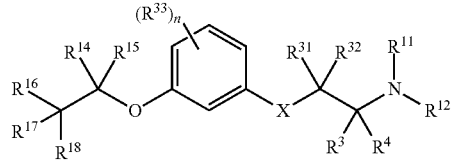

Formula (E)

wherein

X is —S—, —S(=O)—, —S(=O)$_2$—, —N($R^{30}$)—, —C(=O)—, —C(=CH$_2$)—, —C(=N—N$R^{35}$)—, or —C(=N—O$R^{35}$)—;

$R^{31}$ and $R^{32}$ are each independently selected from hydrogen, $C_1$-$C_5$ alkyl, or fluoroalkyl;

$R^3$ and $R^4$ are each independently selected from hydrogen or alkyl; or $R^3$ and $R^4$ together form an imino;

$R^{11}$ and $R^{12}$ are each independently selected from hydrogen, alkyl, carbocyclyl, or —C(=O)$R^{23}$; or $R^{11}$ and $R^{12}$, together with the nitrogen atom to which they are attached, form an N-heterocyclyl;

$R^{23}$ is selected from alkyl, alkenyl, aryl, carbocyclyl, heteroaryl or heterocyclyl;

$R^{14}$ and $R^{15}$ are each independently selected from hydrogen or alkyl;

$R^{16}$ and $R^{17}$ are each independently selected from hydrogen, $C_1$-$C_{13}$ alkyl, halo or fluoroalkyl; or $R^{16}$ and $R^{17}$, together with the carbon atom to which they are attached, form a carbocyclyl;

$R^{30}$, $R^{34}$ and $R^{35}$ are each independently hydrogen or alkyl;

$R^{18}$ is selected from a hydrogen, alkyl, alkoxy, hydroxy, halo or fluoroalkyl;

each $R^{33}$ is independently selected from halogen, OR$^{34}$, alkyl, or fluoroalkyl; and n is 0, 1, 2, 3, or 4.

In a further embodiment is the compound of Formula (E), wherein n is 0 and each $R^{11}$ and $R^{12}$ is hydrogen.

In a further embodiment is the compound of Formula (E), wherein each $R^3$, $R^4$, $R^{14}$ and $R^{15}$ is hydrogen.

In a further embodiment is the compound of Formula (E), wherein $R^{31}$ and $R^{32}$ are each independently hydrogen, or $C_1$-$C_5$ alkyl;

$R^{16}$ and $R^{17}$, together with the carbon atom to which they are attached, form a carbocyclyl; and $R^{18}$ is hydrogen, hydroxy, or alkoxy.

In a further embodiment is the compound of Formula (E), wherein $R^{16}$ and $R^{17}$, together with the carbon atom to which they are attached form cyclopentyl, cyclohexyl or cycloheptyl and $R^{18}$ is hydrogen or hydroxy.

In a further embodiment is the compound of Formula (E), wherein, $R^{31}$ and $R^{32}$ are each independently selected from hydrogen, or $C_1$-$C_5$ alkyl; and $R^{18}$ is hydrogen, hydroxy or alkoxy.

In an additional embodiment is the compound of Formula (A), selected from the group consisting of:

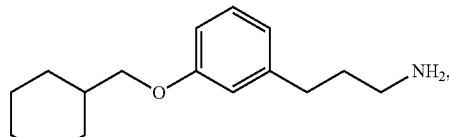

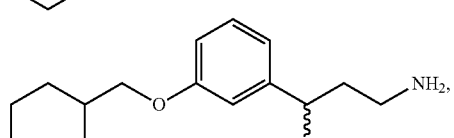

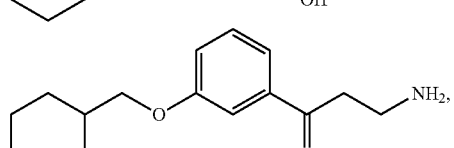

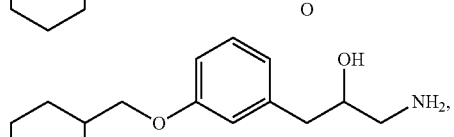

-continued

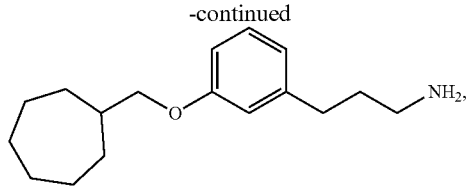

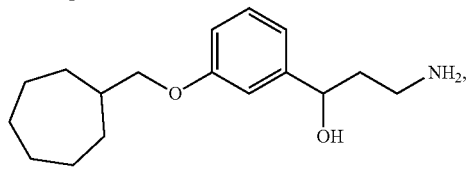

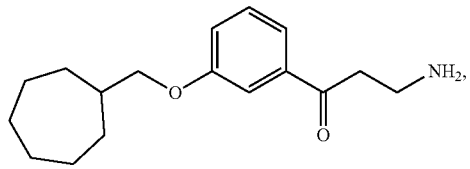

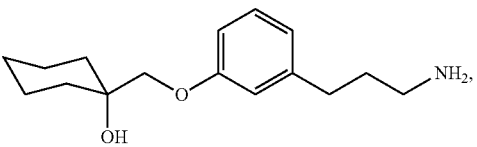

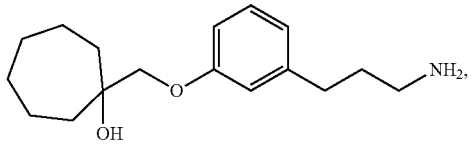

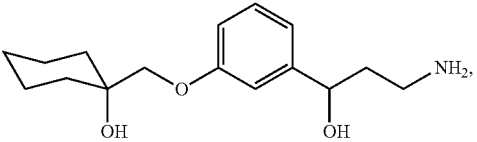

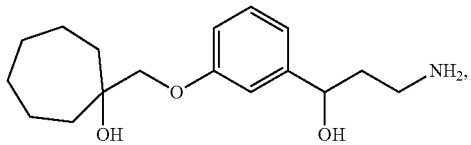

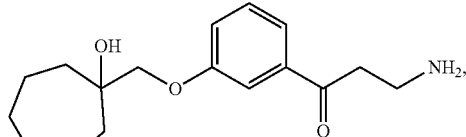

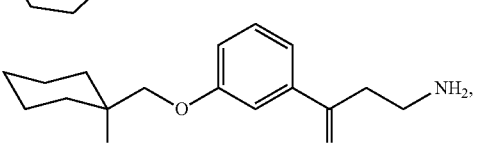

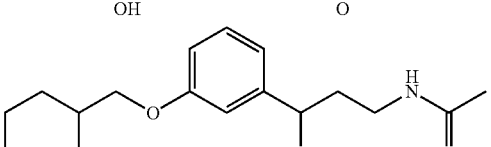

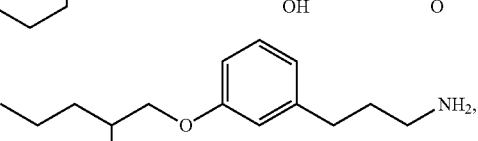

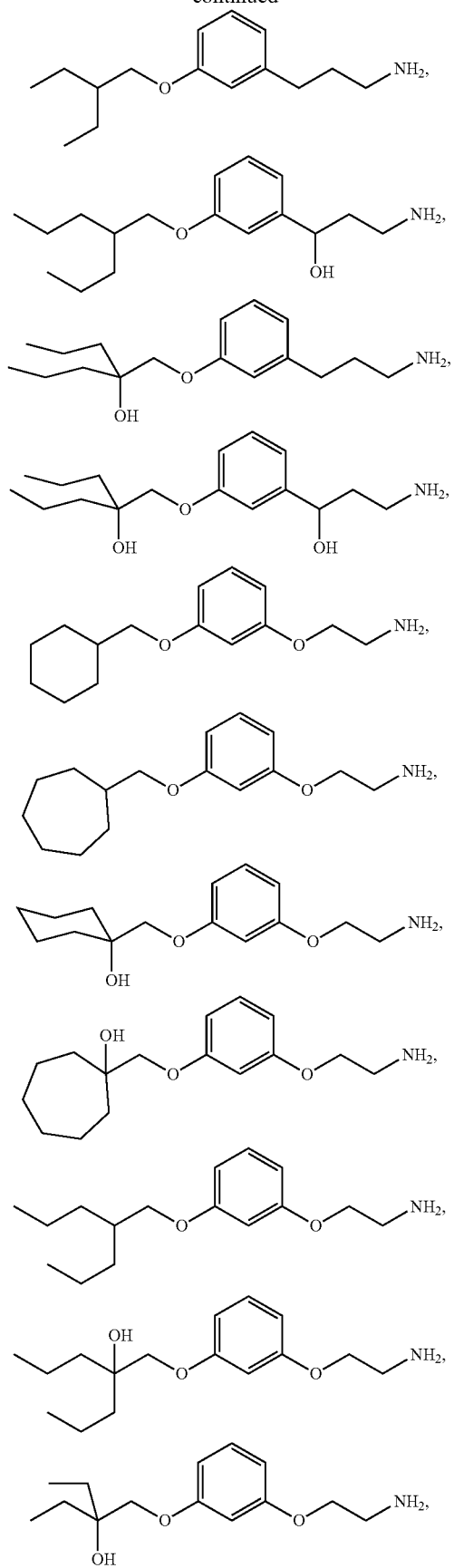
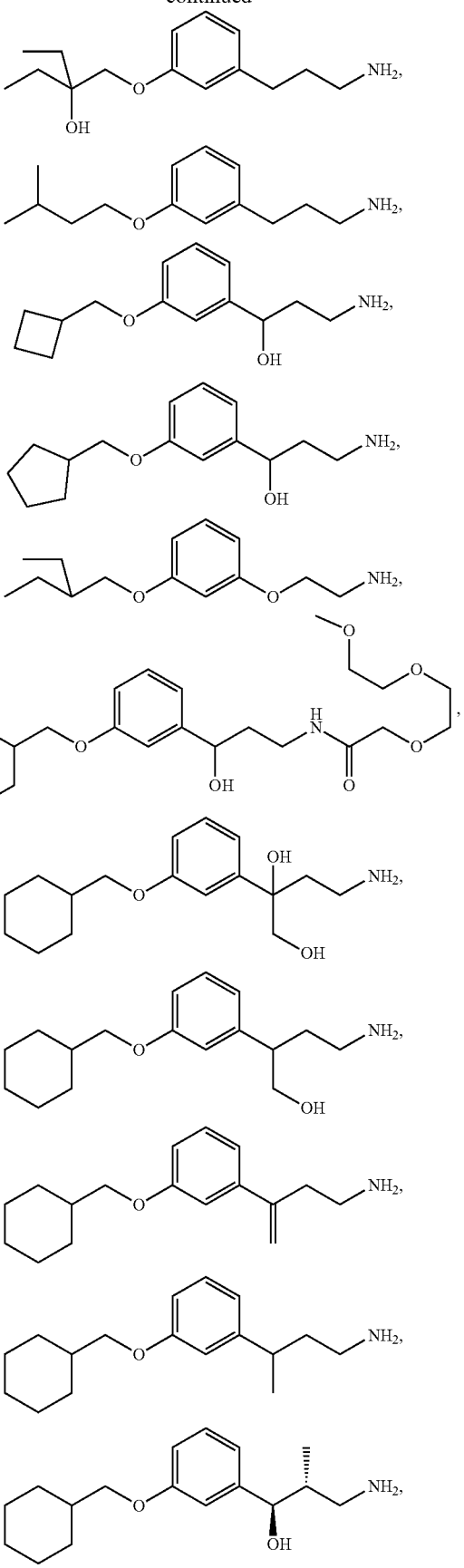

-continued
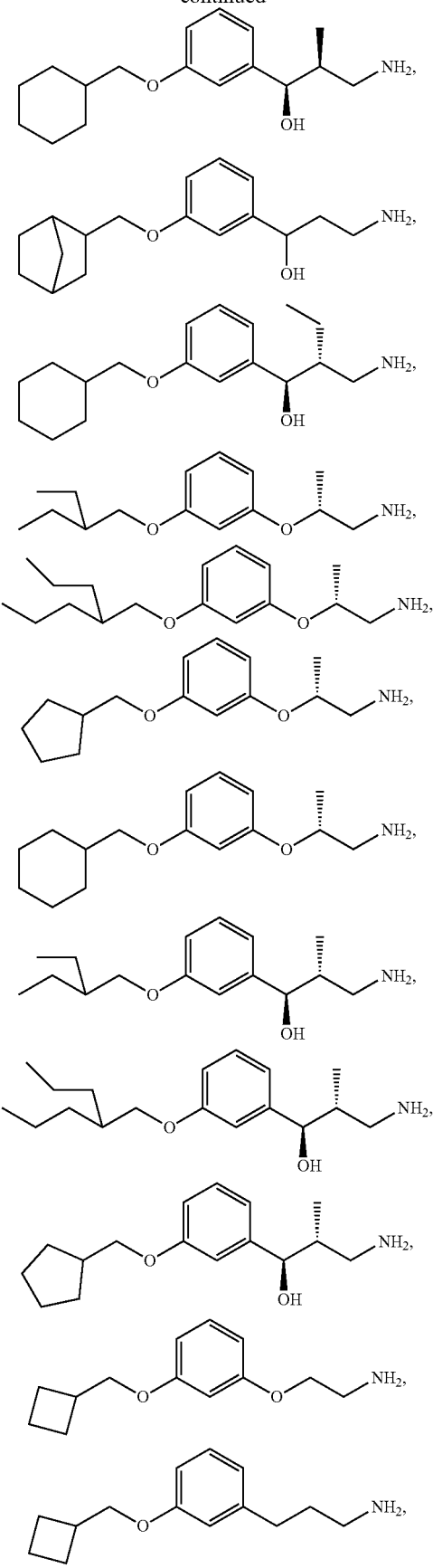
-continued
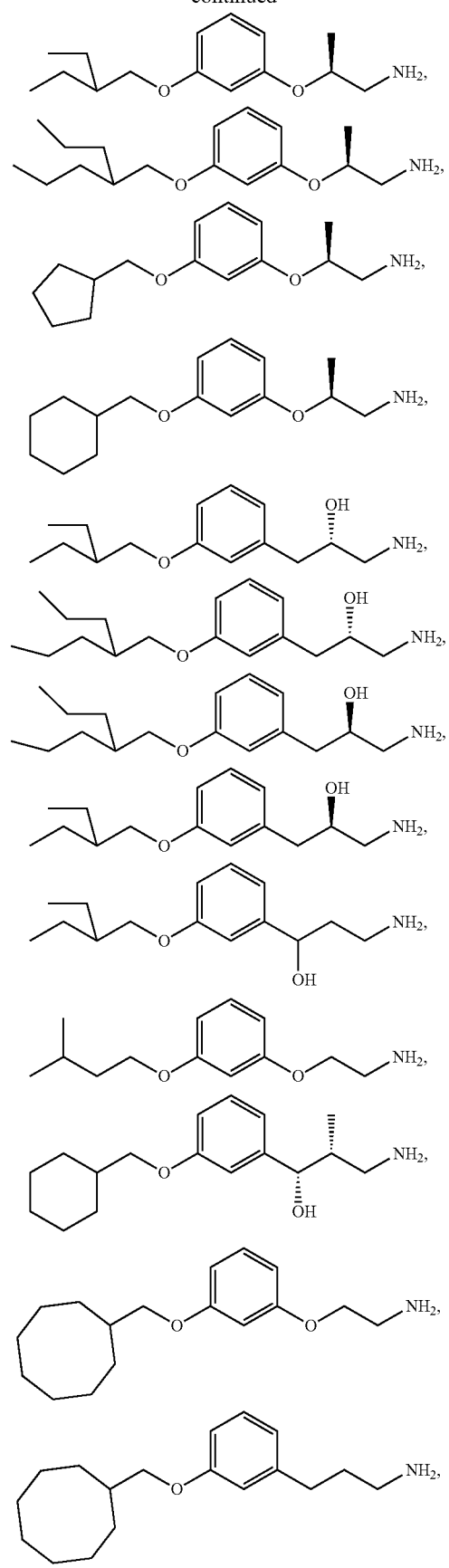

-continued
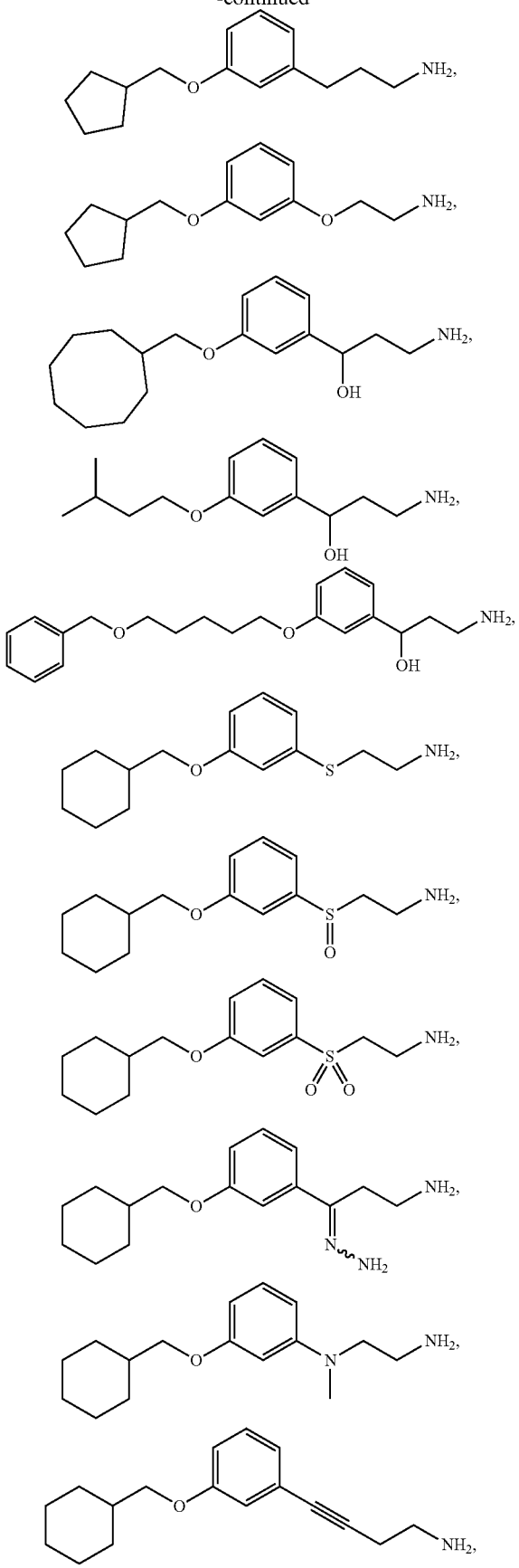
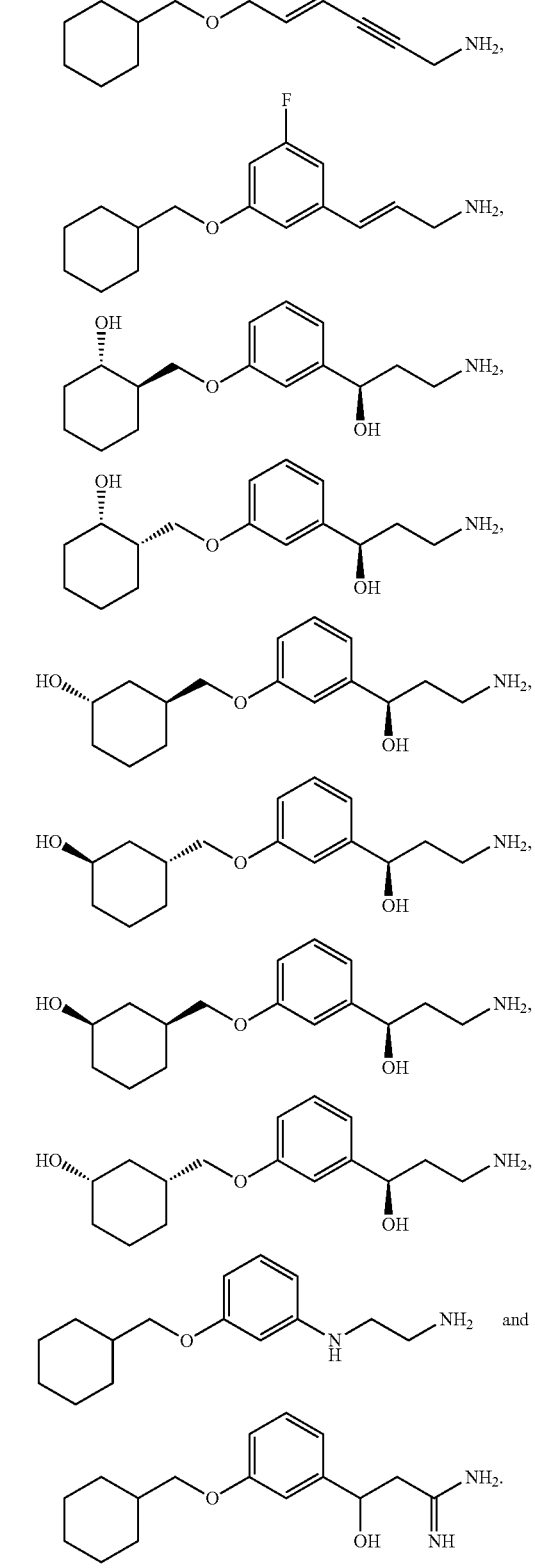
In certain embodiments, an alkoxyphenyl-linked amine derivative compound comprises a meta-substituted linkage terminating in a nitrogen-containing moiety. The linkage comprises linking atoms, including at least two carbon atoms and up to one heteroatom, such as sulfur, oxygen, or nitrogen. These linking atoms form a combination of linearly constructed stable chemical bonds, including single, double, or triple carbon-carbon bonds, carbon-nitrogen bonds, nitrogen-nitrogen bonds, carbon-oxygen bonds, carbon-sulfur bonds, and the like. Thus, the compounds have a structure that can be represented by Formula (I):

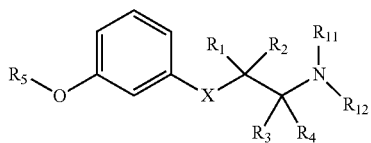

Formula (I)

as a tautomer or a mixture of tautomers, or as a pharmaceutically acceptable salt, hydrate, solvate, N-oxide or prodrug thereof, wherein:

$R_1$ and $R_2$ are each the same or different and independently hydrogen, halogen, alkyl, fluoroalkyl, —$OR_6$, —$NR_7R_8$ or carbocyclyl; or $R_1$ and $R_2$ form an oxo;

$R_3$ and $R_4$ are each the same or different and independently hydrogen or alkyl;

$R_5$ is $C_5$-$C_{15}$ alkyl or carbocyclylalkyl;

$R_6$ is hydrogen or alkyl;

$R_7$ and $R_8$ are each the same or different and independently hydrogen, alkyl, carbocyclyl, or —C(=O)$R_{13}$; or $R_7$ and $R_8$, together with the nitrogen atom to which they are attached, form an N-heterocyclyl;

X is —C($R_9$)($R_{10}$)— or —O—;

$R_9$ and $R_{10}$ are each the same or different and independently hydrogen, halogen, alkyl, fluoroalkyl, —$OR_6$, —$NR_7R_8$ or carbocyclyl; or $R_9$ and $R_{10}$ form an oxo;

$R_{11}$ and $R_{12}$ are each the same or different and independently hydrogen, alkyl, carbocyclyl, or —C(=O)$R_{13}$; or $R_{11}$ and $R_{12}$, together with the nitrogen atom to which they are attached, form an N-heterocyclyl; and $R_{13}$ is alkyl, alkenyl, aryl, carbocyclyl, heteroaryl, or heterocyclyl.

In certain embodiments, each of $R_{11}$ and $R_{12}$ is hydrogen.

In other embodiments, $R_{11}$ is hydrogen and $R_{12}$ is —C(=O)$R_{13}$, wherein $R_{13}$ is alkyl.

In certain embodiments, each of $R_3$ and $R_4$ is hydrogen.

In other certain embodiments, $R_1$, $R_2$, $R_9$ and $R_{10}$ are each independently hydrogen, halogen, alkyl or —$OR_6$, wherein $R_6$ is hydrogen or alkyl.

In another specific embodiment, each of $R_1$, $R_2$, $R_9$ and $R_{10}$ is independently hydrogen or —$OR_6$, wherein $R_6$ is hydrogen or alkyl.

In a specific embodiment, $R_9$ and $R_{10}$ together form oxo.

In certain embodiments, $R_5$ is $C_5$-$C_8$ alkyl.

In one embodiment, $R_5$ is —C($R_{14}$)($R_{15}$)—C($R_{16}$)($R_{17}$)($R_{18}$), and the compound of Formula (I) can be represented by a structure of Formula (II):

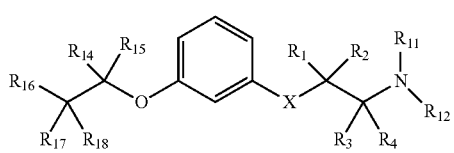

Formula (II)

as a tautomer or a mixture of tautomers, or as a pharmaceutically acceptable salt, hydrate, solvate, N-oxide or prodrug thereof, wherein:

$R_1$ and $R_2$ are each the same or different and independently hydrogen, halogen, alkyl, fluoroalkyl, —$OR_6$, —$NR_7R_8$ or carbocyclyl; or $R_1$ and $R_2$ form an oxo;

$R_3$ and $R_4$ are each the same or different and independently hydrogen or alkyl;

$R_6$ is hydrogen or alkyl;

$R_7$ and $R_8$ are each the same or different and independently hydrogen, alkyl, carbocyclyl or —C(=O)$R_{13}$; or $R_7$ and $R_8$, together with the nitrogen atom to which they are attached, form an N-heterocyclyl;

X is —C($R_9$)($R_{10}$)— or —O—;

$R_9$ and $R_{10}$ are each the same or different and independently hydrogen, halogen, alkyl, fluoroalkyl, —$OR_6$, —$NR_7R_8$ or carbocyclyl; or $R_9$ and $R_{10}$ form an oxo;

$R_{11}$ and $R_{12}$ are each the same or different and independently hydrogen, alkyl, carbocyclyl, or —C(=O)$R_{13}$; or $R_{11}$ and $R_{12}$, together with the nitrogen atom to which they are attached, form an N-heterocyclyl;

$R_{13}$ is alkyl, alkenyl, aryl, carbocyclyl, heteroaryl or heterocyclyl;

$R_{14}$ and $R_{15}$ are each the same or different and independently hydrogen or alkyl;

$R_{16}$ and $R_{17}$ are each the same or different and independently hydrogen, $C_1$-$C_{13}$ alkyl, halo or fluoroalkyl, or $R_{16}$ and $R_{17}$ together with the carbon to which they are attached form a carbocyclyl, heterocyclyl having at least one oxygen ring atom or monocyclic heteroaryl; and $R_{18}$ is hydrogen, alkyl, alkoxy, hydroxy, halo or fluoroalkyl.

In certain embodiments of the compound having a structure represented by Formula (II), each of $R_{11}$ and $R_{12}$ is hydrogen.

In other embodiments, $R_{11}$ is hydrogen and $R_{12}$ is —C(=O)$R_{13}$, wherein $R_{13}$ is alkyl.

In certain embodiments, each of $R_3$, $R_4$, $R_{14}$ and $R_{15}$ is hydrogen.

In certain embodiments, X is —C($R_9$)($R_{10}$)— and each of $R_9$ and $R_{10}$ is independently hydrogen, halogen, alkyl or —$OR_6$, wherein $R_6$ is hydrogen or alkyl.

In further embodiments, each of $R_1$, $R_2$, $R_9$ and $R_{10}$ is independently hydrogen or —$OR_6$, wherein $R_6$ is hydrogen or alkyl, $R_{16}$ and $R_{17}$ together with the carbon to which they are attached form a carbocyclyl, and $R_{18}$ is hydrogen, hydroxy or alkoxy.

In another specific embodiment, X is —C($R_9$)($R_{10}$)— and $R_9$ and $R_{10}$ together form oxo.

In further embodiments, each of $R_1$ and $R_2$ is independently hydrogen or —$OR_6$, wherein $R_6$ is hydrogen or alkyl, $R_9$ and $R_{10}$ together form oxo, $R_{16}$ and $R_{17}$ together with the carbon to which they are attached form a carbocyclyl, and $R_{18}$ is hydrogen, hydroxy or alkoxy.

In further embodiments, $R_{16}$ and $R_{17}$ together with the carbon to which they are attached form cyclohexyl or cycloheptyl, and $R_{18}$ is hydrogen or hydroxy.

In yet other embodiments, each of $R_{16}$ and $R_{17}$ is independently $C_1$-$C_{13}$ alkyl, and $R_{18}$ is hydrogen or hydroxy.

In certain embodiments of the compound of Formula (II), X is —C($R_9$)($R_{10}$)— and the compound has a structure of Formula (IIa):

Formula (IIa)

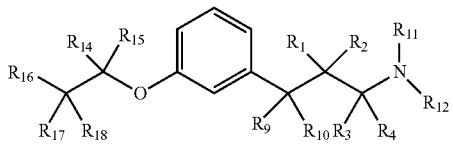

as a tautomer or a mixture of tautomers, or as a pharmaceutically acceptable salt, hydrate, solvate, N-oxide or prodrug thereof, wherein:

$R_1$ and $R_2$ are each the same or different and independently hydrogen, halogen, alkyl, fluoroalkyl, —$OR_6$, —$NR_7R_8$ or carbocyclyl; or $R_1$ and $R_2$ form an oxo;

$R_3$ and $R_4$ are each the same or different and independently hydrogen or alkyl;

$R_6$ is hydrogen or alkyl; $R_7$ and $R_8$ are each the same or different and independently hydrogen, alkyl, carbocyclyl, or —C(=O)$R_{13}$; or $R_7$ and $R_8$, together with the nitrogen atom to which they are attached, form an N-heterocyclyl;

$R_9$ and $R_{10}$ are each the same or different and independently hydrogen, halogen, alkyl, fluoroalkyl, —$OR_6$, —$NR_7R_8$ or carbocyclyl; or $R_9$ and $R_{10}$ form an oxo;

$R_{11}$ and $R_{12}$ are each the same or different and independently hydrogen, alkyl, carbocyclyl, or —C(=O)$R_{13}$; or $R_{11}$ and $R_{12}$, together with the nitrogen atom to which they are attached, form an N-heterocyclyl;

$R_{13}$ is alkyl, alkenyl, aryl, carbocyclyl, heteroaryl or heterocyclyl;

$R_{14}$ and $R_{15}$ are each the same or different and independently hydrogen or alkyl;

$R_{16}$ and $R_{17}$ are each the same or different and independently hydrogen, $C_1$-$C_{13}$ alkyl, halo or fluoroalkyl, or $R_{16}$ and $R_{17}$ together with the carbon to which they are attached form a carbocyclyl, heterocyclyl having at least one oxygen ring atom or monocyclic heteroaryl; and $R_{18}$ is hydrogen, alkyl, alkoxy, hydroxy, halo or fluoroalkyl.

In certain embodiments of the compound having a structure represented by Formula (IIa), each of $R_1$ and $R_{12}$ is hydrogen.

In other embodiments, $R_{11}$ is hydrogen and $R_{12}$ is —C(=O)$R_{13}$, wherein $R_{13}$ is alkyl.

In other embodiments, each of $R_3$, $R_4$, $R_{14}$ and $R_{15}$ is hydrogen.

In a specific embodiment, each of $R_9$ and $R_{10}$ is independently hydrogen, halogen, alkyl or —$OR_6$, wherein $R_6$ is hydrogen or alkyl.

In further embodiments, each of $R_{11}$ and $R_{12}$ is hydrogen, each of $R_1$, $R_2$, $R_9$ and $R_{10}$ is independently hydrogen or —$OR_6$, wherein $R_6$ is hydrogen or alkyl, $R_{16}$ and $R_{17}$ together with the carbon to which they are attached form a carbocyclyl, and $R_{18}$ is hydrogen, hydroxy or alkoxy.

In a further embodiments, $R_{11}$ is hydrogen, $R_{12}$ is —C(=O)$R_{13}$, wherein $R_{13}$ is alkyl, each of $R_1$, $R_2$, $R_9$ and $R_{10}$ is independently hydrogen or —$OR_6$, wherein $R_6$ is hydrogen or alkyl, $R_{16}$ and $R_{17}$ together with the carbon to which they are attached form a carbocyclyl, and $R_{18}$ is hydrogen, hydroxy or alkoxy.

In another specific embodiment, $R_9$ and $R_{10}$ together form oxo.

In further embodiments, each of $R_{11}$ and $R_{12}$ is hydrogen, each of $R_1$ and $R_2$ is independently hydrogen or —$OR_6$, wherein $R_6$ is hydrogen or alkyl, $R_9$ and $R_{10}$ together form oxo, $R_{16}$ and $R_{17}$ together with the carbon to which they are attached form a carbocyclyl, and $R_{18}$ is hydrogen, hydroxy or alkoxy.

In further embodiments, $R_{16}$ and $R_{17}$ together with the carbon to which they are attached form cyclohexyl or cycloheptyl, and $R_{18}$ is hydrogen or hydroxy.

Certain compounds disclosed herein have the structures shown in Table 1. The example number refers to a specific Example herein that describes the preparation of the compound having the structure/name shown.

TABLE 1

| Example number | Structure | Name |
|---|---|---|
| 1 | ![structure] | 3-(3-(cyclohexylmethoxy)phenyl)propan-1-amine |
| 4, 28, 29 | ![structure] | (R and/or S) 3-amino-1-(3-(cyclohexylmethoxy)phenyl)propan-1-ol |
| 5 | ![structure] | 3-amino-1-(3-(cyclohexylmethoxy)phenyl)propan-1-one |

TABLE 1-continued

| Example number | Structure | Name |
|---|---|---|
| 6 | 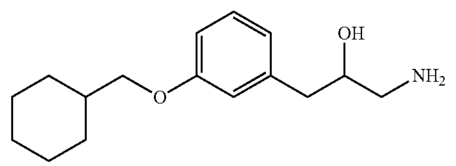 [SMILES: NCC(O)Cc1cccc(OCC2CCCCC2)c1] | 1-amino-3-(3-(cyclohexylmethoxy)phenyl)propan-2-ol |
| 14 | 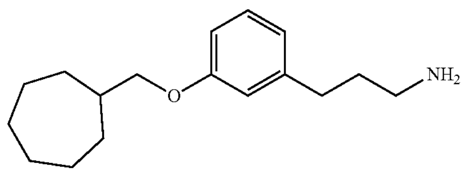 [SMILES: NCCCc1cccc(OCC2CCCCCC2)c1] | 3-(3-(cycloheptylmethoxy)phenyl)propan-1-amine |
| 15 | 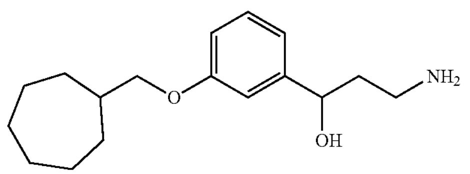 [SMILES: NCCC(O)c1cccc(OCC2CCCCCC2)c1] | 3-amino-1-(3-(cycloheptylmethoxy)phenyl) propan-1-ol |
| 16 | 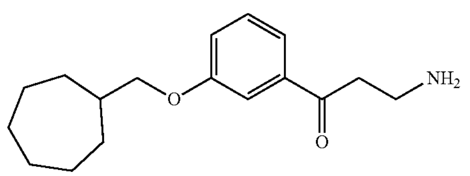 [SMILES: NCCC(=O)c1cccc(OCC2CCCCCC2)c1] | 3-amino-1-(3-(cycloheptylmethoxy)phenyl)propan-1-one |
| 10 | 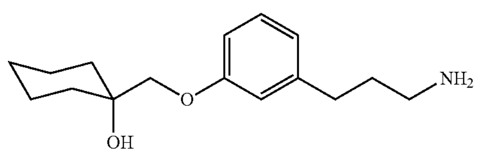 [SMILES: NCCCc1cccc(OCC2(O)CCCCC2)c1] | 1-((3-(3-aminopropyl)phenoxy)methyl)cyclohexanol |
| 11 | 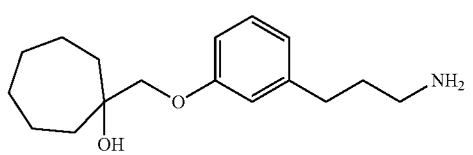 [SMILES: NCCCc1cccc(OCC2(O)CCCCCC2)c1] | 1-((3-(3-aminopropyl)phenoxy)methyl)cycloheptanol |
| 12 | 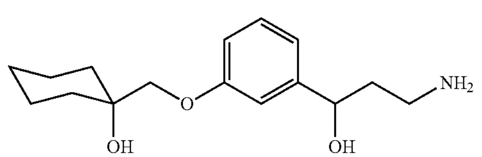 [SMILES: NCCC(O)c1cccc(OCC2(O)CCCCC2)c1] | 1-((3-(3-amino-1-hydroxypropyl)phenoxy)methyl)cyclohexanol |
| 13 | 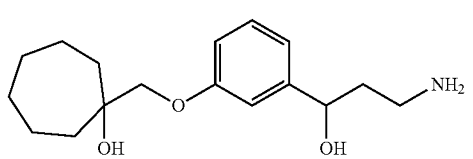 [SMILES: NCCC(O)c1cccc(OCC2(O)CCCCCC2)c1] | 1-((3-(3-amino-1-hydroxypropyl)phenoxy)methyl)cycloheptanol |
| 24 | 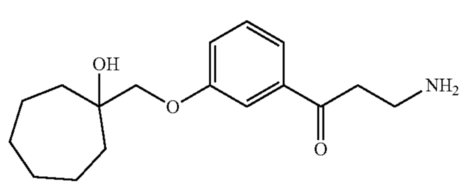 [SMILES: NCCC(=O)c1cccc(OCC2(O)CCCCCC2)c1] | 3-amino-1-(3-(cycloheptylmethoxy)phenyl)propan-1-one |

TABLE 1-continued

| Example number | Structure | Name |
|---|---|---|
| 22 | 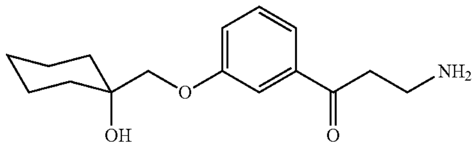 [SMILES: NCCC(=O)c1cccc(OCC2(O)CCCCC2)c1] | 3-amino-1-(3-((1-hydroxycyclohexyl)methoxy)phenyl)propan-1-one |
| 19 | 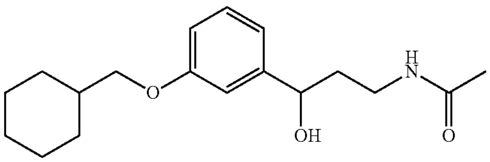 [SMILES: CC(=O)NCCC(O)c1cccc(OCC2CCCCC2)c1] | N-(3-(3-(cyclohexylmethoxy)phenyl)-3-hydroxypropyl)acetamide |
| 34 | 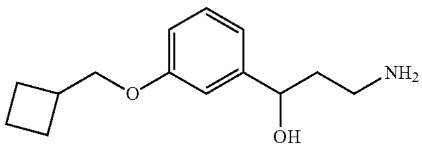 [SMILES: NCCC(O)c1cccc(OCC2CCC2)c1] | 3-amino-1-(3-(cyclobutylmethoxy)phenyl)propan-1-ol |
| 35 | 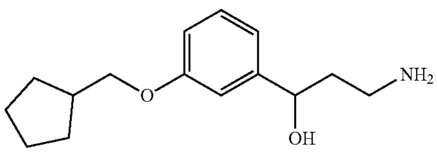 [SMILES: NCCC(O)c1cccc(OCC2CCCC2)c1] | 3-amino-1-(3-(cyclopentylmethoxy)phenyl)propan-1-ol |
| 77 | 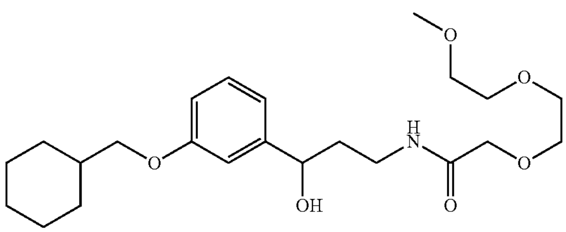 [SMILES: COCCOCCOCC(=O)NCCC(O)c1cccc(OCC2CCCCC2)c1] | N-(3-(3-(cyclohexylmethoxy)phenyl)-3-hydroxypropyl)-2-(2-(2-methoxyethoxy)ethoxy)acetamide |
| 56 | 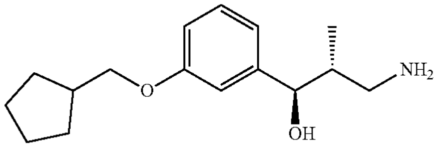 [SMILES: C[C@H](CN)[C@@H](O)c1cccc(OCC2CCCC2)c1] | (1R,2R)-3-amino-1-(3-(cyclopentylmethoxy)phenyl)-2-methylpropan-1-ol |
| 79 | 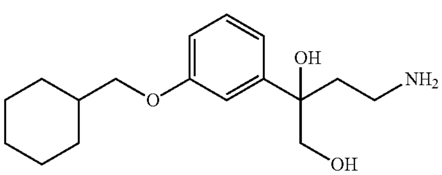 [SMILES: NCCC(O)(CO)c1cccc(OCC2CCCCC2)c1] | 4-amino-2-(3-(cyclohexylmethoxy)phenyl)butane-1,2-diol |
| 80 | 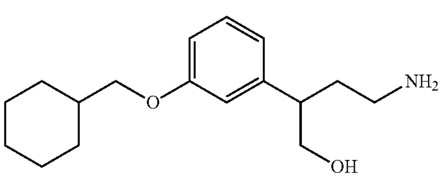 [SMILES: NCCC(CO)c1cccc(OCC2CCCCC2)c1] | 4-amino-2-(3-(cyclohexylmethoxy)phenyl)butan-1-ol |
| 78 | 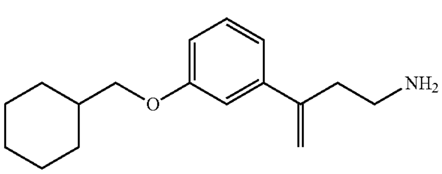 [SMILES: C=C(CCN)c1cccc(OCC2CCCCC2)c1] | 3-(3-(cyclohexylmethoxy)phenyl)but-3-en-1-amine |

TABLE 1-continued

| Example number | Structure | Name |
|---|---|---|
| 81 | 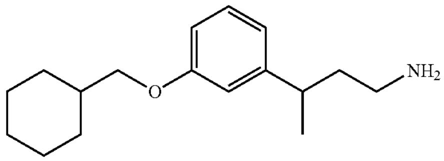 | 3-(3-(cyclohexylmethoxy)phenyl)butan-1-amine |
| 73 | 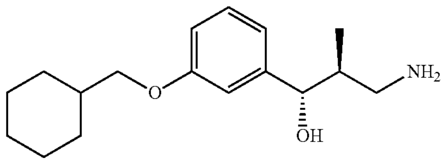 [SMILES: C[C@@H](CN)[C@H](O)c1cccc(OCC2CCCCC2)c1] | (1S,2S)-3-amino-1-(3-(cyclohexylmethoxy)phenyl)-2-methylpropan-1-ol |
| 74 | 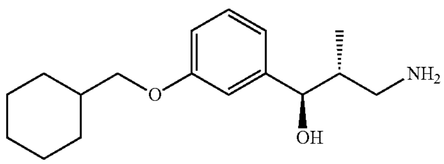 [SMILES: C[C@H](CN)[C@@H](O)c1cccc(OCC2CCCCC2)c1] | (1R,2R)-3-amino-1-(3-(cyclohexylmethoxy)phenyl)-2-methylpropan-1-ol |
| 75 | 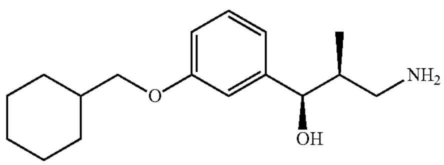 [SMILES: C[C@@H](CN)[C@@H](O)c1cccc(OCC2CCCCC2)c1] | (1R,2S)-3-amino-1-(3-(cyclohexylmethoxy)phenyl)-2-methylpropan-1-ol |
| 48 | 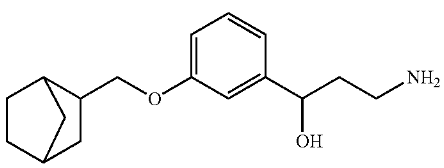 [SMILES: NCCC(O)c1cccc(OCC2CC3CCC2C3)c1] | 3-amino-1-(3-(bicyclo[2.2.1]heptan-2-ylmethoxy)phenyl)propan-1-ol |
| 49 | 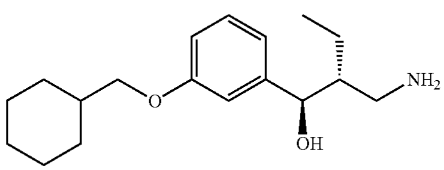 [SMILES: CC[C@H](CN)[C@@H](O)c1cccc(OCC2CCCCC2)c1] | (1R,2R)-2-(aminomethyl)-1-(3-(cyclohexylmethoxy)phenyl)butan-1-ol |
| 60 | 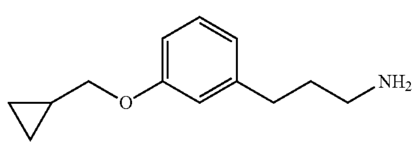 [SMILES: NCCCc1cccc(OCC2CC2)c1] | 3-(3-(cyclopropylmethoxy)phenyl)propan-1-amine |
| 61 | 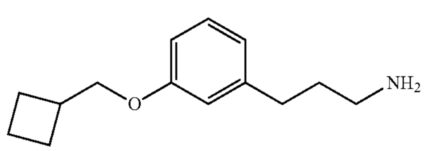 [SMILES: NCCCc1cccc(OCC2CCC2)c1] | 3-(3-(cyclobutylmethoxy)phenyl)propan-1-amine |
| 71 | 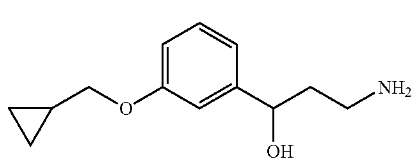 [SMILES: NCCC(O)c1cccc(OCC2CC2)c1] | 3-amino-1-(3-(cyclopropylmethoxy)phenyl)propan-1-ol |

TABLE 1-continued

| Example number | Structure | Name |
|---|---|---|
| 76 | 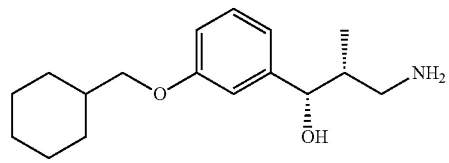 [SMILES: C[C@H](CN)[C@H](O)c1cccc(OCC2CCCCC2)c1] | (1S,2R)-3-amino-1-(3-(cyclohexylmethoxy)phenyl)-2-methylpropan-1-ol |
| 99 | 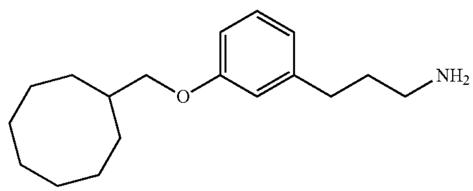 | 3-(3-(cyclooctylmethoxy)phenyl)propan-1-amine |
| 103 | 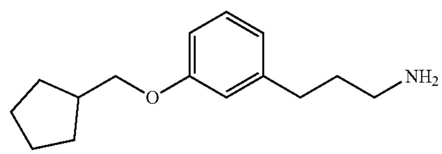 [SMILES: NCCCc1cccc(OCC2CCCC2)c1] | 3-(3-(cyclopentylmethoxy)phenyl)propan-1-amine |
| 106 | 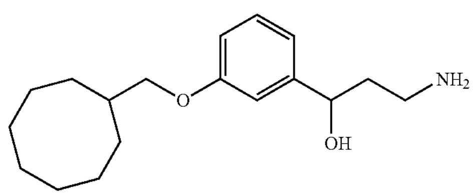 [SMILES: NCCC(O)c1cccc(OCC2CCCCCCC2)c1] | 3-amino-1-(3-(cyclooctylmethoxy)phenyl)propan-1-ol |
| 83 | 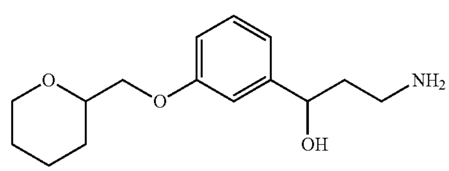 [SMILES: NCCC(O)c1cccc(OCC2CCCCO2)c1] | 3-amino-1-(3-((tetrahydro-2H-pyran-2-yl)methoxy)phenyl)propan-1-ol |
| 122 | 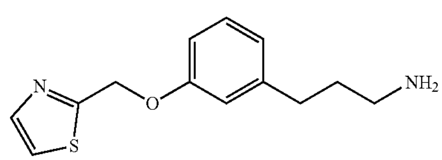 [SMILES: NCCCc1cccc(OCc2nccs2)c1] | 3-(3-(thiazol-2-ylmethoxy)phenyl)propan-1-amine |
| 126 | 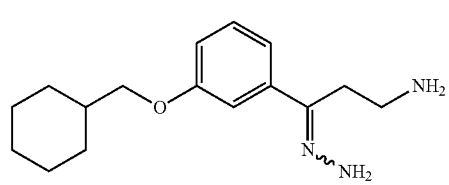 [SMILES: NCCC(=NN)c1cccc(OCC2CCCCC2)c1] | 3-(3-(cyclohexylmethoxy)phenyl)-3-hydrazonopropan-1-amine |
| 130 | 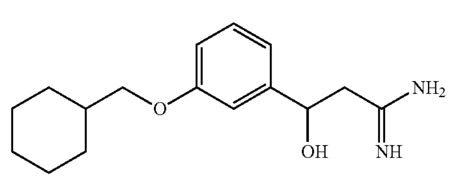 [SMILES: N=C(N)CC(O)c1cccc(OCC2CCCCC2)c1] | 3-(3-(cyclohexylmethoxy)phenyl)-3-hydroxypropanimidamide |

TABLE 1-continued

| Example number | Structure | Name |
|---|---|---|
| 135 | 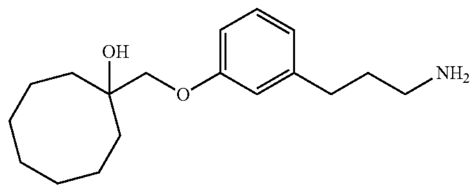 [SMILES: NCCCc1cccc(OCC2(O)CCCCCCC2)c1] | 1-((3-(3-aminopropyl)phenoxy)methyl)cyclooctanol |
| 168 | 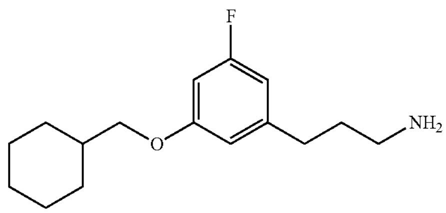 [SMILES: NCCCc1cc(F)cc(OCC2CCCCC2)c1] | 3-(3-(cyclohexylmethoxy)-5-fluorophenyl)propan-1-amine |
| 146 | 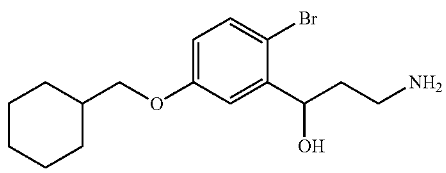 [SMILES: NCCC(O)c1cc(OCC2CCCCC2)ccc1Br] | 3-amino-1-(2-bromo-5-(cyclohexylmethoxy)phenyl)propan-1-ol |
| 147 | 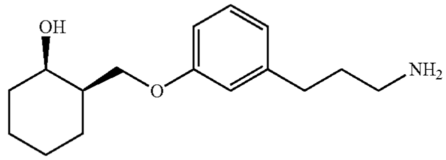 [SMILES: NCCCc1cccc(OC[C@H]2CCCC[C@H]2O)c1] | (1,2-cis)-2-((3-(3-aminopropyl)phenoxy)methyl)cyclohexanol |
| 148 | 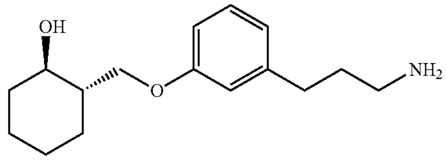 [SMILES: NCCCc1cccc(OC[C@@H]2CCCC[C@H]2O)c1] | (1,2-trans)-2-((3-(3-aminopropyl)phenoxy)methyl)cyclohexanol |
| 162 | 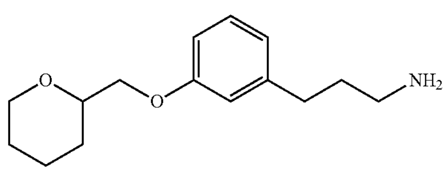 [SMILES: NCCCc1cccc(OCC2CCCCO2)c1] | 3-(3-((tetrahydro-2H-pyran-2-yl)methoxy)phenyl)propan-1-amine |
| 142 | 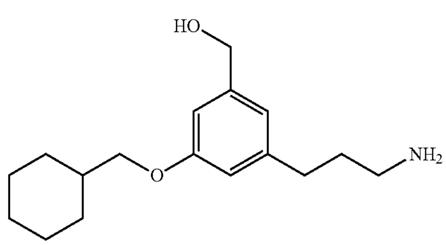 [SMILES: NCCCc1cc(CO)cc(OCC2CCCCC2)c1] | (3-(3-aminopropyl)-5-(cyclohexylmethoxy)phenyl)methanol |
| 169 | 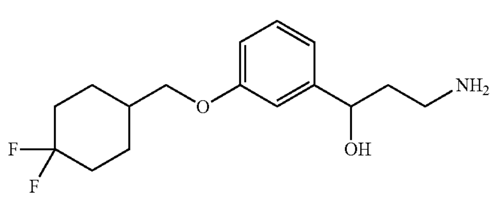 [SMILES: NCCC(O)c1cccc(OCC2CCC(F)(F)CC2)c1] | 3-amino-1-(3-((4,4-difluorocyclohexyl)methoxy)phenyl)propan-1-ol |

TABLE 1-continued

| Example number | Structure | Name |
|---|---|---|
| 170 | 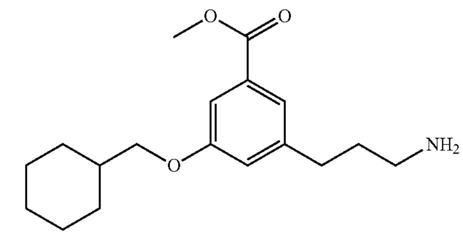 [SMILES: COC(=O)c1cc(CCCN)cc(OCC2CCCCC2)c1] | methyl 3-(3-aminopropyl)-5-(cyclohexylmethoxy)benzoate |
| 174 | 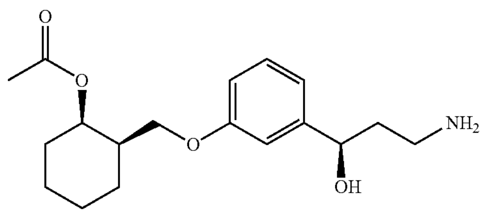 [SMILES: CC(=O)O[C@@H]1CCCC[C@@H]1COc1cccc([C@H](O)CCN)c1] | (1,2-cis)-2-((3-((R)-3-amino-1-hydroxypropyl)phenoxy)methyl)cyclohexyl acetate |
| 173 | 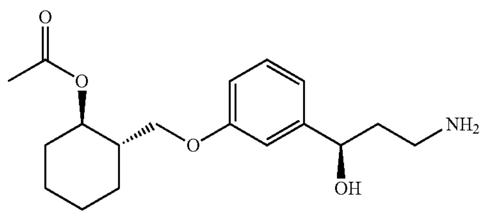 [SMILES: CC(=O)O[C@@H]1CCCC[C@H]1COc1cccc([C@H](O)CCN)c1] | (1,2-trans)-2-((3-((R)-3-amino-1-hydroxypropyl)phenoxy)methyl)cyclohexyl acetate |
| 175 | 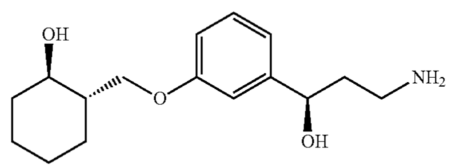 [SMILES: NCC[C@@H](O)c1cccc(OC[C@@H]2CCCC[C@H]2O)c1] | (1,2-trans)-2-((3-((R)-3-amino-1-hydroxypropyl)phenoxy)methyl)cyclohexanol |
| 176 | 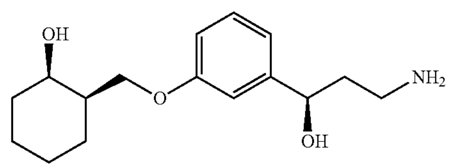 [SMILES: NCC[C@@H](O)c1cccc(OC[C@H]2CCCC[C@H]2O)c1] | (1,2-cis)-2-((3-((R)-3-amino-1-hydroxypropyl)phenoxy)methyl)cyclohexanol |
| 172 | 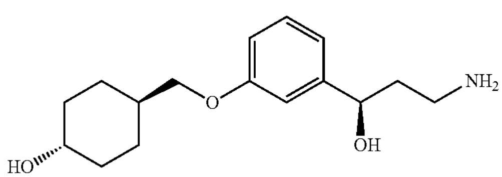 [SMILES: NCC[C@@H](O)c1cccc(OC[C@H]2CC[C@H](O)CC2)c1] | (1,4-trans)-4-((3-((R)-3-amino-1-hydroxypropyl)phenoxy)methyl)cyclohexanol |
| 171 | 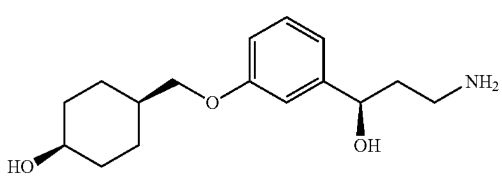 [SMILES: NCC[C@@H](O)c1cccc(OC[C@H]2CC[C@@H](O)CC2)c1] | (1,4-cis)-4-((3-((R)-3-amino-1-hydroxypropyl)phenoxy)methyl)cyclohexanol |
| 177 | 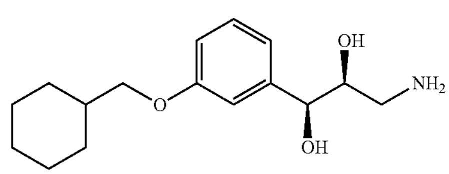 [SMILES: NC[C@H](O)[C@@H](O)c1cccc(OCC2CCCCC2)c1] | (1S,2S)-3-amino-1-(3-(cyclohexylmethoxy)phenyl)propane-1,2-diol |

TABLE 1-continued

| Example number | Structure | Name |
|---|---|---|
| 178 | 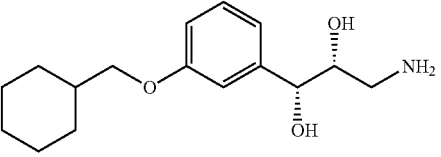 [SMILES: NC[C@@H](O)[C@H](O)c1cccc(OCC2CCCCC2)c1] | (1R,2R)-3-amino-1-(3-(cyclohexylmethoxy)phenyl)propane-1,2-diol |
| 179 | 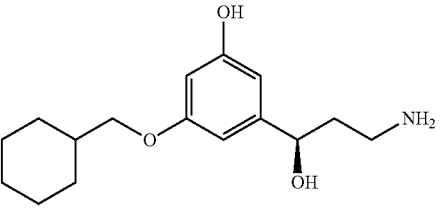 [SMILES: NCC[C@@H](O)c1cc(O)cc(OCC2CCCCC2)c1] | (R)-3-(3-amino-1-hydroxypropyl)-5-(cyclohexylmethoxy)phenol |
| 180 | 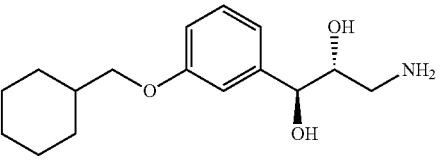 [SMILES: NC[C@@H](O)[C@@H](O)c1cccc(OCC2CCCCC2)c1] | (1S,2R)-3-amino-1-(3-(cyclohexylmethoxy)phenyl)propane-1,2-diol |
| 181 | 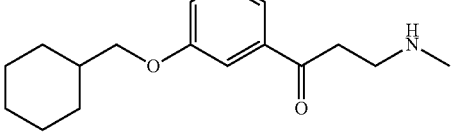 | 1-(3-(cyclohexylmethoxy)phenyl)-3-(methylamino)propan-1-one |
| 182 | 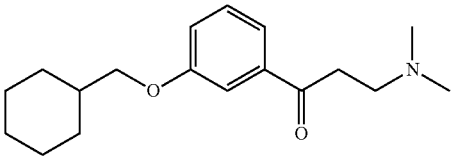 [SMILES: CN(C)CCC(=O)c1cccc(OCC2CCCCC2)c1] | 1-(3-(cyclohexylmethoxy)phenyl)-3-(dimethylamino)propan-1- |
| 184 | 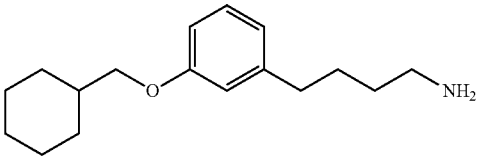 [SMILES: NCCCCc1cccc(OCC2CCCCC2)c1] | 4-(3-(cyclohexylmethoxy)phenyl)butan-1-amine |
| 185 | 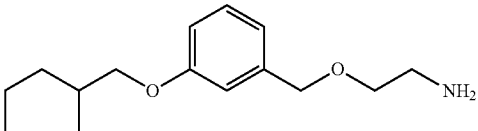 | 2-(3-(cyclohexylmethoxy)benzyloxy)ethanamine |
| 186 | 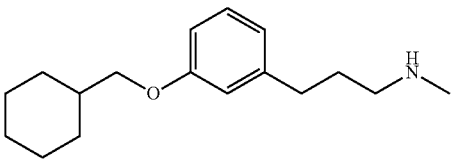 [SMILES: CNCCCc1cccc(OCC2CCCCC2)c1] | 3-(3-(cyclohexylmethoxy)phenyl)-N-methylpropan-1-amine |

TABLE 1-continued

| Example number | Structure | Name |
|---|---|---|
| 187 | 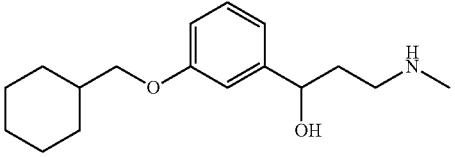 [SMILES: CNCCC(O)c1cccc(OCC2CCCCC2)c1] | 1-(3-(cyclohexylmethoxy)phenyl)-3-(methylamino)propan-1-ol |
| 188 | 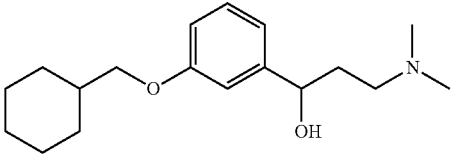 [SMILES: CN(C)CCC(O)c1cccc(OCC2CCCCC2)c1] | 1-(3-(cyclohexylmethoxy)phenyl)-3-(dimethylamino)propan-1-ol |
| 189 | 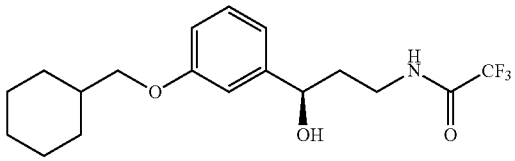 [SMILES: O=C(NCC[C@@H](O)c1cccc(OCC2CCCCC2)c1)C(F)(F)F] | (R)-N-(3-(3-(cyclohexylmethoxy)phenyl)-3-hydroxypropyl)-2,2,2-trifluoroacetamide |
| 190 | 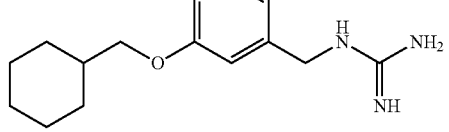 | 1-(3-(cyclohexylmethoxy)benzyl)guanidine |
| 191 | 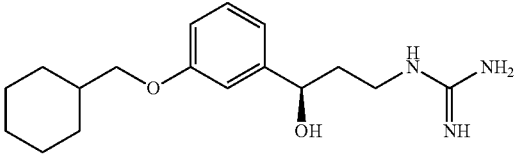 [SMILES: N=C(N)NCC[C@@H](O)c1cccc(OCC2CCCCC2)c1] | (R)-1-(3-(3-(cyclohexylmethoxy)phenyl)-3-hydroxypropyl)guanidine |
| 192 | 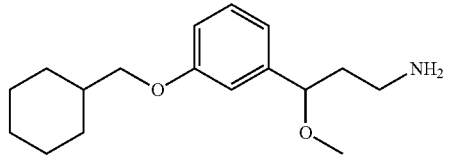 [SMILES: COC(CCN)c1cccc(OCC2CCCCC2)c1] | 3-(3-(cyclohexylmethoxy)phenyl)-3-methoxypropan-1-amine |
| 193 | 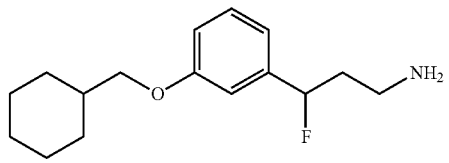 | 3-(3-(cyclohexylmethoxy)phenyl)-3-fluoropropan-1-amine |
| 194 | 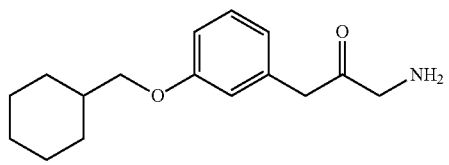 [SMILES: NCC(=O)Cc1cccc(OCC2CCCCC2)c1] | 1-amino-3-(3-(cyclohexylmethoxy)phenyl)propan-2-one |
| 195 | 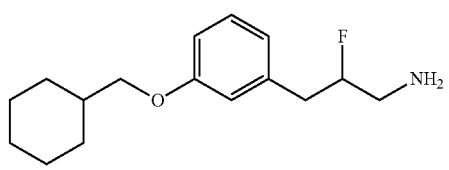 [SMILES: NCC(F)Cc1cccc(OCC2CCCCC2)c1] | 3-(3-(cyclohexylmethoxy)phenyl)-2-fluoropropan-1-amine |

In further embodiments, each of $R_{11}$ and $R_{12}$ is hydrogen, each of $R_1$, $R_2$, $R_9$ and $R_{10}$ is independently hydrogen or —$OR_6$, wherein $R_6$ is hydrogen or alkyl, each of $R_{16}$ and $R_{17}$ is independently hydrogen or $C_1$-$C_{13}$ alkyl, and $R_{18}$ is hydrogen, hydroxy or alkoxy.

In further embodiments, $R_{11}$ is hydrogen, $R_{12}$ is —C(=O)$R_{13}$, wherein $R_{13}$ is alkyl, each of $R_1$, $R_2$, $R_9$ and $R_{10}$ is independently hydrogen or —$OR_6$, wherein $R_6$ is hydrogen or alkyl, each of $R_{16}$ and $R_{17}$ is independently hydrogen or $C_1$-$C_{13}$ alkyl, and $R_{18}$ is hydrogen, hydroxy or alkoxy.

In another specific embodiment, $R_9$ and $R_{10}$ together form oxo.

In further embodiments, each of $R_{11}$ and $R_{12}$ is hydrogen, each of $R_1$ and $R_2$ is independently hydrogen or —$OR_6$, wherein $R_6$ is hydrogen or alkyl, $R_9$ and $R_{10}$ together form oxo, each of $R_{16}$ and $R_{17}$ is independently $C_1$-$C_{13}$ alkyl, and $R_{18}$ is hydrogen, hydroxy or alkoxy.

In further embodiments, $R_{11}$ is hydrogen, $R_{12}$ is —C(=O)$R_{13}$, each of $R_1$ and $R_2$ is independently hydrogen or —$OR_6$, wherein $R_6$ is hydrogen or alkyl, $R_9$ and $R_{10}$ together form oxo, each of $R_{16}$ and $R_{17}$ is independently $C_1$-$C_{13}$ alkyl, and $R_{18}$ is hydrogen, hydroxy or alkoxy.

Certain compounds disclosed herein have the structures shown in Table 2. The example number refers to a specific Example herein that describes the preparation of the compound having the structure/name shown.

TABLE 2

| Example number | Structure | Name |
| --- | --- | --- |
| 2 | 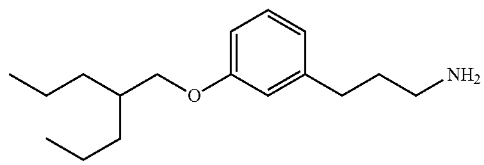 [SMILES: CCCC(CCC)COc1cccc(CCCN)c1] | 3-(3-(2-propylpentyloxy)phenyl)propan-1-amine |
| 3 | 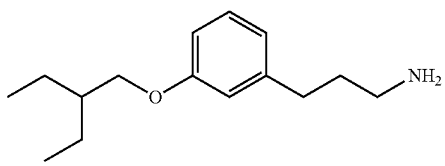 [SMILES: CCC(CC)COc1cccc(CCCN)c1] | 3-(3-(2-ethylbutoxy)phenyl)propan-1-amine |
| 17 | 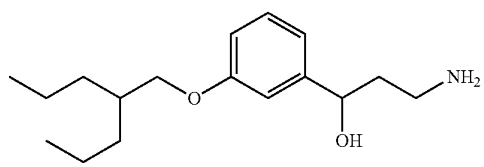 [SMILES: CCCC(CCC)COc1cccc(C(O)CCN)c1] | 3-amino-1-(3-(2-propylpentyloxy)phenyl)propan-1-ol |
| 21 | 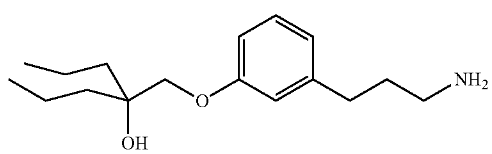 [SMILES: CCCC(O)(CCC)COc1cccc(CCCN)c1] | 4-((3-(3-aminopropyl)phenoxy)methyl)heptan-4-ol |
| 20 | 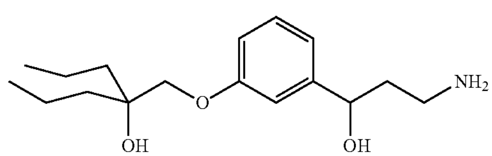 [SMILES: CCCC(O)(CCC)COc1cccc(C(O)CCN)c1] | 4-((3-(3-amino-1-hydroxypropyl)phenoxy)methyl)heptan-4-ol |
| 23 | 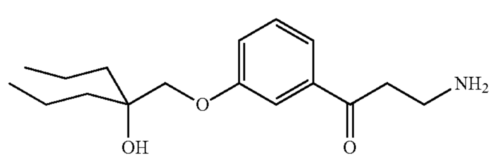 [SMILES: CCCC(O)(CCC)COc1cccc(C(=O)CCN)c1] | 3-amino-1-(3-(2-hydroxy-2-propylpentyloxy)phenyl)propan-1-one |
| 30 | 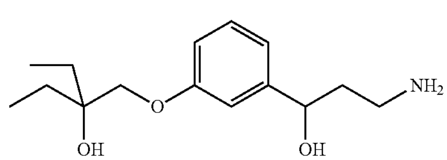 [SMILES: CCC(O)(CC)COc1cccc(C(O)CCN)c1] | 3-((3-(3-amino-1-hydroxypropyl)phenoxy)methyl)pentan-3-ol |

TABLE 2-continued

| Example number | Structure | Name |
|---|---|---|
| 32 | 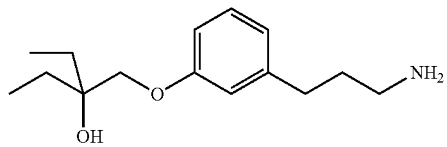 | 3-((3-(3-aminopropyl)phenoxy)methyl)pentan-3-ol |
| 33 | 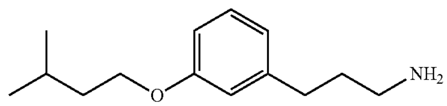 | 3-(3-(isopentyloxy)phenyl)propan-1-amine |
| 39 | 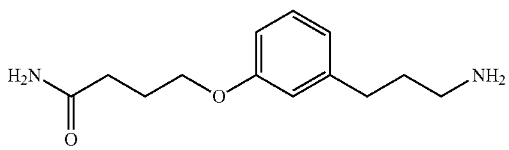 [SMILES: NCCCc1cccc(OCCCC(N)=O)c1] | 4-(3-3-aminopropyl)phenoxy)butanamide |
| 40 | 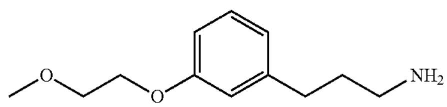 | 3-(3-(2-methoxyethoxy)phenyl)propan-1-amine |
| 41 | 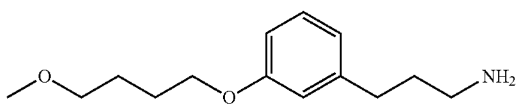 [SMILES: COCCCCOc1cccc(CCCN)c1] | 3-(3-(4-methoxybutoxy)phenyl)propan-1-amine |
| 42 | 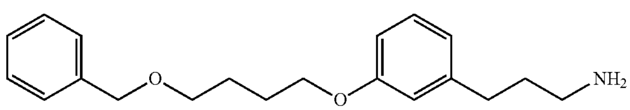 [SMILES: NCCCc1cccc(OCCCCOCc2ccccc2)c1] | 3-(3-(4-(benzyloxy)butoxy)phenyl)propan-1-amine |
| 43 | 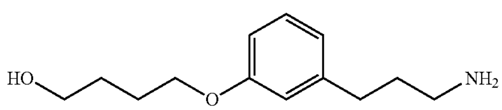 [SMILES: NCCCc1cccc(OCCCCO)c1] | 4-(3-(3-aminopropyl)phenoxy)butan-1-ol |
| 44 | 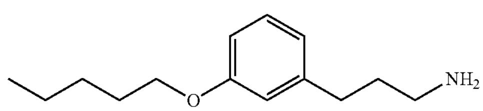 [SMILES: CCCCCOc1cccc(CCCN)c1] | 3-(3-(pentyloxy)phenyl)propan-1-amine |
| 45 | 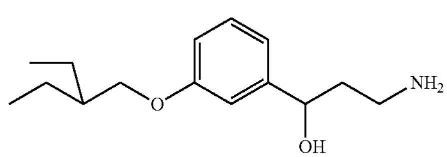 [SMILES: CCC(CC)COc1cccc(C(O)CCN)c1] | 3-amino-1-(3-(2-ethylbutoxy)phenyl)propan-1-ol |
| 72 | 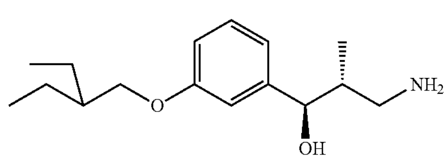 [SMILES: CCC(CC)COc1cccc([C@H](O)[C@H](C)CN)c1] | (1R,2R)-3-amino-1-(3-(2-ethylbutoxy)phenyl)-2-methylpropan-1-ol |
| 54 | 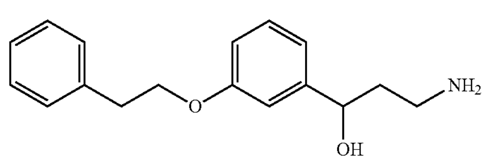 [SMILES: NCCC(O)c1cccc(OCCc2ccccc2)c1] | 3-amino-1-(3-phenethoxyphenyl)propan-1-ol |

TABLE 2-continued

| Example number | Structure | Name |
|---|---|---|
| 55 | 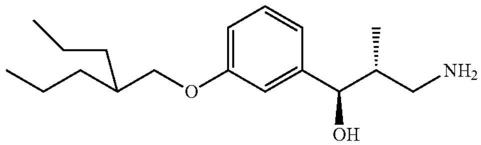 [SMILES: CCCC(CCC)COc1cccc([C@H](O)[C@H](C)CN)c1] | (1R,2R)-3-amino-2-methyl-1-(3-(2-propylpentyloxy)phenyl)propan-1-ol |
| 70 | 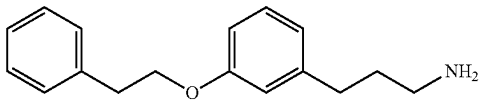 [SMILES: NCCCc1cccc(OCCc2ccccc2)c1] | 3-(3-phenethoxyphenyl)propan-1-amine |
| 66 | 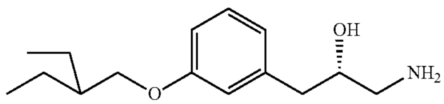 [SMILES: CCC(CC)COc1cccc(C[C@H](O)CN)c1] | (S)-1-amino-3-(3-(2-ethylbutoxy)phenyl)propan-2-ol |
| 67 | 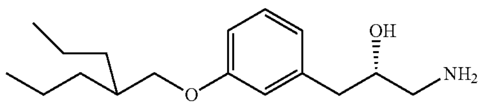 [SMILES: CCCC(CCC)COc1cccc(C[C@H](O)CN)c1] | (S)-1-amino-3-(3-(2-propylpentyloxy)phenyl)propan-2-ol |
| 68 | 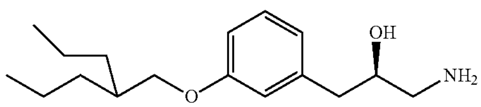 [SMILES: CCCC(CCC)COc1cccc(C[C@@H](O)CN)c1] | (R)-1-amino-3-(3-(2-propylpentyloxy)phenyl)propan-2-ol |
| 69 | 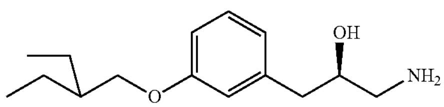 [SMILES: CCC(CC)COc1cccc(C[C@@H](O)CN)c1] | (R)-1-amino-3-(3-(2-ethylbutoxy)phenyl)propan-2-ol |
| 86 | 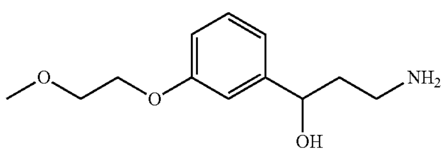 [SMILES: COCCOc1cccc(C(O)CCN)c1] | 3-amino-1-(3-(2-methoxyethoxy)phenyl)propan-1-ol |
| 87 | 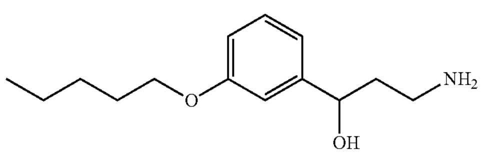 [SMILES: CCCCCOc1cccc(C(O)CCN)c1] | 3-amino-1-(3-(pentyloxy)phenyl)propan-1-ol |
| 88 | 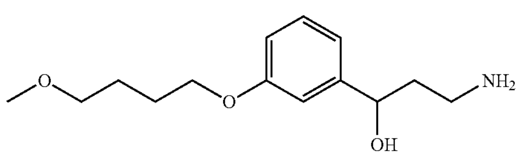 [SMILES: COCCCCOc1cccc(C(O)CCN)c1] | 3-amino-1-(3-(4-methoxybutoxy)phenyl)propan-1-ol |
| 96 | 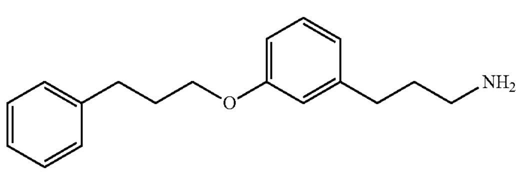 [SMILES: NCCCc1cccc(OCCCc2ccccc2)c1] | 3-(3-(3-phenylpropoxy)phenyl)propan-1-amine |
| 97 | 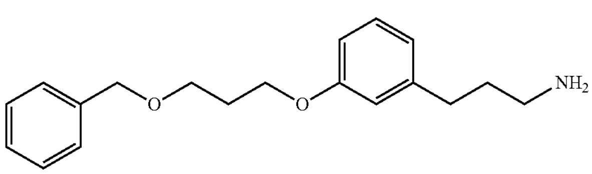 [SMILES: NCCCc1cccc(OCCCOCc2ccccc2)c1] | 3-(3-(3-(benzyloxy)propoxy)phenyl)propan-1-amine |

TABLE 2-continued

| Example number | Structure | Name |
|---|---|---|
| 98 | 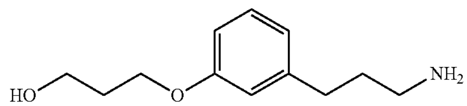 [SMILES: NCCCc1cccc(OCCCO)c1] | 3-(3-(3-aminopropyl)phenoxy)propan-1-ol |
| 102 | 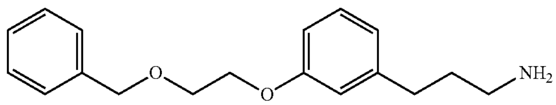 | 3-(3-(2-(benzyloxy)ethoxy)phenyl)propan-1-amine |
| 107 | 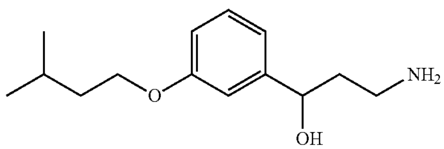 [SMILES: CC(C)CCOc1cccc(C(O)CCN)c1] | 3-amino-1-(3-(isopentyloxy)phenyl)propan-1-ol |
| 108 | 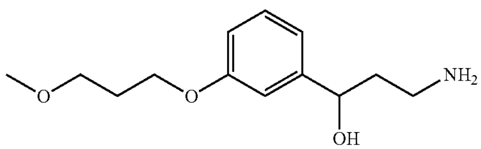 [SMILES: COCCCOc1cccc(C(O)CCN)c1] | 3-amino-1-(3-(3-methoxypropoxy)phenyl)propan-1-ol |
| 109 | 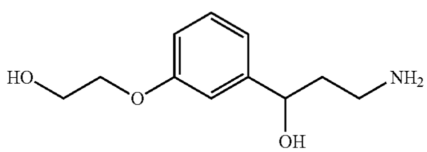 [SMILES: NCCC(O)c1cccc(OCCO)c1] | 3-amino-1-(3-(2-hydroxyethoxy)phenyl)propan-1-ol |
| 110 | 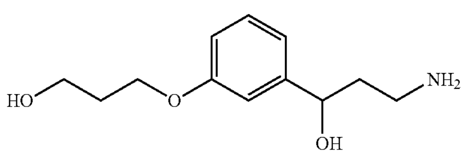 [SMILES: NCCC(O)c1cccc(OCCCO)c1] | 3-amino-1-(3-(3-hydroxypropoxy)phenyl)propan-1-ol |
| 114 | 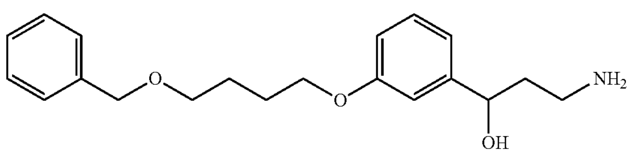 [SMILES: NCCC(O)c1cccc(OCCCCOCc2ccccc2)c1] | 3-amino-1-(3-(4-(benzyloxy)butoxy)phenyl)propan-1-ol |
| 115 | 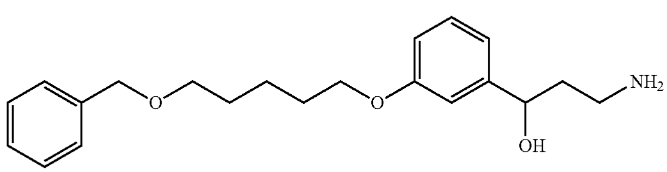 [SMILES: NCCC(O)c1cccc(OCCCCCOCc2ccccc2)c1] | 3-amino-1-(3-(5-(benzyloxy)pentyloxy)phenyl)propan-1-ol |
| 116 | 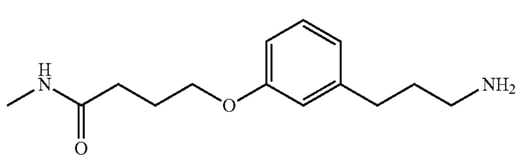 [SMILES: CNC(=O)CCCOc1cccc(CCCN)c1] | 4-(3-(3-aminopropyl)phenoxy)-N-methylbutanamide |
| 117 | 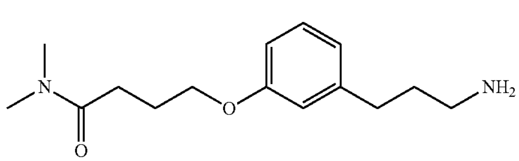 [SMILES: CN(C)C(=O)CCCOc1cccc(CCCN)c1] | 4-(3-(3-aminopropyl)phenoxy)-N,N-dimethylbutanamide |

TABLE 2-continued

| Example number | Structure | Name |
|---|---|---|
| 118 | 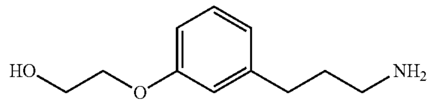 [SMILES: NCCCc1cccc(OCCO)c1] | 2-(3-(3-aminopropyl)phenoxy)ethanol |
| 131 | 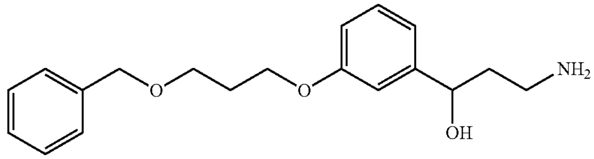 [SMILES: NCCC(O)c1cccc(OCCCOCc2ccccc2)c1] | 3-amino-1-(3-(3-(benzyloxy)propoxy)phenyl)propan-1-ol |
| 132 | 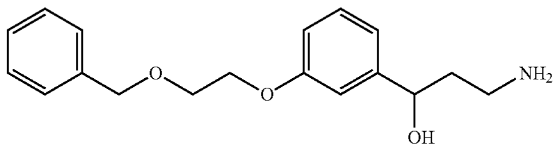 [SMILES: NCCC(O)c1cccc(OCCOCc2ccccc2)c1] | 3-amino-1-(3-(2-(benzyloxy)ethoxy)phenyl)propan-1-ol |
| 136 | 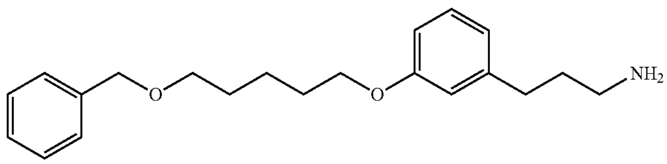 [SMILES: NCCCc1cccc(OCCCCCOCc2ccccc2)c1] | 3-(3-(5-(benzyloxy)pentyloxy)phenyl)propan-1-amine |
| 155 | 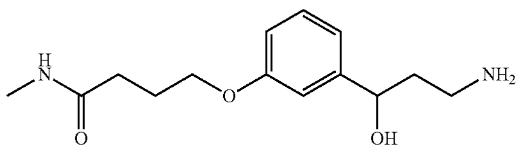 [SMILES: CNC(=O)CCCOc1cccc(C(O)CCN)c1] | 4-(3-(3-amino-1-hydroxypropyl)phenoxy)-N-methylbutanamide |
| 150 | 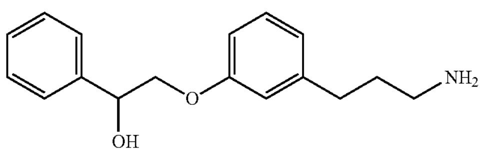 [SMILES: NCCCc1cccc(OCC(O)c2ccccc2)c1] | 2-(3-(3-aminopropyl)phenoxy)-1-phenylethanol |
| 151 | 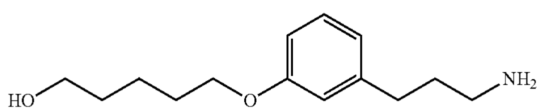 | 5-(3-(3-aminopropyl)phenoxy)pentan-1-ol |
| 152 | 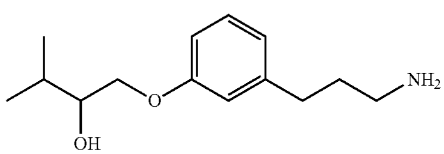 [SMILES: CC(C)C(O)COc1cccc(CCCN)c1] | 1-(3-(3-aminopropyl)phenoxy)-3-methylbutan-2-ol |
| 149 | 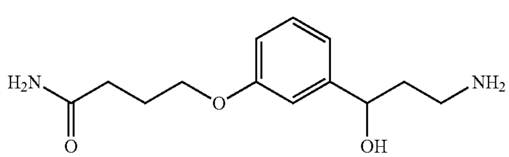 [SMILES: NCCC(O)c1cccc(OCCCC(N)=O)c1] | 4-(3-(3-amino-1-hydroxypropyl)phenoxy)butanamide |
| 157 | 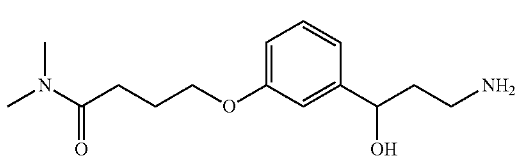 [SMILES: CN(C)C(=O)CCCOc1cccc(C(O)CCN)c1] | 4-(3-(3-amino-1-hydroxypropyl)phenoxy)-N,N-dimethylbutanamide |

TABLE 2-continued

| Example number | Structure | Name |
|---|---|---|
| 158 | 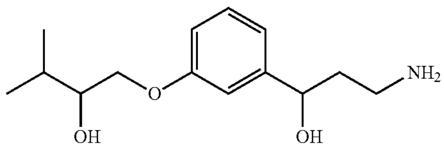 [SMILES: CC(C)C(O)COc1cccc(C(O)CCN)c1] | 1-(3-(3-amino-1-hydroxypropyl)phenoxy)-3-methylbutan-2-ol |
| 161 | 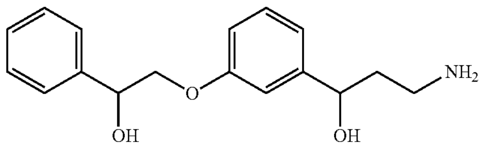 [SMILES: NCCC(O)c1cccc(OCC(O)c2ccccc2)c1] | 3-amino-1-(3-(2-hydroxy-2-phenylethoxy)phenyl)propan-1-ol |
| 163 | 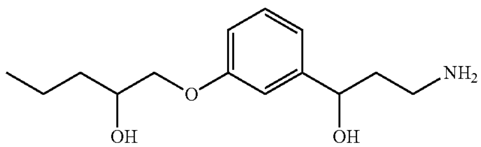 [SMILES: CCCC(O)COc1cccc(C(O)CCN)c1] | 1-(3-(3-amino-1-hydroxypropyl)phenoxy)pentan-2-ol |
| 165 | 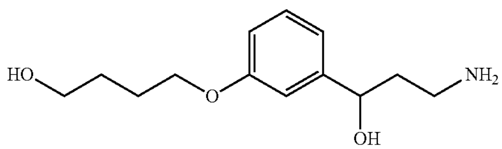 [SMILES: NCCC(O)c1cccc(OCCCCO)c1] | 4-(3-(3-amino-1-hydroxypropyl)phenoxy)butan-1-ol |
| 166 | 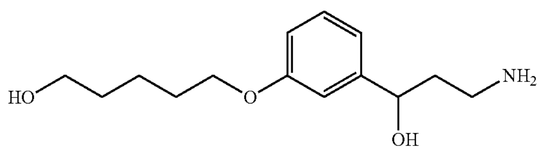 [SMILES: NCCC(O)c1cccc(OCCCCCO)c1] | 5-(3-(3-amino-1-hydroxypropyl)phenoxy)pentan-1-ol |
| 167 | 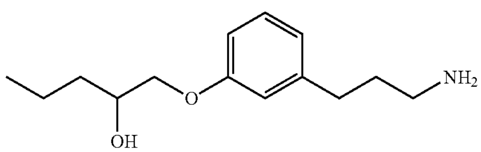 [SMILES: CCCC(O)COc1cccc(CCCN)c1] | 1-(3-(3-aminopropyl)phenoxy)pentan-2-ol |
| 183 | 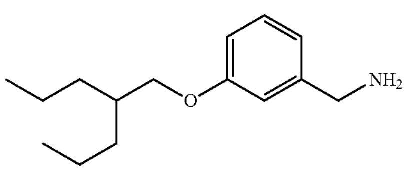 [SMILES: CCCC(CCC)COc1cccc(CN)c1] | (3-(2-propylpentyloxy)phenyl)methanamine |

In certain embodiments of the compound of Formula (II), X is —O—, and the compound has a structure of Formula (IIb):

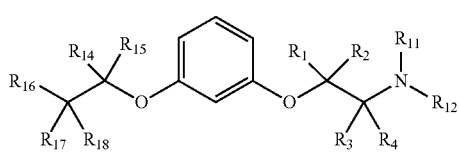

Formula (IIb)

as a tautomer or a mixture of tautomers, or as a pharmaceutically acceptable salt, hydrate, solvate, N-oxide or prodrug thereof, wherein:

$R_1$ and $R_2$ are each the same or different and independently hydrogen, halogen, alkyl, fluoroalkyl, or carbocyclyl;

$R_3$ and $R_4$ are each the same or different and independently hydrogen or alkyl;

$R_{11}$ and $R_{12}$ are each the same or different and independently hydrogen, alkyl, carbocyclyl, or —C(=O)$R_{13}$; or $R_{11}$ and $R_{12}$, together with the nitrogen atom to which they are attached, form an N-heterocyclyl;

$R_{13}$ is alkyl, alkenyl, aryl, carbocyclyl, heteroaryl or heterocyclyl;

$R_{14}$ and $R_{15}$ are each the same or different and independently hydrogen or alkyl;

$R_{16}$ and $R_{17}$ are each the same or different and independently hydrogen, $C_1$-$C_{13}$ alkyl, halo or fluoroalkyl, or $R_{16}$ and $R_{17}$ together with the carbon to which they are attached form a carbocyclyl, heterocyclyl having at least one oxygen ring atom or monocyclic heteroaryl; and $R_{18}$ is hydrogen, alkyl, alkoxy, hydroxy, halo or fluoroalkyl.

In certain embodiments of a compound having the structure of Formula (IIb), each of $R_{11}$ and $R_{12}$ is hydrogen.

In other embodiments, $R_{11}$ is hydrogen and $R_{12}$ is —C(=O)$R_{13}$, wherein $R_{13}$ is alkyl.

In other embodiments, each of $R_3$, $R_4$, $R_{14}$ and $R_{15}$ is hydrogen.

In certain embodiments, each of $R_{11}$ and $R_{12}$ is hydrogen, each of $R_1$ and $R_2$ is independently hydrogen or alkyl, each of $R_3$, $R_4$, $R_{14}$ and $R_{15}$ is hydrogen, $R_{16}$ and $R_{17}$ together with the carbon to which they are attached form a carbocyclyl, and $R_{18}$ is hydrogen, hydroxy or alkoxy.

In certain specific embodiments, $R_{16}$ and $R_{17}$ together with the carbon to which they are attached form cyclohexyl or cycloheptyl, and $R_{18}$ is hydrogen or hydroxy.

Certain compounds disclosed herein have the structures shown in Table 3. The example number refers to a specific Example herein that describes the preparation of the compound having the structure/name shown.

TABLE 3

| Example number | Structure | Name |
|---|---|---|
| 7 | 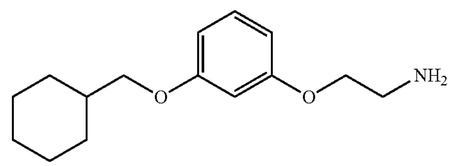 | 2-(3-(cyclohexylmethoxy)phenoxy)ethanamine |
| 9 | 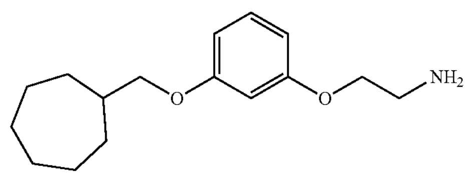 [SMILES: NCCOc1cccc(OCC2CCCCCC2)c1] | 2-(3-(cycloheptylmethoxy)phenoxy)ethanamine |
| 26 | 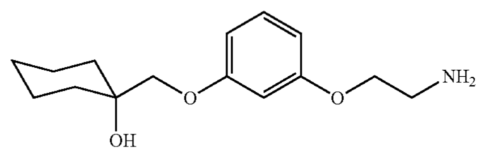 | 1-((3-(2-aminoethoxy)phenoxy)methyl)cyclohexanol |
| 18 | 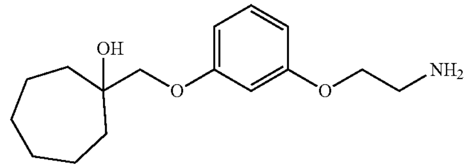 [SMILES: NCCOc1cccc(OCC2(O)CCCCCC2)c1] | 1-((3-(2-aminoethoxy)phenoxy)methyl)cycloheptanol |
| 52 | 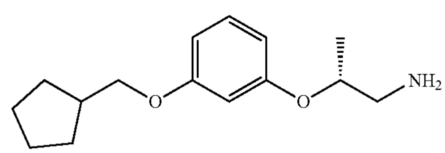 [SMILES: C[C@H](CN)Oc1cccc(OCC2CCCC2)c1] | (R)-2-(3-(cyclopentylmethoxy)phenoxy)propan-1-amine |
| 53 | 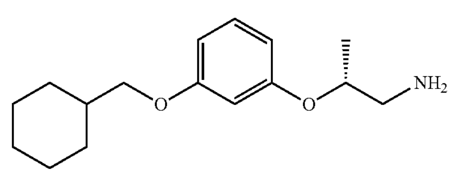 [SMILES: C[C@H](CN)Oc1cccc(OCC2CCCCC2)c1] | (R)-2-(3-(cyclohexylmethoxy)phenoxy)propan-1-amine |
| 57 | 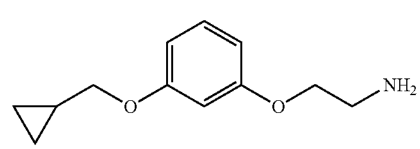 [SMILES: NCCOc1cccc(OCC2CC2)c1] | 2-(3-(cyclopropylmethoxy)phenoxy)ethanamine |
| 58 | 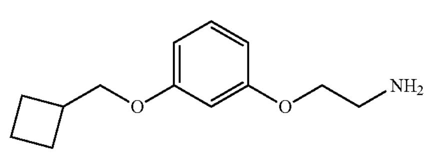 [SMILES: NCCOc1cccc(OCC2CCC2)c1] | 2-(3-(cyclobutylmethoxy)phenoxy)ethanamine |

TABLE 3-continued

| Example number | Structure | Name |
|---|---|---|
| 64 | 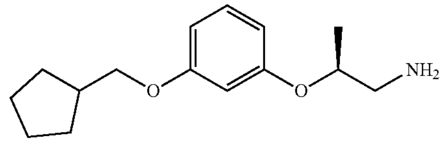 [SMILES: C[C@@H](CN)Oc1cccc(OCC2CCCC2)c1] | (S)-2-(3-(cyclopentylmethoxy)phenoxy)propan-1-amine |
| 65 | 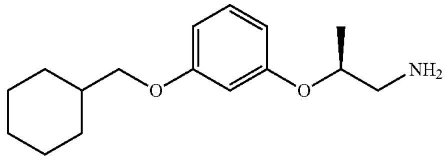 [SMILES: C[C@@H](CN)Oc1cccc(OCC2CCCCC2)c1] | (S)-2-(3-(cyclohexylmethoxy)phenoxy)propan-1-amine |
| 93 | 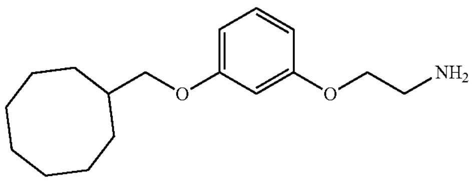 [SMILES: NCCOc1cccc(OCC2CCCCCCC2)c1] | 2-(3-(cyclooctylmethoxy)phenoxy)ethanamine |
| 104 | 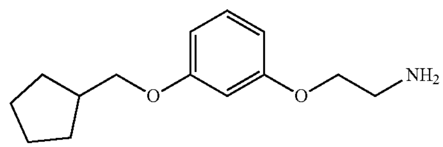 [SMILES: NCCOc1cccc(OCC2CCCC2)c1] | 2-(3-(cyclopentylmethoxy)phenoxy)ethanamine |
| 111 | 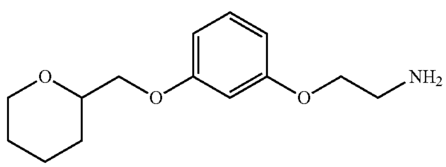 | 2-(3-((tetrahydro-2H-pyran-2-yl)methoxy)phenoxy)ethanamine |
| 154 | 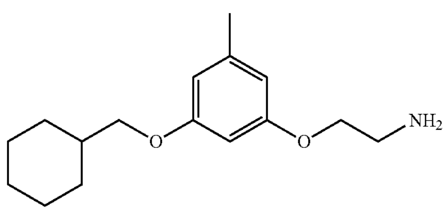 [SMILES: Cc1cc(OCCN)cc(OCC2CCCCC2)c1] | 2-(3-(cyclohexylmethoxy)-5-methylphenoxy)ethanamine |
| 139 | 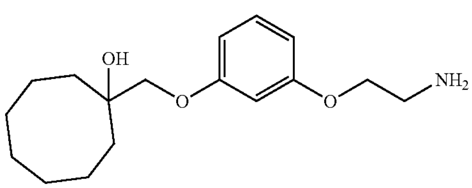 [SMILES: NCCOc1cccc(OCC2(O)CCCCCCC2)c1] | 1-((3-(2-aminoethoxy)phenoxy)methyl)cyclooctanol |
| 160 | 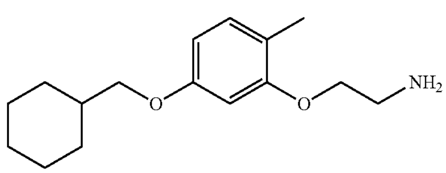 [SMILES: Cc1ccc(OCC2CCCCC2)cc1OCCN] | 2-(5-(cyclohexylmethoxy)-2-methylphenoxy)ethanamine |

TABLE 3-continued

| Example number | Structure | Name |
|---|---|---|
| 164 | 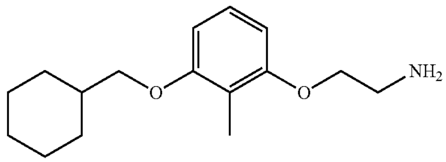 [SMILES: Cc1c(OCCN)cccc1OCC1CCCCC1] | 2-(3-(cyclohexylmethoxy)-2-methylphenoxy)ethanamine |

In certain embodiments, each of $R_{11}$ and $R_{12}$ is hydrogen, each of $R_1$, $R_2$, $R_3$, $R_4$, $R_{14}$ and $R_{15}$ is hydrogen, each of $R_{16}$ and $R_{17}$ is independently hydrogen or $C_1$-$C_{13}$ alkyl, and $R_{18}$ is hydrogen, hydroxy or alkoxy.

In certain embodiments, each of $R_{16}$ and $R_{17}$ is independently $C_1$-$C_{13}$ alkyl, and $R_{18}$ is hydrogen or hydroxy.

Certain compounds disclosed herein have the structures shown in Table 4. The example number refers to a specific Example herein that describes the preparation of the compound having the structure/name shown.

TABLE 4

| Example number | Structure | Name |
|---|---|---|
| 25 | 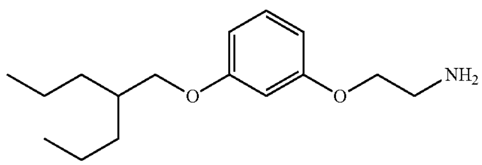 [SMILES: CCCC(CCC)COc1cccc(OCCN)c1] | 2-(3-(2-propylpentyloxy)phenoxy)ethanamine |
| 27 | 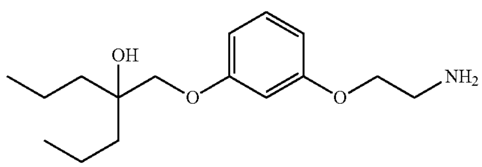 [SMILES: CCCC(O)(CCC)COc1cccc(OCCN)c1] | 4-((3-(2-aminoethoxy)phenoxy)methyl) heptan-4-ol |
| 31 | 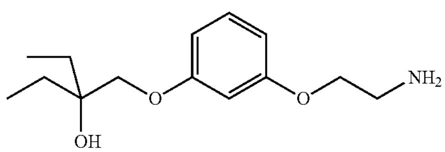 [SMILES: CCC(O)(CC)COc1cccc(OCCN)c1] | 3-((3-(2-aminoethoxy)phenoxy)methyl)pentan-3-ol |
| 36 | 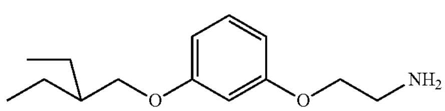 [SMILES: CCC(CC)COc1cccc(OCCN)c1] | 2-(3-(2-ethylbutoxy)phenoxy)ethanamine |
| 46 | 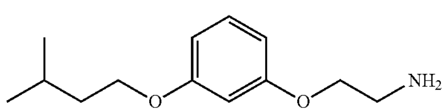 [SMILES: CC(C)CCOc1cccc(OCCN)c1] | 2-(3-(isopentyloxy)phenoxy)ethanamine |
| 47 | 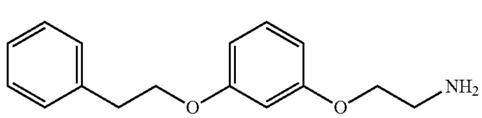 [SMILES: NCCOc1cccc(OCCc2ccccc2)c1] | 2-(3-phenethoxyphenoxy)ethanamine |
| 50 | 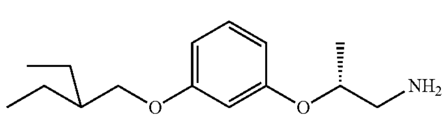 [SMILES: CCC(CC)COc1cccc(O[C@H](C)CN)c1] | (R)-2-(3-(2-ethylbutoxy)phenoxy)propan-1-amine |

TABLE 4-continued

| Example number | Structure | Name |
|---|---|---|
| 51 | 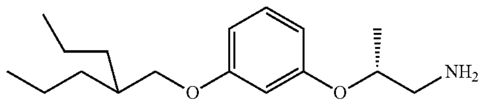 [SMILES: CCCC(CCC)COc1cccc(O[C@H](C)CN)c1] | (R)-2-(3-(2-propylpentyloxy)phenoxy)propan-1-amine |
| 62 | 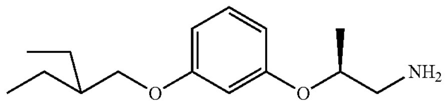 [SMILES: CCC(CC)COc1cccc(O[C@@H](C)CN)c1] | (S)-2-(3-(2-ethylbutoxy)phenoxy)propan-1-amine |
| 63 | 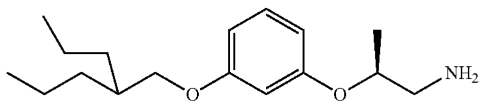 [SMILES: CCCC(CCC)COc1cccc(O[C@@H](C)CN)c1] | (S)-2-(3-(2-propylpentyloxy)phenoxy)propan-1-amine |
| 82 | 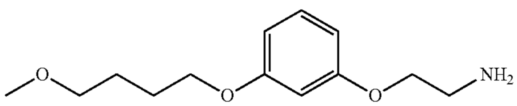 [SMILES: COCCCCOc1cccc(OCCN)c1] | 2-(3-(4-methoxybutoxy)phenoxy)ethanamine |
| 85 | 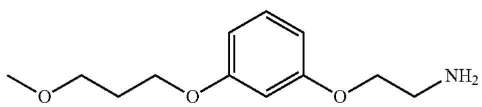 [SMILES: COCCCOc1cccc(OCCN)c1] | 2-(3-(3-methoxypropoxy)phenoxy)ethanamine |
| 89 | 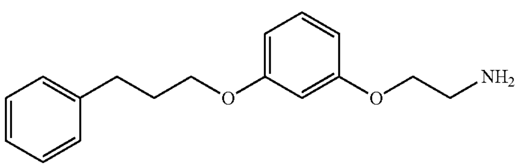 [SMILES: NCCOc1cccc(OCCCc2ccccc2)c1] | 2-(3-(3-phenylpropoxy)phenoxy)ethanamine |
| 90 | 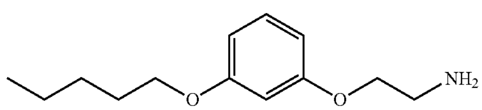 [SMILES: CCCCCOc1cccc(OCCN)c1] | 2-(3-(pentyloxy)phenoxy)ethanamine |
| 94 | 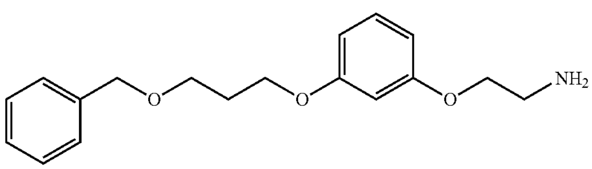 [SMILES: NCCOc1cccc(OCCCOCc2ccccc2)c1] | 2-(3-(3-(benzyloxy)propoxy)phenoxy)ethanamine |
| 95 | 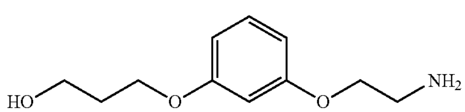 [SMILES: NCCOc1cccc(OCCCO)c1] | 3-(3-(2-aminoethoxy)phenoxy)propan-1-ol |
| 100 | 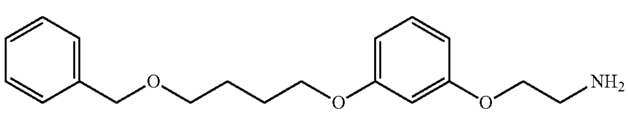 [SMILES: NCCOc1cccc(OCCCCOCc2ccccc2)c1] | 2-(3-(4-(benzyloxy)butoxy)phenoxy)ethanamine |
| 112 | 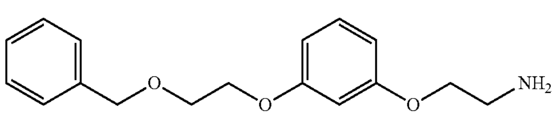 [SMILES: NCCOc1cccc(OCCOCc2ccccc2)c1] | 2-(3-(2-(benzyloxy)ethoxy)phenoxy)ethanamine |
| 113 | 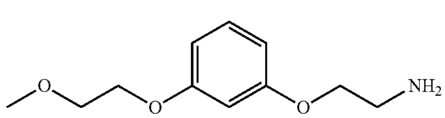 | 2-(3-(2-methoxyethoxy)phenoxy)ethanamine |

TABLE 4-continued

| Example number | Structure | Name |
|---|---|---|
| 133 | 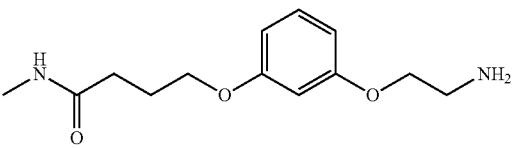 [SMILES: CNC(=O)CCCOc1cccc(OCCN)c1] | 4-(3-(2-aminoethoxy)phenoxy)-N-methylbutanamide |
| 134 | 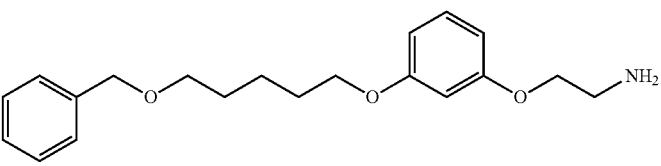 [SMILES: NCCOc1cccc(OCCCCCOCc2ccccc2)c1] | 2-(3-(5-benzyloxy)pentyloxy)phenoxy)ethanamine |
| 138 | 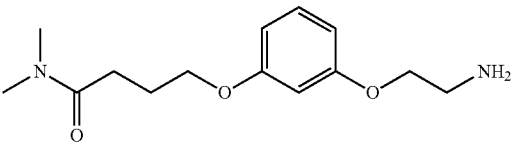 [SMILES: CN(C)C(=O)CCCOc1cccc(OCCN)c1] | 4-(3-(2-aminoethoxy)phenoxy)-N,N-dimethylbutanamide |
| 141 | 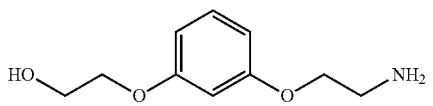 [SMILES: NCCOc1cccc(OCCO)c1] | 2-(3-(2-aminoethoxy)phenoxy)ethanol |
| 143 | 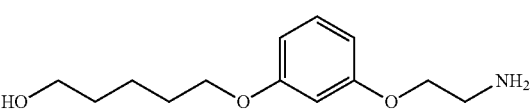 | 5-(3-(2-aminoethoxy)phenoxy)pentan-1-ol |
| 144 | 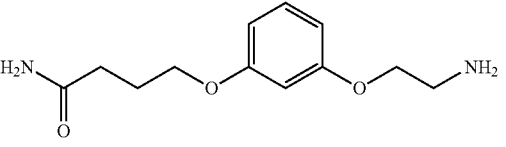 [SMILES: NCCOc1cccc(OCCCC(N)=O)c1] | 4-(3-(2-aminoethoxy)phenoxy)butanamide |
| 145 | 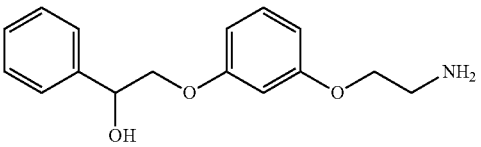 [SMILES: NCCOc1cccc(OCC(O)c2ccccc2)c1] | 2-(3-(2-aminoethoxy)phenoxy)-1-phenylethanol |
| 153 | 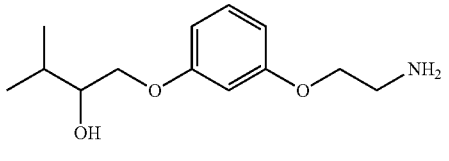 | 1-(3-(2-aminoethoxy)phenoxy)-3-methylbutan-2-ol |
| 156 | 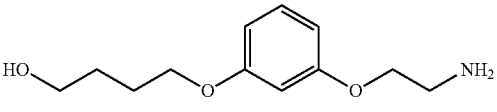 [SMILES: NCCOc1cccc(OCCCCO)c1] | 4-(3-(2-aminoethoxy)phenoxy)butan-1-ol |
| 159 | 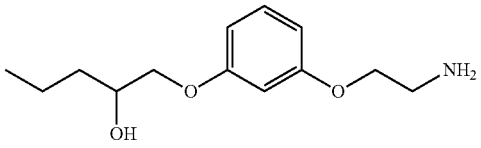 [SMILES: CCCC(O)COc1cccc(OCCN)c1] | 1-(3-2-aminoethoxy)phenoxy)pentan-2-ol |

Certain compounds disclosed herein have the structures shown in Table 5. The example number refers to a specific Example herein that describes the preparation of the compound having the structure/name shown.

TABLE 5

| Example number | Structure | Name |
| --- | --- | --- |
| 37 | 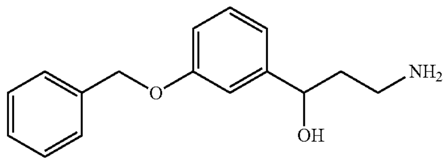 [SMILES: NCCC(O)c1cccc(OCc2ccccc2)c1] | 3-amino-1-(3-(benzyloxy)phenyl)propan-1-ol |
| 38 | 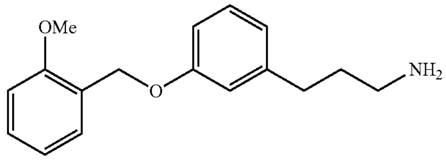 [SMILES: COc1ccccc1COc1cccc(CCCN)c1] | 3-(3-(2-methoxybenzyloxy)phenyl)propan-1-amine |
| 59 | 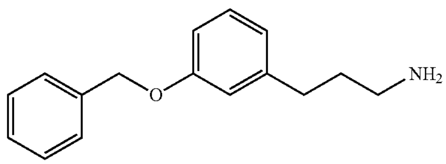 [SMILES: NCCCc1cccc(OCc2ccccc2)c1] | 3-(3-(benzyloxy)phenyl)propan-1-amine |
| 91 | 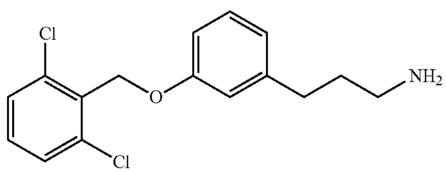 [SMILES: NCCCc1cccc(OCc2c(Cl)cccc2Cl)c1] | 3-(3-(2,6-dichlorobenzyloxy)phenyl)propan-1-amine |
| 92 | 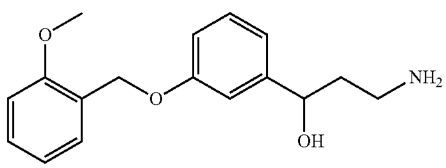 [SMILES: COc1ccccc1COc1cccc(C(O)CCN)c1] | 3-amino-1-(3-(2-methoxybenzyloxy)phenyl)propan-1-ol |
| 105 | 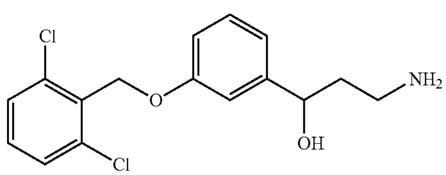 [SMILES: NCCC(O)c1cccc(OCc2c(Cl)cccc2Cl)c1] | 3-amino-1-(3-(2,6-dichlorobenzyloxy)phenyl)propan-1-ol |
| 119 | 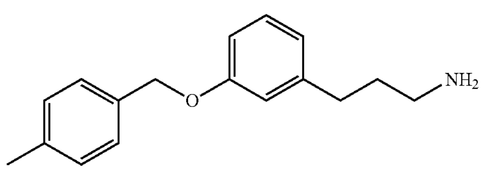 [SMILES: Cc1ccc(COc2cccc(CCCN)c2)cc1] | 3-(3-(4-methylbenzyloxy)phenyl)propan-1-amine |
| 120 | 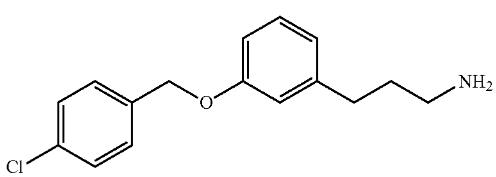 [SMILES: NCCCc1cccc(OCc2ccc(Cl)cc2)c1] | 3-(3-(4-chlorobenzyloxy)phenyl)propan-1-amine |

TABLE 5-continued

| Example number | Structure | Name |
|---|---|---|
| 121 | 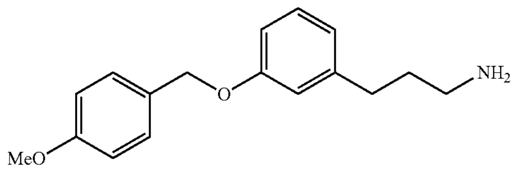 [SMILES: COc1ccc(COc2cccc(CCCN)c2)cc1] | 3-(3-(4-methoxybenzyloxy)phenyl)propan-1-amine |
| 137 | 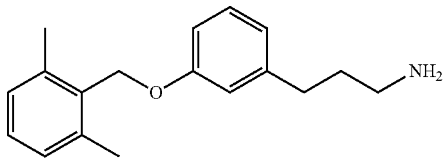 [SMILES: Cc1cccc(C)c1COc1cccc(CCCN)c1] | 3-(3-(2,6-dimethylbenzyloxy)phenyl)propan-1-amine |

Certain compounds disclosed herein have the structures shown in Table 6. The example number refers to a specific Example herein that describes the preparation of the compound having the structure/name shown.

TABLE 6

| Example number | Structure | Name |
|---|---|---|
| 8 | 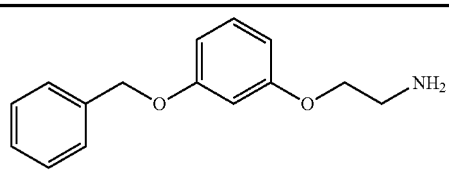 | 2-(3-(benzyloxy)phenoxy)ethanamine |
| 84 | 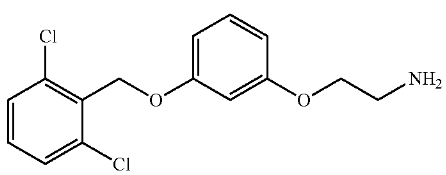 [SMILES: NCCOc1cccc(OCc2c(Cl)cccc2Cl)c1] | 2-(3-(2,6-dichlorobenzyloxy)phenoxy)ethanamine |
| 101 | 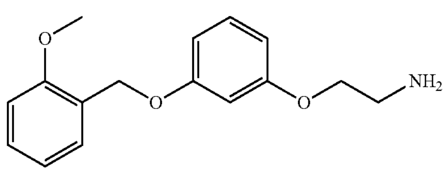 [SMILES: COc1ccccc1COc1cccc(OCCN)c1] | 2-(3-(2-methoxybenzyloxy)phenoxy)ethanamine |
| 140 | 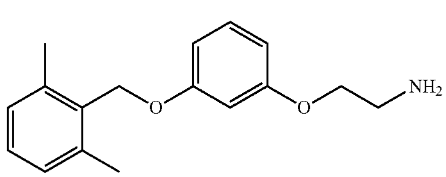 [SMILES: Cc1cccc(C)c1COc1cccc(OCCN)c1] | 2-(3-(2,6-dimethylbenzyloxy)phenoxy)ethanamine |

Certain compounds disclosed herein have the structures shown in Table 7. The example number refers to a specific Example herein that describes the preparation of the compound having the structure/name shown.

TABLE 7

| Example number | Structure | Name |
|---|---|---|
| 123 | 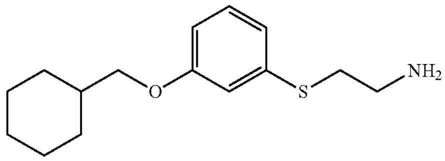 | 2-(3-(cyclohexylmethoxy)phenylthio)ethanamine |
| 124 | 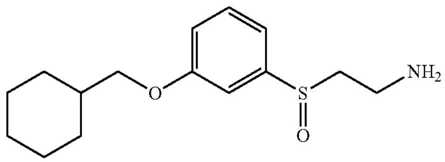 [SMILES: NCCS(=O)c1cccc(OCC2CCCCC2)c1] | 2-(3-(cyclohexylmethoxy)phenylsulfinyl)ethanamine |
| 125 | 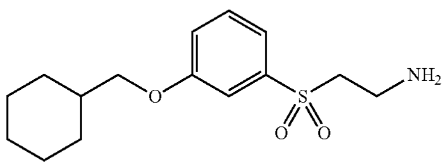 [SMILES: NCCS(=O)(=O)c1cccc(OCC2CCCCC2)c1] | 2-(3-(cyclohexylmethoxy)phenylsulfonyl)ethanamine |
| 128 | 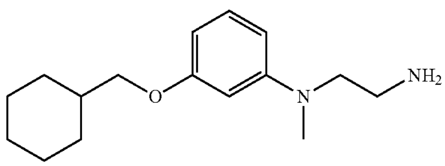 | $N^1$-(3-(cyclohexylmethoxy)phenyl)$N^1$-methylethane-1,2-diamine |
| 129 | 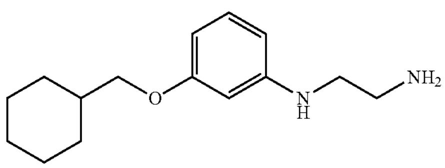 [SMILES: NCCNc1cccc(OCC2CCCCC2)c1] | $N^1$-(3-(cyclohexylmethoxy)phenyl)ethane-1,2-diamine |

Certain compounds disclosed herein have the structures shown in Table 8. The example number refers to a specific Example herein that describes the preparation of the compound having the structure/name shown.

TABLE 8

| Example number | Structure | Name |
|---|---|---|
| 127 | 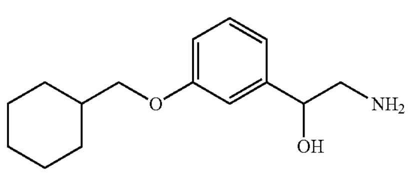 [SMILES: NCC(O)c1cccc(OCC2CCCCC2)c1] | 2-amino-1-(3-(cyclohexylmethoxy)phenyl)ethanol |
| 196 | 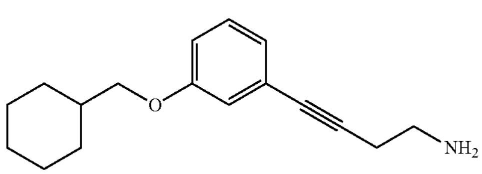 [SMILES: NCCC#Cc1cccc(OCC2CCCCC2)c1] | 4-(3-(cyclohexylmethoxy)phenyl)but-3-yn-1-amine |

TABLE 8-continued

| Example number | Structure | Name |
| --- | --- | --- |
| 197 | 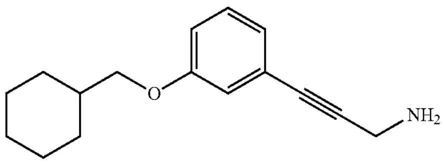 [SMILES: NCC#Cc1cccc(OCC2CCCCC2)c1] | 3-(3-(cyclohexylmethoxy)phenyl)prop-2-yn-1-amine |
| 198 | 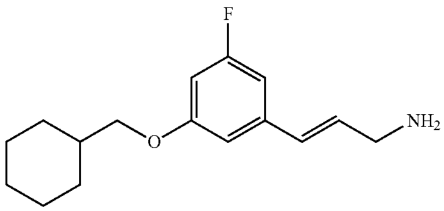 [SMILES: NC/C=C/c1cc(F)cc(OCC2CCCCC2)c1] | 3-(3-(cyclohexylmethoxy)-5-fluorophenyl)prop-2-en-1-amine |

In an additional embodiment is a compound selected from:

127
-continued
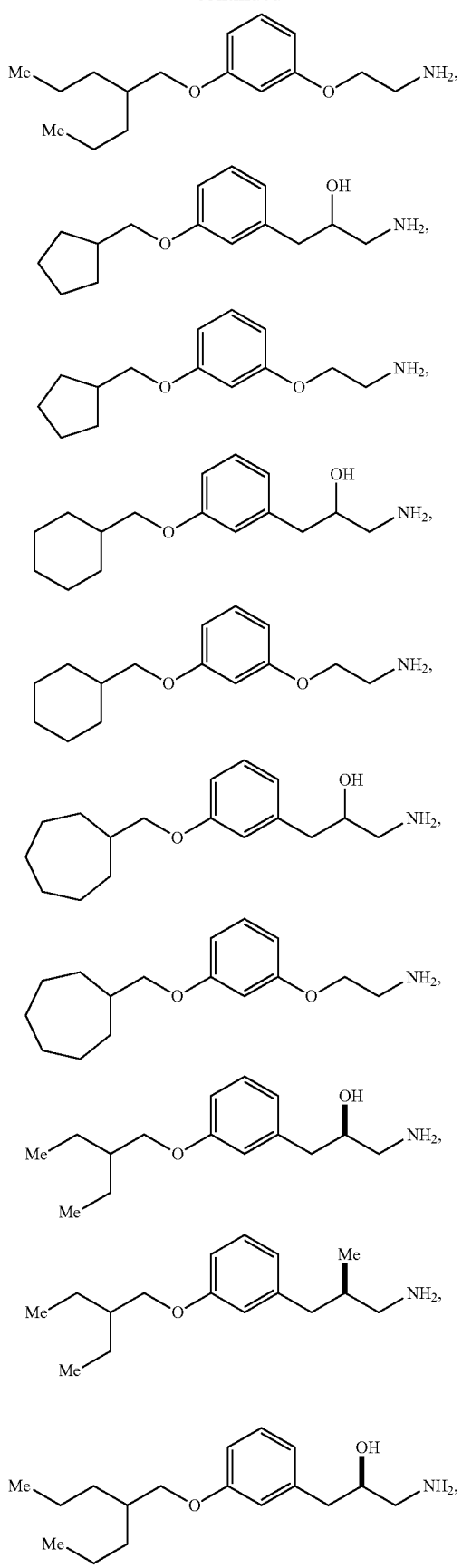
128
-continued
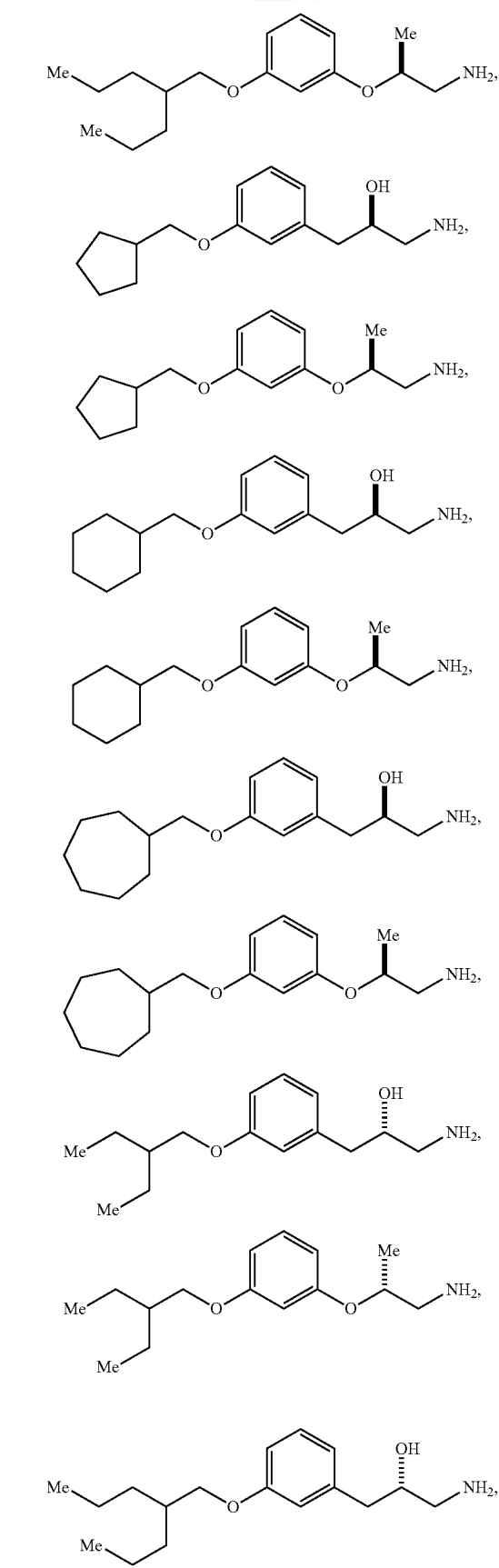

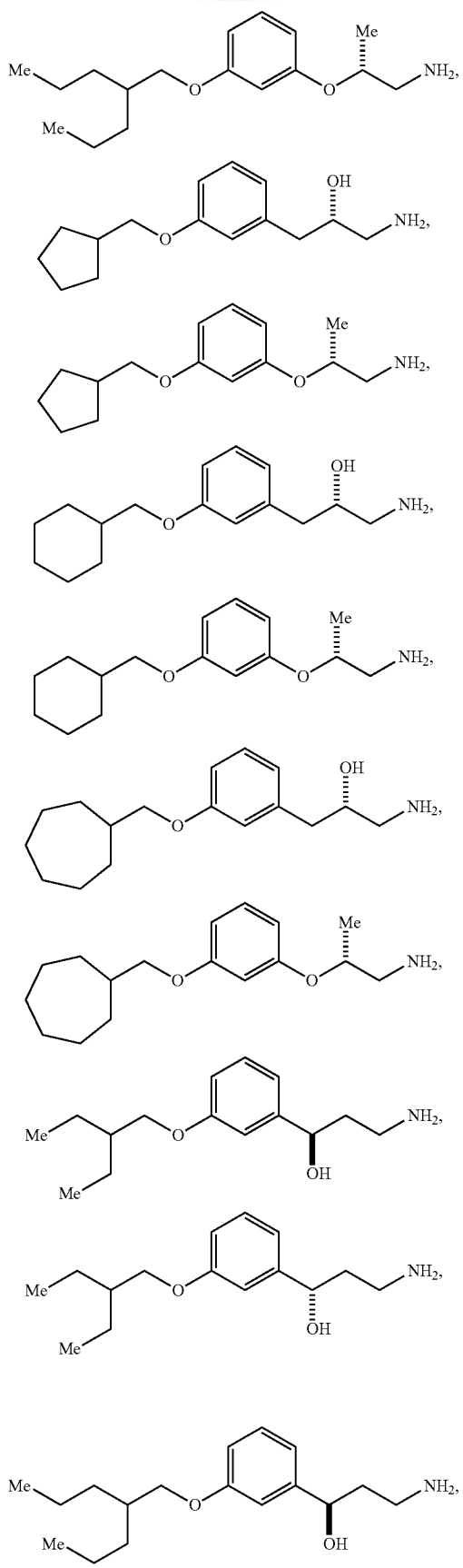
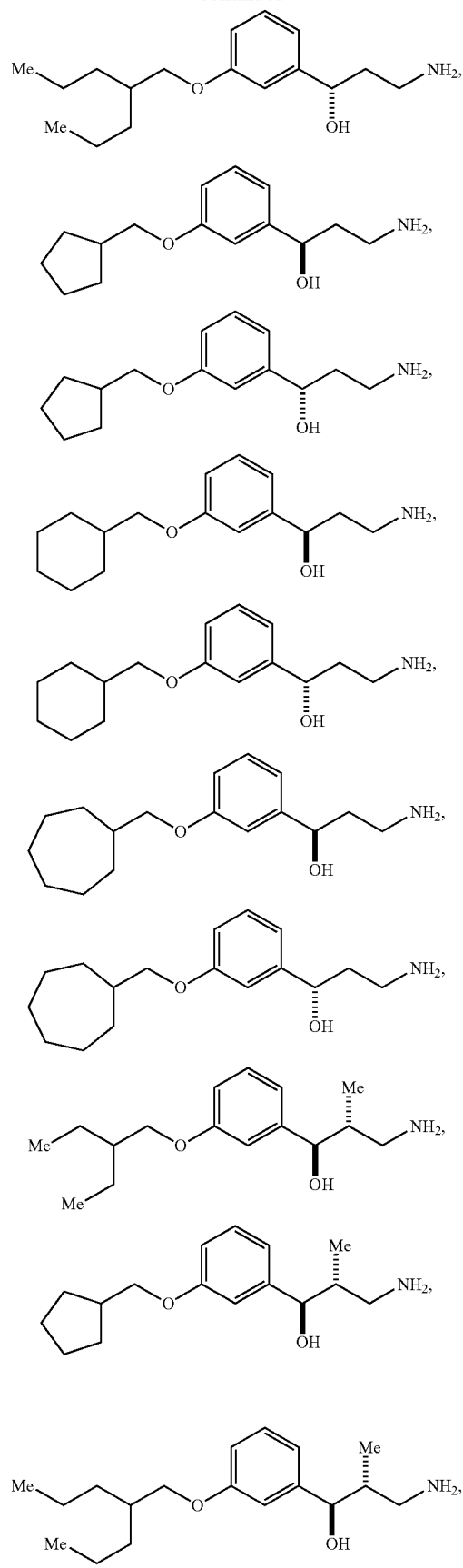

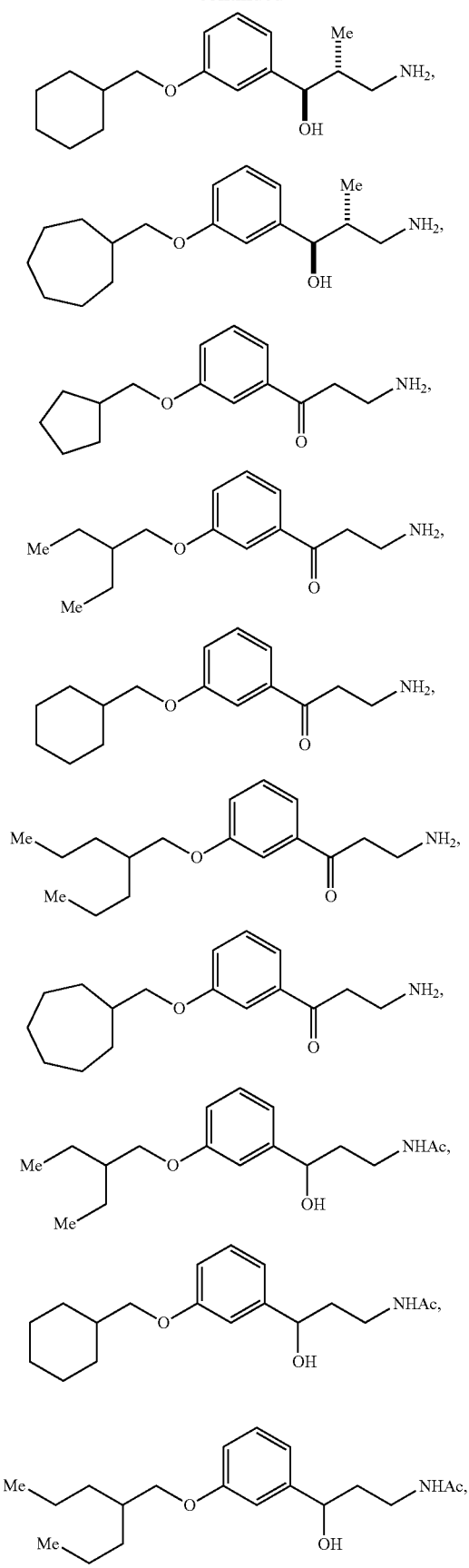
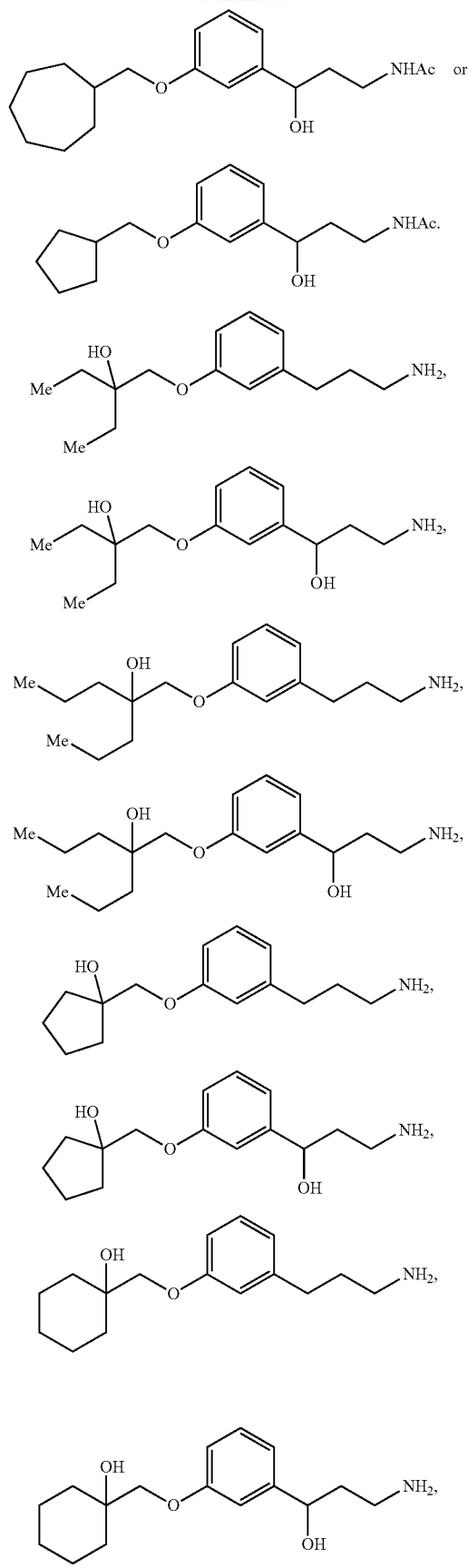

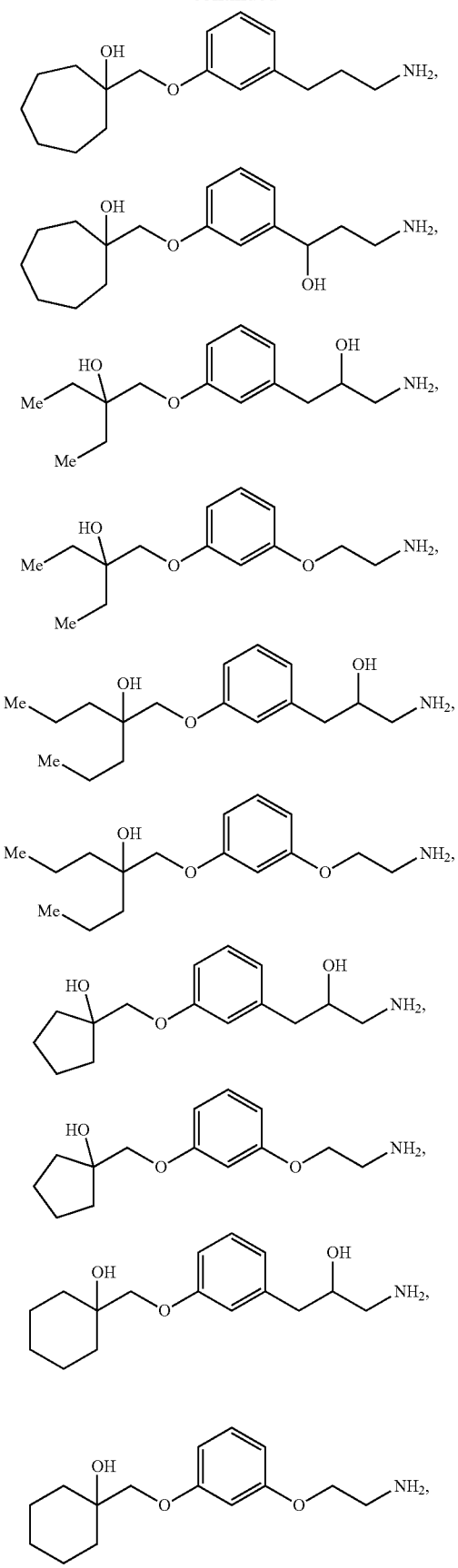
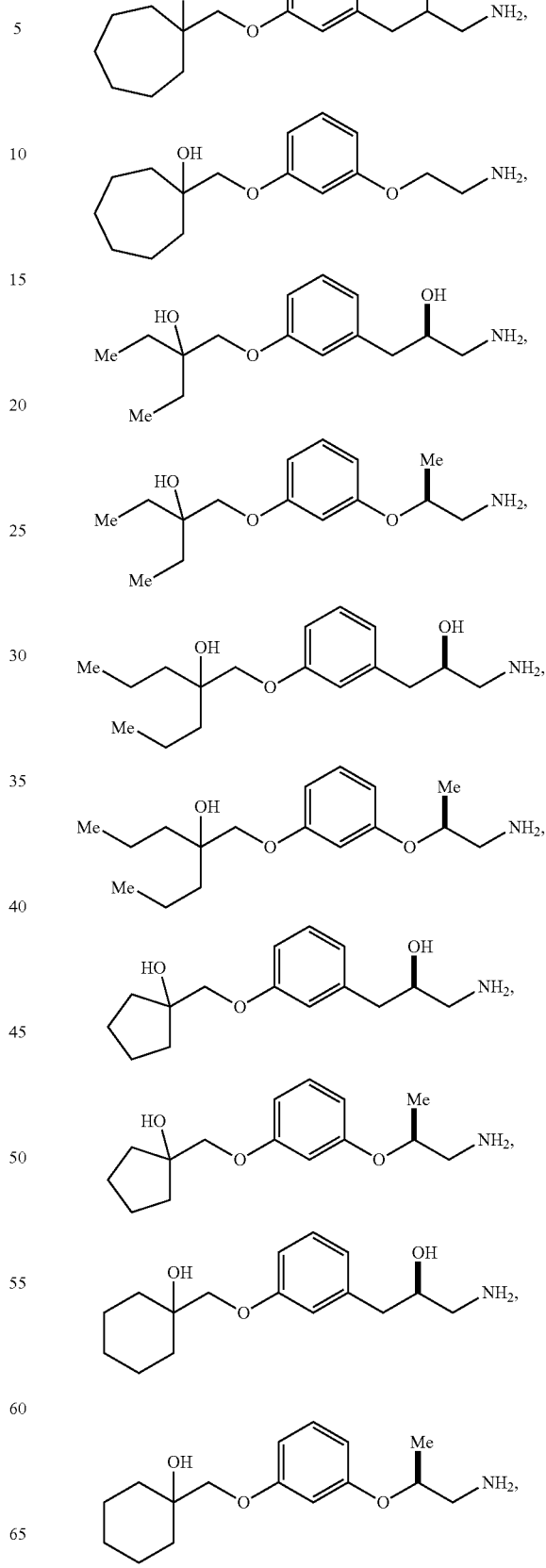

-continued
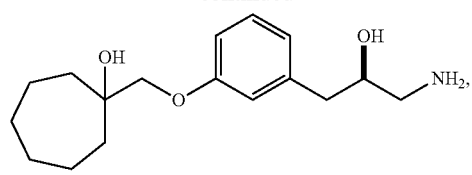
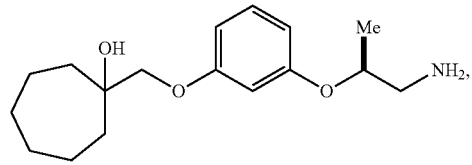
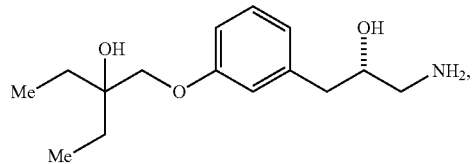
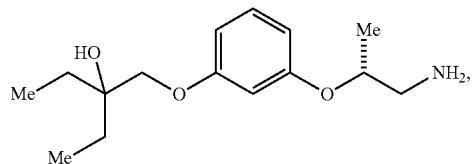
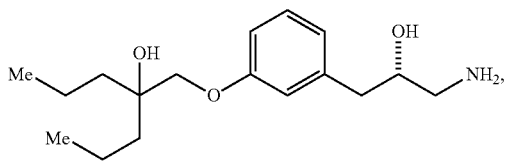
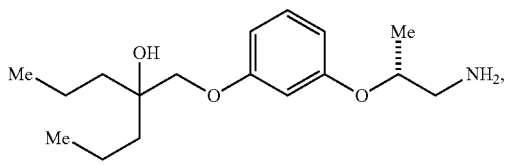
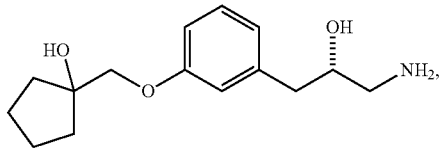
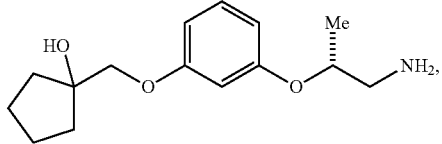
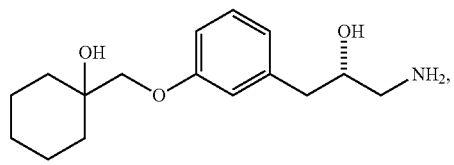
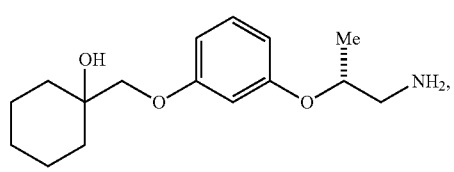
-continued
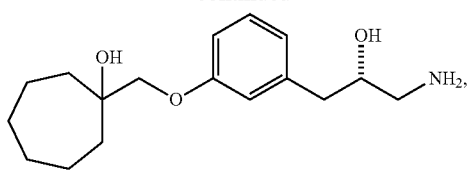
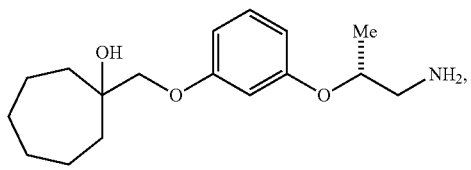
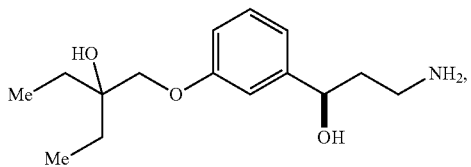
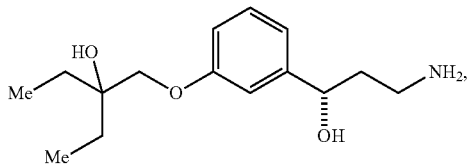
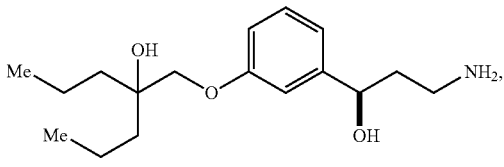
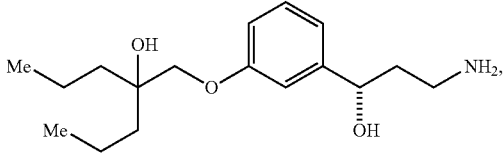
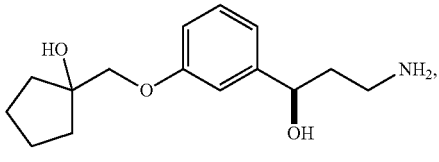
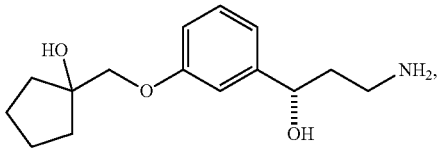
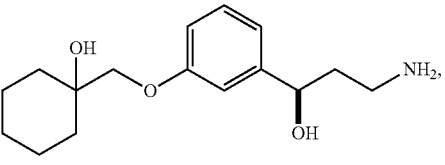
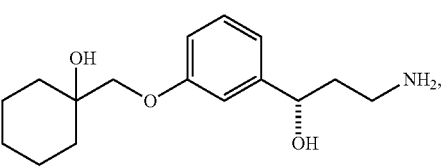

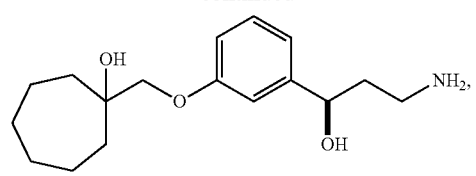
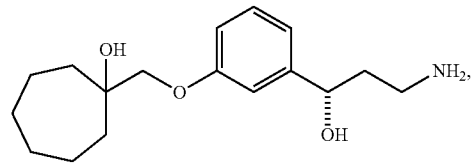
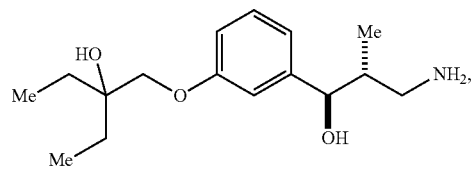
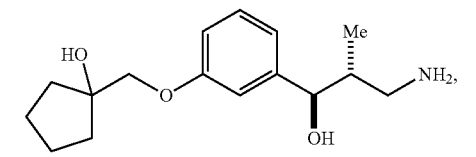
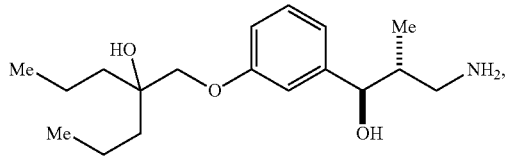
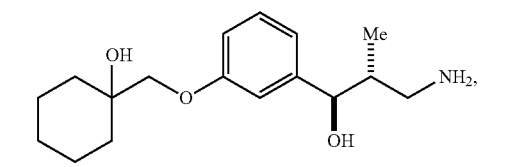
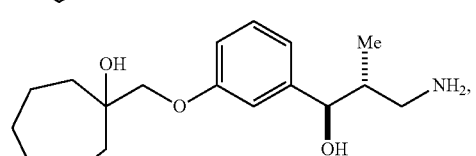
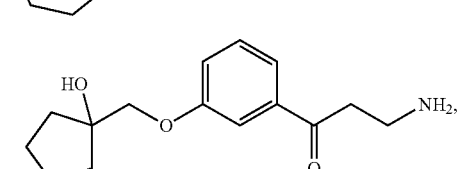
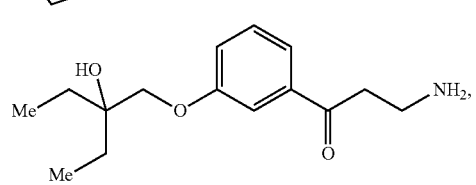
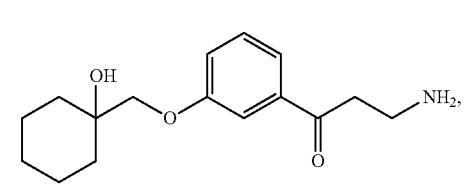
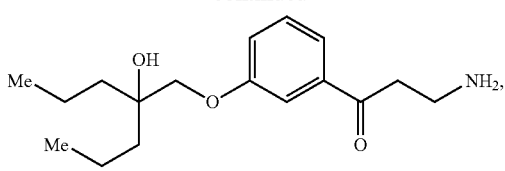
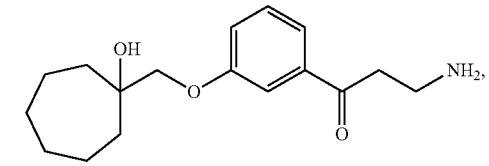
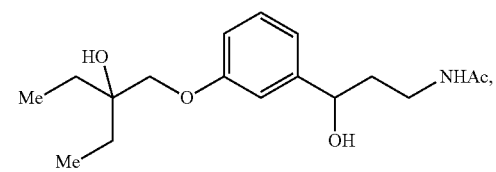
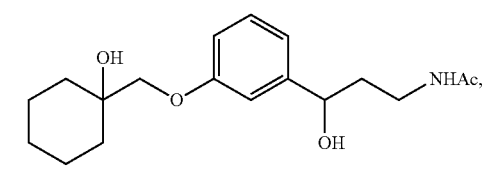
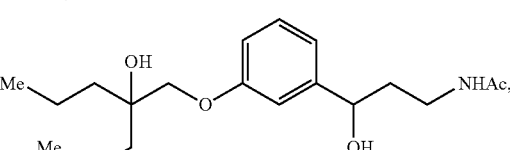
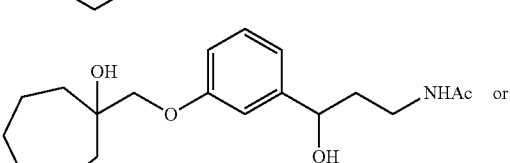
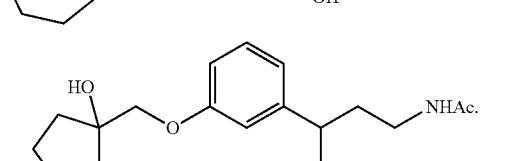
In an additional embodiment is a compound selected from the group consisting of:
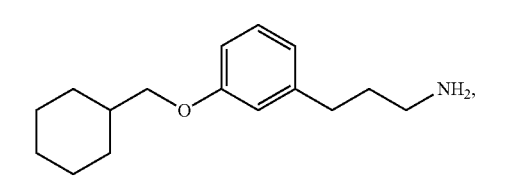
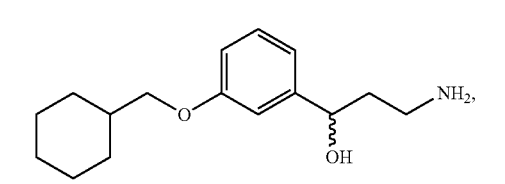

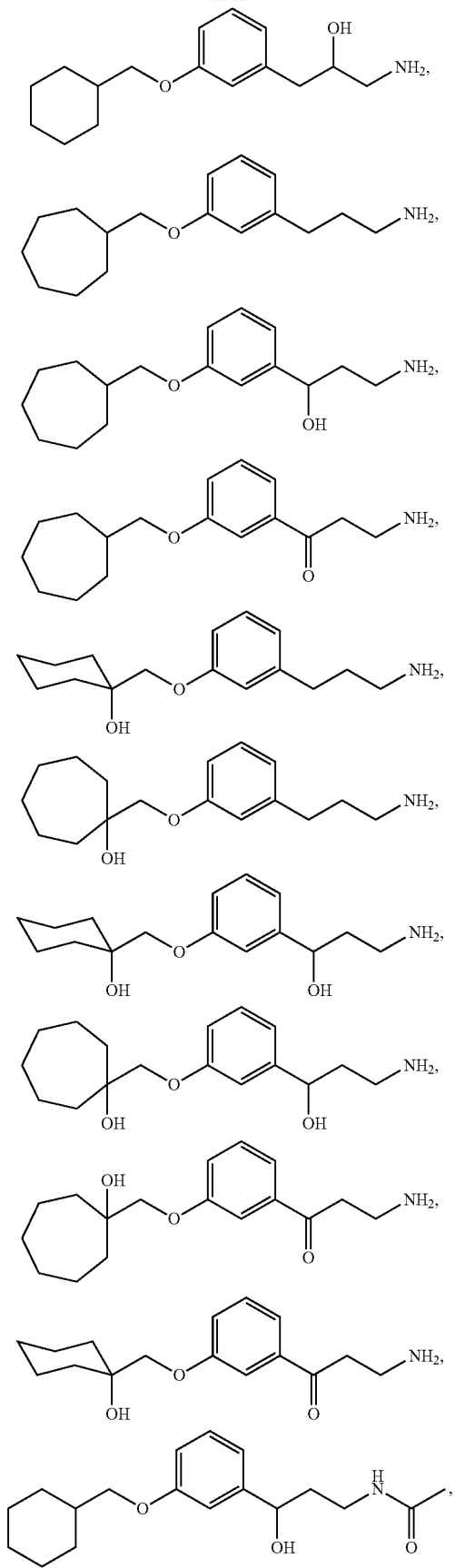
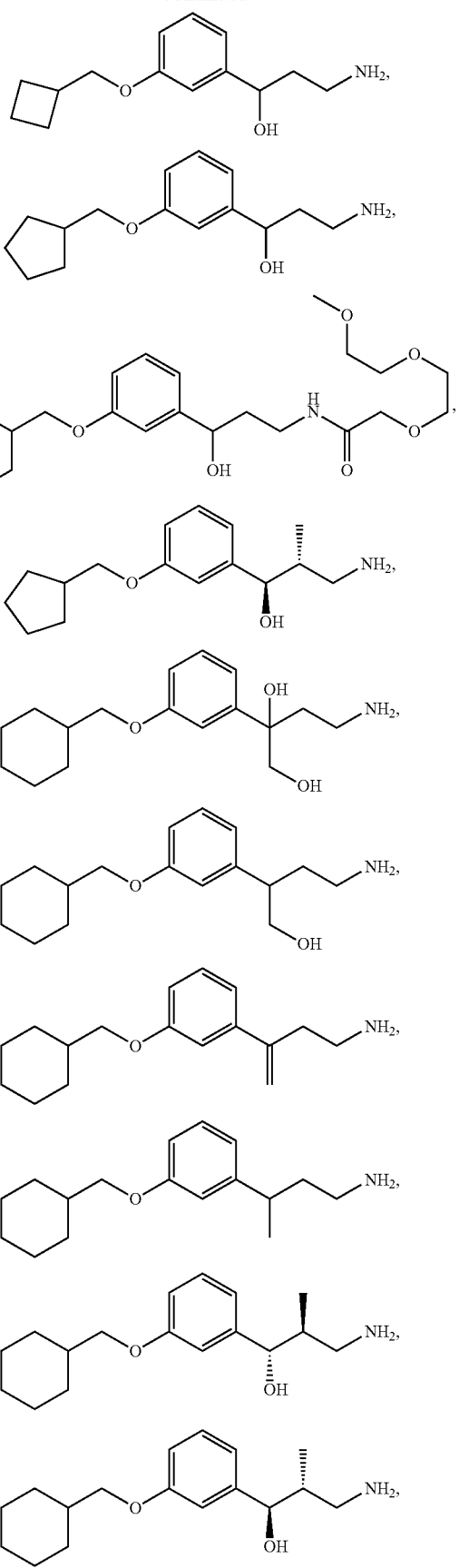

141
-continued
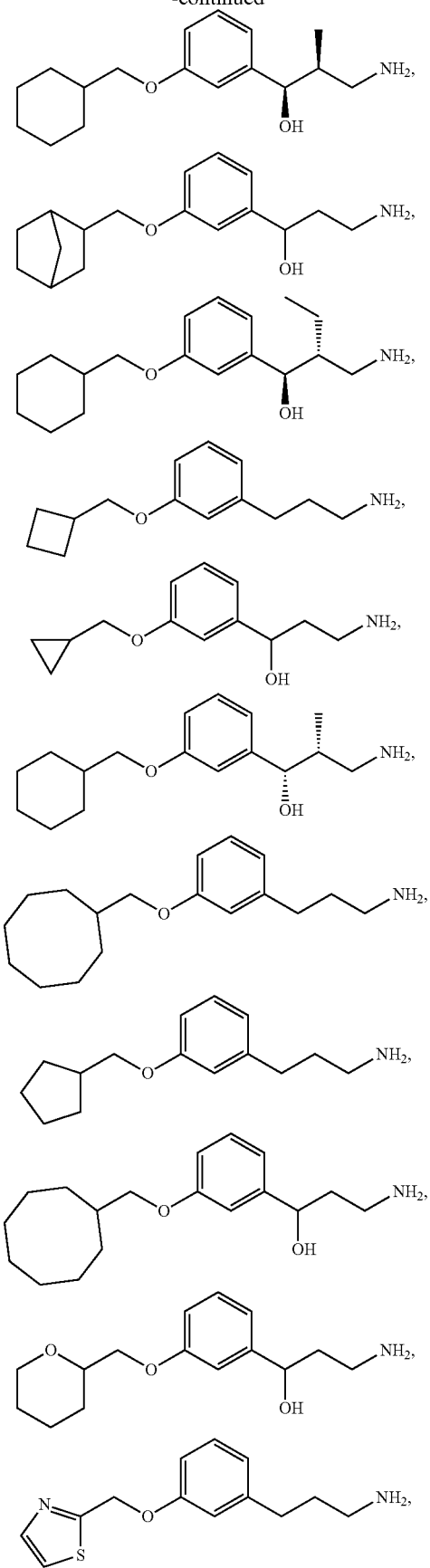
142
-continued
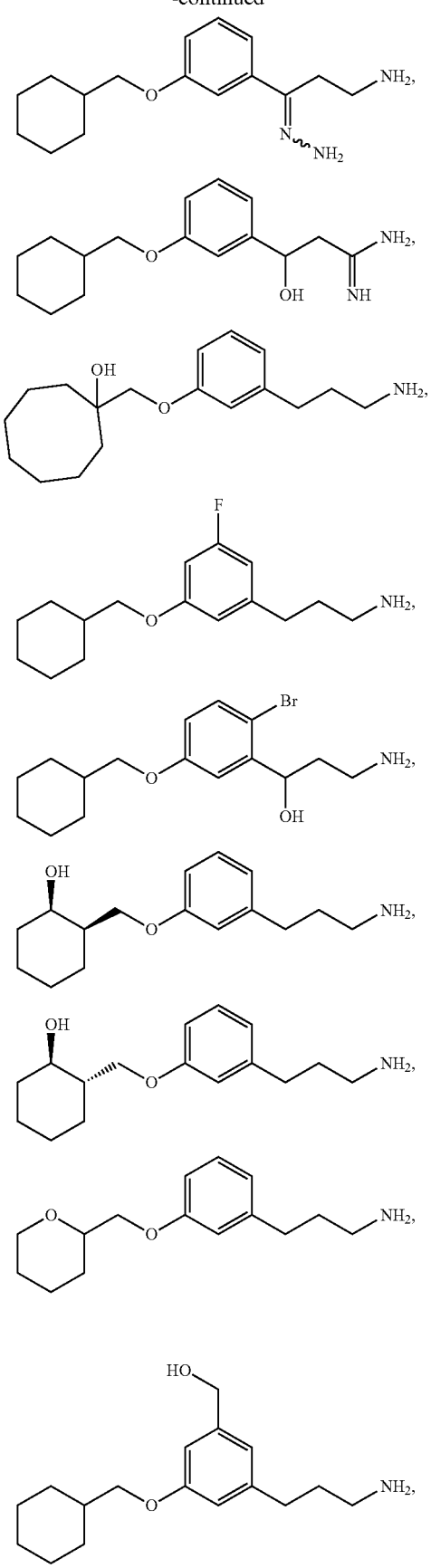

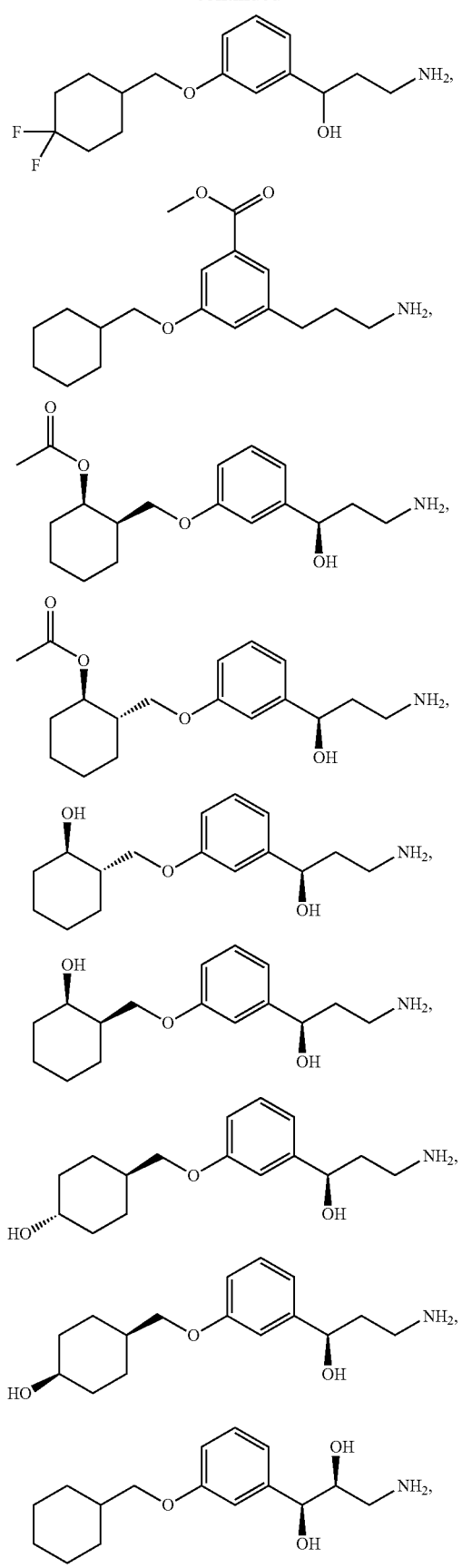
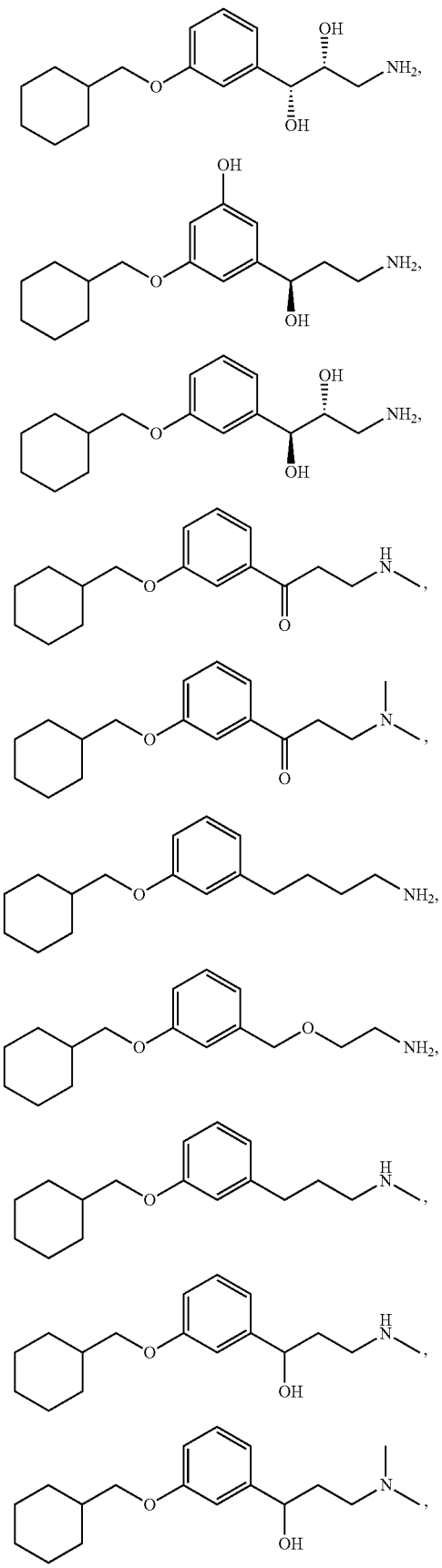

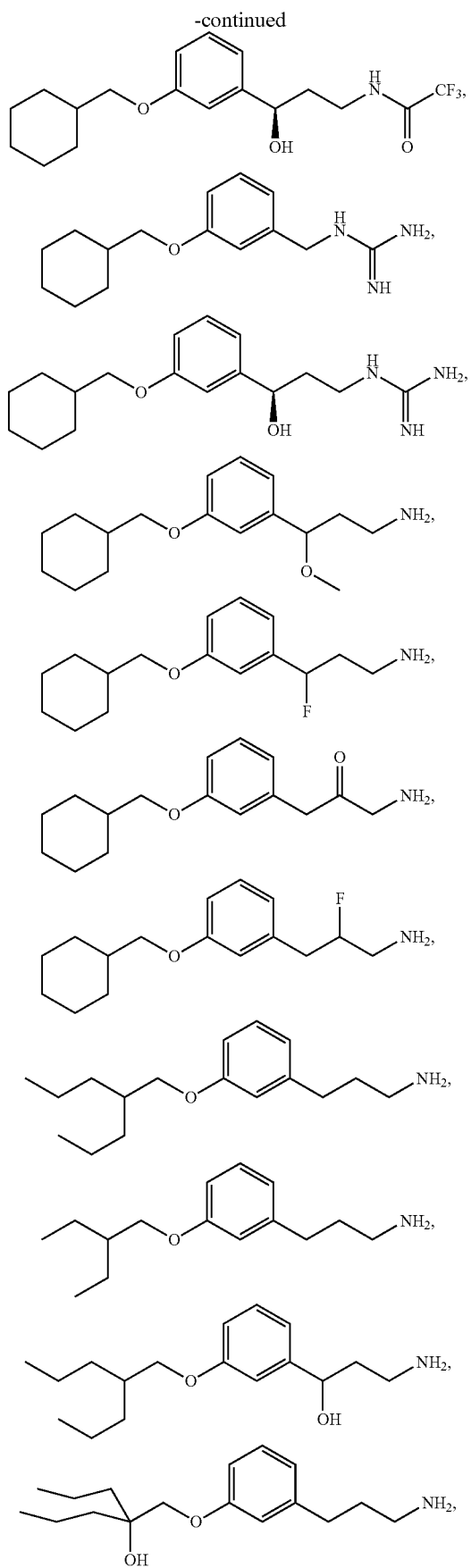
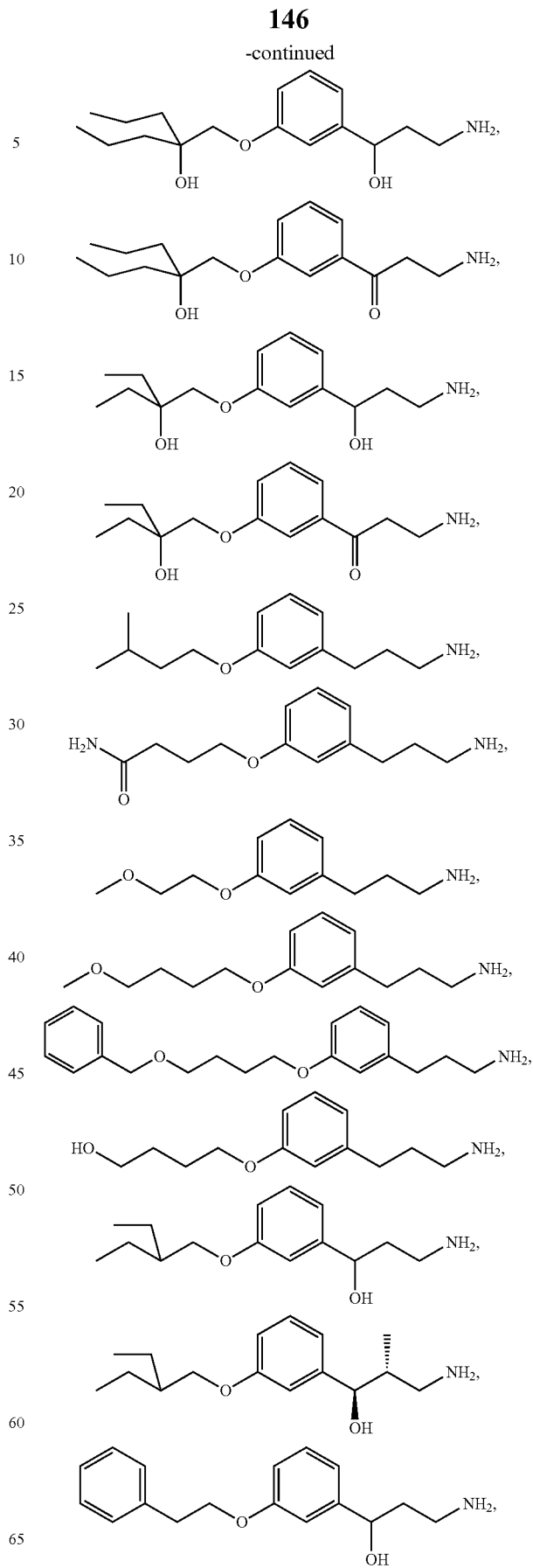

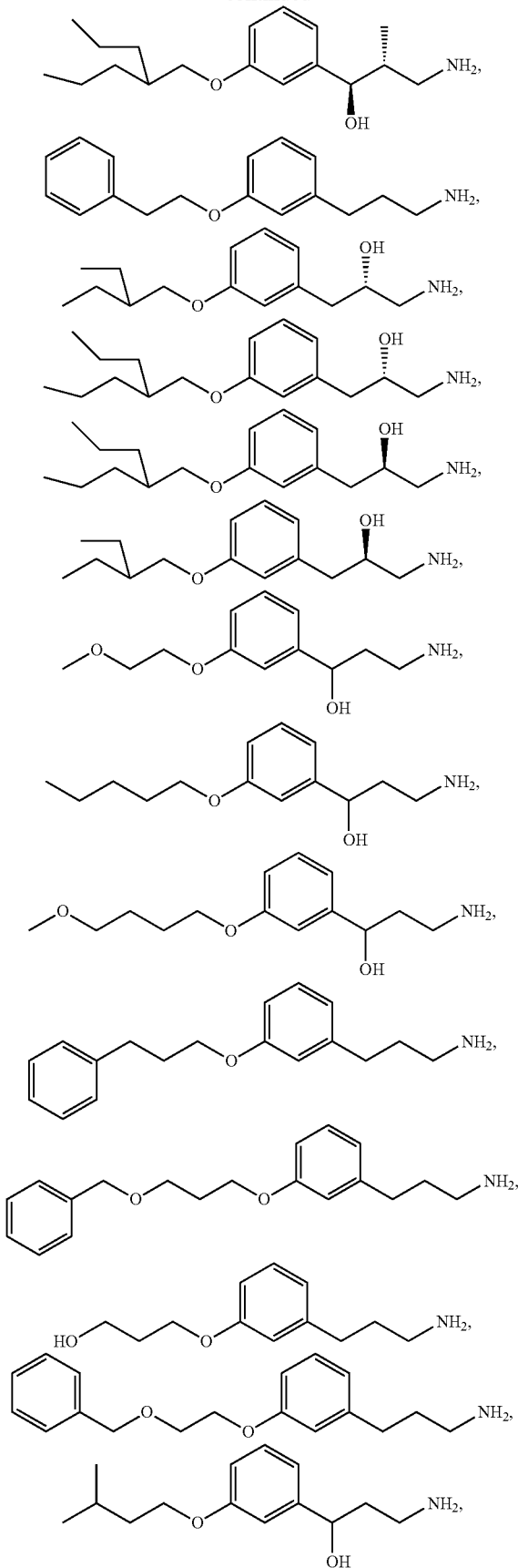
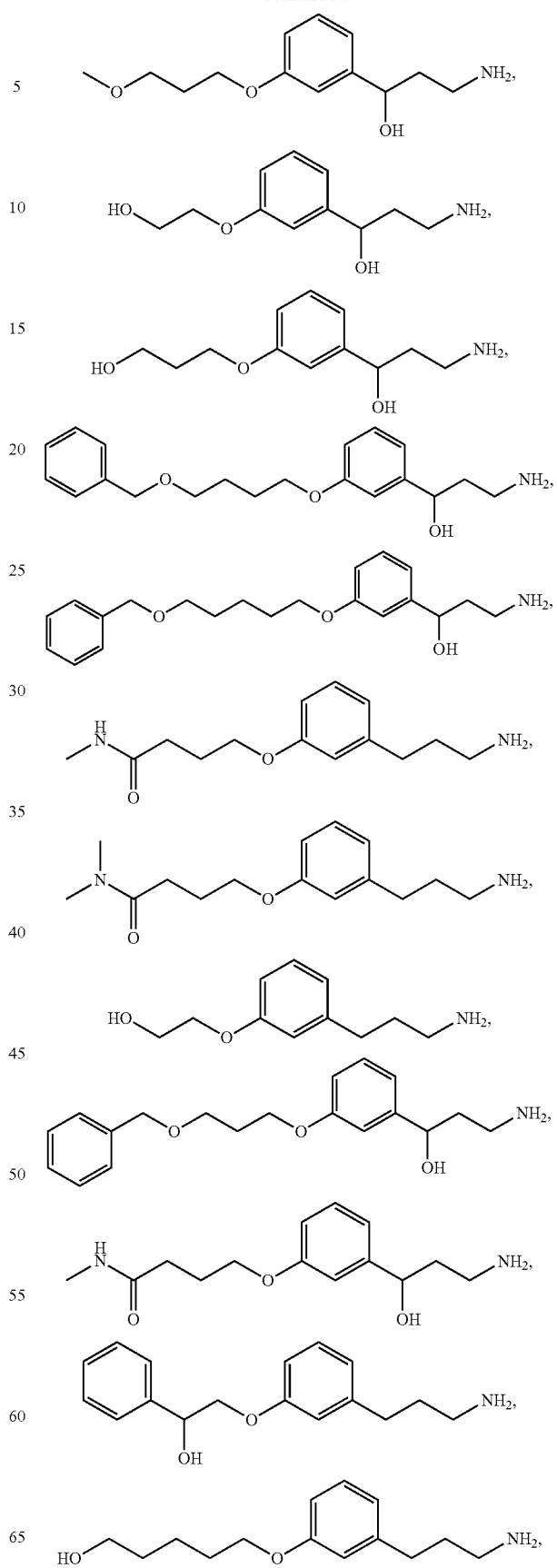

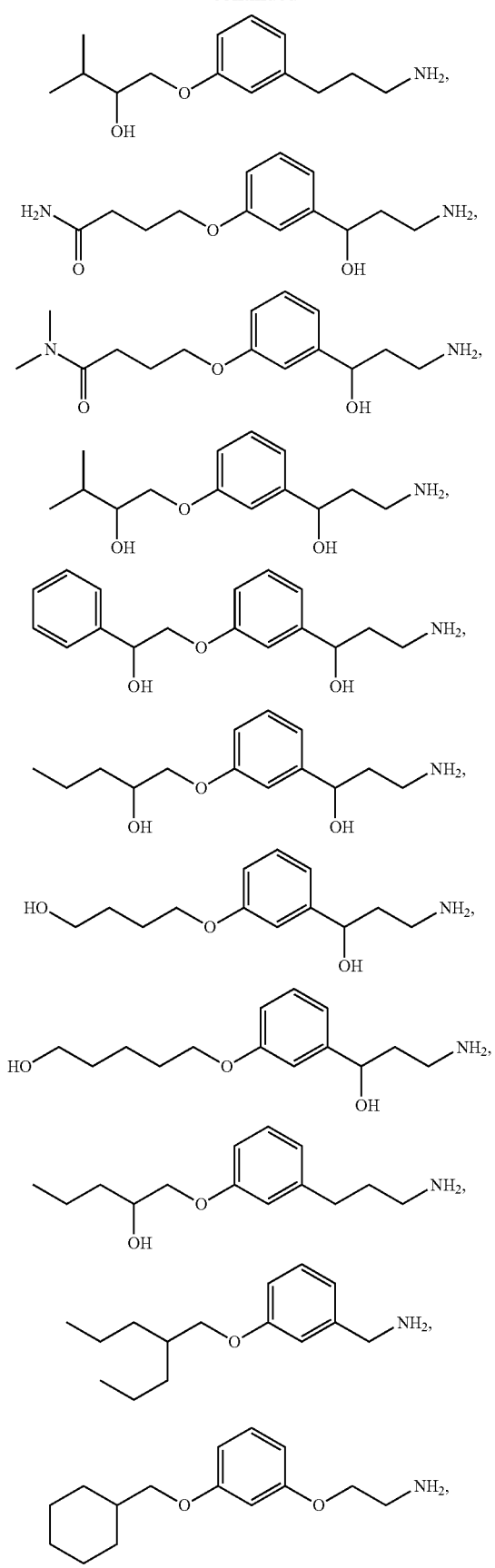
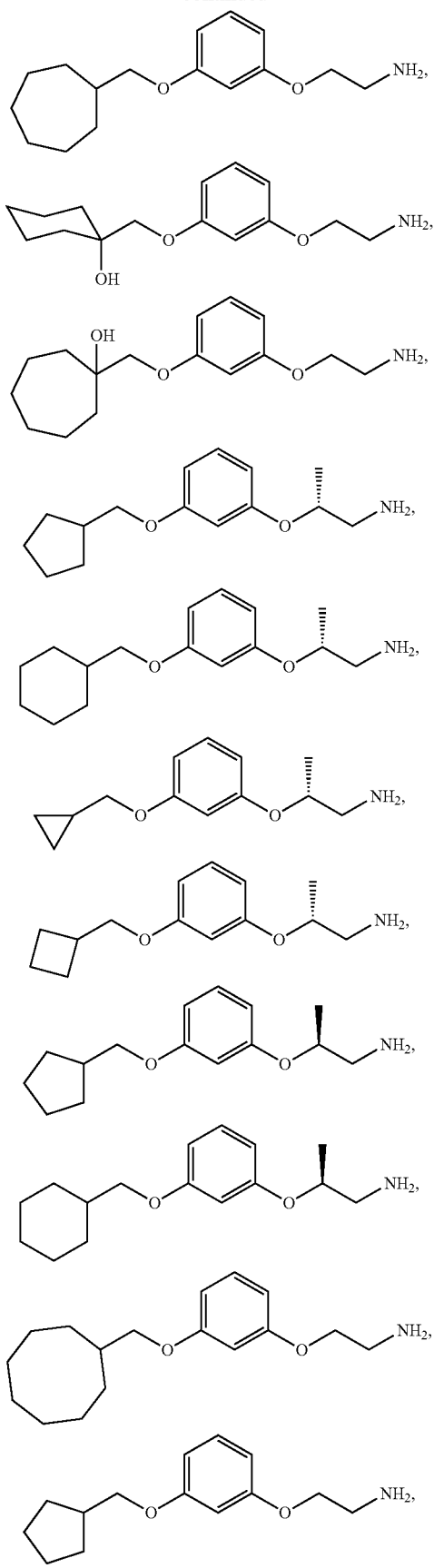

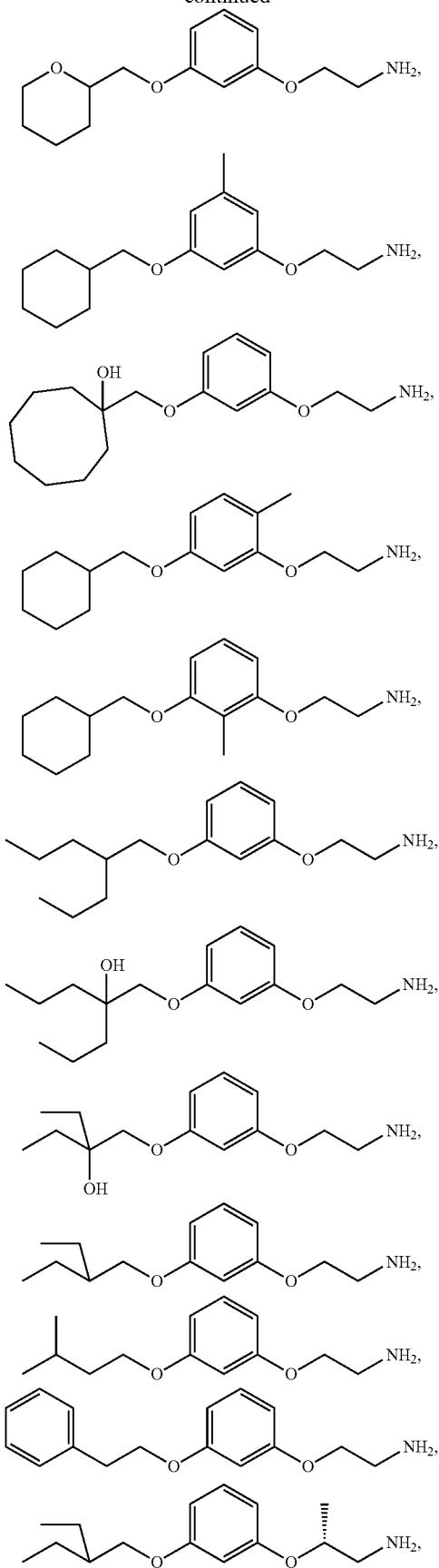
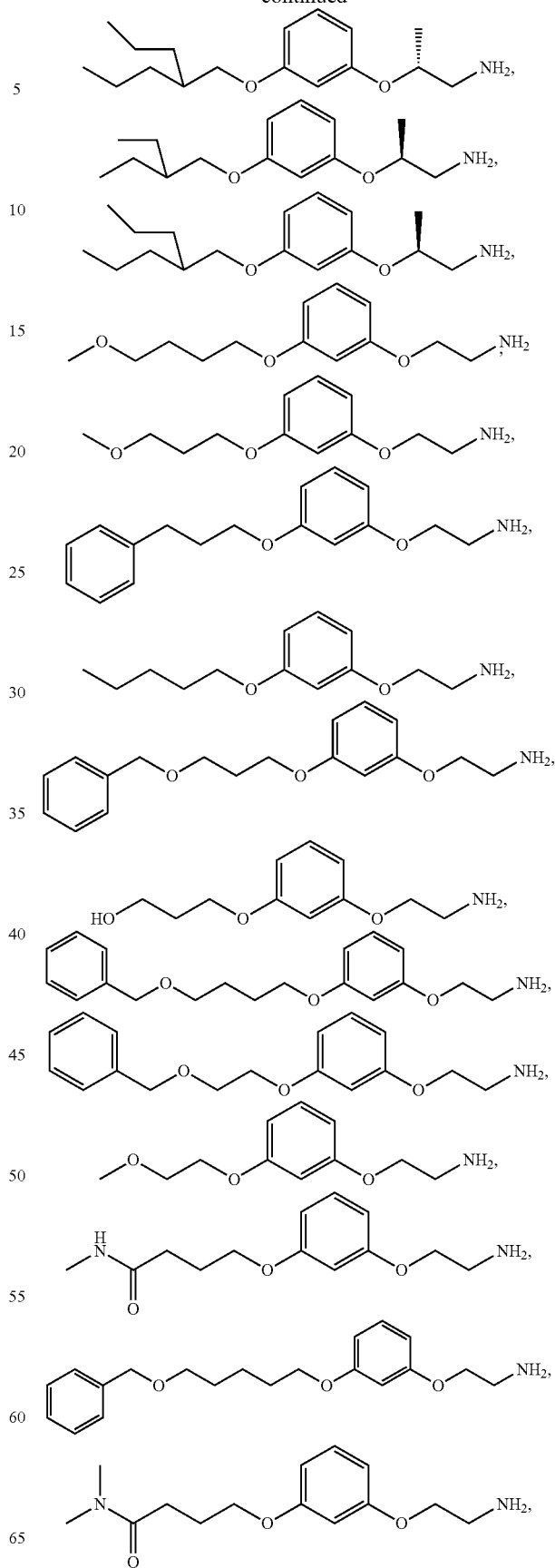

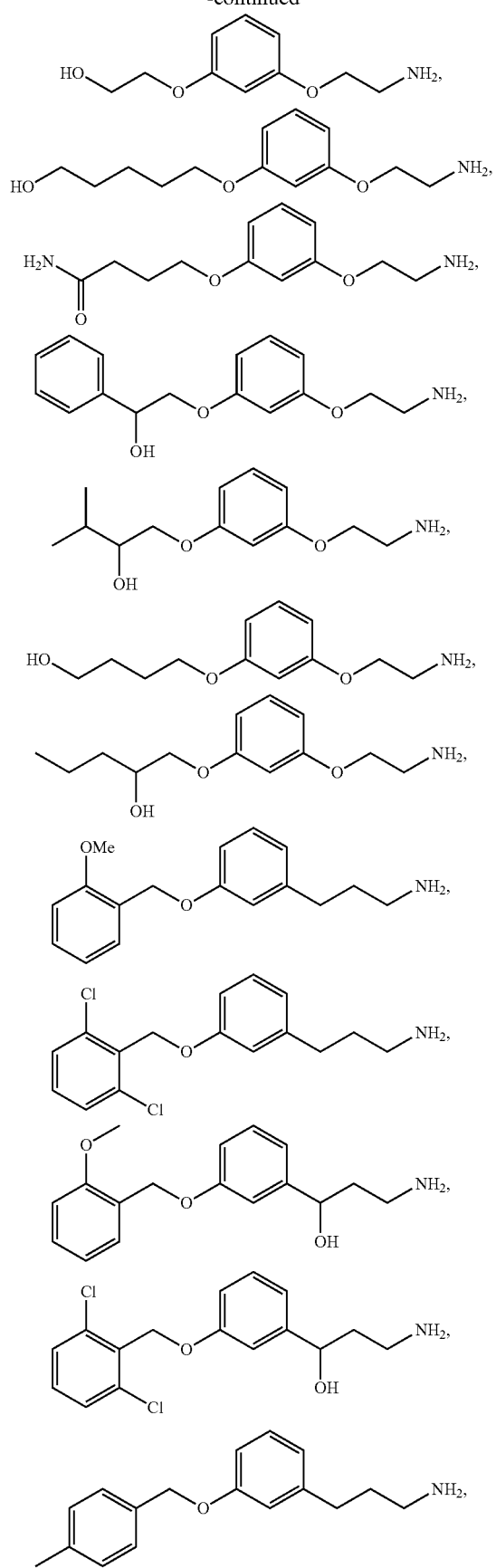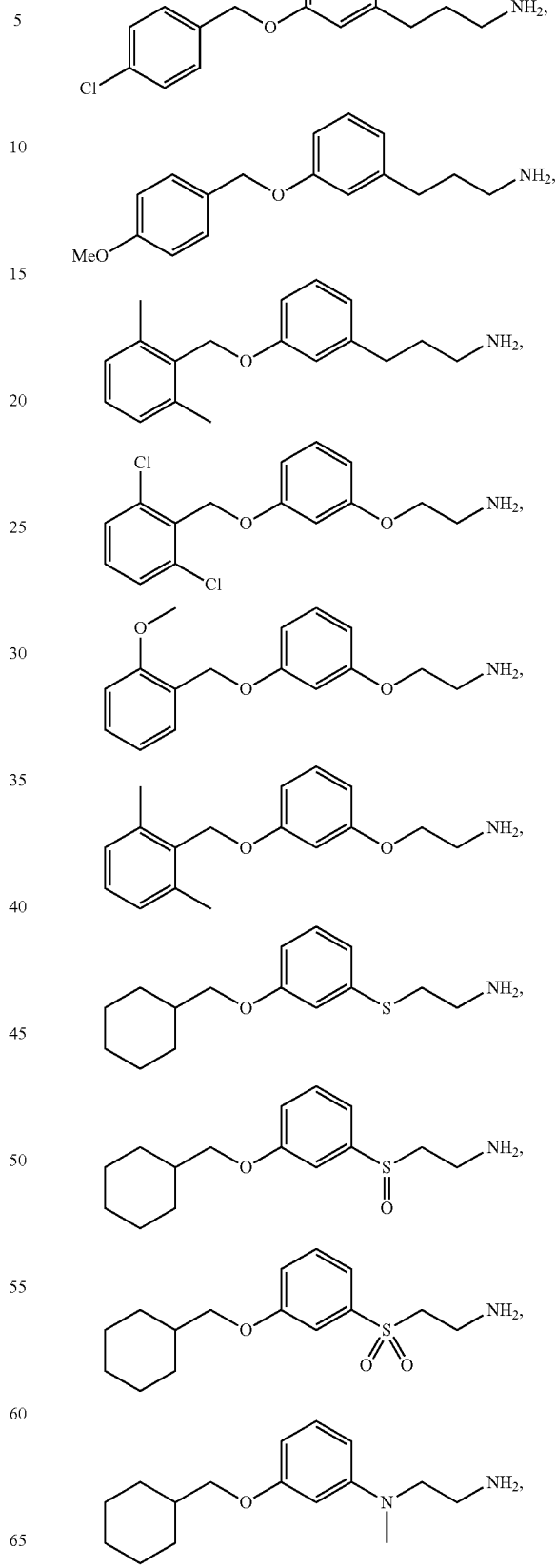

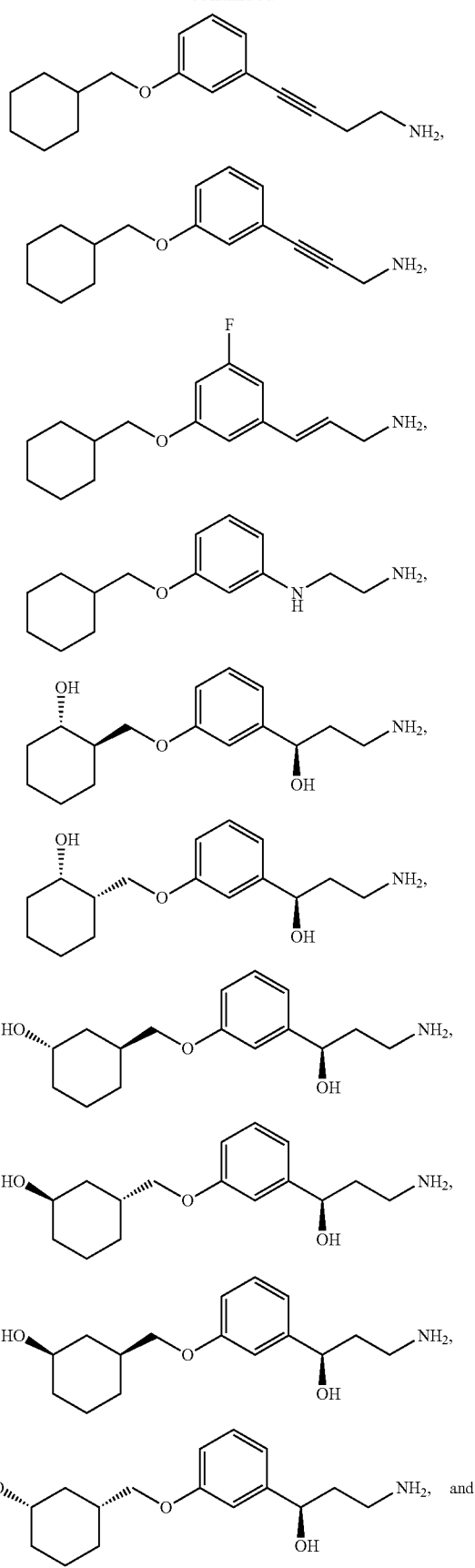

Definitions

As used in the specification and appended claims, unless specified to the contrary, the following terms have the meaning indicated:

As used herein and in the appended claims, the singular forms "a," "and," and "the" include plural referents unless the context clearly dictates otherwise. Thus, for example, reference to "a compound" includes a plurality of such compounds, and reference to "the cell" includes reference to one or more cells (or to a plurality of cells) and equivalents thereof known to those skilled in the art, and so forth. When ranges are used herein for physical properties, such as molecular weight, or chemical properties, such as chemical formulae, all combinations and subcombinations of ranges and specific embodiments therein are intended to be included. The term "about" when referring to a number or a numerical range means that the number or numerical range referred to is an approximation within experimental variability (or within statistical experimental error), and thus the number or numerical range may vary between 1% and 15% of the stated number or numerical range. The term "comprising" (and related terms such as "comprise" or "comprises" or "having" or "including") is not intended to exclude that in other certain embodiments, for example, an embodiment of any composition of matter, composition, method, or process, or the like, described herein, may "consist of" or "consist essentially of" the described features.

"Amino" refers to the —NH$_2$ radical.
"Cyano" refers to the —CN radical.
"Nitro" refers to the —NO$_2$ radical.
"Oxa" refers to the —O— radical.
"Oxo" refers to the =O radical.
"Thioxo" refers to the =S radical.
"Imino" refers to the =N—H radical.
"Hydrazino" refers to the =N—NH$_2$ radical.
"Alkyl" refers to a straight or branched hydrocarbon chain radical consisting solely of carbon and hydrogen atoms, containing no unsaturation, having from one to fifteen carbon atoms (e.g., C$_1$-C$_{15}$ alkyl). In certain embodiments, an alkyl comprises one to thirteen carbon atoms (e.g., C$_1$-C$_{13}$ alkyl). In certain embodiments, an alkyl comprises one to eight carbon atoms (e.g., C$_1$-C$_8$ alkyl). In other embodiments, an alkyl comprises five to fifteen carbon atoms (e.g., C$_5$-C$_{15}$ alkyl). In other embodiments, an alkyl comprises five to eight carbon atoms (e.g., C$_5$-C$_8$ alkyl). The alkyl is attached to the rest of the molecule by a single bond, for example, methyl (Me), ethyl (Et), n-propyl, 1-methylethyl (iso-propyl), n-butyl, n-pentyl, 1,1-dimethylethyl (t-butyl), 3-methylhexyl, 2-methylhexyl, and the like. Unless stated otherwise specifically in the specification, an alkyl group is optionally substituted by one or more of the following substituents: halo, cyano, nitro, oxo, thioxo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —N(R$^a$)C(O)R$^a$, —N(R$^a$)S(O)$_t$R$^a$ (where t is 1 or 2), —S(O)$_t$OR$^a$ (where t is 1 or 2) and —S(O)$_t$N(R$^a$)$_2$ (where t is 1 or 2) where each R$^a$ is independently hydrogen, alkyl, fluoroalkyl, carbocyclyl, carbocyclylalkyl, aryl, aralkyl, heterocyclyl, heterocyclylalkyl, heteroaryl or heteroarylalkyl.

"Alkenyl" refers to a straight or branched hydrocarbon chain radical group consisting solely of carbon and hydrogen atoms, containing at least one double bond, and having from two to twelve carbon atoms. In certain embodiments, an alkenyl comprises two to eight carbon atoms. In other embodiments, an alkenyl comprises two to four carbon atoms. The alkenyl is attached to the rest of the molecule by a single bond, for example, ethenyl (i.e., vinyl), prop-1-enyl (i.e., allyl), but-1-enyl, pent-1-enyl, penta-1,4-dienyl, and the like. Unless stated otherwise specifically in the specification, an alkenyl group is optionally substituted by one or more of the following substituents: halo, cyano, nitro, oxo, thioxo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —N(R$^a$)C(O)R$^a$, —N(R$^a$)S(O)$_t$R$^a$ (where t is 1 or 2), —S(O)$_t$OR$^a$ (where t is 1 or 2) and —S(O)$_t$N(R$^a$)$_2$ (where t is 1 or 2) where each R$^a$ is independently hydrogen, alkyl, fluoroalkyl, carbocyclyl, carbocyclylalkyl, aryl, aralkyl, heterocyclyl, heterocyclylalkyl, heteroaryl or heteroarylalkyl.

"Alkynyl" refers to a straight or branched hydrocarbon chain radical group consisting solely of carbon and hydrogen atoms, containing at least one triple bond, having from two to twelve carbon atoms. In certain embodiments, an alkynyl comprises two to eight carbon atoms. In other embodiments, an alkynyl has two to four carbon atoms. The alkynyl is attached to the rest of the molecule by a single bond, for example, ethynyl, propynyl, butynyl, pentynyl, hexynyl, and the like. Unless stated otherwise specifically in the specification, an alkynyl group is optionally substituted by one or more of the following substituents: halo, cyano, nitro, oxo, thioxo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —N(R$^a$)C(O)R$^a$, —N(R$^a$)S(O)$_t$R$^a$ (where t is 1 or 2), —S(O)$_t$OR$^a$ (where t is 1 or 2) and —S(O)$_t$N(R$^a$)$_2$ (where t is 1 or 2) where each R$^a$ is independently hydrogen, alkyl, fluoroalkyl, carbocyclyl, carbocyclylalkyl, aryl, aralkyl, heterocyclyl, heterocyclylalkyl, heteroaryl or heteroarylalkyl.

"Alkylene" or "alkylene chain" refers to a straight or branched divalent hydrocarbon chain linking the rest of the molecule to a radical group, consisting solely of carbon and hydrogen, containing no unsaturation and having from one to twelve carbon atoms, for example, methylene, ethylene, propylene, n-butylene, and the like. The alkylene chain is attached to the rest of the molecule through a single bond and to the radical group through a single bond. The points of attachment of the alkylene chain to the rest of the molecule and to the radical group can be through one carbon in the alkylene chain or through any two carbons within the chain. Unless stated otherwise specifically in the specification, an alkylene chain is optionally substituted by one or more of the following substituents: halo, cyano, nitro, aryl, cycloalkyl, heterocyclyl, heteroaryl, oxo, thioxo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —N(R$^a$)C(O)R$^a$, —N(R$^a$)S(O)$_t$R$^a$ (where t is 1 or 2), —S(O)$_t$OR$^a$ (where t is 1 or 2) and —S(O)$_t$N(R$^a$)$_2$ (where t is 1 or 2) where each R$^a$ is independently hydrogen, alkyl, fluoroalkyl, carbocyclyl, carbocyclylalkyl, aryl, aralkyl, heterocyclyl, heterocyclylalkyl, heteroaryl or heteroarylalkyl.

"Alkenylene" or "alkenylene chain" refers to a straight or branched divalent hydrocarbon chain linking the rest of the molecule to a radical group, consisting solely of carbon and hydrogen, containing at least one double bond and having from two to twelve carbon atoms, for example, ethenylene, propenylene, n-butenylene, and the like. The alkenylene chain is attached to the rest of the molecule through a double bond or a single bond and to the radical group through a double bond or a single bond. The points of attachment of the alkenylene chain to the rest of the molecule and to the radical group can be through one carbon or any two carbons within the chain. Unless stated otherwise specifically in the specification, an alkenylene chain is optionally substituted by one or more of the following substituents: halo, cyano, nitro, aryl, cycloalkyl, heterocyclyl, heteroaryl, oxo, thioxo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —N(R$^a$)C(O)R$^a$, —N (R$^a$)S(O)$_t$R$^a$ (where t is 1 or 2), —S(O)$_t$OR$^a$ (where t is 1 or 2) and —S(O)$_t$N(R$^a$)$_2$ (where t is 1 or 2) where each R$^a$ is independently hydrogen, alkyl, fluoroalkyl, cycloalkyl, cycloalkylalkyl, aryl (optionally substituted with one or more halo groups), aralkyl, heterocyclyl, heterocyclylalkyl, heteroaryl or heteroarylalkyl, and where each of the above substituents is unsubstituted unless otherwise indicated.

"Aryl" refers to a radical derived from an aromatic monocyclic or multicyclic hydrocarbon ring system by removing a hydrogen atom from a ring carbon atom. The aromatic monocyclic or multicyclic hydrocarbon ring system contains only hydrogen and carbon from six to eighteen carbon atoms, where at least one of the rings in the ring system is fully unsaturated, i.e., it contains a cyclic, delocalized (4n+2) π-electron system in accordance with the Hückel theory. Aryl groups include, but are not limited to, groups such as phenyl, fluorenyl, and naphthyl. Unless stated otherwise specifically in the specification, the term "aryl" or the prefix "ar-" (such as in "aralkyl") is meant to include aryl radicals optionally substituted by one or more substituents independently selected from alkyl, alkenyl, alkynyl, halo, fluoroalkyl, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —R$^b$—OR$^a$, —R$^b$—OC(O)—R$^a$, —R$^b$—N(R$^a$)$_2$, —R$^b$—C(O)R$^a$, —R$^b$—C(O)OR$^a$, —R$^b$—C(O)N(R$^a$)$_2$, —R$^b$—O—R$^c$—C(O)N(R$^a$)$_2$, —R$^b$—N(R$^a$)C(O)OR$^a$, —R$^b$—N(R$^a$)C(O)R$^a$, —R$^b$—N(R$^a$)S(O)$_t$R$^a$ (where t is 1 or 2), —R$^b$—S(O)$_t$OR$^a$ (where t is 1 or 2) and —R$^b$—S(O)$_t$N(R$^a$)$_2$ (where t is 1 or 2), where each R$^a$ is independently hydrogen, alkyl, fluoroalkyl, cycloalkyl, cycloalkylalkyl, aryl (optionally substituted with one or more halo groups), aralkyl, heterocyclyl, heterocyclylalkyl, heteroaryl or heteroarylalkyl, each R$^b$ is independently a direct bond or a straight or branched alkylene or alkenylene chain, and R$^c$ is a straight or branched alkylene or alkenylene chain, and where each of the above substituents is unsubstituted unless otherwise indicated.

"Aralkyl" refers to a radical of the formula —R$^c$-aryl where R$^c$ is an alkylene chain as defined above, for example, benzyl, diphenylmethyl and the like. The alkylene chain part of the aralkyl radical is optionally substituted as described above for an alkylene chain. The aryl part of the aralkyl radical is optionally substituted as described above for an aryl group.

"Aralkenyl" refers to a radical of the formula —R$^d$-aryl where R$^d$ is an alkenylene chain as defined above. The aryl part of the aralkenyl radical is optionally substituted as described above for an aryl group. The alkenylene chain part of the aralkenyl radical is optionally substituted as defined above for an alkenylene group.

"Aralkynyl" refers to a radical of the formula —$R^e$-aryl, where $R^e$ is an alkynylene chain as defined above. The aryl part of the aralkynyl radical is optionally substituted as described above for an aryl group. The alkynylene chain part of the aralkynyl radical is optionally substituted as defined above for an alkynylene chain.

"Carbocyclyl" refers to a stable non-aromatic monocyclic or polycyclic hydrocarbon radical consisting solely of carbon and hydrogen atoms, which may include fused or bridged ring systems, having from three to fifteen carbon atoms. In certain embodiments, a carbocyclyl comprises three to ten carbon atoms. In other embodiments, a carbocyclyl comprises five to seven carbon atoms. The carbocyclyl is attached to the rest of the molecule by a single bond. Carbocyclyl may be saturated, (i.e., containing single C—C bonds only) or unsaturated (i.e., containing one or more double bonds or triple bonds.) A fully saturated carbocyclyl radical is also referred to as "cycloalkyl." Examples of monocyclic cycloalkyls include, e.g., cyclopropyl, cyclobutyl, cyclopentyl, cyclohexyl, cycloheptyl, and cyclooctyl. An unsaturated carbocyclyl is also referred to as "cycloalkenyl." Examples of monocyclic cycloalkenyls include, e.g., cyclopentenyl, cyclohexenyl, cycloheptenyl, and cyclooctenyl. Polycyclic carbocyclyl radicals include, for example, adamantyl, norbornyl (i.e., bicyclo[2.2.1]heptanyl), norbornenyl, decalinyl, 7,7-dimethyl-bicyclo[2.2.1]heptanyl, and the like. Unless otherwise stated specifically in the specification, the term "carbocyclyl" is meant to include carbocyclyl radicals that are optionally substituted by one or more substituents independently selected from alkyl, alkenyl, alkynyl, halo, fluoroalkyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^b$—$OR^a$, —$R^b$—$SR^a$, —$R^b$—OC(O)—$R^a$, —$R^b$—N($R^a$)$_2$, —$R^b$—C(O)$R^a$, —$R^b$—C(O)O$R^a$, —$R^b$—C(O)N($R^a$)$_2$, —$R^b$—O—$R^c$—C(O)N($R^a$)$_2$, —$R^b$—N($R^a$)C(O)O$R^a$, —$R^b$—N($R^a$)C(O)$R^a$, —$R^b$—N($R^a$)S(O)$_t$$R^a$ (where t is 1 or 2), —$R^b$—S(O)$_t$O$R^a$ (where t is 1 or 2) and —$R^b$—S(O)$_t$N($R^a$)$_2$ (where t is 1 or 2), where each $R^a$ is independently hydrogen, alkyl, fluoroalkyl, cycloalkyl, cycloalkylalkyl, aryl, aralkyl, heterocyclyl, heterocyclylalkyl, heteroaryl or heteroarylalkyl, each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"Carbocyclylalkyl" refers to a radical of the formula —$R^c$-carbocyclyl where $R^c$ is an alkylene chain as defined above. The alkylene chain and the carbocyclyl radical is optionally substituted as defined above.

"Halo" or "halogen" refers to bromo, chloro, fluoro or iodo substituents.

"Fluoroalkyl" refers to an alkyl radical, as defined above, that is substituted by one or more fluoro radicals, as defined above, for example, trifluoromethyl, difluoromethyl, 2,2,2-trifluoroethyl, 1-fluoromethyl-2-fluoroethyl, and the like. The alkyl part of the fluoroalkyl radical may be optionally substituted as defined above for an alkyl group.

"Heterocyclyl" refers to a stable 3- to 18-membered non-aromatic ring radical that comprises two to twelve carbon atoms and from one to six heteroatoms selected from nitrogen, oxygen and sulfur. Unless stated otherwise specifically in the specification, the heterocyclyl radical is a monocyclic, bicyclic, tricyclic or tetracyclic ring system, which may include fused or bridged ring systems. The heteroatoms in the heterocyclyl radical may be optionally oxidized. One or more nitrogen atoms, if present, are optionally quaternized. The heterocyclyl radical is partially or fully saturated. The heterocyclyl may be attached to the rest of the molecule through any atom of the ring(s). Examples of such heterocyclyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. Unless stated otherwise specifically in the specification, the term "heterocyclyl" is meant to include heterocyclyl radicals as defined above that are optionally substituted by one or more substituents selected from alkyl, alkenyl, alkynyl, halo, fluoroalkyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^b$—$OR^a$, —$R^b$—$SR^a$, —$R^b$—OC(O)—$R^a$, —$R^b$—N($R^a$)$_2$, —$R^b$—C(O)$R^a$, —$R^b$—C(O)O$R^a$, —$R^b$—C(O)N($R^a$)$_2$, —$R^b$—O—$R^c$—C(O)N($R^a$)$_2$, —$R^b$—N($R^a$)C(O)O$R^a$, —$R^b$—N($R^a$)C(O)$R^a$, —$R^b$—N($R^a$)S(O)$_t$$R^a$ (where t is 1 or 2), —$R^b$—S(O)$_t$O$R^a$ (where t is 1 or 2) and —$R^b$—S(O)$_t$N($R^a$)$_2$ (where t is 1 or 2), where each $R^a$ is independently hydrogen, alkyl, fluoroalkyl, cycloalkyl, cycloalkylalkyl, aryl, aralkyl, heterocyclyl, heterocyclylalkyl, heteroaryl or heteroarylalkyl, each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"N-heterocyclyl" or "N-attached heterocyclyl" refers to a heterocyclyl radical as defined above containing at least one nitrogen and where the point of attachment of the heterocyclyl radical to the rest of the molecule is through a nitrogen atom in the heterocyclyl radical. An N-heterocyclyl radical is optionally substituted as described above for heterocyclyl radicals. Examples of such N-heterocyclyl radicals include, but are not limited to, 1-morpholinyl, 1-piperidinyl, 1-piperazinyl, 1-pyrrolidinyl, pyrazolidinyl, imidazolinyl, and imidazolidinyl.

"C-heterocyclyl" or "C-attached heterocyclyl" refers to a heterocyclyl radical as defined above containing at least one heteroatom and where the point of attachment of the heterocyclyl radical to the rest of the molecule is through a carbon atom in the heterocyclyl radical. A C-heterocyclyl radical is optionally substituted as described above for heterocyclyl radicals. Examples of such C-heterocyclyl radicals include, but are not limited to, 2-morpholinyl, 2- or 3- or 4-piperidinyl, 2-piperazinyl, 2- or 3-pyrrolidinyl, and the like.

"Heterocyclylalkyl" refers to a radical of the formula —$R^c$-heterocyclyl where $R^c$ is an alkylene chain as defined above. If the heterocyclyl is a nitrogen-containing heterocyclyl, the heterocyclyl is optionally attached to the alkyl radical at the nitrogen atom. The alkylene chain of the heterocyclylalkyl radical is optionally substituted as defined above for an alkylene chain. The heterocyclyl part of the heterocyclylalkyl radical is optionally substituted as defined above for a heterocyclyl group.

"Heteroaryl" refers to a radical derived from a 3- to 18-membered aromatic ring radical that comprises two to seventeen carbon atoms and from one to six heteroatoms selected from nitrogen, oxygen and sulfur. As used herein, the heteroaryl radical may be a monocyclic, bicyclic, tricyclic or tetracyclic ring system, wherein at least one of the rings in the ring system is fully unsaturated, i.e., it contains a cyclic, delocalized (4n+2) π-electron system in accordance with the Hückel theory. Heteroaryl includes fused or bridged ring systems. The heteroatom(s) in the heteroaryl radical is optionally oxidized. One or more nitrogen atoms, if present, are optionally quaternized. The heteroaryl is attached to the rest of the molecule through any atom of the ring(s). Examples of heteroaryls include, but are not limited to, azepinyl, acridinyl, benzimidazolyl, benzindolyl, 1,3-benzodioxolyl, benzofuranyl, benzooxazolyl, benzo[d]thiazolyl, benzothiadiazolyl, benzo[b][1,4]dioxepinyl, benzo[b][1,4]oxazinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[h]quinazolinyl, 5,6-dihydrobenzo[h]cinnolinyl, 6,7-dihydro-5H-benzo[6,7]cyclohepta[1,2-c]pyridazinyl, dibenzofuranyl, dibenzothiophenyl, furanyl, furanonyl, furo[3,2-c]pyridinyl, 5,6,7,8,9,10-hexahydrocycloocta[d]pyrimidinyl, 5,6,7,8,9,10-hexahydrocycloocta[d]pyridazinyl, 5,6,7,8,9,10-hexahydrocycloocta[d]pyridinyl, isothiazolyl, imidazolyl, indazolyl, indolyl, indazolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo[4,5]thieno[2,3-d]pyrimidinyl, 6,7,8,9-tetrahydro-5H-cyclohepta[4,5]thieno[2,3-d]pyrimidinyl, 5,6,7,8-tetrahydropyrido[4,5-c]pyridazinyl, thiazolyl, thiadiazolyl, triazolyl, tetrazolyl, triazinyl, thieno[2,3-d]pyrimidinyl, thieno[3,2-d]pyrimidinyl, thieno[2,3-c]pridinyl, and thiophenyl (i.e. thienyl). Unless stated otherwise specifically in the specification, the term "heteroaryl" is meant to include heteroaryl radicals as defined above which are optionally substituted by one or more substituents selected from alkyl, alkenyl, alkynyl, halo, fluoroalkyl, haloalkenyl, haloalkynyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^b$—$OR^a$, —$R^b$—$SR^a$, —$R^b$—OC(O)—$R^a$, —$R^b$—N($R^a$)$_2$, —$R^b$—C(O)$R^a$, —$R^b$—C(O)O$R^a$, —$R^b$—C(O)N($R^a$)$_2$, —$R^b$—O—$R^c$—C(O)N($R^a$)$_2$, —$R^b$—N($R^a$)C(O)O$R^a$, —$R^b$—N($R^a$)C(O)$R^a$, —$R^b$—N($R^a$)S(O)$_t$$R^a$ (where t is 1 or 2), —$R^b$—S(O)$_t$O$R^a$ (where t is 1 or 2) and —$R^b$—S(O)$_t$N($R^a$)$_2$ (where t is 1 or 2), where each $R^a$ is independently hydrogen, alkyl, fluoroalkyl, cycloalkyl, cycloalkylalkyl, aryl, aralkyl, heterocyclyl, heterocyclylalkyl, heteroaryl or heteroarylalkyl, each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"N-heteroaryl" refers to a heteroaryl radical as defined above containing at least one nitrogen and where the point of attachment of the heteroaryl radical to the rest of the molecule is through a nitrogen atom in the heteroaryl radical. An N-heteroaryl radical is optionally substituted as described above for heteroaryl radicals.

"C-heteroaryl" refers to a heteroaryl radical as defined above and where the point of attachment of the heteroaryl radical to the rest of the molecule is through a carbon atom in the heteroaryl radical. A C-heteroaryl radical is optionally substituted as described above for heteroaryl radicals.

"Heteroarylalkyl" refers to a radical of the formula —$R^c$-heteroaryl, where $R^c$ is an alkylene chain as defined above. If the heteroaryl is a nitrogen-containing heteroaryl, the heteroaryl is optionally attached to the alkyl radical at the nitrogen atom. The alkylene chain of the heteroarylalkyl radical is optionally substituted as defined above for an alkylene chain. The heteroaryl part of the heteroarylalkyl radical is optionally substituted as defined above for a heteroaryl group.

The compounds, or their pharmaceutically acceptable salts may contain one or more asymmetric centers and may thus give rise to enantiomers, diastereomers, and other stereoisomeric forms that may be defined, in terms of absolute stereochemistry, as (R)- or (S)- or, as (D)- or (L)- for amino acids. When the compounds described herein contain olefinic double bonds or other centers of geometric asymmetry, and unless specified otherwise, it is intended that the compounds include both E and Z geometric isomers (e.g., cis or trans.) Likewise, all possible isomers, as well as their racemic and optically pure forms, and all tautomeric forms are also intended to be included.

A "stereoisomer" refers to a compound made up of the same atoms bonded by the same bonds but having different three-dimensional structures, which are not interchangeable. It is therefore contemplated that various stereoisomers and mixtures thereof and includes "enantiomers," which refers to two stereoisomers whose molecules are nonsuperimposeable mirror images of one another.

A "tautomer" refers to a proton shift from one atom of a molecule to another atom of the same molecule. The compounds presented herein may exist as tautomers. Tautomers are compounds that are interconvertible by migration of a hydrogen atom, accompanied by a switch of a single bond and adjacent double bond. In solutions where tautomerization is possible, a chemical equilibrium of the tautomers will exist. The exact ratio of the tautomers depends on several factors, including temperature, solvent, and pH. Some examples of tautomeric pairs include:

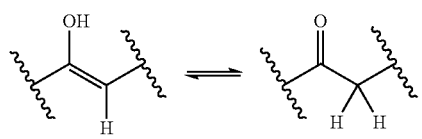

-continued

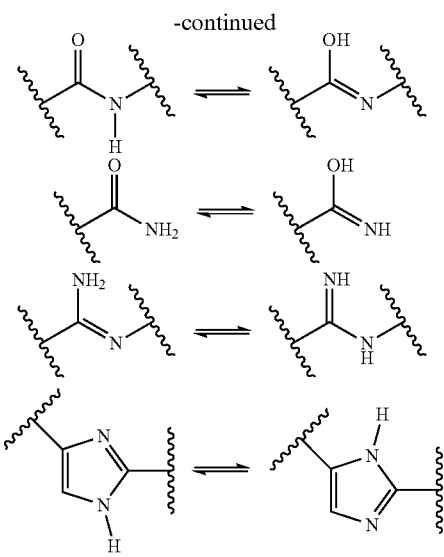

"Optional" or "optionally" means that a subsequently described event or circumstance may or may not occur and that the description includes instances when the event or circumstance occurs and instances in which it does not. For example, "optionally substituted aryl" means that the aryl radical may or may not be substituted and that the description includes both substituted aryl radicals and aryl radicals having no substitution.

"Pharmaceutically acceptable salt" includes both acid and base addition salts. A pharmaceutically acceptable salt of any one of the alkoxyphenyl-linked amine derivative compounds described herein is intended to encompass any and all pharmaceutically suitable salt forms. Preferred pharmaceutically acceptable salts of the compounds described herein are pharmaceutically acceptable acid addition salts and pharmaceutically acceptable base addition salts.

"Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid, hydroiodic acid, hydrofluoric acid, phosphorous acid, and the like. Also included are salts that are formed with organic acids such as aliphatic mono- and dicarboxylic acids, phenyl-substituted alkanoic acids, hydroxy alkanoic acids, alkanedioic acids, aromatic acids, aliphatic and. aromatic sulfonic acids, etc. and include, for example, acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Exemplary salts thus include sulfates, pyrosulfates, bisulfates, sulfites, bisulfites, nitrates, phosphates, monohydrogenphosphates, dihydrogenphosphates, metaphosphates, pyrophosphates, chlorides, bromides, iodides, acetates, trifluoroacetates, propionates, caprylates, isobutyrates, oxalates, malonates, succinate suberates, sebacates, fumarates, maleates, mandelates, benzoates, chlorobenzoates, methylbenzoates, dinitrobenzoates, phthalates, benzenesulfonates, toluenesulfonates, phenylacetates, citrates, lactates, malates, tartrates, methanesulfonates, and the like. Also contemplated are salts of amino acids, such as arginates, gluconates, and galacturonates (see, for example, Berge S. M. et al., "Pharmaceutical Salts," *Journal of Pharmaceutical Science*, 66:1-19 (1997), which is hereby incorporated by reference in its entirety). Acid addition salts of basic compounds may be prepared by contacting the free base forms with a sufficient amount of the desired acid to produce the salt according to methods and techniques with which a skilled artisan is familiar.

"Pharmaceutically acceptable base addition salt" refers to those salts that retain the biological effectiveness and properties of the free acids, which are not biologically or otherwise undesirable. These salts are prepared from addition of an inorganic base or an organic base to the free acid. Pharmaceutically acceptable base addition salts may be formed with metals or amines, such as alkali and alkaline earth metals or organic amines. Salts derived from inorganic bases include, but are not limited to, sodium, potassium, lithium, ammonium, calcium, magnesium, iron, zinc, copper, manganese, aluminum salts and the like. Salts derived from organic bases include, but are not limited to, salts of primary, secondary, and tertiary amines, substituted amines including naturally occurring substituted amines, cyclic amines and basic ion exchange resins, for example, isopropylamine, trimethylamine, diethylamine, triethylamine, tripropylamine, ethanolamine, diethanolamine, 2-dimethylaminoethanol, 2-diethylaminoethanol, dicyclohexylamine, lysine, arginine, histidine, caffeine, procaine, N,N-dibenzylethylenediamine, chloroprocaine, hydrabamine, choline, betaine, ethylenediamine, ethylenedianiline, N-methylglucamine, glucosamine, methylglucamine, theobromine, purines, piperazine, piperidine, N-ethylpiperidine, polyamine resins and the like. See Berge et al., supra.

"Non-retinoid compound" refers to any compound that is not a retinoid. A retinoid is a compound that has a diterpene skeleton possessing a trimethylcyclohexenyl ring and a polyene chain that terminates in a polar end group. Examples of retinoids include retinaldehyde and derived imine/hydrazide/oxime, retinol and any derived ester, retinyl amine and any derived amide, retinoic acid and any derived ester or amide. A non-retinoid compound can comprise though not require an internal cyclic group (e.g., aromatic group). A non-retinoid compound can contain though not require an alkoxyphenyl-linked amine group.

As used herein, "treatment" or "treating," or "palliating" or "ameliorating" are used interchangeably herein. These terms refers to an approach for obtaining beneficial or desired results including but not limited to therapeutic benefit and/or a prophylactic benefit. By "therapeutic benefit" is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient may still be afflicted with the underlying disorder. For prophylactic benefit, the compositions may be administered to a patient at risk of developing a particular disease, or to a patient reporting one or more of the physiological symptoms of a disease, even though a diagnosis of this disease may not have been made.

"Prodrug" is meant to indicate a compound that may be converted under physiological conditions or by solvolysis to a biologically active compound described herein. Thus, the term "prodrug" refers to a precursor of a biologically active compound that is pharmaceutically acceptable. A prodrug may be inactive when administered to a subject, but is converted in vivo to an active compound, for example, by hydrolysis. The prodrug compound often offers advantages of solubility, tissue compatibility or delayed release in a mammalian organism (see, e.g., Bundgard, H., Design of Prodrugs (1985), pp. 7-9, 21-24 (Elsevier, Amsterdam).

A discussion of prodrugs is provided in Higuchi, T., et al., "Pro-drugs as Novel Delivery Systems," A.C.S. Symposium Series, Vol. 14, and in Bioreversible Carriers in Drug Design, ed. Edward B. Roche, American Pharmaceutical Association and Pergamon Press, 1987, both of which are incorporated in full by reference herein.

The term "prodrug" is also meant to include any covalently bonded carriers, which release the active compound in vivo when such prodrug is administered to a mammalian subject. Prodrugs of an active compound, as described herein, may be prepared by modifying functional groups present in the active compound in such a way that the modifications are cleaved, either in routine manipulation or in vivo, to the parent active compound. Prodrugs include compounds wherein a hydroxy, amino or mercapto group is bonded to any group that, when the prodrug of the active compound is administered to a mammalian subject, cleaves to form a free hydroxy, free amino or free mercapto group, respectively. Examples of prodrugs include, but are not limited to, acetate, formate and benzoate derivatives of alcohol or amine functional groups in the active compounds and the like.

Preparation of the Alkoxyphenyl-Linked Amine Derivative Compounds

The compounds used in the reactions described herein are made according to organic synthesis techniques known to those skilled in this art, starting from commercially available chemicals and/or from compounds described in the chemical literature. "Commercially available chemicals" are obtained from standard commercial sources including Acros Organics (Pittsburgh Pa.), Aldrich Chemical (Milwaukee Wis., including Sigma Chemical and Fluka), Apin Chemicals Ltd. (Milton Park UK), Avocado Research (Lancashire U.K.), BDH Inc. (Toronto, Canada), Bionet (Cornwall, U.K.), Chemservice Inc. (West Chester Pa.), Crescent Chemical Co. (Hauppauge N.Y.), Eastman Organic Chemicals, Eastman Kodak Company (Rochester N.Y.), Fisher Scientific Co. (Pittsburgh Pa.), Fisons Chemicals (Leicestershire UK), Frontier Scientific (Logan Utah), ICN Biomedicals, Inc. (Costa Mesa Calif.), Key Organics (Cornwall U.K.), Lancaster Synthesis (Windham N.H.), Maybridge Chemical Co. Ltd. (Cornwall U.K.), Parish Chemical Co. (Orem Utah), Pfaltz & Bauer, Inc. (Waterbury Conn.), Polyorganix (Houston Tex.), Pierce Chemical Co. (Rockford Ill.), Riedel de Haen AG (Hanover, Germany), Spectrum Quality Product, Inc. (New Brunswick, N.J.), TCI America (Portland Oreg.), Trans World Chemicals, Inc. (Rockville Md.), and Wako Chemicals USA, Inc. (Richmond Va.).

Methods known to one of ordinary skill in the art are identified through various reference books and databases. Suitable reference books and treatise that detail the synthesis of reactants useful in the preparation of compounds described herein, or provide references to articles that describe the preparation, include for example, "Synthetic Organic Chemistry", John Wiley & Sons, Inc., New York; S. R. Sandler et al., "Organic Functional Group Preparations," 2nd Ed., Academic Press, New York, 1983; H. O. House, "Modern Synthetic Reactions", 2nd Ed., W. A. Benjamin, Inc. Menlo Park, Calif. 1972; T. L. Gilchrist, "Heterocyclic Chemistry", 2nd Ed., John Wiley & Sons, New York, 1992; J. March, "Advanced Organic Chemistry: Reactions, Mechanisms and Structure", 4th Ed., Wiley-Interscience, New York, 1992. Additional suitable reference books and treatise that detail the synthesis of reactants useful in the preparation of compounds described herein, or provide references to articles that describe the preparation, include for example, Fuhrhop, J. and Penzlin G. "Organic Synthesis: Concepts, Methods, Starting Materials", Second, Revised and Enlarged Edition (1994) John Wiley & Sons ISBN: 3-527-29074-5; Hoffman, R. V. "Organic Chemistry, An Intermediate Text" (1996) Oxford University Press, ISBN 0-19-509618-5; Larock, R. C. "Comprehensive Organic Transformations: A Guide to Functional Group Preparations" 2nd Edition (1999) Wiley-VCH, ISBN: 0-471-19031-4; March, J. "Advanced Organic Chemistry: Reactions, Mechanisms, and Structure" 4th Edition (1992) John Wiley & Sons, ISBN: 0-471-60180-2; Otera, J. (editor) "Modern Carbonyl Chemistry" (2000) Wiley-VCH, ISBN: 3-527-29871-1; Patai, S. "Patai's 1992 Guide to the Chemistry of Functional Groups" (1992) Interscience ISBN: 0-471-93022-9; Quin, L. D. et al. "A Guide to Organophosphorus Chemistry" (2000) Wiley-Interscience, ISBN: 0-471-31824-8; Solomons, T. W. G. "Organic Chemistry" 7th Edition (2000) John Wiley & Sons, ISBN: 0-471-19095-0; Stowell, J. C., "Intermediate Organic Chemistry" 2nd Edition (1993) Wiley-Interscience, ISBN: 0-471-57456-2; "Industrial Organic Chemicals: Starting Materials and Intermediates: An Ullmann's Encyclopedia" (1999) John Wiley & Sons, ISBN: 3-527-29645-X, in 8 volumes; "Organic Reactions" (1942-2000) John Wiley & Sons, in over 55 volumes; and "Chemistry of Functional Groups" John Wiley & Sons, in 73 volumes.

Specific and analogous reactants may also be identified through the indices of known chemicals prepared by the Chemical Abstract Service of the American Chemical Society, which are available in most public and university libraries, as well as through on-line databases (the American Chemical Society, Washington, D.C., may be contacted for more details). Chemicals that are known but not commercially available in catalogs may be prepared by custom chemical synthesis houses, where many of the standard chemical supply houses (e.g., those listed above) provide custom synthesis services. A reference for the preparation and selection of pharmaceutical salts of the alkoxyphenyl-linked amine derivative compounds described herein is P. H. Stahl & C. G. Wermuth "Handbook of Pharmaceutical Salts", Verlag Helvetica Chimica Acta, Zurich, 2002.

Compounds disclosed herein can be prepared in a step-wise manner involving alkylation of a phenol and construction of the linker to the amine.

Alkylation:

Methods A-B below describe various approaches to alkylation.

More specifically, Method A illustrates the construction of an alkoxy intermediate (A-3) through alkylation of a phenol (A-2). The alkylating agent (A-1) comprises a moiety (X) reactive to the acidic hydrogen of phenol. X can be, for example, halogen, mesylate, tosylate, triflate and the like. As shown, the alkylation process eliminates a molecule of HX.

A base can be used to facilitate the deprotonation of the phenol. Suitable bases are typically mild bases such as alkali carbonates (e.g., $K_2CO_3$). Depending on X, other reagents (e.g., $PPh_3$ in combination with DEAD) can be used to facilitate the alkylation process.

METHOD A

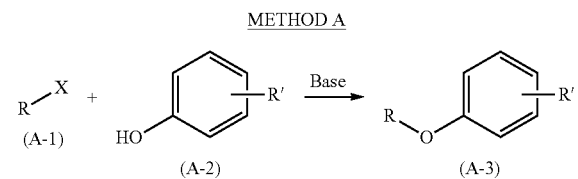

Method B shows the construction of an alkoxy intermediate (A-5) through the ring-opening of an epoxide (A-4).

METHOD B

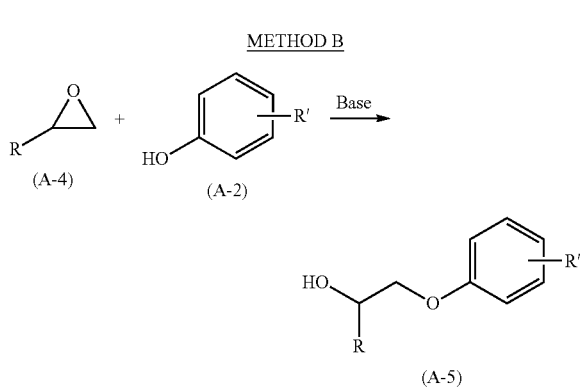

Side Chain Formation and Modification

Methods C-P below describe various approaches to side chain formation and modifications.

Generally speaking, a suitably substituted aryl derivative (e.g., alkoxyphenyl) can be coupled to a diverse range of side chains, which may be further modified to provide the final linkages and the nitrogen-containing moieties of compounds disclosed herein.

Method C illustrates an aldol condensation between an aryl aldehyde or aryl ketone with a nitrile reagent comprising at least one α-hydrogen. The resulting condensation intermediate can be further reduced to an amine (—NH$_2$).

METHOD C

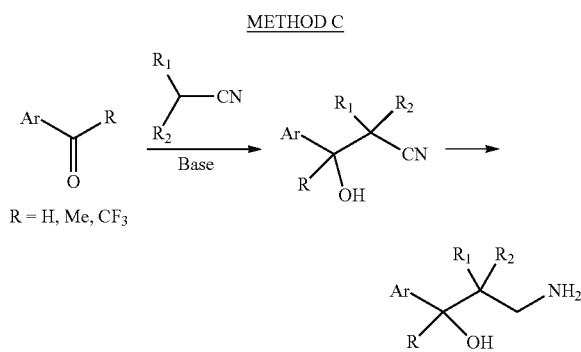

Method D shows an acylation reaction to form a ketone-based linkage. One skilled in the art will recognize that the R' group comprises functional groups that can be further modified.

METHOD D

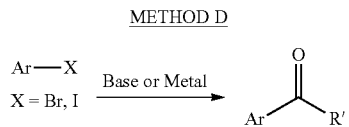

Method E shows a ring-opening reaction of an epoxide reagent to form a 3-carbon side chain linkage. R' can be further modified.

METHOD E

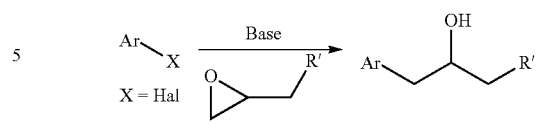

Method F shows the formation of a triple bond linkage based on a Sonogashira reaction. Typically, palladium(0) catalyst is used in combination with a base to couple an aryl halide with a acetylene derivative. R' can be further modified, as described herein. The acetylene linkage can also be further modified, for example, by hydrogenation to provide alkylene or alkenylene linkage.

METHOD F

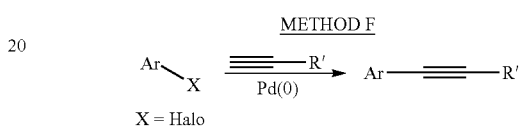

Palladium catalysts suitable for coupling reactions are known to one skilled in the art. Exemplary palladium(0) catalysts include, for example, tetrakis(triphenylphosphine)palladium(0) [Pd(PPh$_3$)$_4$] and tetrakis(tri(o-tolylphosphine)palladium(0), tetrakis(dimethylphenylphosphine)palladium (0), tetrakis(tris-p-methoxyphenylphosphine)palladium(0) and the like. It is understood that a palladium (II) salt can also be used, which generates the palladium (0) catalyst in situ. Suitable palladium (II) salts include, for example, palladium diacetate [Pd(OAc)$_2$], bis(triphenylphosphine)-palladium diacetate and the like.

Method G shows the formation of a double bond linkage based on a Heck reaction. Typically, palladium(0) catalyst is used in combination with a base to couple an aryl halide with a vinyl derivative. R' can be further modified, as described herein.

METHOD G

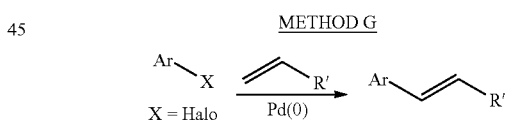

Methods H-P illustrate attachments of side chain moieties by heteroatoms. Method H shows a side chain precursor (R'OH) attached to an aryl derivative via an oxygen atom in a condensation reaction in which a molecule of water is eliminated. R' comprises functional groups that can be further modified to prepare linkages and nitrogen-containing moieties of the compounds disclosed herein.

METHOD H

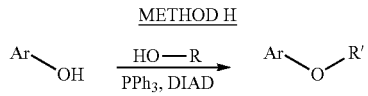

Additional or alternative modifications can be carried out according to the methods illustrated below.

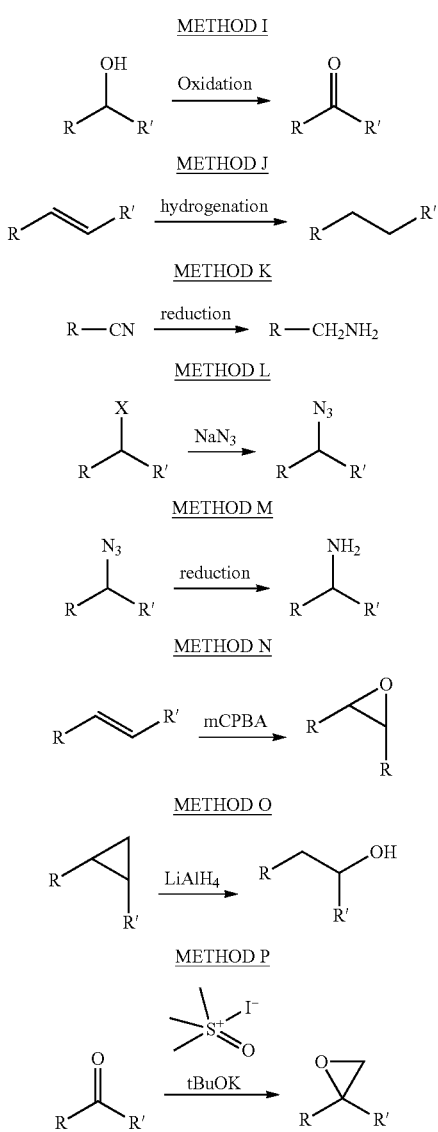

Scheme I illustrates a complete synthetic sequence for preparing a compound disclosed herein.

SCHEME I

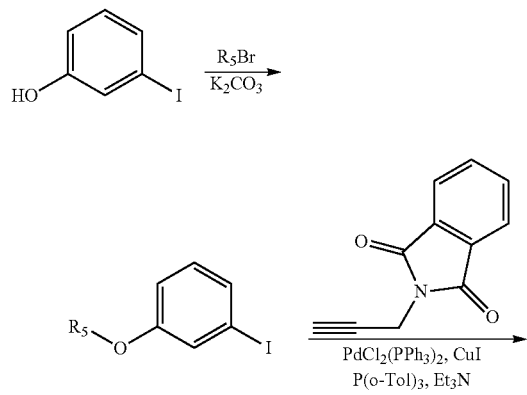

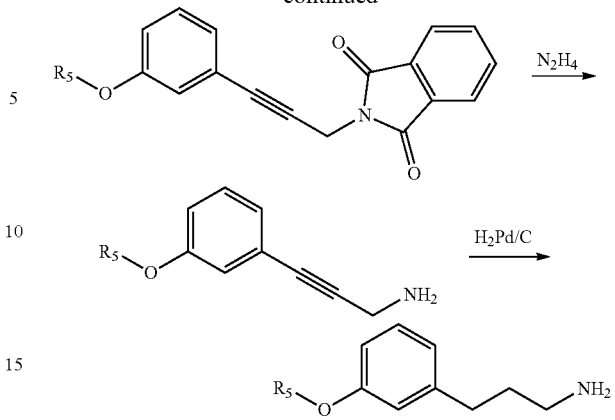

In Scheme I, the alkoxy intermediate is formed via alkylation of a phenol. The side chain is introduced through a Sonogashira coupling. Deprotection of the amine, followed by hydrogenation of the acetylene gives the target compound. Other nitrogen-containing moieties can be further derived from the terminal amine, according to known methods in the art.

In addition to the generic reaction schemes and methods discussed above, other exemplary reaction schemes are also provided to illustrate methods for preparing any compound of Formulae (A)-(E), (I), (II), (IIa), (IIb) described herein or any of its subgenus structures.

Treatment of Ophthalmic Diseases and Disorders

In an additional embodiment is a non-retinoid compound that inhibits an isomerase reaction resulting in production of 11-cis retinol, wherein said isomerase reaction occurs in RPE, and wherein said compound has an $ED_{50}$ value of 1 mg/kg or less when administered to a subject. In a further embodiment is the non-retinoid compound wherein the $ED_{50}$ value is measured after administering a single dose of the compound to said subject for about 2 hours or longer. In a further embodiment is the non-retinoid compound, wherein the non-retinoid compound is an alkoxyl compound. In an additional embodiment is a pharmaceutical composition comprising a pharmaceutically acceptable carrier and a non-retinoid compound as described herein. In an additional embodiment is a method for treating an ophthalmic disease or disorder in a subject, comprising administering to the subject a pharmaceutical composition comprising a pharmaceutically acceptable carrier and a non-retinoid compound as described herein.

In an additional embodiment is a compound that inhibits 11-cis-retinol production with an $IC_{50}$ of about 1 µM or less when assayed in vitro, utilizing extract of cells that express RPE65 and LRAT, wherein the extract further comprises CRALBP, wherein the compound is stable in solution for at least about 1 week at room temperature. In a further embodiment, the compound inhibits 11-cis-retinol production with an $IC_{50}$ of about 0.1 µM or less. In a further embodiment, the compound inhibits 11-cis-retinol production with an $IC_{50}$ of about 0.01 µM or less. In a further embodiment, the compound that inhibits 11-cis-retinol production is a non-retinoid compound. In an additional embodiment is a pharmaceutical composition comprising a pharmaceutically acceptable carrier and a compound that inhibits 11-cis-retinol production as described herein. In an additional embodiment is a method for treating an ophthalmic disease or disorder in a subject, comprising administering to the subject a pharmaceutical composition comprising a pharmaceutically acceptable carrier and a compound that inhibits 11-cis-retinol production as described herein. In an additional embodiment is a method of modulating chromophore flux in a retinoid cycle comprising introducing into a subject a compound that inhibits 11-cis-retinol production as described herein.

In an additional embodiment is a method for treating an ophthalmic disease or disorder in a subject, comprising administering to the subject a compound of Formula (F) or tautomer, stereoisomer, geometric isomer or a pharmaceutically acceptable solvate, hydrate, salt, N-oxide or prodrug thereof:

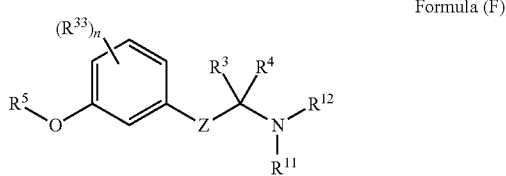

Formula (F)

wherein,

Z is a bond, —C($R^1$)($R^2$)—, —C($R^9$)($R^{10}$)—C($R^1$)($R^2$)—, —X—C($R^{31}$)($R^{32}$)—, —C($R^9$)($R^{10}$)—C($R^1$)($R^2$)—C($R^{36}$)($R^{37}$)— or —X—C($R^{31}$)($R^{32}$)—C($R^1$)($R^2$)—;

$R^1$ and $R^2$ are each independently selected from hydrogen, halogen, $C_1$-$C_5$ alkyl, fluoroalkyl, —$OR^6$ or —$NR^7R^8$; or $R^1$ and $R^2$ together form an oxo;

$R^{31}$ and $R^{32}$ are each independently selected from hydrogen, $C_1$-$C_5$ alkyl, or fluoroalkyl;

$R^{36}$ and $R^{37}$ are each independently selected from hydrogen, halogen, $C_1$-$C_5$ alkyl, fluoroalkyl, —$OR^6$ or —$NR^7R^8$; or $R^{36}$ and $R^{37}$ together form an oxo; or optionally, $R^{36}$ and $R^1$ together form a direct bond to provide a double bond; or optionally, $R^{36}$ and $R^1$ together form a direct bond, and $R^{37}$ and $R^2$ together form a direct bond to provide a triple bond;

$R^3$ and $R^4$ are each independently selected from hydrogen, alkyl, alkenyl, fluoroalkyl, aryl, heteroaryl, carbocyclyl or C-attached heterocyclyl; or $R^3$ and $R^4$ together with the carbon atom to which they are attached, form a carbocyclyl or heterocyclyl; or $R^3$ and $R^4$ together form an imino;

$R^5$ is $C_1$-$C_{15}$ alkyl, carbocyclyalkyl, arylalkyl, heteroaryl alkyl or heterocyclylalkyl;

$R^7$ and $R^8$ are each independently selected from hydrogen, alkyl, carbocyclyl, heterocyclyl, —C(=O)$R^{13}$, $SO_2R^{13}$, $CO_2R^{13}$ or $SO_2NR^{24}R^{25}$; or $R^7$ and $R^8$ together with the nitrogen atom to which they are attached, form an N-heterocyclyl;

X is —O—, —S—, —S(=O)—, —S(=O)$_2$—, —N($R^{30}$)—, —C(=O)—, —C(=CH$_2$)—, —C(=N—N$R^{35}$)—, or —C(=N—O$R^{35}$)—;

$R^9$ and $R^{10}$ are each independently selected from hydrogen, halogen, alkyl, fluoroalkyl, —$OR^{19}$—, —$NR^{20}R^{21}$ or carbocyclyl; or $R^9$ and $R^{10}$ form an oxo; or optionally, $R^9$ and $R^1$ together form a direct bond to provide a double bond; or optionally, $R^9$ and $R^1$ together form a direct bond, and $R^{10}$ and $R^2$ together form a direct bond to provide a triple bond;

$R^{11}$ and $R^{12}$ are each independently selected from hydrogen, alkyl, carbocyclyl, —C(=O)$R^{23}$, —C(NH)NH$_2$, $SO_2R^{23}$, $CO_2R^{23}$ or $SO_2NR^{28}R^{29}$; or $R^{11}$ and $R^{12}$, together with the nitrogen atom to which they are attached, form an N-heterocyclyl;

each $R^{13}$, $R^{22}$ and $R^{23}$ is independently selected from alkyl, heteroalkyl, alkenyl, aryl, aralkyl, carbocyclyl, heteroaryl or heterocyclyl;

$R^6$, $R^{19}$, $R^{30}$, $R^{34}$ and $R^{35}$ are each independently hydrogen or alkyl;

$R^{20}$ and $R^{21}$ are each independently selected from hydrogen, alkyl, carbocyclyl, heterocyclyl, —C(=O)$R^{22}$, $SO_2R^{22}$, $CO_2R^{22}$ or $SO_2NR^{26}R^{27}$; or $R^{20}$ and $R^{21}$ together with the nitrogen atom to which they are attached, form an N-heterocyclyl; and each $R^{24}$, $R^{25}$, $R^{26}$, $R^{27}$, $R^{28}$ and $R^{29}$ is independently selected from hydrogen, alkyl, alkenyl, fluoroalkyl, aryl, heteroaryl, carbocyclyl or heterocyclyl;

each $R^{33}$ is independently selected from halogen, $OR^{34}$, alkyl, or fluoroalkyl; and n is 0, 1, 2, 3, or 4.

In an additional embodiment is a method of modulating chromophore flux in a retinoid cycle comprising introducing into a subject a compound of Formula (F). In a further embodiment is the method resulting in a reduction of lipofuscin pigment accumulated in an eye of the subject. In a further embodiment is the method resulting in a reduction of lipofuscin pigment accumulated in an eye of the subject, wherein the lipofuscin pigment is N-retinylidene-N-retinylethanolamine (A2E).

In a further embodiment is the method of treating an ophthalmic disease or disorder in a subject as described herein resulting in a reduction of lipofuscin pigment accumulated in an eye of the subject. In a further embodiment is the method of treating an ophthalmic disease or disorder in a subject as described herein resulting in a reduction of lipofuscin pigment accumulated in an eye of the subject, wherein the lipofuscin pigment is N-retinylidene-N-retinylethanolamine (A2E).

In a further embodiment is the method of treating an ophthalmic disease or disorder in a subject as described herein, wherein the ophthalmic disease or disorder is age-related macular degeneration or Stargardt's macular dystrophy. In a further embodiment is the method of treating an ophthalmic disease or disorder in a subject as described herein, wherein the ophthalmic disease or disorder is selected from retinal detachment, hemorrhagic retinopathy, retinitis pigmentosa, cone-rod dystrophy, Sorsby's fundus dystrophy, optic neuropathy, inflammatory retinal disease, diabetic retinopathy, diabetic maculopathy, retinal blood vessel occlusion, retinopathy of prematurity, or ischemia reperfusion related retinal injury, proliferative vitreoretinopathy, retinal dystrophy, hereditary optic neuropathy, Sorsby's fundus dystrophy, uveitis, a retinal injury, a retinal disorder associated with Alzheimer's disease, a retinal disorder associated with multiple sclerosis, a retinal disorder associated with Parkinson's disease, a retinal disorder associated with viral infection, a retinal disorder related to light overexposure, myopia, and a retinal disorder associated with AIDS. In a further embodiment is the method of treating an ophthalmic disease or disorder in a subject as described herein resulting in a reduction of lipofuscin pigment accumulated in an eye of the subject. In a further embodiment is the method of treating an ophthalmic disease or disorder in a subject as described herein resulting in a reduction of lipofuscin pigment accumulated in an eye of the subject, wherein the lipofuscin pigment is N-retinylidene-N-retinylethanolamine (A2E).

In another embodiment is a method of inhibiting dark adaptation of a rod photoreceptor cell of the retina comprising contacting the retina with a compound of Formula (F). In another embodiment is a method of inhibiting dark adaptation of a rod photoreceptor cell of the retina comprising contacting the retina with a non-retinoid compound as described herein. In another embodiment is a method of inhibiting dark adaptation of a rod photoreceptor cell of the retina comprising contacting the retina with a compound that inhibits 11-cis-retinol production as described herein.

In another embodiment is a method of inhibiting regeneration of rhodopsin in a rod photoreceptor cell of the retina comprising contacting the retina with a compound of Formula (F). In another embodiment is a method of inhibiting regeneration of rhodopsin in a rod photoreceptor cell of the retina comprising contacting the retina with a non-retinoid compound as described herein. In another embodiment is a method of inhibiting regeneration of rhodopsin in a rod photoreceptor cell of the retina comprising contacting the retina with a compound that inhibits 11-cis-retinol production as described herein.

In another embodiment is a method of reducing ischemia in an eye of a subject comprising administering to the subject a pharmaceutical composition comprising a pharmaceutically acceptable carrier and a compound of Formula (F).

In an additional embodiment is a method of reducing ischemia in an eye of a subject comprising administering to the subject a pharmaceutical composition comprising a pharmaceutically acceptable carrier and a non-retinoid compound as described herein. In an additional embodiment is a method of reducing ischemia in an eye of a subject comprising administering to the subject a pharmaceutical composition comprising a pharmaceutically acceptable carrier and a compound that inhibits 11-cis-retinol production as described herein. In a further embodiment is the method of reducing ischemia in an eye of a subject, wherein the pharmaceutical composition is administered under conditions and at a time sufficient to inhibit dark adaptation of a rod photoreceptor cell, thereby reducing ischemia in the eye.

In an additional embodiment is a method of inhibiting neovascularization in the retina of an eye of a subject comprising administering to the subject a pharmaceutical composition comprising a pharmaceutically acceptable carrier and a non-retinoid compound as described herein. In an additional embodiment is a method of inhibiting neovascularization in the retina of an eye of a subject comprising administering to the subject a pharmaceutical composition comprising a pharmaceutically acceptable carrier and a compound that inhibits 11-cis-retinol production as described herein. In a further embodiment is the method of inhibiting neovascularization in the retina of an eye of a subject, wherein the pharmaceutical composition is administered under conditions and at a time sufficient to inhibit dark adaptation of a rod photoreceptor cell, thereby inhibiting neovascularization in the retina.

In an additional embodiment is a method of inhibiting degeneration of a retinal cell in a retina comprising contacting the retina with a compound of Formula (F). In an additional embodiment is a method of inhibiting degeneration of a retinal cell in a retina comprising contacting the retina with a non-retinoid compound as described herein. In an additional embodiment is a method of inhibiting degeneration of a retinal cell in a retina comprising contacting the retina with a compound that inhibits 11-cis-retinol production as described herein.

In a further embodiment is the method of inhibiting degeneration of a retinal cell in a retina wherein the retinal cell is a retinal neuronal cell. In a further embodiment is the method of inhibiting degeneration of a retinal cell in a retina wherein the retinal neuronal cell is a photoreceptor cell.

In another embodiment is a method of reducing lipofuscin pigment accumulated in a subject's retina comprising administering to the subject a pharmaceutical composition comprising a pharmaceutically acceptable carrier and a compound of Formula (F). In an additional embodiment is a method of reducing lipofuscin pigment accumulated in a subject's retina wherein the lipofuscin is N-retinylidene-N-retinyl-ethanolamine (A2E).

In an additional embodiment is a method of inhibiting reducing lipofuscin pigment accumulated in a subject's retina comprising administering to the subject a pharmaceutical composition comprising a pharmaceutically acceptable carrier and a non-retinoid compound as described herein. In an additional embodiment is a method of reducing lipofuscin pigment accumulated in a subject's retina comprising administering to the subject a pharmaceutical composition comprising a pharmaceutically acceptable carrier and a compound that inhibits 11-cis-retinol production as described herein. In an additional embodiment is a method of reducing lipofuscin pigment accumulated in a subject's retina wherein the lipofuscin is N-retinylidene-N-retinyl-ethanolamine (A2E).

In an additional embodiment is a method of modulating chromophore flux in a retinoid cycle comprising introducing into a subject a pharmaceutical composition comprising a compound of Formula (F). In a further embodiment is the method resulting in a reduction of lipofuscin pigment accumulated in an eye of the subject. In a further embodiment is the method resulting in a reduction of lipofuscin pigment accumulated in an eye of the subject, wherein the lipofuscin pigment is N-retinylidene-N-retinyl-ethanolamine (A2E).

In another embodiment is a method of inhibiting dark adaptation of a rod photoreceptor cell of the retina comprising contacting the retina with a pharmaceutical composition comprising a compound of Formula (F).

In another embodiment is a method of inhibiting regeneration of rhodopsin in a rod photoreceptor cell of the retina comprising contacting the retina with a pharmaceutical composition comprising a compound of Formula (F).

In an additional embodiment is a method of inhibiting degeneration of a retinal cell in a retina comprising contacting the retina with a pharmaceutical composition comprising a compound of Formula (F).

In a further embodiment is the method for treating an ophthalmic disease or disorder in a subject, comprising administering to the subject a compound of Formula (F), wherein the compound of Formula (F) is selected from the group consisting of:

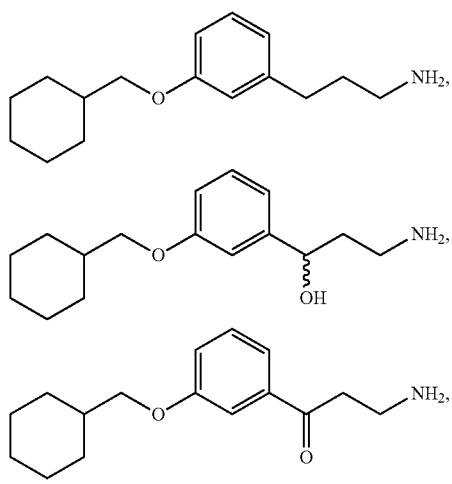

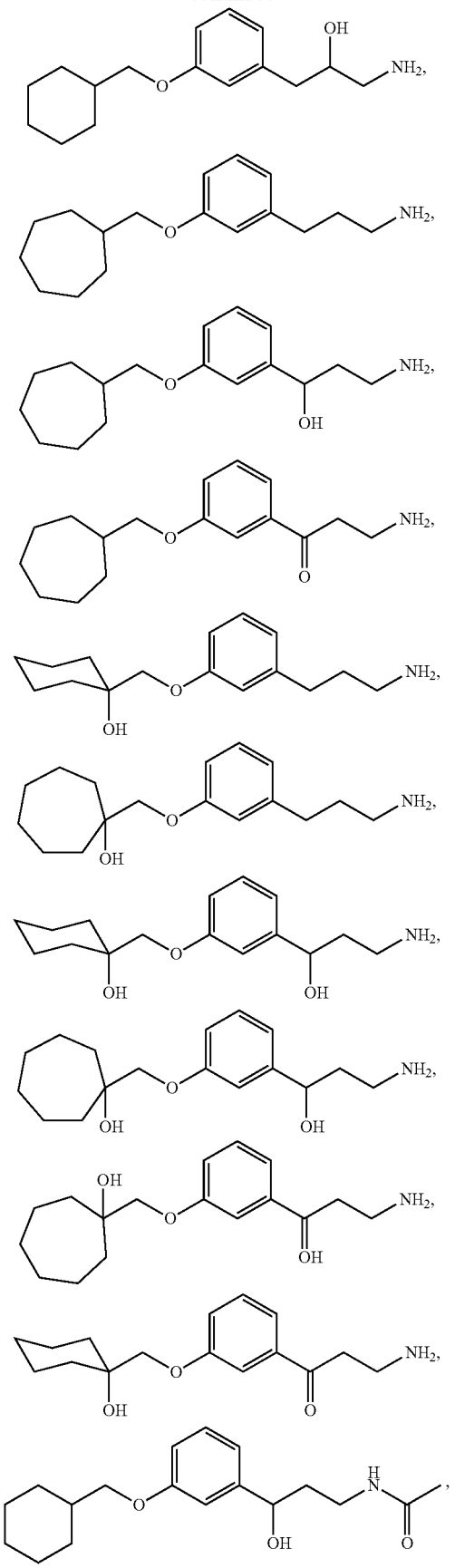
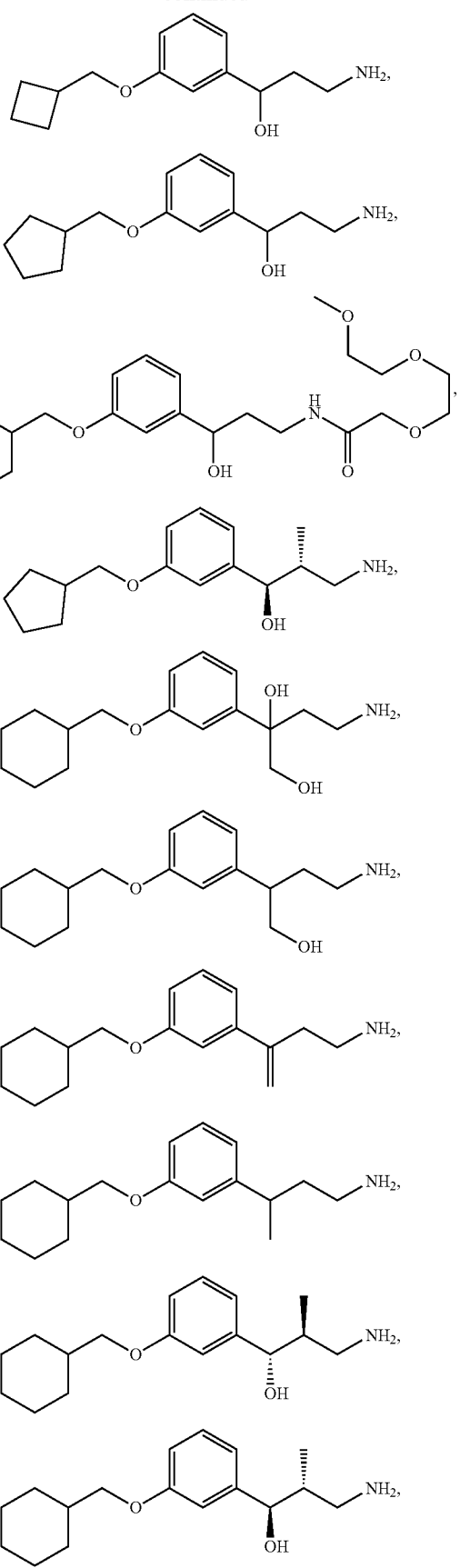

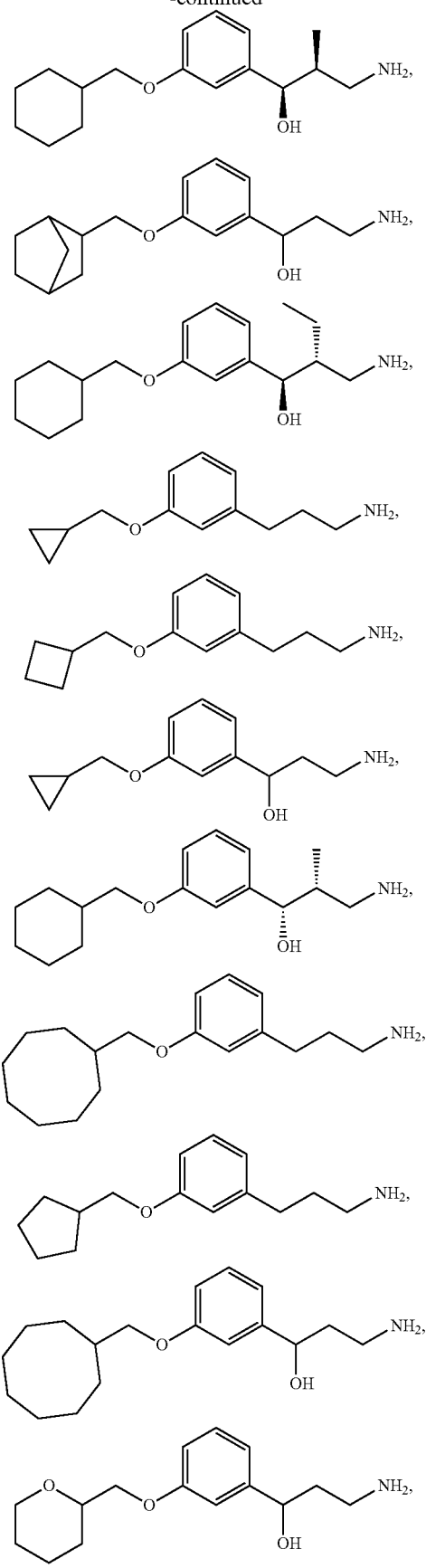
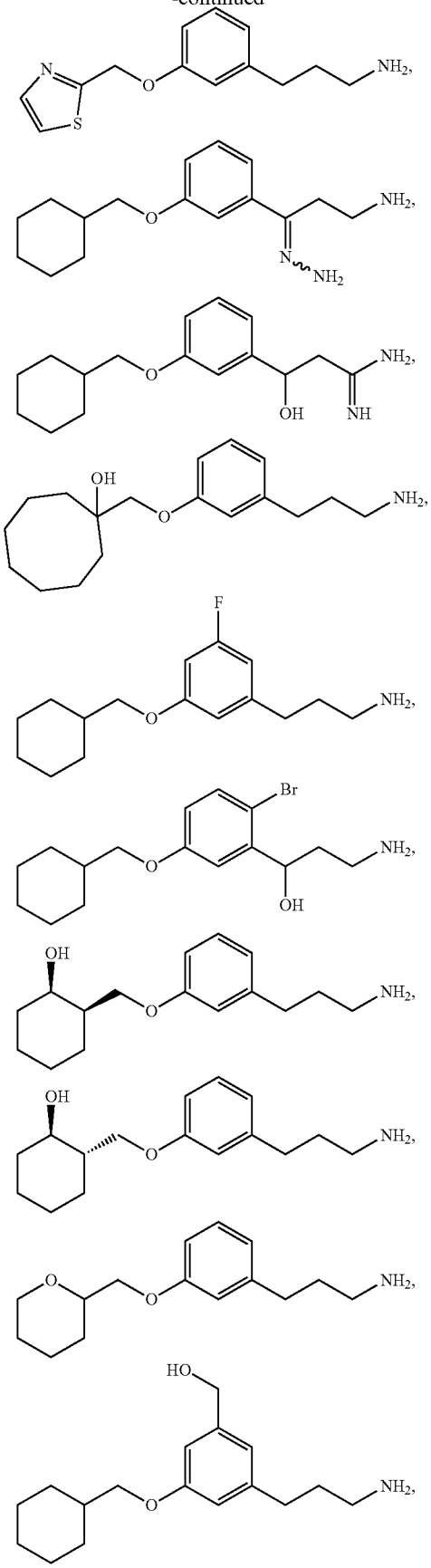

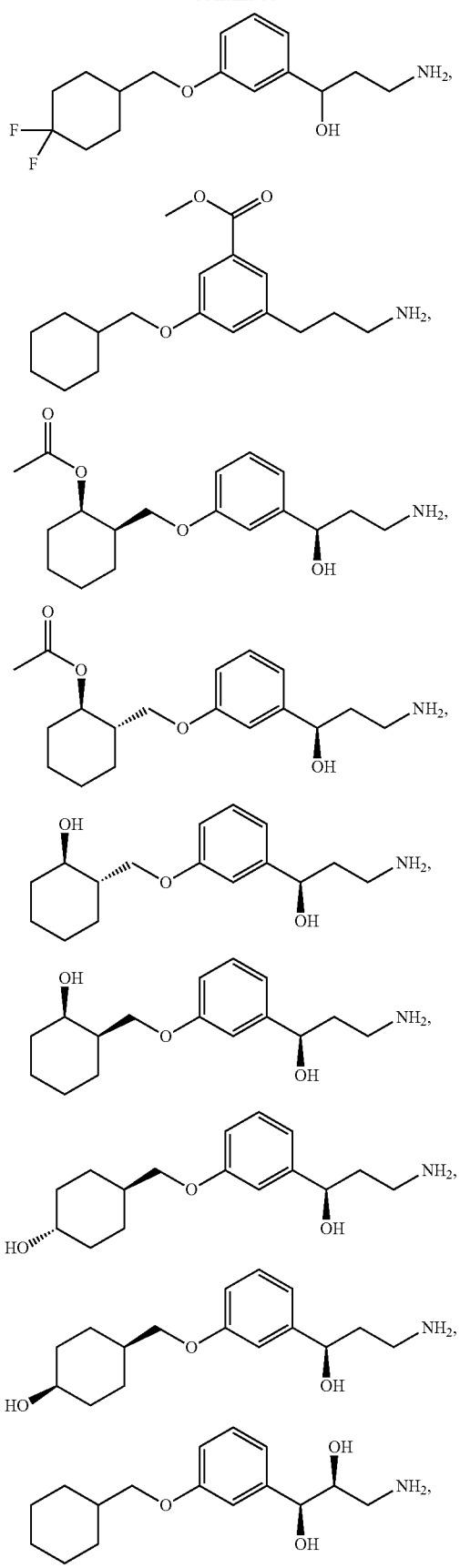
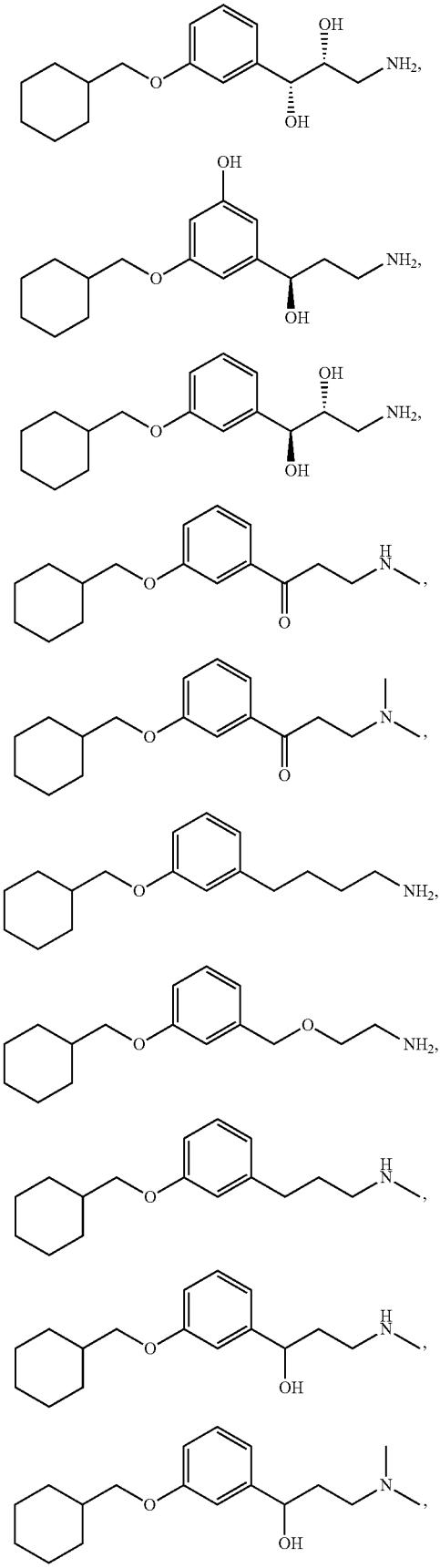

181
-continued
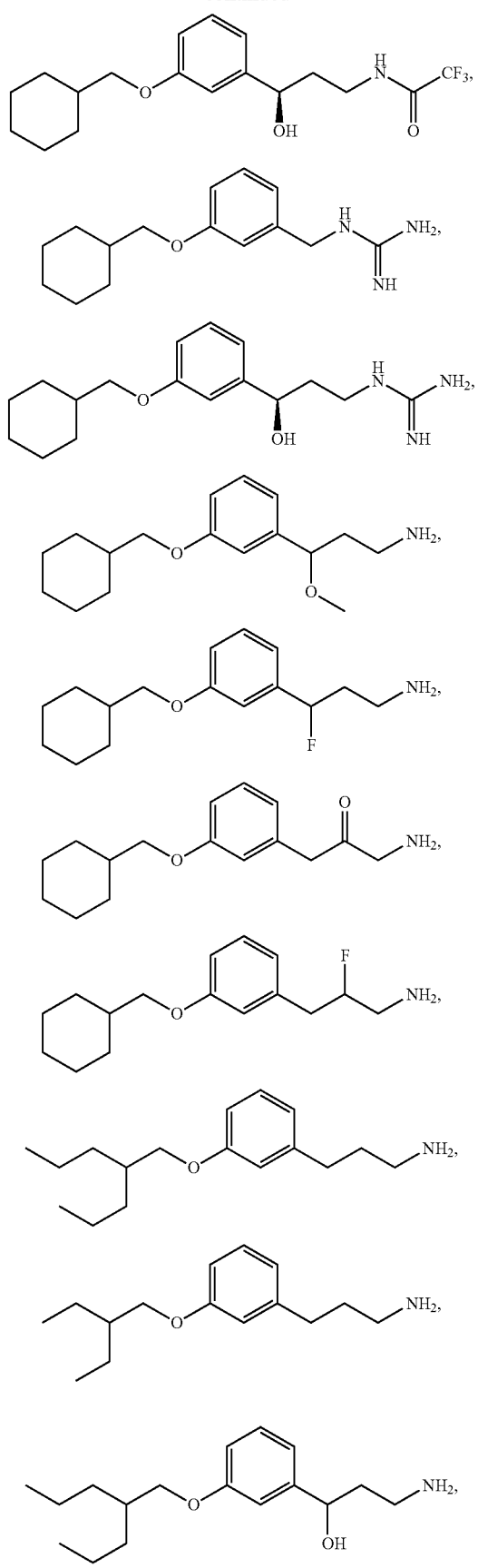
182
-continued
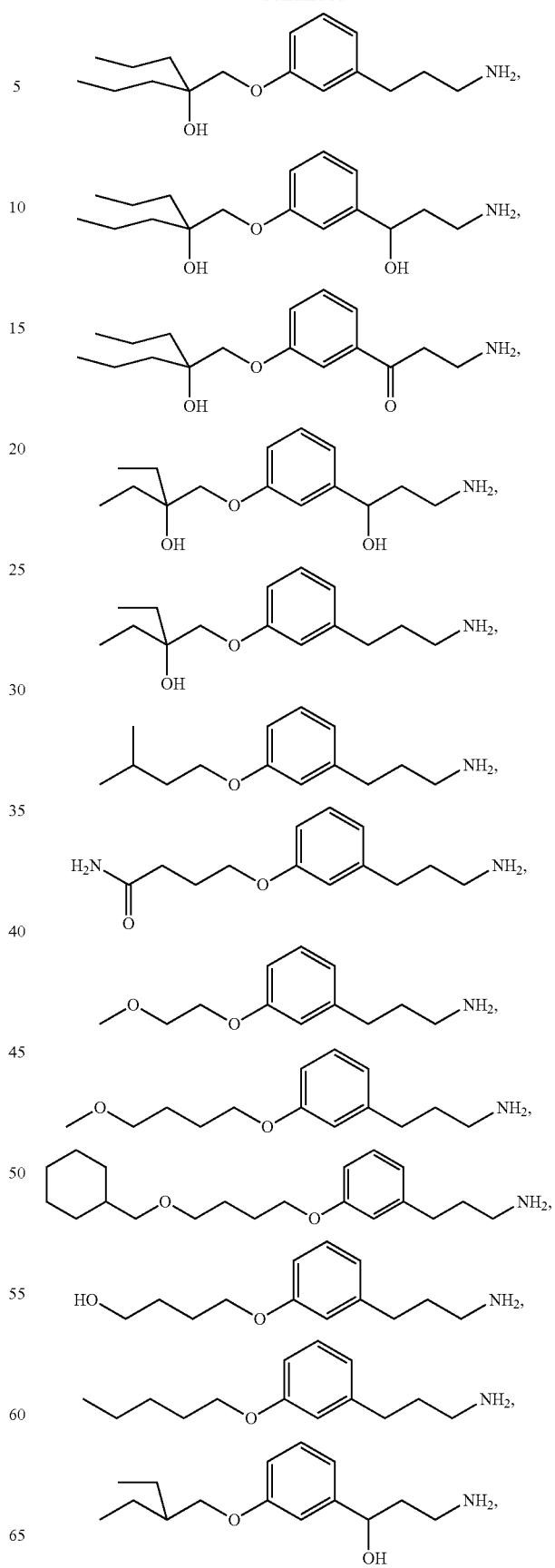

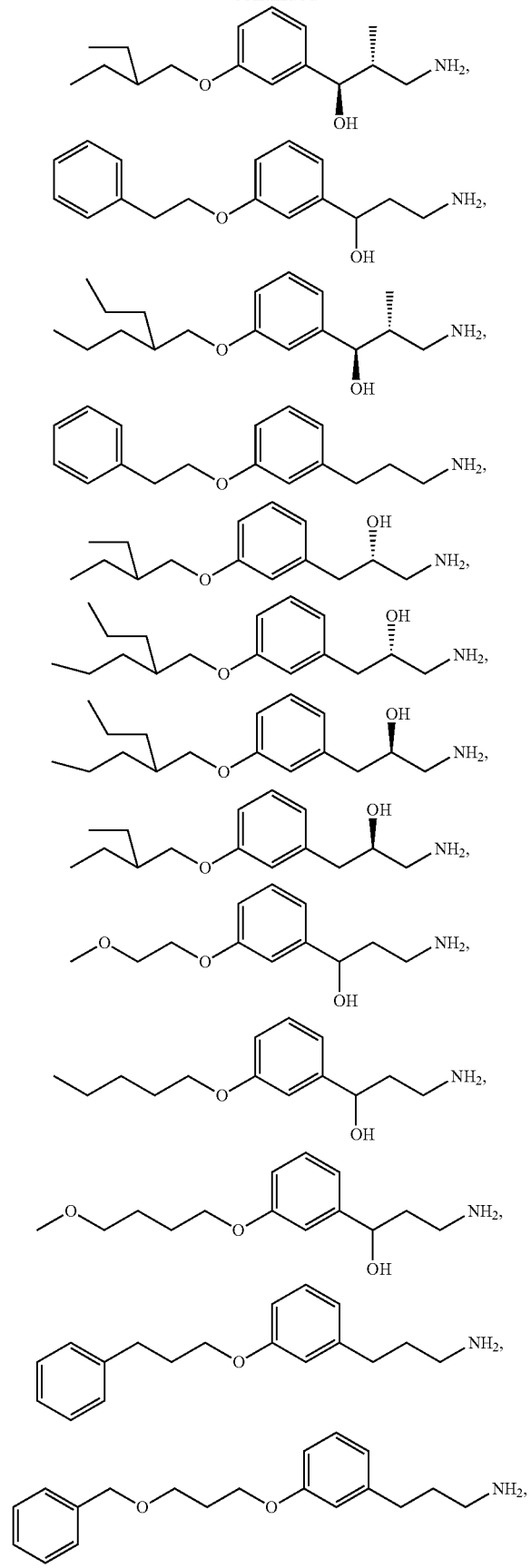
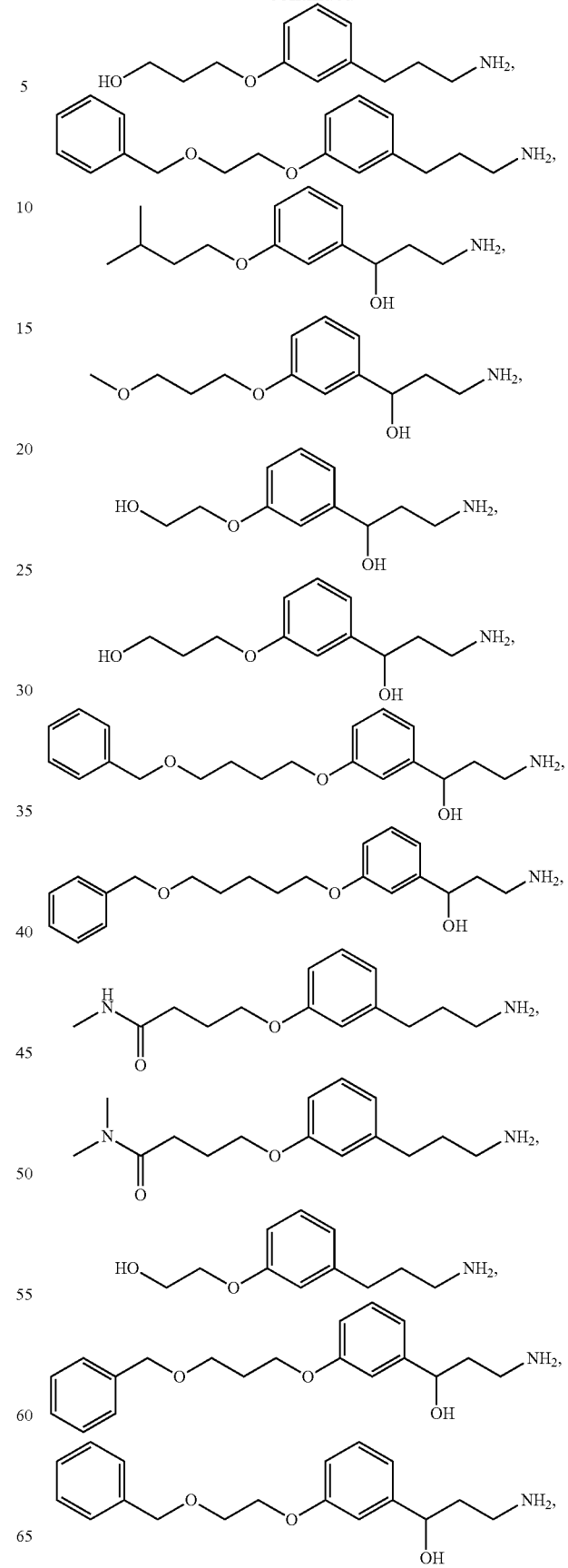

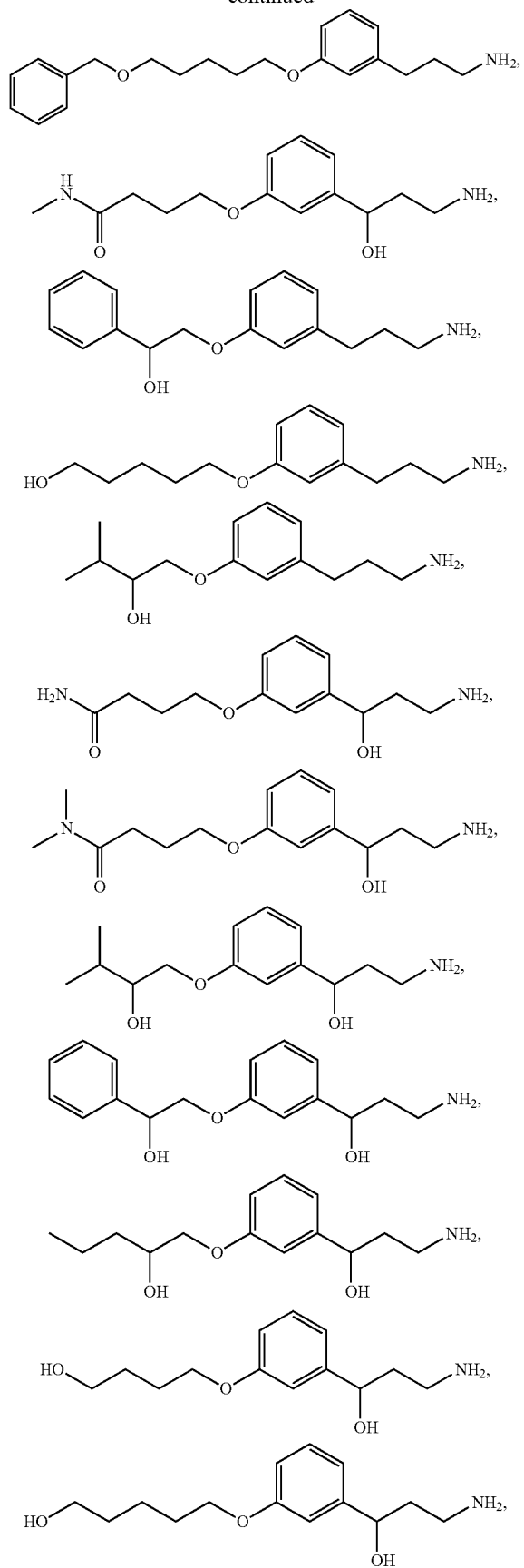
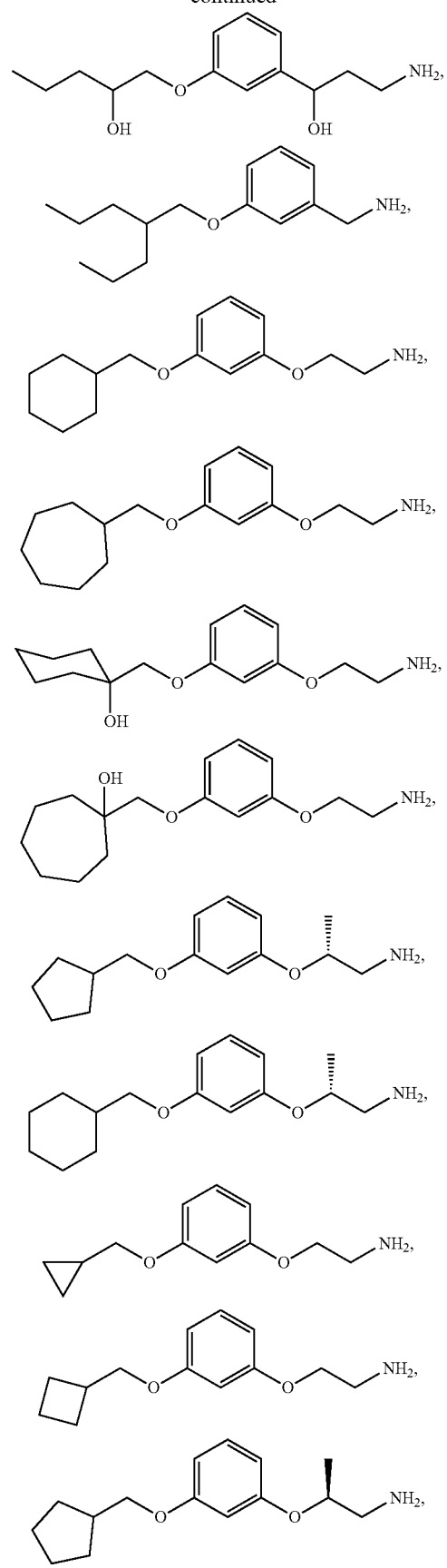

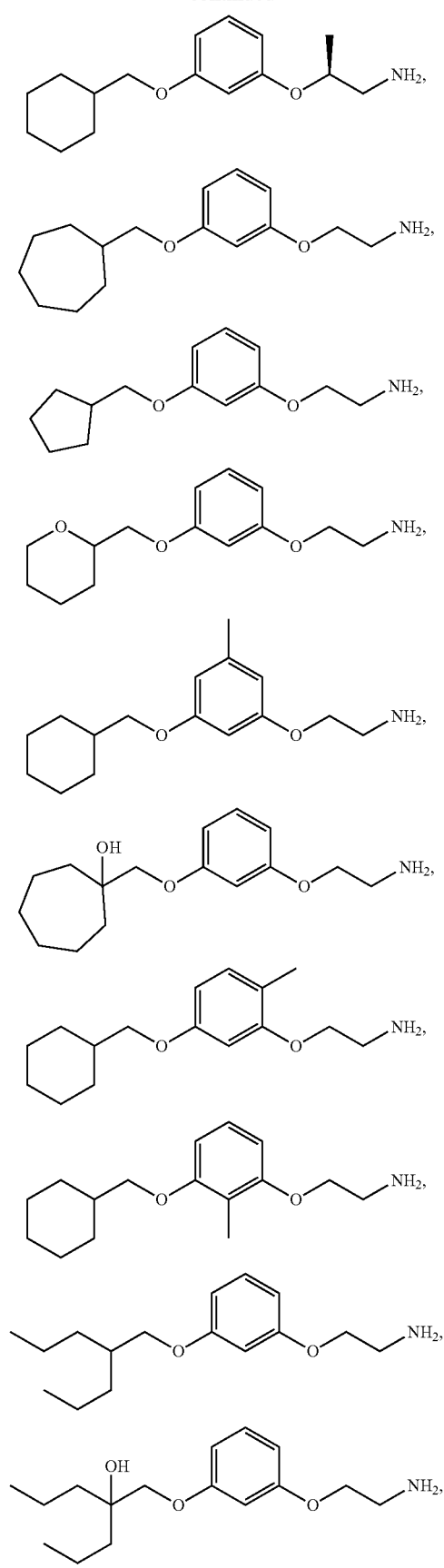

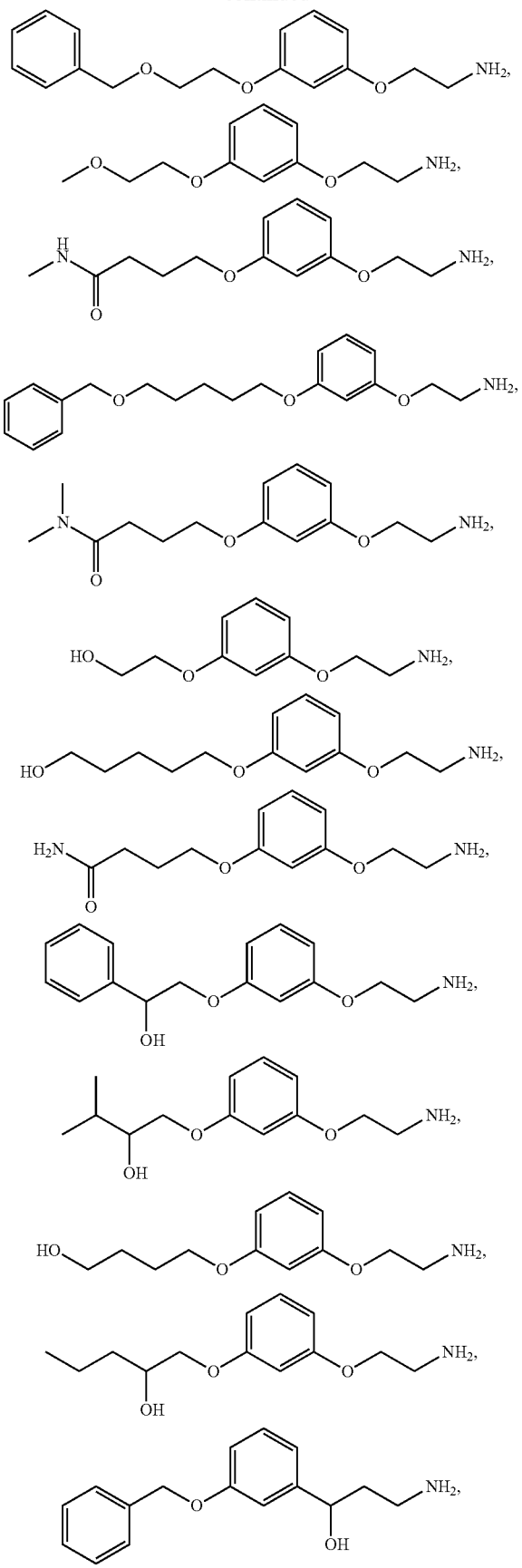
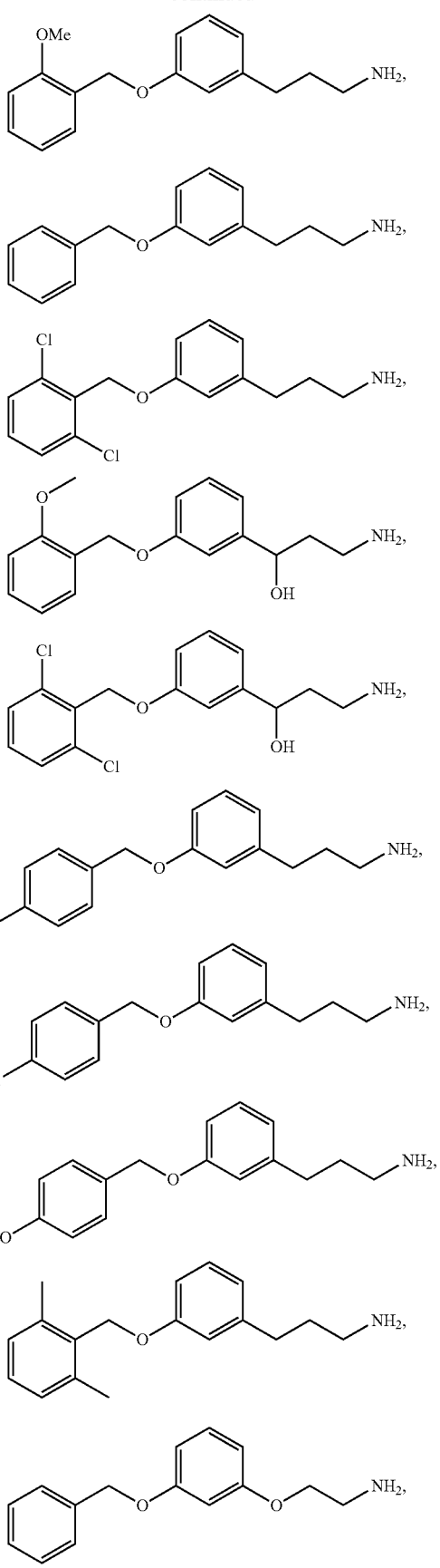

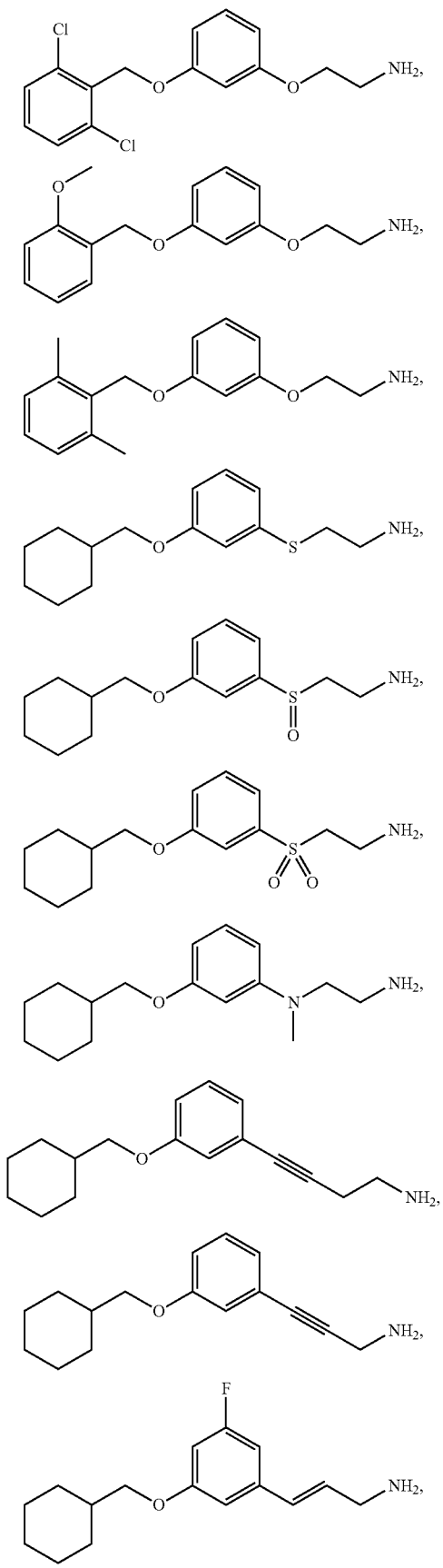
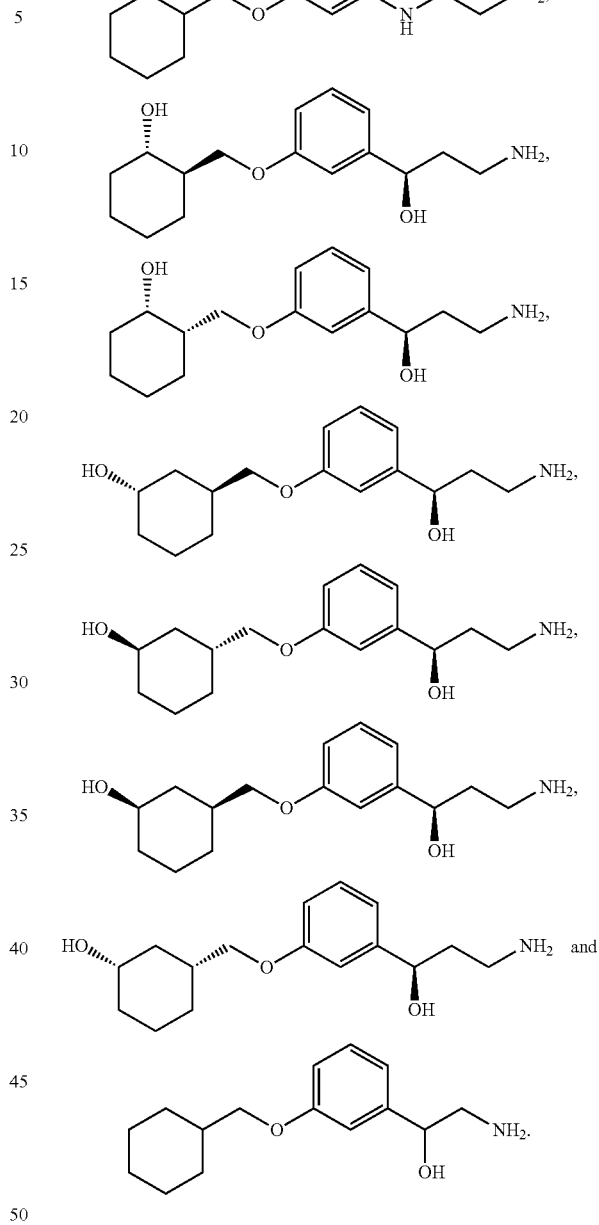

Alkoxyphenyl-linked amine derivative compounds as described in detail herein, including a compound having the structure as set forth in any one of Formulae (A)-(E), (I), (II), (IIa), (IIb), and substructures thereof, and the specific alkoxyphenyl-linked amine compounds described herein that may be useful for treating an ophthalmic disease or disorder may inhibit one or more steps in the visual cycle, for example, by inhibiting or blocking a functional activity of a visual cycle trans-cis isomerase (also including a visual cycle trans-cis isomerohydrolase). The compounds described herein, may inhibit, block, or in some manner interfere with the isomerization step in the visual cycle. In a particular embodiment, the compound inhibits isomerization of an all-trans-retinyl ester; in certain embodiments, the all-trans-retinyl ester is a fatty acid ester of all-trans-retinol, and the compound inhibits isomerization of all-trans-retinol to 11-cis-retinol. The compound may bind to, or in some manner interact with, and inhibit the isomerase activity of at least one visual cycle isomerase, which may also be referred to herein and in the art as a retinal isomerase or an isomerohydrolase. The compound may block or inhibit binding of an all-trans-retinyl ester substrate to an isomerase. Alternatively, or in addition, the compound may bind to the catalytic site or region of the isomerase, thereby inhibiting the capability of the enzyme to catalyze isomerization of an all-trans-retinyl ester substrate. On the basis of scientific data to date, at least one isomerase that catalyzes the isomerization of all-trans-retinyl esters is believed to be located in the cytoplasm of RPE cells. As discussed herein, each step, enzyme, substrate, intermediate, and product of the visual cycle is not yet elucidated (see, e.g., Moiseyev et al., *Proc. Natl. Acad. Sci. USA* 102:12413-18 (2004); Chen et al., *Invest. Ophthalmol. Vis. Sci.* 47:1177-84 (2006); Lamb et al. supra).

A method for determining the effect of a compound on isomerase activity may be performed in vitro as described herein and in the art (Stecher et al., *J Biol Chem* 274:8577-85 (1999); see also Golczak et al., *Proc. Natl. Acad. Sci. USA* 102:8162-67 (2005)). Retinal pigment epithelium (RPE) microsome membranes isolated from an animal (such as bovine, porcine, human, for example) may serve as the source of the isomerase. The capability of the alkoxyphenyl-linked amine derivative compounds to inhibit isomerase may also be determined by an in vivo murine isomerase assay. Brief exposure of the eye to intense light ("photo-bleaching" of the visual pigment or simply "bleaching") is known to photo-isomerize almost all 11-cis-retinal in the retina. The recovery of 11-cis-retinal after bleaching can be used to estimate the activity of isomerase in vivo (see, e.g., Maeda et al., *J. Neurochem* 85:944-956 (2003); Van Hooser et al., *J Biol Chem* 277:19173-82, 2002). Electroretinographic (ERG) recording may be performed as previously described (Haeseleer et al., *Nat. Neurosci.* 7:1079-87 (2004); Sugitomo et al., *J. Toxicol. Sci.* 22 Suppl 2:315-25 (1997); Keating et al., *Documenta Ophthalmologica* 100: 77-92 (2000)). See also Deigner et al., *Science*, 244: 968-971 (1989); Gollapalli et al., *Biochim Biophys Acta.* 1651: 93-101 (2003); Parish, et al., *Proc. Natl. Acad. Sci. USA* 95:14609-13 (1998); Radu, et al., *Proc Natl Acad Sci USA* 101: 5928-33 (2004)). In certain embodiments, compounds that are useful for treating a subject who has or who is at risk of developing any one of the ophthalmic and retinal diseases or disorders described herein have $IC_{50}$ levels (compound concentration at which 50% of isomerase activity is inhibited) as measured in the isomerase assays described herein or known in the art that is less than about 1 µM; in other embodiments, the determined $IC_{50}$ level is less than about 10 nM; in other embodiments, the determined $IC_{50}$ level is less than about 50 nM; in certain other embodiments, the determined $IC_{50}$ level is less than about 100 nM; in other certain embodiments, the determined $IC_{50}$ level is less than about 10 µM; in other embodiments, the determined $IC_{50}$ level is less than about 50 µM; in other certain embodiments, the determined $IC_{50}$ level is less than about 100 µM or about 500 µM; in other embodiments, the determined $IC_{50}$ level is between about 1 µM and 10 µM; in other embodiments, the determined $IC_{50}$ level is between about 1 nM and 10 nM. When adminstered into a subject, one or more compounds of the present invention exhibits an $ED_{50}$ value of about 5 mg/kg, 5 mg/kg or less as ascertained by inhibition of an isomerase reaction that results in production of 11-cis retinol. In some embodiments, the compounds of the present invention have $ED_{50}$ values of about 1 mg/kg when administered into a subject. In other embodiments, the compounds of the present invention have $ED_{50}$ values of about 0.1 mg/kg when administered into a subject. The $ED_{50}$ values can be measured after about 2 hours, 4 hours, 6 hours, 8 hours or longer upon administering a subject compound or a pharmaceutical composition thereof.

The compounds described herein may be useful for treating a subject who has an ophthalmic disease or disorder, particularly a retinal disease or disorder such as age-related macular degeneration or Stargardt's macular dystrophy. In one embodiment, the compounds described herein may inhibit (i.e., prevent, reduce, slow, abrogate, or minimize) accumulation of lipofuscin pigments and lipofuscin-related and/or associated molecules in the eye. In another embodiment, the compounds may inhibit (i.e., prevent, reduce, slow, abrogate, or minimize) N-retinylidene-N-retinyletha-nolamine (A2E) accumulation in the eye. The ophthalmic disease may result, at least in part, from lipofuscin pigments accumulation and/or from accumulation of A2E in the eye. Accordingly, in certain embodiments, methods are provided for inhibiting or preventing accumulation of lipofuscin pigments and/or A2E in the eye of a subject. These methods comprise administering to the subject a composition comprising a pharmaceutically acceptable or suitable excipient (i.e., pharmaceutically acceptable or suitable carrier) and an alkoxyphenyl-linked amine derivative compound as described in detail herein, including a compound having the structure as set forth in any one of Formulae (A)-(E), (I), (II), (IIa), (IIb), and substructures thereof, and the specific alkoxyphenyl-linked amine compounds described herein.

Accumulation of lipofuscin pigments in retinal pigment epithelium (RPE) cells has been linked to progression of retinal diseases that result in blindness, including age-related macular degeneration (De Laey et al., *Retina* 15:399-406 (1995)). Lipofuscin granules are autofluorescent lysosomal residual bodies (also called age pigments). The major fluorescent species of lipofuscin is A2E (an orange-emitting fluorophore), which is a positively charged Schiff-base condensation-product formed by all-trans retinaldehyde with phosphatidylethanolamine (2:1 ratio) (see, e.g., Eldred et al., *Nature* 361:724-6 (1993); see also, Sparrow, *Proc. Natl. Acad. Sci.* USA 100:4353-54 (2003)). Much of the indigestible lipofuscin pigment is believed to originate in photoreceptor cells; deposition in the RPE occurs because the RPE internalize membranous debris that is discarded daily by the photoreceptor cells. Formation of this compound is not believed to occur by catalysis by any enzyme, but rather A2E forms by a spontaneous cyclization reaction. In addition, A2E has a pyridinium bisretinoid structure that once formed may not be enzymatically degraded. Lipofuscin, and thus A2E, accumulate with aging of the human eye and also accumulate in a juvenile form of macular degeneration called Stargardt's disease, and in several other congenital retinal dystrophies.

A2E may induce damage to the retina via several different mechanisms. At low concentrations, A2E inhibits normal proteolysis in lysosomes (Holz et al., *Invest. Ophthalmol. Vis. Sci.* 40:737-43 (1999)). At higher, sufficient concentrations, A2E may act as a positively charged lysosomotropic detergent, dissolving cellular membranes, and may alter lysosomal function, release proapoptotic proteins from mitochondria, and ultimately kill the RPE cell (see, e.g., Eldred et al., supra; Sparrow et al., *Invest. Ophthalmol. Vis. Sci.* 40:2988-95 (1999); Holz et al., supra; Finneman et al., *Proc. Natl. Acad. Sci. USA* 99:3842-347 (2002); Suter et al., *J. Biol. Chem.* 275:39625-30 (2000)). A2E is phototoxic and initiates blue light-induced apoptosis in RPE cells (see, e.g., Sparrow et al., *Invest. Ophthalmol. Vis. Sci.* 43:1222-27 (2002)). Upon exposure to blue light, photooxidative products of A2E are formed (e.g., epoxides) that damage cellular macromolecules, including DNA (Sparrow et al., *J. Biol. Chem.* 278(20):18207-13 (2003)). A2E self-generates singlet oxygen that reacts with A2E to generate epoxides at carbon-carbon double bonds (Sparrow et al., supra). Generation of oxygen reactive species upon photoexcitation of A2E causes oxidative damage to the cell, often resulting in cell death. An indirect method of blocking formation of A2E by inhibiting biosynthesis of the direct precursor of A2E, all-trans-retinal, has been described (see U.S. Patent Application Publication No. 2003/0032078). However, the usefulness of the method described therein is limited because generation of all-trans retinal is an important component of the visual cycle. Other therapies described include neutralizing damage caused by oxidative radical species by using superoxide-dismutase mimetics (see, e.g., U.S. Patent Application Publication No. 2004/0116403) and inhibiting A2E-induced cytochrome C oxidase in retinal cells with negatively charged phospholipids (see, e.g., U.S. Patent Application Publication No. 2003/0050283).

The alkoxyphenyl-linked amine derivative compounds described herein may be useful for preventing, reducing, inhibiting, or decreasing accumulation (i.e., deposition) of A2E and A2E-related and/or derived molecules in the RPE. Without wishing to be bound by theory, because the RPE is critical for the maintenance of the integrity of photoreceptor cells, preventing, reducing, or inhibiting damage to the RPE may inhibit degeneration (i.e., enhance the survival or increase or prolong cell viability) of retinal neuronal cells, particularly, photoreceptor cells. Compounds that bind specifically to or interact with A2E, A2E-related and/or derived molecules, or that affect A2E formation or accumulation may also reduce, inhibit, prevent, or decrease one or more toxic effects of A2E or of A2E-related and/or derived molecules that result in retinal neuronal cell (including a photoreceptor cell) damage, loss, or neurodegeneration, or in some manner decrease retinal neuronal cell viability. Such toxic effects include induction of apoptosis, self-generation of singlet oxygen and generation of oxygen reactive species; self-generation of singlet oxygen to form A2E-epoxides that induce DNA lesions, thus damaging cellular DNA and inducing cellular damage; dissolving cellular membranes; altering lysosomal function; and effecting release of proapoptotic proteins from mitochondria.

In other embodiments, the compounds described herein may be used for treating other ophthalmic diseases or disorders, for example, glaucoma, cone-rod dystrophy, retinal detachment, hemorrhagic or hypertensive retinopathy, retinitis pigmentosa, optic neuropathy, inflammatory retinal disease, proliferative vitreoretinopathy, genetic retinal dystrophies, traumatic injury to the optic nerve (such as by physical injury, excessive light exposure, or laser light), hereditary optic neuropathy, neuropathy due to a toxic agent or caused by adverse drug reactions or vitamin deficiency, Sorsby's fundus dystrophy, uveitis, a retinal disorder associated with Alzheimer's disease, a retinal disorder associated with multiple sclerosis; a retinal disorder associated with viral infection (cytomegalovirus or herpes simplex virus), a retinal disorder associated with Parkinson's disease, a retinal disorder associated with AIDS, or other forms of progressive retinal atrophy or degeneration. In another specific embodiment, the disease or disorder results from mechanical injury, chemical or drug-induced injury, thermal injury, radiation injury, light injury, laser injury. The subject compounds are useful for treating both hereditary and non-hereditary retinal dystrophy. These methods are also useful for preventing ophthalmic injury from environmental factors such as light-induced oxidative retinal damage, laser-induced retinal damage, "flash bomb injury," or "light dazzle", refractive errors including but not limited to myopia (see, e.g., Quinn G E et al. *Nature* 1999; 399:113-114; Zadnik K et al. *Nature* 2000; 404:143-144; Gwiazda J et al. *Nature* 2000; 404: 144), etc.

In other embodiments, methods are provided herein for inhibiting neovascularization (including but not limited to neovascular glycoma) in the retina using any one or more of the alkoxyphenyl-linked amine derivative compound as described in detail herein, including a compound having the structure as set forth in any one of Formulae (A)-(E), (I), (II), (IIa), (IIb), and substructures thereof, and the specific alkoxyphenyl-linked amine compounds described herein. In certain other embodiments, methods are provided for reducing hypoxia in the retina using the compounds described herein. These methods comprise administering to a subject, in need thereof, a composition comprising a pharmaceutically acceptable or suitable excipient (i.e., pharmaceutically acceptable or suitable carrier) and a alkoxyphenyl-linked amine derivative compound as described in detail herein, including a compound having the structure as set forth in any one of Formulae (I), (II), (IIa), (IIb), and substructures thereof, and the specific alkoxyphenyl-linked amine compounds described herein.

Merely by way of explanation and without being bound by any theory, and as discussed in further detail herein, dark-adapted rod photoreceptors engender a very high metabolic demand (i.e., expenditure of energy (ATP consumption) and consumption of oxygen). The resultant hypoxia may cause and/or exacerbate retinal degeneration, which is likely exaggerated under conditions in which the retinal vasculature is already compromised, including, but not limited to, such conditions as diabetic retinopathy, macular edema, diabetic maculopathy, retinal blood vessel occlusion (which includes retinal venous occlusion and retinal arterial occlusion), retinopathy of prematurity, ischemia reperfusion related retinal injury, as well as in the wet form of age-related macular degeneration (AMD). Furthermore, retinal degeneration and hypoxia may lead to neovascularization, which in turn may worsen the extent of retinal degeneration. The alkoxyphenyl amine derivative compounds described herein that modulate the visual cycle can be administered to prevent, inhibit, and/or delay dark adaptation of rod photoreceptor cells, and may therefore reduce metabolic demand, thereby reducing hypoxia and inhibiting neovascularization.

By way of background, oxygen is a critical metabolite for preservation of retinal function in mammals, and retinal hypoxia may be a factor in many retinal diseases and disorders that have ischemia as a component. In most mammals (including humans) with dual vascular supply to the retina, oxygenation of the inner retina is achieved through the intraretinal microvasculature, which is sparse compared to the choriocapillaris that supplies oxygen to the RPE and photoreceptors. The different vascular supply networks create an uneven oxygen tension across the thickness of the retina (Cringle et al., *Invest. Ophthalmol. Vis. Sci.* 43:1922-27 (2002)). Oxygen fluctuation across the retinal layers is related to both the differing capillary densities and disparity in oxygen consumption by various retinal neurons and glia.

Local oxygen tension can significantly affect the retina and its microvasculature by regulation of an array of vasoactive agents, including, for example, vascular endothelial growth factor (VEGF). (See, e.g., Werdich et al., *Exp. Eye Res.* 79:623 (2004); Arden et al., *Br. J Ophthalmol.* 89:764

(2005)). Rod photoreceptors are believed to have the highest metabolic rate of any cell in the body (see, e.g., Arden et al., supra). During dark adaptation, the rod photoreceptors recover their high cytoplasmic calcium levels via cGMP-gated calcium channels with concomitant extrusion of sodium ions and water. The efflux of sodium from the cell is an ATP-dependent process, such that the retinal neurons consume up to an estimated five times more oxygen under scotopic (i.e., dark adapted), compared with photopic (i.e., light adapted) conditions. Thus, during characteristic dark adaptation of photoreceptors, the high metabolic demand leads to significant local reduction of oxygen levels in the dark-adapted retina (Ahmed et al, *Invest. Ophthalmol. Vis. Sci.* 34:516 (1993)).

Without being bound by any one theory, retinal hypoxia may be further increased in the retina of subjects who have diseases or conditions such as, for example, central retinal vein occlusion in which the retinal vasculature is already compromised. Increasing hypoxia may increase susceptibility to sight-threatening, retinal neovascularization. Neovascularization is the formation of new, functional microvascular networks with red blood cell perfusion, and is a characteristic of retinal degenerative disorders, including, but not limited to, diabetic retinopathy, retinopathy of prematurity, wet AMD and central retinal vein occlusions. Preventing or inhibiting dark adaptation of rod photoreceptor cells, thereby decreasing expenditure of energy and consumption of oxygen (i.e., reducing metabolic demand), may inhibit or slow retinal degeneration, and/or may promote regeneration of retinal cells, including rod photoreceptor cells and retinal pigment epithelial (RPE) cells, and may reduce hypoxia and may inhibit neovascularization.

Methods are described herein for inhibiting (i.e., reducing, preventing, slowing or retarding, in a biologically or statistically significant manner) degeneration of retinal cells (including retinal neuronal cells as described herein and RPE cells) and/or for reducing (i.e., preventing or slowing, inhibiting, abrogating in a biologically or statistically significant manner) retinal ischemia. Methods are also provided for inhibiting (i.e., reducing, preventing, slowing or retarding, in a biologically or statistically significant manner) neovascularization in the eye, particularly in the retina. Such methods comprise contacting the retina, and thus, contacting retinal cells (including retinal neuronal cells such as rod photoreceptor cells, and RPE cells) with at least one of the alkoxyphenyl amine derivative compounds described herein that inhibits at least one visual cycle trans-cis isomerase (which may include inhibition of isomerization of an all-trans-retinyl ester), under conditions and at a time that may prevent, inhibit, or delay dark adaptation of a rod photoreceptor cell in the retina. As described in further detail herein, in particular embodiments, the compound that contacts the retina interacts with an isomerase enzyme or enzymatic complex in a RPE cell in the retina and inhibits, blocks, or in some manner interferes with the catalytic activity of the isomerase. Thus, isomerization of an all-trans-retinyl ester is inhibited or reduced. The at least one strenyl derivative compound (or composition comprising at least one compound) may be administered to a subject who has developed and manifested an ophthalmic disease or disorder or who is at risk of developing an ophthalmic disease or disorder, or to a subject who presents or who is at risk of presenting a condition such as retinal neovascularization or retinal ischemia.

By way of background, the visual cycle (also called retinoid cycle) refers to the series of enzyme and light-mediated conversions between the 11-cis and all-trans forms of retinol/retinal that occur in the photoreceptor and retinal pigment epithelial (RPE) cells of the eye. In vertebrate photoreceptor cells, a photon causes isomerization of the 11-cis-retinylidene chromophore to all-trans-retinylidene coupled to the visual opsin receptors. This photoisomerization triggers conformational changes of opsins, which, in turn, initiate the biochemical chain of reactions termed phototransduction (Filipek et al., *Annu. Rev. Physiol.* 65 851-79 (2003)). After absorption of light and photoisomerization of 11-cis-retinal to all-trans retinal, regeneration of the visual chromophore is a critical step in restoring photoreceptors to their dark-adapted state. Regeneration of the visual pigment requires that the chromophore be converted back to the 11-cis-configuration (reviewed in McBee et al., *Prog. Retin. Eye Res.* 20:469-52 (2001)). The chromophore is released from the opsin and reduced in the photoreceptor by retinol dehydrogenases. The product, all-trans-retinol, is trapped in the adjacent retinal pigment epithelium (RPE) in the form of insoluble fatty acid esters in subcellular structures known as retinosomes (Imanishi et al., *J. Cell Biol.* 164:373-78 (2004)).

During the visual cycle in rod receptor cells, the 11-cis retinal chromophore within the visual pigment molecule, which is called rhodopsin, absorbs a photon of light and is isomerized to the all-trans configuration, thereby activating the phototransduction cascade. Rhodopsin is a G-protein coupled receptor (GPCR) that consists of seven membrane-spanning helices that are interconnected by extracellular and cytoplasmic loops. When the all-trans form of the retinoid is still covalently bound to the pigment molecule, the pigment is referred to as metarhodopsin, which exists in different forms (e.g., metarhodopsin I and metarhodopsin II). The all-trans retinoid is then hydrolyzed and the visual pigment is in the form of the apoprotein, opsin, which is also called apo-rhodopsin in the art and herein. This all-trans retinoid is transported or chaperoned out of the photoreceptor cell and across the extracellular space to the RPE cells, where the retinoid is converted to the 11-cis isomer. The movement of the retinoids between the RPE and photoreceptors cells is believed to be accomplished by different chaperone polypeptides in each of the cell types. See Lamb et al., *Progress in Retinal and Eye Research* 23:307-80 (2004).

Under light conditions, rhodopsin continually transitions through the three forms, rhodopsin, metarhodopsin, and apo-rhodopsin. When most of the visual pigment is in the rhodopsin form (i.e., bound with 11-cis retinal), the rod photoreceptor cell is in a "dark-adapted" state. When the visual pigment is predominantly in the metarhodopsin form (i.e., bound with all-trans-retinal), the state of the photoreceptor cell is referred to as a "light-adapted," and when the visual pigment is apo-rhodopsin (or opsin) and no longer has bound chromophore, the state of the photoreceptor cell is referred to as "rhodopsin-depleted." Each of the three states of the photoreceptor cell has different energy requirements, and differing levels of ATP and oxygen are consumed. In the dark-adapted state, rhodopsin has no regulatory effect on cation channels, which are open, resulting in an influx of cations ($Na^+/K^+$ and $Ca^{2+}$). To maintain the proper level of these cations in the cell during the dark state, the photoreceptor cells actively transport the cations out of the cell via ATP-dependent pumps. Thus maintenance of this "dark current" requires a large amount of energy, resulting in high metabolic demand. In the light-adapted state, metarhodopsin triggers an enzymatic cascade process that results in hydrolysis of GMP, which in turn, closes cation-specific channels in the photoreceptor cell membrane. In the rhodopsin-depleted state, the chromophore is hydrolyzed from metarhodopsin to form the apoprotein, opsin (apo-rhodopsin), which partially regulates the cation channels such that the rod photoreceptor cells exhibit an attenuated current compared with the photoreceptor in the dark-adapted state, resulting in a moderate metabolic demand.

Under normal light conditions, the incidence of rod photoreceptors in the dark adapted state is small, in general, 2% or less, and the cells are primarily in the light-adapted or rhodopsin-depleted states, which overall results in a relatively low metabolic demand compared with cells in the dark-adapted state. At night, however, the relative incidence of the dark-adapted photoreceptor state increases profoundly, due to the absence of light adaptation and to the continued operation of the "dark" visual cycle in RPE cells, which replenishes the rod photoreceptor cells with 11-cis-retinal. This shift to dark adaptation of the rod photoreceptor causes an increase in metabolic demand (that is, increased ATP and oxygen consumption), leading ultimately to retinal hypoxia and subsequent initiation of angiogenesis. Most ischaemic insults to the retina therefore occur in the dark, for example, at night during sleep.

Without being bound by any theory, therapeutic intervention during the "dark" visual cycle may prevent retinal hypoxia and neovascularization that are caused by high metabolic activity in the dark-adapted rod photoreceptor cell. Merely by way of one example, altering the "dark" visual cycle by administering any one of the compounds described herein, which is an isomerase inhibitor, rhodopsin (i.e., 11-cis retinal bound) may be reduced or depleted, preventing or inhibiting dark adaptation of rod photoreceptors. This in turn may reduce retinal metabolic demand, attenuating the nighttime risk of retinal ischemia and neovascularization, and thereby inhibiting or slowing retinal degeneration.

In one embodiment, at least one of the compounds described herein (i.e., an alkoxyphenyl-linked amine derivative compound as described in detail herein, including a compound having the structure as set forth in any one of Formulae (A)-(E), (I), (II), (IIa), (IIb), and substructures thereof, and the specific alkoxyphenyl-linked amine compounds described herein) that, for example, blocks, reduces, inhibits, or in some manner attenuates the catalytic activity of a visual cycle isomerase in a statistically or biologically significant manner, may prevent, inhibit, or delay dark adaptation of a rod photoreceptor cell, thereby inhibiting (i.e., reducing, abrogating, preventing, slowing the progression of, or decreasing in a statistically or biologically significant manner) degeneration of retinal cells (or enhancing survival of retinal cells) of the retina of an eye. In another embodiment, the alkoxyphenyl-linked amine derivative compounds may prevent or inhibit dark adaptation of a rod photoreceptor cell, thereby reducing ischemia (i.e., decreasing, preventing, inhibiting, slowing the progression of ischemia in a statistically or biologically significant manner). In yet another embodiment, any one of the alkoxyphenyl-linked amine derivative compounds described herein may prevent dark adaptation of a rod photoreceptor cell, thereby inhibiting neovascularization in the retina of an eye. Accordingly, methods are provided herein for inhibiting retinal cell degeneration, for inhibiting neovascularization in the retina of an eye of a subject, and for reducing ischemia in an eye of a subject wherein the methods comprise administering at least one alkoxyphenyl-linked amine derivative compound described herein, under conditions and at a time sufficient to prevent, inhibit, or delay dark adaptation of a rod photoreceptor cell. These methods and compositions are therefore useful for treating an ophthalmic disease or disorder including, but not limited to, diabetic retinopathy, diabetic maculopathy, retinal blood vessel occlusion, retinopathy of prematurity, or ischemia reperfusion related retinal injury.

The alkoxyphenyl-linked amine derivative compounds described herein (i.e., an alkoxyphenyl-linked amine derivative compound as described in detail herein, including a compound having the structure as set forth in any one of Formulae (A)-(E), (I), (II), (IIa), (IIb), and substructures thereof, and the specific alkoxyphenyl-linked amine compounds described herein) may prevent (i.e., delay, slow, inhibit, or decrease) recovery of the visual pigment chromophore, which may prevent or inhibit or retard the formation of retinals and may increase the level of retinyl esters, which perturbs the visual cycle, inhibiting regeneration of rhodopsin, and which prevents, slows, delays or inhibits dark adaptation of a rod photoreceptor cell. In certain embodiments, when dark adaptation of rod photoreceptor cells is prevented in the presence of the compound, dark adaptation is substantially prevented, and the number or percent of rod photoreceptor cells that are rhodopsin-depleted or light adapted is increased compared with the number or percent of cells that are rhodopsin-depleted or light-adapted in the absence of the agent. Thus, in certain embodiments when dark adaptation of rod photoreceptor cells is prevented (i.e., substantially prevented), only at least 2% of rod photoreceptor cells are dark-adapted, similar to the percent or number of cells that are in a dark-adapted state during normal, light conditions. In other certain embodiments, at least 5-10%, 10-20%, 20-30%, 30-40%, 40-50%, 50-60%, or 60-70% of rod photoreceptor cells are dark-adapted after administration of an agent. In other embodiments, the compound acts to delay dark adaptation, and in the presence of the compound dark adaptation of rod photoreceptor cells may be delayed 30 minutes, one hour, two hours, three hours, or four hours compared to dark adaptation of rod photoreceptors in the absence of the compound. By contrast, when an alkoxyphenyl-linked amine derivative compound is administered such that the compound effectively inhibits isomerization of substrate during light-adapted conditions, the compound is administered in such a manner to minimize the percent of rod photoreceptor cells that are dark-adapted, for example, only 2%, 5%, 10%, 20%, or 25% of rod photoreceptors are dark-adapted (see e.g., U.S. Patent Application Publication No. 2006/0069078; Patent Application No. PCT/US2007/002330).

In the retina in the presence of at least one alkoxyphenyl-linked amine derivative compound, regeneration of rhodopsin in a rod photoreceptor cell may be inhibited or the rate of regeneration may be reduced (i.e., inhibited, reduced, or decreased in a statistically or biologically significant manner), at least in part, by preventing the formation of retinals, reducing the level of retinals, and/or increasing the level of retinyl esters. To determine the level of regeneration of rhodopsin in a rod photoreceptor cell, the level of regeneration of rhodopsin (which may be called a first level) may be determined prior to permitting contact between the compound and the retina (i.e., prior to administration of the agent). After a time sufficient for the compound and the retina and cells of the retina to interact, (i.e., after administration of the compound), the level of regeneration of rhodopsin (which may be called a second level) may be determined. A decrease in the second level compared with the first level indicates that the compound inhibits regeneration of rhodopsin. The level of rhodopsin generation may be determined after each dose, or after any number of doses, and ongoing throughout the therapeutic regimen to characterize the effect of the agent on regeneration of rhodopsin.

In certain embodiments, the subject in need of the treatments described herein, may have a disease or disorder that results in or causes impairment of the capability of rod photoreceptors to regenerate rhodopsin in the retina. By way of example, inhibition of rhodopsin regeneration (or reduction of the rate of rhodopsin regeneration) may be symptomatic in patients with diabetes. In addition to determining the level of regeneration of rhodopsin in the subject who has diabetes before and after administration of an alkoxyphenyl-linked amine derivative compound described herein, the effect of the compound may also be characterized by comparing inhibition of rhodopsin regeneration in a first subject (or a first group or plurality of subjects) to whom the compound is administered, to a second subject (or second group or plurality of subjects) who has diabetes but who does not receive the agent.

In another embodiment, a method is provided for preventing or inhibiting dark adaptation of a rod photoreceptor cell (or a plurality of rod photoreceptor cells) in a retina comprising contacting the retina and at least one of the alkoxyphenyl-linked amine derivative compounds described herein (i.e., a compound as described in detail herein, including a compound having the structure as set forth in any one of Formulae (I), (II), (IIa), (IIb), and substructures thereof, and the specific alkoxyphenyl-linked amine compounds described herein), under conditions and at a time sufficient to permit interaction between the agent and an isomerase present in a retinal cell (such as an RPE cell). A first level of 11-cis-retinal in a rod photoreceptor cell in the presence of the compound may be determined and compared to a second level of 11-cis-retinal in a rod photoreceptor cell in the absence of the compound. Prevention or inhibition of dark adaptation of the rod photoreceptor cell is indicated when the first level of 11-cis-retinal is less than the second level of 11-cis-retinal.

Inhibiting regeneration of rhodopsin may also include increasing the level of 11-cis-retinyl esters present in the RPE cell in the presence of the compound compared with the level of 11-cis-retinyl esters present in the RPE cell in the absence of the compound (i.e., prior to administration of the agent). A two-photon imaging technique may be used to view and analyze retinosome structures in the RPE, which structures are believed to store retinyl esters (see, e.g., Imanishi et al., *J. Cell Biol.* 164:373-83 (2004), Epub 2004 January 26.). A first level of retinyl esters may be determined prior to administration of the compound, and a second level of retinyl esters may be determined after administration of a first dose or any subsequent dose, wherein an increase in the second level compared to the first level indicates that the compound inhibits regeneration of rhodopsin.

Retinyl esters may be analyzed by gradient HPLC according to methods practiced in the art (see, for example, Mata et al., *Neuron* 36:69-80 (2002); Trevino et al. *J. Exp. Biol.* 208:4151-57 (2005)). To measure 11-cis and all-trans retinals, retinoids may be extracted by a formaldehyde method (see, e.g., Suzuki et al., *Vis. Res.* 28:1061-70 (1988); Okajima and Pepperberg, *Exp. Eye Res.* 65:331-40 (1997)) or by a hydroxylamine method (see, e.g., Groenendijk et al., *Biochim. Biophys. Acta.* 617:430-38 (1980)) before being analyzed on isocratic HPLC (see, e.g., Trevino et al., supra). The retinoids may be monitored spectrophotometrically (see, e.g., Maeda et al., *J. Neurochem.* 85:944-956 (2003); Van Hooser et al., *J. Biol. Chem.* 277:19173-82 (2002)).

In another embodiment of the methods described herein for treating an ophthalmic disease or disorder, for inhibiting retinal cell degeneration (or enhancing retinal cell survival), for inhibiting neovascularization, and for reducing ischemia in the retina, preventing or inhibiting dark adaptation of a rod photoreceptor cell in the retina comprises increasing the level of apo-rhodopsin (also called opsin) in the photoreceptor cell. The total level of the visual pigment approximates the sum of rhodopsin and apo-rhodopsin and the total level remains constant. Therefore, preventing, delaying, or inhibiting dark adaptation of the rod photoreceptor cell may alter the ratio of apo-rhodopsin to rhodopsin. In particular embodiments, preventing, delaying, or inhibiting dark adaptation by administering an alkoxyphenyl-linked amine derivative compound described herein may increase the ratio of the level of apo-rhodopsin to the level of rhodopsin compared to the ratio in the absence of the agent (for example, prior to administration of the agent). An increase in the ratio (i.e., a statistically or biologically significant increase) of apo-rhodopsin to rhodopsin indicates that the percent or number of rod photoreceptor cells that are rhodopsin-depleted is increased and that the percent or number of rod photoreceptor cells that are dark-adapted is decreased. The ratio of apo-rhodopsin to rhodopsin may be determined throughout the course of therapy to monitor the effect of the agent.

Determining or characterizing the capability of compound to prevent, delay, or inhibit dark adaptation of a rod photoreceptor cell may be determined in animal model studies. The level of rhodopsin and the ratio of apo-rhodopsin to rhodopsin may be determined prior to administration (which may be called a first level or first ratio, respectively) of the agent and then after administration of a first or any subsequent dose of the agent (which may be called a second level or second ratio, respectively) to determine and to demonstrate that the level of apo-rhodopsin is greater than the level of apo-rhodopsin in the retina of animals that did not receive the agent. The level of rhodopsin in rod photoreceptor cells may be performed according to methods practiced in the art and provided herein (see, e.g., Yan et al. *J. Biol. Chem.* 279:48189-96 (2004)).

A subject in need of such treatment may be a human or may be a non-human primate or other animal (i.e., veterinary use) who has developed symptoms of an ophthalmic disease or disorder or who is at risk for developing an ophthalmic disease or disorder. Examples of non-human primates and other animals include but are not limited to farm animals, pets, and zoo animals (e.g., horses, cows, buffalo, llamas, goats, rabbits, cats, dogs, chimpanzees, orangutans, gorillas, monkeys, elephants, bears, large cats, etc.).

Also provided herein are methods for inhibiting (reducing, slowing, preventing) degeneration and enhancing retinal neuronal cell survival (or prolonging cell viability) comprising administering to a subject a composition comprising a pharmaceutically acceptable carrier and an alkoxyphenyl-linked amine derivative compound described in detail herein, including a compound having any one of the structures set forth in Formulae (I), (II), (IIa) and (IIb) substructures thereof, and specific alkoxyphenyl-linked amine compounds recited herein. Retinal neuronal cells include photoreceptor cells, bipolar cells, horizontal cells, ganglion cells, and amacrine cells. In another embodiment, methods are provided for enhancing survival or inhibiting degeneration of a mature retinal cell such as a RPE cell or a Miller glial cell. In other embodiments, a method for preventing or inhibiting photoreceptor degeneration in an eye of a subject are provided. A method that prevents or inhibits photoreceptor degeneration may include a method for restoring photoreceptor function in an eye of a subject.

Such methods comprise administering to the subject a composition comprising an alkoxyphenyl-linked amine derivative compound as described herein and a pharmaceutically or acceptable carrier (i.e., excipient or vehicle). More specifically, these methods comprise administering to a subject a pharmaceutically acceptable excipient and an alkoxyphenyl-linked amine derivative compound described herein, including a compound having any one of the structures set forth in Formulae (I), (II), (IIa) and (IIb) or substructures thereof described herein. Without wishing to be bound by theory, the compounds described herein may inhibit an isomerization step of the retinoid cycle (i.e., visual cycle) and/or may slow chromophore flux in a retinoid cycle in the eye.

The ophthalmic disease may result, at least in part, from lipofuscin pigment(s) accumulation and/or from accumulation of N-retinylidene-N-retinylethanolamine (A2E) in the eye. Accordingly, in certain embodiments, methods are provided for inhibiting or preventing accumulation of lipofuscin pigment(s) and/or A2E in the eye of a subject. These methods comprise administering to the subject a composition comprising a pharmaceutically acceptable carrier and an alkoxyphenyl-linked amine compound as described in detail herein, including a compound having the structure as set forth in any one of Formulae (A)-(E), (I), (II), (IIa) and (IIb) or substructures thereof.

An alkoxyphenyl-linked amine compound can be administered to a subject who has an excess of a retinoid in an eye (e.g., an excess of 11-cis-retinol or 11-cis-retinal), an excess of retinoid waste products or intermediates in the recycling of all-trans-retinal, or the like. Methods described herein and practiced in the art may be used to determine whether the level of one or more endogenous retinoids in a subject are altered (increased or decreased in a statistically significant or biologically significant manner) during or after administration of any one of the compounds described herein. Rhodopsin, which is composed of the protein opsin and retinal (a vitamin A form), is located in the membrane of the photoreceptor cell in the retina of the eye and catalyzes the only light-sensitive step in vision. The 11-cis-retinal chromophore lies in a pocket of the protein and is isomerized to all-trans retinal when light is absorbed. The isomerization of retinal leads to a change of the shape of rhodopsin, which triggers a cascade of reactions that lead to a nerve impulse that is transmitted to the brain by the optic nerve.

Methods of determining endogenous retinoid levels in a vertebrate eye, and an excess or deficiency of such retinoids, are disclosed in, for example, U.S. Patent Application Publication No: 2005/0159662 (the disclosure of which is incorporated by reference herein in its entirety). Other methods of determining endogenous retinoid levels in a subject, which is useful for determining whether levels of such retinoids are above the normal range, and include for example, analysis by high pressure liquid chromatography (HPLC) of retinoids in a biological sample from a subject. For example, retinoid levels can be determined in a biological sample that is a blood sample (which includes serum or plasma) from a subject. A biological sample may also include vitreous fluid, aqueous humor, intraocular fluid, subretinal fluid, or tears.

For example, a blood sample can be obtained from a subject, and different retinoid compounds and levels of one or more of the retinoid compounds in the sample can be separated and analyzed by normal phase high pressure liquid chromatography (HPLC) (e.g., with a HP 1100 HPLC and a Beckman, Ultrasphere-Si, 4.6 mm×250 mm column using 10% ethyl acetate/90% hexane at a flow rate of 1.4 ml/minute). The retinoids can be detected by, for example, detection at 325 nm using a diode-array detector and HP Chemstation A.03.03 software. An excess in retinoids can be determined, for example, by comparison of the profile of retinoids (i.e., qualitative, e.g., identity of specific compounds, and quantitative, e.g., the level of each specific compound) in the sample with a sample from a normal subject. Persons skilled in the art who are familiar with such assays and techniques and will readily understand that appropriate controls are included.

As used herein, increased or excessive levels of endogenous retinoid, such as 11-cis-retinol or 11-cis-retinal, refer to levels of endogenous retinoid higher than those found in a healthy eye of a young vertebrate of the same species. Administration of an alkoxyphenyl-linked amine derivative compound and reduce or eliminate the requirement for endogenous retinoid. In certain embodiments, the level of endogenous retinoid may be compared before and after any one or more doses of an alkoxyphenyl-linked amine compound is administered to a subject to determine the effect of the compound on the level of endogenous retinoids in the subject.

In another embodiment, the methods described herein for treating an ophthalmic disease or disorder, for inhibiting neovascularization, and for reducing ischemia in the retina comprise administering at least one of the alkoxyphenyl-linked amine compounds described herein, thereby effecting a decrease in metabolic demand, which includes effecting a reduction in ATP consumption and in oxygen consumption in rod photoreceptor cells. As described herein, consumption of ATP and oxygen in a dark-adapted rod photoreceptor cell is greater than in rod photoreceptor cells that are light-adapted or rhodopsin-depleted; thus, use of the compounds in the methods described herein may reduce the consumption of ATP in the rod photoreceptor cells that are prevented, inhibited, or delayed from dark adaptation compared with rod photoreceptor cells that are dark-adapted (such as the cells prior to administration or contact with the compound or cells that are never exposed to the compound).

The methods described herein that may prevent or inhibit dark adaptation of a rod photoreceptor cell may therefore reduce hypoxia (i.e., reduce in a statistically or biologically significant manner) in the retina. For example, the level of hypoxia (a first level) may be determined prior to initiation of the treatment regimen, that is, prior to the first dosing of the compound (or a composition, as described herein, comprising the compound). The level of hypoxia (for example, a second level) may be determined after the first dosing, and/or after any second or subsequent dosing to monitor and characterize hypoxia throughout the treatment regimen. A decrease (reduction) in the second (or any subsequent) level of hypoxia compared to the level of hypoxia prior to initial administration indicates that the compound and the treatment regiment prevent dark adaptation of the rod photoreceptor cells and may be used for treating ophthalmic diseases and disorders. Consumption of oxygen, oxygenation of the retina, and/or hypoxia in the retina may be determined using methods practiced in the art. For example, oxygenation of the retina may be determined by measuring the fluorescence of flavoproteins in the retina (see, e.g., U.S. Pat. No. 4,569,354). Another exemplary method is retinal oximetry that measures blood oxygen saturation in the large vessels of the retina near the optic disc. Such methods may be used to identify and determine the extent of retinal hypoxia before changes in retinal vessel architecture can be detected.

A biological sample may be a blood sample (from which serum or plasma may be prepared), biopsy specimen, body fluids (e.g., vitreous fluid, aqueous humor, intraocular fluid, subretinal fluid, or tears), tissue explant, organ culture, or any other tissue or cell preparation from a subject or a biological source. A sample may further refer to a tissue or cell preparation in which the morphological integrity or physical state has been disrupted, for example, by dissection, dissociation, solubilization, fractionation, homogenization, biochemical or chemical extraction, pulverization, lyophilization, sonication, or any other means for processing a sample derived from a subject or biological source. The subject or biological source may be a human or non-human animal, a primary cell culture (e.g., a retinal cell culture), or culture adapted cell line, including but not limited to, genetically engineered cell lines that may contain chromosomally integrated or episomal recombinant nucleic acid sequences, immortalized or immortalizable cell lines, somatic cell hybrid cell lines, differentiated or differentiatable cell lines, transformed cell lines, and the like. Mature retinal cells, including retinal neuronal cells, RPE cells, and Miller glial cells, may be present in or isolated from a biological sample as described herein. For example, the mature retinal cell may be obtained from a primary or long-term cell culture or may be present in or isolated from a biological sample obtained from a subject (human or non-human animal).

Retinal Cells

The retina is a thin layer of nervous tissue located between the vitreous body and choroid in the eye. Major landmarks in the retina are the fovea, the macula, and the optic disc. The retina is thickest near the posterior sections and becomes thinner near the periphery. The macula is located in the posterior retina and contains the fovea and foveola. The foveola contains the area of maximal cone density and, thus, imparts the highest visual acuity in the retina. The foveola is contained within the fovea, which is contained within the macula.

The peripheral portion of the retina increases the field of vision. The peripheral retina extends anterior to the ciliary body and is divided into four regions: the near periphery (most posterior), the mid-periphery, the far periphery, and the ora serrata (most anterior). The ora serrata denotes the termination of the retina.

The term neuron (or nerve cell) as understood in the art and used herein denotes a cell that arises from neuroepithelial cell precursors. Mature neurons (i.e., fully differentiated cells) display several specific antigenic markers. Neurons may be classified functionally into four groups: (1) afferent neurons (or sensory neurons) that transmit information into the brain for conscious perception and motor coordination; (2) motor neurons that transmit commands to muscles and glands; (3) interneurons that are responsible for local circuitry; and (4) projection interneurons that relay information from one region of the brain to anther region and therefore have long axons. Interneurons process information within specific subregions of the brain and have relatively shorter axons. A neuron typically has four defined regions: the cell body (or soma); an axon; dendrites; and presynaptic terminals. The dendrites serve as the primary input of information from other neural cells. The axon carries the electrical signals that are initiated in the cell body to other neurons or to effector organs. At the presynaptic terminals, the neuron transmits information to another cell (the postsynaptic cell), which may be another neuron, a muscle cell, or a secretory cell.

The retina is composed of several types of neuronal cells. As described herein, the types of retinal neuronal cells that may be cultured in vitro by this method include photoreceptor cells, ganglion cells, and interneurons such as bipolar cells, horizontal cells, and amacrine cells. Photoreceptors are specialized light-reactive neural cells and comprise two major classes, rods and cones. Rods are involved in scotopic or dim light vision, whereas photopic or bright light vision originates in the cones. Many neurodegenerative diseases, such as AMD, that result in blindness affect photoreceptors.

Extending from their cell bodies, the photoreceptors have two morphologically distinct regions, the inner and outer segments. The outer segment lies furthermost from the photoreceptor cell body and contains disks that convert incoming light energy into electrical impulses (phototransduction). The outer segment is attached to the inner segment with a very small and fragile cilium. The size and shape of the outer segments vary between rods and cones and are dependent upon position within the retina. See Hogan, "Retina" in *Histology of the Human Eye: an Atlas and Text Book* (Hogan et al. (eds). WB Saunders; Philadelphia, Pa. (1971)); *Eye and Orbit*, $8^{th}$ Ed., Bron et al., (Chapman and Hall, 1997).

Ganglion cells are output neurons that convey information from the retinal interneurons (including horizontal cells, bipolar cells, amacrine cells) to the brain. Bipolar cells are named according to their morphology, and receive input from the photoreceptors, connect with amacrine cells, and send output radially to the ganglion cells. Amacrine cells have processes parallel to the plane of the retina and have typically inhibitory output to ganglion cells. Amacrine cells are often subclassified by neurotransmitter or neuromodulator or peptide (such as calretinin or calbindin) and interact with each other, with bipolar cells, and with photoreceptors. Bipolar cells are retinal interneurons that are named according to their morphology; bipolar cells receive input from the photoreceptors and sent the input to the ganglion cells. Horizontal cells modulate and transform visual information from large numbers of photoreceptors and have horizontal integration (whereas bipolar cells relay information radially through the retina).

Other retinal cells that may be present in the retinal cell cultures described herein include glial cells, such as Müller glial cells, and retinal pigment epithelial cells (RPE). Glial cells surround nerve cell bodies and axons. The glial cells do not carry electrical impulses but contribute to maintenance of normal brain function. Müller glia, the predominant type of glial cell within the retina, provide structural support of the retina and are involved in the metabolism of the retina (e.g., contribute to regulation of ionic concentrations, degradation of neurotransmitters, and remove certain metabolites (see, e.g., Kljavin et al., *J. Neurosci.* 11:2985 (1991))). Müller's fibers (also known as sustentacular fibers of retina) are sustentacular neuroglial cells of the retina that run through the thickness of the retina from the internal limiting membrane to the bases of the rods and cones where they form a row of junctional complexes.

Retinal pigment epithelial (RPE) cells form the outermost layer of the retina, separated from the blood vessel-enriched choroids by Bruch's membrane. RPE cells are a type of phagocytic epithelial cell, with some functions that are macrophage-like, which lies immediately below the retinal photoreceptors. The dorsal surface of the RPE cell is closely apposed to the ends of the rods, and as discs are shed from the rod outer segment they are internalized and digested by RPE cells. Similar process occurs with the disc of the cones. RPE cells also produce, store, and transport a variety of factors that contribute to the normal function and survival of photoreceptors. Another function of RPE cells is to recycle vitamin A as it moves between photoreceptors and the RPE during light and dark adaptation in the process known as the visual cycle.

Described herein is an exemplary long-term in vitro cell culture system permits and promotes the survival in culture of mature retinal cells, including retinal neurons, for at least 2-4 weeks, over 2 months, or for as long as 6 months. The cell culture system may be used for identifying and characterizing the alkoxyphenyl-linked amine derivative compounds that are useful in the methods described herein for treating and/or preventing an ophthalmic disease or disorder or for preventing or inhibiting accumulation in the eye of lipofuscin(s) and/or A2E. Retinal cells are isolated from non-embryonic, non-tumorigenic tissue and have not been immortalized by any method such as, for example, transformation or infection with an oncogenic virus. The cell culture system comprises all the major retinal neuronal cell types (photoreceptors, bipolar cells, horizontal cells, amacrine cells, and ganglion cells), and also may include other mature retinal cells such as retinal pigment epithelial cells and Müller glial cells.

For example, a blood sample can be obtained from a subject, and different retinoid compounds and levels of one or more of the retinoid compounds in the sample can be separated and analyzed by normal phase high pressure liquid chromatography (HPLC) (e.g., with a HP 1100 HPLC and a Beckman, Ultrasphere-Si, 4.6 mm×250 mm column using 10% ethyl acetate/90% hexane at a flow rate of 1.4 ml/minute). The retinoids can be detected by, for example, detection at 325 nm using a diode-array detector and HP Chemstation A.03.03 software. An excess in retinoids can be determined, for example, by comparison of the profile of retinoids (i.e., qualitative, e.g., identity of specific compounds, and quantitative, e.g., the level of each specific compound) in the sample with a sample from a normal subject. Persons skilled in the art who are familiar with such assays and techniques and will readily understand that appropriate controls are included.

As used herein, increased or excessive levels of endogenous retinoid, such as 11-cis-retinol or 11-cis-retinal, refer to levels of endogenous retinoid higher than those found in a healthy eye of a young vertebrate of the same species. Administration of an alkoxyphenyl-linked amine derivative compound and reduce or eliminate the requirement for endogenous retinoid.

In Vivo and In Vitro Methods for Determining Therapeutic Effectiveness of Compounds In one embodiment, methods are provided for using the compounds described herein for enhancing or prolonging retinal cell survival, including retinal neuronal cell survival and RPE cell survival. Also provided herein are methods for inhibiting or preventing degeneration of a retinal cell, including a retinal neuronal cell (e.g., a photoreceptor cell, an amacrine cell, a horizontal cell, a bipolar cell, and a ganglion cell) and other mature retinal cells such as retinal pigment epithelial cells and Müller glial cells using the compounds described herein. Such methods comprise, in certain embodiments, administration of an alkoxyphenyl-linked amine derivative compound as described herein. Such a compound is useful for enhancing retinal cell survival, including photoreceptor cell survival and retinal pigment epithelia survival, inhibiting or slowing degeneration of a retinal cell, and thus increasing retinal cell viability, which can result in slowing or halting the progression of an ophthalmic disease or disorder or retinal injury, which are described herein.

The effect of an alkoxyphenyl-linked amine derivative compound on retinal cell survival (and/or retinal cell degeneration) may be determined by using cell culture models, animal models, and other methods that are described herein and practiced by persons skilled in the art. By way of example, and not limitation, such methods and assays include those described in Oglivie et al., *Exp. Neurol.* 161:675-856 (2000); U.S. Pat. No. 6,406,840; WO 01/81551; WO 98/12303; U.S. Patent Application No. 2002/0009713; WO 00/40699; U.S. Pat. Nos. 6,117,675; 5,736,516; WO 99/29279; WO 01/83714; WO 01/42784; U.S. Pat. Nos. 6,183,735; 6,090,624; WO 01/09327; U.S. Pat. No. 5,641,750; U.S. Patent Application Publication No. 2004/0147019; and U.S. Patent Application Publication No. 2005/0059148.

Compounds described herein that may be useful for treating an ophthalmic disease or disorder (including a retinal disease or disorder) may inhibit, block, impair, or in some manner interfere with one or more steps in the visual cycle (also called the retinoid cycle herein and in the art). Without wishing to be bound by a particular theory, an alkoxyphenyl-linked amine derivative may inhibit or block an isomerization step in the visual cycle, for example, by inhibiting or blocking a functional activity of a visual cycle trans-cis isomerase. The compounds described herein may inhibit, directly or indirectly, isomerization of all-trans-retinol to 11-cis-retinol. The compounds may bind to, or in some manner interact with, and inhibit the isomerase activity of at least one isomerase in a retinal cell. Any one of the compounds described herein may also directly or indirectly inhibit or reduce the activity of an isomerase that is involved in the visual cycle. The compound may block or inhibit the capability of the isomerase to bind to one or more substrates, including but not limited to, an all-trans-retinyl ester substrate or all-trans-retinol. Alternatively, or in addition, the compound may bind to the catalytic site or region of the isomerase, thereby inhibiting the capability of the enzyme to catalyze isomerization of at least one substrate. On the basis of scientific data to date, an at least one isomerase that catalyzes the isomerization of a substrate during the visual cycle is believed to be located in the cytoplasm of RPE cells. As discussed herein, each step, enzyme, substrate, intermediate, and product of the visual cycle is not yet elucidated. While a polypeptide called RPE65, which has been found in the cytoplasm and membrane bound in RPE cells, is hypothesized to have isomerase activity (and has also been referred to in the art as having isomerohydrolase activity) (see, e.g., Moiseyev et al., *Proc. Natl. Acad. Sci. USA* 102:12413-18 (2004); Chen et al., *Invest. Ophthalmol. Vis. Sci.* 47:1177-84 (2006)), other persons skilled in the art believe that the RPE65 acts primarily as a chaperone for all-trans-retinyl esters (see, e.g., Lamb et al. supra).

Exemplary methods are described herein and practiced by persons skilled in the art for determining the level of enzymatic activity of a visual cycle isomerase in the presence of any one of the compounds described herein. A compound that decreases isomerase activity may be useful for treating an ophthalmic disease or disorder. Thus, methods are provided herein for detecting inhibition of isomerase activity comprising contacting (i.e., mixing, combining, or in some manner permitting the compound and isomerase to interact) a biological sample comprising the isomerase and an alkoxyphenyl-linked amine derivative compound described herein and then determining the level of enzymatic activity of the isomerase. A person having skill in the art will appreciate that as a control, the level of activity of the isomerase in the absence of a compound or in the presence of a compound known not to alter the enzymatic activity of the isomerase can be determined and compared to the level of activity in the presence of the compound. A decrease in the level of isomerase activity in the presence of the compound compared to the level of isomerase activity in the absence of the compound indicates that the compound may be useful for treating an ophthalmic disease or disorder, such as age-related macular degeneration or Stargardt's disease. A decrease in the level of isomerase activity in the presence of the compound compared to the level of isomerase activity in the absence of the compound indicates that the compound may also be useful in the methods described herein for inhibiting or preventing dark adaptation, inhibiting neovascularization and reducing hypoxia and thus useful for treating an ophthalmic disease or disorder, for example, diabetic retinopathy, diabetic maculopathy, retinal blood vessel occlusion, retinopathy of prematurity, or ischemia reperfusion related retinal injury.

The capability of an alkoxyphenyl-linked amine compound described herein to inhibit or to prevent dark adaptation of a rod photoreceptor cell by inhibiting regeneration of rhodopsin may be determined by in vitro assays and/or in vivo animal models. By way of example, inhibition of regeneration may be determined in a mouse model in which a diabetes-like condition is induced chemically or in a diabetic mouse model (see, e.g., Phipps et al., *Invest. Ophthalmol. Vis. Sci.* 47:3187-94 (2006); Ramsey et al., *Invest. Ophthalmol. Vis. Sci.* 47:5116-24 (2006)). The level of rhodopsin (a first level) may be determined (for example, spectrophotometrically) in the retina of animals prior to administration of the agent and compared with the level (a second level) of rhodopsin measured in the retina of animals after administration of the agent. A decrease in the second level of rhodopsin compared with the first level of rhodopsin indicates that the agent inhibits regeneration of rhodopsin. The appropriate controls and study design to determine whether regeneration of rhodopsin is inhibited in a statistically significant or biologically significant manner can be readily determined and implemented by persons skilled in the art.

Methods and techniques for determining or characterizing the effect of any one of the compounds described herein on dark adaptation and rhodopsin regeneration in rod photoreceptor cells in a mammal, including a human, may be performed according to procedures described herein and practiced in the art. For example, detection of a visual stimulus after exposure to light (i.e., photobleaching) versus time in darkness may be determined before administration of the first dose of the compound and at a time after the first dose and/or any subsequent dose. A second method for determining prevention or inhibition of dark adaptation by the rod photoreceptor cells includes measurement of the amplitude of at least one, at least two, at least three, or more electroretinogram components, which include, for example, the a-wave and the b-wave. See, for example, Lamb et al., supra; Asi et al., *Documenta Ophthalmologica* 79:125-39 (1992).

Inhibiting regeneration of rhodopsin by an alkoxyphenyl-linked amine compound described herein comprises reducing the level of the chromophore, 11-cis-retinal, that is produced and present in the RPE cell, and consequently reducing the level of 11-cis-retinal that is present in the photoreceptor cell. Thus, the compound, when permitted to contact the retina under suitable conditions and at a time sufficient to prevent dark adaptation of a rod photoreceptor cell and to inhibit regeneration of rhodopsin in the rod photoreceptor cell, effects a reduction in the level of 11-cis-retinal in a rod photoreceptor cell (i.e., a statistically significant or biologically significant reduction). That is, the level of 11-cis retinal in a rod photoreceptor cell is greater prior to administration of the compound when compared with the level of 11-cis-retinal in the photoreceptor cell after the first and/or any subsequent administration of the compound. A first level of 11-cis-retinal may be determined prior to administration of the compound, and a second level of 11-cis-retinal may be determined after administration of a first dose or any subsequent dose to monitor the effect of the compound. A decrease in the second level compared to the first level indicates that the compound inhibits regeneration of rhodopsin and thus inhibits or prevents dark adaptation of the rod photoreceptor cells.

An exemplary method for determining or characterizing the capability of an alkoxyphenyl-linked amine compound to reduce retinal hypoxia includes measuring the level of retinal oxygenation, for example, by Magnetic Resonance Imaging (MRI) to measure changes in oxygen pressure (see, e.g., Luan et al., *Invest. Ophthalmol. Vis. Sci.* 47:320-28 (2006)). Methods are also available and routinely practiced in the art to determine or characterize the capability of compounds described herein to inhibit degeneration of a retinal cell (see, e.g., Wenzel et al., *Prog. Retin. Eye Res.* 24:275-306 (2005)).

Animal models may be used to characterize and identify compounds that may be used to treat retinal diseases and disorders. A recently developed animal model may be useful for evaluating treatments for macular degeneration has been described by Ambati et al. (*Nat. Med.* 9:1390-97 (2003); Epub 2003 Oct. 19). This animal model is one of only a few exemplary animal models presently available for evaluating a compound or any molecule for use in treating (including preventing) progression or development of a retinal disease or disorder. Animal models in which the ABCR gene, which encodes an ATP-binding cassette transporter located in the rims of photoreceptor outer segment discs, may be used to evaluate the effect of a compound. Mutations in the ABCR gene are associated with Stargardt's disease, and heterozygous mutations in ABCR have been associated with AMD. Accordingly, animals have been generated with partial or total loss of ABCR function and may used to characterize the alkoxyphenyl-linked amine compounds described herein. (See, e.g., Mata et al., *Invest. Ophthalmol. Sci.* 42:1685-90 (2001); Weng et al., *Cell* 98:13-23 (1999); Mata et al., *Proc. Natl. Acad. Sci. USA* 97:7154-49 (2000); US 2003/0032078; U.S. Pat. No. 6,713,300). Other animal models include the use of mutant ELOVL4 transgenic mice to determine lipofuscin accumulation, electrophysiology, and photoreceptor degeneration, or prevention or inhibition thereof (see, e.g., Karan et al., *Proc. Natl. Acad. Sci. USA* 102:4164-69 (2005)).

The effect of any one of the compounds described herein may be determined in a diabetic retinopathy animal model, such as described in Luan et al. or may be determined in a normal animal model, in which the animals have been light or dark adapted in the presence and absence of any one of the compounds described herein. Another exemplary method for determining the capability of the agent to reduce retinal hypoxia measures retinal hypoxia by deposition of a hydroxyprobe (see, e.g., de Gooyer et al. (*Invest. Ophthalmol. Vis. Sci.* 47:5553-60 (2006)). Such a technique may be performed in an animal model using Rho$^-$/Rho$^-$ knockout mice (see de Gooyer et al., supra) in which at least one compound described herein is administered to group(s) of animals in the presence and absence of the at least one compound, or may be performed in normal, wildtype animals in which at least one compound described herein is administered to group(s) of animals in the presence and absence of the at least one compound. Other animal models include models for determining photoreceptor function, such as rat models that measure elctroretinographic (ERG) oscillatory potentials (see, e.g., Liu et al., *Invest. Ophthalmol. Vis. Sci.* 47:5447-52 (2006); Akula et al., *Invest. Ophthalmol. Vis. Sci.* 48:4351-59 (2007); Liu et al., *Invest. Ophthalmol. Vis. Sci.* 47:2639-47 (2006); Dembinska et al., *Invest. Ophthalmol. Vis. Sci.* 43:2481-90 (2002); Penn et al., *Invest. Ophthalmol. Vis. Sci.* 35:3429-35 (1994); Hancock et al., *Invest. Ophthalmol. Vis. Sci.* 45:1002-1008 (2004)).

A method for determining the effect of a compound on isomerase activity may be performed in vitro as described herein and in the art (Stecher et al., *J. Biol. Chem.* 274: 8577-85 (1999); see also Golczak et al., *Proc. Natl. Acad. Sci. USA* 102:8162-67 (2005)). Retinal pigment epithelium (RPE) microsome membranes isolated from an animal (such as bovine, porcine, human, for example) may serve as the source of the isomerase. The capability of the alkoxyphenyl-linked amine derivative compounds to inhibit isomerase may also be determined by an in vivo murine isomerase assay. Brief exposure of the eye to intense light ("photo-bleaching" of the visual pigment or simply "bleaching") is known to photo-isomerize almost all 11-cis-retinal in the retina. The recovery of 11-cis-retinal after bleaching can be used to estimate the activity of isomerase in vivo (see, e.g., Maeda et al., *J. Neurochem.* 85:944-956 (2003); Van Hooser et al., *J. Biol. Chem.* 277:19173-82, 2002). Electroretinographic (ERG) recording may be performed as previously described (Haeseleer et al., *Nat. Neurosci.* 7:1079-87 (2004); Sugitomo et al., *J. Toxicol. Sci.* 22 Suppl 2:315-25 (1997); Keating et al., *Documenta Ophthalmologica* 100: 77-92 (2000)). See also Deigner et al., *Science,* 244: 968-971 (1989); Gollapalli et al., *Biochim. Biophys. Acta* 1651: 93-101 (2003); Parish, et al., *Proc. Natl. Acad. Sci. USA* 95:14609-13 (1998); Radu et al., *Proc Natl Acad Sci USA* 101: 5928-33 (2004).

Cell culture methods, such as the method described herein, are also useful for determining the effect of a compound described herein on retinal neuronal cell survival. Exemplary cell culture models are described herein and described in detail in U.S. Patent Application Publication No. US 2005-0059148 and U.S. Patent Application Publication No. US2004-0147019 (which are incorporated by reference in their entirety), which are useful for determining the capability of an alkoxyphenyl-linked amine derivative compound as described herein to enhance or prolong survival of neuronal cells, particularly retinal neuronal cells, and of retinal pigment epithelial cells, and inhibit, prevent, slow, or retard degeneration of an eye, or the retina or retinal cells thereof, or the RPE, and which compounds are useful for treating ophthalmic diseases and disorders.

The cell culture model comprises a long-term or extended culture of mature retinal cells, including retinal neuronal cells (e.g., photoreceptor cells, amacrine cells, ganglion cells, horizontal cells, and bipolar cells). The cell culture system and methods for producing the cell culture system provide extended culture of photoreceptor cells. The cell culture system may also comprise retinal pigment epithelial (RPE) cells and Müller glial cells.

The retinal cell culture system may also comprise a cell stressor. The application or the presence of the stressor affects the mature retinal cells, including the retinal neuronal cells, in vitro, in a manner that is useful for studying disease pathology that is observed in a retinal disease or disorder. The cell culture model provides an in vitro neuronal cell culture system that will be useful in the identification and biological testing of an alkoxyphenyl-linked amine derivative compound that is suitable for treatment of neurological diseases or disorders in general, and for treatment of degenerative diseases of the eye and brain in particular. The ability to maintain primary, in vitro-cultured cells from mature retinal tissue, including retinal neurons over an extended period of time in the presence of a stressor enables examination of cell-to-cell interactions, selection and analysis of neuroactive compounds and materials, use of a controlled cell culture system for in vitro CNS and ophthalmic tests, and analysis of the effects on single cells from a consistent retinal cell population.

The cell culture system and the retinal cell stress model comprise cultured mature retinal cells, retinal neurons, and a retinal cell stressor, which may be used for screening and characterizing an alkoxyphenyl-linked amine derivative compound that are capable of inducing or stimulating the regeneration of CNS tissue that has been damaged by disease. The cell culture system provides a mature retinal cell culture that is a mixture of mature retinal neuronal cells and non-neuronal retinal cells. The cell culture system comprises all the major retinal neuronal cell types (photoreceptors, bipolar cells, horizontal cells, amacrine cells, and ganglion cells), and may also include other mature retinal cells such as RPE and Miller glial cells. By incorporating these different types of cells into the in vitro culture system, the system essentially resembles an "artificial organ" that is more akin to the natural in vivo state of the retina.

Viability of one or more of the mature retinal cell types that are isolated (harvested) from retinal tissue and plated for tissue culture may be maintained for an extended period of time, for example, from two weeks up to six months. Viability of the retinal cells may be determined according to methods described herein and known in the art. Retinal neuronal cells, similar to neuronal cells in general, are not actively dividing cells in vivo and thus cell division of retinal neuronal cells would not necessarily be indicative of viability. An advantage of the cell culture system is the ability to culture amacrine cells, photoreceptors, and associated ganglion projection neurons and other mature retinal cells for extended periods of time, thereby providing an opportunity to determine the effectiveness of an alkoxyphenyl-linked amine derivative compound described herein for treatment of retinal disease.

The biological source of the retinal cells or retinal tissue may be mammalian (e.g., human, non-human primate, ungulate, rodent, canine, porcine, bovine, or other mammalian source), avian, or from other genera. Retinal cells including retinal neurons from post-natal non-human primates, post-natal pigs, or post-natal chickens may be used, but any adult or post-natal retinal tissue may be suitable for use in this retinal cell culture system.

In certain instances, the cell culture system may provide for robust long-term survival of retinal cells without inclusion of cells derived from or isolated or purified from non-retinal tissue. Such a cell culture system comprises cells isolated solely from the retina of the eye and thus is substantially free of types of cells from other parts or regions of the eye that are separate from the retina, such as the ciliary body, iris, choroid, and vitreous. Other cell culture methods include the addition of non-retinal cells, such as ciliary body cell and/or stem cells (which may or may not be retinal stem cells) and/or additional purified glial cells.

The in vitro retinal cell culture systems described herein may serve as physiological retinal models that can be used to characterize aspects of the physiology of the retina. This physiological retinal model may also be used as a broader general neurobiology model. A cell stressor may be included in the model cell culture system. A cell stressor, which as described herein is a retinal cell stressor, adversely affects the viability or reduces the viability of one or more of the different retinal cell types, including types of retinal neuronal cells, in the cell culture system. A person skilled in the art would readily appreciate and understand that as described herein a retinal cell that exhibits reduced viability means that the length of time that a retinal cell survives in the cell culture system is reduced or decreased (decreased lifespan) and/or that the retinal cell exhibits a decrease, inhibition, or adverse effect of a biological or biochemical function (e.g., decreased or abnormal metabolism; initiation of apoptosis; etc.) compared with a retinal cell cultured in an appropriate control cell system (e.g., the cell culture system described herein in the absence of the cell stressor). Reduced viability of a retinal cell may be indicated by cell death; an alteration or change in cell structure or morphology; induction and/or progression of apoptosis; initiation, enhancement, and/or acceleration of retinal neuronal cell neurodegeneration (or neuronal cell injury).

Methods and techniques for determining cell viability are described in detail herein and are those with which skilled artisans are familiar. These methods and techniques for determining cell viability may be used for monitoring the health and status of retinal cells in the cell culture system and for determining the capability of the alkoxyphenyl-linked amine derivative compounds described herein to alter (preferably increase, prolong, enhance, improve) retinal cell or retinal pigment epithelial cell viability or retinal cell survival.

The addition of a cell stressor to the cell culture system is useful for determining the capability of an alkoxyphenyl-linked amine derivative compound to abrogate, inhibit, eliminate, or lessen the effect of the stressor. The retinal cell culture system may include a cell stressor that is chemical (e.g., A2E, cigarette smoke concentrate); biological (for example, toxin exposure; beta-amyloid; lipopolysaccharides); or non-chemical, such as a physical stressor, environmental stressor, or a mechanical force (e.g., increased pressure or light exposure) (see, e.g., US 2005-0059148).

The retinal cell stressor model system may also include a cell stressor such as, but not limited to, a stressor that may be a risk factor in a disease or disorder or that may contribute to the development or progression of a disease or disorder, including but not limited to, light of varying wavelengths and intensities; A2E; cigarette smoke condensate exposure; oxidative stress (e.g., stress related to the presence of or exposure to hydrogen peroxide, nitroprusside, $Zn^{++}$, or $Fe^{++}$); increased pressure (e.g., atmospheric pressure or hydrostatic pressure), glutamate or glutamate agonist (e.g., N-methyl-D-aspartate (NMDA); alpha-amino-3-hydroxy-5-methylisoxazole-4-proprionate (AMPA); kainic acid; quisqualic acid; ibotenic acid; quinolinic acid; aspartate; trans-1-aminocyclopentyl-1,3-dicarboxylate (ACPD)); amino acids (e.g., aspartate, L-cysteine; beta-N-methylamine-L-alanine); heavy metals (such as lead); various toxins (for example, mitochondrial toxins (e.g., malonate, 3-nitropropionic acid; rotenone, cyanide); MPTP (1-methyl-4-phenyl-1,2,3,6,-tetrahydropyridine), which metabolizes to its active, toxic metabolite MPP+ (1-methyl-4-phenylpryidine)); 6-hydroxydopamine; alpha-synuclein; protein kinase C activators (e.g., phorbol myristate acetate); biogenic amino stimulants (for example, methamphetamine, MDMA (3-4 methylenedioxymethamphetamine)); or a combination of one or more stressors. Useful retinal cell stressors include those that mimic a neurodegenerative disease that affects any one or more of the mature retinal cells described herein. A chronic disease model is of particular importance because most neurodegenerative diseases are chronic. Through use of this in vitro cell culture system, the earliest events in long-term disease development processes may be identified because an extended period of time is available for cellular analysis.

A retinal cell stressor may alter (i.e., increase or decrease in a statistically significant manner) viability of retinal cells such as by altering survival of retinal cells, including retinal neuronal cells and RPE cells, or by altering neurodegeneration of retinal neuronal cells and/or RPE cells. Preferably, a retinal cell stressor adversely affects a retinal neuronal cell or RPE cell such that survival of a retinal neuronal cell or RPE cell is decreased or adversely affected (i.e., the length of time during which the cells are viable is decreased in the presence of the stressor) or neurodegeneration (or neuron cell injury) of the cell is increased or enhanced. The stressor may affect only a single retinal cell type in the retinal cell culture or the stressor may affect two, three, four, or more of the different cell types. For example, a stressor may alter viability and survival of photoreceptor cells but not affect all the other major cell types (e.g., ganglion cells, amacrine cells, horizontal cells, bipolar cells, RPE, and Miller glia). Stressors may shorten the survival time of a retinal cell (in vivo or in vitro), increase the rapidity or extent of neurodegeneration of a retinal cell, or in some other manner adversely affect the viability, morphology, maturity, or lifespan of the retinal cell.

The effect of a cell stressor (in the presence and absence of an alkoxyphenyl-linked amine derivative compound) on the viability of retinal cells in the cell culture system may be determined for one or more of the different retinal cell types. Determination of cell viability may include evaluating structure and/or a function of a retinal cell continually at intervals over a length of time or at a particular time point after the retinal cell culture is prepared. Viability or long term survival of one or more different retinal cell types or one or more different retinal neuronal cell types may be examined according to one or more biochemical or biological parameters that are indicative of reduced viability, such as apoptosis or a decrease in a metabolic function, prior to observation of a morphological or structural alteration.

A chemical, biological, or physical cell stressor may reduce viability of one or more of the retinal cell types present in the cell culture system when the stressor is added to the cell culture under conditions described herein for maintaining the long-term cell culture. Alternatively, one or more culture conditions may be adjusted so that the effect of the stressor on the retinal cells can be more readily observed. For example, the concentration or percent of fetal bovine serum may be reduced or eliminated from the cell culture when cells are exposed to a particular cell stressor (see, e.g., US 2005-0059148). Alternatively, retinal cells cultured in media containing serum at a particular concentration for maintenance of the cells may be abruptly exposed to media that does not contain any level of serum.

The retinal cell culture may be exposed to a cell stressor for a period of time that is determined to reduce the viability of one or more retinal cell types in the retinal cell culture system. The cells may be exposed to a cell stressor immediately upon plating of the retinal cells after isolation from retinal tissue. Alternatively, the retinal cell culture may be exposed to a stressor after the culture is established, or any time thereafter. When two or more cell stressors are included in the retinal cell culture system, each stressor may be added to the cell culture system concurrently and for the same length of time or may be added separately at different time points for the same length of time or for differing lengths of time during the culturing of the retinal cell system. An alkoxyphenyl-linked amine compound may be added before the retinal cell culture is exposed to a cell stressor, may be added concurrently with the cell stressor, or may be added after exposure of the retinal cell culture to the stressor.

Photoreceptors may be identified using antibodies that specifically bind to photoreceptor-specific proteins such as opsins, peripherins, and the like. Photoreceptors in cell culture may also be identified as a morphologic subset of immunocytochemically labeled cells by using a pan-neuronal marker or may be identified morphologically in enhanced contrast images of live cultures. Outer segments can be detected morphologically as attachments to photoreceptors.

Retinal cells including photoreceptors can also be detected by functional analysis. For example, electrophysiology methods and techniques may be used for measuring the response of photoreceptors to light. Photoreceptors exhibit specific kinetics in a graded response to light. Calcium-sensitive dyes may also be used to detect graded responses to light within cultures containing active photoreceptors. For analyzing stress-inducing compounds or potential neurotherapeutics, retinal cell cultures can be processed for immunocytochemistry, and photoreceptors and/or other retinal cells can be counted manually or by computer software using photomicroscopy and imaging techniques. Other immunoassays known in the art (e.g., ELISA, immunoblotting, flow cytometry) may also be useful for identifying and characterizing the retinal cells and retinal neuronal cells of the cell culture model system described herein.

The retinal cell culture stress models may also be useful for identification of both direct and indirect pharmacologic agent effects by the bioactive agent of interest, such as an alkoxyphenyl-linked amine derivative compound as described herein. For example, a bioactive agent added to the cell culture system in the presence of one or more retinal cell stressors may stimulate one cell type in a manner that enhances or decreases the survival of other cell types. Cell/cell interactions and cell/extracellular component interactions may be important in understanding mechanisms of disease and drug function. For example, one neuronal cell type may secrete trophic factors that affect growth or survival of another neuronal cell type (see, e.g., WO 99/29279).

In another embodiment, an alkoxyphenyl-linked amine derivative compound is incorporated into screening assays comprising the retinal cell culture stress model system described herein to determine whether and/or to what level or degree the compound increases or prolongs viability (i.e., increases in a statistically significant or biologically significant manner) of a plurality of retinal cells. A person skilled in the art would readily appreciate and understand that as described herein a retinal cell that exhibits increased viability means that the length of time that a retinal cell survives in the cell culture system is increased (increased lifespan) and/or that the retinal cell maintains a biological or biochemical function (normal metabolism and organelle function; lack of apoptosis; etc.) compared with a retinal cell cultured in an appropriate control cell system (e.g., the cell culture system described herein in the absence of the compound). Increased viability of a retinal cell may be indicated by delayed cell death or a reduced number of dead or dying cells; maintenance of structure and/or morphology; lack of or delayed initiation of apoptosis; delay, inhibition, slowed progression, and/or abrogation of retinal neuronal cell neurodegeneration or delaying or abrogating or preventing the effects of neuronal cell injury. Methods and techniques for determining viability of a retinal cell and thus whether a retinal cell exhibits increased viability are described in greater detail herein and are known to persons skilled in the art.

In certain embodiments, a method is provided for determining whether an alkoxyphenyl-linked amine derivative compound, enhances survival of photoreceptor cells. One method comprises contacting a retinal cell culture system as described herein with an alkoxyphenyl-linked amine compound under conditions and for a time sufficient to permit interaction between the retinal neuronal cells and the compound. Enhanced survival (prolonged survival) may be measured according to methods described herein and known in the art, including detecting expression of rhodopsin.

The capability of an alkoxyphenyl-linked amine derivative compound to increase retinal cell viability and/or to enhance, promote, or prolong cell survival (that is, to extend the time period in which retinal cells, including retinal neuronal cells, are viable), and/or impair, inhibit, or impede degeneration as a direct or indirect result of the herein described stress may be determined by any one of several methods known to those skilled in the art. For example, changes in cell morphology in the absence and presence of the compound may be determined by visual inspection such as by light microscopy, confocal microscopy, or other microscopy methods known in the art. Survival of cells can also be determined by counting viable and/or nonviable cells, for instance. Immunochemical or immunohistological techniques (such as fixed cell staining or flow cytometry) may be used to identify and evaluate cytoskeletal structure (e.g., by using antibodies specific for cytoskeletal proteins such as glial fibrillary acidic protein, fibronectin, actin, vimentin, tubulin, or the like) or to evaluate expression of cell markers as described herein. The effect of an alkoxyphenyl-linked amine derivative compound on cell integrity, morphology, and/or survival may also be determined by measuring the phosphorylation state of neuronal cell polypeptides, for example, cytoskeletal polypeptides (see, e.g., Sharma et al., *J. Biol. Chem.* 274:9600-06 (1999); Li et al., *J. Neurosci.* 20:6055-62 (2000)). Cell survival or, alternatively cell death, may also be determined according to methods described herein and known in the art for measuring apoptosis (for example, annexin V binding, DNA fragmentation assays, caspase activation, marker analysis, e.g., poly(ADP-ribose) polymerase (PARP), etc.).

In the vertebrate eye, for example, a mammalian eye, the formation of A2E is a light-dependent process and its accumulation leads to a number of negative effects in the eye. These include destabilization of retinal pigment epithelium (RPE) membranes, sensitization of cells to blue-light damage, and impaired degradation of phospholipids. Products of the oxidation of A2E (and A2E related molecules) by molecular oxygen (oxiranes) were shown to induce DNA damage in cultured RPE cells. All these factors lead to a gradual decrease in visual acuity and eventually to vision loss. If reducing the formation of retinals during vision processes were possible, this reduction would lead to decreased amounts of A2E in the eye. Without wishing to be bound by theory, decreased accumulation of A2E may reduce or delay degenerative processes in the RPE and retina and thus may slow down or prevent vision loss in dry AMD and Stargardt's Disease.

In another embodiment, methods are provided for treating and/or preventing degenerative diseases and disorders, including neurodegenerative retinal diseases and ophthalmic diseases, and retinal diseases and disorders as described herein. A subject in need of such treatment may be a human or non-human primate or other animal who has developed symptoms of a degenerative retinal disease or who is at risk for developing a degenerative retinal disease. As described herein a method is provided for treating (which includes preventing or prophylaxis) an ophthalmic disease or disorder by administrating to a subject a composition comprising a pharmaceutically acceptable carrier and an alkoxyphenyl-linked amine derivative compound (e.g., a compound having the structure of any one of Formulae (I), (II), (IIa) and (IIb), and substructures thereof.) As described herein, a method is provided for enhancing survival of neuronal cells such as retinal neuronal cells, including photoreceptor cells, and/or inhibiting degeneration of retinal neuronal cells by administering the pharmaceutical compositions described herein comprising an alkoxyphenyl-linked amine derivative compound.

Enhanced survival (or prolonged or extended survival) of one or more retinal cell types in the presence of an alkoxyphenyl-linked amine derivative compound indicates that the compound may be an effective agent for treatment of a degenerative disease, particularly a retinal disease or disorder, and including a neurodegenerative retinal disease or disorder. Cell survival and enhanced cell survival may be determined according to methods described herein and known to a skilled artisan including viability assays and assays for detecting expression of retinal cell marker proteins. For determining enhanced survival of photoreceptor cells, opsins may be detected, for instance, including the protein rhodopsin that is expressed by rods.

In another embodiment, the subject is being treated for Stargardt's disease or Stargardt's macular degeneration. In Stargardt's disease, which is associated with mutations in the ABCA4 (also called ABCR) transporter, the accumulation of all-trans-retinal has been proposed to be responsible for the formation of a lipofuscin pigment, A2E, which is toxic towards retinal cells and causes retinal degeneration and consequently loss of vision.

In yet another embodiment, the subject is being treated for age-related macular degeneration (AMD). In various embodiments, AMD can be wet- or dry-form. In AMD, vision loss primarily occurs when complications late in the disease either cause new blood vessels to grow under the macula or the macula atrophies. Without intending to be bound by any particular theory, the accumulation of all-trans-retinal has been proposed to be responsible for the formation of a lipofuscin pigment, N-retinylidene-N-retinylethanolamine (A2E) and A2E related molecules, which are toxic towards RPE and retinal cells and cause retinal degeneration and consequently loss of vision.

A neurodegenerative retinal disease or disorder for which the compounds and methods described herein may be used for treating, curing, preventing, ameliorating the symptoms of, or slowing, inhibiting, or stopping the progression of, is a disease or disorder that leads to or is characterized by retinal neuronal cell loss, which is the cause of visual impairment. Such a disease or disorder includes but is not limited to age-related macular degeneration (including dry-form and wet-form of macular degeneration) and Stargardt's macular dystrophy.

Age-related macular degeneration as described herein is a disorder that affects the macula (central region of the retina) and results in the decline and loss of central vision. Age-related macular degeneration occurs typically in individuals over the age of 55 years. The etiology of age-related macular degeneration may include both environmental influences and genetic components (see, e.g., Lyengar et al., Am. J Hum. Genet. 74:20-39 (2004) (Epub 2003 December 19); Kenealy et al., Mol. Vis. 10:57-61 (2004); Gorin et al., Mol. Vis. 5:29 (1999)). More rarely, macular degeneration occurs in younger individuals, including children and infants, and generally, these disorders results from a genetic mutation. Types of juvenile macular degeneration include Stargardt's disease (see, e.g., Glazer et al., Ophthalmol. Clin. North Am. 15:93-100, viii (2002); Weng et al., Cell 98:13-23 (1999)); Doyne's honeycomb retinal dystrophy (see, e.g., Kermani et al., Hum. Genet. 104:77-82 (1999)); Sorsby's fundus dystrophy, Malattia Levintinese, fundus flavimaculatus, and autosomal dominant hemorrhagic macular dystrophy (see also Seddon et al., Ophthalmology 108:2060-67 (2001); Yates et al., J. Med. Genet. 37:83-7 (2000); Jaakson et al., Hum. Mutat. 22:395-403 (2003)). Geographic atrophy of the RPE is an advanced form of non-neovascular dry-type age-related macular degeneration, and is associated with atrophy of the choriocapillaris, RPE, and retina.

Stargardt's macular degeneration, a recessive inherited disease, is an inherited blinding disease of children. The primary pathologic defect in Stargardt's disease is also an accumulation of toxic lipofuscin pigments such as A2E in cells of the retinal pigment epithelium (RPE). This accumulation appears to be responsible for the photoreceptor death and severe visual loss found in Stargardt's patients. The compounds described herein may slow the synthesis of 11-cis-retinaldehyde (11 cRAL or retinal) and regeneration of rhodopsin by inhibiting isomerase in the visual cycle. Light activation of rhodopsin results in its release of all-trans-retinal, which constitutes the first reactant in A2E biosynthesis. Treatment with alkoxyphenyl-linked amine derivative compounds may inhibit lipofuscin accumulation and thus delay the onset of visual loss in Stargardt's and AMD patients without toxic effects that would preclude treatment with an alkoxyphenyl-linked amine derivative compound. The compounds described herein may be used for effective treatment of other forms of retinal or macular degeneration associated with lipofuscin accumulation.

Administration of an alkoxyphenyl-linked amine derivative compound to a subject can prevent formation of the lipofuscin pigment, A2E (and A2E related molecules), that is toxic towards retinal cells and causes retinal degeneration. In certain embodiments, administration of an alkoxyphenyl-linked amine derivative compound can lessen the production of waste products, e.g., lipofuscin pigment, A2E (and A2E related molecules), ameliorate the development of AMD (e.g., dry-form) and Stargardt's disease, and reduce or slow vision loss (e.g., choroidal neovascularization and/or chorioretinal atrophy). In previous studies, with 13-cis-retinoic acid (Accutane® or Isotretinoin), a drug commonly used for the treatment of acne and an inhibitor of 11-cis-retinol dehydrogenase, has been administered to patients to prevent A2E accumulation in the RPE. However, a major drawback in this proposed treatment is that 13-cis-retinoic acid can easily isomerize to all-trans-retinoic acid. All-trans-retinoic acid is a very potent teratogenic compound that adversely affects cell proliferation and development. Retinoic acid also accumulates in the liver and may be a contributing factor in liver diseases.

In yet other embodiments, an alkoxyphenyl-linked amine derivative compound is administered to a subject such as a human with a mutation in the ABCA4 transporter in the eye. The alkoxyphenyl-linked amine derivative compound can also be administered to an aging subject. As used herein, an aging human subject is typically at least 45, or at least 50, or at least 60, or at least 65 years old. In Stargardt's disease, which is associated with mutations in the ABCA4 transporter, the accumulation of all-trans-retinal has been proposed to be responsible for the formation of a lipofuscin pigment, A2E (and A2E related molecules), that is toxic towards retinal cells and causes retinal degeneration and consequently loss of vision. Without wishing to be bound by theory, an alkoxyphenyl-linked amine derivative compound described herein may be a strong inhibitor of an isomerase involved in the visual cycle. Treating patients with an alkoxyphenyl-linked amine derivative compound as described herein may prevent or slow the formation of A2E (and A2E related molecules) and can have protective properties for normal vision.

In other certain embodiments, one or more of the compounds described herein may be used for treating other ophthalmic diseases or disorders, for example, glaucoma, retinal detachment, hemorrhagic retinopathy, retinitis pigmentosa, an inflammatory retinal disease, proliferative vitreoretinopathy, retinal dystrophy, hereditary optic neuropathy, Sorsby's fundus dystrophy, uveitis, a retinal injury, optical neuropathy, and retinal disorders associated with other neurodegenerative diseases such as Alzheimer's disease, multiple sclerosis, Parkinson's disease or other neurodegenerative diseases that affect brain cells, a retinal disorder associated with viral infection, or other conditions such as AIDS. A retinal disorder also includes light damage to the retina that is related to increased light exposure (i.e., overexposure to light), for example, accidental strong or intense light exposure during surgery; strong, intense, or prolonged sunlight exposure, such as at a desert or snow covered terrain; during combat, for example, when observing a flare or explosion or from a laser device, and the like. Retinal diseases can be of degenerative or non-degenerative nature. Non-limiting examples of degenerative retinal diseases include age-related macular degeneration, and Stargardt's macular dystrophy. Examples of non-degenerative retinal diseases include but are not limited hemorrhagic retinopathy, retinitis pigmentosa, optic neuropathy, inflammatory retinal disease, diabetic retinopathy, diabetic maculopathy, retinal blood vessel occlusion, retinopathy of prematurity, or ischemia reperfusion related retinal injury, proliferative vitreoretinopathy, retinal dystrophy, hereditary optic neuropathy, Sorsby's fundus dystrophy, uveitis, a retinal injury, a retinal disorder associated with Alzheimer's disease, a retinal disorder associated with multiple sclerosis, a retinal disorder associated with Parkinson's disease, a retinal disorder associated with viral infection, a retinal disorder related to light overexposure, and a retinal disorder associated with AIDS.

In other certain embodiments, at least one of the compounds described herein may be used for treating, curing, preventing, ameliorating the symptoms of, or slowing, inhibiting, or stopping the progression of, certain ophthalmic diseases and disorders including but not limited to diabetic retinopathy, diabetic maculopathy, diabetic macular edema, retinal ischemia, ischemia-reperfusion related retinal injury, and retinal blood vessel occlusion (including venous occlusion and arterial occlusion).

Diabetic retinopathy is a leading cause of blindness in humans and is a complication of diabetes. Diabetic retinopathy occurs when diabetes damages blood vessels inside the retina. Non-proliferative retinopathy is a common, usually mild form that generally does not interfere with vision. Abnormalities are limited to the retina, and vision is impaired only if the macula is involved. If left untreated retinopathy can progress to proliferative retinopathy, the more serious form of diabetic retinopathy. Proliferative retinopathy occurs when new blood vessels proliferate in and around the retina. Consequently, bleeding into the vitreous, swelling of the retina, and/or retinal detachment may occur, leading to blindness.

Other ophthalmic diseases and disorders that may be treated using the methods and compositions described herein include diseases, disorders, and conditions that are associated with, exacerbated by, or caused by ischemia in the retina. Retinal ischemia includes ischemia of the inner retina and the outer retina. Retinal ischemia can occur from either choroidal or retinal vascular diseases, such as central or branch retinal vision occlusion, collagen vascular diseases and thrombocytopenic purpura. Retinal vasculitis and occlusion is seen with Eales disease and systemic lupus erythematosus.

Retinal ischemia may be associated with retinal blood vessel occlusion. In the United States, both branch and central retinal vein occlusions are the second most common retinal vascular diseases after diabetic retinopathy. About 7% to 10% of patients who have retinal venous occlusive disease in one eye eventually have bilateral disease. Visual field loss commonly occurs from macular edema, ischemia, or vitreous hemorrhage secondary to disc or retinal neovascularization induced by the release of vascular endothelial growth factor.

Arteriolosclerosis at sites of retinal arteriovenous crossings (areas in which arteries and veins share a common adventitial sheath) causes constriction of the wall of a retinal vein by a crossing artery. The constriction results in thrombus formation and subsequent occlusion of the vein. The blocked vein may lead to macular edema and hemorrhage secondary to breakdown in the blood-retina barrier in the area drained by the vein, disruption of circulation with turbulence in venous flow, endothelial damage, and ischemia. Clinically, areas of ischemic retina appear as feathery white patches called cotton-wool spots.

Branch retinal vein occlusions with abundant ischemia cause acute central and paracentral visual field loss corresponding to the location of the involved retinal quadrants. Retinal neovascularization due to ischemia may lead to vitreous hemorrhage and subacute or acute vision loss.

Two types of central retinal vein occlusion, ischemic and nonischemic, may occur depending on whether widespread retinal ischemia is present. Even in the nonischemic type, the macula may still be ischemic. Approximately 25% central retinal vein occlusion is ischemic. Diagnosis of central retinal vein occlusion can usually be made on the basis of characteristic ophthalmoscopic findings, including retinal hemorrhage in all quadrants, dilated and tortuous veins, and cotton-wool spots. Macular edema and foveal ischemia can lead to vision loss. Extracellular fluid increases interstitial pressure, which may result in areas of retinal capillary closure (i.e., patchy ischemic retinal whitening) or occlusion of a cilioretinal artery.

Patients with ischemic central retinal vein occlusion are more likely to present with a sudden onset of vision loss and have visual acuity of less than 20/200, a relative afferent pupillary defect, abundant intraretinal hemorrhages, and extensive nonperfusion on fluorescein angiography. The natural history of ischemic central retinal vein occlusion is associated with poor outcomes: eventually, approximately two-thirds of patients who have ischemic central retinal vein occlusion will have ocular neovascularization and one-third will have neovascular glaucoma. The latter condition is a severe type of glaucoma that may lead to rapid visual field and vision loss, epithelial edema of the cornea with secondary epithelial erosion and predisposition to bacterial keratitis, severe pain, nausea and vomiting, and, eventually, phthisis bulbi (atrophy of the globe with no light perception).

As used herein, a patient (or subject) may be any mammal, including a human, that may have or be afflicted with a neurodegenerative disease or condition, including an ophthalmic disease or disorder, or that may be free of detectable disease. Accordingly, the treatment may be administered to a subject who has an existing disease, or the treatment may be prophylactic, administered to a subject who is at risk for developing the disease or condition. Treating or treatment refers to any indicia of success in the treatment or amelioration of an injury, pathology or condition, including any objective or subjective parameter such as abatement; remission; diminishing of symptoms or making the injury, pathology, or condition more tolerable to the patient; slowing in the rate of degeneration or decline; making the final point of degeneration less debilitating; or improving a subject's physical or mental well-being.

The treatment or amelioration of symptoms can be based on objective or subjective parameters; including the results of a physical examination. Accordingly, the term "treating" includes the administration of the compounds or agents described herein to treat pain, hyperalgesia, allodynia, or nociceptive events and to prevent or delay, to alleviate, or to arrest or inhibit development of the symptoms or conditions associated with pain, hyperalgesia, allodynia, nociceptive events, or other disorders. The term "therapeutic effect" refers to the reduction, elimination, or prevention of the disease, symptoms of the disease, or sequelae of the disease in the subject. Treatment also includes restoring or improving retinal neuronal cell functions (including photoreceptor function) in a vertebrate visual system, for example, such as visual acuity and visual field testing etc., as measured over time (e.g., as measured in weeks or months). Treatment also includes stabilizing disease progression (i.e., slowing, minimizing, or halting the progression of an ophthalmic disease and associated symptoms) and minimizing additional degeneration of a vertebrate visual system. Treatment also includes prophylaxis and refers to the administration of an alkoxyphenyl-linked amine derivative compound to a subject to prevent degeneration or further degeneration or deterioration or further deterioration of the vertebrate visual system of the subject and to prevent or inhibit development of the disease and/or related symptoms and sequelae.

Various methods and techniques practiced by a person skilled in the medical and ophthalmological arts to determine and evaluate a disease state and/or to monitor and assess a therapeutic regimen include, for example, fluorescein angiogram, fundus photography, indocyanine green dye tracking of the choroidal circulatory system, opthalmoscopy, optical coherence tomography (OCT), and visual acuity testing.

A fluorescein angiogram involves injecting a fluorescein dye intravenously and then observing any leakage of the dye as it circulates through the eye. Intravenous injection of indocyanine green dye may also be used to determine if vessels in the eye are compromised, particularly in the choroidal circulatory system that is just behind the retina. Fundus photography may be used for examining the optic nerve, macula, blood vessels, retina, and the vitreous. Microaneurysms are visible lesions in diabetic retinopathy that may be detected in digital fundus images early in the disease (see, e.g., U.S. Patent Application Publication No. 2007/0002275). An ophthalmoscope may be used to examine the retina and vitreous. Opthalmoscopy is usually performed with dilated pupils, to allow the best view inside the eye. Two types of ophthalmoscopes may be used: direct and indirect. The direct ophthalmoscope is generally used to view the optic nerve and the central retina. The periphery, or entire retina, may be viewed by using an indirect ophthalmoscope. Optical coherence tomography (OCT) produces high resolution, high speed, non-invasive, cross-sectional images of body tissue. OCT is noninvasive and provides detection of microscopic early signs of disruption in tissues.

A subject or patient refers to any vertebrate or mammalian patient or subject to whom the compositions described herein can be administered. The term "vertebrate" or "mammal" includes humans and non-human primates, as well as experimental animals such as rabbits, rats, and mice, and other animals, such as domestic pets (such as cats, dogs, horses), farm animals, and zoo animals. Subjects in need of treatment using the methods described herein may be identified according to accepted screening methods in the medical art that are employed to determine risk factors or symptoms associated with an ophthalmic disease or condition described herein or to determine the status of an existing ophthalmic disease or condition in a subject. These and other routine methods allow the clinician to select patients in need of therapy using the methods and formulations described herein.

Pharmaceutical Compositions

In certain embodiments, an alkoxylphenyl-linked amine derivative compound may be administered as a pure chemical. In other embodiments, the alkoxyphenyl-linked amine derivative compound can be combined with a pharmaceutically suitable or acceptable carrier (also referred to herein as a pharmaceutically suitable (or acceptable) excipient, physiologically suitable (or acceptable) excipient, or physiologically suitable (or acceptable) carrier) selected on the basis of a chosen route of administration and standard pharmaceutical practice as described, for example, in *Remington: The Science and Practice of Pharmacy* (Gennaro, 21$^{st}$ Ed. Mack Pub. Co., Easton, Pa. (2005)), the disclosure of which is hereby incorporated herein by reference, in its entirety.

Accordingly, provided herein is a pharmaceutical composition comprising one or more alkoxylphenyl linked amine derivative compounds, or a stereoisomer, prodrug, pharmaceutically acceptable salt, hydrate, solvate, acid salt hydrate, N-oxide or isomorphic crystalline form thereof, of a compound described herein, together with one or more pharmaceutically acceptable carriers and, optionally, other therapeutic and/or prophylactic ingredients. The carrier(s) (or excipient(s)) is acceptable or suitable if the carrier is compatible with the other ingredients of the composition and not deleterious to the recipient (i.e., the subject) of the composition. A pharmaceutically acceptable or suitable composition includes an ophthalmologically suitable or acceptable composition.

Thus, another embodiment provides a pharmaceutical composition comprising a pharmaceutically acceptable excipient and a compound having a structure of Formulae (A)-(E), (I), (II), (IIa), (IIb):

Accordingly, in one embodiment, a compound is provided that has a structure of Formula (I):

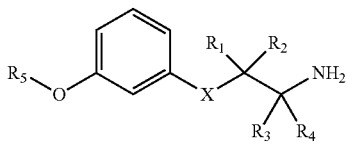

Formula (I)

as a tautomer or a mixture of tautomers, or as a pharmaceutically acceptable salt, hydrate, solvate, N-oxide or prodrug thereof, wherein:

$R_1$ and $R_2$ are each the same or different and independently hydrogen, halogen, alkyl, fluoroalkyl, —$OR_6$, —$NR_7R_8$ or carbocyclyl; or $R_1$ and $R_2$ form an oxo;

$R_3$ and $R_4$ are each the same or different and independently hydrogen or alkyl;

$R_5$ is alkyl, carbocyclylalkyl, heterocyclylalkyl wherein the heterocyclyl comprises at least one oxygen, or heteroarylalkyl wherein the heteroaryl is monocyclic;

$R_6$ is hydrogen or alkyl;

$R_7$ and $R_8$ are each the same or different and independently hydrogen, alkyl, carbocyclyl, or —C(=O)$R_9$; or $R_7$ and $R_8$, together with the nitrogen atom to which they are attached, form an N-heterocyclyl;

X is —C($R_9$)($R_{10}$)— or —O—;

$R_9$ and $R_{10}$ are each the same or different and independently hydrogen, halogen, alkyl, fluoroalkyl, —$OR_6$, —$NR_{11}R_{12}$ or carbocyclyl; or $R_9$ and $R_{10}$ form an oxo;

$R_{11}$ and $R_{12}$ are each the same or different and independently hydrogen, alkyl, carbocyclyl, or —C(=O)$R_{13}$; or $R_{11}$ and $R_{12}$, together with the nitrogen atom to which they are attached, form an N-heterocyclyl;

$R_{13}$ is alkyl, alkenyl, aryl, carbocyclyl, heteroaryl or heterocyclyl.

Various embodiments further provide pharmaceutical compositions comprising a pharmaceutically acceptable excipient and a compound of any one of Formulae (II), (IIa) and (IIb):

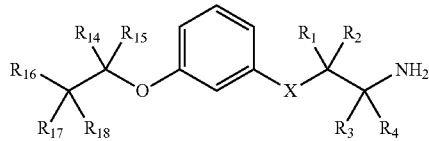

Formula (II)

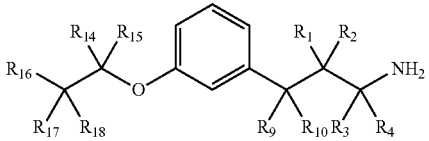

Formula (IIa)

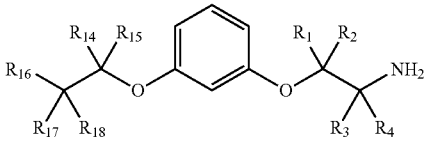

Formula (IIb)

wherein each of $R_1$, $R_2$, $R_3$, $R_4$, $R_5$, $R_9$, $R_{10}$, $R_{14}$, $R_{15}$, $R_{16}$, $R_{17}$ and $R_{18}$ are as defined above and herein.

In an additional embodiment is a pharmaceutical composition comprising a pharmaceutically acceptable carrier and a compound of Formula (A) or tautomer, stereoisomer, geometric isomer, or pharmaceutically acceptable solvate, hydrate, salt, N-oxide or prodrug thereof:

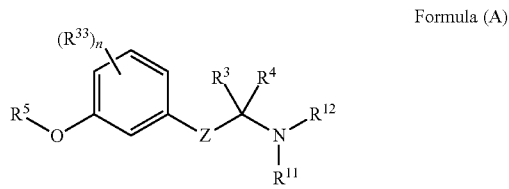

Formula (A)

wherein,

Z is —C($R^9$)($R^{10}$)—C($R^1$)($R^2$)—, —X—C($R^{31}$)($R^{32}$)—, —C($R^9$)($R^{10}$)—C($R^1$)($R^2$)—C($R^{36}$)($R^{37}$)— or —X—C($R^{31}$)($R^{32}$)—C($R^1$)($R^2$)—;

$R^1$ and $R^2$ are each independently selected from hydrogen, halogen, $C_1$-$C_5$ alkyl, fluoroalkyl, —$OR^6$ or —$NR^7R^8$; or $R^1$ and $R^2$ together form an oxo;

$R^{31}$ and $R^{32}$ are each independently selected from hydrogen, $C_1$-$C_5$ alkyl, or fluoroalkyl;

$R^{36}$ and $R^{37}$ are each independently selected from hydrogen, halogen, $C_1$-$C_5$ alkyl, fluoroalkyl, —$OR^6$ or —$NR^7R^8$; or $R^{36}$ and $R^{37}$ together form an oxo; or optionally, $R^{36}$ and $R^1$ together form a direct bond to provide a double bond; or optionally, $R^{36}$ and $R^1$ together form a direct bond, and $R^{37}$ and $R^2$ together form a direct bond to provide a triple bond;

$R^3$ and $R^4$ are each independently selected from hydrogen, alkyl, alkenyl, fluoroalkyl, aryl, heteroaryl, carbocyclyl or C-attached heterocyclyl; or $R^3$ and $R^4$ together with the carbon atom to which they are attached, form a carbocyclyl or heterocyclyl; or $R^3$ and $R^4$ together form an imino;

$R^5$ is $C_5$-$C_{15}$ alkyl or carbocyclalkyl;

$R^7$ and $R^8$ are each independently selected from hydrogen, alkyl, carbocyclyl, heterocyclyl, —C(=O)$R^{13}$, $SO_2R^{13}$, $CO_2R^{13}$ or $SO_2NR^{24}R^{25}$; or $R^7$ and $R^8$ together with the nitrogen atom to which they are attached, form an N-heterocyclyl;

X is —O—, —S—, —S(=O)—, —S(=O)$_2$—, —N($R^{30}$)—, —C(=O)—, —C(=CH$_2$)—, —C(=N—N$R^{35}$)—, or —C(=N—O$R^{35}$)—;

$R^9$ and $R^{10}$ are each independently selected from hydrogen, halogen, alkyl, fluoroalkyl, —$OR^{19}$—, —$NR^{20}R^{21}$ or carbocyclyl; or $R^9$ and $R^{10}$ form an oxo; or optionally, $R^9$ and $R^1$ together form a direct bond to provide a double bond; or optionally, $R^9$ and $R^1$ together form a direct bond, and $R^{10}$ and $R^2$ together form a direct bond to provide a triple bond;

$R^{11}$ and $R^{12}$ are each independently selected from hydrogen, alkyl, carbocyclyl, —C(=O)$R^{23}$, —C(NH)NH$_2$, $SO_2R^{23}$, $CO_2R^{23}$ or $SO_2NR^{28}R^{29}$; or $R^{11}$ and $R^{12}$, together with the nitrogen atom to which they are attached, form an N-heterocyclyl;

each $R^{13}$, $R^{22}$ and $R^{23}$ is independently selected from alkyl, heteroalkyl, alkenyl, aryl, aralkyl, carbocyclyl, heteroaryl or heterocyclyl;

$R^6$, $R^{19}$, $R^{30}$, $R^{34}$ and $R^{35}$ are each independently hydrogen or alkyl;

$R^{20}$ and $R^{21}$ are each independently selected from hydrogen, alkyl, carbocyclyl, heterocyclyl, —C(=O)$R^{22}$, $SO_2R^{22}$, $CO_2R^{22}$ or $SO_2NR^{26}R^{27}$; or $R^{20}$ and $R^{21}$ together with the nitrogen atom to which they are attached, form an N-heterocyclyl;

each $R^{24}$, $R^{25}$, $R^{26}$, $R^{27}$, $R^{28}$ and $R^{29}$ is independently selected from hydrogen, alkyl, alkenyl, fluoroalkyl, aryl, heteroaryl, carbocyclyl or heterocyclyl;

each $R^{33}$ is independently selected from halogen, $OR^{34}$, alkyl, or fluoroalkyl; and n is 0, 1, 2, 3, or 4; with the provision that $R^5$ is not 2-(cyclopropyl)-1-ethyl or an unsubstituted normal alkyl.

A pharmaceutical composition (e.g., for oral administration or delivery by injection, or combined devices, or for application as an eye drop) may be in the form of a liquid or solid. A liquid pharmaceutical composition may include, for example, one or more of the following: sterile diluents such as water for injection, saline solution, preferably physiological saline, Ringer's solution, isotonic sodium chloride, fixed oils that may serve as the solvent or suspending medium, polyethylene glycols, glycerin, propylene glycol or other solvents; antibacterial agents; antioxidants; chelating agents; buffers and agents for the adjustment of tonicity such as sodium chloride or dextrose. A parenteral preparation can be enclosed in ampoules, disposable syringes or multiple dose vials made of glass or plastic. Physiological saline is commonly used as an excipient, and an injectable pharmaceutical composition or a composition that is delivered ocularly is preferably sterile.

At least one alkoxyphenyl-linked amine derivative compound can be administered to human or other nonhuman vertebrates. In certain embodiments, the compound is substantially pure, in that it contains less than about 5% or less than about 1%, or less than about 0.1%, of other organic small molecules, such as contaminating intermediates or by-products that are created, for example, in one or more of the steps of a synthesis method. In other embodiments, a combination of one or more alkoxyphenyl-linked amine derivative compounds can be administered.

An alkoxyphenyl-linked amine derivative compound can be delivered to a subject by any suitable means, including, for example, orally, parenterally, intraocularly, intravenously, intraperitoneally, intranasally (or other delivery methods to the mucous membranes, for example, of the nose, throat, and bronchial tubes), or by local administration to the eye, or by an intraocular or periocular device. Modes of local administration can include, for example, eye drops, intraocular injection or periocular injection. Periocular injection typically involves injection of the synthetic isomerization inhibitor, i.e., alkoxyphenyl-linked amine derivative compound under the conjunctiva or into the Tennon's space (beneath the fibrous tissue overlying the eye). Intraocular injection typically involves injection of the alkoxyphenyl-linked amine derivative compound into the vitreous. In certain embodiments, the administration is non-invasive, such as by eye drops or oral dosage form, or as a combined device.

An alkoxyphenyl-linked amine derivative compound can be formulated for administration using pharmaceutically acceptable (suitable) carriers or vehicles as well as techniques routinely used in the art. A pharmaceutically acceptable or suitable carrier includes an ophthalmologically suitable or acceptable carrier. A carrier is selected according to the solubility of the alkoxyphenyl-linked amine derivative compound. Suitable ophthalmological compositions include those that are administrable locally to the eye, such as by eye drops, injection or the like. In the case of eye drops, the formulation can also optionally include, for example, ophthalmologically compatible agents such as isotonizing agents such as sodium chloride, concentrated glycerin, and the like; buffering agents such as sodium phosphate, sodium acetate, and the like; surfactants such as polyoxyethylene sorbitan mono-oleate (also referred to as Polysorbate 80), polyoxyl stearate 40, polyoxyethylene hydrogenated castor oil, and the like; stabilization agents such as sodium citrate, sodium edentate, and the like; preservatives such as benzalkonium chloride, parabens, and the like; and other ingredients. Preservatives can be employed, for example, at a level of from about 0.001 to about 1.0% weight/volume. The pH of the formulation is usually within the range acceptable to ophthalmologic formulations, such as within the range of about pH 4 to 8.

For injection, the alkoxyphenyl-linked amine derivative compound can be provided in an injection grade saline solution, in the form of an injectable liposome solution, slow-release polymer system or the like. Intraocular and periocular injections are known to those skilled in the art and are described in numerous publications including, for example, Spaeth, Ed., *Ophthalmic Surgery: Principles of Practice*, W. B. Sanders Co., Philadelphia, Pa., 85-87, 1990.

For delivery of a composition comprising at least one of the compounds described herein via a mucosal route, which includes delivery to the nasal passages, throat, and airways, the composition may be delivered in the form of an aerosol. The compound may be in a liquid or powder form for intramucosal delivery. For example, the composition may be delivered via a pressurized aerosol container with a suitable propellant, such as a hydrocarbon propellant (e.g., propane, butane, isobutene). The composition may be delivered via a non-pressurized delivery system such as a nebulizer or atomizer.

Suitable oral dosage forms include, for example, tablets, pills, sachets, or capsules of hard or soft gelatin, methylcellulose or of another suitable material easily dissolved in the digestive tract. Suitable nontoxic solid carriers can be used which include, for example, pharmaceutical grades of mannitol, lactose, starch, magnesium stearate, sodium saccharin, talcum, cellulose, glucose, sucrose, magnesium carbonate, and the like. (See, e.g., *Remington: The Science and Practice of Pharmacy* (Gennaro, 21$^{st}$ Ed. Mack Pub. Co., Easton, Pa. (2005)).

The alkoxyphenyl-linked amine derivative compounds described herein may be formulated for sustained or slow-release. Such compositions may generally be prepared using well known technology and administered by, for example, oral, periocular, intraocular, rectal or subcutaneous implantation, or by implantation at the desired target site. Sustained-release formulations may contain an agent dispersed in a carrier matrix and/or contained within a reservoir surrounded by a rate controlling membrane. Excipients for use within such formulations are biocompatible, and may also be biodegradable; preferably the formulation provides a relatively constant level of active component release. The amount of active compound contained within a sustained-release formulation depends upon the site of implantation, the rate and expected duration of release, and the nature of the condition to be treated or prevented.

Systemic drug absorption of a drug or composition administered via an ocular route is known to those skilled in the art (see, e.g., Lee et al., *Int. J. Pharm.* 233:1-18 (2002)). In one embodiment, an alkoxyphenyl-linked amine derivative compound is delivered by a topical ocular delivery method (see, e.g., *Curr. Drug Metab.* 4:213-22 (2003)). The composition may be in the form of an eye drop, salve, or ointment or the like, such as, aqueous eye drops, aqueous ophthalmic suspensions, non-aqueous eye drops, and non-aqueous ophthalmic suspensions, gels, ophthalmic ointments, etc. For preparing a gel, for example, carboxyvinyl polymer, methyl cellulose, sodium alginate, hydroxypropyl cellulose, ethylene maleic anhydride polymer and the like can be used.

The dose of the composition comprising at least one of the alkoxyphenyl-linked amine derivative compounds described herein may differ, depending upon the patient's (e.g., human) condition, that is, stage of the disease, general health status, age, and other factors that a person skilled in the medical art will use to determine dose. When the composition is used as eye drops, for example, one to several drops per unit dose, preferably 1 or 2 drops (about 50 µl per 1 drop), may be applied about 1 to about 6 times daily.

Pharmaceutical compositions may be administered in a manner appropriate to the disease to be treated (or prevented) as determined by persons skilled in the medical arts. An appropriate dose and a suitable duration and frequency of administration will be determined by such factors as the condition of the patient, the type and severity of the patient's disease, the particular form of the active ingredient, and the method of administration. In general, an appropriate dose and treatment regimen provides the composition(s) in an amount sufficient to provide therapeutic and/or prophylactic benefit (e.g., an improved clinical outcome, such as more frequent complete or partial remissions, or longer disease-free and/or overall survival, or a lessening of symptom severity). For prophylactic use, a dose should be sufficient to prevent, delay the onset of, or diminish the severity of a disease associated with neurodegeneration of retinal neuronal cells and/or degeneration of other mature retinal cells such as RPE cells. Optimal doses may generally be determined using experimental models and/or clinical trials. The optimal dose may depend upon the body mass, weight, or blood volume of the patient.

The doses of the alkoxyphenyl-linked amine derivative compounds can be suitably selected depending on the clinical status, condition and age of the subject, dosage form and the like. In the case of eye drops, an alkoxyphenyl-linked amine derivative compound can be administered, for example, from about 0.01 mg, about 0.1 mg, or about 1 mg, to about 25 mg, to about 50 mg, to about 90 mg per single dose. Eye drops can be administered one or more times per day, as needed. In the case of injections, suitable doses can be, for example, about 0.0001 mg, about 0.001 mg, about 0.01 mg, or about 0.1 mg to about 10 mg, to about 25 mg, to about 50 mg, or to about 90 mg of the alkoxyphenyl-linked amine derivative compound, one to seven times per week. In other embodiments, about 1.0 to about 30 mg of the alkoxyphenyl-linked amine derivative compound can be administered one to seven times per week.

Oral doses can typically range from 1.0 to 1000 mg, one to four times, or more, per day. An exemplary dosing range for oral administration is from 10 to 250 mg one to three times per day. If the composition is a liquid formulation, the composition comprises at least 0.1% active compound at particular mass or weight (e.g., from 1.0 to 1000 mg) per unit volume of carrier, for example, from about 2% to about 60%.

In certain embodiments, at least one alkoxyphenyl-linked amine compound described herein may be administered under conditions and at a time that inhibits or prevents dark adaptation of rod photoreceptor cells. In certain embodiments, the compound is administered to a subject at least 30 minutes (half hour), 60 minutes (one hour), 90 minutes (1.5 hour), or 120 minutes (2 hours) prior to sleeping. In certain embodiments, the compound may be administered at night before the subject sleeps. In other embodiments, a light stimulus may be blocked or removed during the day or under normal light conditions by placing the subject in an environment in which light is removed, such as placing the subject in a darkened room or by applying an eye mask over the eyes of the subject. When the light stimulus is removed in such a manner or by other means contemplated in the art, the agent may be administered prior to sleeping.

The doses of the compounds that may be administered to prevent or inhibit dark adaptation of a rod photoreceptor cell can be suitably selected depending on the clinical status, condition and age of the subject, dosage form and the like. In the case of eye drops, the compound (or the composition comprising the compound) can be administered, for example, from about 0.01 mg, about 0.1 mg, or about 1 mg, to about 25 mg, to about 50 mg, to about 90 mg per single dose. In the case of injections, suitable doses can be, for example, about 0.0001 mg, about 0.001 mg, about 0.01 mg, or about 0.1 mg to about 10 mg, to about 25 mg, to about 50 mg, or to about 90 mg of the compound, administered any number of days between one to seven days per week prior to sleeping or prior to removing the subject from all light sources. In certain other embodiments, for administration of the compound by eye drops or injection, the dose is between 1-10 mg (compound)/kg (body weight of subject) (i.e., for example, 80-800 mg total per dose for a subject weighing 80 kg). In other embodiments, about 1.0 to about 30 mg of compound can be administered one to seven times per week. Oral doses can typically range from about 1.0 to about 1000 mg, administered any number of days between one to seven days per week. An exemplary dosing range for oral administration is from about 10 to about 800 mg once per day prior to sleeping. In other embodiments, the composition may be delivered by intravitreal administration.

Also provided are methods of manufacturing the compounds and pharmaceutical compositions described herein. A composition comprising a pharmaceutically acceptable excipient or carrier and at least one of the alkoxyphenyl-linked amine derivative compounds described herein may be prepared by synthesizing the compound according to any one of the methods described herein or practiced in the art and then formulating the compound with a pharmaceutically acceptable carrier. Formulation of the composition will be appropriate and dependent on several factors, including but not limited to, the delivery route, dose, and stability of the compound.

Other embodiments and uses will be apparent to one skilled in the art in light of the present disclosures. The following examples are provided merely as illustrative of various embodiments and shall not be construed to limit the invention in any way.

EXAMPLES

Unless otherwise noted, reagents and solvents were used as received from commercial suppliers. Anhydrous solvents were used for synthetic transformations generally considered sensitive to moisture. Flash column chromatography and thin layer chromatography (TLC) were performed on silica gel unless otherwise noted. Gradient flash column chromatography was performed on a Biotage instrument. Proton and carbon nuclear magnetic resonance spectra were obtained on a Varian 400/54 spectrometer at 400 MHz for proton and 125 MHz for carbon, as noted. Spectra are given in ppm (δ) and coupling constants, J, are reported in Hertz (Hz). Residual protonated solvent was used as the reference peak for proton and carbon spectra.

RP HPLC analyses were obtained using a Gemini C18 column (150×4.6 mm, 5μ, Phenomenex) with detection at 220 nm using a standard solvent gradient program.

| Method 1 | | | |
|---|---|---|---|
| Time (min) | Flow (mL/min) | % A | % B |
| 0.0 | 1.0 | 70.0 | 30.0 |
| 6.0 | 1.0 | 20.0 | 80.0 |
| 9.0 | 1.0 | 5.0 | 95.0 |
| 11.0 | 1.0 | 70.0 | 30.0 |
| 15.0 | 1.0 | 30.0 | 30.0 |

A = Water with 0.05% Trifluoroacetic Acid
B = Acetonitrile with 0.05% Trifluoroacetic Acid

| Method 2 | | | |
|---|---|---|---|
| Time (min) | Flow (mL/min) | % A | % B |
| 0.0 | 1.0 | 70.0 | 30.0 |
| 14.2 | 1.0 | 20.0 | 80.0 |
| 17.0 | 1.0 | 5.0 | 95.0 |
| 20.0 | 1.0 | 70.0 | 30.0 |
| 24.0 | 1.0 | 30.0 | 30.0 |

A = Water with 0.05% Trifluoroacetic Acid
B = Acetonitrile with 0.05% Trifluoroacetic Acid Chiral HPLC Analyses were obtained using a Chiralpak IA column (4.6 mm×250 mm, 5μ) with diode array detection. The eluent used was 95% heptanes, 5% EtOH: 0.1% ethanesulfonic acid. The flow rate was 1 mL/min; column temperature was 25° C.

The following Examples 1-196 describe the preparation of a compound described herein.

Example 1

Preparation of 3-(3-(cyclohexylmethoxy)phenyl)propan-1-amine

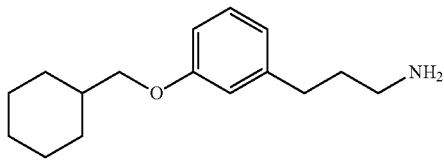 [SMILES: NCCCc1cccc(OCC2CCCCC2)c1]

3-(3-(Cyclohexylmethoxy)phenyl)propan-1-amine was prepared following the method shown in Scheme 1:

SCHEME 1

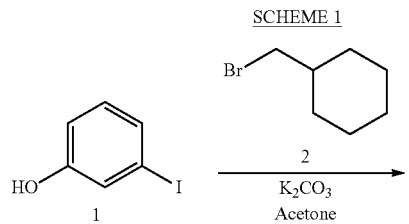

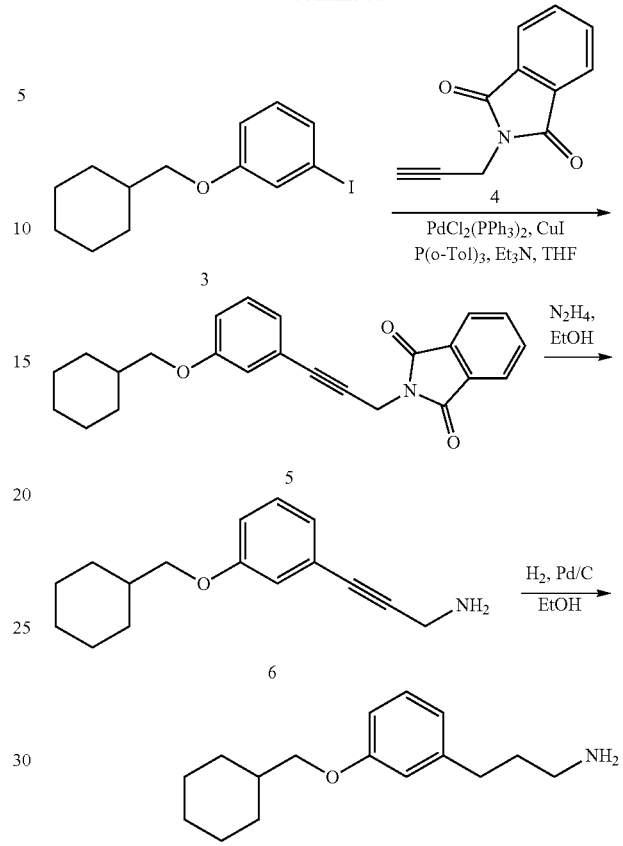

Step 1:

A mixture of 3-iodophenol (1) (1.1 g, 5 mmol), bromide 2 (2.1 mL, 15 mmol) and potassium carbonate (2.07 g, 15 mmol) in acetone (20 mL) was heated under reflux overnight. The mixture was cooled to room temperature and then concentrated under reduced pressure. The mixture was partitioned between EtOAc and water and the organic layer was washed with 10% aqueous sodium hydroxide, then brine, dried over $MgSO_4$ and concentrated under reduced pressure. Purification by flash chromatography (0 to 30% EtOAc-hexanes gradient) gave ether 3 as a clear oil. Yield (1.08 g, 68%): $^1$H NMR (400 MHz, DMSO-$d_6$) δ 7.13-7.26 (m, 2H), 7.03 (t, J=8.0 Hz, 1H), 6.92 (dq, J=8.4, 2.4 Hz, 1H), 3.74 (d, J=6.4 Hz, 2H), 1.60-1.77 (m, 6H), 0.95-1.28 (m, 5H).

Step 2:

Preparation of acetylene 4: To an ice cold mixture of propargyl bromide (50 g of an 80% solution in toluene, 336 mmol) in DMF (200 mL) under argon was added potassium phthalimide (64.7 g, 350 mmol) via a funnel. The funnel was rinsed with additional DMF (50 mL). The reaction mixture was allowed to warm to room temperature and then stirred overnight. After solids were removed from the mixture by filtration through Celite, the filtrate was concentrated under reduced pressure. The residue was partitioned between EtOAc and water and the combined organics were washed with water and saturated aqueous $NaHCO_3$ and dried over $MgSO_4$. The solution was concentrated under reduced pressure to give an off-white solid. The product was suspended in water, sonicated and the resulting solid was collected by filtration. After drying under vacuum, the solid was triturated with hexanes, collected by filtration and dried to give acetylene 4 as a slightly off-white solid. Yield (49.7 g, 80%):

¹H NMR (400 MHz, DMSO-d₆) δ 7.85-7.93 (m, 4H), 4.38 (d, J=6.0 Hz, 2H), 3.26-3.34 (m, 1H).

A mixture of iodide 3 (1.00 g, 3.16 mmol), acetylene 4 (0.643 g, 3.5 mmol), bis(triphenylphosphine)palladium (II) dichloride (0.042 g, 0.06 mmol, copper (I) iodide (0.011 g, 0.06 mmol), tri-(o-tolyl)phosphine (0.037 g, 0.12 mmol) and triethylamine (3 mL) in THF (10 mL) was degassed (vac/argon) and stirred at 55° C. under argon for 16 h. The mixture was concentrated under reduced pressure and then diluted with a small quantity of dichloromethane. Purification by flash chromatography (5 to 40% EtOAc-hexanes gradient) gave phthalimide 5 as a light yellow oil. Yield (0.7 g, 59%): ¹H NMR (400 MHz, DMSO-d₆) δ 7.85-7.93 (m, 4H), 7.20-7.24 (m, 1H), 6.90-6.96 (m, 3H), 4.60 (s, 2H), 3.74 (d, J=5.6 Hz, 2H), 1.60-1.76 (m, 6H), 0.94-1.26 (m, 5H).

Step 3:

To a solution of phthalimide 5 (0.7 g, 1.85 mmol) in EtOH (10 mL) was added hydrazine monohydrate (0.5 mL) and the mixture was stirred at 55° C. for 6 h. The mixture was cooled to room temperature then filtered. The filtrate was concentrated under reduced pressure and the residue suspended in EtOAc (50 mL) and the product collected by filtration to give amine 6 which was used without further purification in the next step.

Step 4:

To a solution of amine 6 (previous step) in EtOH (10 mL) under argon was added 10% Pd/C (0.1 g). The flask was filled with hydrogen and the mixture stirred under a balloon of hydrogen overnight. The mixture was filtered through a 0.45 µm filter and the filtrate was concentrated under reduced pressure. Purification by flash chromatography (80 to 100% (9:1 EtOAc: 7M NH₃ in MeOH)-hexanes gradient) gave Example 1 as a clear oil. Yield (0.192 g, 42% for two steps): ¹H NMR (400 MHz, DMSO-d₆) δ 7.13 (t, J=8.0 Hz, 1H), 6.73-6.78 (m, 3H), 3.79 (d, J=5.6 Hz, 2H), 2.47-2.55 (m, 2H), 1.71-1.75 (m, 1H), 1.55-1.63 (m, 2H), 1.26-1.40 (m, 9H), 0.84-0.87 (m, 5H).

Example 2

Preparation of 3-(3-(2-propylpentyloxy)phenyl)propan-1-amine

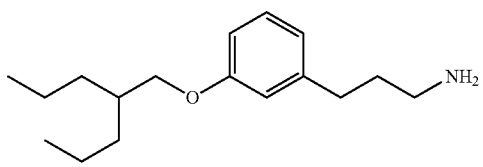 [SMILES: CCCC(CCC)COc1cccc(CCCN)c1]

3-(3-(2-Propylpentyloxy)phenyl)propan-1-amine was prepared following the method shown in Scheme 2:

SCHEME 2

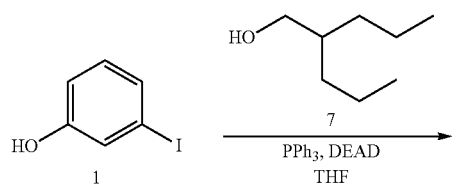

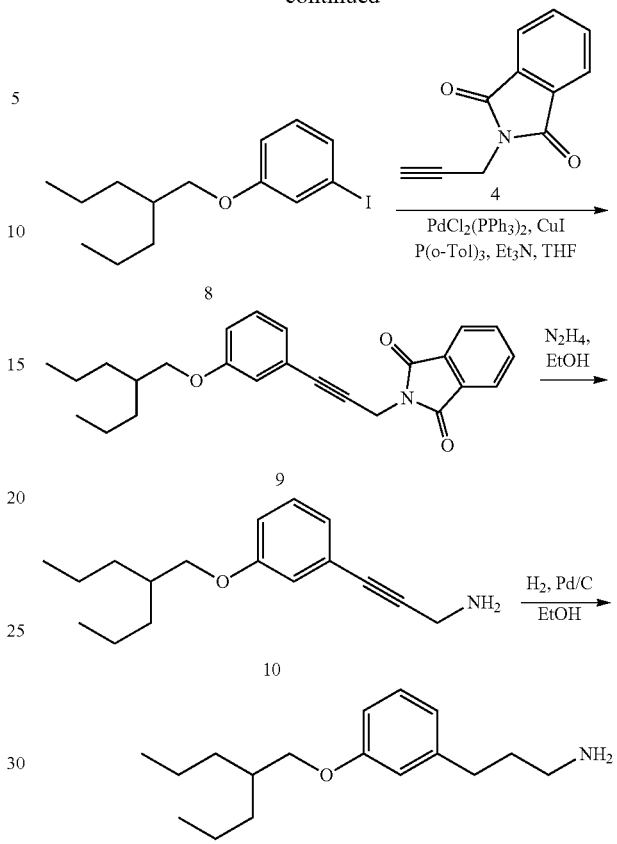

Step 1:

To a solution of phenol 1 (0.66 g, 3 mmol), alcohol 7 (0.49 mL, 3.1 mmol, and PPh₃ (0.865 g, 3.3 mmol) in THF (7 mL) under argon was added diethyl azodicarboxylate (0.44 mL, 3.3 mmol) dropwise with rapid stirring. The mixture was stirred at room temperature for 2.5 h. The mixture was concentrated. Purification by flash chromatography (5 to 50% EtOAc-hexanes gradient) gave ether 8 as a clear oil. Yield (0.995 g, quant): ¹H NMR (400 MHz, DMSO-d₆) δ 7.24-7.26 (m, 2H), 7.01-7.06 (m, 1H), 6.91-6.94 (m, 1H), 3.81 (d, J=6.0 Hz, 2H), 1.70-1.73 (m, 1H), 1.25-1.38 (m, 8H), 0.84-0.87 (m, 6H).

Step 2:

Coupling of ether 8 with acetylene 4 following the method described in Example 1 gave phthalimide 9 as a light yellow solid. Yield (0.77 g, 69%): ¹H NMR (400 MHz, DMSO-d₆) δ 7.85-7.93 (m, 4H), 7.20-7.24 (m, 1H), 6.91-6.96 (m, 3H), 4.60 (s, 2H), 3.80 (d, J=6.0 Hz, 2H), 1.69-1.71 (m, 1H), 1.23-1.37 (m, 8H), 0.82-0.85 (m, 6H).

Step 3:

Deprotection of phthalimide 9 with hydrazine following the method used in Example 1 gave amine 10 which was used without further purification in the next step.

Step 4:

Hydrogenation of alkyne 10 following the method used in Example 1 gave Example 2. Yield (0.291 g, 56% two steps): ¹H NMR (400 MHz, DMSO-d₆) δ 7.12 (t, J=8.0 Hz, 1H), 6.67-6.71 (m, 3H), 3.70 (d, J=6.0 Hz, 2H), 2.47-2.52 (m, 8H), 1.55-1.80 (m, 8H), 1.12-1.32 (m, 5H), 0.96-1.06 (m, 2H).

Example 3

Preparation of
3-(3-(2-ethylbutoxy)phenyl)propan-1-amine

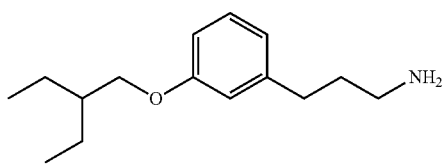 [SMILES: CCC(CC)COc1cccc(CCCN)c1]

3-(3-(2-Ethylbutoxy)phenyl)propan-1-amine was prepared following the method used in Example 1.

Step 1:

Alkylation of phenol 1 with 1-bromo-2-ethylbutane gave 1-(2-ethylbutoxy)-3-iodobenzene as a clear oil. Yield (1.29 g, 85%): $^1$H NMR (400 MHz, DMSO-$d_6$) δ 7.24-7.28 (m, 2H), 7.04 (t, J=8.0, 1H), 6.94 (dq, J=8.0, 0.8, 1H), 3.83 (d, J=5.6, 2H), 1.55-1.59 (m, 1H), 1.28-1.44 (m, 4H), 0.86 (t, J=7.2, 6H).*

Step 2:

Coupling of 1-(2-ethylbutoxy)-3-iodobenzene with acetylene 4 gave 2-(3-(3-(2-ethylbutoxy)phenyl)prop-2-ynyl)isoindoline-1,3-dione as a light orange solid. Yield (0.80 g, 53%): $^1$H NMR (400 MHz, DMSO-$d_6$) δ 7.85-7.93 (m, 4H), 7.22 (dd, J=9.2, 7.6 Hz, 1H), 6.92-6.96 (m, 3H), 4.60 (s, 2H), 3.81 (d, J=6.0 Hz, 2H), 1.53-1.59 (m, 1H), 1.30-1.43 (m, 4H), 0.85 (t, J=7.2 Hz, 6H).

Step 3:

Deprotection of 2-(3-(3-(2-ethylbutoxy)phenyl)prop-2-ynyl)isoindoline-1,3-dione with hydrazine gave 3-(3-(2-ethylbutoxy)phenyl)prop-2-yn-1-amine which was used without further purification in the next step.

Step 4:

Hydrogenation of 3-(3-(2-ethylbutoxy)phenyl)prop-2-yn-1-amine gave Example 3 as a clear oil. Yield (0.320 g, 63% two steps): $^1$H NMR (400 MHz, DMSO-$d_6$) δ 7.13 (t, J=7.6 Hz, 1H), 6.69-6.73 (m, 3H), 3.81 (d, J=6.0 Hz, 2H), 2.47-2.55 (m, 4H), 1.55-1.62 (m, 3H), 1.33-1.45 (m, 6H), 0.87 (t, J=7.6 Hz, 6H).

Example 4

Preparation of
3-amino-1-(3-(cyclohexylmethoxy)phenyl)propan-1-ol

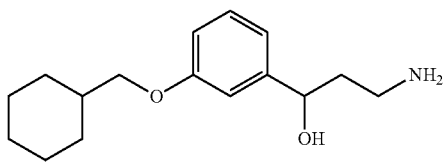

3-Amino-1-(3-(cyclohexylmethoxy)phenyl)propan-1-ol was prepared following the method shown in Scheme 3:

SCHEME 3

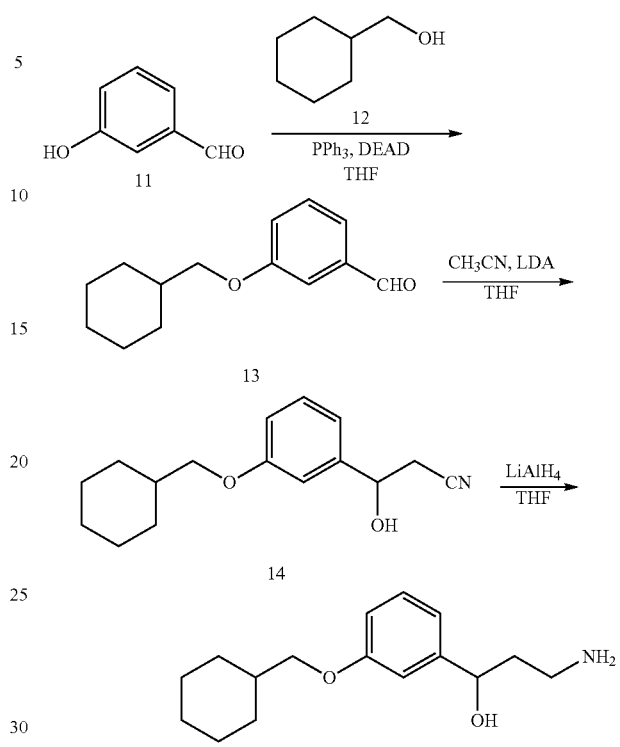

Step 1:

Coupling of 3-hydroxybenzaldehyde (11) (2.3 g, 18.9 mmol) with cyclohexylmethanol (12) (2.1 g, 18.9 mmol) was conducted following the procedure given for Example 2 except that the addition of diethyl azodicarboxylate was carried out at 0° C. and the reaction was stirred at room temperature overnight. The reaction mixture was concentrated under reduced pressure and the residue was triturated with diethyl ether (100 mL). The resulting white ppt was removed by filtration. Trituration and filtration was repeated. The filtrate was re-filtered through silica (eluent 10% EtOAc-hexanes) and concentrated under reduced pressure to give a pale yellow oil. Purification by flash chromatography (0 to 20% EtOAc-hexanes gradient) followed by prep TLC (25% EtOAc-hexanes) of impure fractions gave ether 13 as a pale yellow oil. Yield (1.6 g, 39%): $^1$H NMR (400 MHz, DMSO-$d_6$) δ 9.95 (s, 1H), 7.45-7.5 (m, 2H), 7.38-7.39 (m, 1H), 7.22-7.25 (m, 1H), 3.82 (d, J=6.4 Hz, 2H), 1.74-1.81 (m, 2H), 1.58-1.73 (m, 4H), 1.10-1.28 (m, 3H), 0.98-1.08 (m, 2H).

Step 2:

To a −78° C. solution of acetonitrile (0.578 mL, 10.99 mmol) in anhydrous THF (20 mL) under argon, was added a solution of LDA (5.85 mL of a 2M solution in THF, 11.73 mmol) dropwise. The resulting mixture was stirred at −78° C. for 1 h. A solution of aldehyde 13 (1.6 g, 7.3 mmol) in THF (20 mL) was added dropwise. The reaction mixture was allowed to warm to room temperature over 30 min. The reaction was quenched with water (50 mL) and the mixture was extracted with EtOAc. The organic layer was washed with brine, dried over $Na_2SO_4$ and concentrated under reduced pressure. Purification by flash chromatography (20 to 60% EtOAc-hexanes gradient) gave alcohol 14 as a yellow oil. Yield (1.3 g, 68%): $^1$H NMR (400 MHz, CDCl$_3$) δ 7.27-7.31 (m, 1H), 6.92-6.95 (m, 2H), 6.85-6.88 (m, 1H), 5.00 (t, J=6.4 Hz, 1H), 3.76 (d, J=6.4 Hz, 2H), 2.77 (d, J=1.6 Hz, 1H), 2.75 (s, 1H), 1.82-1.89 (m, 2H), 1.68-1.82 (m, 4H), 1.14-1.36 (m, 4H), 1.01-1.10 (m, 2H).

Step 3:

To an ice cold solution of nitrile 14 (1.3 g, 5 mmol) in dry THF (20 mL) under argon was added LiAlH₄ (5 mL of a 2M solution in THF, 10 mmol) dropwise. The reaction mixture was stirred at 0° C. for 30 min. The reaction was quenched by the addition of saturated aqueous Na₂SO₄ until gas evolution ceased. The mixture was filtered through Celite and the Celite rinsed with THF. The solution was concentrated under reduced pressure. Purification by flash chromatography (5 to 10% 7 M NH₃ in MeOH-EtOAc) gave Example 4 as a colorless oil. Yield (0.705 g, 53%): ¹H NMR (400 MHz, CDCl₃) δ 7.22 (t, J=8.0 Hz, 1H), 6.95 (t, J=1.6 Hz, 1H), 6.90 (d, J=7.6 Hz, 1H), 6.77 (ddd, J=8.0, 2.4, 0.8 Hz, 1H), 4.90 (dd, J=8.8, 3.2 Hz, 1H), 3.75 (d, J=6.4 Hz, 2H), 3.12 (br s, 2H), 3.06 (ddd, J=12.4, 6.0, 4.0 Hz, 1H), 2.90-2.96 (m, 1H), 1.82-1.89 (m, 3H), 1.67-1.81 (m, 6H), 1.15-1.34 (m, 3H), 0.99-1.09 (m, 2H).

Example 5

Preparation of 3-amino-1-(3-(cyclohexylmethoxy)phenyl)propan-1-one

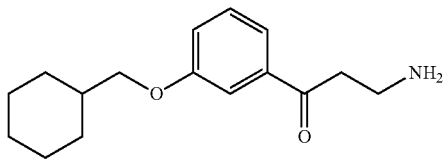 [SMILES: NCCC(=O)c1cccc(OCC2CCCCC2)c1]

3-Amino-1-(3-(cyclohexylmethoxy)phenyl)propan-1-one was prepared starting from 3-amino-1-(3-(cyclohexylmethoxy)phenyl)propan-1-ol following the method shown in Scheme 4:

SCHEME 4

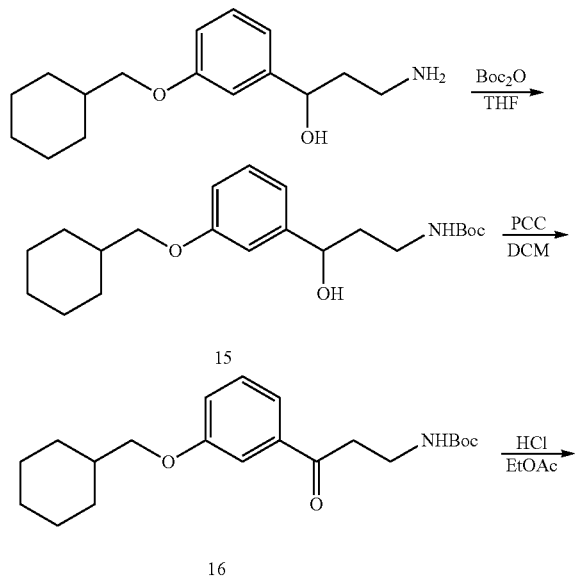

Step 1:

To a solution of 3-amino-1-(3-(cyclohexylmethoxy)phenyl)propan-1-ol (0.300 g, 1.14 mmol) in THF (5 mL) was added Boc₂O (0.249 g, 1.14 mmol). The reaction mixture was stirred for 30 min, then diluted with EtOAc, washed with water and brine, dried over Na₂SO₄ and concentrated under reduced pressure. Product 15 was used in the next step without purification.

Step 2:

To a solution of compound 15 (approx. 1.14 mmol) in dichloromethane (5 mL) was added pyridinium chlorochromate (0.295 g, 1.14 mmol). The mixture was stirred for 1 h at room temp, then Celite was added and the mixture stirred. The mixture was filtered and the filtrate was concentrated under reduced pressure. Purification by flash chromatography (EtOAc-hexanes) gave ketone 16 which was used in the next step without purification.

Step 3:

To a solution of ketone 16 (approx. 1.14 mmol) in EtOAc was added HCl (2.7 ml of a 4.2 M solution in EtOAc, 11.4 mmol). Stirring at room temperature gave a white ppt which was collected by filtration and dried under vacuum. A second batch of ppt was recovered from the filtrate after cooling to 4° C. to give the Example 5 hydrochloride as a white powder. Yield (0.190 g, 56% for three steps): ¹H NMR (400 MHz, DMSO-d₆) δ 8.04 (br s, 3H), 7.52 (dt, J=7.6, 1.2 Hz, 1H), 7.44 (t, J=8.0 Hz, 1H), 7.40 (dd, J=2.4, 1.6 Hz, 1H), 7.22, (ddd, J=8.0, 2.4, 0.8 Hz, 1H), 3.83 (d, J=6.0 Hz, 2H), 3.41 (t, J=6.4 Hz, 2H), 3.11 (t, J=6.4 Hz, 2H), 1.78-1.81 (m, 2H), 1.62-1.74 (m, 4H), 1.10-1.30 (m, 3H), 0.99-1.09 (m, 2H).

Example 6

Preparation of 1-amino-3-(3-(cyclohexylmethoxy)phenyl)propan-2-ol

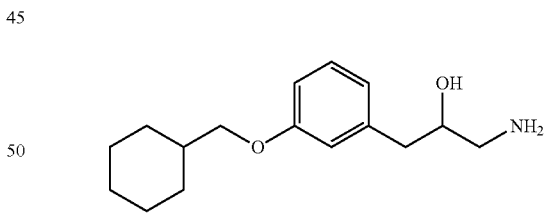

1-Amino-3-(3-(cyclohexylmethoxy)phenyl)propan-2-ol was prepared following the method shown in Scheme 5:

SCHEME 5

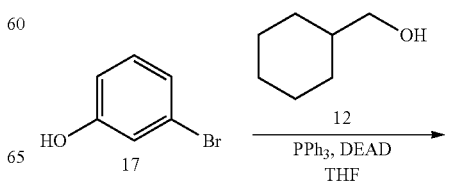

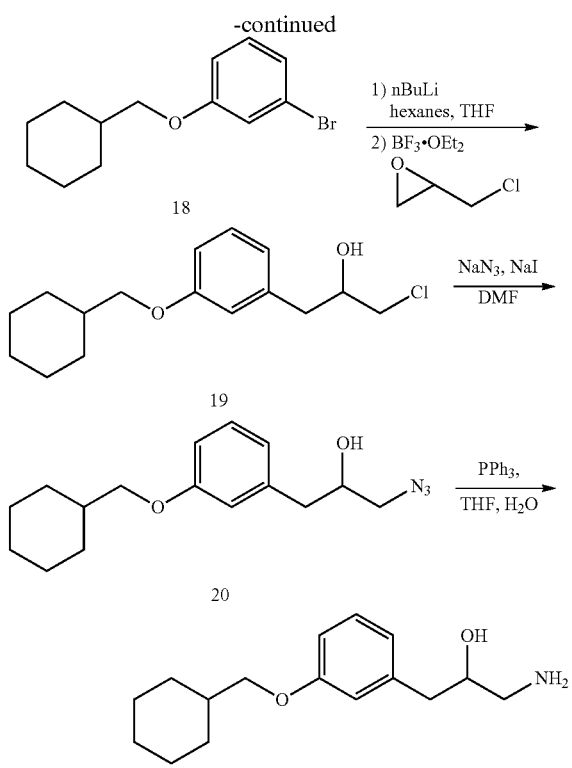

Step 1:

Coupling of 3-bromophenol (17) (5.0 g, 28.9 mmol) with cyclohexylmethanol (12) (3.3 g, 28.9 mmol) was conducted following the procedure given for Example 2 except that the reaction was stirred at room temperature overnight. The reaction mixture was concentrated under reduced pressure then triturated with 20% diethyl ether-hexanes. The suspension was filtered and the filtrate was concentrated under reduced pressure. Purification by flash chromatography (100% hexanes) gave ether 18 a clear liquid. Yield (5.03 g, 65%): $^1$H NMR (400 MHz, DMSO-$d_6$) δ 7.20 (t, J=8.0 Hz, 1H), 7.10 (t, J=2.0 Hz, 1H), 7.06-7.09 (m, 1H), 6.91 (dq, J=8.4, 0.8 Hz, 1H), 3.76 (d, J=6.4 Hz, 2H), 1.60-2.47 (m, 6H), 1.11-1.27 (m, 3H), 0.95-1.05 (m, 2H).

Step 2:

Ether 18 (2.5 g, 9.29 mmol) was placed in a round bottom flask and dried in a vacuum oven at 40° C. for 3 h, then cooled under $N_2$. Anhydrous THF (20 mL) was added and the solution was cooled to −78° C., n-BuLi (6.4 mL of a 1.6 M solution in hexanes, 10.2 mmol) was added dropwise over 5 min. After the mixture was stirred for 10 min at −78° C., $BF_3$-diethyl etherate (1.3 mL, 10.35 mmol) was added followed by the addition of a solution of epichlorohydrin (0.73 mL, 9.31 mmol) in THF (5 mL) dropwise in portions over 11 min. The reaction mixture was stirred for 45 min at −78° C. then quenched with the dropwise addition of water (5 mL). After warming to room temperature, the mixture was partitioned between MTBE and water and the organic layer was washed with water and brine and dried over $Na_2SO_4$. Purification by flash chromatography (EtOAc:hexanes 1:8, with pre-adsorbtion onto silica gel) gave chlorohydrin 19 in ca. 90% purity. Yield (1.11 g, 42%): $^1$H NMR (400 MHz, DMSO-$d_6$) δ 7.15 (t, J=7.9 Hz, 1H), 6.72-6.77 (m, 3H), 5.14 (d, J=5.5 Hz, 1H), 3.83-3.87 (m, 1H), 3.72 (d, J=6.3 Hz, 2H), 3.53 (dd, J=11.0, 4.5 Hz, 1H), 3.43 (dd, J=11.0, 5.5 Hz, 1H), 2.75 (dd, J=13.5, 5.3 Hz, 1H), 2.62 (dd, J=13.5, 7.4 Hz, 1H), 1.62-1.79 (m, 6H), 1.12-1.28 (m, 3H), 0.84-1.06 (m, 2H).

Step 3:

To a solution of chlorohydrin 19 (1.11 g, 3.92 mmol) in anhydrous DMF (30 mL) under $N_2$ was added $NaN_3$ (1.28 g, 19.6 mmol) and NaI (0.147 g, 2.26 mmol). The mixture was heated at 75° C. overnight. After cooling to room temperature, the mixture was diluted with EtOAc and washed with water, 5% aqueous LiCl and brine. The solution was dried over $Na_2SO_4$ and concentrated under reduced pressure. The product was dried in a vacuum oven at 40° C. for 2 h to give azide 20 as a brown oil which was used without purification. Yield (1.11 g, 97% crude).

Step 4:

To a solution of azide 20 (1.11 g, 3.84 mmol) in THF (30 mL) under $N_2$ was added $PPh_3$ (1.01 g, 3.85 mmol) and water (10 mL). The reaction mixture was heated at 50° C. for 24 h. After cooling to room temperature, the mixture was partitioned between 10% aqueous $NaHCO_3$ and dichloromethane. The aqueous layer was re-extracted with dichloromethane and the combined organics were washed with brine then dried with $Na_2SO_4$ and concentrated under reduced pressure. Purification by flash chromatography (100% dichloromethane then 85:14:1 (dichloromethane:EtOH:$NH_4OH$) gave a colorless oil which was dried in a vacuum oven at 40° C. overnight to give Example 6 as a pale yellow oil which formed an amorphous white solid upon standing. Yield (0.70 g, 69%): $^1$H NMR (400 MHz, DMSO-$d_6$) δ 7.12 (t, J=7.9 Hz, 1H), 6.68-6.74 (m, 3H), 3.71 (d, J=6.5 Hz, 2H), 3.50-3.52 (m, 1H), 2.62 (dd, J=13.3, 5.7 Hz, 1H), 2.49-2.52 (m, 1H), 2.45-2.47 (m, 1H), 2.37 (dd, J=12.7, 6.8 Hz, 1H), 1.62-1.80 (m, 6H), 1.16-1.26 (m, 3H), 0.99-1.05 (m, 2H).

Example 7

Preparation of 2-(3-(cyclohexylmethoxy)phenoxy)ethanamine

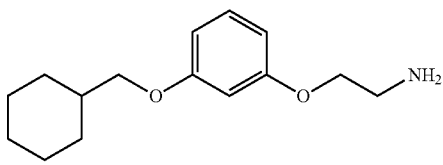 [SMILES: NCCOc1cccc(OCC2CCCCC2)c1]

2-(3-(Cyclohexylmethoxy)phenoxy)ethanamine was prepared following the method shown in Scheme 6.

SCHEME 6

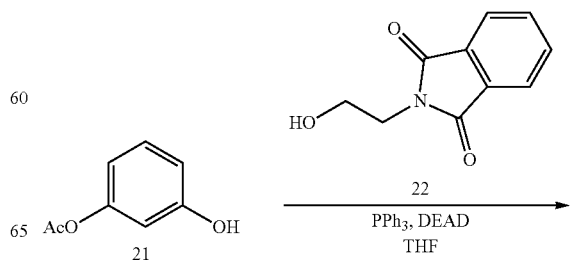

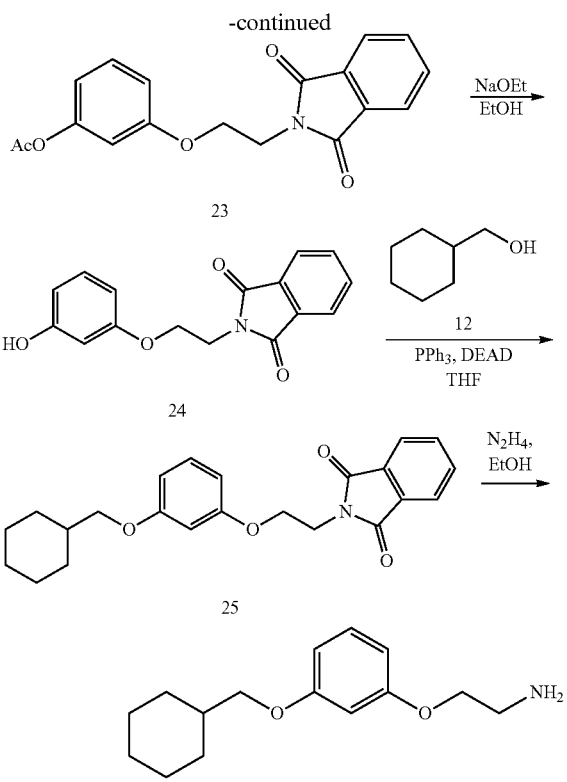

Step 1:

To a solution of phenol 21 (1.74 g, 11.44 mmol), alcohol 22 (2.25 g, 11.77 mmol) and PPh₃ (3.30 g, 12.58 mmol) in anhydrous THF (60 mL) was added a solution of diethyl azodicarboxylate (2.30 g, 13.2 mmol) in THF (20 mL). The reaction mixture was stirred at room temperature for 15 min then concentrated under reduced pressure. Hexanes was added to the gummy solid to form a suspension. EtOAc was slowly added until the solid changed to a fine precipitate which was removed by filtration. The filtrate was concentrated under reduced pressure. Purification by flash chromatography (10 to 70% EtOAc-hexanes gradient, loading as a concentrated solution in CH$_2$Cl$_2$) gave ether 23. Yield (1.30 g, 38%): $^1$H NMR (400 MHz, CDCl$_3$) δ 7.85-7.86 (m, 2H), 7.71-7.74 (m, 2H), 7.23 (t, J=8.0 Hz, 1H), 6.75 (dq, J=8.4, 0.8 Hz, 1H), 6.66 (dq, J=8.0, 0.8 Hz, 1H), 6.62 (t, J=2.4 Hz, 1H), 4.19 (t, J=6 Hz, 2H), 4.10 (t, J=6 Hz, 2H), 2.26 (s, 3H).

Step 2:

Ether 23 (1.34 g, 4.11 mmol) was dissolved in hot EtOH (30 mL). After cooling to room temperature, NaOEt in EtOH (2 mL of a 2.68 M solution, 5.36 mmol) was added and the mixture was stirred at room temperature under argon for 35 min. Additional NaOEt solution in EtOH (2.68 M, 0.60 mL, 1.6 mmol) was added and the mixture was stirred for a further 35 min. Solutions of aqueous NaHSO$_4$ (3.0 mL), saturated aqueous NH$_4$Cl (10 mL) and brine (50 mL) were added. The mixture was extracted with EtOAc, and the extract was washed with brine, dried over MgSO$_4$, filtered and concentrated under reduced pressure. Purification by flash chromatography (10 to 100% EtOAc-hexanes gradient) gave phenol 24. Yield (0.4921 g, 42%): $^1$H NMR (400 MHz, CDCl$_3$) δ 7.84-7.86 (m, 2H), 7.71-7.73 (m, 2H), 7.07 (t, J=8.0 Hz, 1H), δ 6.39-6.46 (m, 3H), 5.35 (br s, 1H), 4.19 (t, J=5.2 Hz, 2H), 4.09 (t, J=5.2 Hz, 2H).

Step 3:

To an ice cold solution of PPh$_3$ (0.498 g, 1.90 mmol) in anhydrous THF (3 mL) was added a solution of diethyl azodicarboxylate (0.3508 g, 2.0 mmol) in THF (2 mL). The ice-cold mixture was stirred for 10 min. A solution of cyclohexylmethanol (0.1182 g, 1.04 mmol) in THF (2 mL) was added, followed by a solution of phenol 24 (0.2841 g, 0.9993 mmol) in THF (2 mL). The mixture was allowed to warm to room temperature, then additional cyclohexylmethanol (0.1194 g, 1.308 mmol) and diethyl azodicarboxylate (0.354 g, 2.0 mmol) were added and the mixture was stirred briefly. The reaction mixture was concentrated under reduced pressure. Purification by flash chromatography (10 to 100% EtOAc-hexanes gradient, loading as a concentrated solution in dichloromethane, repeated twice) gave ether 25. Yield (0.1983 g, 52%): $^1$H NMR (400 MHz, CDCl$_3$) δ 7.78-7.81 (m, 2H), 7.63-7.76 (m, 2H), 7.04 (t, J=8.0 Hz, 1H), 6.35-6.41 (m, 3H), 4.13 (t, J=5.6 Hz, 2H), 4.03 (t, J=5.6 Hz, 2H), 3.62 (d, J=6.4 Hz, 2H), 1.59-1.79 (m, 5H), 1.07-1.27 (m, 4H), 0.85-0.99 (m, 2H).

Step 4:

To a solution of ether 25 (0.1443 g, 0.379 mmol) in EtOH (5 mL) at room temperature was added hydrazine hydrate (0.1128 g, 2.26 mmol). The mixture was heated under reflux for 2 h. The reaction mixture was concentrated under reduced pressure and the residue was triturated with hexanes. The precipitate was removed by filtration through Celite and the filtrate was concentrated under reduced pressure. Purification by flash chromatography (75 to 100% (5:5:1 hexane:EtOAc:7M NH$_3$ in MeOH) hexanes) gave Example 7 as a colorless oil. Yield (0.0337, g, 36%): $^1$H NMR (400 MHz, DMSO-d$_6$) δ 7.10-7.14 (m, 1H), 6.43-6.47 (m, 3H), 3.86 (t, J=6.0 Hz, 2H), 3.72 (d, J=6.4 Hz, 2H), 2.82 (d, J=5.6 Hz, 2H), 1.61-1.75 (m, 5H), 1.48 (br s, 2H), 1.10-1.28 (m, 4H), 0.95-1.05 (m, 2H).

Example 8

Preparation of 2-(3-(benzyloxy)phenoxy)ethanamine

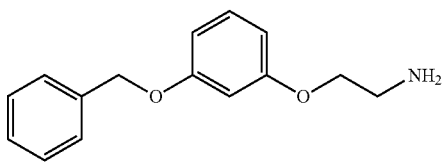 [SMILES: NCCOc1cccc(OCc2ccccc2)c1]

2-(3-(Benzyloxy)phenoxy)ethanamine was prepared following the method used in Example 7.

Step 1:

To a suspension of acetate 23 (3.10 g, 9.50 mmol) in MeOH (20 mL) was added 6M aqueous HCl (10 mL). The mixture was stirred at room temperature for 10 min then heated at 60° C. for 15 min. Additional MeOH (10 mL) was added and the mixture was heated until all material was dissolved. Additional 6M HCl (5 mL) was added and the mixture was heated initially, then at 60° C. for 15 min. After cooling, the mixture was concentrated under reduced pressure. Water (ca. 50 mL) was added to the mixture and the resultant precipitate was collected by filtration, washed with water and hexanes then dried in a vacuum dessicator to give phenol 24. Yield (2.27 g, 84%).

Step 2:

Phenol 24 was coupled with benzyl alcohol following the method used in Example 2 except that the reaction mixture was stirred for at room temperature for 1 h then at 60° C. for 1 h. The mixture was concentrated under reduced pressure. Hexanes was added to the residue to form a suspension. EtOAc was slowly added until the gummy solid turned to a precipitate which was removed by filtration and the filtrate concentrated under reduced pressure. Purification by chromatography (10 to 40% EtOAc-hexanes gradient) gave 2-(2-(3-(benzyloxy)phenoxy)ethyl)isoindoline-1,3-dione contaminated with benzyl alcohol. The crude mixture was triturated with hexanes and the product collected by filtration to give 2-(2-(3-(benzyloxy)phenoxy)ethyl)isoindoline-1,3-dione as a fine crystalline powder. Yield (0.7110 g, 65%): $^1$H NMR (400 MHz, CDCl$_3$) δ 7.86-7.87 (m, 2H), 7.71-7.74 (m, 2H), 7.29-7.42 (m, 5H), 7.14 (t, J=8.0 Hz, 1H), 6.48-6.57 (m, 3H), 5.01 (s, 2H), 4.21 (t, J=5.6 Hz, 2H), 4.10 (t, J=6.0 Hz, 2H).

Step 3:

2-(2-(3-(Benzyloxy)phenoxy)ethyl)isoindoline-1,3-dione was deprotected following the method used in Example 7 except that the reaction mixture was heated at 60° C. for 23 h. Example 8 was isolated as a colorless oil. Yield (0.3913 g, 85%): $^1$H NMR (400 MHz, CDCl$_3$) δ 7.31-7.45 (m, 5H), 7.18 (t, J=8.0 Hz, 1H), 6.52-6.61 (m, 3H), 5.05 (s, 2H), 3.96 (t, J=5.6 Hz, 2H), 3.06 (t, J=6.0 Hz, 2H), 1.34 (br s, 2H).

Example 9

Preparation of 2-(3-(cycloheptylmethoxy)phenoxy)ethanamine

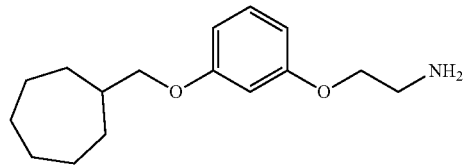

2-(3-(Cycloheptylmethoxy)phenoxy)ethanamine was prepared following the method used in Example 7.

Step 1:

To an ice-cold solution of cycloheptane carboxylic acid (83 g, 0.58 mol) in THF (350 mL) was added BH$_3$-THF (700 mL of a 1M solution in THF, 0.70 mol) dropwise. The reaction mixture was stirred at 0° C. for 30 min. After warming to room temperature, the reaction was quenched with the addition of MeOH (300 mL) initially dropwise then more quickly. The mixture was concentrated under reduced pressure. The residue was partitioned between EtOAc and aqueous NaHCO$_3$, washed with brine, dried over MgSO$_4$ and concentrated under reduced pressure. Purification by distillation (96° C. at 19 Torr) gave pure cycloheptylmethanol. Yield (58.3 g, 78%). $^1$HNMR (DMSO-d$^6$) δ 4.36 (dt, J=3.5, 1.9 Hz, 1H), 3.13 (t, J=6.0 Hz, 2H), 1.34-1.69 (m, 11H), 1.02-1.10 (m, 2H).

Step 2:

Phenol 24 was coupled with cycloheptylmethanol following the method used in Example 2 except that the reaction mixture was stirred at room temperature for 10 min then at 60° C. for 1 h. After cooling to room temperature, the mixture was concentrated under reduced pressure then 10% EtOAc-hexanes was added. The mixture was sonicated and stirred, and the precipitate was removed by filtration. The filtrate was concentrated under reduced pressure. Purification by chromatography (20% EtOAc-hexanes) gave 2-(2-(3-(cycloheptylmethoxy)phenoxy)ethyl)isoindoline-1,3-dione. Yield (0.3465 g, 51%): $^1$H NMR (400 MHz, CDCl$_3$) δ 7.85-7.87 (m, 2H), 7.71-7.73 (m, 2H), 7.11 (t, J=8.0 Hz, 1H), 6.42-6.48 (m, 3H), 4.20 (t, J=4.4 Hz, 2H), 4.10 (t, J=5.2 Hz, 2H), 3.67 (d, J=6.0 Hz, 2H), 1.79-1.95 (m, 3H), 1.42-1.71 (m, 8H), 1.20-1.34 (m, 2H).

Step 3:

2-(2-(3-(Cycloheptylmethoxy)phenoxy)ethyl)isoindoline-1,3-dione was deprotected following the method used in Example 7 except that the reaction mixture was heated at 60° C. for 16 h. Example 9 was isolated as a colorless oil. Yield (0.3913 g, 85%): $^1$H NMR (400 MHz, DMSO-d$_6$) δ 7.15 (t, J=8.0 Hz, 1H), 6.47-6.51 (m, 3H), 3.97 (t, J=4.8 Hz, 2H), 3.71 (d, J=6.8 Hz, 2H), 3.06 (t, J=5.2 Hz, 2H), 1.82-2.0 (m, 3H), 1.24-1.73 (m, 12H).

Example 10

Preparation of 1-((3-(3-aminopropyl)phenoxy)methyl)cyclohexanol

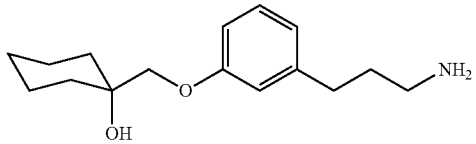 [SMILES: NCCCc1cccc(OCC2(O)CCCCC2)c1]

1-((3-(3-Aminopropyl)phenoxy)methyl)cyclohexanol was prepared following the method described in Scheme 7.

SCHEME 7

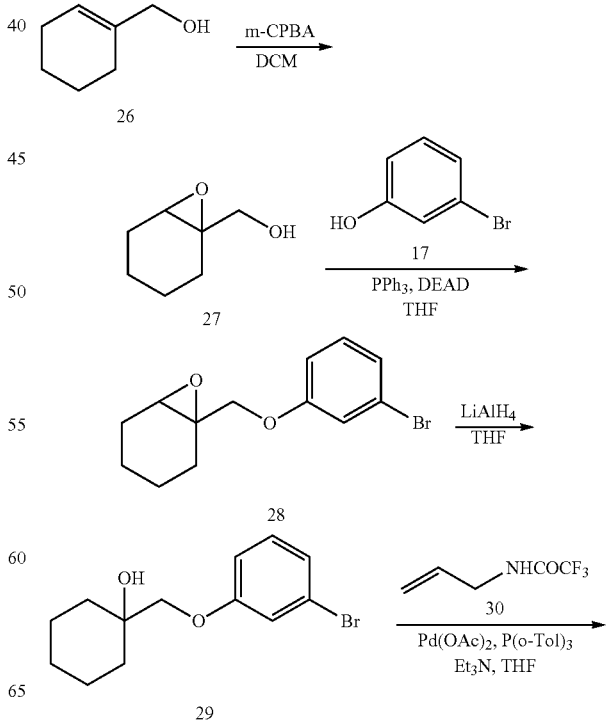

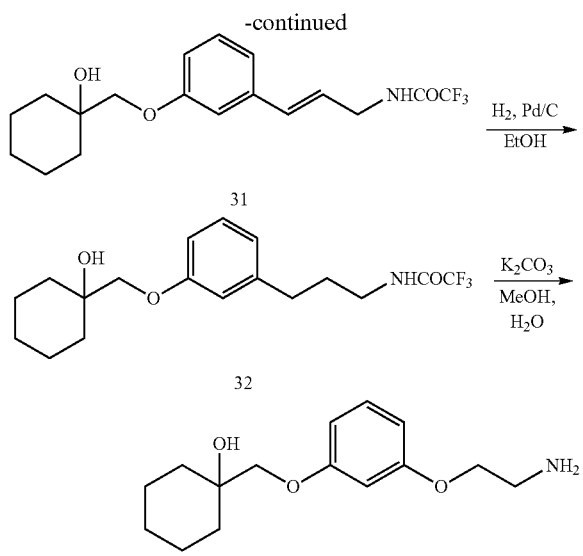

Step 1:

Preparation of cyclohexenylmethanol (26): To a 0° C. solution of 1-cyclohexene-1-carboxylic acid (5.0 g, 39.7 mmol) in diethyl ether (100 mL) under argon was added a solution of LiAlH$_4$ (22 mL of a 2M solution in THF, 44.0 mmol) dropwise. After the reaction mixture was allowed to warm to room temperature, it was stirred overnight. The mixture was then quenched with the dropwise addition of water (10 mL) while stirring. The organic layer was separated, dried over MgSO$_4$ and concentrated under reduced pressure to give cyclohexenylmethanol (26). Yield (3.6 g, 82% crude): $^1$H NMR (400 MHz, DMSO-d$_6$) δ 4.71 (t, J=5.6 Hz, 1H), 3.31 (t, J=5.6 Hz, 2H), 2.98 (t, J=2.0 Hz, 1H), 1.68-1.77 (m, 4H), 1.11-1.38 (m, 4H).

Step 2:

To a suspension of cyclohexenylmethanol (26) (1.76 g, 15.69 mmol) and Na$_2$CO$_3$ (5.05 g, 47.6 mmol) in dichloromethane (20 mL) was added meta-chloroperoxybenzoic acid (77% maximum, 4.58 g, <20.4 mmol) slowly. Gas evolution occurred. Additional dichloromethane (10 mL) was added and the reaction was stirred overnight. The mixture was partitioned between EtOAc and water. The combined organics were washed with water and brine, dried over MgSO$_4$ and concentrated under reduced pressure to give epoxide 27. Yield (1.59 g, 79%): $^1$H NMR (400 MHz, CDCl$_3$) δ 3.67 (d, J=12.4 Hz, 1H), 3.57 (d, J=12 Hz, 1H), 3.42 (d, J=6.4, 1H), 3.25 (d, J=3.2, 1H), 1.65-2.0 (m, 4H), 1.41-1.52 (m, 2H), 1.22-1.32 (m, 2H).

Step 3:

Epoxide 27 was coupled with 3-bromophenol following the method used in Example 2 except that the reaction mixture was stirred for 1 h at room temperature. The reaction mixture was concentrated under reduced pressure. Hexanes was added to the residue. The mixture was sonicated and stirred, and the precipitate was filtered off. After concentration under reduced pressure, purification by flash chromatography (20% EtOAc-hexanes) gave epoxide 28. Yield (1.3649 g, 68%): $^1$H NMR (400 MHz, CDCl$_3$) δ 7.07-7.15 (m, 3H), 6.83-6.86 (m, 1H), 3.93 (q, J=10.4 Hz, 2H), 3.19 (d, J=3.2 Hz, 1H), 1.56-2.04 (m, 4H), 1.42-1.54 (m, 2H), 1.23-1.38 (m, 2H).

Step 4:

Epoxide 28 was reduced to alcohol 29 following the method used in Example 4 except that the LiAlH$_4$ (1.25 equiv.) was added in two aliquots 20 min apart and the mixture was stirred for 45 min. Workup as in Example 4 provided crude compound which was purified by flash chromatography (10 to 30% EtOAc-hexanes gradient) to give alcohol 29. Yield (1.0589 g, 78%): $^1$H NMR (400 MHz, CDCl$_3$) δ 7.08-7.16 (m, 3H), 6.84-6.86 (m, 1H), 3.79 (s, 2H), 2.04 (s, 1H), 1.49-2.03 (m, 10H).

Step 5:

Preparation of N-allyl-2,2,2-trifluoroacetamide (30): To an ice-cold solution of ethyl trifluoroacetate (15 mL, 142.2 mmol) in THF (40 mL) was added allylamine (12 mL, 57.1 mmol). The reaction was allowed to warm to room temperature then stirred for 55 min. After the mixture was concentrated under reduced pressure, the residue was dried under vacuum to give acetamide 30. Yield (18.79 g, 98%): $^1$H NMR (400 MHz, CDCl$_3$) δ 6.46 (br s, 1H), 5.79-5.89 (m, 1H), 5.23-5.29 (m, 2H), 3.98 (t, J=5.6 Hz, 2H).

A mixture of alcohol 29 (1.0589 g, 3.71 mmol), N-allyl-2,2,2-trifluoroacetamide (30) (0.6505 g, 4.25 mmol), tri-(o-tolyl)phosphine (0.0631 g, 0.207 mmol), Pd(OAc)$_2$ (0.0558 g, 0.249 mmol), Et$_3$N (3 mL, 21.5 mmol) and anhydrous DMF (10 mL) was degassed by bubbling with argon and heated at 90° C. for 20 h. After cooling to room temperature, the mixture was concentrated under reduced pressure. EtOAc was added to the residue and the resulting precipitate was filtered off. The filtrate was concentrated under reduced pressure. Purification by flash chromatography (10 to 70% EtOAc-hexanes gradient) gave alcohol 31. Yield (0.8051 g, 61%): $^1$H NMR (400 MHz, CDCl$_3$) δ 7.21-7.25 (m, 1H), 6.96 (d, J=7.6 Hz, 1H), 6.92 (t, J=1.6 Hz, 1H), 6.82-6.85 (m, 1H), 6.55 (d, J=16 Hz, 1H), 6.46 (bs, 1H), 6.13-6.20 (m, 1H), 4.09-4.15 (m, 2H), 3.81 (s, 2H), 2.10 (s, 1H), 1.49-2.04 (m, 10H).

Step 6:

A solution of alcohol 31 (0.8051 g, 2.25 mmol) in EtOH (10 mL) was degassed with vacuum/argon then 10% Pd/C (0.1049 g) was added. The mixture was degassed again then put under H$_2$ at atmospheric pressure. This procedure was repeated then the reaction mixture was stirred at room temperature for 2 h. The solids were removed by filtration through filter paper and the filtrate was concentrated under reduced pressure. Purification by flash chromatography (10 to 50% EtOAc-hexanes gradient) gave amide 32. (Yield 0.7023 g, 87%): $^1$H NMR (400 MHz, CDCl$_3$) δ 7.24-7.29 (m, 1H), 6.75-7.19 (m, 3H), 6.18 (br s, 1H), 3.80 (s, 2H), 3.39 (q, J=6.8 Hz, 2H), 2.66 (t, J=7.6 Hz, 2H), 2.09 (s, 1H), 1.90-1.97 (m, 2H), 1.51-1.75 (m, 10H).

Step 7:

To a solution of amide 32 (0.7023 g, 1.95 mmol) in MeOH (16 mL) was added K$_2$CO$_3$ (1.3911 g, 10.07 mmol). Water (7 mL) was added until all material dissolved. The mixture was stirred under argon at room temperature for 15 h. The mixture was concentrated under reduced pressure and the residue was partitioned between EtOAc and brine. The combined organics were washed with brine, dried over MgSO$_4$, and concentrated under reduced pressure. Purification by flash chromatography (9:9:2 EtOAc:hexanes:7M NH$_3$ in MeOH) provided Example 10. Yield (0.3192 g, 62%): $^1$H NMR (400 MHz, DMSO-d$_6$) δ 7.13 (t, J=8 Hz, 1H), 6.69-6.74 (m, 3H), 4.30 (br s, 1H), 3.66 (s, 2H), 2.47-2.55 (m, 4H), 1.38-1.63 (m, 12H), 1.30 (br s, 2H).

Example 11

Preparation of 1-((3-(3-aminopropyl)phenoxy)methyl)cycloheptanol

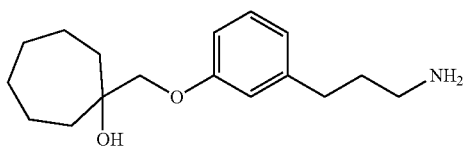 [SMILES: NCCCc1cccc(OCC2(O)CCCCCC2)c1]

1-((3-(3-aminopropyl)phenoxy)methyl)cycloheptanol was prepared following the method described in Scheme 8:

SCHEME 8

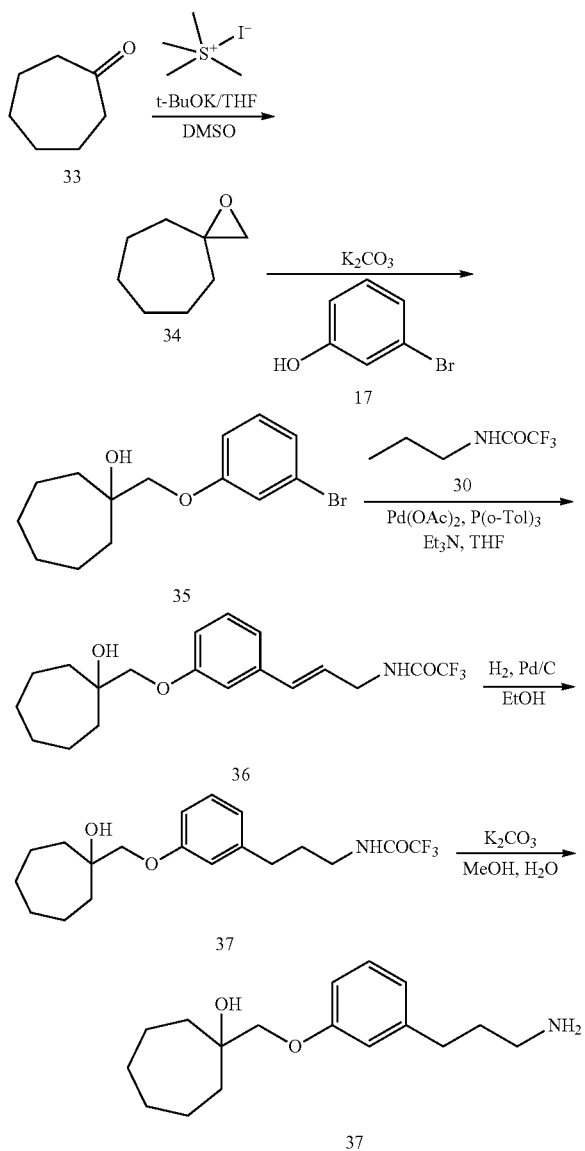

Step 1:
To a suspension of cycloheptanone (2.88 g, 25.68 mmol) and trimethyl sulfoxonium iodide (2.88 g, 27.22 mmol) in DMSO (15 mL) was added potassium tert-butoxide (27 mL of a 1M solution in THF, 27.0 mmol). The reaction mixture was stirred under argon at room temperature for 16 h. The mixture was concentrated under reduced pressure and partitioned between 25% EtOAc-hexanes and brine. The combined organics were washed with water and brine, dried over MgSO$_4$, and concentrated under reduced pressure to give epoxide 34. Yield (2.86 g, 88%): $^1$H NMR (400 MHz, CDCl$_3$) δ 2.58 (s, 2H), 1.26-1.72 (m, 12H).

Step 2:
A suspension of epoxide 34 (1.033 g, 8.185 mmol), K$_2$CO$_3$ (1.6135 g, 11.67 mmol) and 3-bromophenol (1.6665 g, 9.632 mmol) was heated without solvent at 120° C. for 23 h. After cooling to room temperature, the mixture was partitioned between EtOAc and water. The combined organics were washed twice with 10% aqueous NaOH, dried over MgSO$_4$, and concentrated under reduced pressure. Purification by flash chromatography (20-40% EtOAc-hexanes gradient) gave alcohol 35 contaminated with ca. 10% 3-bromophenol. Yield (1.59 g, 65%): $^1$H NMR (400 MHz, CDCl$_3$) δ 7.08-7.16 (m, 3H), 6.84-6.87 (m, 1H), 3.76 (s, 2H), 2.09 (s, 1H), 1.43-1.84 (m, 12H).

Step 3:
Alcohol 35 was coupled with N-allyl-2,2,2-trifluoroacetamide (30) following the method used in Example 10 except that it was heated for 18 h. Purification by flash chromatography (20 to 50% EtOAc-hexanes gradient) gave amide 36 as a pale yellow solid. Yield (0.81 g, 63%). $^1$H NMR (400 MHz, CDCl$_3$) δ 7.24 (t, J=7.6 Hz, 1H), 6.96 (d, J=8 Hz, 1H), 6.92 (t, J=2 Hz, 1H), 6.84 (dd, J=7.6, 2.0 Hz, 1H), 6.55 (d, J=15.6 Hz, 1H), 6.49 (br s, 1H), 6.17 (dt, J=15.6, 6.8 Hz, 1H), 4.14 (t, J=6 Hz, 2H), 3.78 (s, 2H), 2.16 (s, 1H), 1.41-1.85 (m, 12H).

Step 4:
Amide 36 was hydrogenated following the method used in Example 10 except that it was allowed to react for 80 min. Purification by flash chromatography (20 to 50% EtOAc-hexanes gradient) gave amide 37 which crystallized upon standing to give white crystals. Yield (0.7850 g, 97%): $^1$H NMR (400 MHz, CDCl$_3$) δ 7.21 (t, J=7.6 Hz, 1H), 6.75-6.79 (m, 3H), 6.20 (br s, 1H), 3.76 (s, 2H), 3.39 (q, J=6.8 Hz, 2H), 2.67 (t, J=7.6 Hz, 2H), 2.14 (s, 1H), 1.42-1.95 (m, 14H).

Step 5:
Amide 37 was deprotected following the method used in Example 10 except that it was allowed to react for 22.5 h. Purification by flash chromatography (5:5:1 EtOAc:hexanes:7M NH$_3$ in MeOH) gave Example 11 as a colorless oil which crystallized upon drying to form white crystals. Yield (0.2715 g, 47%): $^1$H NMR (400 MHz, DMSO-d$_6$) δ 7.13 (t, J=8 Hz, 1H), 6.73-6.89 (m, 3H), 4.32 (br s, 1H), 3.65 (s, 2H), 2.47-2.55 (m, 4H), 1.32-1.72 (m, 16H).

Example 12

Preparation of 1-((3-(3-amino-1-hydroxypropyl)phenoxy)methyl)cyclohexanol

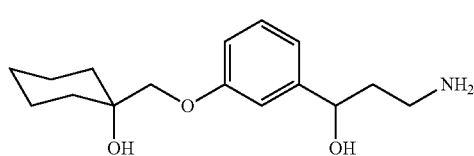 [SMILES: NCCC(O)c1cccc(OCC2(O)CCCCC2)c1]

Step 1:

3-Hydroxybenzaldehyde (11) was coupled with alcohol 27 following the method used in Example 2 except that alcohol 27 was used as the limiting reagent and the mixture was stirred for 64 h. Purification by flash chromatography (10 to 30% EtOAc-hexanes gradient) gave 3-(7-oxabicyclo [4.1.0]heptan-1-ylmethoxy)-benzaldehyde as an oil. Yield (0.90 g, 52%): $^1$H NMR (400 MHz, CDCl$_3$) δ 9.98 (s, 1H), 7.40-7.48 (m, 3H), 7.19-7.22 (m, 1H), 4.07 (d, J=10.4 Hz, 1H), 4.03 (d, J=10.4 Hz, 1H), 3.22 (t, J=3.6 Hz, 1H), 1.90-2.04 (m, 4H), 1.48-1.51 (m, 2H), 1.24-1.40 (m, 2H).

Step 2:

To a −78° C. solution of acetonitrile (240 uL, 4.6 mmol) in THF under argon was added a solution of LDA (2.2 mL of a 2M solution in heptane/THF/ethylbenzene, 4.4 mmol). The resulting mixture was stirred at −78° C. for 30 min. In a separate flask, a solution of 3-(7-oxabicyclo[4.1.0]heptan-1-ylmethoxy)benzaldehyde (0.90 g, 4.1 mmol) in THF was cooled to −78° C. under argon. The freshly made lithium acetonitrile solution described above was added dropwise. The reaction mixture was stirred at −78° C. for 30 min then allowed to warm to room temperature overnight. The mixture was quenched with the addition of brine followed by 1M HCl (4 mL). The layers were separated and the aqueous layer was extracted with EtOAc. The combined organics were dried over MgSO$_4$ and concentrated under reduced pressure. Purification by flash chromatography (10 to 75% EtOAc-hexanes gradient) gave 3-(3-(7-oxabicyclo[4.1.0]heptan-1-ylmethoxy)phenyl)-3-hydroxypropane-nitrile as an oil. Yield (0.340 g, 32%): $^1$H NMR (400 MHz, CDCl$_3$) δ 7.30 (t, J=8.0 Hz, 1H), 6.88-6.91 (m, 3H), 5.01 (br s, 1H), 3.92-4.02 (m, 2H), 3.01 (d, J=2.0 Hz, 1H), 2.76 (d, J=6.4 Hz, 2H), 2.34 (br s, 1H), 1.84-2.05 (m, 4H), 1.42-1.56 (m, 2H), 1.24-1.40 (m, 2H).

Step 3:

To an ice cold mixture of 3-(3-(7-oxabicyclo[4.1.0]heptan-1-ylmethoxy)phenyl)-3-hydroxypropanenitrile (0.340 g, 1.3 mmol) in THF was added LiAlH$_4$ (1.95 mL of a 2M solution in THF, 3.9 mmol). After warming to room temperature, the reaction was stirred for 2 h. The mixture was chilled over ice and quenched with the addition of solutions of saturated aqueous Na$_2$SO$_4$ (0.5 mL) and NH$_3$ (1 mL of a 7M solution in MeOH). After stirring for 15 min, the mixture was dried over Na$_2$SO$_4$ and concentrated under reduced pressure. Purification by flash chromatography (2:2:1 EtOAc:hexanes:7M NH$_3$ in MeOH) gave Example 12 as an oil. Yield (0.240 g, 66%): $^1$H NMR (400 MHz, DMSO-d$_6$) δ 7.16 (t, J=7.6 Hz, 1H), 6.87 (d, J=2.0 Hz, 1H), 6.83 (d, J=7.6 Hz, 1H), 6.73-6.75 (m, 1H), 4.61 (t, J=6.4 Hz, 1H), 4.31 (br s, 1H), 3.67 (s, 2H), 3.28 (br s, 1H), 2.57-2.65 (m, 2H), 1.38-1.63 (m, 12H), 1.18-1.22 (m, 2H).

Example 13

Preparation of 1-((3-(3-amino-1-hydroxypropyl) phenoxy)methyl)cycloheptanol

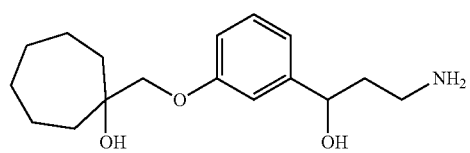 [SMILES: NCCC(O)c1cccc(OCC2(O)CCCCCC2)c1]

1-((3-(3-Amino-1-hydroxypropyl)phenoxy)methyl)cycloheptanol was prepared following the method used in Scheme 9:

SCHEME 9

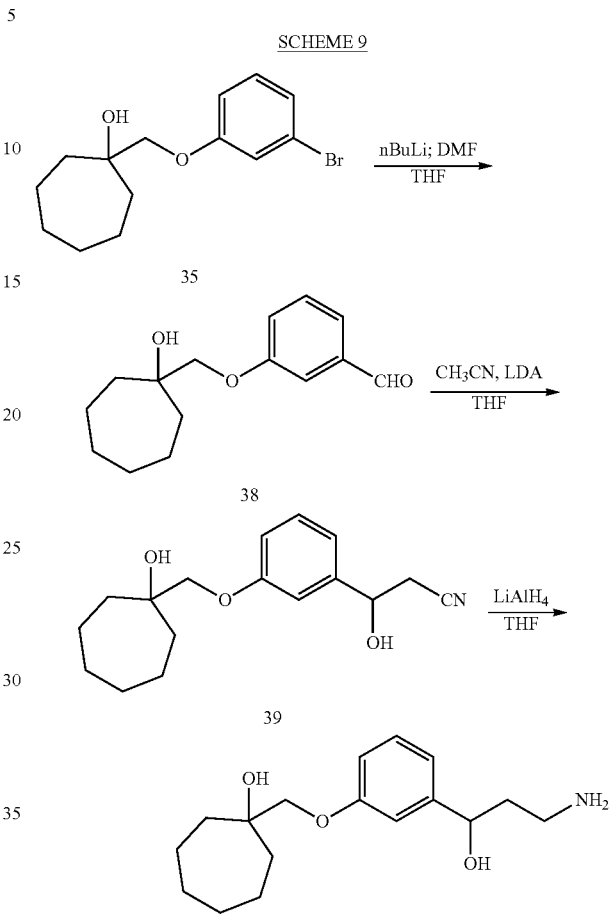

Step 1:

To a −78° C. solution of alcohol 35 (550 mg, 1.83 mmol) in THF under argon was added n-BuLi (1.8 ml of a 2.5 M solution in hexanes, 4.0 mmol) dropwise. After stirring the reaction mixture for 25 min, DMF (0.6 ml, 7.3 mmol) was added. The resulting mixture was stirred at −78° C. for 1 h. 1M aqueous HCl (2 mL) was added followed by EtOAc (50 ml). The organic layer was separated, washed with brine, dried over Na$_2$SO$_4$ and concentrated under reduced pressure. Purification by flash chromatography (5, 30, 50% EtOAc-hexanes step gradient) gave aldehyde 38 as a colorless oil. Yield (0.160 g, 35%): $^1$H NMR (400 MHz, CDCl$_3$) δ 9.98 (s, 1H), 7.41-7.47 (m, 3H), 7.20-7.23 (m, 1H), 3.84 (s, 2H), 1.42-1.83 (m, 12H).

Step 2:

To a −78° C. solution of LDA (3.3 mL of a 2M solution in THF, 6.6 mmol) in THF (10 mL) was added acetonitrile (0.34 mL, 6.6 mmol). After stirring for 30 min at −78° C., a solution of aldehyde 38 (0.16 g, 0.65 mmol) in THF (5 mL) was added. The resulting mixture was stirred for 45 min then quenched with a solution of aqueous NH$_4$OAc. After warming to room temperature, the mixture was extracted with EtOAc. The combined organics were dried over Na$_2$SO$_4$ and concentrated under reduced pressure. Purification by flash chromatography (10, 30, 50, 75% EtOAc-hexanes step gradient) gave alcohol 39 as a colorless oil. Yield (0.14 g, 75%): $^1$H NMR (400 MHz, CDCl$_3$) δ 7.31 (t, J=8.0 Hz, 1H), 6.89-6.99 (m, 3H), 5.02 (t, J=7.2 Hz, 1H), 3.78 (s, 2H), 2.77 (d, J=5.6 Hz, 2H), 2.32 (br s, 1H), 2.11 (br s, 1H), 1.42-1.85 (m, 12H).

Step 3:

Alcohol 39 was reduced following the method used in Example 12 except that the reaction mixture was stirred at 0° C. for 1.5 h. After the mixture was quenched, NH$_3$ (3 mL of a 7M solution in MeOH) and EtOAc were added, and the mixture was dried over Na$_2$SO$_4$ and concentrated under reduced pressure. Purification by chromatography (2:2:1 EtOAc:hexanes:7M NH$_3$-MeOH) gave Example 13 as a colorless oil. Yield (0.090 g, 64%): $^1$H NMR (400 MHz, CDCl$_3$) δ 7.24-7.28 (m, 1H), 7.05 (br s, 1H), 6.95 (t, J=7.2 Hz, 1H), 6.82 (t, J 7.2 Hz, 1H), 4.97 (t, J=8.8 Hz, 1H), 3.81 (s, 2H), 2.98-3.20 (m, 2H), 1.42-2.07 (m, 18H).

Example 14

Preparation of 3-(3-(cycloheptylmethoxy)phenyl)propan-1-amine

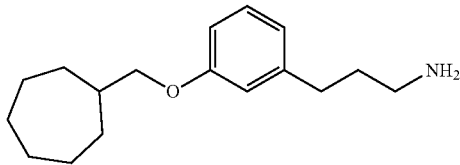

3-(3-(Cycloheptylmethoxy)phenyl)propan-1-amine was prepared following the method described in Example 10.

Step 1:

Cycloheptylmethanol was coupled with 3-bromophenol following the method used in Example 10. After concentration under reduced pressure, hexanes was added. The mixture was stirred and sonicated then the precipitate was removed by filtration and the solids washed with hexanes. The combined filtrates were concentrated under reduced pressure. Purification by flash chromatography (10 to 50% EtOAc-hexanes gradient) gave ((3-bromophenoxy)methyl)cycloheptane. (Yield 1.0697 g, 56%): $^1$H NMR (400 MHz, CDCl$_3$) δ 7.12 (t, J=8.4, 1H), 7.06-7.04 (m, 2H), 6.82 (dq, J=8.0, 1.2, 1H), 3.70 (d, J=6.4, 2H), 1.91-1.98 (m, 1H), 1.81-1.88 (m, 2H), 1.42-1.72 (m, 8H), 1.24-1.34 (m, 2H).

Step 2

((3-Bromophenoxy)methyl)cycloheptane was coupled with N-allyl-2,2,2-trifluoroacetamide following the method used in Example 10 except that the mixture was heated for 23 h. After cooling to room temperature, the reaction mixture was concentrated under reduced pressure and partitioned between EtOAc and water. The combined organics were washed with water and brine, dried over MgSO$_4$ and concentrated under reduced pressure. Purification by flash chromatography (10% EtOAc-hexanes) gave (E)-N-(3-(3-(cycloheptylmethoxy)phenyl)allyl)-2,2,2-trifluoroacetamide. Yield (0.7015 g, 52%): $^1$H NMR (400 MHz, CDCl$_3$) δ 7.23 (t, J=7.6 Hz, 1H), 6.90-6.94 (m, 2H), 6.81 (dd, J=8.4, 1.6 Hz, 1H), 6.56 (d, J=15.6 Hz, 1H), 6.39 (br s, 1H), 6.12-6.19 (m, 1H), 4.13 (t, J=6.0 Hz, 2H), 3.73 (d, J=9.6 Hz, 2H), 1.92-2.10 (m, 1H), 1.82-1.90 (m, 2H), 1.42-1.76 (m, 8H), 1.24-1.36 (m, 2H).

Step 3:

(E)-N-(3-(3-(cycloheptylmethoxy)phenyl)allyl)-2,2,2-trifluoroacetamide was hydrogenated following the method used in Example 10. After hydrogenation the solids were removed by filtration through silica gel (EtOAc rinse) and concentrated under reduced pressure. Purification by flash chromatography (0 to 50% EtOAc-hexanes) gave N-(3-(3-(cycloheptylmethoxy)phenyl)propyl)-2,2,2-trifluoroacetamide. Yield (0.55 g, 78%): $^1$H NMR (400 MHz, CDCl$_3$) δ 7.19 (t, J=7.6 Hz, 1H), 6.71-6.76 (m, 3H), 6.19 (br s, 1H), 3.69-3.73 (m, 2H), 3.89 (q, J=6.8 Hz, 2H), 2.65 (t, J=7.2 Hz, 2H), 1.82-2.10 (m, 4H), 1.44-1.74 (m, 8H), 1.20-1.34 (m, 3H).

Step 4:

N-(3-(3-(cycloheptylmethoxy)phenyl)propyl)-2,2,2-trifluoroacetamide was deprotected following the method used in Example 10 except that the MeOH:water mixture was 4:1. After the extractive work up, the residue was dissolved in hexanes, filtered through Celite and concentrated under reduced pressure. Example 14 was isolated in pure form without further manipulation. $^1$H NMR (400 MHz, CDCl$_3$) δ 7.17 (t, J=7.6 Hz, 1H), 6.70-6.76 (m, 3H), 3.71 (d, J=6.8 Hz, 2H), 2.74 (t, J=7.2 Hz, 2H), 2.62 (t, J=8 Hz, 2H), 1.43-2.02 (m, 15H), 1.23-1.33 (m, 2H).

Example 15

Preparation of 3-amino-1-(3-(cycloheptylmethoxy)phenyl)propan-1-ol

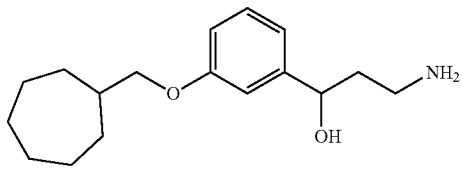 [SMILES: NCCC(O)c1cccc(OCC2CCCCCC2)c1]

3-Amino-1-(3-(cycloheptylmethoxy)phenyl)propan-1-ol was prepared following the method used in Example 12.

Step 1:

To an ice-cold solution of cycloheptylmethanol (5.244 g, 40.9 mmol), triphenylphosphine (10.73 g, 40.9 mmol) and 3-hydroxybenzaldehyde (11) (5.0 g, 40.9 mmol) in THF (50 mL) was added diethyl azodicarboxylate (9.097 g, 44.99 mmol). The reaction mixture was allowed to warm to room temperature and stirred overnight. The mixture was concentrated under reduced pressure, and the residue was suspended in 20% diethyl ether-hexanes. Solids were removed by filtration then the mixture was concentrated under reduced pressure. Purification by flash chromatography (5% EtOAc-hexanes) gave 3-(cycloheptylmethoxy)benzaldehyde as a colorless oil. Yield (3.9 g, 41%): $^1$H NMR (400 MHz, DMSO-d$_6$) δ 9.95 (s, 1H), 7.46-7.51 (m, 2H), 7.39-7.40 (m, 1H), 7.25 (dt, J=6.8, 2.6 Hz, 1H), 3.81 (d, J=6.8 Hz, 2H), 1.88-1.93 (m, 1H), 1.76-1.82 (m, 2H), 1.22-1.68 (m, 10H).

Step 2:

To a −78° C. solution of LDA (10 mL of a 2M solution in heptane/THF/ethylbenzene, 20.09 mmol) in THF (30 mL) was added acetonitrile (0.97 mL, 18.41 mmol) dropwise over ca. 2 min. After stirring for 15 min, a solution of 3-(cycloheptylmethoxy)benzaldehyde (3.89 g, 16.74 mmol) in THF (20 mL) was added. The reaction was allowed to warm to 0° C. over 2 h then quenched with the addition of saturated aqueous NH$_4$Cl (30 mL). The mixture was extracted with EtOAc twice. The combined organics were dried over Na$_2$SO$_4$ and concentrated under reduced pressure. Purification by flash chromatography (20% EtOAc-hexanes)

gave 3-(3-(cycloheptylmethoxy)phenyl)-3-hydroxypropanenitrile as a colorless oil. Yield (2.102 g, 46%): $^1$H NMR (400 MHz, DMSO-$d_6$) δ 7.22 (t, J=8.0 Hz, 1H), 6.95 (d, J=2.4 Hz, 1H), 6.93 (d, J=8.0 Hz, 1H), 6.81 (ddd, J=8.4, 2.4, 0.8 Hz, 1H), 5.89 (d, J=4.4 Hz, 1H), 4.83 (dt, J=6.4, 4.8 Hz, 1H), 3.71 (d, J=6.8 Hz, 2H), 2.86 (dd, J=16.8, 5.0 Hz, 1H), 2.78 (dd, J=16.4, 6.6 Hz, 1H), 1.86-1.92 (m, 1H), 1.76-1.82 (m, 2H), 1.61-1.67 (m, 2H), 1.37-1.59 (m, 6H), 1.20-1.30 (m, 2H).*

Step 3:

3-(3-(Cycloheptylmethoxy)phenyl)-3-hydroxypropanenitrile was reduced following the method used in Example 4 except that the reaction was stirred for 1 h at room temperature. The mixture was quenched with saturated aqueous $Na_2SO_4$, dried with $Na_2SO_4$, and concentrated under reduced pressure. Purification by chromatography (10% 7M $NH_3$ in MeOH-dichloromethane) gave Example 15 as a colorless oil. Yield (1.23 g, 58%): $^1$H NMR (400 MHz, DMSO-$d_6$) δ 7.16 (t, J=8.0 Hz, 1H), 6.85 (d, J=2.8 Hz, 1H), 6.84 (d, J=8.0 Hz, 1H), 6.71 (ddd, J=8.4, 2.8, 0.8 Hz, 1H), 4.60 (t, J=6.4 Hz, 1H), 3.70 (d, J=6.8 Hz, 2H), 2.56-2.65 (m, 2H), 1.85-1.91 (m, 1H), 1.75-1.81 (m, 2H), 1.37-1.68 (m, 10H), 1.20-1.29 (m, 2H).

Example 16

Preparation of 3-amino-1-(3-(cycloheptylmethoxy)phenyl)propan-1-one

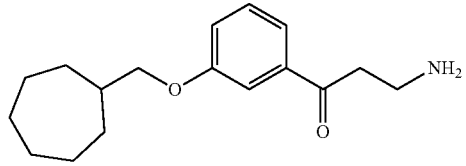 [SMILES: NCCC(=O)c1cccc(OCC2CCCCCC2)c1]

3-amino-1-(3-(cycloheptylmethoxy)phenyl)propan-1-one was prepared following the method used in Example 5.

Step 1:

Protection of 3-amino-1-(3-(cycloheptylmethoxy)phenyl)propan-1-ol was conducted following the method used in Example 5 except that the reaction mixture was stirred overnight. After the mixture was concentrated under reduced pressure, purification by flash chromatography (30% EtOAc-hexanes) gave tert-butyl 3-(3-(cycloheptylmethoxy)phenyl)-3-hydroxypropylcarbamate as a clear oil. Yield (0.552 g, 81%): $^1$H NMR (400 MHz, DMSO-$d_6$) δ 7.17 (t, J=7.6 Hz, 1H), 6.83-6.85 (m, 2H), 6.71-6.75 (m, 2H), 5.13 (br s, 1H), 4.49 (t, J=6.4 Hz, 1H), 3.71 (d, J=6.4 Hz, 2H), 2.94 (m, 2H), 1.86-1.91 (m, 1H), 1.76-1.82 (m, 2H), 1.61-1.66 (m, 4H), 1.37-1.59 (m, 6H), 1.35 (s, 9H), 1.20-1.29 (m, 2H).

Step 2:

To a solution of tert-butyl 3-(3-(cycloheptylmethoxy)phenyl)-3-hydroxypropylcarbamate (0.550 g, 1.46 mmol) in dichloromethane (20 mL) was added Celite (est. 3-4 g) and pyridinium chlorochromate (0.377 g, 1.75 mmol). After stirring overnight at room temperature, the solids were removed by filtration and the filtrate was concentrated under reduced pressure. Purification by flash chromatography (5% EtOAc-hexanes) gave tert-butyl 3-(3-(cycloheptylmethoxy)phenyl)-3-oxopropylcarbamate as a clear oil. Yield (0.50 g, 91%): $^1$H NMR (400 MHz, DMSO-$d_6$) δ 7.49 (d, J=7.6 Hz, 1H), 7.41 (d, J=8.0 Hz, 1H), 7.39 (dd, J=4.4, 2.2 Hz, 1H), 7.18 (dd, J=7.6, 2.4 Hz, 1H), 6.78 (t, J=5.6 Hz, 1H), 3.80 (d, J=6.4 Hz, 2H), 3.24 (dt, J=6.6, 6.0 Hz, 2H), 3.10 (t, J=6.8 Hz, 2H), 1.86-1.97 (m, 1H), 1.77-1.83 (m, 2H), 1.16-1.68 (m, 19H).*

Step 3:

HCl gas was bubbled for 1-2 min through an ice-cold solution of tert-butyl 3-(3-(cycloheptylmethoxy)phenyl)-3-oxopropylcarbamate (0.495 g, 1.318 mmol) in EtOAc (ca. 20 mL). The reaction mixture was warmed to room temperature. After stirring overnight, the mixture was diluted with diethyl ether (ca. 30 mL). The white solid was collected by filtration, washed with diethyl ether and hexanes and dried under vacuum for 4 h. Example 16 was isolated as a white solid. Yield (0.285 g, 69%): $^1$H NMR (400 MHz, DMSO-$d_6$) δ 8.05 (br s, 3H), 7.52 (dt, J=8.0, 1.2 Hz, 1H), 7.44 (t, J=8.0 Hz, 1H), 7.40 (t, J=2.4 Hz, 1H), 7.23 (ddd, J=8.4, 2.8, 1.2 Hz, 1H), 3.81 (d, J=6.4 Hz, 2H), 3.41 (t, J=6.4 Hz, 2H), 3.10 (q, J=5.6 Hz, 2H), 1.88-1.95 (m, 1H), 1.76-1.83 (m, 2H), 1.61-1.69 (m, 2H), 1.38-1.59 (m, 6H), 1.22-1.31 (m, 2H).*

Example 17

Preparation of 3-amino-1-(3-(2-propylpentyloxy)phenyl)propan-1-ol

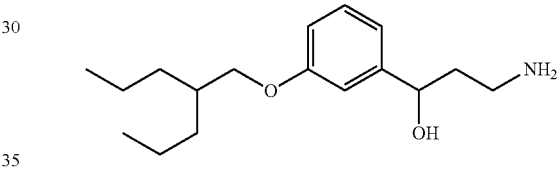

3-Amino-1-(3-(2-propylpentyloxy)phenyl)propan-1-ol was prepared following the methods used in Examples 4 and 20.

Step 1:

Coupling of 3-hydroxybenzaldehyde with 4-heptanol was conducted following the method used for Example 4. Purification by flash chromatography (5% EtOAc-hexanes) gave 3-(2-propylpentyloxy)benzaldehyde as a pale yellow oil. Yield (1.55 g, 54%): $^1$H NMR (400 MHz, DMSO-$d_6$) δ 9.95 (s, 1H), 7.46-7.51 (m, 2H), 7.40-7.41 (m, 1H), 7.25 (dt, J=6.8, 2.8 Hz, 1H), 3.90 (d, J=5.6 Hz, 2H), 1.74-1.79 (m, 1H), 1.27-1.43 (m, 8H), 0.86 (t, J=7.0 Hz, 6H).

Step 2:

Reaction of 3-(2-propylpentyloxy)benzaldehyde with acetonitrile was conducted following the method used for Example 20. Purification by flash chromatography (20% EtOAc-hexanes) gave 3-hydroxy-3-(3-(2-propylpentyloxy)phenyl)propanenitrile as a clear oil. Yield (1.05 g, 59%): $^1$H NMR (DMSO-$d^6$) δ 7.21 (t, J=8.0 Hz, 1H), 6.92-6.95 (m, 2H), 6.81 (ddd, J=8.0, 2.4, 0.8 Hz, 1H), 5/87 (br s, 1H), 4.82 (t, J=6.4 Hz, 1H), 3.81 (d, J=5.6 Hz, 1H), 2.86 (dd, J=16.8, 5.0 Hz, 1H), 2.77 (dd, J=17.2, 6.8 Hz, 1H), 1.74 (quint., J=5.6 Hz, 1H), 1.26-1.40 (m, 8H), 0.84-0.87 (m, 6H).

Step 3:

Reduction of 3-hydroxy-3-(3-(2-propylpentyloxy)phenyl)-propanenitrile and purification of the resulting product was conducted following the procedure given for Example 15. 3-Amino-1-(3-(2-propylpentyloxy)phenyl)propan-1-ol was isolated as a clear oil. Yield (0.515 g, 50%): $^1$H NMR (400 MHz, DMSO-$d_6$) δ 7.20 (t, J=7.8 Hz, 1H), 6.85-6.89 (m, 2H), 6.76 (ddd, J=10.8, 3.2, 1.2 Hz, 1H), 4.64 (t, J=8.4

Hz, 2H), 3.83 (d, J=7.2 Hz, 2H), 3.37-3.42 (m, 1H), 2.60-2.70 (m, 2H), 1.75-1.78 (m, 1H), 1.64 (q, J=8.8 Hz, 2H), 1.28-1.45 (m, 8H), 0.87-0.92 (m, 6H).*

Example 18

Preparation of 1-((3-(2-aminoethoxy)phenoxy)methyl)cycloheptanol

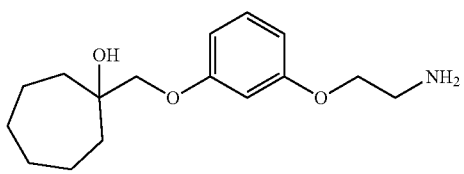 [SMILES: NCCOc1cccc(OCC2(O)CCCCCC2)c1]

1-((3-(2-Aminoethoxy)phenoxy)methyl)cycloheptanol was prepared following the method described in Scheme 10:

SCHEME 10

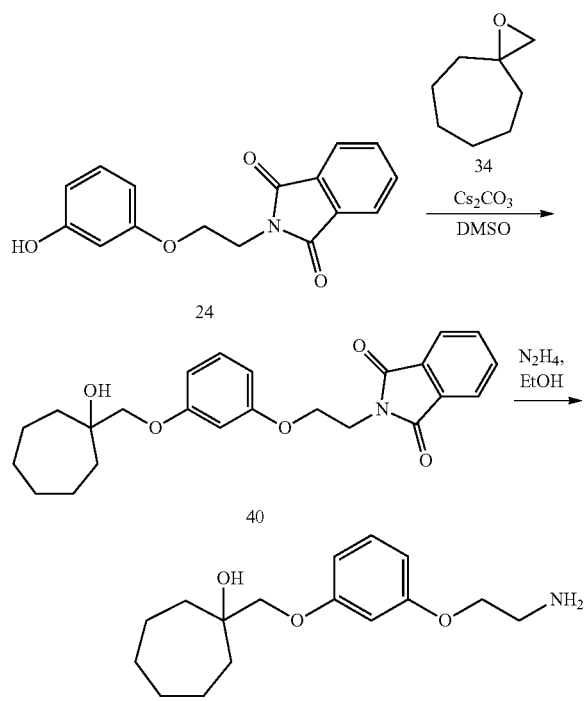

Step 1:

A mixture of epoxide 34 (300 mg, 2.4 mmol), phenol 24 (0.750 g, 2.64 mmol), Cs₂CO₃ (0.860 g, 2.64 mmol) and DMSO (1 mL) was heated at 120° C. for 16 h. After cooling to room temperature, 1M aqueous HCl (2.6 mL) was added. The reaction mixture was partitioned between EtOAc and water. The combined organics were washed with brine, dried over Na₂SO₄, and concentrated under reduced pressure. Purification by flash chromatography (5, 30, 50% EtOAc-hexanes step gradient) gave compound 40 as an oil. Yield (0.130 g, 13%): ¹H NMR (400 MHz, DMSO-d₆) δ 7.85-7.88 (m, 2H), 7.71-7.74 (m, 2H), 7.14 (t, J=8.0 Hz, 1H), 6.47-6.50 (m, 3H), 4.22 (t, J=5.6 Hz, 2H), 4.12 (t, J=5.6 Hz, 2H), 3.73 (s, 2H), 1.25-2.05 (m, 13H).

Step 2:

To a mixture of compound 40 (0.110 g, 0.27 mmol) in EtOH (10 ml) was added hydrazine hydrate (1 ml, 17.7 mmol). The resulting mixture was stirred at room temperature for 4 h. After concentration under reduced pressure, the residue was partitioned between EtOAc and water. The combined organics were washed with brine, dried over Na₂SO₄, and concentrated under reduced pressure. Purification by flash chromatography (5:5:1 EtOAc:hexanes:7M NH₃ in MeOH) gave Example 18 as a solid. Yield (0.040 g, 53%): ¹H NMR (400 MHz, DMSO-d₆) δ 7.13 (t, J=10.4 Hz, 1H), 6.44-6.52 (m, 3H), 4.36 (s, 1H), 3.87 (t, J=7.6 Hz, 2H), 3.66 (s, 2H), 2.83 (t, J=7.6 Hz, 1H), 1.32-1.74 (m, 15H).

Example 19

Preparation of N-(3-(3-(cyclohexylmethoxy)phenyl)-3-hydroxypropyl)-acetamide

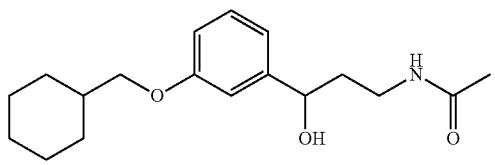 [SMILES: CC(=O)NCCC(O)c1cccc(OCC2CCCCC2)c1]

N-(3-(3-(cyclohexylmethoxy)phenyl)-3-hydroxypropyl)acetamide was prepared following the method shown in Scheme 11:

SCHEME 11

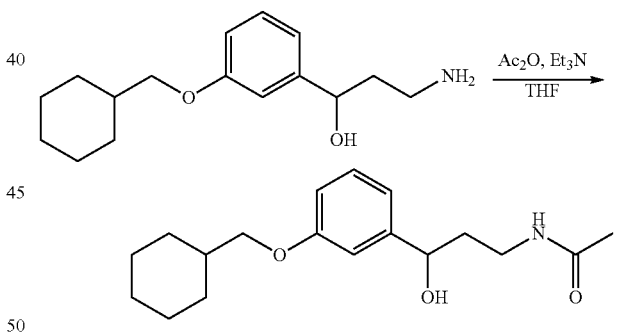

To a solution of 3-amino-1-(3-(cyclohexylmethoxy)phenyl)propan-1-ol (0.91 g, 3.5 mmol) in THF (3 ml) at room temperature was added triethylamine (730 ul, 5.3 mmol), and a solution of acetic anhydride (39 mg, 3.8 mmol) in THF (2 mL). The reaction was stirred at room temperature for 2 h then partitioned between EtOAc and water. The combined organic layers were washed with water and brine, then dried over Na₂SO₄ and concentrated under reduced pressure to give Example 19 as a white waxy solid. Yield (0.100 g, 9%): ¹H NMR (400 MHz, DMSO-d₆) δ 7.75 (t, J=4.8 Hz, 1H), 7.17 (t, J=7.6, 1H), 6.82-6.84 (m, 2H), 6.73 (dd, J=8.0, 1.6 Hz, 1H), 5.16 (d, J=4.4 Hz, 1H), 4.49 (dt, J=6.4, 4.8 Hz, 1H), 3.72 (d, J=6.0 Hz, 2H), 2.99-3.08 (m, 2H), 1.73-1.81 (m, 5H), 1.61-1.71 (m, 6H), 1.08-1.28 (m, 3H), 0.96-1.06 (m, 2H).*

Example 20

Preparation of 4-((3-(3-amino-1-hydroxypropyl)phenoxy)methyl)heptan-4-ol

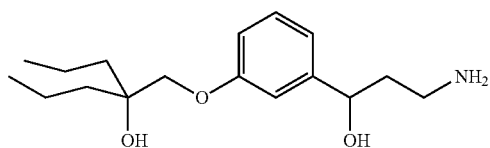 [SMILES: CCCC(O)(CCC)COc1cccc(C(O)CCN)c1]

4-((3-(3-Amino-1-hydroxypropyl)phenoxy)methyl)heptan-4-ol was prepared following the method shown in Scheme 12:

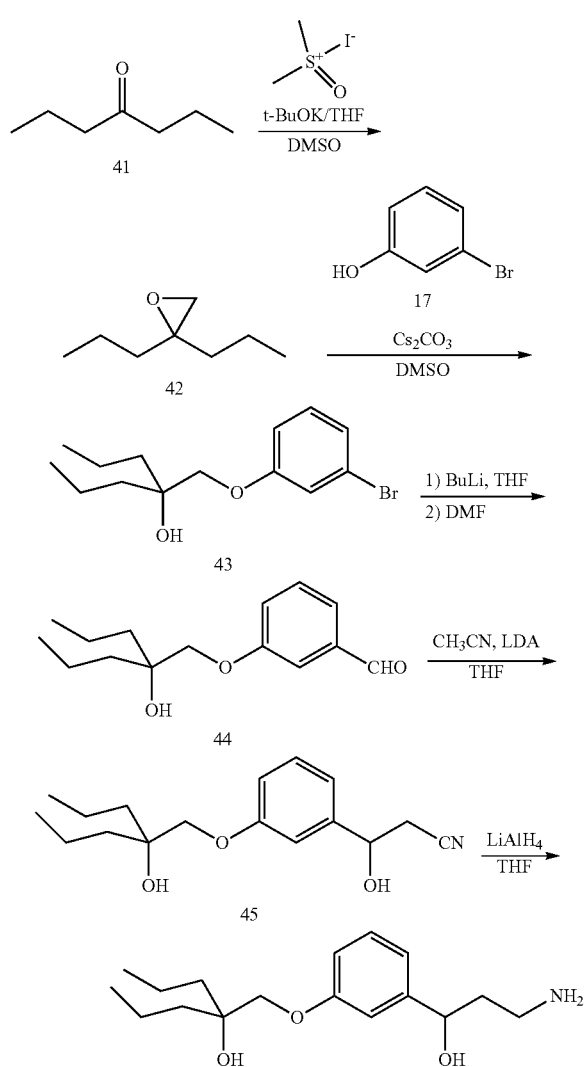

Step 1:

Heptan-4-one (41) was reacted with trimethyl sulfoxonium iodide following the method used in Example 11 to give epoxide 42. This compound was carried on to the next step without further purification.

Step 2:

Epoxide 42 was reacted with 3-bromophenol (17) following the method used in Example 18. After cooling to room temperature, the reaction mixture was partitioned between EtOAc and water. The combined organics were washed with water and brine, dried over $Na_2SO_4$ and concentrated under reduced pressure. Purification by flash chromatography (5, 20, 30, 50% EtOAc-hexanes step gradient) gave bromide 43 as an oil. Yield (0.670 g, 57%): $^1H$ NMR (400 MHz, DMSO-$d_6$) δ 7.24 (t, J=10.8 Hz, 1H), 7.10-7.16 (m, 2H), 6.94-6.98 (m, 1H), 4.38 (s, 1H), 3.74 (s, 2H), 1.44-1.49 (m, 4H), 1.22-1.39 (m, 4H), 0.87 (t, J=9.6 Hz, 6H).

Step 3:

Bromide 43 was carbonylated following the method used in Example 13 except that initial reaction time with n-BuLi was 45 min. Purification by flash chromatography (3, 19, 30, 50% EtOAc-hexanes step gradient) gave aldehyde 44 as an oil. Yield (0.250 g, 45%): $^1H$ NMR (400 MHz, DMSO-$d_6$) δ 9.99 (s, 1H), 7.74-7.55 (m, 3H), 7.28-7.32 (m, 1H), 4.45 (s, 1H), 3.81 (s, 2H), 1.47-1.50 (m, 4H), 1.30-1.39 (m, 4H), 0.87 (t, J=9.6 Hz, 6H).

Step 4:

Aldehyde 44 was reacted with acetonitrile following the method used in Example 13. Purification by flash chromatography (7, 30, 50, 75% EtOAc-hexanes step gradient) gave nitrile 45 as an oil. Yield (0.105 g, 36%): $^1H$ NMR (400 MHz, DMSO-$d_6$) δ 7.26 (t, J=10.4 Hz, 1H), 6.96-7.00 (m, 2H), 6.84 (dd, J=10.8, 2.4 Hz, 1H), 5.94 (d, J=6.0 Hz, 1H), 4.87 (q, J=8.4 Hz, 1H), 4.40 (s, 1H), 3.72 (s, 2H), 2.83-2.89 (m, 2H), 1.46-1.51 (m, 4H), 1.30-1.41 (m, 4H), 0.87 (t, J=9.2 Hz, 6H).

Step 5:

Nitrile 45 was reduced following the method used in Example 12 except that the reaction was stirred for 1.5 h after allowing to warm to room temperature. The reaction mixture was quenched with the addition of saturated aqueous $Na_2SO_4$. $NH_3$-MeOH (3 mL of a 7 M solution) was added, the mixture was dried over solid $Na_2SO_4$, and concentrated under reduced pressure. Purification by flash chromatography (EtOAc:hexanes:(7 M $NH_3$ in MeOH) 4:4:1.2) gave Example 20 as an oil. Yield (0.080 g, 79%): $^1H$ NMR (400 MHz, DMSO-$d_6$) δ 7.20 (t, J=10.4 Hz, 1H), 6.86-6.90 (m, 2H), 6.74-6.80 (m, 1H), 4.63 (d, J=8.8 Hz, 1H), 4.34 (s, 1H), 3.70 (s, 2H), 3.37-3.42 (m, 2H), 2.62-2.67 (m, 1H), 1.22-1.67 (m, 12H), 0.87 (t, J=9.2 Hz, 6H).

Example 21

Preparation of 4-((3-(3-aminopropyl)phenoxy)methyl)heptan-4-ol

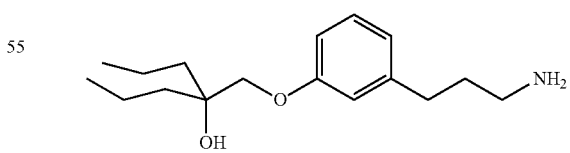

4-((3-(3-aminopropyl)phenoxy)methyl)heptan-4-ol was prepared following the method described in Example 32 and Scheme 16 and by the method used in Example 18.

Step 1:

Coupling of 2,2-dipropyloxirane (0.36 g, 2.8 mmol) with compound 58 (0.5 g, 1.78 mmol) following the method used in Example 18 gave 2-(3-(3-(2-hydroxy-2-propylpentyloxy)

phenyl)propyl)isoindoline-1,3-dione which was directly used in the subsequent reaction without purification.

Step 2:

Deprotection of 2-(3-(3-(2-hydroxy-2-propylpentyloxy)phenyl)propyl)isoindoline-1,3-dione following the method used in Example 18 gave 4-((3-(3-aminopropyl)phenoxy)methyl)heptan-4-ol as a colorless oil. Yield (0.28 g, 56% in 2 steps): $^1$H NMR (400 MHz, MeOD) δ 7.16 (t, J=8.4 Hz, 1H), 6.74-6.79 (m, 3H), 5.47 (s, 1H), 3.76 (s, 2H), 2.73 (t, J=7.6 Hz, 2H), 2.63 (t, J=7.6 Hz, 2H), 1.78-1.86 (m, 2H), 1.55-1.60 (m, 4H), 1.32-1.42 (m, 4H), 0.92 (t, J=7.2 Hz, 6H).

Example 22

Preparation of 3-amino-1-(3-((1-hydroxycyclohexyl)methoxy)phenyl)propan-1-one

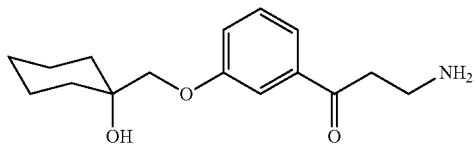 [SMILES: NCCC(=O)c1cccc(OCC2(O)CCCCC2)c1]

3-Amino-1-(3-((1-hydroxycyclohexyl)methoxy)phenyl)propan-1-one is prepared following the method described in Scheme 13.

SCHEME 13

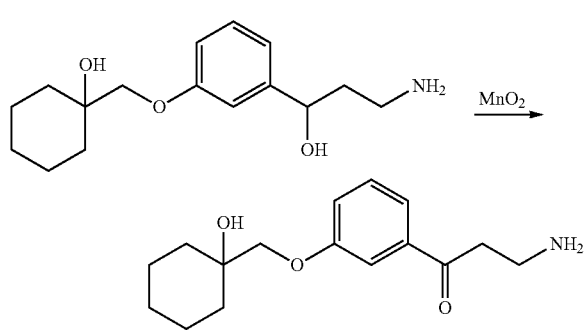

Example 23

Preparation of 3-amino-1-(3-((1-hydroxycycloheptyl)methoxy)phenyl)propan-1-one

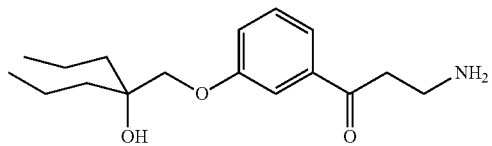 [SMILES: CCCC(O)(CCC)COc1cccc(C(=O)CCN)c1]

3-Amino-1-(3-((1-hydroxycycloheptyl)methoxy)phenyl)propan-1-one was prepared following the method described in Example 5.

Step 1:

Protection of Example 20 gave tert-butyl 3-hydroxy-3-(3-(2-hydroxy-2-propylpentyloxy)phenyl)propylcarbamate which was used in the next step without purification.

Step 2:

Oxidation of tert-butyl 3-hydroxy-3-(3-(2-hydroxy-2-propylpentyloxy)phenyl)propylcarbamate gave tert-butyl 3-(3-(2-hydroxy-2-propylpentyloxy)phenyl)-3-oxopropylcarbamate as a colorless oil. Yield (0.058 g, 86% in 2 steps): $^1$H NMR (400 MHz, MeOD) δ 7.56 (d, J=7.6 Hz, 1H), 7.50 (t, J=2.0 Hz, 1H), 7.39 (t, J=8.0 Hz, 1H), 7.19 (dd, J=8.0, 2.0 Hz, 1H), 3.85 (s, 2H), 3.42 (t, J=4.2 Hz, 2H), 3.18 (t, J=6.4 Hz, 2H), 1.57-2.0 (m, 4H), 1.35-1.41 (m, 13H), 0.84-0.97 (m, 6H).

Step 3:

Deprotection of tert-butyl 3-(3-(2-hydroxy-2-propylpentyloxy)phenyl)-3-oxopropylcarbamate gave Example 23 as a white solid. Yield (0.03 g, 65%): $^1$H NMR (400 MHz, MeOD) δ 7.60 (d, J=8.0 Hz, 1H), 7.54 (t, J=2.0 Hz, 1H), 7.44 (t, J=8.0 Hz, 1H), 7.23-7.26 (m, 1H), 3.85 (s, 2H), 3.24-3.45 (m, 4H), 1.56-1.64 (m, 4H), 1.35-1.44 (m, 4H), 0.93 (t, J=7.6 Hz, 6H).

Example 24

Preparation of 3-amino-1-(3-(2-hydroxy-2-propylpentyloxy)phenyl)propan-1-one

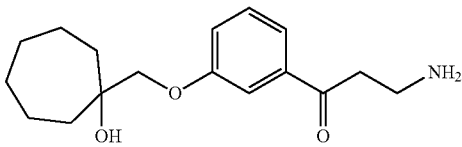 [SMILES: NCCC(=O)c1cccc(OCC2(O)CCCCCC2)c1]

3-Amino-1-(3-(2-hydroxy-2-propylpentyloxy)phenyl)propan-1-one was prepared following the method described in Example 5.

Step 1:

Protection of 1-((3-(3-amino-1-hydroxypropyl)phenoxy)methyl)cycloheptanol gave tert-butyl 3-hydroxy-3-(3-((1-hydroxycycloheptyl)methoxy)phenyl)propylcarbamate which was used in the next step without purification.

Step 2:

Oxidation of tert-butyl 3-hydroxy-3-(3-((1-hydroxycycloheptyl)methoxy)phenyl)propylcarbamate gave tert-butyl 3-(3-((1-hydroxycycloheptyl)methoxy)phenyl)-3-oxopropylcarbamate as a colorless oil. Yield (0.095 g, 89% in 2 steps): $^1$H NMR (400 MHz, MeOD) δ 7.51-7.57 (m, 2H), 7.39 (t, J=8.4 Hz, 1H), 7.19 (dd, J=7.2, 1.6 Hz, 1H), 3.82 (s, 2H), 3.42 (t, J=6.4 Hz, 2H), 3.17 (t, J=6.8 Hz, 2H), 1.48-1.86 (m, 12H), 1.41 (s, 9H).

Step 3:

Deprotection of tert-butyl 3-(3-((1-hydroxycycloheptyl)methoxy)phenyl)-3-oxopropylcarbamate gave Example 24 as a white solid. Yield (0.05 g, 66%): $^1$H NMR (400 MHz, MeOD) δ 7.55-7.62 (m, 2H), 7.44 (t, J=8.0 Hz, 1H), 7.19 (ddd, J=8.0, 2.4, 0.8 Hz, 1H), 3.82 (s, 2H), 3.43 (t, J=5.6 Hz, 2H), 3.32 (t, J=5.6 Hz, 2H), 1.44-1.88 (m, 12H).

Example 25

Preparation of 2-(3-(2-propylpentyloxy)phenoxy)ethanamine

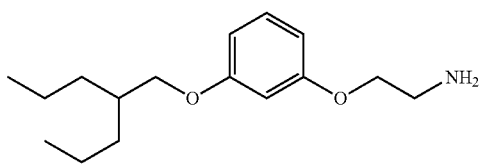 [SMILES: CCCC(CCC)COc1cccc(OCCN)c1]

2-(3-(2-Propylpentyloxy)phenoxy)ethanamine was prepared following the method described in Examples 2 and 18.

Step 1:

Coupling of 2-propylpentylmethanesulfonate (0.2 g, 1.1 mmol) with compound 24 (0.28 g, 1.1 mmol) following the method used in Example 18 gave 2-(2-(3-(2-propylpentyloxy)phenoxy)ethyl)isoindoline-1,3-dione as a colorless oil. Yield (0.21 g, 53%): $^1$H NMR (400 MHz, CDCl$_3$) δ 7.82-7.88 (m, 2H), 7.68-7.74 (m, 2H), 7.10 (t, J=8.0 Hz, 1H), 6.40-6.48 (m, 3H), 4.19 (t, J=6.0 Hz, 2H), 4.10 (dd, J=6.0 Hz, 2H), 3.76 (d, J=6.0 Hz, 2H), 1.70-1.80 (m, 1H), 1.50-1.80 (m, 8H), 0.86-0.92 (m, 6H).

Step 2:

Deprotection of 2-(2-(3-(2-propylpentyloxy)phenoxy)ethyl)isoindoline-1,3-dione following the method used in Example 18 gave Example 25 as a colorless oil. Yield (0.11 g, 82%): $^1$H NMR (400 MHz, DMSO) δ 7.11 (t, J=8.0 Hz, 1H), 6.42-6.48 (m, 3H), 3.85 (t, J=5.6 Hz, 2H), 3.78 (d, J=6.0 Hz, 2H), 2.81 (t, J=6.0 Hz, 2H), 1.65-1.75 (m, 1H), 1.48 (brs, 2H), 1.20-1.40 (m, 8H), 0.85 (t, J=7.2 Hz, 6H).

Example 26

Preparation of 1-((3-(2-aminoethoxy)phenoxy)methyl)cyclohexanol

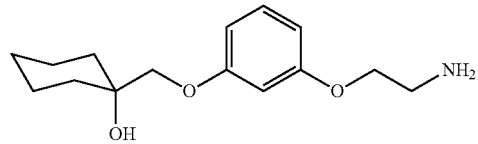 [SMILES: NCCOc1cccc(OCC2(O)CCCCC2)c1]

1-((3-(2-aminoethoxy)phenoxy)methyl)cyclohexanol was prepared following the method described in Example 18.

Step 1:

Coupling of 1-oxaspiro[2.5]octane (0.34 g, 3 mmol) with phenol 24 (0.28 g, 1 mmol) following the method used in Example 18 gave 2-(2-(3-((1-hydroxycyclohexyl)methoxy)phenoxy)ethyl)isoindoline-1,3-dione that was directly used in subsequent reaction without purification.

Step 2:

Deprotection of 2-(2-(3-((1-hydroxycyclohexyl)methoxy)phenoxy)ethyl)isoindoline-1,3-dione following the method used in Example 18 gave 1-((3-(2-aminoethoxy)phenoxy)methyl)cyclohexanol as a colorless oil. Yield (0.22 g, 83% in 2 steps): $^1$H NMR (400 MHz, MeOD) δ 7.13 (t, J=8.0 Hz, 1H), 6.48-6.55 (m, 3H), 5.47 (d, J=1.2 Hz, 1H), 3.79 (t, J=5.2 Hz, 2H), 3.74 (d, J=1.2 Hz, 2H), 3.33 (m, 2H), 1.44-1.76 (m, 10H), 1.24-1.36 (m, 2H).

Example 27

Preparation of 4-((3-(2-aminoethoxy)phenoxy)methyl)heptan-4-ol

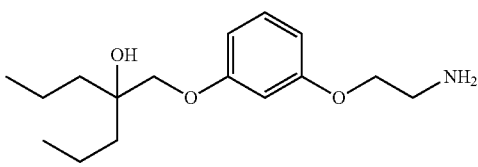 [SMILES: CCCC(O)(CCC)COc1cccc(OCCN)c1]

4-((3-(2-aminoethoxy)phenoxy)methyl)heptan-4-ol was prepared following the method described in Example 18.

Example 28

Preparation of (R)-3-amino-1-(3-(cyclohexylmethoxy)phenyl)propan-1-ol

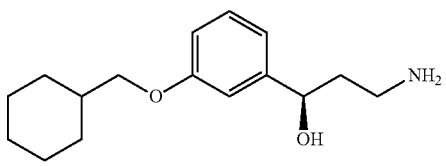 [SMILES: NCC[C@@H](O)c1cccc(OCC2CCCCC2)c1]

(R)-3-Amino-1-(3-(cyclohexylmethoxy)phenyl)propan-1-ol was prepared following the method shown in Scheme 14:

SCHEME 14

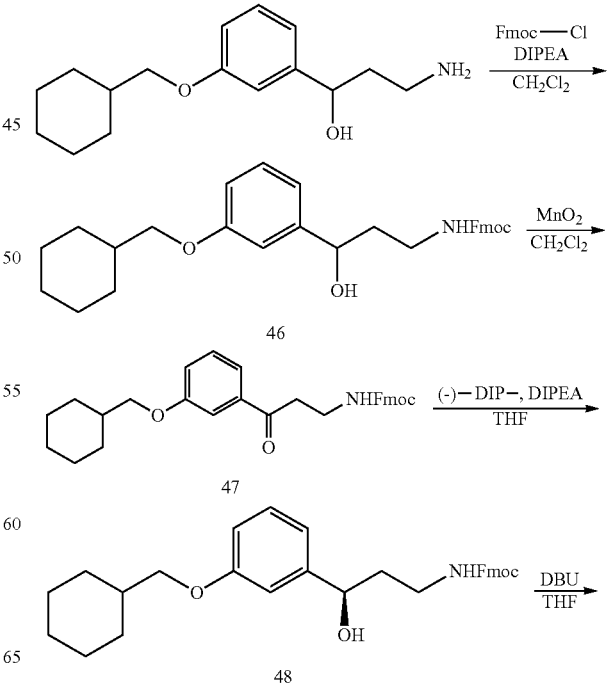

-continued

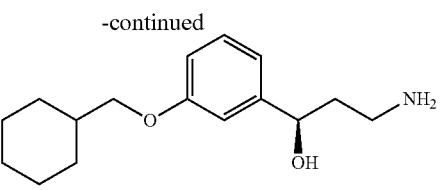

Step 1:

To a solution of 3-amino-1-(3-(cyclohexylmethoxy)phenyl)propan-1-ol (3.76 g, 14.3 mmol) in CH$_2$Cl$_2$ (40 mL) was added diisopropylethylamine (3.0 mL, 17.2 mmol) and a solution of 9-fluorenylmethoxycarbonyl chloride (4.09 g, 15.8 mmol) in CH$_2$Cl$_2$ (5 mL). The reaction mixture was stirred for 30 min then concentrated under reduced pressure. Purification by flash chromatography (20 to 70% EtOAc-hexanes gradient) gave alcohol 46 as an oil. Yield (5.02 g, 72%): $^1$H NMR (400 MHz, DMSO-d$_6$) δ 7.90 (d, J=10.0 Hz, 2H), 7.70 (d, J=10.0 Hz, 2H), 7.42 (t, J=9.6 Hz, 1H), 7.18-7.36 (m, 4H), 6.75-6.89 (m, 3H), 5.21 (d, J=6.0 Hz, 1H), 4.53 (q, J=6.4 Hz, 1H), 4.20-4.32 (m, 3H), 3.74 (d, J=8.0 Hz, 2H), 3.06 (q, J=9.2 Hz, 2H), 1.69-1.82 (m, 8H), 0.98-1.30 (m, 6H).

Step 2:

To a solution of alcohol 46 in CH$_2$Cl$_2$ (50 mL) was added MnO$_2$ (18.2 g, 209 mmol) and the mixture was stirred at room temperature overnight. Additional MnO$_2$ (5.02 g, 57.8 mmol) and CH$_2$Cl$_2$ (40 mL) were added and stirring was continued for 64 h. Solids were removed from the mixture by filtration and the filtrate was concentrated under reduced pressure. Purification by flash chromatography (10 to 50% EtOAc-hexanes gradient) gave ketone 47 as an oil. Yield (3.49 g, 70%): $^1$H NMR (400 MHz, DMSO-d$_6$) δ 7.85 (d, J=7.6 Hz, 2H), 7.64 (d, J=7.6 Hz, 2H), 7.49 (d, J=7.6 Hz, 1H), 7.36-7.41 (m, 3H), 7.26-31 (m, 3H), 7.15-7.20 (m, 1H), 4.26 (d, J=6.8 Hz, 2H), 4.14-4.18 (m, 1H), 3.79 (q, J=6.0 Hz, 2H), 3.26-3.34 (m, 2H), 3.14 (t, J=6.4 Hz, 2H), 1.60-1.84 (m, 6H), 0.91-1.26 (m, 6H).

Step 3:

Preparation of (−)-B-chlorodiisopinocampheylborane solution ((−)-DIP-Cl): To an ice-cold solution of (−)-α-pinene (7.42 g, 54.56 mmol) in hexanes (5 mL) under argon was added chloroborane-methyl sulfide complex (2.55 mL, 24.46 mmol) over 1.5 min. The mixture was stirred for 2.5 min then allowed to warm to room temperature over 3 min. The reaction mixture was heated at 30° C. for 2.5 h. The resulting solution was approximately 1.5 M.

To a −25° C. solution of ketone 47 (1.23 g, 2.53 mmol) and diisopropyl ethylamine (0.110 mL, 0.63 mmol) in THF (10 mL) was added a solution of (−)-DIP-Cl (3.0 mL of the 1.5 M solution prepared above, 4.5 mmol). The reaction mixture was allowed to warm to 0° C. over 11 min, then to room temperature over 45 min. It was stirred at room temperature for 2 h then partitioned between EtOAc and saturated aqueous NaHCO$_3$. The combined organics were washed with brine, dried over MgSO$_4$ and concentrated under reduced pressure. Purification by flash chromatography (10 to 70% EtOAc-hexanes gradient) gave alcohol 48. Yield (0.896 g, 73%).

Step 4:

To a solution of alcohol 48 (0.896 g, 1.85 mmol) in THF (10 mL) was added 1,8-diazabicyclo[5.4.0]undec-7-ene (0.31 mL, 2.07 mmol). The mixture was stirred at room temperature for 30 min then concentrated under reduced pressure. Purification by flash chromatography (50:10:40 to 0:20:80 hexanes:7 M NH$_3$ in MeOH:EtOAc gradient) gave Example 21 as an oil. Yield (0.280 g, 58%): The $^1$H NMR data was consistent with that of Example 4. Chiral HPLC 96.9% major enantiomer (AUC), t$_R$=29.485 min (minor enantiomer: 3.1%, t$_R$=37.007 min). [α]$_D$=+19.66 (26.7° C., c=1.125 g/100 mL in EtOH).

Determination of the Absolute Stereochemistry

The absolute stereochemistry of Example 28 was determined by the method shown in Scheme 15 where Example 28 and (R)-3-amino-1-phenylpropan-1-ol were synthesized from a common intermediate (phenol 53). The optical rotation of (R)-3-amino-1-phenylpropan-1-ol matched the value reported in the literature (Mitchell, D.; Koenig, T. M. *Synthetic Communications*, 1995, 25(8), 1231-1238.).

SCHEME 15

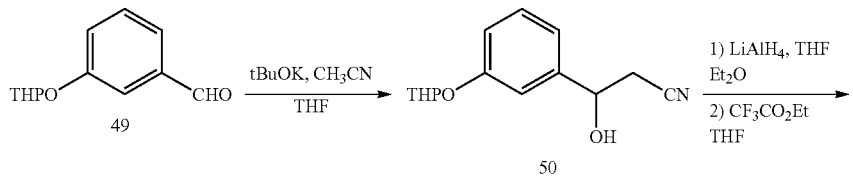

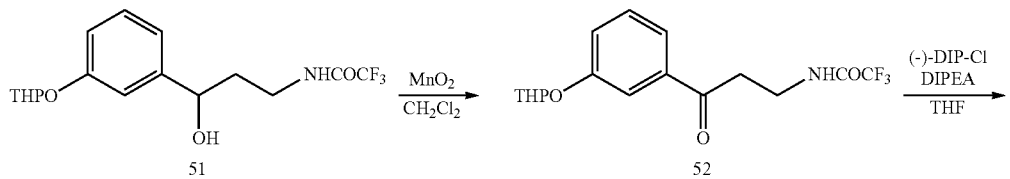

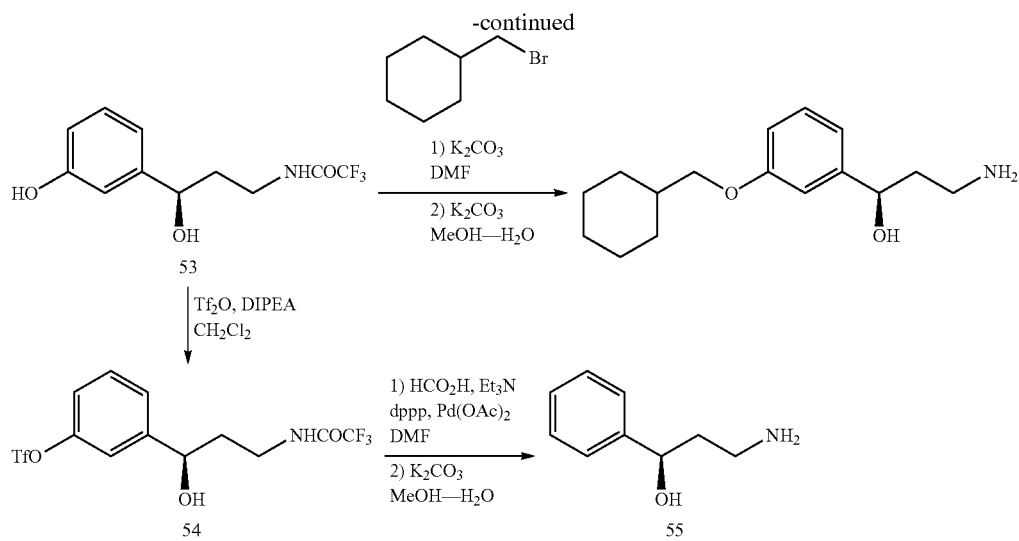

Step 1:

To a −50° C. solution of potassium tert-butoxide (26 mL of a 1.0 M solution in THF, 26 mmol) in THF (10 mL) was added acetonitrile (1.25 mL, 23.75 mmol) over 5 min then the mixture was stirred for 45 min. A solution of aldehyde 49 (4.11 g, 19.93 mmol) in THF (10 mL) was added over 3-5 min. The reaction was stirred at −50° C. for 10 min then allowed to warm to 0° C. and stirred for 25 min. A solution of 30% aqueous NH$_4$Cl (30 mL) was added and the mixture was allowed to warm to room temperature. The mixture was extracted with MTBE and the combined organics were washed with water and brine, dried over MgSO$_4$ and concentrated under reduced pressure. Purification by flash chromatography (10 to 70% EtOAc-hexanes gradient) gave nitrile 50 as an oil. Yield (2.78 g, 57%): $^1$H NMR (400 MHz, DMSO-d$_6$) δ 7.21-7.25 (m, 1H), 7.04 (d, J=8.8 Hz, 1H), 6.99 (t, J=6.4 Hz, 1H), 6.91 (dd, J=8.4, 2.0 Hz, 1H), 5.90 (dd, J=4.4, 2.0 Hz, 1H), 5.43 (t, J=2.8 Hz, 1H), 4.82 (q, J=5.2 Hz, 1H), 3.74 (t, J=9.2 Hz, 1H), 3.49-3.53 (m, 1H), 2.73-2.88 (m, 2H), 1.49-1.88 (m, 6H).

Step 2:

To an ice-cold solution of nitrile 50 (2.78 g, 11.25 mmol) in diethyl ether (50 mL) was added a solution of LiAlH$_4$ (10 mL of a 2.0 M in THF, 20 mmol) and the reaction was stirred for 10 min. The reaction mixture was quenched with the slow addition of saturated aqueous Na$_2$SO$_4$ then stirred at 0° C. until white precipitate formed (~40 min). The solution was dried over MgSO$_4$ and concentrated under reduced pressure to give 3-amino-1-(3-(tetrahydro-2H-pyran-2-yloxy)phenyl)propan-1-ol as an oil. This material was used in the next synthetic step without purification. Yield (2.87 g, quant.).

To a solution of 3-amino-1-(3-(tetrahydro-2H-pyran-2-yloxy)phenyl)propan-1-ol (2.87 g, ~11.25 mmol) in THF (20 mL) was added ethyl trifluoroacetate (2.7 mL, 22.6 mmol). The reaction mixture was stirred at room temperature for 50 min then concentrated under reduced pressure. Purification by flash chromatography (10 to 50% EtOAc-hexanes gradient) gave trifluoroacetamide 51 as an oil. Yield (3.05 g, 78% for two steps): $^1$H NMR (400 MHz, DMSO-d$_6$) δ 9.32 (br s, 1H), 7.18-7.22 (m, 1H), 6.96 (t, J=6.4 Hz, 1H), 6.91 (dd, J=7.6, 3.6 Hz, 1H), 6.84 (dd, J=8.4, 2.0 Hz, 1H), 5.41 (d, J=2.8 Hz, 1H), 5.29 (dd, J=4.4, 2.0 Hz, 1H), 4.48-4.56 (m, 1H), 3.71-3.77 (m, 1H), 3.49-3.54 (m, 1H), 3.22 (q, J=5.2 Hz, 2H), 1.48-1.87 (m, 8H).

Step 3:

To a solution of trifluoroacetamide 51 (3.05 g, 8.78 mmol) in CH$_2$Cl$_2$ (50 mL) was added MnO$_2$ (20.18 g, 232 mmol) and the mixture was stirred at room temperature for 67 h. The solids were removed by filtration and the filtrate was concentrated under reduced pressure to give ketone 52 as an oil. This material was used in the next synthetic step without purification. Yield (2.4737 g, 82%): $^1$H NMR (400 MHz, DMSO-d$_6$) δ 9.40 (br s, 1H), 7.53-7.58 (m, 2H), 7.43 (t, J=6.4 Hz, 1H), 7.26-7.29 (m, 1H), 5.54 (t, J=3.64 Hz, 1H), 3.69-3.74 (m, 1H), 3.28-3.56 (m, 3H), 3.27 (t, J=7.2 Hz, 2H), 1.50-1.87 (m, 6H).

Step 4:

To an ice-cold solution of ketone 52 (1.95 g, 5.65 mmol) in THF (12 mL) was added diisopropylethylamine (0.25 mL, 1.44 mmol) and (−)-DIP-Cl (preparation described above; 6.0 mL of a 1.67 M solution in hexanes, 10.2 mmol). The reaction mixture was stirred at 0° C. for 2 h, then additional (−)-DIP-Cl (2.0 mL, 3.3 mmol) was added. The reaction mixture was stirred for 15 min then more (−)-DIP-Cl (2.0 mL, 3.3 mmol) was added. After stirring for another hour, more (−)-DIP-Cl (1.0 mL, 1.7 mmol) was added and stirring was continued for 15 min. The reaction mixture was poured into saturated aqueous NaHCO$_3$ and extracted with EtOAc. The combined organics were washed with saturated aqueous NaHCO$_3$ and brine, dried over Na$_2$SO$_4$ and concentrated under reduced pressure. Purification by flash chromatography twice (10 to 100% EtOAc-hexanes gradient; 30 to 80% EtOAc-hexanes gradient) gave phenol 53 as an oil. Yield (1.23 g, 83%): $^1$H NMR (400 MHz, CDCl$_3$) δ 7.43 (br s, 1H), 7.22 (t, J=6.4 Hz, 1H), 6.82-6.87 (m, 2H), 6.76 (dd, J=8.0, 3.6 Hz, 1H), 5.49 (s, 1H), 4.79-4.83 (m, 1H), 3.59-3.66 (m, 1H), 3.37-3.44 (m, 1H), 2.48 (d, J=2.4 Hz, 1H), 1.92-1.99 (m, 2H).

Step 5:

To a solution of phenol 53 (0.2004 g, 0.76 mmol) in DMF (5 mL) was added K$_2$CO$_3$ (0.1278 g, 0.93 mmol) and (bromomethyl)cyclohexane (0.1547 g, 0.87 mmol). The mixture was stirred at 50° C. for 25 min, then at 60° C. for 4 h, 20 min. After cooling to room temperature, the mixture was concentrated under reduced pressure. Purification by flash chromatography (10 to 50% EtOAc-hexanes gradient)

gave (R)—N-(3-(3-(cyclohexylmethoxy)phenyl)-3-hydroxypropyl)-2,2,2-trifluoroacetamide as an oil. Yield (0.0683 g, 25%): $^1$H NMR (400 MHz, CDCl$_3$) δ 7.47 (br s, 1H), 7.24 (t, J=6.4 Hz, 1H), 6.79-6.87 (m, 3H), 4.80-4.81 (m, 1H), 3.73 (d, J=6.4 Hz, 2H), 3.57-3.64 (m, 1H), 3.34-3.40 (m, 1H), 2.63 (s, 1H), 1.68-2.01 (m, 8H), 1.17-1.34 (m, 3H), 0.99-1.09 (m, 2H).

Step 6:

To a solution of (R)—N-(3-(3-(cyclohexylmethoxy)phenyl)-3-hydroxypropyl)-2,2,2-trifluoroacetamide (0.0683 g, 0.19 mmol) in MeOH—H$_2$O (2:1, 6 mL) was added K$_2$CO$_3$ (1.22 mmol) and the mixture was stirred at room temperature for 10 min. The reaction was then heated at 50° C. for 1 h. After cooling to room temperature, the mixture was concentrated under reduced pressure. Purification by flash chromatography (50:10:40 to 0:20:80 hexanes:7 M NH$_3$ in MeOH:EtOAc gradient) gave Example 28 as an oil. Yield (0.0353 g, 71%): the $^1$H NMR was consistent with that of Example 4. [α]$_D$=+17.15 (23.8° C., c=1.765 g/100 mL in EtOH).

Preparation of (R)-3-amino-1-phenylpropan-1-ol from Phenol 53

Step 1:

To an ice-cold solution of phenol 53 (0.3506 g, 1.33 mmol) in CH$_2$Cl$_2$ (10 mL) was added diisopropylethylamine (0.7 mL, 4.0 mmol) and a solution of trifluoromethanesulfonic anhydride (0.23 mL, 1.37 mmol) in CH$_2$Cl$_2$ (0.75 mL). The reaction mixture was stirred at 0° C. for 1.5 h. The mixture was partitioned between CH$_2$Cl$_2$ and water and the combined organics were washed with water and brine, dried over MgSO$_4$, filtered through Celite and the filtrate was concentrated under reduced pressure. Purification by flash chromatography (10 to 80% EtOAc-hexanes gradient) gave triflate 54 as an oil. Yield (0.4423 g, 84%).

Step 2:

To a solution of triflate 54 (0.4380 g, 1.1 mmol) in DMF (6 mL) was added triethylamine (0.8 mL, 5.7 mmol) then formic acid (0.17 mL, 4.4 mmol) slowly and the mixture was stirred for 3 min. 1,3-Bis(diphenylphosphino)propane (dppp, 0.0319 g, 0.077 mmol) and palladium acetate (0.0185 g, 0.082 mmol) were added and the mixture was degassed three times (vacuum/argon cycle). The reaction was heated at 60° C. for 2 h, 20 min then concentrated under reduced pressure. Purification by flash chromatography (10 to 70% EtOAc-hexanes gradient) gave (R)-2,2,2-trifluoro-N-(3-hydroxy-3-phenylpropyl)acetamide as an oil. Yield (0.2348 g, 86%): $^1$H NMR (400 MHz, CDCl$_3$) δ 9.33 (br s, 1H), 7.51 (t, J=7.6 Hz, 1H), 7.44 (d, J=8.0 Hz, 1H), 7.39 (s, 1H), 7.33 (ddd, J=8.4, 2.8, 0.8 Hz, 1H), 5.59 (d, J=4.8 Hz, 1H), 4.66 (dt, J=8.0, 4.4 Hz, 1H), 3.19-3.28 (m, 2H), 1.71-1.86 (m, 2H).

(R)-2,2,2-Trifluoro-N-(3-hydroxy-3-phenylpropyl)acetamide was deprotected according to the method for the synthesis of Example 28, Scheme 15. Purification by flash chromatography (50:10:40 to 0:20:80 hexanes:7 M NH$_3$ in MeOH:EtOAc gradient) gave (R)-3-amino-1-phenylpropan-1-ol as an oil. Yield (0.1035 g, 72%): $^1$H NMR (400 MHz, CDCl$_3$) δ 7.31-7.38 (m, 4H), 7.21-7.25 (m, 1H), 4.94 (dd, J=8.8, 3.2 Hz, 1H), 3.05-3.10 (m, 1H), 2.91-2.97 (m, 1H), 2.62 (br s, 3H), 1.82-1.89 (m, 1H), 1.70-1.79 (m, 1H).

Alternatively, (R)-3-Amino-1-(3-(cyclohexylmethoxy)phenyl)propan-1-ol was prepared by the following procedure. Borane-methyl sulfide complex (2.80 L, 31.3 mol) was charged to a solution of 3-(3-(cyclohexylmethoxy)phenyl)-3-hydroxypropanenitrile (6.20 kg, 23.9 mol) in THF (17.9 L) keeping the temperature below 67° C. and allowing methyl sulfide/THF to distill off. Once the addition was complete the methyl sulfide/THF distillation was continued until ~6 L has been collected. The removed volume was replaced by charging 6 L additional THF. The reaction mixture was heated at reflux (66-68° C.) until the reaction was found to be complete by HPLC (usually ~2 h). The reaction mixture was cooled to ~15° C. and the reaction quenched by the addition of 8.1 L of 3 N hydrochloric acid while keeping the temperature below 50° C. The resulting mixture was allowed to cool to ambient temperature while stirring for 18-24 h. The pH of the reaction mixture was adjusted to 12 by the addition of ~2.1 L of 50% aq. sodium hydroxide in portions, diluted with 9 L of water, and extracted with 25 L of MTBE. The organic solution was washed with 20 L of 1 N aq. sodium hydroxide, 20 L of 5% aq. sodium chloride, and 10 L of 25% aq. sodium chloride. The MTBE solution was dried over 1 kg of anhydrous sodium sulfate and filtered to remove the drying agent. An additional 6 L of MTBE was used to aid in the filtration. (R)-Mandelic acid (3.60 kg, 23.7 mol) was added to the combined filtrates and this mixture was heated to ~50° C. Once a clear homogeneous solution was observed the mixture was allowed to cool. Seed crystals (6.0 g) were added at 40° C. The mixture was further cooled to 10° C., the product was collected by filtration and washed with two 3 L portions of MTBE. The product was dried in a vacuum oven at 30-35° C. to yield 3.60 kg (36.4%) of (R)-3-amino-1-(3-(cyclohexylmethoxy)phenyl)propan-1-ol mandelate as a white crystalline solid. (R)-3-Amino-1-(3-(cyclohexylmethoxy)phenyl)propan-1-ol mandelate (3.60 kg) was dissolved in 25.2 L of water/2-propanol (9:1) by heating to 55-60° C. The solution was slowly cooled and seeded with 5.5 g seed crystals at 50-52° C. This mixture was cooled to 10° C., the product collected by filtration, and washed with two 3.6 L portions of water/2-propanol (9:1). The white crystalline solid was dried in a vacuum oven at 30-35° C. to give 3.40 kg (91.6%) of (R)-3-amino-1-(3-(cyclohexylmethoxy)phenyl)propan-1-ol mandelate. A solution of (R)-3-amino-1-(3-(cyclohexylmethoxy)phenyl)propan-1-ol mandelate (3.25 kg, 7.82 mol) in 17 L isopropyl acetate (iPrOAc) was extracted twice with 1 N aq. sodium hydroxide (17 L and 8.5 L) followed by 25% aq. sodium chloride (8.5 L) and dried over 300 g of anhydrous sodium sulfate. This solution was filtered to remove the drying agent and polished by filtration through a secondary 0.45 micron filter. Additional iPrOAc (6.0 L) was used to aid in the filtration. The combined filtrates were warmed to 40° C. and hydrogen chloride in 2-propanol (4.52 M, 2.10 L, 9.49 mol) was added while keeping the temperature between 40 and 50° C. An additional 11 L iPrOAc were added and the mixture was cooled to 0-5° C. The product was collected by filtration, washed with two 1.7 L portions of iPrOAc, and dried in a vacuum oven (35-45° C.) to yield 2.10 kg (89.4%) (R)-3-amino-1-(3-(cyclohexylmethoxy)phenyl)propan-1-ol hydrochloride.

Example 29

Preparation of (S)-3-amino-1-(3-(cyclohexylmethoxy)phenyl)propan-1-ol

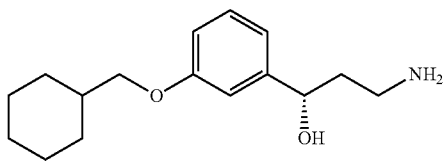 [SMILES: NCC[C@H](O)c1cccc(OCC2CCCCC2)c1]

(S)-3-Amino-1-(3-(cyclohexylmethoxy)phenyl)propan-1-ol was prepared following the method used in Example 28.

Step 1:

Ketone 47 was reduced with (+)-B-chlorodiisopinocampheylborane as described for Example 28 to give (S)-(9H-fluoren-9-yl)methyl 3-(3-(cyclohexylmethoxy)phenyl)-3-hydroxypropylcarbamate. Yield (1.33 g, 98%).

Step 2:

The Fmoc protecting group was removed from (S)-(9H-fluoren-9-yl)methyl 3-(3-(cyclohexylmethoxy)phenyl)-3-hydroxypropylcarbamate following the method used in Example 28 to give Example 29 as an oil. Yield (0.397 g, 55%). The $^1$H NMR data was consistent with that of Example 4. Chiral HPLC 96.6% major enantiomer (AUC), $t_R$=36.289 min (minor enantiomer: 3.4%, $t_R$=29.036 min). [α]D=−21.05 (26.4° C., c=1.18 g/100 mL in EtOH).

Example 30

Preparation of 3-((3-(3-amino-1-hydroxypropyl)phenoxy)methyl)pentan-3-ol

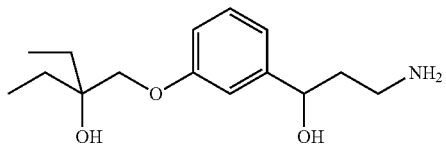 [SMILES: CCC(O)(CC)COc1cccc(C(O)CCN)c1]

3-((3-(3-Amino-1-hydroxypropyl)phenoxy)methyl)pentan-3-ol was prepared following the method described in Example 13.

Step 1:

2,2-Diethyloxirane (6.5 g of a 60% crude, 40 mmol), 3-bromophenol (5.7 g, 33 mmol), and cesium carbonate (12.0 g, 37 mmol) were combined in anhydrous DMSO (20 mL) in a sealed pressure tube and the reaction was stirred and heated at 120° C. for 2 d. Crude product was extracted from water with diethyl ether. The combined organic was washed with brine, dried over Na$_2$SO$_4$, filtered and concentrated under reduced vacuum. Purification by flash chromatography (0-20% EtOAc/hexanes gradient) gave 3-((3-bromophenoxy)methyl)pentan-3-ol as a colorless oil. Yield (7.1 g, 79%): NMR (400 MHz, CDCl$_3$) δ 7.19 (t, J=8.0 Hz, 1H), 7.05-7.12 (m, 2H), 6.90-6.94 (m, 1H), 4.31 (s, 1H), 3.71 (s, 2H), 1.41-1.55 (m, 4H), 0.80 (t, J=7.6 Hz, 6H).

Step 2:

3-((3-Bromophenoxy)methyl)pentan-3-ol was carbonylated following the method used in Example 13. Purification by flash chromatography (10, 30, 50, 65% EtOAc-hexanes step gradient) gave 3-(2-ethyl-2-hydroxybutoxy) benzaldehyde as an oil. Yield (0.19 g, 23%): $^1$H NMR (400 MHz, CDCl$_3$) δ 9.97 (s, 1H), 7.40-7.47 (m, 3H), 7.18-7.22 (m, 1H), 3.88 (s, 2H), 1.63-1.69 (m, 4H), 0.93 (t, J=7.6 Hz, 6H).

Step 3:

3-(2-Ethyl-2-hydroxybutoxy)benzaldehyde was reacted with acetonitrile following the method used in Example 13. Purification by flash chromatography (30, 40, 50, 75% EtOAc-hexanes step gradient) gave 3-(3-(2-ethyl-2-hydroxybutoxy)phenyl)-3-hydroxypropanenitrile as an oil. Yield (0.17 g, 79%): $^1$H NMR (400 MHz, CDCl$_3$) δ 7.23 (t, J=8.0 Hz, 1H), 6.96-6.98 (m, 2H), 6.88-6.91 (m, 1H), 5.02 (t, J=6.4 Hz, 1H), 3.83 (s, 2H), 2.76 (d, J=6.8 Hz, 2H), 1.62-1.68 (m, 4H), 0.92 (t, J=7.6 Hz, 6H).

Step 4:

3-(3-(2-Ethyl-2-hydroxybutoxy)phenyl)-3-hydroxypropanenitrile was reduced following the method used in Example 13. The reaction mixture was quenched with the addition of saturated aqueous Na$_2$SO$_4$. NH$_3$-MeOH (4 mL of a 7 M solution) was added, the mixture was dried over solid Na$_2$SO$_4$, and concentrated under reduced pressure gave Example 30 as an oil. Yield (0.034 g, 22%): $^1$H NMR (400 MHz, MeOD) δ 7.22 (t, J=10.04 Hz, 1H), 6.90-6.96 (m, 2H), 6.81 (dd, J=8.4, 1.6 Hz, 1H), 4.07 (t, J=6.4 Hz, 1H), 3.80 (s, 2H), 3.54-3.57 (m, 2H), 1.56-1.70 (m, 6H), 0.91 (t, J=8.0 Hz, 6H).

Example 31

Preparation of 3-((3-(2-aminoethoxy)phenoxy)methyl)pentan-3-ol

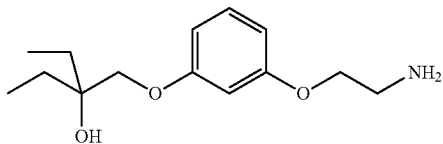 [SMILES: CCC(O)(CC)COc1cccc(OCCN)c1]

3-((3-(2-Aminoethoxy)phenoxy)methyl)pentan-3-ol was prepared following the method used in Example 18.

Step 1:

Coupling of 2,2-diethyloxirane (0.34 g, 3 mmol) with compound 24 (0.28 g, 1 mmol) following the method used in Example 18 gave 2-(2-(3-(2-ethyl-2-hydroxybutoxy)phenoxy)ethyl)isoindoline-1,3-dione that was directly used in subsequent reaction without purification. Yield (0.16 g, 42%): $^1$H NMR (400 MHz, CDCl$_3$) δ 7.48-7.57 (m, 3H), 7.16 (t, J=8.0 Hz, 1H), 6.49-6.58 (m, 3H), 4.16 (t, J=4.8 Hz, 2H), 3.86 (q, J=5.2 Hz, 2H), 3.80 (s, 2H), 1.60-1.66 (m, 4H), 0.89-0.93 (m, 6H).

Step 2:

Deprotection of 2-(2-(3-(2-ethyl-2-hydroxybutoxy)phenoxy)ethyl)isoindoline-1,3-dione following the method used in Example 18 gave Example 31 as a colorless oil. Yield (0.08 g, 86%): $^1$H NMR (400 MHz, MeOD) δ 7.14 (t, J=6.8 Hz, 1H), 6.51-6.53 (m, 3H), 3.98 (t, J=5.2 Hz, 2H), 3.77 (s, 2H), 1.60-1.66 (m, 4H), 0.90 (t, J=7.6 Hz, 6H),

Example 32

Preparation of 3-((3-(3-aminopropyl)phenoxy)methyl)pentan-3-ol

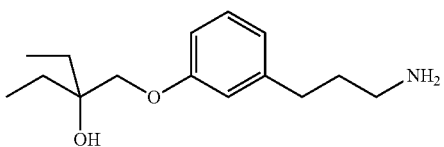 [SMILES: CCC(O)(CC)COc1cccc(CCCN)c1]

3-((3-(3-Aminopropyl)phenoxy)methyl)pentan-3-ol was prepared following the method shown in Scheme 16.

for 5 h, the reaction was cooled to room temperature. The mixture was concentrated under reduced pressure then triturated with EtOAc. The solids were removed by filtration and the filtrate concentrated under reduced pressure. Purification by flash chromatography (10 to 50% EtOAc-hexanes gradient) gave allyl amine 56 as a grey solid. Yield (5.59 g, 69%): $^1$H NMR (400 MHz, CDCl$_3$) δ 7.84-7.87 (m, 2H), 7.70-7.74 (m, 2H), 7.19 (t, J=8.0 Hz, 1H), 7.05 (t, J=2.0 Hz, 1H), 6.97 (d, J=7.8 Hz, 1H), 6.91-6.93 (m, 1H), 6.61 (d, J=15.8 Hz, 1H), 6.24 (dt, J=15.8, 6.5 Hz, 1H), 5.40 (t, J=3.1 Hz, 1H), 4.43 (dd, J=6.5, 1.2 Hz, 1H), 3.85-3.91 (m, 1H), 3.56-3.61 (m, 1H), 1.94-2.12 (m, 1H), 1.81-1.85 (m, 2H), 1.55-1.72 (m, 4H).

Step 2:

A suspension of allyl amine 56 (5.59 g, 15.4 mmol) in EtOH (40 mL) and THF (20 mL) was purged with vacuum/

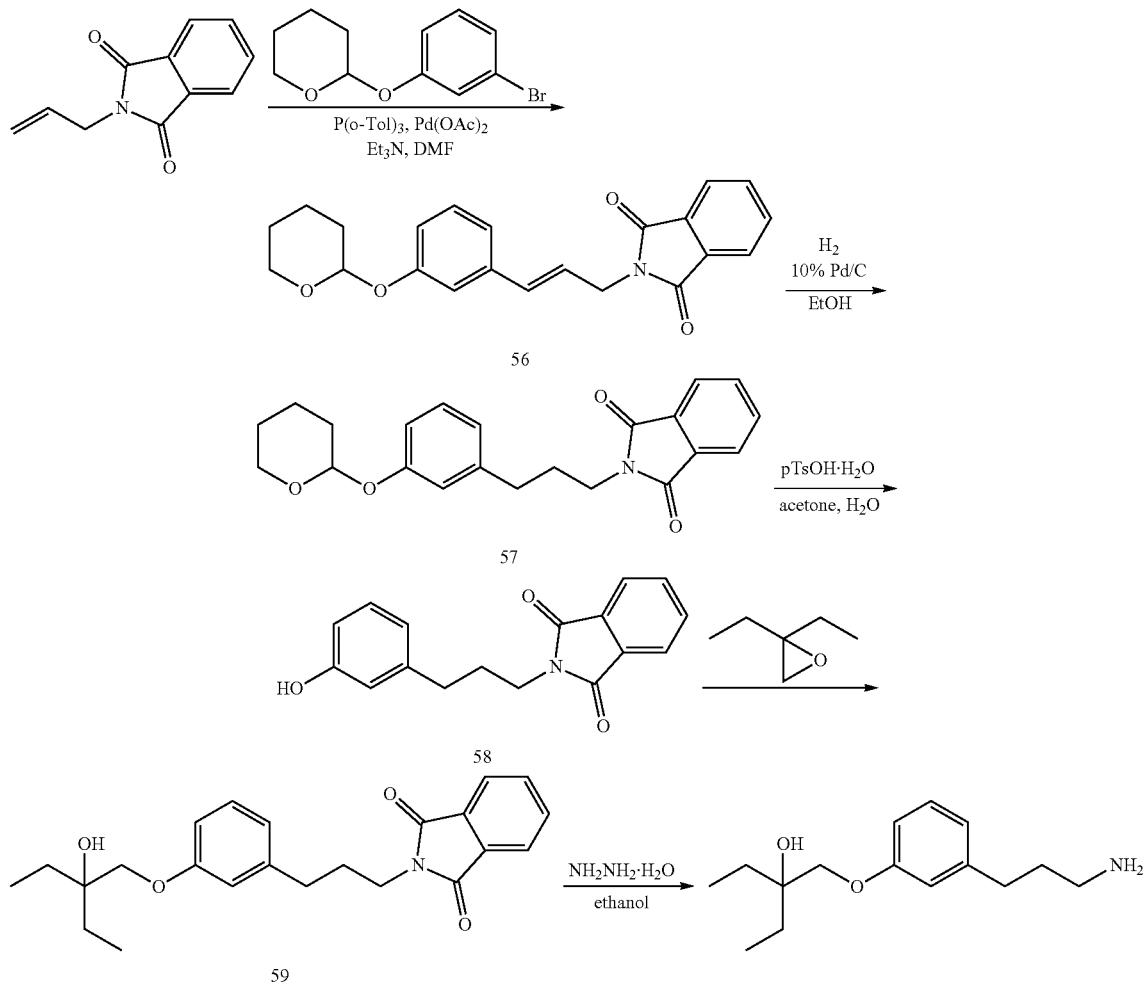

SCHEME 16

Step 1:

A solution of 2-(3-bromophenoxy)tetrahydro-2H-pyran (5.70 g, 22.2 mmol), 2-allylisoindoline-1,3-dione (4.15 g, 22.2 mmol), and tri-(o-tolyl)phosphine (0.1723 g, 0.57 mmol) in anhydrous DMF (50 mL) was degassed by bubbling with argon then put under vacuum/argon purge three times. Triethylamine (7 mL) was added and the mixture purged twice. Pd(OAc)$_2$ (0.1447 g, 0.65 mmol) was added and the mixture purged three times. After heating at 90° C.

argon three times then 10% Pd/C (0.29 g) was added. The mixture was put under vacuum then under hydrogen (balloon) for 4.5 h. The hydrogen balloon was removed and the mixture was stirred overnight. The mixture was put under vacuum then vented to the atmosphere. The solids were removed by filtration through filter paper and the filtrate concentrated under reduced pressure to give phthalimide 57 as an oil. This product was used without purification. Yield (5.52 g, 98%): $^1$H NMR (400 MHz, CDCl$_3$) δ 7.80-7.83 (m, 2H), 7.68-7.72 (m, 2H), 7.15 (t, J=7.8 Hz, 1H), 6.88 (t, J=2.0 Hz, 1H), 6.80-6.85 (m, 2H), 5.39 (t, J=3.1 Hz, 1H), 3.87-3.93 (m, 1H), 3.69-3.76 (m, 2H), 3.57-3.62 (m, 1H), 2.65 (m, 2H), 1.97-2.06 (m, 2H), 1.82-1.86 (m, 2H), 1.57-1.69 (m, 4H).

Step 3:

To a solution of phthalimide 57 (5.52 g, 15.1 mmol) in acetone-water (4:1, 50 mL) was added p-toluenesulfonic acid monohydrate (0.34 g, 1.8 mmol). The mixture was stirred for 2 h at room temperature. After removal of the volatiles under reduced pressure, the aqueous suspension was diluted with additional water. The precipitate was collected by filtration and washed with water and hexanes. Phenol 58 was dried under vacuum overnight and isolated as a white solid. Yield (3.98 g, 93%): $^1$H NMR (400 MHz, CDCl$_3$) δ 7.81-7.84 (m, 2H), 7.68-7.71 (m, 2H), 7.10 (t, J=7.8 Hz, 1H), 6.75 (m, 1H), 6.68 (t, J=1.8 Hz, 1H), 6.60-6.62 (m, 1H), 5.06 (s, 1H), 3.74 (t, J=7.0 Hz, 2H), 2.64 (t, J=7.4 Hz, 2H), 1.99-2.04 (m, 2H).

Example 33

Preparation of 3-(3-(isopentyloxy)phenyl)propan-1-amine

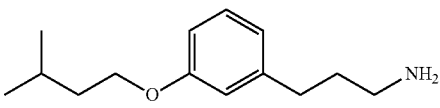 [SMILES: CC(C)CCOc1cccc(CCCN)c1]

3-(3-(Isopentyloxy)phenyl)propan-1-amine was prepared following the method shown in Scheme 17

SCHEME 17

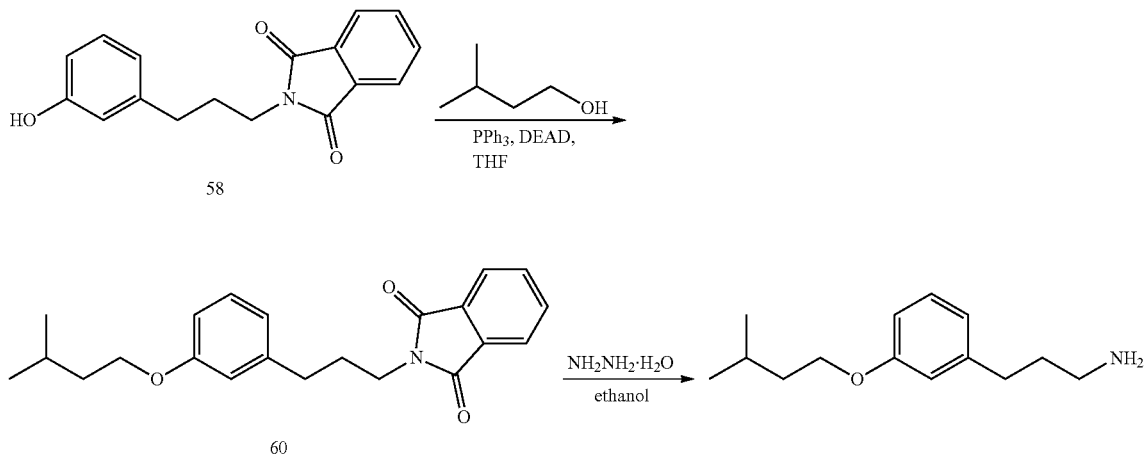

Step 4:

Reaction of 2-(3-(3-hydroxyphenyl)propyl)isoindoline-1,3-dione with 2,2-diethyloxirane following method described in Example 18 gave 2-(3-(3-(2-ethyl-2-hydroxybutoxy)phenyl)propyl)isoindoline-1,3-dione. $^1$H NMR (400 MHz, CDCl$_3$) δ 7.75-7.88 (m, 4H), 7.06 (t, J=6.8 Hz, 1H), 6.72-6.76 (m, 2H), 6.61 (d, J=8.4 Hz, 1H), 3.74 (s, 2H), 3.69 (t, J=6.4 Hz, 2H), 2.63 (t, J=7.2 Hz, 2H), 1.95-2.05 (m, 2H), 1.61-1.66 (m, 4H), 0.91 (t, J=7.6 Hz, 6H).

Step 5:

Deprotection of 2-(3-(3-(2-ethyl-2-hydroxybutoxy)phenyl)propyl)isoindoline-1,3-dione using hydrazine hydrate following the method described in Example 18 gave Example 32. $^1$H NMR (400 MHz, DMSO-d$_6$) δ 7.13 (t, J=6.8 Hz, 1H), 6.69-6.73 (m, 3H), 4.28 (brs, 1H), 3.66 (s, 2H), 2.99 (t, J=4.8 Hz, 2H), 2.47-2.55 (m, 4H), 1.45-1.51 (m, 4H), 0.80 (t, J=7.6 Hz, 6H).

Step 1:

To a mixture of phenol 58 (1 g, 3.6 mmol), iso-amyl alcohol (0.3 mL, 3.7 mmol) and triphenyl phosphine (1.02 g, 3.8 mmol) in THF (5 mL) was added DEAD (0.75 mL, 4.2 mmol) as a solution in THF (5 mL). The mixture was stirred at room temperature for 24 h and concentrated under reduced pressure. Purification by flash chromatography (0 to 10% EtOAc-hexanes gradient) gave ether 60 as yellow oil. Yield (0.418 g, 33%): $^1$H NMR (400 MHz, CDCl$_3$) δ 7.79-7.87 (m, 2H), 7.68-7.74 (m, 2H), 7.10-7.17 (m, 1H), 6.72-6.80 (m, 2H), 6.65-6.69 (m, 1H), 3.95 (t, J=6.8 Hz, 2H), 3.75 (t, J=7.0 Hz, 2H), 2.65 (t, J=7.8 Hz, 2H), 2.00-2.09 (m, 2H), 1.80-1.90 (m, 1H), 1.62-1.70 (m, 2H), 0.92-1.01 (m, 6H).

Step 2:

To a solution of phthalimide 60 (0.410 g, 1.2 mmol) in EtOH (10 mL) was added hydrazine monohydrate (0.2 mL) and the mixture was stirred at 55° C. for 6 h. The mixture was cooled to room temperature and filtered. The filtrate was concentrated under reduced pressure and the residue suspended in water and extracted with DCM. The organic layer was dried over anhydrous Na$_2$SO$_4$, filtered and concentrated under reduced pressure. Purification by flash chromatography (0 to 10% 7N NH$_3$/methanol-CH$_2$Cl$_2$) afforded Example 33 as yellow oil. Yield (0.260 g, 98%): $^1$H NMR (400 MHz, DMSO-d$_6$) δ 7.15-7.21 (m, 1H), 6.70-6.78 (m, 3H), 3.95 (t, J=6.6, 2H), 2.51-2.59 (m, 4H), 1.75-1.83 (m, 3H), 1.59-1.66 (m, 5H), 0.92-0.98 (m, 6H). $^{13}$C NMR (100 MHz, DMSO-d$_6$) δ 158.9, 143.6, 129.2, 120.4, 114.5, 111.5, 65.6, 40.6, 37.5, 33.8, 32.5, 31.5, 24.6, 22.5. MS: 222 [M+1]$^+$.

Example 34

Preparation of 3-amino-1-(3-(cyclobutylmethoxy)phenyl)propan-1-ol

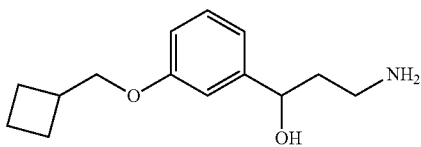 [SMILES: NCCC(O)c1cccc(OCC2CCC2)c1]

3-Amino-1-(3-(cyclobutylmethoxy)phenyl)propan-1-ol was prepared following the method shown in Scheme 18.

SCHEME 18

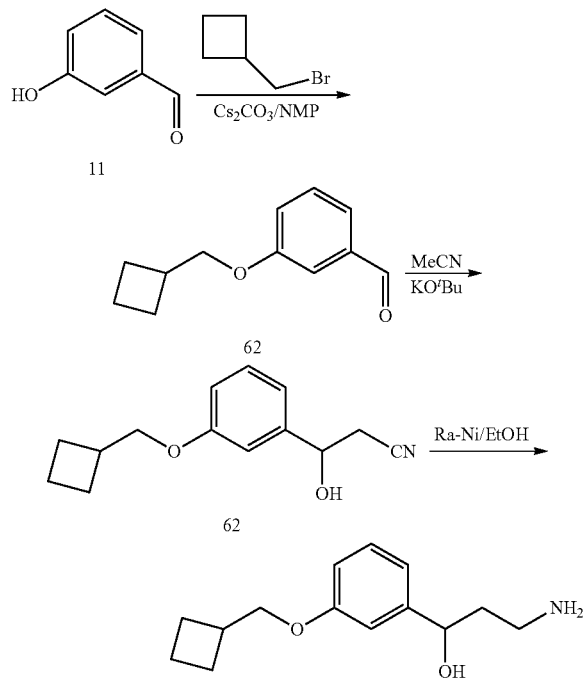

Step 1:

A mixture of 3-hydroxybenzaldehyde (11) (1.5 g, 12.2 mmol), cyclobutylmethyl bromide (2.19 g, 14.7 mmol) and cesium carbonate (5.98 g, 18.4 mmol) in NMP (15 mL) was heated at 60° C. overnight. The mixture was cooled to room temperature and then poured into ice-water. This mixture was extracted EtOAc and the organic layer was washed with water, then brine, dried over Na$_2$SO$_4$ and concentrated under reduced pressure. Purification by flash chromatography (0 to 10% EtOAc-hexanes gradient) gave ether 61 as clear oil. Yield (1.7 g, 49%): $^1$H NMR (400 MHz, CDCl$_3$) δ 9.97 s, 1H), 7.43-7.46 (m, 2H), 7.38-7.46 (m, 2H), 7.39 (d, J=2.0, 1H), 7.16-7.20 (m, 1H), 3.99 (d, J=6.8, 2H), 2.72-2.83 (m, 1H), 2.12-2.20 (m, 1H), 1.83-2.02 (m, 5H).

Step 2:

To a stirred suspension of t-BuOK (1.308 g, 10 mmol) in THF (10 mL), cooled to −50° C., was added acetonitrile (0.51 mL, 9.8 mmol), dropwise over a period of 5 min. The resulting mixture was stirred at −50° C. for 30 min following which a solution of 61 (1.7 g, mmol) in THF (10 mL) was added slowly, over a period of 10 min. This was then allowed to warm to 0° C. and stirred for another 3 h during which the reaction was found to be complete. The reaction was quenched by slow addition of ice-water and the mixture extracted with EtOAc. The combined organics were washed with water, brine and dried over Na$_2$SO$_4$. The solution was concentrated under reduced pressure. Purification by flash column chromatography (0 to 20% EtOAc-hexanes gradient) gave nitrile 62. Yield (1.07 g, 52%): $^1$H NMR (400 MHz, CDCl$_3$) δ 7.27-7.32 (m, 1H), 6.93-6.97 (m, 2H), 6.86-6.90 (d, J=8.0 Hz, 1H), 5.01 (m, 1H), 3.94 (d, J=11.6 Hz, 2H), 2.70-2.82 (m, 3H), 2.30-2.33 (m, 1H), 2.10-2.20 (m, 2H), 1.80-2.00 (m, 4H).

Step 3:

To a solution of nitrile 61 (1.07 g, 4.6 mmol) in EtOH (10 mL) was added conc. NH$_4$OH (1 mL) followed by the addition of freshly washed Raney-Ni (100 mg). The resulting mixture was stirred at 40° C. for 4 h under a hydrogen balloon. The mixture was filtered through celite and washed with EtOAc. The combined filtrate was concentrated under reduced pressure. Purification by flash chromatography (0 to 15% (9:1 MeOH—NH$_3$)-DCM gradient) gave Example 34 as a clear oil. Yield (0.4 g, 38%): $^1$H NMR (400 MHz, DMSO-d$_6$) δ 7.19 (t, J=7.6 Hz, 1H), 6.85-6.90 (m, 2H), 6.75 (dd, J=5.6, 4.0 Hz, 1H), 4.60 (t, J=6.4 Hz, 1H), 3.91 (d, J=6.8 Hz, 2H), 2.58-2.65 (m, 3H), 2.03-2.10 (m, 2H), 1.79-1.95 (m, 4H), 1.58-1.65 (m, 2H). $^{13}$C NMR (100 MHz, DMSO-d$_6$) δ 158.6, 148.3, 128.9, 117.8, 112.4, 111.7, 71.3, 71.2, 42.2, 34.0, 24.4, 18.1. MS: 236 [M+1]$^+$.

Example 35

Preparation of 3-amino-1-(3-(cyclopentylmethoxy)phenyl)propan-1-ol

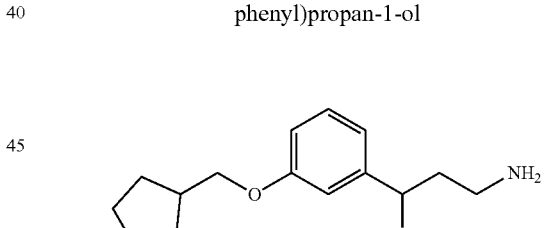

3-Amino-1-(3-(cyclopentyllmethoxy)phenyl)propan-1-ol was prepared following the method described in Example 71.

Step 1:

Coupling of 3-hydroxybenzaldehyde (11) (8.46 g, 69.3 mmol) with cyclopentanemethanol (5.0 g, 69.3 mmol) gave 3-(cyclopentylmethoxy)benzaldehyde as a colorless oil. Yield (0.87 g, 7%): $^1$H NMR (400 MHz, CDCl$_3$) δ 9.96 (s, 1H), 7.42-7.44 (m, 2H), 7.37-7.39 (m, 1H), 7.14-7.20 (m, 1H), 3.88 (d, J=7.2 Hz, 2H), 2.37 (dddd, J=8 Hz, 1H), 1.78-1.90 (m, 2H), 1.54-1.70 (m, 4H), 1.30-1.42 (m, 2H).

Step 2:

Aldol condensation with acetonitrile and 3-(cyclopentylmethoxy)benzaldehyde gave 3-(3-(cyclopentylmethoxy)phenyl)-3-hydroxypropanenitrile as a colorless oil. Yield (0.4 g, 38%): $^1$H NMR (400 MHz, CDCl$_3$) δ 7.22-7.28 (m, 1H), 6.88-6.94 (m, 2H), 6.82-6.88 (m, 1H), 4.95 (t, J=6.4

Hz, 1H), 3.81 (d, J=6.4 Hz, 2H), 2.83 (brs, 1H), 2.71 (d, J=6.4 Hz, 2H), 2.33 (dddd, J=7.2 Hz, 1H), 1.76-1.88 (m, 2H), 1.50-1.68 (m, 4H), 1.28-1.40 (m, 2H).

Step 3:

Reduction of 3-(3-(cyclopentylmethoxy)phenyl)-3-hydroxypropanenitrile gave Example 35 as a colorless oil. Yield (0.086 g, 21%): $^1$H NMR (400 MHz, CDCl$_3$) δ 7.21 (t, J=8.0 Hz, 1H), 6.94-6.97 (m, 1H), 6.88-6.92 (m, 1H), 6.74-6.89 (m, 1H), 4.90 (dd, J=8.8, 3.2 Hz, 1H), 3.75 (d, J=6.4 Hz, 2H), 3.02-3.09 (m, 1H), 3.02 (br s, 3H), 2.87-2.96 (m, 1H), 2.28-2.40 (m, 1H), 1.68-1.88 (m, 4H), 1.51-1.68 (m, 4H), 1.29-1.40 (m, 2H).

Example 36

Preparation of 2-(3-(2-ethylbutoxy)phenoxy)ethanamine

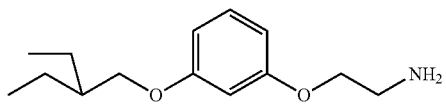 [SMILES: CCC(CC)COc1cccc(OCCN)c1]

2-(3-(2-Ethylbutoxy)phenoxy)ethanamine was prepared following the method described.

Step 1:

Coupling of 2-ethylbutyl 4-methylbenzenesulfonate (0.5 g, 1.95 mmol) with compound 24 (0.5 g, 1 mmol) following the method used in Example 18 gave 2-(2-(3-(2-ethylbutoxy)phenoxy)ethyl)isoindoline-1,3-dione as a colorless oil. Yield (0.2 g, 31%): $^1$H NMR (400 MHz, CDCl$_3$) δ 7.84-7.86 (m, 2H), 7.68-7.72 (m, 2H), 7.10 (t, J=7.2 Hz, 1H), 6.42-6.48 (m, 3H), 4.20 (t, J=5.6 Hz, 2H), 4.08-4.12 (m, 2H), 3.78 (d, J=5.6 Hz, 2H), 1.59-1.66 (m, 1H), 1.38-1.50 (m, 4H), 0.90 (t, J=7.6 Hz, 6H).

Step 2:

Deprotection of 2-(2-(3-(2-ethylbutoxy)phenoxy)ethyl)isoindoline-1,3-dione following the method used in Example 18 gave Example 36 as a colorless oil. Yield (0.2 g, 31%): $^1$H NMR (400 MHz, DMSO-d$_6$) δ 7.12 (t, J=8.0 Hz, 1H), 6.20-6.48 (m, 3H), 3.86 (t, J=6.0 Hz, 2H), 3.80 (d, J=5.2 Hz, 2H), 2.82 (t, J=5.6 Hz, 2H), 1.46-1.61 (m, 3H), 1.32-1.46 (m, 4H), 0.86 (t, J=7.4 Hz, 6H).

Example 37

Preparation of 3-amino-1-(3-(benzyloxy)phenyl)propan-1-ol

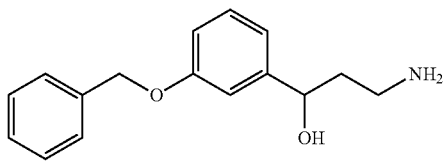 [SMILES: NCCC(O)c1cccc(OCc2ccccc2)c1]

3-Amino-1-(3-(benzyloxy)phenyl)propan-1-ol is prepared following the method described in Example 34.

Example 38

Preparation of 3-(3-(2-methoxybenzyloxy)phenyl)propan-1-amine

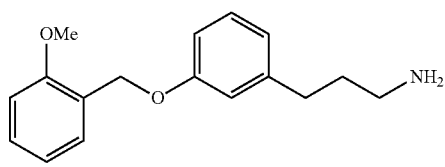 [SMILES: COc1ccccc1COc1cccc(CCCN)c1]

3-(3-(2-Methoxybenzyloxy)phenyl)propan-1-amine was prepared following the method described in Example 33.

Step 1:

Mitsunobu coupling of 2-methoxybenzylalcohol with phenol 58 gave 2-(3-(3-(2-methoxybenzyloxy)phenyl)propyl)isoindoline-1,3-dione as a colorless oil. Yield (0.26 g, 61%). $^1$H NMR (400 MHz, CDCl$_3$) δ 7.78-7.84 (m, 2H), 7.66-7.72 (m, 2H), 7.43-7.47 (m, 1H), 7.24-7.31 (m, 1H), 7.14 (t, J=8.0 Hz, 1H), 6.94-6.99 (m, 1H), 6.88-6.91 (m, 1H), 6.82-6.85 (m, 1H), 6.74-6.80 (m, 2H), 5.06 (s, 2H), 3.81 (s, 3H), 3.74 (t, J=7.2 Hz, 2H), 2.66 (t, J=7.6 Hz, 2H), 1.98-2.07 (m, 2H).

Step 2:

Hydrazine deprotection of 2-(3-(3-(2-methoxybenzyloxy)phenyl)propyl)isoindoline-1,3-dione gave Example 38 as a yellow oil. Yield (0.137 g, 81%). $^1$H NMR (400 MHz, DMSO) δ 7.34-7.38 (m, 1H), 7.27-7.33 (m, 1H), 7.14 (t, J=8.0 Hz, 1H), 7.00-7.03 (m, 1H), 6.91-6.96 (m, 1H), 6.78-6.82 (m, 1H), 6.72-6.78 (m, 2H), 4.99 (s, 2H), 3.78 (s, 3H), 2.45-2.55 (m, 4H), 1.58 (dddd, J=7.2, 2H), 1.33 (brs, 2H).

Example 39

Preparation of 4-(3-(3-aminopropyl)phenoxy)butanamide

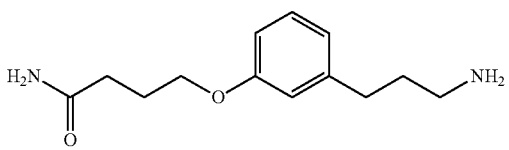

4-(3-(3-Aminopropyl)phenoxy)butanamide was prepared following the method shown in Scheme 19

SCHEME 19

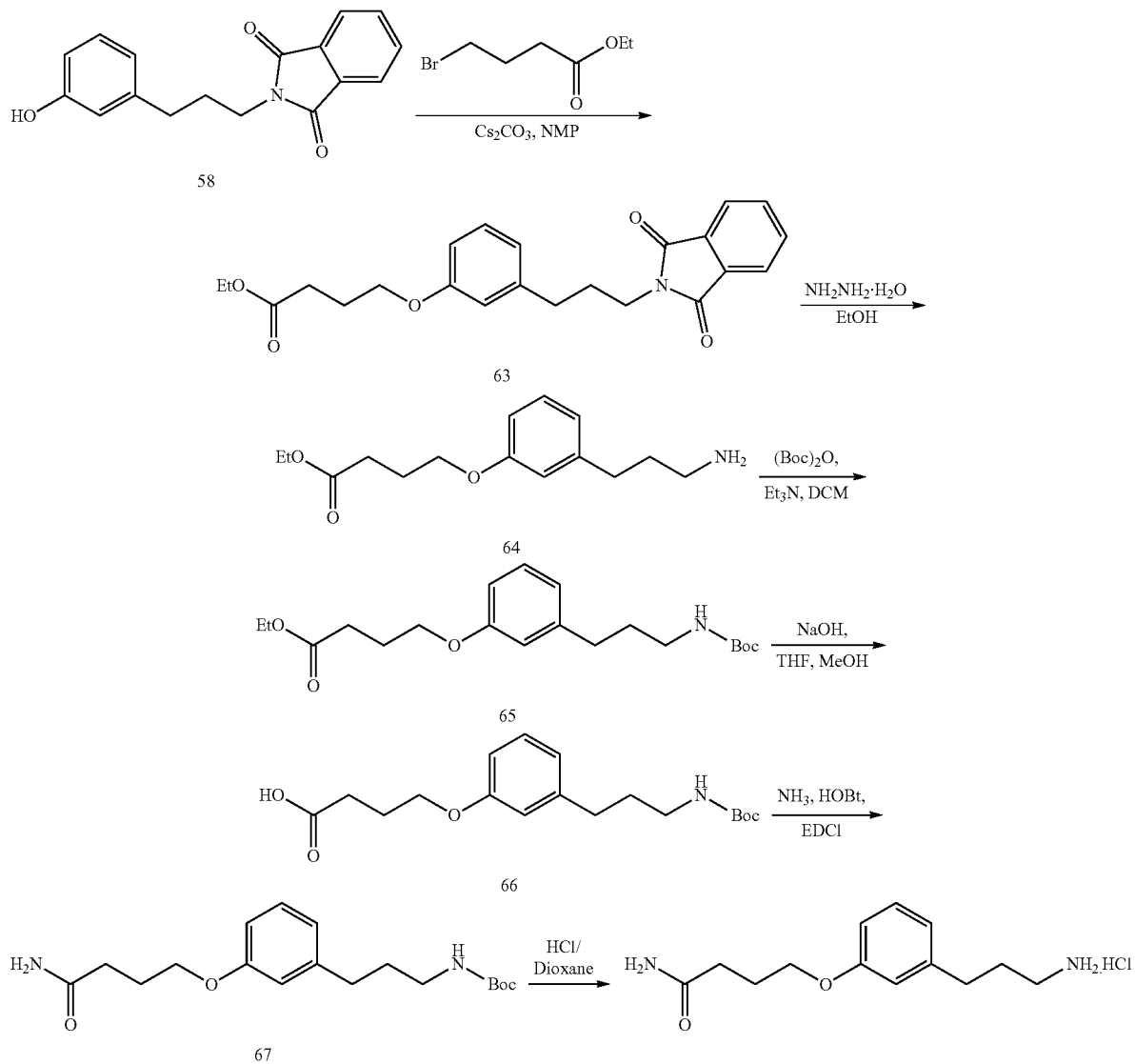

Step 1:

A mixture of 2-[3-(3-hydroxyphenyl)propyl]isoindole-1,3-dione (58) (5 g, 17.5 mmol), 4-bromoethyl butyrate (3.0 mL, 21 mmol) and cesium carbonate (6.2 g, 35 mmol) in NMP (10 mL) was warmed to 70° C. for 12 h. The mixture was cooled to room temperature and then poured into ice-water. This was extracted with EtOAc and the organic layer was washed with water, then brine, dried over $Na_2SO_4$ and concentrated under reduced pressure. Purification by flash chromatography (0 to 10% EtOAc-hexanes gradient) gave ether 63 as clear oil. Yield (5.6 g, 81%): $^1$H NMR (400 MHz, $CDCl_3$) δ 7.81-7.83 (m, 2H), 7.69-7.71 (m, 2H), 7.11-7.16 (m, 1H), 6.77 (d, J=7.2 Hz, 1H), 6.72 (s, 1H), 6.65 (d, J=8.0 Hz, 1H), 4.14 (q, J=7.2 Hz, 2H), 3.97 (t, J=6.0 Hz, 2H), 3.74 (t, J=6.8 Hz, 2H), 2.63 (t, J=7.6 Hz, 2H), 2.50 (t, J=7.2 Hz, 2H), 2.00-2.12 (m, 4H), 1.26 (t, J=7.2 Hz, 3H).

Step 2:

To a solution of phthalimide 63 (5.6 g, 14 mmol) in EtOH (20 mL) was added hydrazine monohydrate (1 mL) and the mixture was stirred at 55° C. for 6 h. The mixture was cooled to room temperature and filtered. The filtrate was concentrated under reduced pressure and the residue suspended in water and extracted with DCM. The organic layer was dried over anhydrous $Na_2SO_4$, filtered and concentrated under reduced pressure. Purification by flash chromatography (0 to 10% 7N $NH_3$/methanol-$CH_2Cl_2$) afforded amine 64 as yellow oil. Yield (3.07 g, crude): $^1$H NMR (400 MHz, $CDCl_3$) δ 7.16-7.20 (m, 1H), 6.77 (d, J=7.2 Hz, 1H), 6.69-6.73 (m, 2H), 4.14 (q, J=7.2 Hz, 2H), 3.99 (t, J=6.0 Hz, 2H), 2.70-2.80 (m, 2H), 2.62 (t, J=7.4 Hz, 2H), 2.51 (t, J=7.2 Hz, 2H), 2.07-2.12 (m, 2H), 1.72-1.80 (m, 2H), 1.26 (t, J=7.2 Hz, 3H).

Step 3:

To a solution of amine 64 (3.0 g, 11.3 mmol) in DCM (100 mL) was added triethylamine (5 mL, 40 mmol). To this was added $(Boc)_2O$ (2.8 mL, 15 mmol). The resulting mixture was stirred at room temperature overnight. The mixture was quenched by the addition of water and extracted with DCM. The organic layer was washed with satd. $NaHCO_3$ solution, dried over anhydrous $Na_2SO_4$, filtered and concentrated under reduced pressure. Purification by flash chromatography (0 to 20% EtOAc-hexanes gradient) afforded Boc protected amine 65 as yellow oil. Yield (3.412 g, 83%): $^1$H NMR (400 MHz, CDCl$_3$) δ 7.15-7.20 (m, 1H), 6.75 (d, J=7.6 Hz, 1H), 6.69-6.73 (m, 2H), 4.14 (q, J=7.2 Hz, 2H), 3.99 (t, J=6.0 Hz, 2H), 3.13-3.16 (m, 2H), 2.60 (t, J=7.6 Hz, 2H), 2.51 (t, J=7.2 Hz, 2H), 2.08-2.13 (m, 2H), 1.77-1.82 (m, 2H), 1.44 (s, 9H), 1.26 (t, J=7.2 Hz, 3H).

Step 4:

To the ester 65 (3.4 g, 12.8 mmol) in THF (80 mL) and MeOH (20 mL) was added 1N NaOH (2.5 mL, 25.7 mmol) and stirred at room temperature overnight. After evaporating the solvent, the mixture was carefully neutralized to pH 6 by the addition of cold dilute HCl. After extraction with DCM, the organic layer was washed with water, dried over anhydrous Na$_2$SO$_4$, filtered and concentrated under reduced pressure. The crude acid 66 was directly utilized for further transformation. Yield (3.1 g, crude): $^1$H NMR (400 MHz, CDCl$_3$) δ 7.14-7.18 (m, 1H), 6.70-6.77 (m, 3H), 4.04 (t, J=6.0 Hz, 2H), 3.13-3.15 (m, 2H), 2.55-2.63 (m, 2H), 2.08-2.14 (m, 2H), 1.76-1.83 (m, 2H), 1.45 (s, 9H).

Step 9:

A mixture of acid 66 (1.0 g, 2.96 mmol), HOBt (0.725 g, 3.3 mmol) and EDCI (0.915 g, 6 mmol) in DCM (40 mL) was stirred at room temperature for 2 h. To this was added ammonia in methanol (5 mL, 2M) and the reaction mixture was allowed to stir for further 3 h during which the reaction was found to be complete. The mixture was quenched by the addition of water and extracted with DCM. The organic layer was washed with brine, dried over anhydrous Na$_2$SO$_4$, filtered and concentrated under reduced pressure. Purification by flash chromatography (0 to 2% DCM-Methanol gradient) afforded amide 67 as yellow oil. Yield (0.66 g, 66%): $^1$H NMR (400 MHz, CDCl$_3$) δ 7.14-7.18 (m, 1H), 6.70-6.75 (m, 3H), 3.92 (t, J=6.4 Hz, 2H), 2.88-2.93 (m, 2H), 2.49-2.51 (m, 2H), 2.21 (t, J=7.6 Hz, 2H), 1.88-1.92 (m, 2H), 1.63-1.67 (m, 2H), 1.37 (s, 9H).

Step 10:

To a solution of compound 67 (0.66 g, 2.0 mmol) in THF (10 mL) was added HCl in Dioxane (5 mL, 4 M) and the resulting mixture was stirred at room temperature overnight. The solvent was removed under reduced pressure and solid obtained was triturated with diethyl ether and dried to give Example 39 hydrochloride as a yellow solid. Yield (0.360 g, 66%): $^1$H NMR (400 MHz, DMSO-d$_6$) δ 7.17-7.21 (m, 1H), 6.73-6.77 (m, 3H), 3.91 (t, J=6.4 Hz, 2H), 2.75 (t, J=7.6 Hz, 2H), 2.58 (t, J=7.6 Hz, 2H), 2.21 (t, J=7.6 Hz, 2H), 1.85-1.92 (m, 2H), 1.79-1.85 (m, 2H). $^{13}$C NMR (100 MHz, DMSO-d$_6$) δ 174.2, 159.1, 142.9, 129.8, 120.9, 115.0, 112.4, 67.2, 38.7, 32.3, 31.8, 29.0, 25.2. MS: 237 [M+1]$^+$.

Example 40

Preparation of 3-(3-(2-methoxyethoxy)phenyl)propan-1-amine

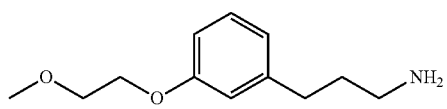

3-(3-(2-Methoxyethoxy)phenyl)propan-1-amine was prepared following the method described in Example 33.

Step 1:

Mitsunobu reaction of phenol 58 with 2-methoxyethanol gave 2-(3-(3-(2-methoxyethoxy)phenyl)propyl)isoindoline-1,3-dione as a clear oil. Yield (0.225 g, 19%): $^1$H NMR (400 MHz, DMSO-d$_6$) 7.81-7.84 (m, 2H), 7.67-7.72 (m, 2H), 7.10-7.16 (m, 1H), 6.76-6.80 (m, 2H), 6.67-6.72 (m, 1H), 4.07-4.11 (m, 2H), 3.70-3.76 (m, 4H), 3.45 (s, 3H), 2.55 (t, J=7.6 Hz, 2H), 1.98-2.05 (m, 2H).

Step 2:

Phthalimide cleavage of 2-(3-(3-(2-methoxyethoxy)phenyl)propyl)isoindoline-1,3-dione gave Example 77 as off-white semi-solid. Yield (0.24 g, 94%): $^1$H NMR (400 MHz, DMSO-d$_6$) δ 7.14-7.19 (m, 1H), 6.72-6.78 (m, 3H), 4.04-4.07 (m, 2H), 3.64 (t, J=4.8 Hz, 2H), 3.30 (s, 3H), 2.48-2.60 (m, 4H), 1.58-1.68 (m, 2H). $^{13}$C NMR (100 MHz, DMSO-d$_6$) δ 158.9, 144.3, 129.7, 121.1, 114.9, 111.9, 70.9, 67.1, 58.6, 41.4, 35.1, 33.0. MS: 210 [M+1]$^+$.

Example 41

Preparation of 3-(3-(4-methoxybutoxy)phenyl)propan-1-amine

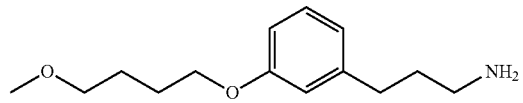 [SMILES: COCCCCOc1cccc(CCCN)c1]

3-(3-(4-Methoxybutoxy)phenyl)propan-1-amine was prepared following the method described in Example 33.

Step 1:

Mitsunobu reaction of phenol 58 with 4-methoxybutanol gave 2-(3-(3-(4-methoxybutoxy)phenyl)propyl)isoindoline-1,3-dione as yellow oil. Yield (0.840 g, 66%): $^1$H NMR (400 MHz, CDCl$_3$) δ 7.80-7.85 (m, 2H), 7.68-7.72 (m, 2H), 7.11-7.17 (m, 1H), 6.72-6.79 (m, 2H), 6.65 (dd, J=8.2, 2.4 Hz, 1H), 3.95 (t, J=6.2 Hz, 2H), 3.75 (t, J=6.8 Hz, 2H), 3.44 (t, J=6.4 Hz, 2H), 3.35 (s, 3H), 2.65 (t, J=7.2 Hz, 2H), 1.98-2.06 (m, 2H), 1.70-1.86 (m, 4H).

Step 2:

Phthalimide cleavage of 2-(3-(3-(4-methoxybutoxy)phenyl)propyl)isoindoline-1,3-dione gave Example 41 as pale yellow oil. Yield (0.36 g, 59%): $^1$H NMR (400 MHz, DMSO-d$_6$) δ 7.13-7.18 (m, 1H), 6.69-6.76 (m, 3H), 3.94 (t, J=6.4 Hz, 2H), 3.37 (t, J=6.4 Hz, 2H), 3.23 (s, 3H), 2.48-2.58 (m, 4H), 1.63-1.76 (m, 2H), 1.58-1.67 (m, 4H). $^{13}$C NMR (100 MHz, DMSO-d$_6$) δ 158.6, 143.9, 129.1, 120.4, 114.4, 111.5, 71.5, 66.9, 57.8, 41.2, 35.1, 32.6, 25.7, 25.6: MS: 238 [M+1]$^+$.

Example 42

Preparation of 3-(3-(4-(benzyloxy)butoxy)phenyl)propan-1-amine

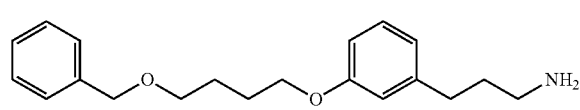

3-(3-(4-(Benzyloxy)butoxy)phenyl)propan-1-amine was prepared following the method described in Example 33.

Step 1:

Mitsunobu reaction of phenol 58 with 4-benzyloxybutanol gave 2-(3-(3-(4-(benzyloxy)butoxy)phenyl)propyl)isoindoline-1,3-dione as yellow oil. Yield (0.830 g, 54%): $^1$H NMR (400 MHz, CDCl$_3$) δ 7.81-7.85 (m, 2H), 7.70-7.74 (m, 2H), 7.28-7.35 (m, 5H), 7.10-7.16 (m, 1H), 6.77 (d, J=8.2 Hz, 1H), 6.73 (s, 1H), 6.65 (dd, J=7.6, 2.4 Hz, 1H), 4.52 (s, 2H), 3.94 (t, J=6.0 Hz, 2H), 3.74 (t, J=7.2 Hz, 2H), 3.55 (t, J=6.4 Hz, 2H), 2.63 (t, J=7.6 Hz, 2H), 2.00-2.08 (m, 2H), 1.82-1.90 (m, 2H), 1.76-1.81 (m, 2H).

Step 2:

Phthalimide cleavage of 2-(3-(3-(4-(benzyloxy)butoxy)phenyl) propyl)isoindoline-1,3-dione gave Example 42 as yellow oil. Yield (0.34 g, 50%): $^1$H NMR (400 MHz, DMSO-d$_6$) δ 7.24-7.37 (m, 5H), 7.12-7.18 (m, 1H), 6.68-6.75 (m, 3H), 4.46 (s, 2H), 3.95 (t, J=6.0 Hz, 2H), 3.48 (t, J=6.0 Hz, 2H), 2.51-2.56 (m, 2H), 1.55-1.80 (m, 6H). $^{13}$C NMR (100 MHz, DMSO-d$_6$) δ 158.6, 143.9, 138.7, 129.1, 128.2, 127.4, 127.3, 120.4, 114.4, 111.5, 71.8, 69.3, 66.9, 41.1, 325.0, 32.6, 25.8, 25.7. MS: 314 [M+1]$^+$.

Example 43

Preparation of 4-(3-(3-aminopropyl)phenoxy)butan-1-ol

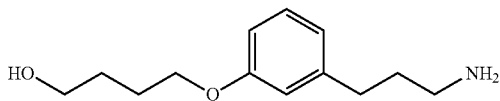 [SMILES: NCCCc1cccc(OCCCCO)c1]

4-(3-(3-Aminopropyl)phenoxy)butan-1-ol was prepared following the method described below.

The debenzylation of Example 42 using 10% Pd/C in EtOH gave Example 43 as an off-white solid. Yield (0.120 g, 51%): $^1$H NMR (400 MHz, CDCl$_3$) δ 7.14-7.18 (m, 1H), 6.71-6.75 (m, 3H), 3.93 (t, J=6.4 Hz, 2H), 3.42 (t, J=6.4 Hz, 2H), 2.50-2.58 (m, 4H), 1.69-1.76 (m, 2H), 1.52-1.58 (m, 2H). $^{13}$C NMR (100 MHz, DMSO-d$_6$) δ 158.7, 143.9, 129.2, 120.4, 114.5, 111.5, 67.1, 60.4, 41.2, 35.0, 32.6, 29.0, 25.5. MS: 224 [M+1]+.

Example 44

Preparation of 3-(3-(pentyloxy)phenyl)propan-1-amine

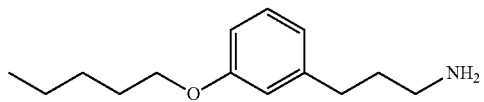 [SMILES: CCCCCOc1cccc(CCCN)c1]

3-(3-(Pentyloxy)phenyl)propan-1-amine was prepared following the method described in Example 59.

Step 1:

Alkylation reaction of phenol 58 with pentyl bromide gave 2-(3-(3-(pentyloxy)phenyl)propyl)isoindoline-1,3-dione as yellow oil. Yield (0.549 g, 46%): $^1$H NMR (400 MHz, CDCl$_3$) δ 7.81-7.84 (m, 2H), 7.69-7.72 (m, 2H), 7.11-7.16 (m, 1H), 6.76 (d, J=7.6 Hz, 1H), 6.73 (s, 1H), 6.66 (dd, J=7.8, 2.2 Hz, 1H), 3.91 (t, J=6.8 Hz, 2H), 3.74 (t, J=7.2 Hz, 2H), 2.65 (t, J=7.6 Hz, 2H), 2.01-2.07 (m, 2H), 1.73-1.78 (m, 2H), 1.34-1.48 (m, 4H), 0.92 (t, J=7.2 Hz, 3H).

Step 2:

Phthalimide cleavage of 2-(3-(3-(pentyloxy)phenyl)propyl) isoindoline-1,3-dione gave Example 44 as yellow oil. Yield (0.220 g, 59%): $^1$H NMR (400 MHz, DMSO-d$_6$) δ 7.16-7.20 (m, 1H), 6.76 (d, J=7.6 Hz, 1H), 6.71-6.74 (m, 2H), 3.94 (t, J=6.4 Hz, 2H), 2.73 (t, J=6.8 Hz, 2H), 2.62 (t, J=7.6 Hz, 2H), 1.74-1.81 (m, 4H), 1.34-1.47 (m, 4H), 0.93 (t, J=7.2 Hz, 3H). $^{13}$C NMR (100 MHz, DMSO-d$_6$) δ 159.1, 144.3, 129.6, 120.9, 114.9, 111.9, 67.6, 41.6, 35.4, 33.1, 28.9, 28.2, 22.4, 14.4. MS: 222 [M+1]+.

Example 45

Preparation of 3-amino-1-(3-(2-ethylbutoxy)phenyl)propan-1-ol

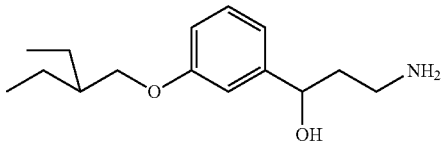 [SMILES: CCC(CC)COc1cccc(C(O)CCN)c1]

3-Amino-1-(3-(2-ethylbutoxy)phenyl)propan-1-ol was prepared following the method described in Example 4.

Step 1:

Coupling of 2-ethylbutan-1-ol with cyclohexylmethanol 3-hydroxybenzaldehyde gave 3-(2-ethylbutoxy)benzaldehyde. $^1$H NMR (400 MHz, CDCl$_3$) δ 9.96 (s, 1H), 7.38-7.43 (m, 3H), 7.13-7.19 (m, 1H), 3.90 (d, J=6.0 Hz, 2H), 1.63-1.73 (m, 1H), 1.42-1.52 (m, 4H), 0.93 (t, J=6.0 Hz, 6H).

Step 2:

Reaction of 3-(2-ethylbutoxy)benzaldehyde with acetonitrile in the presence of LDA gave 3-(3-(2-ethylbutoxy)phenyl)-3-hydroxypropanenitrile. $^1$H NMR (400 MHz, DMSO-d$_6$) δ 7.22 (t, J=7.2 Hz, 1H), 6.92-6.96 (m, 2H), 6.81-6.83 (m, 1H), 5.89 (brs, 1H), 4.83 (brs, 1H), 3.82 (d, J=6.4 Hz, 2H), 2.73-2.90 (m, 2H), 1.56-1.64 (m, 1H), 1.31-1.44 (m, 4H), 0.87 (t, J=7.6 Hz, 6H).

Step 3:

Reduction of 3-(3-(2-ethylbutoxy)phenyl)-3-hydroxypropanenitrile using lithium aluminum hydride gave Example 45 as a colorless oil. $^1$H NMR (400 MHz, MeOD) δ 7.20 (t, J=7.6 Hz, 1H), 6.88-6.92 (m, 2H), 6.78 (d, J=8.0 Hz, 1H), 4.68 (t, J=6.0 Hz, 1H), 3.86 (d, J=7.2 Hz, 2H), 2.68-2.79 (m, 2H), 1.78-1.90 (m, 2H), 1.58-1.66 (m, 1H), 1.43-1.52 (m, 4H), 0.93 (t, J=7.2 Hz, 6H).

Example 46

Preparation of 2-(3-(isopentyloxy)phenoxy)ethanamine

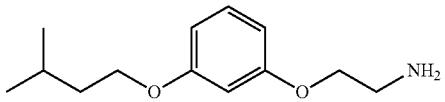 [SMILES: CC(C)CCOc1cccc(OCCN)c1]

2-(3-(Isopentyloxy)phenoxy)ethanamine was prepared following the method described in Example 7.

Step 1:

Reaction of phenol 24 (1 g, 3.6 mmol) with isoamyl alcohol following the method used in Example 7 except that the reaction was allowed to proceed for 24 h gave ether 2-(2-(3-(isopentyloxy)phenoxy)ethyl)isoindoline-1,3-dione as yellow oil. Yield (0.50 g, 40%): $^1$H NMR (400 MHz, CDCl$_3$) δ 7.83-7.89 (m, 2H), 7.70-7.74 (m, 2H), 7.12 (t, J=8.1 Hz, 1H), 6.42-6.49 (m, 3H), 4.20 (t, J=6 Hz, 2H), 4.12 (t, J=6 Hz, 2H), 3.92 (t, J=6.8 Hz, 2H), 1.77-1.85 (m, 1H), 1.64 (q, J=6.8 Hz, 2H), 0.91-0.97 (d, J=6.8 Hz, 6H).

Step 2:

Deprotection of 2-(2-(3-(isopentyloxy)phenoxy)ethyl)isoindoline-1,3-dione following the method used in Example 7 except that the reaction was run at 75° C. for 6 h gave Example 46 as yellow oil. Yield (0.150 g, 47%): $^1$H NMR (400 MHz, DMSO-d$_6$) δ 7.14 (t, J=8 Hz, 1H), 6.46-6.51 (m, 3H), 3.95 (t, J=6.6 Hz, 2H), 3.87 (t, J=5.8 Hz, 2H), 2.84 (bs, 2H), 1.70-1.82 (m, 1H), 1.56-1.61 (q, J=6.8 Hz, 2H), 0.92 (d, J=6.4 Hz, 6H). $^{13}$C NMR (100 MHz, DMSO-d$_6$) 160.4, 160.3, 130.3, 107.1, 107.0, 101.5, 70.6, 66.2, 41.4, 37.9, 25.0, 22.9. MS: 224 [M+1]$^+$.

Example 47

Preparation of 2-(3-phenethoxyphenoxy)ethanamine

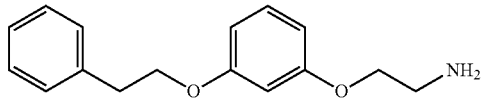 [SMILES: NCCOc1cccc(OCCc2ccccc2)c1]

2-(3-Phenethoxyphenoxy)ethanamine was prepared following the method described in Example 46.

Step 1:

Mitsunobu reaction of phenol 24 with phenethylalcohol gave 2-(2-(3-phenethoxyphenoxy)ethyl)isoindoline-1,3-dione as yellow oil. Yield (0.50 g, 36%). The crude product was directly utilized for further step.

Step 2:

Phthalimide cleavage of 2-(2-(3-phenethoxyphenoxy)ethyl)isoindoline-1,3-dione gave Example 47 as yellow oil. Yield (0.17 g, 51%): $^1$H NMR (400 MHz, DMSO-d$_6$) δ 7.28-7.32 (m, 4H), 7.22-7.28 (m, 1H), 7.15 (t, J=8.4 Hz, 1H), 6.46-6.52 (m, 3H), 4.16 (t, J=6.8 Hz, 2H), 3.87 (t, J=5.6 Hz, 2H), 3.01 (t, J=6.8 Hz, 2H), 2.8 (t, J=5.6 Hz, 2H), 2.0 (bs, 2H). $^{13}$C NMR (100 MHz, DMSO-d$_6$) 159.9, 159.6, 138.4, 129.9, 128.9, 128.3, 126.2, 106.8, 106.7, 101.2, 69.9, 68.1, 40.8, 34.9. MS: 258 [M+1]+.

Example 48

Preparation of 3-amino-1-(3-(bicyclo[2.2.1]heptan-2-ylmethoxy)phenyl)propan-1-ol

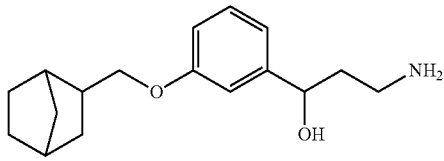 [SMILES: NCCC(O)c1cccc(OCC2CC3CCC2C3)c1]

3-Amino-1-(3-(bicyclo[2.2.1]heptan-2-ylmethoxy)phenyl)propan-1-ol was prepared following the method described for Example 4.

Step 1.

Condensation of bicyclo[2.2.1]heptan-2-ylmethanol with 3-hydroxybenzaldehyde (11) under Mitsunobu conditions was performed following the method given in Example 2. The product was purified by flash chromatography (5 to 30% EtOAc/hexane gradient) to give 3-(bicyclo[2.2.1]heptan-2-ylmethoxy)benzaldehyde as a colorless oil. Yield (0.88 g, 32%). $^1$H NMR (400 MHz, DMSO-d$_6$) δ 9.95 (s, 1H), 7.38-7.50 (m, 3H), 7.22-7.28 (m, 1H), 4.01 (m, 1H), 3.88-3.93 (m, 1H), 3.70-3.80 (m, 1H), 2.15-2.29 (m, 2H), 1.67-1.90 (m, 1H), 1.40-1.52 (m, 2H), 1.24-1.40 (m, 2H), 1.05-1.21 (m, 2H), 0.75 (ddd, J=2.3, 5.1, 12.1 Hz, 1H).

Step 2.

Addition of acetonitrile to 3-(bicyclo[2.2.1]heptan-2-ylmethoxy)benzaldehyde following the procedure given for Example 4 gave 3-(3-(bicyclo[2.2.1]heptan-2-ylmethoxy)phenyl)-3-hydroxypropanenitrile as a colorless oil. Yield (1.09 g, quant.). $^1$H NMR (400 MHz, DMSO-d$_6$) δ 7.19-7.24 (m, 1H), 6.90-6.97 (m, 2H), 6.77-6.83 (m, 1H), 5.88 (d, J=4.5 Hz, 1H), 4.80-4.85 (m, 1H), 3.91 (dd, J=7.0, 9.8 Hz, 1H), 3.78-3.84 (m, 1H), 3.54-3.61 (m, 1H), 2.74-2.89 (m, 2H), 2.15-2.28 (m, 3H), 1.68-1.75 (m, 1H), 1.40-1.51 (m, 2H), 1.24-1.38 (m, 3H), 0.70-0.75 (m, 1H).

Step 3.

To a solution of 3-(3-(bicyclo[2.2.1]heptan-2-ylmethoxy)phenyl)-3-hydroxypropanenitrile (1.09 g, 4.02 mmol) in anhydrous THF (15 mL) was added borane-dimethyl sulfide (0.5 mL, 5.27 mmol) and the reaction mixture was heated under reflux for 1 hour, then left to stir at room temperature for 15 hrs. Saturated aqueous NaHCO$_3$ (20 mL) was added followed by MTBE and the mixture was stirred for 1 hour. Layers were separated, organic layer washed with brine, dried over anhydrous MgSO$_4$ and concentrated under reduced pressure. The residue was purified by flash chromatography (5% 7N NH$_3$/MeOH in CH$_2$Cl$_2$) to give Example 53 as a colorless oil. Yield (0.446 g, 43%). $^1$H NMR (400 MHz, DMSO-d$_6$) δ 7.13-7.18 (m, 1H), 6.80-6.87 (m, 2H), 6.70-6.76 (m, 1H), 4.59 (t, J=6.5 Hz, 1H), 3.86-3.93 (m 0.75H), 3.76-3.83 (m, 0.75H), 3.58-3.69 (m, 0.5H), 2.53-2.66 (m, 2H), 2.15-2.29 (m, 2H), 1.53-1.88 (m, 4H), 1.40-1.50 (m, 2H), 1.00-1.40 (m, 8H), 0.72 (m, 1H).

Example 49

Preparation of (1R,2R)-2-(aminomethyl)-1-(3-(cyclohexylmethoxy)phenyl)butan-1-ol

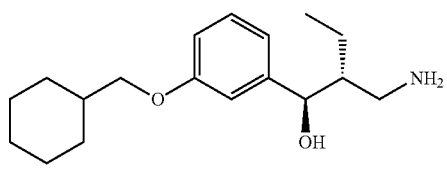 [SMILES: CC[C@H](CN)[C@@H](O)c1cccc(OCC2CCCCC2)c1]

(1R,2R)-2-(Aminomethyl)-1-(3-(cyclohexylmethoxy)phenyl)butan-1-ol was prepared following the method used in Example 72.

Step 1:

Condensation of (R)-4-benzyl-3-butyryloxazolidin-2-one with aldehyde 13 following the method described in Example 45 gave (R)-4-benzyl-3-((S)-2-((R)-(3-(cyclohexylmethoxy)phenyl)(trimethylsilyloxy)methyl)butanoyl)oxazolidin-2-one as a colorless oil. Yield (1.69 g, quant.). $^1$H NMR (400 MHz, DMSO-$d_6$) δ 7.22-7.34 (m, 6H), 6.90-6.943 (m, 2H), 6.82-6.85 (m, 1H), 4.85 (d, J=9.4 Hz, 1H), 4.73 (tt, J=2.9 Hz, 8.0 Hz, 1H), 4.29 (t, J=8.2 Hz, 1H), 4.21 (dt, J=4.1 Hz, 9.2 Hz, 1H), 4.11 (dd, J=2.7 Hz, 8.8 Hz, 1H), 3.72-3.79 (m, 2H), 3.08 (dd, J=2.9 Hz, 13.3 Hz, 1H), 2.84 (dd, J=8.2 Hz, 13.5 Hz, 1H), 1.60-1.79 (m, 6H), 1.29-1.38 (m, 1H), 1.07-1.25 (m, 4H), 0.96-1.06 (m, 2H), 0.65 (t, J=7.4 Hz, 3H), −0.12 (s, 9H).

Step 2:

Oxazolidinone cleavage of (R)-4-benzyl-3-((S)-2-((R)-(3-(cyclohexylmethoxy)phenyl)(trimethylsilyloxy)methyl)butanoyl)oxazolidin-2-one following the method described in Example 45 gave (R)-2-((R)-(3-(cyclohexylmethoxy)phenyl)-(trimethylsilyloxy)methyl)butan-1-ol as colorless oil. Yield (0.273 g, 21%). $^1$H NMR (400 MHz, DMSO-$d_6$) δ 7.17 (t, J=7.6 Hz, 1H), 6.73-6.80 (m, 3H), 4.64 (d, J=6.5 Hz, 1H), 4.19 (t, J=5.1 Hz, 1H), 3.41-3.47 (m, 1H), 3.32-3.37 (m, 1H), 1.58-1.79 (m, 6H), 1.48 (m, 1H), 0.99-1.26 (m, 7H), 0.76 (t, J=7.6 Hz, 3H), −0.06 (s, 9H).

Step 3:

Mitsunobu reaction following the method described in Example 45 gave 2-((R)-2-((R)-(3-(cyclohexylmethoxy)phenyl)(trimethylsilyloxy)methyl)butyl)isoindoline-1,3-dione as a colorless oil. Yield (0.289 g, 80%). $^1$H NMR (400 MHz, DMSO-$d_6$) δ 7.74 (m, 4H), 7.09 (t, J=8.0 Hz, 1H), 6.78-6.82 (m, 2H), 6.56-6.60 (m, 1H), 4.76 (d, J=4.3 Hz, 1H), 3.63-3.72 (m, 2H), 3.57 (dd, J=13.7 Hz, 6.5 Hz, 1H), 3.45 (dd, J=13.9 Hz, 8.0 Hz, 1H), 2.13-2.21 (m, 1H), 1.57-1.80 (m, 6H), 0.96-1.30 (m, 7H), 0.85 (t, J=7.6 Hz, 3H), −0.03 (s, 9H).

Step 4:

TMS deprotection of ether following the method described in Example 45 gave 2-((R)-2-((R)-(3-(cyclohexylmethoxy)phenyl)(hydroxy)methyl)butyl)isoindoline-1,3-dione as a colorless oil. The product was not isolated and was taken to the next step without further purification.

Step 5:

Phthalimide cleavage of the imide was performed following the method described in Example 45 to give Example 49 as a colorless oil. Yield (0.112 g, 66% for two steps). $^1$H NMR (400 MHz, DMSO-$d_6$) δ 7.16 (t, J=7.6 Hz, 1H), 6.78-6.82 (m, 2H), 6.70-6.74 (m, 1H), 4.48 (d, J=6.5 Hz, 1H), 3.72 (d, J=6.3 Hz, 2H), 2.70 (dd, J=4.3 Hz, 12.5 Hz, 1H), 2.54 (dd, J=5.9 Hz, 12.5 Hz, 1H), 1.58-1.81 (m, 6H), 1.33-1.41 (m, 1H), 1.08-1.27 (m, 5H), 0.96-1.06 (m, 2H), 0.77 (t, J=7.4 Hz, 3H); $^{13}$C NMR (400 MHz, DMSO-$d_6$) δ 159.3, 147.9, 129.4, 119.4, 113.3, 113.1, 76.4, 73.2, 48.5, 42.2, 37.9, 30.0, 26.7, 26.0, 21.7, 12.2; ESI MS m/z 292.4 [M+H]$^+$; Chiral HPLC: 6.98 min, 99.1% ee; RP-HPLC: 97.3%, $t_R$=5.06 min; Chiral HPLC 99.6% (AUC), $t_R$=7.0 min. (Method 1)

Example 50

Preparation of (R)-2-(3-(2-ethylbutoxy)phenoxy)propan-1-amine

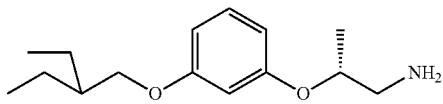 [SMILES: CCC(CC)COc1cccc(O[C@H](C)CN)c1]

(R)-2-(3-(2-Ethylbutoxy)phenoxy)propan-1-amine was prepared following the method shown in Scheme 20

SCHEME 20

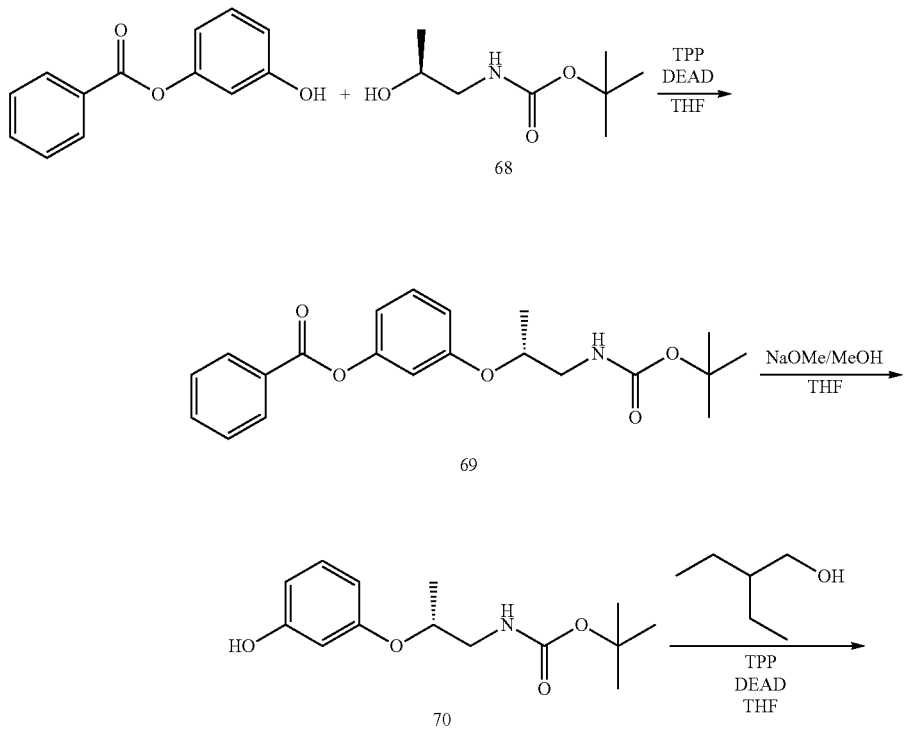

-continued

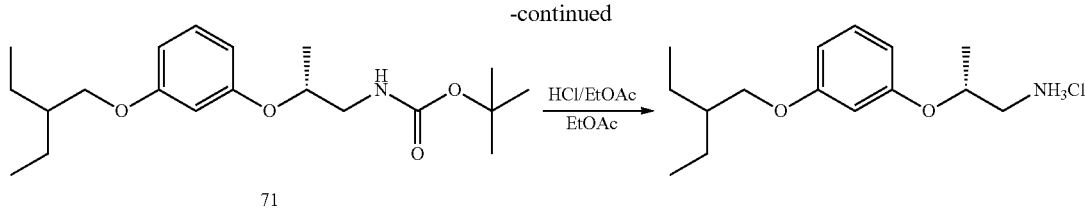

71

Step 1:

Alkylation of phenyl benzoate with alcohol 68 following the method and purification used in Example 4 (except that no silica filtration was performed), gave the benzoate (69) as a colorless oil. Yield (8.6 g, 41%). $^1$H NMR (400 MHz, CDCl$_3$) δ 8.18-8.20 (m, 2H), 7.60-7.65 (m, 1H), 7.46-7.53 (m, 2H), 7.30 (t, J=8.0 MHz, 1H), 6.76-6.83 (m, 3H), 4.90-4.98 (m, 1H), 4.42-4.52 (m, 1H), 3.42-3.52 (m, 1H), 3.18-3.28 (m, 1H), 1.43 (s, 9H), 1.28 (d, J=6.4 MHz, 3H).

Step 2:

Sodium methoxide (6.1 mL of a 30% solution in MeOH) was added to a solution of benzoate 69 (3.9 g, 10.5 mmol) in MeOH (100 mL). The reaction was stirred overnight then extracted from water with dichloromethane. The combined organics were washed with brine, dried over sodium sulfate, filtered, and concentrated under reduced pressure. The residue was purified by flash chromatography (10-15% ethyl acetate/hexanes gradient), giving phenol (70) as a colorless oil. (Yield (1.75 g, 64%). $^1$H NMR (400 MHz, CDCl$_3$) δ 7.04-7.10 (m, 2H), 6.40-6.48 (m, 3H), 5.02-5.10 (m, 1H), 4.34-4.44 (m, 1H), 3.38-3.48 (m, 1H), 3.16-3.26 (m, 1H), 1.43 (s, 9H), 1.21 (d, J=6.0 MHz, 3H).

Step 3:

Alkylation of phenol 70 with 2-ethylbutan-1-ol following the method and purification used in Example 55 gave phenyl ether 71 as a colorless oil. Yield (0.254 g, 43%). $^1$H NMR (400 MHz, CDCl$_3$) δ 7.11-7.17 (m, 1H), 6.44-6.52 (m, 3H), 4.86-4.98 (m, 1H), 4.41-4.49 (m, 1H), 3.81 (d, J=5.6 MHz, 2H), 3.42-3.51 (m, 1H), 3.16-3.26 (m, 1H), 1.59-1.69 (m, 1H), 1.36-1.54 (m, 4H), 1.43 (s, 9H), 1.26 (d, J=6.0 MHz, 3H), 0.92 (t, J=7.6 MHz, 6H).

Step 4:

Deprotection of phenyl ether 71 following the method used in Example 5 gave Example 50 hydrochloride as a white solid. Yield (0.213 g, quant.). $^1$H NMR (400 MHz, CDCl$_3$) δ 8.09 (brs, 3H), 7.12-7.18 (m, 1H), 6.52-6.56 (m, 3H), 4.58-4.66 (m, 1H), 3.80 (d, J=6.0 MHz, 2H), 2.91-3.08 (m, 2H), 1.52-1.64 (m, 1H), 1.28-1.40 (m, 4H), 1.21 (d, J=6 MHz, 3H), 0.85 (t, J=7.2 MHz, 6H).

Example 51

Preparation of (R)-2-(3-(2-propylpentyloxy)phenoxy)propan-1-amine

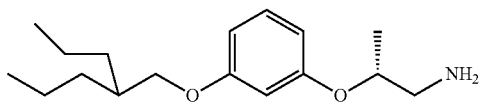 [SMILES: CCCC(CCC)COc1cccc(O[C@H](C)CN)c1]

(R)-2-(3-(2-Propylpentyloxy)phenoxy)propan-1-amine was prepared following the method described in Example 50.

Step 1:

Alkylation of phenol 70 with 2-propylpentan-1-ol gave (R)-tert-butyl 2-(3-(2-propylpentyloxy)phenoxy)propylcarbamate as a colorless oil. Yield (0.331, 52%). $^1$H NMR (400 MHz, CDCl$_3$) δ 7.11-7.17 (m, 1H), 6.44-6.52 (m, 3H), 4.91 (bs, 1H), 4.41-4.49 (m, 1H), 3.79 (d, J=5.6 MHz, 2H), 3.42-3.51 (m, 1H), 3.16-3.26 (m, 1H), 1.74-1.82 (m, 1H), 1.43 (s, 9H), 1.28-1.42 (m, 8H), 1.26 (d, J=6.0 MHz, 3H), 0.88-0.93 (m, 6H).

Step 2:

Deprotection of (R)-tert-butyl 2-(3-(2-propylpentyloxy) phenoxy) propylcarbamate gave Example 51 hydrochloride as a white solid. Yield (0.198 g, 60%). $^1$H NMR (400 MHz, CDCl$_3$) δ 8.11 (brs, 3H), 7.12-7.18 (m, 1H), 6.50-6.56 (m, 3H), 4.58-4.66 (m, 1H), 3.80 (d, J=5.6 MHz, 2H), 2.91-3.08 (m, 2H), 1.66-1.76 (m, 1H), 1.24-1.40 (m, 8H), 1.22 (d, J=6 MHz, 3H), 0.85 (t, J=7.2 MHz, 6H).

Example 52

Preparation of (R)-2-(3-(cyclopentylmethoxy)phenoxy)propan-1-amine

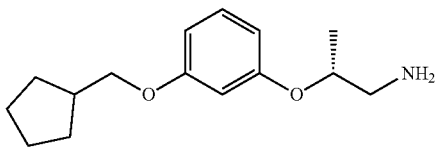 [SMILES: C[C@H](CN)Oc1cccc(OCC2CCCC2)c1]

(R)-2-(3-(Cyclopentylmethoxy)phenoxy)propan-1-amine was prepared following the method described in Example 50.

Step 1:

Alkylation of phenol 70 with cyclopentylmethanol gave (R)-tert-butyl 2-(3-(cyclopentylmethoxy)phenoxy)propylcarbamate as a colorless oil. Yield (0.116 g, 20%). $^1$H NMR (400 MHz, CDCl$_3$) δ 7.11-7.17 (m, 1H), 6.44-6.52 (m, 3H), 4.91 (bs, 1H), 4.41-4.49 (m, 1H), 3.79 (d, J=5.6 MHz, 2H), 3.42-3.51 (m, 1H), 3.16-3.26 (m, 1H), 1.74-1.82 (m, 1H), 1.43 (s, 9H), 1.28-1.42 (m, 8H), 1.26 (d, J=6.0 MHz, 3H), 0.88-0.93 (m, 6H).

Step 2:

Deprotection of (R)-tert-butyl 2-(3-(cyclopentylmethoxy) phenoxy)propylcarbamate gave (R)-2-(3-(cyclopentylmethoxy)phenoxy)propan-1-amine hydrochloride as an impure white solid which was carried forward without purification.

Step 3:

A solution of (R)-2-(3-(cyclopentylmethoxy)phenoxy) propan-1-amine hydrochloride in ethyl acetate was washed with saturated aqueous sodium bicarbonate. The combined organics were washed with brine, dried over sodium sulfate, filtered, and concentrated under reduce pressure. The residue was purified by flash chromatography (5% (7N NH$_3$ in MeOH)/EtOAc), giving Example 52 as a colorless oil. Yield (0.025 g, 30% from Boc-protected). $^1$H NMR (400 MHz, CDCl$_3$) δ 7.10-7.16 (m, 1H), 6.46-6.51 (m, 3H), 4.27-4.36 (m, 1H), 3.78 (d, J=6.8 MHz, 2H), 2.87 (brs, 2H), 2.26-2.40 (m, 1H), 1.76-1.88 (m, 2H), 1.50-1.70 (m, 4H), 1.28-1.40 (m, 4H), 1.25 (d, J=6.4 MHz, 3H).

Example 53

Preparation of (R)-2-(3-(cyclohexylmethoxy)phenoxy)propan-1-amine

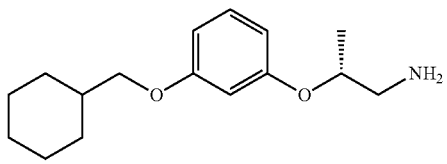 [SMILES: C[C@H](CN)Oc1cccc(OCC2CCCCC2)c1]

(R)-2-(3-(Cyclohexylmethoxy)phenoxy)propan-1-amine was prepared following the method described in Example 52.

Step 1:
Alkylation of phenol 70 with cyclohexylmethanol gave (R)-tert-butyl 2-(3-(cyclohexylmethoxy)phenoxy)propylcarbamate as a colorless oil. $^1$H NMR (400 MHz, CDCl$_3$) δ 7.09-7.15 (m, 1H), 6.43-6.50 (m, 3H), 4.95 (bs, 1H), 4.38-4.48 (m, 1H), 3.70 (d, J=6.4 MHz, 2H), 3.38-3.48 (m, 1H), 3.16-3.25 (m, 1H), 1.80-1.90 (m, 2H), 1.60-1.80 (m, 4H), 1.42 (s, 9H), 1.10-1.34 (m, 6H), 0.96-1.1 (m, 2H).

Step 2:
Deprotection of ((R)-tert-butyl 2-(3-(2-propylpentyloxy)phenoxy) propylcarbamate gave (R)-tert-butyl 2-(3-(cyclohexylmethoxy)phenoxy)propylcarbamate hydrochloride as an impure white solid which was carried forward without purification.

Step 3:
(R)-tert-butyl 2-(3-(cyclohexylmethoxy)phenoxy)propylcarbamate hydrochloride was neutralized following the method and purification used in Example 52, to give Example 53 as a colorless oil. Yield (0.043 g, 28% from Boc-protected). $^1$H NMR (400 MHz, CDCl$_3$) δ 7.10-7.16 (m, 1H), 6.45-6.51 (m, 3H), 4.27-4.36 (m, 1H), 3.71 (d, J=6.4 MHz, 2H), 2.87 (d, J=5.6 MHz, 2H), 1.80-1.90 (m, 2H), 1.64-1.80 (m, 4H), 1.34 (s, 2H), 1.12-1.32 (m, 4H), 1.25 (d, J=6.4 MHz, 2H), 0.96-1.08 (m, 2H).

Example 54

Preparation of 3-amino-1-(3-phenethoxyphenyl)propan-1-ol

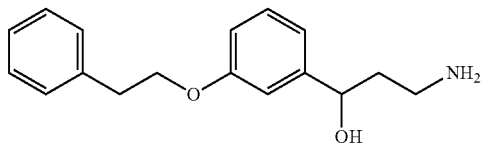 [SMILES: NCCC(O)c1cccc(OCCc2ccccc2)c1]

3-Amino-1-(3-phenethoxyphenyl)propan-1-ol was prepared following the method described in Example 34 and 48.

Step 1:
Alkylation of 3-hydroxybenzaldehyde with phenethyl bromide was done following the method used in Example 34, except that DMF was used as the reaction solvent, to give 3-phenethoxybenzaldehyde as a clear oil. Yield (0.98 g, 54%): $^1$H NMR (400 MHz, CDCl$_3$) δ 9.96 (s, 1H), 7.21-7.48 (m, 8H), 7.18-7.20 (m, 1H), 4.24 (t, J=7.0 Hz, 2H), 3.13 (t, J=7.0 Hz, 2H).

Step 2:
Addition of acetonitrile to 3-phenethoxybenzaldehyde gave 3-hydroxy-3-(3-phenethoxyphenyl)propanenitrile as a yellow oil. Yield (0.80 g, 80%): $^1$H NMR (400 MHz, CDCl$_3$) δ 7.23-7.38 (m, 6H), 6.93-6.97 (m, 2H), 6.88 (dd, J=7.6, 1.8 Hz, 1H), 5.00 (t, J=6.0 Hz, 1H), 4.18 (t, J=7.2 Hz, 2H), 3.12 (t, J=7.2 Hz, 2H), 2.75 (d, J=6.4 Hz, 2H).

Step 3 Reduction of 3-hydroxy-3-(3-phenethoxyphenyl)propanenitrile following the method used in Example 48 gave Example 54 as a colorless oil. Yield (0.37 g, 46%): $^1$H NMR (400 MHz, DMSO-d$_6$) δ 7.10-7.28 (m, 6H), 6.85 (d, J=8.0 Hz, 1H), 6.82 (s, 1H), 6.76 (dd, J=8.0, 2.0 Hz, 1H), 4.57-4.62 (m, 1H), 4.04 (t, J=6.2 Hz, 2H), 2.97 (t, J=6.2 Hz, 2H), 2.74-2.86 (m, 2H), 1.78-1.84 (m, 2H). $^{13}$C NMR (100 MHz, DMSO-d$_6$) δ 158.4, 147.0, 138.4, 129.3, 129.0, 128.4, 126.3, 117.8, 112.8, 111.7, 69.7, 68.1, 36.6, 35.0, 21.1. MS: 272 [M+1]$^+$.

Example 55

Preparation of (1R,2R)-3-amino-2-methyl-1-(3-(2-propylpentyloxy)phenyl)propan-1-ol

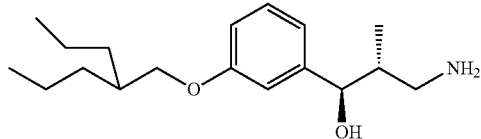 [SMILES: CCCC(CCC)COc1cccc([C@H](O)[C@H](C)CN)c1]

(1R,2R)-3-Amino-2-methyl-1-(3-(2-propylpentyloxy) phenyl)propan-1-ol was prepared following the method described for Example 72.

Step 1.
2-((2R,3R)-3-Hydroxy-3-(3-hydroxyphenyl)-2-methylpropyl)isoindoline-1,3-dione (82) was reacted with 2-propylpentyl methanesulfonate following the method described for Example 72 to give 2-((2R,3R)-3-hydroxy-2-methyl-3-(3-(2-propylpentyloxy)phenyl)propyl)isoindoline-1,3-dione as a colorless oil. Yield (0.414 g, 79%). $^1$H NMR (400 MHz, DMSO-d$_6$) δ 7.75-7.80 (m, 4H), 7.13 (t, J=7.8 Hz, 1H), 6.83-6.88 (m, 2H), 6.67-6.70 (m, 1H), 5.30 (d, J=4.3 Hz, 1H), 4.38-4.41 (m, 1H), 3.78 (d, J=5.7 Hz, 2H), 3.70 (dd, J=5.3, 13.5 Hz, 1H), 3.41 (dd, J=9.4, 13.7 Hz, 1H), 2.21-2.28 (m, 1H), 1.67-1.75 (m, 1H), 1.23-1.42 (m, 8H), 0.85 (t, J=6.7 Hz, 6H), 0.65 (d, J=6.8 Hz, 3H).

Step 2.
2-((2R,3R)-3-Hydroxy-2-methyl-3-(3-(2-propylpentyloxy)phenyl)propyl)isoindoline-1,3-dion was deprotected following the method used in Example 72 to give crude amine which was purified by chromatography using gradient of 20% 7N NH$_3$/MeOH in EtOAc/hexanes (50 to 100%) to give Example 55 as colorless oil. Yield (0.085 g, 31%). $^1$H NMR (400 MHz, MeOD-d$_4$) δ 7.20 (t, J=7.8 Hz, 1H), 6.85-6.91 (m, 2H), 6.79 (ddd, J=1.0, 2.5, and 8.2 Hz, 1H), 4.37 (d, J=7.8 Hz, 1H), 3.85 (d, J=5.7 Hz, 2H), 2.83 (dd, J=5.9, 12.7 Hz, 1H), 2.67 (dd, J=5.9, 12.7 Hz, 1H), 1.75-1.87 (m, 2H), 1.31-1.48 (m, 8H), 0.92 (t, J=6.8 Hz, 6H), 0.73

(d, J=7.0 Hz, 3H); $^{13}$C NMR (100 MHz, MeOH-d$_4$) δ 159.6, 145.7, 128.9, 119.0, 113.2, 112.8, 78.6, 70.6, 45.2, 42.0, 37.7, 33.8, 19.9, 14.0, 13.6; LC-MS (ESI+) 294.4 [M+H]$^+$; RP-HPLC: 94.9%, t$_R$=5.43 min; Chiral HPLC 96.6% (AUC), t$_R$=6.53 min.

Example 56

Preparation of (1R,2R)-3-amino-1-(3-(cyclopentylmethoxy)phenyl)-2-methylpropan-1-ol

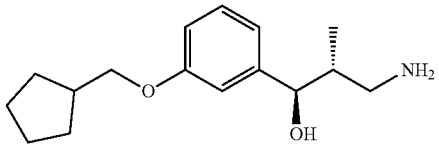 [SMILES: C[C@H](CN)[C@@H](O)c1cccc(OCC2CCCC2)c1]

(1R,2R)-3-Amino-1-(3-(cyclopentylmethoxy)phenyl)-2-methylpropan-1-ol was prepared following the method described for Example 72.
Step 1.
2-((2R,3R)-3-Hydroxy-3-(3-hydroxyphenyl)-2-methylpropyl)isoindoline-1,3-dione (82) was reacted with cyclopentylmethyl methanesulfonate following the method described for Example 72 to give 2-((2R,3R)-3-(3-(cyclopentylmethoxy)phenyl)-3-hydroxy-2-methylpropyl)isoindoline-1,3-dione as a colorless oil. Yield (0.295 g, 61%). $^1$H NMR (400 MHz, DMSO-d$_6$) δ 7.75-7.80 (m, 4H), 7.13 (t, J=7.8 Hz, 1H), 6.83-6.88 (m, 2H), 6.66-6.69 (m, 1H), 5.30 (d, J=4.5 Hz, 1H), 4.38-4.41 (m, 1H), 3.77 (d, J=7.0 Hz, 2H), 3.70 (dd, J=5.5, 13.7 Hz, 1H), 3.40 (dd, J=9.4, 13.7 Hz, 1H), 2.20-2.30 (m, 2H), 1.70-1.78 (m, 2H), 1.46-1.62 (m, 4H), 1.26-1.34 (m, 2H), 0.65 (d, J=6.85 Hz, 3H).
Step 2.
2-((2R,3R)-3-(3-(Cyclopentylmethoxy)phenyl)-3-hydroxy-2-methylpropyl)isoindoline-1,3-dione was deprotected following the method used in Example 72 to give crude amine which was purified by chromatography using gradient of 20% 7N NH$_3$/MeOH in EtOAc/hexanes (50 to 100%) to give Example 56 as a colorless oil. Yield (0.102 g, 53%). $^1$H NMR (400 MHz, MeOD-d$_4$) δ 7.20 (t, J=7.8 Hz, 1H), 6.85-6.91 (m, 2H), 6.79 (ddd, J=0.8, 2.5, and 8.0 Hz, 1H), 4.37 (d, J=7.8 Hz, 1H), 3.83 (d, J=6.8 Hz, 2H), 2.82 (dd, J=5.9, 12.7 Hz, 1H), 2.66 (dd, J=6.1, 12.7 Hz, 1H), 2.28-2.39 (m, 1H), 1.77-1.88 (m, 3H), 1.54-1.71 (m, 4H), 1.33-1.42 (m, 2H), 0.73 (d, J=6.9 Hz, 3H); $^{13}$C NMR (100 MHz, MeOH-d$_4$) δ 159.6, 145.7, 128.9, 119.0, 113.2, 112.8, 78.6, 72.0, 45.2, 42.1, 39.3, 29.3, 25.25, 13.9; LC-MS (ESI+) 264.5 [M+H]$^+$; RP-HPLC: 97.7%, t$_R$=4.22 min; Chiral HPLC 98.7% (AUC), t$_R$=8.77 min.

Example 57

Preparation of 2-(3-(cyclopropylmethoxy)phenoxy)ethanamine

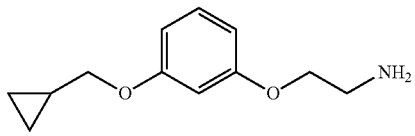 [SMILES: NCCOc1cccc(OCC2CC2)c1]

2-(3-(Cyclopropylmethoxy)phenoxy)ethanamine was prepared following the method used in Example 46.
Step 1:
A mixture of phenol 24 (1.0 g, 3.5 mmol), (bromomethyl)cyclopropane (0.52 mL, 5.3 mmol) and cesium carbonate (1.72 g, 5.3 mmol) in NMP (20 mL) was heated at 75° C. overnight. The mixture was cooled to room temperature and partitioned between DCM and water. The organic layer was washed with water, then brine, dried over Na$_2$SO$_4$ and concentrated under reduced pressure. Purification by flash chromatography (0 to 30% EtOAc-hexanes gradient) gave 2-(2-(3-(cyclopropylmethoxy)phenoxy)ethyl)isoindoline-1,3-dione as yellow oil. Yield (0.710 g, 59%): $^1$H NMR (400 MHz, CDCl$_3$) δ 7.83-7.89 (m, 2H), 7.67-7.75 (m, 2H), 7.12 (t, J=8 Hz, 1H), 6.42-6.49 (m, 3H), 4.2 (t, J=5.6 Hz, 2H), 4.09 (t, J=5.6 Hz, 2H), 3.74 (d, J=6.8 Hz, 2H), 1.18-1.12 (m, 1H), 0.58-0.64 (m, 2H), 0.30-0.33 (m, 2H).
Step 2:
Deprotection of 2-(2-(3-(cyclopropylmethoxy)phenoxy)ethyl)isoindoline-1,3-dione gave Example 57 as a yellow oil. Yield (0.254 g, 59%): $^1$H NMR (400 MHz, DMSO-d$_6$) δ 7.18 (t, J=8 Hz, 1H), 6.45-6.5 (m, 3H), 3.88 (t, J=5.6 Hz, 2H), 3.77 (d, J=7.2 Hz, 2H), 2.84 (t, J=5.6 Hz, 2H), 1.71 (bs, 2H), 1.15-1.24 (m, 1H), 0.53-0.57 (m, 2H), 0.29-0.31 (m, 2H). $^{13}$C NMR (100 MHz, DMSO-d$_6$) 159.9, 159.8, 129.9, 106.7, 106.6, 101.1, 71.9, 70.1, 40.9, 10.2, 3.1. MS: 208 [M+1]$^+$.

Example 58

Preparation of 2-(3-(cyclobutylmethoxy)phenoxy)ethanamine

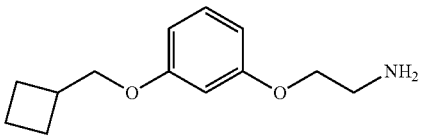 [SMILES: NCCOc1cccc(OCC2CCC2)c1]

2-(3-(Cyclobutylmethoxy)phenoxy)ethanamine was prepared following the method used in Example 57.
Step 1:
Alkylation of phenol 24 with (bromomethyl)cyclobutane gave 2-(2-(3-(cyclobutylmethoxy)phenoxy)ethyl)isoindoline-1,3-dione as semi-solid. Yield (0.720 g, 58%): $^1$H NMR (400 MHz, CDCl$_3$) δ 7.83-7.87 (m, 2H), 7.71-7.74 (m, 2H), 7.11 (t, J=8 Hz, 1H), 6.42-6.48 (m, 3H), 4.20 (t, J=5.6 Hz, 2H), 4.12-4.08 (m, 2H), 3.87 (d, J=6.4 Hz, 2H), 2.71-2.74 (m, 1H), 2.07-2.04 (m, 2H), 1.84-1.93 (m, 4H).
Step 2:
Deprotection of 2-(2-(3-(cyclobutylmethoxy)phenoxy)ethyl)isoindoline-1,3-dione gave Example 58 as pale yellow oil. Yield (0.316 g, 72%): $^1$H NMR (400 MHz, DMSO-d$_6$) δ 7.14 (t, J=8 Hz, 1H), 6.5 (d, J=2.4 Hz, 1H), 6.46-6.48 (m, 2H), 3.86-3.92 (m, 4H), 2.84 (t, J=6 Hz, 2H), 2.64-2.75 (m, 1H), 2.02-2.09 (m, 2H), 1.87-1.92 (m, 2H), 1.77-1.84 (m, 2H). $^{13}$C NMR (100 MHz, DMSO-d$_6$) 160.0, 159.9, 129.9, 106.7, 106.6, 101.1, 71.4, 70.0, 40.9, 34.0, 24.4, 18.1, 25.5. MS: 222 [M+1]$^+$.

Example 59

Preparation of 3-(3-(benzyloxy)phenyl)propan-1-amine

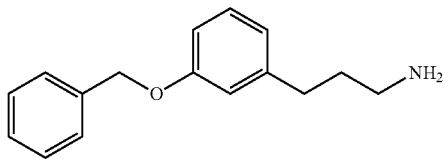 [SMILES: NCCCc1cccc(OCc2ccccc2)c1]

3-(3-(Benzyloxy)phenyl)propan-1-amine was prepared following the method used in Example 33.

Step 1:

Instead of a Mitsunobu reaction, the ether was formed by alkylation as described. A suspension of phenol 58 (1 g, 3.5 mmol), benzyl bromide (0.3 mL, 3.5 mmol), cesium carbonate (1.158 g, 3.5 mmol) in NMP (3.5 mL) was heated at 70° C. for 24 h. The reaction mixture was quenched by the addition of water, extracted with DCM, washed with water, and dried over anhy. $Na_2SO_4$. Filtration and concentration under reduced pressure gave the crude product, which was purified by flash chromatography (hexane-ethyl acetate (0-30%) gradients) to give 2-(3-(3-(benzyloxy)phenyl)propyl) isoindoline-1,3-dione as a white solid. Yield (0.708 g, 55%): $^1$H NMR (400 MHz, DMSO-$d_6$) δ 7.81-7.84 (m, 2H), 7.69-7.72 (m, 2H), 7.30-7.44 (m, 5H), 7.13-7.18 (m, 1H), 6.83-6.85 (m, 1H), 6.80 (d, J=7.6 Hz, 1H), 6.74 (dd, J=7.8, 2.0, 1H), 5.03 (s, 2H), 3.74 (t, J=7.2 Hz, 2H), 2.67 (t, J=7.6 Hz, 2H), 2.0-2.08 (m, 2H).

Step 2:

Phthalimide cleavage of 2-(3-(3-(benzyloxy)phenyl) propyl)isoindoline-1,3-dione gave Example 59 as off-white semi-solid. Yield (0.51 g, 78%): $^1$H NMR (400 MHz, DMSO-$d_6$) δ 7.40-7.45 (m, 2H), 7.34-7.39 (m, 2H), 7.30-7.32 (m, 1H), 7.15-7.19 (m, 1H), 6.84 (s, 1H), 6.67-6.82 (m, 2H), 5.06 (s, 2H), 2.51-2.58 (m, 4H), 1.58-1.64 (m, 2H). $^{13}$C NMR (100 MHz, DMSO-$d_6$) δ 158.8, 144.4, 137.7, 129.7, 128.9, 128.2, 128.1, 121.3, 115.3, 112.3, 69.5, 41.4, 35.1, 33.0. MS: 242 [M+1]$^+$.

Example 60

Preparation of 3-(3-(cyclopropylmethoxy)phenyl)propan-1-amine

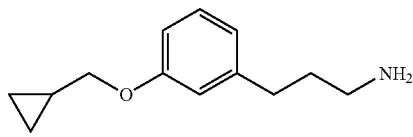 [SMILES: NCCCc1cccc(OCC2CC2)c1]

3-(3-(Cyclopropylmethoxy)phenyl)propan-1-amine was prepared following the method used in Example 59.

Step 1:

Alkylation reaction of phenol 58 with cyclopropylmethylbromide gave 2-(3-(3-(cyclopropylmethoxy)phenyl)propyl)isoindoline-1,3-dione as yellow oil. Yield (0.410 g, 36%): $^1$H NMR (400 MHz, CDCl$_3$) δ 7.81-7.84 (m, 2H), 7.69-7.72 (m, 2H), 7.11-7.16 (m, 1H), 6.73-6.78 (m, 2H), 6.67 (dd, J=8.0, 2.4 Hz, 1H), 6.73 (s, 1H), 6.65 (dd, J=7.6, 2.4 Hz, 1H), 4.52 (s, 2H), 3.94 (t, J=6.0 Hz, 2H), 3.72-3.78 (m, 4H), 2.65 (t, J=7.6 Hz, 2H), 1.98-2.07 (m, 2H), 1.24-1.28 (m, 1H), 0.62-0.66 (m, 2H), 0.32-0.36 (m, 2H).

Step 2:

Phthalimide cleavage of 2-(3-(3-(cyclopropylmethoxy) phenyl)propyl)isoindoline-1,3-dione gave Example 60 as yellow oil. Yield (0.34 g, 50%): $^1$H NMR (400 MHz, DMSO-$d_6$) δ 7.12-7.17 (m, 1H), 6.69-6.74 (m, 3H), 3.77 (d, J=6.8 Hz, 2H), 2.49-2.58 (m, 4H), 1.58-1.73 (m, 2H), 1.15-1.22 (m, 1H), 0.52-0.58 (m, 2H), 0.26-0.30 (m, 2H). $^{13}$C NMR (100 MHz, DMSO-$d_6$) δ 158.7, 143.8, 129.2, 120.4, 114.5, 111.6, 71.8, 41.0, 34.7, 32.6, 10.2, 3.4. MS: 206 [M+1]$^+$.

Example 61

Preparation of 3-(3-(cyclobutylmethoxy)phenyl)propan-1-amine

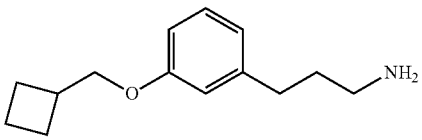 [SMILES: NCCCc1cccc(OCC2CCC2)c1]

3-(3-(Cyclobutylmethoxy)phenyl)propan-1-amine was prepared following the method used in Example 59.

Step 1:

Alkylation reaction of phenol 58 with cyclobutylmethyl bromide gave 2-(3-(3-(cyclobutylmethoxy)phenyl)propyl) isoindoline-1,3-dione as yellow oil. Yield (0.430 g, 34%): $^1$H NMR (400 MHz, CDCl$_3$) δ 7.82-7.84 (m, 2H), 7.69-7.71 (m, 2H), 7.11-7.16 (m, 1H), 6.73-6.78 (m, 2H), 6.66 (dd, J=7.6, 2.4 Hz, 1H), 3.88 (d, J=6.4 Hz, 2H), 3.75 (t, J=7.2 Hz, 2H), 2.70-2.79 (m, 1H), 2.66 (t, J=8.0 Hz, 2H), 2.10-2.17 (m, 2H), 2.00-2.07 (m, 2H), 1.82-1.98 (m, 4H).

Step 2:

Phthalimide cleavage of 2-(3-(3-(cyclobutylmethoxy) phenyl)propyl)isoindoline-1,3-dione gave Example 61 as yellow oil. Yield (0.119 g, 48%): $^1$H NMR (400 MHz, DMSO-$d_6$) δ 7.13-7.17 (m, 1H), 6.70-6.75 (m, 3H), 3.90 (d, J=6.8 Hz, 2H), 2.62-2.71 (m, 1H), 2.49-2.56 (m, 4H), 2.02-2.09 (m, 2H), 1.78-1.92 (m, 4H), 1.59-1.66 (m, 2H). $^{13}$C NMR (100 MHz, DMSO-$d_6$) δ 159.3, 144.3, 129.6, 120.9, 114.9, 112.0, 71.7, 41.4, 35.1, 34.5, 33.0, 24.9, 18.6. MS: 220 [M+1]$^+$.

Example 62

Preparation of (S)-2-(3-(2-ethylbutoxy)phenoxy) propan-1-amine

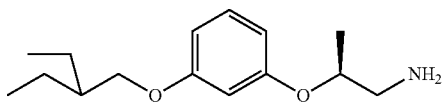

(S)-2-(3-(2-Ethylbutoxy)phenoxy)propan-1-amine was prepared following the method shown in Scheme 21.

SCHEME 21

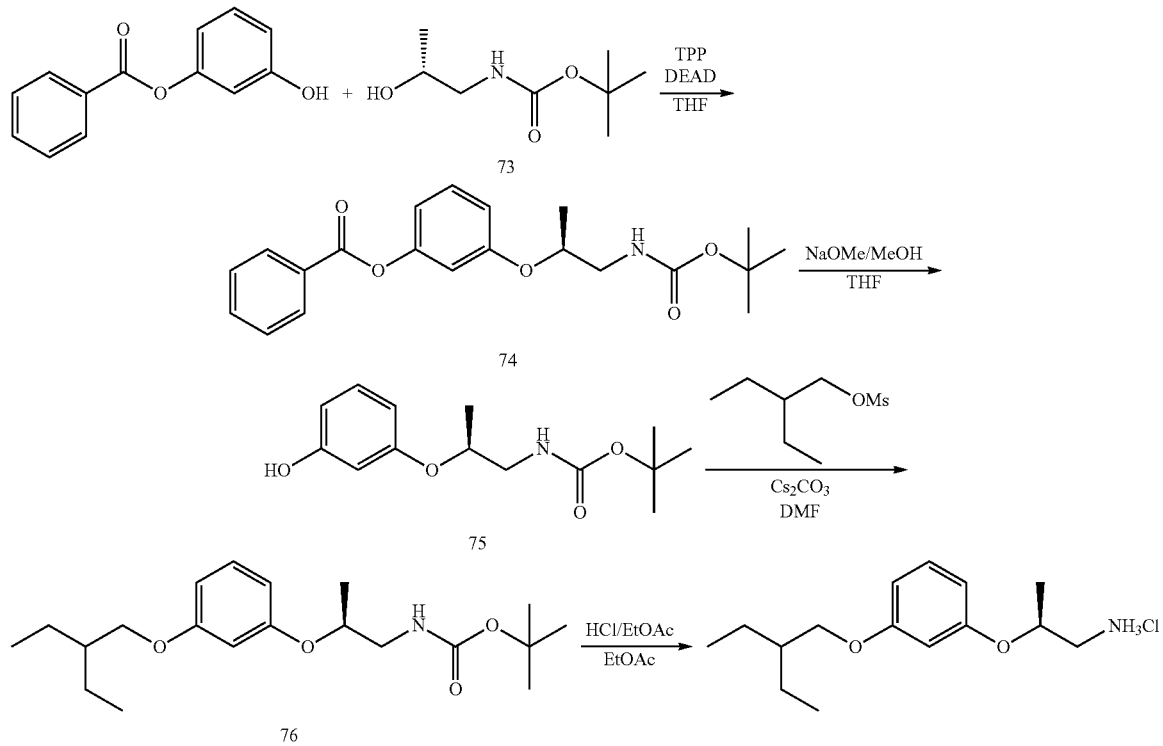

Step 1:

Alkylation of phenol 67 with alcohol 73 following the method and purification used for Example 50 gave the benzoate 74 as a colorless oil. Yield (12.7 g, 60%). $^1$H NMR (400 MHz, CDCl$_3$) δ 8.18-8.21 (m, 2H), 7.60-7.66 (m, 1H), 7.46-7.53 (m, 2H), 7.30 (t, J=8.0 Hz, 1H), 6.76-6.83 (m, 3H), 4.86-4.98 (m, 1H), 4.44-4.52 (m, 1H), 3.42-3.52 (m, 1H), 3.18-3.28 (m, 1H), 1.43 (s, 9H), 1.28 (d, J=6.4 Hz, 3H).

Step 2:

Deacylation of the benzoate 74 following the procedure and purification used for Example 50, gave the phenol 75 as a glassy colorless oil. Yield (4.7 g, 66%). $^1$H NMR (400 MHz, CDCl$_3$) δ 7.04-7.10 (m, 1H), 6.93 (brs, 1H), 6.40-6.48 (m, 3H), 4.88-5.07 (m, 1H), 4.34-4.44 (m, 1H), 3.38-3.48 (m, 1H), 3.16-3.26 (m, 1H), 1.43 (s, 9H), 1.21 (d, J=6.0 Hz, 3H).

Step 3:

Phenol 75 (0.605 g, 2.27 mmol), 2-ethylbutyl methanesulfonate (0.504 g, 2.8 mmol), and cesium carbonate (1.1 g, 3.4 mmol) were combined in DMF (5 mL) and stirred at room temperature overnight. The reaction was extracted from saturated aqueous ammonium chloride with ethyl acetate and the combined organics washed with brine, dried over Na$_2$SO$_4$, filtered, and concentrated under reduced pressure. Purification by flash chromatography (EtOAc/hexanes 0-10% gradient) gave phenyl ether 76 as a colorless oil. Yield (0.527 g, 66%). $^1$H NMR (400 MHz, CDCl$_3$) δ 7.11-7.17 (m, 1H), 6.44-6.52 (m, 3H), 4.92 (brs, 1H), 4.41-4.49 (m, 1H), 3.81 (d, J=5.6 Hz, 2H), 3.42-3.51 (m, 1H), 3.16-3.26 (m, 1H), 1.59-1.69 (m, 1H), 1.36-1.54 (m, 4H), 1.43 (s, 9H), 1.26 (d, J=6.0 Hz, 3H), 0.92 (t, J=6.4 Hz, 6H).

Step 4:

Deprotection of phenyl ether 76 following the method used in Example 5 gave the Example 62 hydrochloride as a tan solid. Yield (0.213 g, quant.). $^1$H NMR (400 MHz, CDCl$_3$) δ 8.36 (brs, 3H), 7.06-7.12 (m, 1H), 6.46-6.58 (m, 3H), 4.64-4.74 (m, 1H), 3.78 (d, J=5.6 Hz, 2H), 2.84-3.06 (m, 2H), 1.56-1.67 (m, 1H), 1.34-1.52 (m, 4H), 1.22 (d, J=6 Hz, 3H), 0.90 (t, J=7.2 Hz, 6H).

Example 63

Preparation of (S)-2-(3-(2-propylpentyloxy)phenoxy)propan-1-amine

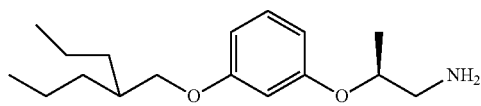 [SMILES: CCCC(CCC)COc1cccc(O[C@@H](C)CN)c1]

(S)-2-(3-(2-Propylpentyloxy)phenoxy)propan-1-amine was prepared following the method described in Example 62.

Step 1:

Alkylation of phenol 75 with 2-propylpentyl methanesulfonate gave (S)-tert-butyl 2-(3-(2-propylpentyloxy)phenoxy)propylcarbamate as a colorless oil. Yield (0.331 g, 52%). $^1$H NMR (400 MHz, CDCl$_3$) δ 7.11-7.17 (m, 1H), 6.44-6.52 (m, 3H), 4.91 (bs, 1H), 4.41-4.49 (m, 1H), 3.79 (d, J=5.6 Hz, 2H), 3.42-3.51 (m, 1H), 3.16-3.26 (m, 1H), 1.74-1.82 (m, 1H), 1.43 (s, 9H), 1.28-1.42 (m, 8H), 1.26 (d, J=6.0 Hz, 3H), 0.88-0.93 (m, 6H).

Step 2:

Deprotection of (S)-tert-butyl 2-(3-(2-propylpentyloxy)phenoxy) propylcarbamate gave Example 63 hydrochloride as a white solid. Yield (0.198 g, 60%). $^1$H NMR (400 MHz, CDCl$_3$) δ 8.36 (brs, 3H), 7.09 (t, J=8.0 Hz, 1H), 6.44-6.58 (m, 3H), 4.63-4.74 (m, 1H), 3.76 (d, J=5.6 Hz, 2H), 2.82-3.06 (m, 2H), 1.70-1.80 (m, 1H), 1.24-1.45 (m, 8H), 1.22 (d, J=6 Hz, 3H), 0.89 (t, J=7.2 Hz, 6H).

Example 64

Preparation of (S)-2-(3-(cyclopentylmethoxy)phenoxy)propan-1-amine

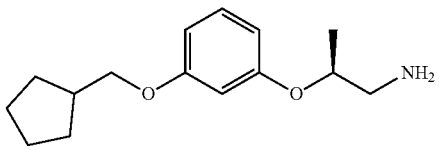 [SMILES: C[C@@H](CN)Oc1cccc(OCC2CCCC2)c1]

(S)-2-(3-(Cyclopentylmethoxy)phenoxy)propan-1-amine was prepared following the method described in Example 62.

Step 1:

Alkylation of phenol 75 with cyclopentylmethyl methanesulfonate gave (S)-tert-butyl 2-(3-(cyclopentylmethoxy)phenoxy)propylcarbamate as a colorless oil. Yield (0.331 g, 52%). $^1$H NMR (400 MHz, CDCl$_3$) δ 7.10-7.16 (m, 1H), 6.44-6.52 (m, 3H), 4.92 (bs, 1H), 4.41-4.49 (m, 1H), 3.79 (d, J=6.8 Hz, 2H), 3.40-3.51 (m, 1H), 3.16-3.26 (m, 1H), 2.26-2.38 (m, 1H), 1.76-1.86 (m, 2H), 1.52-1.68 (m, 4H), 1.43 (s, 9H), 1.28-1.38 (m, 2H), 1.25 (d, J=6.0 Hz, 3H).

Step 2:

Deprotection of (S)-tert-butyl 2-(3-(cyclopentylmethoxy)phenoxy) propylcarbamate gave Example 64 hydrochloride as a white solid. Yield (0.198 g, 60%). $^1$H NMR (400 MHz, CDCl$_3$) δ 8.32 (brs, 3H), 7.05-7.13 (m, 1H), 6.42-6.58 (m, 3H), 4.62-4.73 (m, 1H), 3.76 (d, J=6.8 Hz, 2H), 2.80-3.04 (m, 2H), 2.22-2.36 (m, 1H), 1.74-1.86 (m, 2H), 1.50-1.66 (m, 4H), 1.22-1.38 (m, 2H), 1.20 (d, J=6.0 Hz, 3H).

Example 65

Preparation of (S)-2-(3-(cyclohexylmethoxy)phenoxy)propan-1-amine

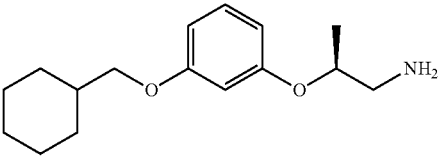 [SMILES: C[C@@H](CN)Oc1cccc(OCC2CCCCC2)c1]

(S)-2-(3-(Cyclohexylmethoxy)phenoxy)propan-1-amine was prepared following the method described in Example 62.

Step 1:

Alkylation of phenol 75 with cyclohexylmethyl methanesulfonate gave (S)-tert-butyl 2-(3-(cyclohexylmethoxy)phenoxy)propylcarbamate as a colorless oil. Yield (0.331 g, 52%). $^1$H NMR (400 MHz, CDCl$_3$) δ 7.13 (t, J=8.4 Hz, 1H), 6.43-6.50 (m, 3H), 4.92 (bs, 1H), 4.38-4.48 (m, 1H), 3.70 (d, J=6.4 Hz, 2H), 3.40-3.50 (m, 1H), 3.16-3.25 (m, 1H), 1.80-1.90 (m, 2H), 1.64-1.80 (m, 4H), 1.42 (s, 9H), 1.12-1.34 (m, 6H), 0.96-1.08 (m, 2H).

Step 3:

Deprotection of (S)-tert-butyl 2-(3-(cyclohexylmethoxy)phenoxy) propylcarbamate gave Example 64 hydrochloride as a white solid. Yield (0.198 g, 60%). $^1$H NMR (400 MHz, CDCl$_3$) δ 8.37 (brs, 3H), 7.06-7.12 (m, 1H), 6.44-6.58 (m, 3H), 4.62-4.72 (m, 1H), 3.68 (d, J=6.4 Hz, 2H), 2.82-3.02 (m, 2H), 1.78-1.86 (m, 2H), 1.64-1.78 (m, 4H), 1.10-1.34 (m, 4H), 1.21 (d, J=6.0 Hz, 2H), 0.94-1.07 (m, 2H),

Example 66

Preparation of (S)-1-amino-3-(3-(2-ethylbutoxy)phenyl)propan-2-ol

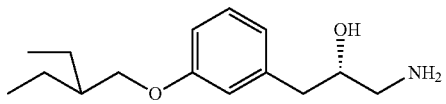 [SMILES: CCC(CC)COc1cccc(C[C@H](O)CN)c1]

(S)-1-Amino-3-(3-(2-ethylbutoxy)phenyl)propan-2-ol was prepared following the method described in Example 6.

Step 1:

Coupling of 3-bromophenol (17) (5.0 g, 28.9 mmol) with 2-ethylbutan-1-ol (3.25 g, 31.79 mmol) was conducted following the procedure given for Example 6. The reaction mixture was concentrated under reduced pressure then triturated with diethyl ether. The suspension was filtered and the filtrate was concentrated under reduced pressure. Purification by flash chromatography (100% hexanes) gave 1-bromo-3-(2-ethylbutoxy)benzene a clear liquid. Yield (5.04 g, 62%): $^1$H NMR (400 MHz, DMSO-d$_6$) δ 7.20 (t, J=8.0 Hz, 1H), 7.11 (t, J=2.2 Hz, 1H), 7.07 (dd, J=8.0, 2.0 Hz, 1H), 6.92 (dd, J=8.4, 2.6 Hz, 1H), 3.84 (d, J=5.6 Hz, 2H), 1.61-1.53 (m, 1H), 1.46-1.30 (m, 4H), 0.86 (t, J=7.4 Hz, 6H).

Step 2:

Metallation of 1-bromo-3-(2-ethylbutoxy)benzene followed by addition to (R)-(−)-epichlorohydrin gave (S)-1-chloro-3-(3-(2-ethylbutoxy)phenyl)propan-2-ol. Yield (1.57 g, 60%): $^1$H NMR (400 MHz, DMSO-d$_6$) δ 7.14 (t, J=7.8 Hz, 1H), 6.78-6.73 (m, 3H), 5.13 (d, J=5.2 Hz, 1H), 3.88-3.83 (m, 1H), 3.80 (d, J=6.0 Hz, 2H), 3.52 (dd, J=10.8, 4.6 Hz, 1H), 3.43 (dd, J=11.0, 5.8 Hz, 1H), 2.74 (dd, J=13.8, 5.0 Hz, 1H), 2.62 (dd, J=13.6, 7.6 Hz, 1H), 1.61-1.55 (m, 1H), 1.47-1.31 (m, 4H), 0.86 (t, J=7.2 Hz, 6H).

Step 3:

Treatment of (S)-1-chloro-3-(3-(2-ethylbutoxy)phenyl)propan-2-ol with sodium azide following the method used in Example 6 gave (S)-1-azido-3-(3-(2-ethylbutoxy)phenyl)propan-2-ol which was used without further purification.

Step 4:

Reduction of (S)-1-azido-3-(3-(2-ethylbutoxy)phenyl)propan-2-ol following the procedure used in example 6 gave Example 66. Yield (0.95 g, 64%): $^1$H NMR (400 MHz, DMSO-d$_6$) δ 7.11 (t, J=7.6 Hz, 1H), 6.75-6.69 (m, 3H), 3.79 (d, J=5.6 Hz, 2H), 3.53-3.47 (m, 1H), 2.62 (dd, J=13.4, 5.8 Hz, 1H), 2.40 (dd, obs., 1H), 2.47 (dd, obs., 1H), 2.36 (dd, J=12.8, 6.8 Hz, 1H), 1.62-1.53 (m, 1H), 1.47-1.31 (m, 4H), 0.86 (t, J=7.4 Hz, 6H).

Example 67

Preparation of (S)-1-amino-3-(3-(2-propylpenty-loxy)phenyl)propan-2-ol

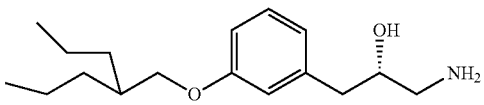 [SMILES: CCCC(CCC)COc1cccc(C[C@H](O)CN)c1]

(S)-1-Amino-3-(3-(2-propylpentyloxy)phenyl)propan-2-ol was prepared following the method described in Example 66.

Step 1:

Coupling of 3-bromophenol (17) (5.0 g, 28.9 mmol) with 2-propylpentan-1-ol (4.14 g, 31.79 mmol) gave 1-bromo-3-(2-propylpentyloxy)benzene as clear liquid. Yield (5.42 g, 60%): $^1$H NMR (400 MHz, DMSO-$d_6$) δ 7.19 (t, J=8.0 Hz, 1H), 7.10 (t, J=2.2 Hz, 1H), 7.07 (dd, J=8.0 2.0 Hz, 1H), 6.91 (dd, J=8.4, 2.4 Hz, 1H), 3.83 (d, J=5.6 Hz, 2H), 1.74-1.70 (m, 1H), 1.38-1.24 (m, 8H), 0.84 (t, J=7.0 Hz, 6H).

Step 2:

Metallation of 1-bromo-3-(2-propylpentyloxy)benzene followed by addition of (R)-(−)-epichlorohydrin gave (S)-1-chloro-3-(3-(2-propylpentyloxy)phenyl)propan-2-ol Yield (1.52 g, 58%): $^1$H NMR (400 MHz, DMSO-$d_6$) δ 7.14 (t, J=7.8 Hz, 1H), 6.77-6.72 (m, 3H), 5.14 (d, J=5.6 Hz, 1H), 3.88-3.81 (m, 1H), 3.78 (d, J=5.6 Hz, 2H), 3.52 (dd, J=10.8, 4.4 Hz, 1H), 3.43 (dd, J=11.2, 5.6 Hz, 1H), 2.74 (dd, J=13.6, 5.2 Hz, 1H), 2.60, (dd, J=13.6, 7.6 Hz, 1H), 1.75-1.69 (m, 1H), 1.39-1.25 (m, 8H), 0.85 (t, J=7.0 Hz, 6H).

Step 3:

Treatment of (S)-1-chloro-3-(3-(2-propylpentyloxy)phenyl)propan-2-ol with sodium azide following the method used in Example 66 gave (S)-1-azido-3-(3-(2-propylpentyloxy)phenyl)propan-2-ol which was used without further purification.

Step 4:

Reduction of (S)-1-azido-3-(3-(2-propylpentyloxy)phenyl)propan-2-ol was prepared following the procedure given for example 66 gave Example 67. Yield (1.02 g, 70%): $^1$H NMR (400 MHz, DMSO-$d_6$) δ 7.11 (t, J=7.8 Hz, 1H), 6.74-6.68 (m, 3H), 3.78 (d, J=6.0 Hz, 2H), 3.53-3.47 (m, 1H), 2.62 (dd, J=13.6, 5.8 Hz, 1H), 2.51 (dd, obs., 1H), 2.47 (dd, obs., 1H), 2.37 (dd, J=13.6, 6.8 Hz, 1H), 1.74-1.69 (m, 1H), 1.40-1.25 (m, 8H), 0.85 (t, J=7.0 Hz, 6H).

Example 68

Preparation of (R)-1-amino-3-(3-(2-propylpenty-loxy)phenyl)propan-2-ol

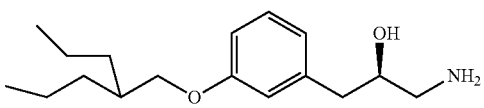 [SMILES: CCCC(CCC)COc1cccc(C[C@@H](O)CN)c1]

(R)-1-Amino-3-(3-(2-propylpentyloxy)phenyl)propan-2-ol was prepared following the method described in Example 66.

Step 1:

Metallation of 1-bromo-3-(2-propylpentyloxy)benzene followed by addition of (S)-(+)-epichlorohydrin gave (R)-1-chloro-3-(3-(2-propylpentyloxy)phenyl)propan-2-ol. Yield (1.55 g, 59%): $^1$H NMR (400 MHz, DMSO-$d_6$) δ 7.14 (t, J=7.8 Hz, 1H), 6.77-6.72 (m, 3H), 5.13 (d, J=4.8 Hz, 1H), 3.88-3.82 (m, 1H), 3.78 (d, J=5.6 Hz, 2H), 3.52 (dd, J=10.8, 4.4 Hz, 1H), 3.43 (dd, J=10.8, 5.6 Hz, 1H), 2.74 (dd, J=13.6, 5.2 Hz, 1H), 2.61 (dd, J=13.2, 7.4 Hz, 1H), 1.74-1.69 (m, 1H), 1.39-1.25 (m, 8H), 0.85 (t, J=7.0 Hz, 6H).

Step 2:

Treatment of (R)-1-chloro-3-(3-(2-propylpentyloxy)phenyl)propan-2-ol with sodium azide following the method used in Example 66 gave (R)-1-azido-3-(3-(2-propylpentyloxy)phenyl)propan-2-ol which was used without further purification.

Step 3:

Reduction of (R)-1-azido-3-(3-(2-propylpentyloxy)phenyl)propan-2-ol was prepared following the procedure given for example 66 gave Example 68. Yield (1.05 g, 71%): $^1$H NMR (400 MHz, DMSO-$d_6$) δ 7.11 (t, J=7.8 Hz, 1H), 6.75-6.68 (m, 3H), 3.78 (d, J=5.6 Hz, 2H), 3.55-3.49 (m, 1H), 2.64 (dd, J=13.2, 5.6 Hz, 1H), 2.52 (dd, obs., 1H), 2.48 (dd, obs., 1H), 2.37 (dd, J=12.8, 7.0 Hz, 1H), 1.75-1.69 (m, 1H), 1.40-1.25 (m, 8H), 0.86 (t, J=7.0 Hz, 6H).

Example 69

Preparation of (R)-1-amino-3-(3-(2-ethylbutoxy)phenyl)propan-2-ol

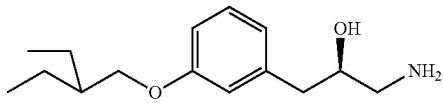 [SMILES: CCC(CC)COc1cccc(C[C@@H](O)CN)c1]

(R)-1-Amino-3-(3-(2-ethylbutoxy)phenyl)propan-2-ol was prepared following the method described in Example 6.

Step 1:

Metallation of 1-bromo-3-(2-ethylbutoxy)benzene followed by addition to (S)-(+)-epichlorohydrin gave (R)-1-chloro-3-(3-(2-ethylbutoxy)phenyl)propan-2-ol. Yield (1.55 g, 59%): $^1$H NMR (400 MHz, DMSO-$d_6$) δ 7.14 (t, J=7.8 Hz, 1H), 6.77-6.72 (m, 3H), 5.13 (d, J=4.8 Hz, 1H), 3.88-3.82 (m, 1H), 3.78 (d, J=5.6 Hz, 2H), 3.52 (dd, J=10.8, 4.4 Hz, 1H), 3.43 (dd, J=10.8, 5.6 Hz, 1H), 2.74 (dd, J=13.6, 5.2 Hz, 1H), 2.61 (dd, J=13.2, 7.4 Hz, 1H), 1.74-1.69 (m, 1H), 1.39-1.25 (m, 8H), 0.85 (t, J=7.0 Hz, 6H).

Step 2:

Treatment of (R)-1-chloro-3-(3-(2-ethylbutoxy)phenyl)propan-2-ol with sodium azide following the method used in Example 66 gave (R)-1-azido-3-(3-(2-ethylbutoxy)phenyl)propan-2-ol which was used without further purification.

Step 3:

Reduction of (R)-1-azido-3-(3-(2-ethylbutoxy)phenyl)propan-2-ol following the procedure used in Example 66 gave Example 69. Yield (1.05 g, 71%): $^1$H NMR (400 MHz, DMSO-$d_6$) δ 7.11 (t, J=7.8 Hz, 1H), 6.75-6.68 (m, 3H), 3.78 (d, J=5.6 Hz, 2H), 3.55-3.49 (m, 1H), 2.64 (dd, J=13.2, 5.6 Hz, 1H), 2.52 (dd, obs., 1H), 2.48 (dd, obs., 1H), 2.37 (dd, J=12.8, 7.0 Hz, 1H), 1.75-1.69 (m, 1H), 1.40-1.25 (m, 8H), 0.86 (t, J=7.0 Hz, 6H).

Example 70

Preparation of 3-(3-phenethoxyphenyl)propan-1-amine

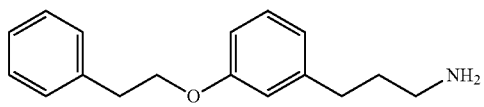 [SMILES: NCCCc1cccc(OCCc2ccccc2)c1]

3-(3-Phenethoxyphenyl)propan-1-amine was prepared following the method described in Example 33.

Step 1:

Mitsunobu reaction of phenol 58 with phenethyl alcohol gave 2-(3-(3-phenethoxyphenyl)propyl)isoindoline-1,3-dione as yellow oil. Yield (0.360 g, 30%): $^1$H NMR (400 MHz, CDCl$_3$) δ 7.77-7.81 (m, 2H), 7.66-7.71 (m, 2H), 7.22-7.34 (m, 6H), 6.71-6.78 (m, 2H), 6.65 (dd, J=7.2, 2.0 Hz, 1H), 3.87 (t, J=6.8, 2H), 3.74 (t, J=7.2 Hz, 2H), 2.88 (t, J=6.4 Hz, 2H), 2.65 (t, J=7.2 Hz, 2H), 1.98-2.06 (m, 2H).

Step 2:

Phthalimide cleavage of 2-(3-(3-phenethoxyphenyl) propyl)isoindoline-1,3-dione gave 3-(3-phenethoxyphenyl)propan-1-amine as yellow oil. Yield (0.220 g, 59%): $^1$H NMR (400 MHz, DMSO-d$_6$) δ 7.30-7.34 (m, 4H), 7.20-7.24 (m, 1H), 7.12-7.18 (m, 1H), 6.71-6.77 (m, 3H), 4.15 (t, J=6.8 Hz, 2H), 3.01 (t, J=6.8 Hz, 2H), 2.48-2.58 (m, 4H), 1.60-1.68 (m, 2H). $^{13}$C NMR (100 MHz, DMSO-d$_6$) δ 143.7, 138.4, 129.2, 128.9, 128.3, 126.2, 120.6, 114.5, 111.6, 67.9, 40.6, 35.6, 33.8, 32.4. MS: 256 [M+1]$^+$.

Example 71

Preparation of 3-amino-1-(3-(cyclopropylmethoxy)phenyl)propan-1-ol

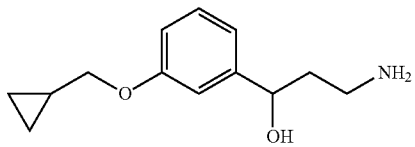 [SMILES: NCCC(O)c1cccc(OCC2CC2)c1]

3-Amino-1-(3-(cyclopropylmethoxy)phenyl)propan-1-ol was prepared following the method described in Scheme 22.

SCHEME 22

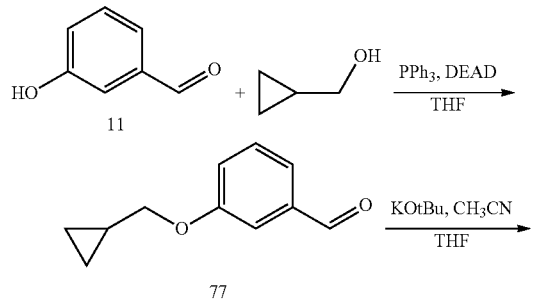

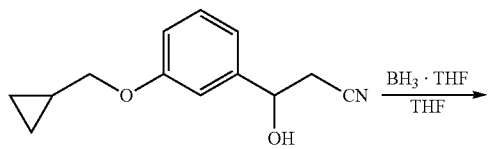

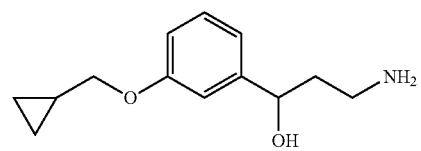

Step 1:

Coupling of 3-hydroxybenzaldehyde (11) (8.46 g, 69.3 mmol) with cyclopropylcarbinol (5.0 g, 69.3 mmol) was conducted following the procedure given for Example 4. The reaction mixture was concentrated under reduced pressure and the residue was triturated with diethyl ether. The resulting white precipitate was removed by filtration. Trituration and filtration was repeated. Purification by flash chromatography (0 to 10% EtOAc-hexanes gradient) was carried out twice, gave phenyl ether 77 as a colorless oil. Yield (0.87 g, 7%): $^1$H NMR (400 MHz, CDCl$_3$) δ 9.62 (s, 1H), 7.08-7.10 (m, 2H), 7.01-7.04 (m, 1H), 6.81-6.87 (m, 1H), 3.52 (d, J=7.2 Hz, 2H), 0.89-0.99 (m, 1H), 0.29-0.34 (m, 2H), 0.0-0.04 (m, 2H).

Step 2:

To a –50° C. solution of potassium tert-butoxide (5.9 mL of a 1M solution in THF, 5.9 mmol) under argon, was added anhydrous acetonitrile (0.22 g, 5.4 mmol), dropwise, and the reaction stirred for 15 min at –50° C. To this was added, dropwise, a solution of phenyl ether 77 (0.865 g, 4.9 mmol) in anhydrous THF (3 mL) with continued stirring at –50° C. for 30 min. The reaction mixture was allowed to warm to room temperature then quenched with saturated aqueous NH$_4$Cl (20 mL). The mixture was extracted with EtOAc, and the organic layer washed with brine, dried over Na$_2$SO$_4$, and concentrated under reduced pressure. Purification by flash chromatography (0 to 30% EtOAc-hexanes gradient) gave hydroxynitrile 78 as a colorless oil. Yield (0.4 g, 38%): $^1$H NMR (400 MHz, CDCl$_3$) δ 6.92-6.98 (m, 1H), 6.58-6.64 (m, 2H), 6.52-6.56 (m, 1H), 4.64 (t, J=7.2 Hz, 1H), 3.47 (d, J=7.2 Hz, 2H), 2.48 (brs, 1H), 2.40 (d, J=7.2 Hz, 2H), 0.86-0.98 (m, 1H), 0.26-0.38 (m, 2H), –0.06-0.04 (m, 2H).

Step 3:

To a solution of hydroxynitrile 78 (0.36 g, 1.56 mmol) in dry THF (3 mL) under argon was added borane-tetrahydrofuran complex (2 mL, 2.0 mmol) slowly. The reaction was stirred at reflux for 2 h, then quenched by the addition of saturated aqueous NaHCO$_3$ (5 mL). The mixture was extracted with EtOAc, and the organic layer washed with brine, dried over Na$_2$SO$_4$, and concentrated under reduced pressure. Purification by flash chromatography (5% (7 M NH$_3$/MeOH)/dichloromethane) gave Example 71 as a colorless oil. Yield (0.086 g, 21%): $^1$H NMR (400 MHz, CDCl$_3$) δ 6.88-6.97 (m, 1H), 6.57-6.66 (m, 2H), 6.44-6.56 (m, 1H), 4.59 (d, J=8.0, 1H), 3.48 (d, J=7.2, 2H), 2.70-2.80 (m, 1H), 2.56-2.66 (m, 1H), 2.50 (br s, 2H), 1.48-1.58 (m, 1H), 1.34-1.46 (m, 1H), 0.86-0.98 (m, 1H), 0.26-0.34 (m, 2H), −0.04-0.04 (m, 2H).

Example 72

Preparation of (1R,2R)-3-amino-1-(3-(2-ethylbutoxy)phenyl)-2-methylpropan-1-ol

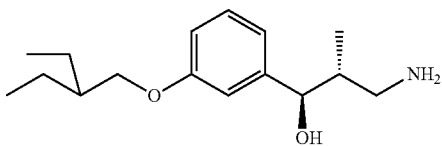 [SMILES: CCC(CC)COc1cccc([C@H](O)[C@H](C)CN)c1]

(1R,2R)-3-Amino-1-(3-(2-ethylbutoxy)phenyl)-2-methylpropan-1-ol was prepared following the method shown in Scheme 23.

SCHEME 23

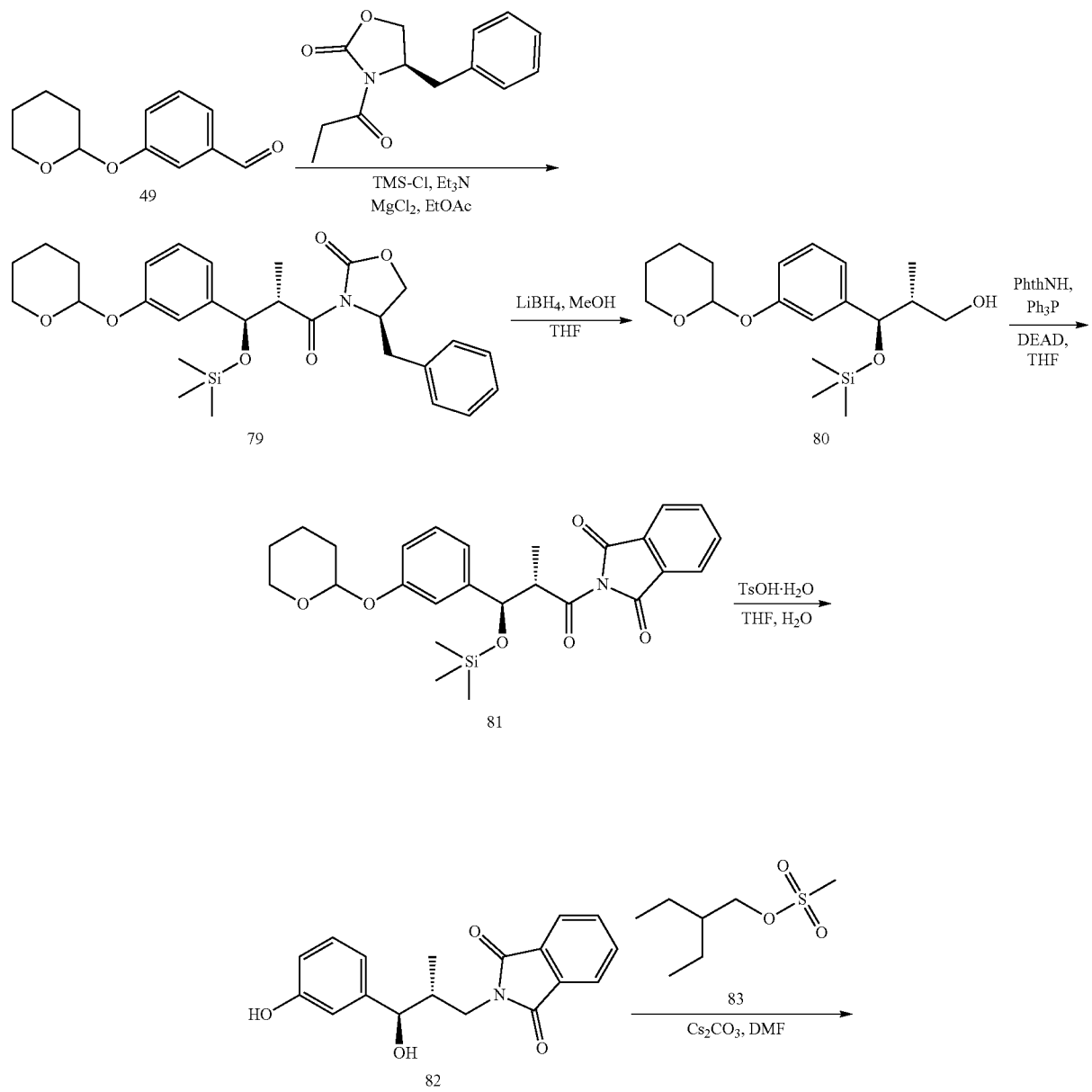

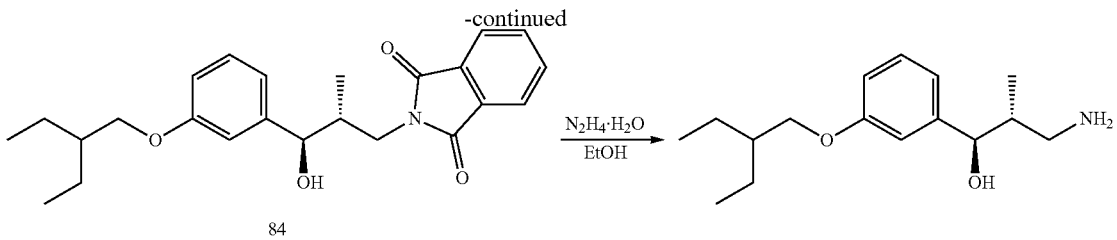

84

Step 1.

Condensation of (R)-4-benzyl-3-propionyloxazolidin-2-one with 3-(tetrahydro-2H-pyran-2-yloxy)benzaldehyde (49) following the method used in Example 45 gave oxazolidinone 79 as colorless oil. Yield (19.11 g, quant.). $^1$H NMR (400 MHz, DMSO-$d_6$) δ 7.34-7.45 (m, 6H), 7.03-7.145 (m, 3H), 5.54 (dt, J=3.2, 6.9 Hz, 1H), 4.98 (dd, J=1.2, 9.6 Hz, 1H), 4.79-4.84 (m, 1H), 4.40 (t, J=8.6 Hz, 1H), 4.23 (dd, J=2.9, 8.8 Hz, 1H), 4.09-4.20 (m, 1H), 3.82-3.88 (m, 1H), 3.59-3.65 (m, 1H), 3.13 (dd, J=3.2, 13.5 Hz, 1H), 3.02 (dd, J=7.4, 13.5 Hz, 1H), 1.80-2.00 (m, 3H), 1.60-1.74 (m, 3H), 0.86 (d, J=7.0 Hz, 3H), 0.00 (d, J=1.2 Hz, 9H).

Step 2.

To a cooled (0° C.) suspension of LiBH$_4$ (6.57 g, 301.7 mmol) in anhydrous THF (75 mL) was added MeOH (6.2 mL) and the mixture was stirred at 0° C. for 20 mins. After that a solution of oxazolidinone 79 (19.1 g, 37.3 mmol) in anhydrous THF (170 mL) was added and reaction mixture was stirred at 0° C. for 4 hrs. Solution of NH$_4$Cl (25%, 100 mL) was added slowly to reaction mixture for over 1 hr and left to stir at room temperature for 15 hrs. Layers were separated, aqueous layer extracted with MTBE, combined organic layers washed with saturated brine, dried with anhydrous MgSO$_4$, filtered and concentrated under reduced pressure. The residue was purified by flash chromatography (5 to 30% EtOAc/hexane gradient) to give the alcohol 80 as colorless oil. Yield (8.57 g, 68%). $^1$H NMR (400 MHz, CDCl$_3$) δ 7.22 (dt, J=2.9, 7.8 Hz, 1H), 6.98-7.02 (m, 1H), 6.87-7.02 (m, 2H), 5.41 (dt, J=3.3, 8.4 Hz, 1H), 4.49 (dd, J=5.7, 6.8 Hz, 1H), 3.87-3.94 (m, 1H), 3.56-3.67 (m, 3H), 1.90-2.06 (m, 2H), 1.85-1.89 (m, 2H), 1.58-1.73 (m, 3H), 0.81 (dd, J=5.1, 7.0 Hz, 3H), 0.00 (s, 9H).

Step 3.

Mitsunobu reaction of alcohol 80 with phthalimide following the method used in Example 45 gave phthalimide 81 as a colorless oil. Yield (10.39 g, 91%). $^1$H NMR (400 MHz, DMSO-$d_6$) δ 7.76-7.92 (m, 4H), 7.13-7.19 (m, 1H), 6.93-6.98 (m, 1H), 6.86-6.91 (m, 1H), 6.76-6.83 (m, 1H), 5.37 (dt, J=3.3, 15.5 Hz, 1H), 4.57 (t, J=5.5 Hz, 1H), 3.62-3.77 (m, 2H), 3.47-3.53 (m, 1H), 3.40 (ddd, J=1.4, 9.2, 13.7 Hz, 1H), 2.24-2.31 (m, 1H), 1.65-1.89 (m, 3H), 1.44-1.64 (m, 3H), 0.64 (dd, J=3.5, 6.9 Hz, 3H), -0.06 (s, 9H).

Step 4.

A mixture of THP-protected phenol 81 (4.10 g, 8.51 mmol) and p-toluenesulfonic acid monohydrate (0.36 g, 1.9 mmol) in THF (40 mL) and water (10 mL) was stirred at room temperature for 15 hrs. Solvent was removed in vacuum, the residue was treated with 20% hexane/EtOA. The precipitate was filtered off, washed with hexane, then with 20% EtOAc/hexane. Purification of the precipitate by flash chromatography (40 to 100% EtOAc/hexane gradient) gave the phenol 82 as a white solid. Yield (1.74 g, 83%). $^1$H NMR (400 MHz, DMSO-$d_6$) δ 9.21 (s, 1H), 7.76-7.83 (m, 4H), 7.05 (t, J=7.8 Hz, 1H), 6.68-6.74 (m, 2H), 6.55 (ddd, J=1.0, 2.4, 8.0 Hz, 1H), 5.26 (d, J=4.1 Hz, 1H), 4.32 (dd, J=4.1, 6.3 Hz, 1H), 3.69 (dd, J=5.1, 13.7 Hz, 1H), 3.42 (dd, J=9.8, 13.5 Hz, 1H), 2.15-2.22 (m, 1H), 0.61 (d, J=6.8 Hz, 3H).

Step 5.

A mixture of mesylate 83 (0.230 g, 1.28 mmol), phenol 82 (0.348 g, 1.12 mmol) and Cs$_2$CO$_3$ (0.502 g, 1.54 mmol) in anhydrous DMF (7 mL) was stirred under argon at 60° C. for 24 hrs. Aqueous NH$_4$Cl (25%, 100 mL) and the product was extracted twice with EtOAc. Combined organic layer were washed with saturated brine, dried over anhydrous MgSO$_4$, filtered and concentrated under reduced pressure. The residue was purified by flash chromatography (10 to 50% EtOAc/hexane gradient) to give ether 83 as a colorless oil. Yield (0.216 g, 49%). $^1$H NMR (400 MHz, DMSO-$d_6$) δ 7.75-7.80 (m, 4H), 7.14 (t, J=7.8 Hz, 1H), 6.83-6.88 (m, 2H), 6.67-6.70 (m, 1H), 5.30 (d, J=4.3 Hz, 1H), 4.38-4.41 (m, 1H), 3.79 (d, J=5.9 Hz, 2H), 3.70 (dd, J=5.5, 13.7 Hz, 1H), 3.41 (dd, J=9.4, 13.7 Hz, 1H), 2.20-2.30 (m, 1H), 1.54-1.62 (m, 1H), 1.31-1.47 (m, 4H), 0.87 (t, J=7.4 Hz, 6H), 0.65 (d, J=6.8 Hz, 3H).

Step 6.

Phthalimide 83 was deprotected following the method used in Example 45 to give crude amine which was purified by chromatography using gradient of 20% 7N NH$_3$/MeOH in EtOAc/hexanes (50 to 100%) to give Example 72 as a colorless oil. Yield (0.051 g, 23%). $^1$H NMR (400 MHz, MeOD-$d_4$) δ 7.20 (t, J=7.8 Hz, 1H), 6.85-6.91 (m, 2H), 6.79 (ddd, J=0.8, 2.5, 8.2 Hz, 1H), 4.37 (d, J=7.8 Hz, 1H), 3.87 (d, J=5.5 Hz, 2H), 2.83 (dd, J=5.7, 12.7 Hz, 1H), 2.66 (dd, J=5.9, 12.7 Hz, 1H), 1.78-1.88 (m, 1H), 1.58-1.67 (m, 1H), 1.39-1.56 (m, 4H), 0.93 (t, J=7.4 Hz, 6H), 0.73 (d, J=6.8 Hz, 3H); $^{13}$C NMR (100 MHz, MeOH-$d_4$) δ 159.6, 145.7, 128.9, 119.0, 113.2, 112.8, 78.6, 69.8, 45.2, 42.1, 41.3, 23.3, 14.0, 10.3; LC-MS (ESI+) 266.3 [M+H]$^+$; RP-HPLC: 94.9%, $t_R$=4.56 min; Chiral HPLC 97.9% (AUC), $t_R$=7.20 min.

Example 73

Preparation of (1S,2S)-3-amino-1-(3-(cyclohexylmethoxy)phenyl)-2-methylpropan-1-ol

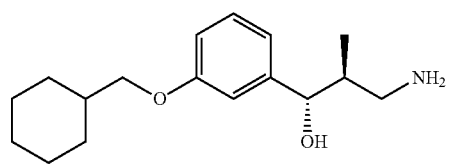 [SMILES: C[C@@H](CN)[C@H](O)c1cccc(OCC2CCCCC2)c1]

3-((1S,2S)-3-Amino-1-(3-(cyclohexylmethoxy)phenyl)-2-methylpropan-1-ol was prepared following the method shown in Scheme 24.

SCHEME 24

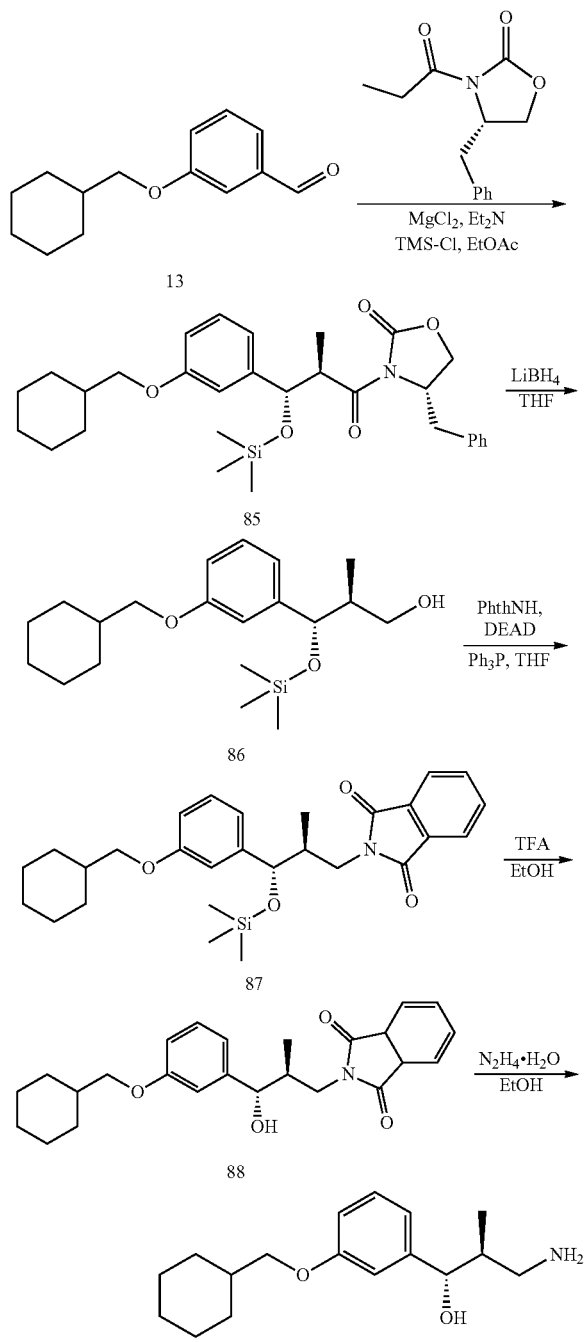

Step 1:

To a mixture of (S)-4-benzyl-3-propionyloxazolidin-2-one (2.16 g, 9.26 mmol), anhydrous MgCl₂ (0.104 g, 1.09 mmol) and 3-(cyclohexylmethoxy)benzaldehyde (13) (2.22 g, 10.2 mmol) in EtOAc (20 mL) was added Et₃N (2.7 mL, 19.4 mmol) followed by chlorotrimethylsilane (1.8 mL, 14.2 mmol). The reaction mixture was stirred under argon at room temperature for 24 hrs and then filtered through a layer of a silica gel, which was further washed with EtOAc. The filtrate was concentrated under reduced pressure and the residue was purified by flash chromatography (1 to 30% EtOAc/hexane gradient) to give imide 85 as a colorless oil. Yield (4.63 g, quant.). $^1$H NMR (400 MHz, DMSO-d₆) δ 7.22-7.34 (m, 6H), 6.88-6.93 (m, 2H), 6.81-6.84 (m, 1H), 4.87 (d, J=9.4 Hz, 1H), 4.71 (m, 1H), 4.29 (t, J=8.6 Hz, 1H), 4.12 (dd, J=3.0 Hz, 8.6 Hz, 1H), 4.05 (dd, J=7.0 Hz, 9.4 Hz, 1H), 3.75 (m, 2H), 3.03 (dd, J=3.0 Hz, 13.5 Hz, 1H), 2.91 (dd, J=7.6 Hz, 13.5 Hz, 1H), 1.60-1.79 (m, 6H), 1.08-1.26 (m, 3H), 0.96-1.08 (m, 2H), 0.74 (d, J=7.04 Hz, 3H), −0.10 (s, 9H).

Step 2:

To a solution of imide 85 (2.01 g, 4.45 mmol) in anhydrous THF (30 mL) was added a solution of LiBH₄ in THF (2M, 5 mL, 10 mmol) under argon. The reaction mixture was stirred for 18 hrs at room temperature and a saturated aqueous solution of NH₄Cl (15 mL) was slowly added followed by MTBE. The mixture was stirred for 15 mins, layers were separated, organic layer was washed with brine, dried over anhydrous MgSO₄, filtered and concentrated under reduced pressure. The residue was purified by flash chromatography (5 to 40% EtOAc/hexane gradient) to give alcohol 86 as colorless oil. Yield (0.57 g, 37%). $^1$H NMR (400 MHz, DMSO-d₆) δ 7.16 (t, J=7.8 Hz, 1H), 6.73-6.80 (m, 3H), 4.49 (d, J=7.0 Hz, 1H), 4.30 (t, J=5.3 Hz, 1H), 3.69-3.76 (m, 2H), 3.38-3.43 (m, 1H), 3.22-3.28 (m, 1H), 1.61-1.80 (m, 7H), 1.11-1.27 (m, 3H), 0.96-1.07 (m, 2H), 0.61 (d, J=6.9 Hz, 3H), −0.07 (s, 9H).

Step 3:

To a cold (0° C.) solution of alcohol 86 (0.57 g, 1.63 mmol), phthalimide (0.35 g, 2.38 mmol) and Ph₃P (0.72 g, 2.75 mmol) in anhydrous THF (20 mL) under argon was added solution of diethyl azodicarboxylate (0.5 mL, 3.00 mmol) in anhydrous THF (3 mL). The reaction mixture was stirred for 1 hour under argon while warming to room temperature and then the solvent was removed in vacuum, the residue was dissolved in dichloromethane/hexane and purified by flash chromatography (5 to 30% EtOAc/hexane gradient) to give phthalimide 87 as colorless oil. Yield (0.62 g, 80%). $^1$H NMR (400 MHz, DMSO-d₆) δ 7.78 (m, 4H), 7.14 (t, J=8.0 Hz, 1H), 6.80-6.84 (m, 2H), 6.66-6.69 (m, 1H), 4.57 (d, J=6.1 Hz, 1H), 3.63-3.74 (m, 3H), 3.40 (dd, J=13.7 Hz, 9.2 Hz, 1H), 2.25-2.32 (m, 1H), 1.61-1.79 (m, 6H), 1.12-1.27 (m, 3H), 0.96-1.08 (m, 2H), 0.64 (d, J=6.9 Hz, 3H), −0.05 (s, 9H).

Step 4:

To a solution of TMS ether 87 (0.62 g, 1.29 mmol) in EtOH (abs, 20 mL) was added trifluoroacetic acid (25 µL). The reaction mixture was stirred at room temperature for 50 mins, concentrated under reduced pressure, re-evaporated with EtOAc then with hexane to give alcohol 88 as a colorless oil. Yield (0.58 g, quant.). The product was taken to the next step without further purification. $^1$H NMR (400 MHz, DMSO-d₆) δ 7.76-7.80 (m, 4H), 7.13 (t, J=7.6 Hz, 1H), 6.82-6.86 (m, 2H), 6.65-6.68 (m, 1H), 4.40 (d, J=6.1 Hz, 1H), 3.67-3.74 (m, 3H), 3.40 (dd, J=13.7 Hz, 9.4 Hz, 1H), 2.21-2.28 (m, 1H), 1.61-1.79 (m, 6H), 1.10-1.27 (m, 3H), 0.97-1.10 (m, 2H), 0.65 (d, J=6.9 Hz, 3H).

Step 5:

Phthalimide cleavage of alcohol 88 was performed following the method described in Example 1 except that the reaction mixture was stirred at 40° C. for 18 hrs. The product was purified by flash chromatography using 4% 7N $NH_3$/MeOH in dichloromethane to give Example 73 as a colorless oil. Yield (0.29 g, 80%). $^1$H NMR (400 MHz, DMSO-$d_6$) δ 7.15 (t, J=7.6 Hz, 1H), 6.78-6.80 (m, 2H), 6.73 (ddd, J=1.0 Hz, 2.5 Hz and 8.2 Hz, 1H), 4.30 (d, J=7.4 Hz, 1H), 3.72 (d, J=6.5 Hz, 2H), 2.57-2.59 (m, 2H), 1.57-1.79 (m, 7H), 1.11-1.27 (m, 3H), 0.96-1.08 (m, 2H), 0.59 (d, J=6.9 Hz, 3H); $^{13}$C NMR (100 MHz, DMSO-$d_6$) δ 159.2, 147.4, 129.3, 119.6, 113.4, 113.3, 78.3, 73.2, 46.2, 42.5, 37.9, 26.7, 26.0, 16.9, 15.4; ESI MS m/z 278.2 [M+H]$^+$. Chiral HPLC 97.7% (AUC), $t_R$=8.8 min.

Example 74

Preparation of (1R,2R)-3-amino-1-(3-(cyclohexylmethoxy)phenyl)-2-methylpropan-1-ol

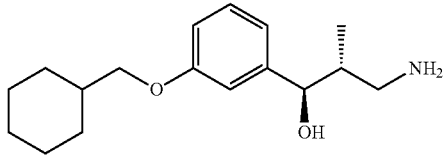 [SMILES: C[C@H](CN)[C@@H](O)c1cccc(OCC2CCCCC2)c1]

3-((1R,2R)-3-Amino-1-(3-(cyclohexylmethoxy)phenyl)-2-methylpropan-1-ol was prepared following the method used in Example 73.

Step 1:

Condensation of (R)-4-benzyl-3-propionyloxazolidin-2-one with aldehyde 13 following the method described in Example 45 gave (S)-4-benzyl-3-((2S,3R)-3-(3-(cyclohexylmethoxy)phenyl)-2-methyl-3-(trimethylsilyloxy)propanoyl)oxazolidin-2-one as a colorless oil. Yield (4.30 g, quant.). $^1$H NMR (400 MHz, DMSO-$d_6$) δ 7.22-7.34 (m, 6H), 6.88-6.93 (m, 2H), 6.81-6.84 (m, 1H), 4.87 (d, J=9.4 Hz, 1H), 4.71 (m, 1H), 4.29 (t, J=8.6 Hz, 1H), 4.12 (dd, J=3.0 Hz, 8.6 Hz, 1H), 4.05 (dd, J=7.0 Hz, 9.4 Hz, 1H), 3.75 (m, 2H), 3.03 (dd, J=3.0 Hz, 13.5 Hz, 1H), 2.91 (dd, J=7.6 Hz, 13.5 Hz, 1H), 1.60-1.79 (m, 6H), 1.08-1.26 (m, 3H), 0.96-1.08 (m, 2H), 0.74 (d, J=7.04 Hz, 3H), −0.10 (s, 9H).

Step 2:

Oxazolidinone cleavage of imide following the method described in Example 73 gave (2R,3R)-3-(3-(cyclohexylmethoxy)phenyl)-2-methyl-3-(trimethylsilyloxy)propan-1-ol as colorless oil. Yield (0.77 g, 45%). $^1$H NMR (400 MHz, DMSO-$d_6$) δ 7.16 (t, J=7.8 Hz, 1H), 6.73-6.80 (m, 3H), 4.49 (d, J=7.0 Hz, 1H), 4.30 (t, J=5.3 Hz, 1H), 3.69-3.76 (m, 2H), 3.38-3.43 (m, 1H), 3.22-3.28 (m, 1H), 1.61-1.80 (m, 7H), 1.11-1.27 (m, 3H), 0.96-1.07 (m, 2H), 0.61 (d, J=6.9 Hz, 3H), −0.07 (s, 9H).

Step 3:

Mitsunobu reaction following the method described in Example 73 gave 2-((2S,3S)-3-(3-(cyclohexylmethoxy)phenyl)-2-methyl-3-(trimethylsilyloxy)propyl)isoindoline-1,3-dione as a colorless oil. Yield (0.58 g, 60%). $^1$H NMR (400 MHz, DMSO-$d_6$) δ 7.78 (m, 4H), 7.14 (t, J=8.0 Hz, 1H), 6.80-6.84 (m, 2H), 6.66-6.69 (m, 1H), 4.57 (d, J=6.1 Hz, 1H), 3.63-3.74 (m, 3H), 3.40 (dd, J=13.7 Hz, 9.2 Hz, 1H), 2.25-2.32 (m, 1H), 1.61-1.79 (m, 6H), 1.12-1.27 (m, 3H), 0.96-1.08 (m, 2H), 0.64 (d, J=6.9 Hz, 3H), −0.05 (s, 9H).

Step 4:

TMS deprotection of ether following the method described in Example 73 gave 2-((2S,3S)-3-(3-(cyclohexylmethoxy)phenyl)-3-hydroxy-2-methylpropyl)isoindoline-1,3-dione as a colorless oil. Yield (0.58 g, quant.). The product was taken to the next step without further purification. $^1$H NMR (400 MHz, DMSO-$d_6$) δ 7.76-7.80 (m, 4H), 7.13 (t, J=7.6 Hz, 1H), 6.82-6.86 (m, 2H), 6.65-6.68 (m, 1H), 4.40 (d, J=6.1 Hz, 1H), 3.67-3.74 (m, 3H), 3.40 (dd, J=13.7 Hz, 9.4 Hz, 1H), 2.21-2.28 (m, 1H), 1.61-1.79 (m, 6H), 1.10-1.27 (m, 3H), 0.97-1.10 (m, 2H), 0.65 (d, J=6.9 Hz, 3H).

Step 5:

Phthalimide cleavage of imide was performed following the method described in Example 73 to give Example 74 as a colorless oil. Yield 0.232 g (69%). $^1$H NMR (400 MHz, DMSO-$d_6$) δ 7.15 (t, J=7.6 Hz, 1H), 6.78-6.80 (m, 2H), 6.73 (ddd, J=1.0 Hz, 2.5 Hz and 8.2 Hz, 1H), 4.30 (d, J=7.4 Hz, 1H), 3.72 (d, J=6.5 Hz, 2H), 2.57-2.59 (m, 2H), 1.57-1.79 (m, 7H), 1.11-1.27 (m, 3H), 0.96-1.08 (m, 2H), 0.59 (d, J=6.9 Hz, 3H); $^{13}$C NMR (100 MHz, DMSO-$d_6$) δ 159.2, 147.4, 129.3, 119.6, 113.4, 113.3, 78.3, 73.2, 46.2, 42.5, 37.9, 26.7, 26.0, 16.9, 15.4; ESI MS m/z 278.3 [M+H]$^+$. Chiral HPLC 97.5% (AUC), $t_R$=8.3 min.

Example 75

Preparation of (1R,2S)-3-amino-1-(3-(cyclohexylmethoxy)phenyl)-2-methylpropan-1-ol

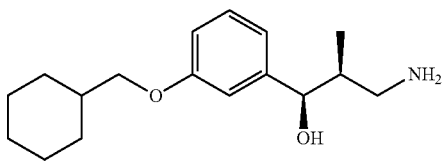 [SMILES: C[C@@H](CN)[C@@H](O)c1cccc(OCC2CCCCC2)c1]

3-((1R,2S)-3-Amino-1-(3-(cyclohexylmethoxy)phenyl)-2-methylpropan-1-ol was prepared following the method shown in Scheme 25.

SCHEME 25

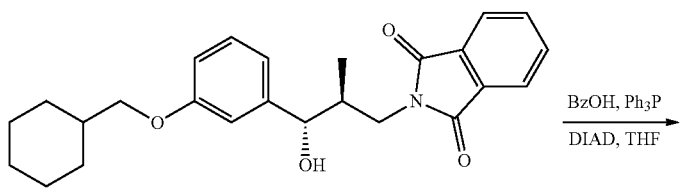

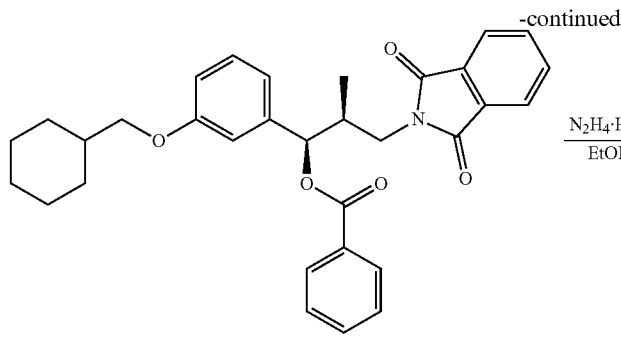

89

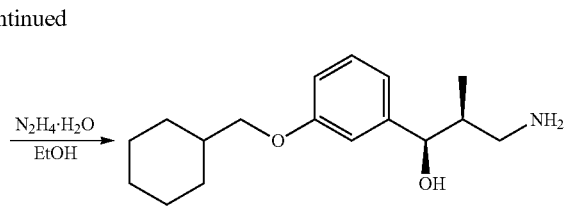

Step 1.

To a cold (0° C.) solution of Ph$_3$P (0.315 g, 1.20 mmol) in anhydrous THF (3 mL) was added a solution of DIAD (0.252 g, 1.24 mmol) in anhydrous THF (3 mL) under Ar. The reaction mixture was stirred at 0° C. for 5 mins after which white precipitate of Ph$_3$P-DIAD complex formed. To this suspension a solution of 2-((2S,3S)-3-(3-(cyclohexylmethoxy)phenyl)-3-hydroxy-2-methylpropyl)isoindoline-1,3-dione (88) (0.403 g, 0.99 mmol) in anhydrous THF (3 mL) was added followed by a solution of benzoic acid (0.134 g, 1.10 mmol) in anhydrous THF (3 mL). An additional amount in THF (2 mL) was added to reaction mixture which was stirred at 0° C. for 20 mins, and allowed to warm to room temperature over 30 mins. The mixture was concentrated under reduced pressure, and the residue was purified by flash chromatography (10 to 100% EtOAc/hexane gradient) to give benzoate 89 as a white foam. Yield (0.316 g, 63%). $^1$H NMR (400 MHz, DMSO-d$_6$) δ 8.00-8.03 (m, 2H), 7.76-7.80 (m, 4H), 7.63-7.68 (m, 1H), 7.50-7.54 (m, 2H), 7.18 (t, J=8.0 Hz, 1H), 6.83-6.85 (m, 2H), 6.72-6.76 (m, 1H), 5.81 (d, J=4.5 Hz, 1H), 3.68-3.74 (m, 3H), 3.50 (dd, J=6.8 Hz, 13.9 Hz, 1H), 2.50-2.53 (m, 1H), 1.58-1.75 (m, 6H), 1.06-1.24 (m, 3H), 0.95-1.02 (m, 2H), 0.93 (d, J=6.9 Hz, 3H).

Step 2.

Deprotection of imidobenzoate 89 following the method described in Example 33 except that 5× molar excess of hydrazine monohydrate was used gave Example 75 as a colorless oil. Yield (0.030 g, 15%). $^1$H NMR (400 MHz, DMSO-d$_6$) δ 7.15 (t, J=8.0 Hz, 1H), 6.78-6.81 (m, 2H), 6.88-6.72 (m, 1H), 4.60 (d, J=4.1 Hz, 1H), 3.71 (d, J=6.5 Hz, 2H), 2.56 (dd, J=6.3 Hz, 12.5 Hz, 1H), 2.40 (dd, J=6.1 Hz, 12.5 Hz, 1H), 1.50-1.84 (m, 7H), 1.08-1.27 (m, 4H), 0.96-1.07 (m, 2H), 0.66 (d, J=6.9 Hz, 3H). ESI MS m/z 278.6 [M+H]$^+$. Chiral HPLC: 97.8%, t$_R$=9.13 min.

Example 76

Preparation of (1S,2R)-3-amino-1-(3-(cyclohexylmethoxy)phenyl)-2-methylpropan-1-ol

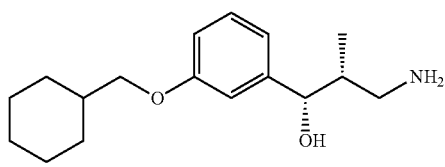 [SMILES: C[C@H](CN)[C@H](O)c1cccc(OCC2CCCCC2)c1]

(1S,2R)-3-amino-1-(3-(cyclohexylmethoxy)phenyl)-2-methylpropan-1-ol was prepared following the method described for Example 75.

Step 1:

Mitsunobu reaction following the method described in Example 75 gave (1S,2R)-1-(3-(cyclohexylmethoxy)phenyl)-3-(1,3-dioxoisoindolin-2-yl)-2-methylpropyl benzoate as a white foam. Yield (0.456 g, 76%). $^1$H NMR (400 MHz, DMSO-d$_6$) δ 8.00-8.03 (m, 2H), 7.76-7.80 (m, 4H), 7.63-7.68 (m, 1H), 7.50-7.54 (m, 2H), 7.18 (t, J=8.0 Hz, 1H), 6.83-6.85 (m, 2H), 6.72-6.76 (m, 1H), 5.81 (d, J=4.5 Hz, 1H), 3.68-3.74 (m, 3H), 3.50 (dd, J=6.8 Hz, 13.9 Hz, 1H), 2.50-2.53 (m, 1H), 1.58-1.75 (m, 6H), 1.06-1.24 (m, 3H), 0.95-1.02 (m, 2H), 0.93 (d, J=6.9 Hz, 3H).

Step 2:

Deprotection of (1S,2R)-1-(3-(cyclohexylmethoxy)phenyl)-3-(1,3-dioxoisoindolin-2-yl)-2-methylpropyl benzoate following the method described in Example 75 gave N-((2R,3S)-3-(3-(cyclohexylmethoxy)phenyl)-3-hydroxy-2-methylpropyl)benzamide as a colorless oil. Yield (0.179 g, 52%). $^1$H NMR (400 MHz, DMSO-d$_6$) δ 8.37 (t, J=5.7 Hz, 1H), 7.77-7.82 (m, 2H), 7.39-7.52 (m, 3H), 7.17 (t, J=15.7 Hz, 1H), 6.80-6.87 (m, 2H), 6.70-6.74 (m, 1H), 5.14 (d, J=4.7 Hz, 1H), 4.56 (t, J=4.3 Hz, 1H), 3.72 (d, J=6.3 Hz, 2H), 3.24-3.32 (m, 1H), 3.10-3.18 (m, 1H), 1.95-2.05 (m, 1H), 1.58-1.80 (m, 6H), 1.08-1.28 (m, 3H), 0.94-1.58 (m, 2H), 0.69 (d, J=6.9 Hz, 3H).

Step 3:

A mixture of N-((2R,3S)-3-(3-(cyclohexylmethoxy)phenyl)-3-hydroxy-2-methylpropyl)benzamide (0.179 g, 0.47 mmol), hydrazine monohydrate (0.2 mL), aqueous solution of NaOH (50% w/w, 0.5 mL) and NaOEt (30% in MeOH, 1 mL) was heated at 60° C. under argon for 6 days. The reaction mixture was concentrated under reduced pressure, brine added and the product was extracted into MTBE. The mixture was concentrated under reduced pressure and the residue was purified by flash chromatography (5% 7N NH/MeOH in CH$_2$Cl$_2$) to give Example 76 as a colorless oil. Yield (0.049 g, 38%). $^1$H NMR (400 MHz, DMSO-d$_6$) δ 7.15 (t, J=8.0 Hz, 1H), 6.78-6.81 (m, 2H), 6.88-6.72 (m, 1H), 4.60 (d, J=4.1 Hz, 1H), 3.71 (d, J=6.5 Hz, 2H), 2.56 (dd, J=6.3 Hz, 12.5 Hz, 1H), 2.40 (dd, J=6.1 Hz, 12.5 Hz, 1H), 1.50-1.84 (m, 7H), 1.08-1.27 (m, 4H), 0.96-1.07 (m, 2H), 0.66 (d, J=6.9 Hz, 3H); ESI MS 278.5 [M+H]$^+$. Chiral HPLC: 92.6%, t$_R$=10.0 min.

Example 77

Preparation of N-(3-(3-(cyclohexylmethoxy)phenyl)-3-hydroxypropyl)-2-(2-(2-methoxyethoxy)ethoxy)acetamide

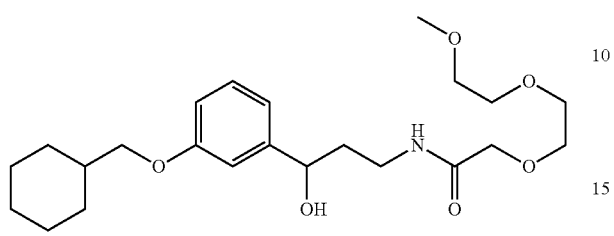

N-(3-(3-(Cyclohexylmethoxy)phenyl)-3-hydroxypropyl)-2-(2-(2-methoxyethoxy)ethoxy)acetamide was prepared following the method shown in Scheme 26.

SCHEME 26

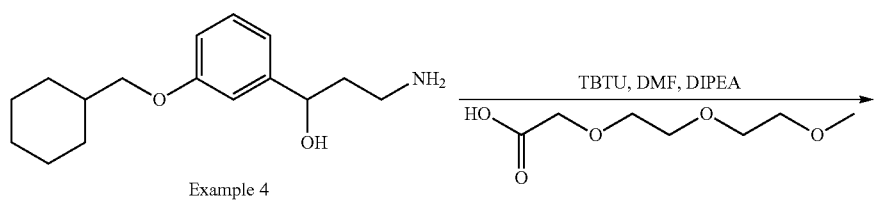

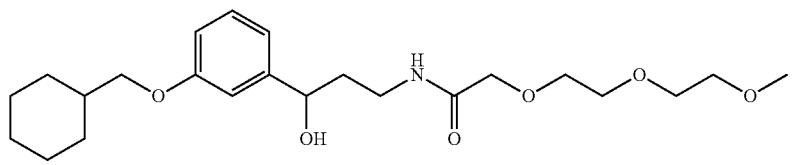

Step 1:

To a mixture of 2-(2-(2-methoxyethoxy)ethoxy)acetic acid (0.6 g, 3.34 mmol), TBTU (1.2 g, 4.0 mmol) and DIPEA (1.3 ml, 4.0 mmol) in DMF (20 ml) was added 3-amino-1-(3-(cyclohexylmethoxy)phenyl)propan-1-ol (1.0 g, 3.34 mmol). The resulting mixture was stirred for 18 hr at room temperature. The reaction mixture was then diluted with ethyl acetate (100 ml), washed with water (2×100 ml), brine (100 ml), dried (Na$_2$SO$_4$) and concentrated under reduced pressure. Purification by flash chromatography (10 to 50% EtOAc-hexanes gradient) gave Example 77 as a colorless oil. Yield (0.7 g, 50%): $^1$H NMR (400 MHz, DMSO-d$_6$) δ 7.65 (t, J=5.6 Hz, 1H), 7.17 (t, J=7.6 Hz, 1H), 6.82-6.85 (m, 2H), 6.72-6.75 (m, 1H), 5.22 (d, J=4.8 Hz, 1H), 4.48-4.52 (m, 1H), 3.82 (s, 2H), 3.72 (d, J=6.4 Hz, 2H), 3.42-3.52 (m, 2H), 3.39-3.41 (m, 2H), 3.30 (s, 3H), 3.12-3.17 (m, 2H), 2.86 (s, 2H), 2.66 (s, 2H), 1.61-1.79 (m, 8H), 1.08-1.28 (m, 3H), 0.98-1.06 (m, 2H).

Example 78

Preparation of 3-(3-(cyclohexylmethoxy)phenyl)but-3-en-1-amine

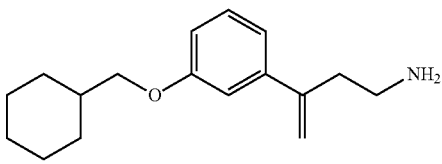 [SMILES: C=C(CCN)c1cccc(OCC2CCCCC2)c1]

3-(3-(Cyclohexylmethoxy)phenyl)but-3-en-1-amine was prepared following the method shown in Scheme 27.

SCHEME 27

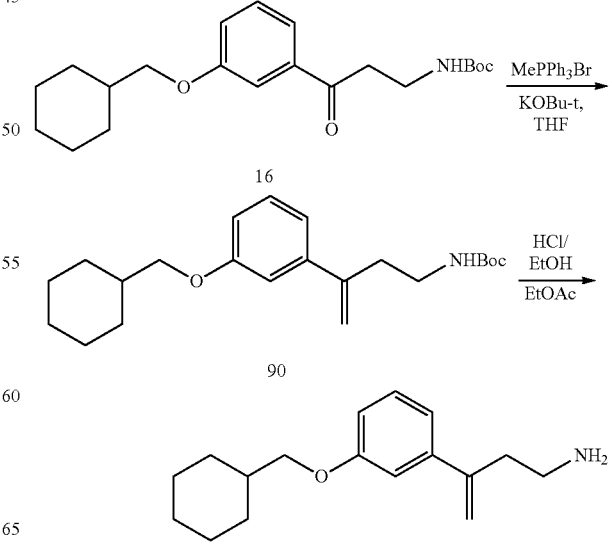

Step 1:

To a suspension of the methyltriphenylphosponium bromide (1.2 g, 3.32 mmol) in THF (10 ml) was added KOBu-t (1 M in THF, 6.1 mmol) at room temperature. After stirring for 30 mins, compound 16 (1.0 g, 2.77 mmol) was added. The resulting mixture was stirred at room temperature for 18 hrs and added AcOH (0.18 g, 2.77 mmol). The mixture was filtered and concentrated under reduced pressure. Purification by flash chromatography (15 to 50% EtOAc-hexanes gradient) gave olefin 90 as a colorless oil. Yield (0.56 g, 56%): $^1$H NMR (400 MHz, CDCl$_3$) δ 7.22 (t, J=7.6 Hz, 1H), 6.91-6.96 (m, 2H), 6.79-6.81 (m, 1H), 5.35 (d, J=1.2 Hz, 1H), 5.08 (d, J=1.2 Hz, 1H), 4.51 (bs, 1H), 3.75 (d, J=6.4 Hz, 2H), 2.67 (t, J=7.8 Hz, 2H), 1.66-1.91 (m, 7H), 1.42 (s, 9H), 1.15-1.35 (m, 4H), 1.01-1.10 (m, 2H).

Step 2:

Deprotection of tert-butyl 3-(3-(cyclohexylmethoxy)phenyl)but-3-enylcarbamate following the method used in Example 5 gave Example 78 as a white solid. Yield (0.1 g, 82%): $^1$H NMR (400 MHz, DMSO-d$_6$) δ 7.82 (bs, 3H), 7.25 (t, J=8.0 Hz, 1H), 6.85-7.03 (m, 3H), 5.46 (s, 1H), 5.14 (s, 1H), 3.76 (d, J=6.4 Hz, 2H), 2.79-2.88 (m, 2H), 2.74 (t, J=6.8 Hz, 2H), 1.60-1.84 (m, 6H), 1.13-1.28 (m, 3H), 0.98-1.08 (m, 2H).

Example 79

Preparation of 4-amino-2-(3-(cyclohexylmethoxy)phenyl)butane-1,2-diol

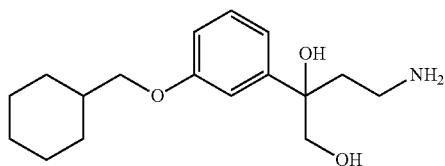 [SMILES: NCCC(O)(CO)c1cccc(OCC2CCCCC2)c1]

4-Amino-2-(3-(cyclohexylmethoxy)phenyl)butane-1,2-diol was prepared following the method shown in Scheme 28.

Step 1:

Epoxidation of tert-butyl 3-(3-(cyclohexylmethoxy)phenyl)but-3-enylcarbamate (90) following the method used in Example 10 gave tert-butyl 2-(2-(3-(cyclohexylmethoxy)phenyl)oxiran-2-yl)ethylcarbamate (91) as a colorless oil. Yield (0.07 g, 64%): $^1$H NMR (400 MHz, DMSO-d$_6$) δ 7.22 (t, J=7.6 Hz, 1H), 6.86-6.90 (m, 2H), 6.79-6.82 (m, 1H), 6.37 (t, J=5.4 Hz, 1H), 3.74 (d, J=6.4 Hz, 2H), 2.93 (d, J=6.4 Hz, 1H), 2.89 (qt, J=5.6 Hz, 2H), 2.66 (d, J=5.2 Hz, 1H), 2.18-2.26 (m, 1H), 1.61-1.84 (m, 7H), 1.33 (s, 9H), 1.13-1.24 (m, 4H), 0.98-1.08 (m, 2H).

Step 2:

To a mixture of tert-butyl 2-(2-(3-(cyclohexylmethoxy)phenyl)oxiran-2-yl)ethylcarbamate (91) (0.04 g, 0.11 mmol) in DCM (3 ml) was added water (0.1 ml) and TFA (0.8 ml). The resulting mixture was stirred for 2 hr at room temperature and concentrated under reduced pressure. Purification by flash chromatography (15% 7M NH$_3$ in Methanol-DCM) gave Example 79 as a colorless oil. Yield (0.03 g, 93%): $^1$H NMR (400 MHz, MeOD) δ 7.28 (t, J=8.4 Hz, 1H), 6.90-6.93 (m, 2H), 6.84-6.87 (m, 1H), 3.76 (d, J=6.0 Hz, 2H), 3.65 (d, J=6.8 Hz, 2H), 3.19-3.26 (m, 1H), 2.86-2.95 (m, 1H), 2.30-2.39 (m, 2H), 1.67-1.89 (m, 7H), 1.20-1.48 (m, 4H), 1.02-1.13 (m, 2H).

Example 80

Preparation of 4-amino-2-(3-(cyclohexylmethoxy)phenyl)butan-1-ol

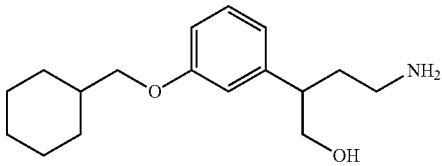 [SMILES: NCCC(CO)c1cccc(OCC2CCCCC2)c1]

4-Amino-2-(3-(cyclohexylmethoxy)phenyl)butan-1-ol was prepared following the method shown in Scheme 29.

SCHEME 28

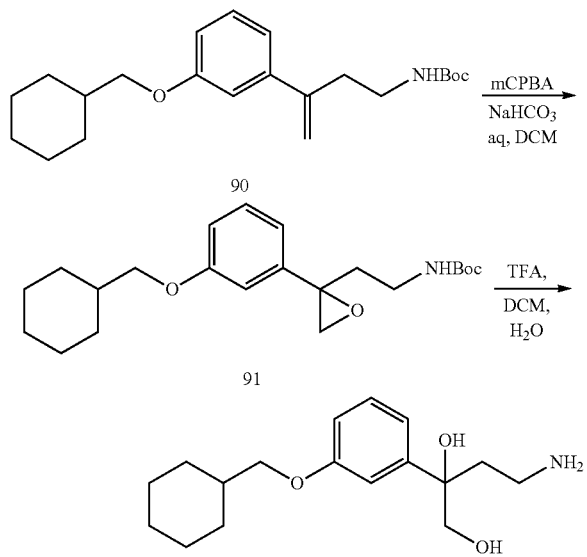

SCHEME 29

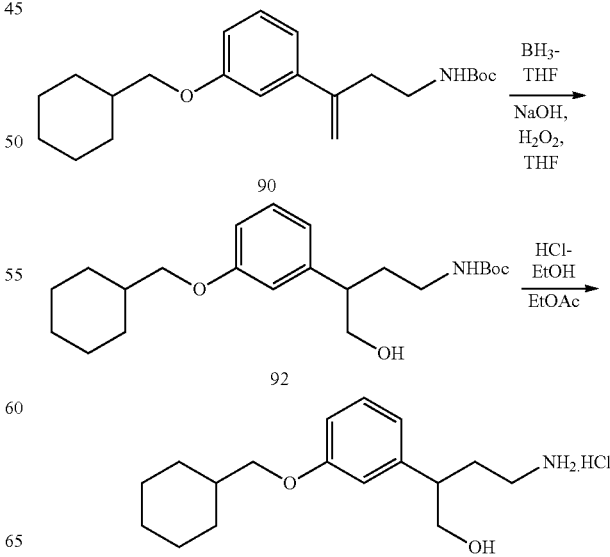

Step 1:

To a solution of tert-butyl 3-(3-(cyclohexylmethoxy)phenyl)but-3-enylcarbamate (90) (0.32 g, 0.89 mmol) in THF (10 ml) was added BH$_3$ (1 M in THF, 2.4 ml, 2.4 mmol) at room temperature. After stirring for 4 hr, aqueous NaOH (1 M, 6.0 ml, 6.0 mmol) was added and the mixture was stirred at 60° C. for 2.5 hrs and room temperature for 18 hr. The mixture was added H$_2$O$_2$ (6 ml, 30%) and stirred at 50° C. for 2 hr. The reaction mixture was extracted with ethyle acetate (2×50 ml). Ethyle acetate part was washed with brine (50 ml), dried (Na$_2$SO$_4$) and concentrated under reduced pressure. Purification by flash chromatography (30 to 75% EtOAc-hexanes gradient) gave tert-butyl 3-(3-(cyclohexylmethoxy)phenyl)-4-hydroxybutylcarbamate (92) as a colorless oil. Yield (0.2 g, 60%): $^1$H NMR (400 MHz, MeOD) δ 7.17 (t, J=8.0 Hz, 1H), 6.73-6.78 (m, 3H), 3.74 (d, J=6.4 Hz, 2H), 3.58-3.68 (m, 2H), 2.91 (t, J=7.8 Hz, 2H), 2.66-2.76 (m, 1H), 1.85-2.00 (m, 3H), 1.67-1.78 (m, 5H), 1.39 (s, 9H), 1.20-1.35 (m, 3H), 1.01-1.14 (m, 2H).

Step 2:

Deprotection of tert-butyl 3-(3-(cyclohexylmethoxy)phenyl)-4-hydroxybutylcarbamate (92) following the method used in Example 5 gave Example 80 hydrochloride as a white solid. Yield (0.06 g, 72%): $^1$H NMR (400 MHz, MeOD) δ 7.21 (t, J=8.2 Hz, 1H), 6.76-6.83 (m, 3H), 3.74 (d, J=6.4 Hz, 2H), 3.60-3.72 (m, 2H), 2.70-2.78 (m, 3H), 2.12-2.21 (m, 1H), 1.68-1.98 (m, 7H), 1.20-1.46 (m, 3H), 1.02-1.14 (m, 2H).

Example 81

Preparation of 3-(3-(cyclohexylmethoxy)phenyl)butan-1-amine

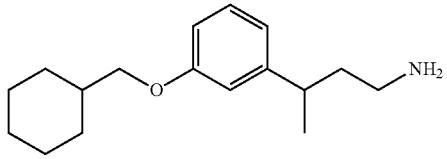

3-(3-(Cyclohexylmethoxy)phenyl)butan-1-amine was prepared following the methods used in Examples 10 and 5.

Step 1:

Hydrogenation of tert-butyl 3-(3-(cyclohexylmethoxy)phenyl)but-3-enylcarbamate following the method used in Example 10 gave tert-butyl 3-(3-(cyclohexylmethoxy)phenyl)butylcarbamate as a colorless oil. Yield (0.23 g, 92%): $^1$H NMR (400 MHz, CDCl$_3$) δ 7.17 (t, J=8.2 Hz, 1H), 6.68-6.75 (m, 3H), 3.69-3.74 (m, 4H), 2.95-3.08 (m, 2H), 2.65-2.74 (m, 1H), 1.65-1.86 (m, 7H), 1.41 (s, 9H), 1.15-1.35 (m, 3H), 0.98-1.09 (m, 2H).

Step 2:

Deprotection of tert-butyl 3-(3-(cyclohexylmethoxy)phenyl)butylcarbamate following the method used in Example 5 gave Example 83 hydrochloride as a white solid. Yield (0.07 g, 90%): $^1$H NMR (400 MHz, DMSO-d$_6$) δ 7.67 (bs, 3H), 7.18 (t, J=8.0 Hz, 1H), 6.71-6.76 (m, 3H), 3.72 (d, J=6.4 Hz, 2H), 2.70-2.75 (m, 1H), 1.60-1.82 (m, 8H), 1.10-1.26 (m, 6H), 0.96-1.06 (m, 2H).

Example 82

Preparation of 2-(3-(4-methoxybutoxy)phenoxy)ethanamine

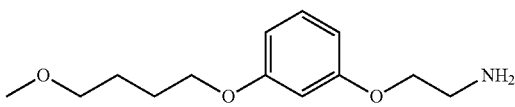

2-(3-(4-Methoxybutoxy)phenoxy)ethanamine was prepared following the method described in Example 7.

Step 1:

Mitsunobu reaction of phenol 24 with 4-methoxybutanol gave 2-(2-(3-(4-methoxybutoxy)phenoxy)ethyl)isoindoline-1,3-dione as yellow oil. Yield (0.58 g, 44%): $^1$H NMR (400 MHz, CDCl$_3$) δ 7.85-7.88 (m, 2H), 7.71-7.74 (m, 2H), 7.11 (t, J=8.4 Hz, 1H), 6.42-6.47 (m, 3H), 4.20 (t, J=5.6 Hz, 2H), 4.10 (t, J=5.6 Hz, 2H), 3.92 (t, J=6 Hz, 2H), 3.42 (t, J=6 Hz, 2H), 3.34 (s, 3H), 1.74-1.86 (m, 2H), 1.6-1.74 (m, 2H).

Step 2:

Phthalimide cleavage of 2-(2-(3-(4-methoxybutoxy)phenoxy) ethyl) isoindoline-1,3-dione gave Example 82 as pale yellow oil. Yield (0.241 g, 66%). $^1$H NMR (400 MHz, DMSO-d$_6$) δ 7.14 (t, J=8 Hz, 1H), 6.45-6.51 (m, 3H), 3.93 (t, J=6.4 Hz, 2H), 3.87 (t, J=5.6 Hz, 2H), 3.35 (t, J=6.4 Hz, 2H), 3.23 (s, 3H), 2.84 (t, J=5.6 Hz, 2H), 1.71-1.86 (m, 2H), 1.58-1.71 (m, 2H). $^{13}$C NMR (100 MHz, DMSO-d$_6$) 159.9, 159.8, 129.9, 106.7, 106.6, 101.1, 71.5, 70.2, 67.1, 57.8, 40.9, 25.6, 25.5. MS: 240 [M+1]$^+$.

Example 83

Preparation of 3-amino-1-(3-((tetrahydro-2H-pyran-2-yl)methoxy)phenyl)propan-1-ol

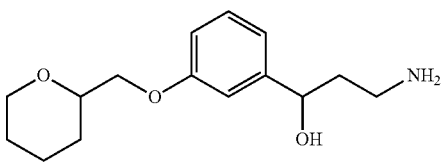 [SMILES: NCCC(O)c1cccc(OCC2CCCCO2)c1]

3-Amino-1-(3-((tetrahydro-2H-pyran-2-yl)methoxy)phenyl)propan-1-ol was prepared following the method used in Example 34.

Step 1:

Alkylation of 3-bromobenzaldehyde with methanesulfonic acid tetrahydro-pyran-2-ylmethyl ester gave 3-((tetrahydro-2H-pyran-2-yl)methoxy) benzaldehyde as a clear oil. Yield (1.4 g, 77%): $^1$H NMR (400 MHz, CDCl$_3$) δ 9.96 (s, 1H), 7.39-7.47 (m, 3H), 7.20-7.25 (m, 1H), 3.92-4.09 (m, 4H), 3.39-3.77 (m, 1H), 1.89-1.94 (m, 1H), 1.42-1.71 (m, 5H).

Step 2:

Addition of acetonitrile to 3-((tetrahydro-2H-pyran-2-yl)methoxy)benzaldehyde gave 3-hydroxy-3-(3-((tetrahydro-2H-pyran-2-yl)methoxy)phenyl)propanenitrile as a yellow oil. Yield (1.1 g, 66%): $^1$H NMR (400 MHz, CDCl$_3$) δ 7.26-7.31 (m, 1H), 6.93-6.99 (m, 2H), 6.87-6.92 (m, 1H), 4.97-5.03 (m, 1H), 3.68-4.01 (m, 4H), 3.47-3.55 (m, 1H), 2.75 (d, J=6.4, 2H), 1.90-1.93 (m, 1H), 1.43-1.71 (m, 5H).

Step 3:

Reduction of 3-hydroxy-3-(3-((tetrahydro-2H-pyran-2-yl)methoxy)phenyl)propanenitrile with BH$_3$.DMS gave Example 83 as a colorless oil. Yield (0.59 g, 53%): $^1$H NMR (400 MHz, DMSO-d$_6$) δ 7.15-7.21 (m, 1H), 6.84-6.88 (m, 2H), 6.73-6.77 (m, 1H), 4.62 (t, J=6.2, 1H), 3.85-3.91 (m, 3H), 3.58-362 (m, 1H), 3.32-3.42 (m, 1H), 2.55-2.68 (m, 2H), 1.79-1.83 (m, 1H), 1.25-1.66 (m, 7H). $^{13}$C NMR (100 MHz, DMSO-d$_6$) δ 158.4, 148.3, 128.9, 117.9, 112.4, 111.7, 75.4, 71.2, 70.8, 67.3, 42.4, 40.1, 27.7, 25.5, 22.6. MS: 266 [M+1]$^+$.

Example 84

Preparation of 2-(3-(2,6-dichlorobenzyloxy)phenoxy)ethanamine

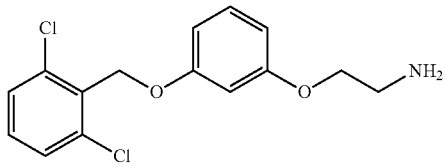 [SMILES: NCCOc1cccc(OCc2c(Cl)cccc2Cl)c1]

2-(3-(2,6-Dichlorobenzyloxy)phenoxy)ethanamine was prepared following the method described in Example 94.

Step 1:

Alkylation reaction of phenol 24 with 2,6-dichlorobenzyl bromide gave 2-(2-(3-(2,6-dichlorobenzyloxy)phenoxy)ethyl)isoindoline-1,3-dione as yellow oil. Yield (0.73 g, 47%): $^1$H NMR (400 MHz, CDCl$_3$) δ 7.85-7.88 (m, 2H), 7.71-7.82 (m, 2H), 7.32-7.36 (m, 2H), 7.22 (d, J=8.4 Hz, 2H), 7.15-7.19 (m, 1H), 6.60 (d, J=8.4 Hz, 2H), 6.58 (s, 1H), 6.52 (d, J=8.0 Hz, 2H), 5.22 (s, 2H), 4.22 (d, J=5.6 Hz, 2H), 4.11 (t, J=5.6 Hz, 2H).

Step 2:

Phthalimide cleavage of 2-(2-(3-(2,6-dichlorobenzyloxy) phenoxy) ethyl)isoindoline-1,3-dione gave Example 84 as yellow oil. Yield (0.27 g, 53%): $^1$H NMR (400 MHz, DMSO-d$_6$) δ 7.55-7.58 (m, 2H), 7.45-7.49 (m, 1H), 7.18-7.22 (m, 1H), 6.62-6.64 (m, 2H), 6.56 (dd, J=8.0, 2.0 Hz, 1H), 5.20 (s, 2H), 3.90 (t, J=5.8 Hz, 2H), 2.85 (t, J=5.8 Hz, 2H), $^{13}$C NMR (100 MHz, DMSO-d$_6$) δ 160.0, 159.6, 136.0, 131.7, 131.5, 130.0, 128.8, 107.4, 106.7, 101.3, 70.2, 64.9, 40.9. MS: 312 [M+1]$^+$.

Example 85

Preparation of 2-(3-(3-methoxypropoxy)phenoxy)ethanamine

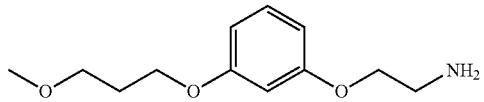 [SMILES: COCCCOc1cccc(OCCN)c1]

2-(3-(3-Methoxypropoxy)phenoxy)ethanamine was prepared following the method described in Example 94.

Step 1:

Alkylation reaction of phenol 24 with methanesulfonic acid 3-methoxy-propyl ester gave 2-(2-(3-(3-methoxypropoxy)phenoxy)ethyl)isoindoline-1,3-dione as yellow oil. Yield (1.1 g, 88%): $^1$H NMR (400 MHz, CDCl$_3$) δ 7.85-7.87 (m, 2H), 7.71-7.74 (m, 2H), 7.10-7.14 (m, 1H), 6.43-6.49 (m, 3H), 4.19 (t, J=6.0 Hz, 2H), 4.10 (t, J=5.2 Hz, 2H), 3.98 (t, J=6.4 Hz, 2H), 3.53 (t, J=6.0 Hz, 2H), 3.34 (s, 3H), 1.92-2.04 (m, 2H).

Step 2:

Phthalimide cleavage of 2-(2-(3-(3-methoxypropoxy) phenoxy) ethyl)isoindoline-1,3-dione gave Example 85 as yellow oil. Yield (0.209 g, 33%): $^1$H NMR (400 MHz, DMSO-d$_6$) δ 7.12-7.17 (m, 1H), 6.45-6.50 (m, 3H), 3.98 (t, J=6.4 Hz, 2H), 3.87 (t, J=6.0 Hz, 2H), 3.45 (t, J=6.0 Hz, 2H), 3.24 (s, 3H), 2.84 (t, J=5.6 Hz, 2H), 1.89-1.95 (m, 2H). $^{13}$C NMR (100 MHz, DMSO-d$_6$) δ 159.9, 159.8, 129.9, 106.7, 106.6, 101.1, 70.2, 68.5, 64.5, 57.9, 41.0, 28.9. MS: 226 [M+1]$^+$.

Example 86

Preparation of 3-amino-1-(3-(2-methoxyethoxy)phenyl)propan-1-ol

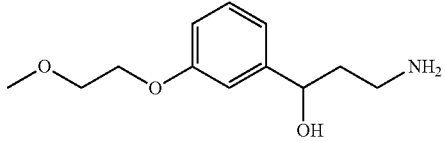 [SMILES: COCCOc1cccc(C(O)CCN)c1]

3-Amino-1-(3-(2-methoxyethoxy)phenyl)propan-1-ol was prepared following the method described in Example 54.

Step 1:

Alkylation of 3-hydroxybenzaldehyde with methanesulfonic acid 2-methoxy-ethyl ester gave 3-(2-methoxyethoxy)benzaldehyde as a clear oil. Yield (0.96 g, 66%): $^1$H NMR (400 MHz, CDCl$_3$) δ 9.97 (s, 1H), 7.41-7.48 (m, 3H), 7.22-7.24 (m, 1H), 4.18 (t, J=4.8 Hz, 2H), 3.78 (t, J=4.8 Hz, 2H), 3.47 (s, 3H).

Step 2:

Addition of acetonitrile to 3-(2-methoxy-ethoxy)benzaldehyde gave 3-(3-(2-methoxy-ethoxy)-phenyl)-3-hydroxy-propionitrile as yellow oil. Yield (1.4 g, 63%): $^1$H NMR (400 MHz, CDCl$_3$) δ 7.27-7.32 (m, 1H), 6.95-7.0 (m, 2H), 6.91 (dd, J=8.0, 1.8 Hz, 1H), 5.0 (t, J=6.2 Hz, 1H), 4.12 (t, J=4.8 Hz, 2H), 3.76 (t, J=4.8 Hz, 2H), 3.48 (s, 3H), 2.75 (d, J=6.2 Hz, 2H).

Step 3:

Reduction of 3-(3-(2-methoxy-ethoxy)-phenyl)-3-hydroxy-propionitrile with BH$_3$-DMS gave Example 86 as colorless oil. Yield (0.45 g, 36%): $^1$H NMR (400 MHz, DMSO-d$_6$) δ 7.18-7.22 (m, 1H), 6.86-6.89 (m, 2H), 6.76 (dd, J=8.4, 2.0 Hz, 1H), 4.63 (t, J=6.4 Hz, 1H), 4.06 (t, J=5.2 Hz, 1H), 3.65 (t, J=5.2 Hz, 2H), 3.30 (s, 3H), 2.58-2.66 (m, 2H), 1.60-1.65 (m, 2H). $^{13}$C NMR (100 MHz, DMSO-d$_6$) δ 158.3, 148.3, 129.0, 118.0, 112.4, 111.7, 71.2, 70.4, 66.7, 58.2, 42.3. MS: 226 [M+1]$^+$.

Example 87

Preparation of 3-amino-1-(3-(pentyloxy)phenyl)propan-1-ol

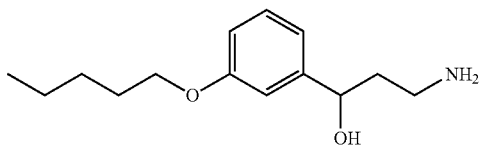 [SMILES: CCCCCOc1cccc(C(O)CCN)c1]

3-Amino-1-(3-(pentyloxy)phenyl)propan-1-ol was prepared following the method described in Example 34.

Step 1:

Alkylation of 3-hydroxybenzaldehyde (11) with 1-bromopentane gave 3-pentyloxybenzaldehyde as a clear oil. Yield (1.65 g, 69%): $^1$H NMR (400 MHz, CDCl$_3$) δ 9.97 (s, 1H), 7.42-7.45 (m, 2H), 7.37-7.39 (m, 1H), 7.15-7.19 (m, 1H), 4.01 (t, J=6.4 Hz, 2H), 1.78-1.85 (m, 2H), 1.34-1.50 (m, 4H), 0.95 (t, J=6.8 Hz, 3H).

Step 2:

Addition of acetonitrile to 3-pentyloxybenzaldehyde gave 3-hydroxy-3-(3-pentyloxyphenyl)propionitrile as a yellow oil. Yield (1.11 g, 67%): $^1$H NMR (400 MHz, CDCl$_3$) δ 7.30 (d, J=7.6 Hz, 1H), 6.92-6.98 (m, 2H), 6.87 (d, J=7.6 Hz, 1H), 5.02 (m, 1H), 3.98 (t, J=6.4 Hz, 2H), 2.76 (d, J=6.0 Hz, 2H), 1.75-1.83 (m, 2H), 1.32-1.49 (m, 4H), 0.92 (t, J=6.8 Hz, 3H).

Step 3:

Reduction of 3-hydroxy-3-(3-pentyloxyphenyl)propionitrile with Raney-Ni gave Example 87 as a colorless oil. Yield (0.310 g, 28%): $^1$H NMR (400 MHz, DMSO-d$_6$) δ 7.16-7.21 (m, 1H), 6.84-6.88 (m, 2H), 6.74 (d, J=7.6 Hz, 1H), 4.62 (t, J=6.4 Hz, 1H), 3.93 (t, J=6.4 Hz, 2H), 2.57-2.65 (m, 2H), 1.67-1.73 (m, 2H), 1.60-1.66 (m, 2H), 1.30-1.43 (m, 4H), 0.90 (t, J=6.8 Hz, 3H). $^{13}$C NMR (100 MHz, DMSO-d$_6$) δ 158.5, 148.2, 128.9, 117.7, 112.3, 111.7, 71.2, 67.2, 42.4, 38.9, 28.4, 27.7, 21.9, 13.9. MS: 238 [M+1]$^+$.

Example 88

Preparation of 3-amino-1-(3-(4-methoxybutoxy)phenyl)propan-1-ol

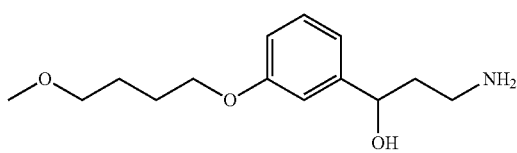 [SMILES: COCCCCOc1cccc(C(O)CCN)c1]

3-Amino-1-(3-(4-methoxybutoxy)phenyl)propan-1-ol was prepared following the method described in Example 34.

Example 89

Preparation of 2-(3-(3-phenylpropoxy)phenoxy)ethanamine

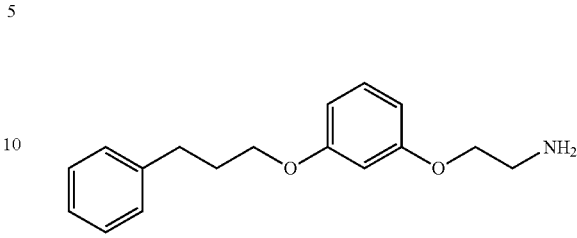

2-(3-(3-Phenylpropoxy)phenoxy)ethanamine was prepared following the method described in Example 94.

Step 1:

Alkylation reaction of phenol 24 with 1-bromo-3-phenylpropane gave 2-(2-(3-(3-phenylpropoxy)phenoxy)ethyl)isoindoline-1,3-dione as yellow oil. Yield (1.4 g, 98%): $^1$H NMR (400 MHz, CDCl$_3$) δ 7.84-7.86 (m, 2H), 7.71-7.74 (m, 2H), 7.27-7.32 (m, 1H), 7.16-7.23 (m, 4H), 7.10-7.15 (m, 1H), 6.46-6.49 (m, 2H), 6.42-6.45 (m, 1H), 4.20 (t, J=5.6 Hz, 2H), 4.10 (t, J=5.8 Hz, 2H), 3.91 (t, J=5.8 Hz, 2H), 2.78 (t, J=8.0 Hz, 2H), 2.0-2.09 (m, 2H).

Step 2:

Phthalimide cleavage of 2-(2-(3-(3-phenylpropoxy)phenoxy) ethyl)isoindoline-1,3-dione gave Example 89 as yellow oil. Yield (0.263 g, 25%): $^1$H NMR (400 MHz, DMSO-d$_6$) δ 7.27-7.30 (m, 2H), 7.20-7.24 (m, 2H), 7.16-7.19 (m, 1H), 7.13-7.15 (m, 1H), 6.46-6.51 (m, 3H), 3.93 (t, J=6.4 Hz, 2H), 3.87 (t, J=5.8 Hz, 2H), 2.84 (t, J=5.8 Hz, 2H), 2.73 (t, J=7.6 Hz, 2H), 1.96-2.03 (m, 2H). $^{13}$C NMR (100 MHz, DMSO-d$_6$) δ 159.9, 159.8, 141.4, 129.9, 128.3, 125.8, 106.7, 106.6, 101.1, 70.2, 66.6, 40.9, 31.4, 30.3. MS: 272 [M+1]$^+$.

Example 90

Preparation of 2-(3-(pentyloxy)phenoxy)ethanamine

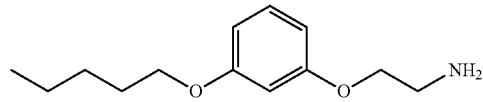 [SMILES: CCCCCOc1cccc(OCCN)c1]

2-(3-(Pentyloxy)phenoxy)ethanamine was prepared following the method described in Example 94.

Step 1:

Alkylation of phenol 24 with pentyl bromide gave 2-(2-(3-(pentyloxy)phenoxy)ethyl)isoindoline-1,3-dione as yellow oil. Yield (1.0 g, 80%): $^1$H NMR (400 MHz, CDCl$_3$) δ 7.84-7.87 (m, 2H), 7.70-7.74 (m, 2H), 7.10-7.14 (m, 1H), 6.42-6.48 (m, 3H), 4.20 (t, J=5.6 Hz, 2H), 4.10 (t, J=5.6 Hz, 2H), 3.89 (t, J=6.6 Hz, 2H), 1.71-1.78 (m, 2H), 1.34-1.45 (m, 4H), 0.92 (t, J=7.2 Hz, 3H).

Step 2:

Phthalimide cleavage of 2-(2-(3-(pentyloxy)phenoxy) ethyl)isoindoline-1,3-dione gave Example 90 as yellow oil. Yield (0.346 g, 38%): $^1$H NMR (400 MHz, DMSO-d$_6$) δ 7.12-7.16 (m, 1H), 6.45-6.49 (m, 3H), 3.92 (t, J=6.6 Hz, 2H), 3.89 (t, J=6.6 Hz, 2H), 2.84 (t, J=5.8 Hz, 2H), 1.65-1.72 (m, 2H), 1.31-1.42 (m, 4H), 0.92 (t, J=7.2 Hz, 3H). $^{13}$C NMR (100 MHz, DMSO-d$_6$) δ 159.9, 159.8, 129.9, 106.6, 106.5, 101.1, 70.2, 67.3, 41.0, 28.4, 27.7, 21.9, 13.9. MS: 224 [M+1]$^+$.

Example 91

Preparation of 3-(3-(2,6-dichlorobenzyloxy)phenyl)propan-1-amine

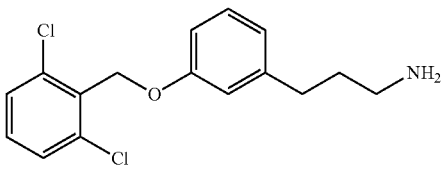

3-(3-(2,6-Dichlorobenzyloxy)phenyl)propan-1-amine was prepared following the method described in Example 59.

Step 1:
Alkylation reaction of phenol 58 with 2,6-dichlorobenzylbromide gave 2-(3-(3-(2,6-dichlorobenzyloxy)phenyl)propyl)isoindoline-1,3-dione as yellow oil. Yield (0.780 g, 51%): $^1$H NMR (400 MHz, CDCl$_3$) δ 7.82-7.85 (m, 2H), 7.69-7.72 (m, 2H), 7.35-7.38 (m, 1H), 6.86-6.79 (m, 2H), 6.81 (s, 1H), 6.80 (dd, J=8.2, 2.4 Hz, 1H), 5.25 (s, 2H), 3.76 (t, J=6.2 Hz, 2H), 2.68 (t, J=7.6 Hz, 2H), 2.00-2.09 (m, 2H).

Step 2:
Phthalimide cleavage of 2-(3-(3-(2,6-dichlorobenzyloxy)phenyl)propyl)isoindoline-1,3-dione gave Example 8 as pale yellow oil. Yield (0.36 g, 59%): $^1$H NMR (400 MHz, DMSO-d$_6$) δ 7.55-7.58 (m, 2H), 7.44-7.49 (m, 1H), 7.19-7.24 (m, 1H), 6.85-6.88 (m, 2H), 6.81-6.84 (m, 2H), 5.20 (s, 2H), 2.50-2.60 (m, 4H), 1.60-1.69 (m, 2H). $^{13}$C NMR (100 MHz, DMSO-d$_6$) δ 158.5, 144.1, 136.0, 131.8, 131.5, 129.3, 128.8, 121.3, 114.6, 111.7, 64.7, 41.1, 34.9, 32.6. MS: 310 [M+1]$^+$.

Example 92

Preparation of 3-amino-1-(3-(2-methoxybenzyloxy) phenyl)propan-1-ol

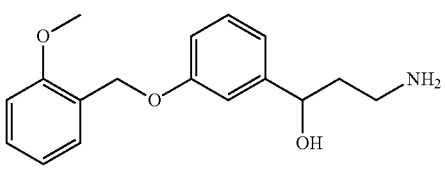 [SMILES: COc1ccccc1COc1cccc(C(O)CCN)c1]

3-Amino-1-(3-(2-methoxybenzyloxy)phenyl)propan-1-ol amine was prepared following the method described in Example 108.

Step 1:
Alkylation of 3-hydroxybenzaldehyde (11) with methanesulfonic acid 2-methoxy-benzyl ester gave 3-(2-methoxybenzyloxy)benzaldehyde as a clear oil. Yield (1.62 g, 81%): $^1$H NMR (400 MHz, CDCl$_3$) δ 9.97 (s, 1H), 7.41-7.53 (m, 4H), 7.26-7.36 (m, 2H), 6.92-7.0 (m, 2H), 5.17 (s, 2H), 3.85 (s, 3H).

Step 2:
Addition of acetonitrile to 3-(2-methoxybenzyloxy) benzaldehyde gave 3-(3-(2-methoxybenzyloxy)phenyl)-3-hydroxypropanenitrile as yellow oil. Yield (0.88 g, 47%): $^1$H NMR (400 MHz, CDCl$_3$) δ 7.42-7.46 (m, 1H), 7.27-7.31 (m, 2H), 6.90-7.06 (m, 5H), 5.12 (s, 2H), 5.01 (m, 1H), 3.87 (s, 3H), 2.76-2.82 (m, 2H).

Step 3:
Reduction of 3-(3-(2-methoxybenzyloxy)phenyl)-3-hydroxypropanenitrile with BH$_3$.DMS gave Example 8 as a colorless oil. Yield (0.48 g, 54%): $^1$H NMR (400 MHz, DMSO-d$_6$) δ 7.07-7.41 (m, 4H), 6.90-6.93 (m, 3H), 6.81 (dd, J=2.0, 2.4 Hz, 1H), 5.03 (s, 2H), 4.63 (t, J=6.4 Hz, 1H), 3.82 (s, 3H), 2.57-2.67 (m, 2H), 1.58-1.65 (m, 2H). $^{13}$C NMR (100 MHz, DMSO-d$_6$) δ 158.3, 156.8, 148.3, 129.2, 128.9, 124.8, 120.3, 118.0, 112.6, 111.9, 110.8, 71.2, 64.3, 55.4, 42.3. MS: 288 [M+1]$^+$.

Example 93

Preparation of 2-(3-(cyclooctylmethoxy)phenoxy)ethanamine

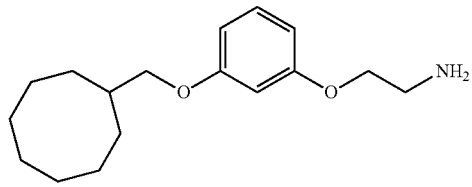

2-(3-(Cyclooctylmethoxy)phenoxy)ethanamine amine was prepared following the method described in Example 94.

Step 1:
Alkylation reaction of phenol 24 with methanesulfonic acid cyclooctylmethyl ester gave 2-(2-(3-(cyclooctylmethoxy)phenoxy)ethyl)isoindoline-1,3-dione as yellow oil. Yield (0.920 g, 64%): $^1$H NMR (400 MHz, CDCl$_3$) δ 7.85-7.87 (m, 2H), 7.71-7.73 (m, 2H), 7.09-7.11 (m, 1H), 6.42-6.46 (m, 3H), 4.20 (t, J=5.6 Hz, 2H), 4.11 (t, J=5.6 Hz, 2H), 3.65 (d, J=6.8 Hz, 2H), 1.92-1.99 (m, 1H), 1.21-1.80 (m, 14H).

Step 2:
Phthalimide cleavage of 2-(2-(3-(cyclooctylmethoxy) phenoxy) ethyl)isoindoline-1,3-dione gave Example 93 as yellow oil. Yield (0.260 g, 42%): $^1$H NMR (400 MHz, DMSO-d$_6$) δ 7.11-7.16 (m, 1H), 6.46-6.49 (m, 3H), 3.88 (t, J=5.6 Hz, 2H), 3.70 (d, J=6.8 Hz, 2H), 2.84 (t, J=5.6 Hz, 2H), 1.89-1.94 (m, 1H), 1.30-1.75 (m, 14). $^{13}$C NMR (100 MHz, DMSO-d$_6$) δ 160.5, 160.4, 130.3, 107.2, 107.1, 101.7, 73.5, 70.6, 41.4, 37.3, 29.2, 27.0, 26.3, 25.4. MS: 264 [M+1]$^+$.

Example 94

Preparation of 2-(3-(3-(benzyloxy)propoxy)phenoxy)ethanamine

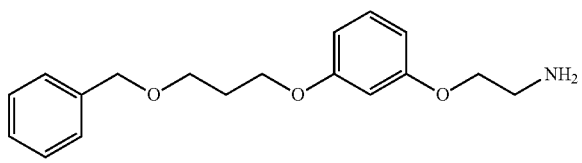 [SMILES: NCCOc1cccc(OCCCOCc2ccccc2)c1]

2-(3-(3-(Benzyloxy)propoxy)phenoxy)ethanamine was prepared following the method described in Example 7.

Step 1:

The suspension of phenol 24 (1 g, 3.5 mmol), methanesulfonic acid 3-benzyloxypropyl ester (0.3 mL, 3.5 mmol), cesium carbonate (1.158 g, 3.5 mmol) in DMF (3.5 mL) was heated at 70° C. for 24 h. The reaction was quenched by the addition of water. It was extracted with DCM, washed with water, dried over anhy. Na$_2$SO$_4$ filtered and concentrated under reduced pressure to give the crude. Purification of the crude by flash chromatography (hexane-ethyl acetate gradients) gave 2-(2-(3-(3-(benzyloxy)propoxy) phenoxy)ethyl)isoindoline-1,3-dione as a yellow oil. Yield (0.560 g, 37%): $^1$H NMR (400 MHz, DMSO-d$_6$) δ 7.84-7.87 (m, 2H), 7.70-7.73 (m, 2H), 7.28-7.36 (m, 5H), 7.01-7.15 (m, 1H), 6.43-6.48 (m, 3H), 4.51 (s, 2H), 4.20 (t, J=5.6 Hz, 2H), 4.11 (t, J=5.6 Hz, 2H), 4.05 (t, J=6.4 Hz, 2H), 3.61-3.70 (m, 2H), 2.03-2.10 (m, 2H).

Step 4:

Phthalimide cleavage of 2-(2-(3-(3-(benzyloxy)propoxy) phenoxy)ethyl)isoindoline-1,3-dione following the method used in Example 75 gave Example 94 as yellow oil. Yield (0.205 g, 53%): $^1$H NMR (400 MHz, DMSO-d$_6$) δ 7.25-7.34 (m, 5H), 7.11-7.17 (m, 1H), 6.46-6.51 (m, 3H), 4.48 (s, 2H), 4.02 (t, J=6.4 Hz, 2H), 3.87 (t, J=6.0 Hz, 2H), 3.58 (t, J=6.4 Hz, 2H), 2.84 (t, J=6.0 Hz, 2H), 1.94-2.00 (m, 2H). $^{13}$C NMR (100 MHz, DMSO-d$_6$) δ 159.9, 159.8, 138.5, 129.9, 128.2, 127.4, 127.3, 106.8, 106.7, 101.1, 71.9, 70.2, 66.3, 64.5, 40.9, 29.1. MS: 302 [M+1]$^+$.

Example 95

Preparation of 3-(3-(2-aminoethoxy)phenoxy)propan-1-ol

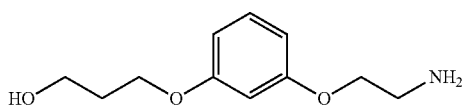

3-(3-(2-Aminoethoxy)phenoxy)propan-1-ol was prepared following the method described in Example 94.

Step 1:

Alkylation of phenol 24 with 3-chloro-prop-1-ol gave 2-(2-(3-(3-(hydroxy)propoxy)phenoxy)ethyl)isoindoline-1,3-dione as yellow oil. Yield (0.70 g, 57%): $^1$H NMR (400 MHz, CDCl$_3$) δ 7.84-7.89 (m, 2H), 7.70-7.75 (m, 2H), 7.10-7.15 (m, 1H), 6.43-6.50 (m, 3H), 4.21 (t, J=5.8 Hz, 2H), 4.08-4.13 (m, 4H), 3.82-3.87 (m, 2H), 1.19-2.05 (m, 2H).

Step 2:

Phthalimide cleavage of 2-(2-(3-(3-(hydroxy)propoxy) phenoxy) ethyl)isoindoline-1,3-dione gave Example 95 as yellow oil. Yield (0.135 g, 31%): $^1$H NMR (400 MHz, DMSO-d$_6$) δ 7.12-7.17 (m, 1H), 6.46-6.50 (m, 3H), 3.99 (t, J=6.4 Hz, 2H), 3.88 (t, J=5.8 Hz, 2H), 3.50-3.55 (m, 2H), 2.84 (t, J=5.8 Hz, 2H), 1.80-1.87 (m, 3H), $^{13}$C NMR (100 MHz, DMSO-d$_6$) δ 160.4, 130.4, 107.1, 101.5, 70.6, 64.9, 57.7, 41.4, 32.6. MS: 212 [M+1]$^+$.

Example 96

Preparation of 3-(3-(3-phenylpropoxy)phenyl)propan-1-amine

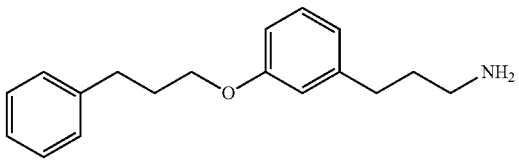 [SMILES: NCCCc1cccc(OCCCc2ccccc2)c1]

3-(3-(3-Phenylpropoxy)phenyl)propan-1-amine was prepared following the method described in Example 59.

Step 1:

Alkylation of phenol 24 with 3-bromo-1-propanol gave 2-(3-(3-(3-phenylpropoxy)phenyl)propyl)isoindoline-1,3-dione as yellow oil. Yield (0.800 g, 56%): $^1$H NMR (400 MHz, CDCl$_3$) δ 7.80-7.84 (m, 2H), 7.69-7.72 (m, 2H), 7.27-7.32 (m, 2H), 7.19-7.25 (m, 2H), 7.12-7.17 (m, 2H), 6.77 (d, J=7.6 Hz, 1H), 6.74 (s, 1H), 6.66 (d, J=8.4 Hz, 1H), 3.94 (t, J=6.4 Hz, 2H), 3.75 (t, J=7.2 Hz, 2H), 2.81 (t, J=7.2 Hz, 2H), 2.66 (t, J=7.2 Hz, 2H), 1.99-2.13 (m, 4H).

Step 2:

Phthalimide cleavage of 2-(3-(3-(3-phenylpropoxy)phenyl) propyl)isoindoline-1,3-dione gave Example 96 as yellow oil. Yield (0.35 g, 66%): $^1$H NMR (400 MHz, DMSO-d$_6$) δ 7.27-7.31 (m, 2H), 7.20-7.24 (m, 2H), 7.14-7.19 (m, 2H), 6.70-6.76 (m, 3H), 3.93 (t, J=6.0 Hz, 2H), 2.73 (t, J=7.6 Hz, 2H), 2.50-2.55 (m, 4H), 1.96-2.03 (m, 2H), 1.57-1.64 (m, 2H). $^{13}$C NMR (100 MHz, DMSO-d$_6$) δ 158.6, 143.9, 141.4, 129.2, 128.3, 125.8, 120.5, 114.5, 111.5, 66.4, 41.2, 35.0, 32.6, 31.5, 30.4. MS: 270 [M+1]$^+$.

Example 97

Preparation of 3-(3-(3-(benzyloxy)propoxy)phenyl)propan-1-amine

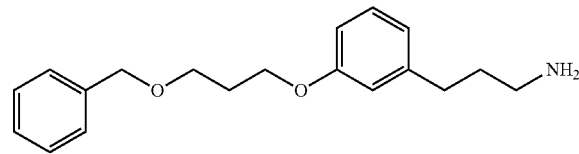 [SMILES: NCCCc1cccc(OCCCOCc2ccccc2)c1]

3-(3-(3-(Benzyloxy)propoxy)phenyl)propan-1-amine was prepared following the method described in Example 59.

Step 1:

Alkylation reaction of phenol 58 with methane sulfonic acid 3-benzyloxy-propyl ester gave 2-(3-(3-(3-(benzyloxy) propoxy)phenyl)propyl)isoindoline-1,3-dione as yellow oil. Yield (0.643 g, 44%): $^1$H NMR (400 MHz, DMSO-d$_6$) δ 7.80-7.83 (m, 2H), 7.68-7.72 (m, 2H), 7.27-7.35 (m, 5H), 7.12-7.16 (m, 1H), 6.77 (d, J=7.6, 1H), 6.73 (s, 1H), 6.66 (d, J=8.0, 1H), 4.53 (s, 2H), 4.06 (t, J=6.0 Hz, 2H), 3.77 (t, J=6.2 Hz, 2H), 3.68 (t, J=5.0 Hz, 2H), 2.65 (t, J=7.8 Hz, 2H), 2.0-2.10 (m, 4H).

Step 2:

Phthalimide cleavage of 2-(3-(3-(3-(benzyloxy)propoxy) phenyl)propyl)isoindoline-1,3-dione gave Example 97 as pale yellow oil. Yield (0.370 g, 86%): $^1$H NMR (400 MHz, DMSO-d$_6$) δ 7.26-7.35 (m, 5H), 7.13-7.18 (m, 1H), 6.70-6.76 (m, 3H), 4.48 (s, 2H), 4.02 (t, J=6.2 Hz, 2H), 3.58 (t, J=6.2 Hz, 2H), 2.46-2.56 (m, 4H), 1.94-2.0 (m, 2H), 1.57-1.64 (m, 2H). $^{13}$C NMR (100 MHz, DMSO-d$_6$) δ 158.6, 143.9, 138.5, 129.2, 128.2, 127.4, 127.3, 120.5, 114.5, 111.5, 71.9, 66.3, 64.3, 41.1, 35.0, 32.6, 29.2. MS: 300 [M+1]$^+$.

Example 98

Preparation of 3-(3-(3-aminopropyl)phenoxy)propan-1-ol

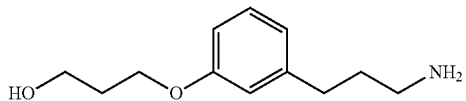 [SMILES: NCCCc1cccc(OCCCO)c1]

3-(3-(3-Aminopropyl)phenoxy)propan-1-ol was prepared following the method described in Example 59.
Step 1:
Alkylation reaction of phenol 58 with 3-bromo-1-propanol gave 2-(3-(3-(3-hydroxypropoxy)phenyl)propyl)isoindoline-1,3-dione as yellow oil. Yield (0.300 g, 25%): $^1$H NMR (400 MHz, CDCl$_3$) δ 7.80-7.83 (m, 2H), 7.69-7.71 (m, 2H), 7.12-7.16 (m, 1H), 6.78 (d, J=7.6 Hz, 1H), 6.76 (s, 1H), 6.65 (dd, J=8.0, 2.4 Hz, 1H), 4.10 (d, J=6.0 Hz, 2H), 3.84-3.89 (m, 2H), 3.73 (t, J=7.2 Hz, 2H), 2.65 (t, J=8.0 Hz, 2H), 1.98-2.05 (m, 4H).
Step 2:
Phthalimide cleavage of 2-(3-(3-(3-hydroxypropoxy)phenyl) propyl)isoindoline-1,3-dione gave Example 98 as yellow oil. Yield (0.124 g, 67%): $^1$H NMR (400 MHz, DMSO-d$_6$) δ 7.13-7.18 (m, 1H), 6.70-6.75 (m, 3H), 3.99 (t, J=6.4 Hz, 2H), 3.55 (t, J=6.2 Hz, 2H), 2.50-2.57 (m, 4H), 1.80-1.87 (m, 2H), 1.58-1.65 (m, 2H). $^{13}$C NMR (100 MHz, DMSO-d$_6$) δ 158.7, 143.9, 129.2, 120.4, 114.4, 111.4, 111.5, 64.3, 57.3, 41.1, 34.9, 32.6, 32.2. MS: 210 [M+1]$^+$.

Example 99

Preparation of 3-(3-(cyclooctylmethoxy)phenyl)propan-1-amine

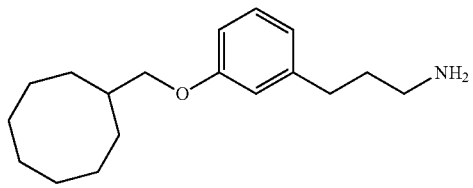

3-(3-(Cyclooctylmethoxy)phenyl)propan-1-amine was prepared following the method described in Example 59.
Step 1:
Mitsunobu reaction of phenol 58 with cyclooctane methanol gave 2-(3-(3-(cyclooctylmethoxy)phenyl)propyl)isoindoline-1,3-dione as yellow oil. Yield (0.920 g, 65%): $^1$H NMR (400 MHz, CDCl$_3$) δ 7.80-7.86 (m, 2H), 7.68-7.73 (m, 2H), 7.10-7.13 (m, 1H), 6.72-6.79 (m, 2H), 6.64-6.68 (m, 1H), 3.65 (d, J=6.4 Hz, 2H), 2.64 (t, J=7.6 Hz, 2H), 1.98-2.06 (m, 4H), 1.65-1.78 (m, 7H), 1.56-1.64 (m, 5H), 1.30-1.40 (m, 3H).

Step 2:
Phthalimide cleavage of 2-(3-(3-(cyclooctylmethoxy) phenyl) propyl)isoindoline-1,3-dione gave 3-(3-(cyclooctylmethoxy)phenyl)propan-1-amine as off white oil. Yield (0.380 g, 59%): $^1$H NMR (400 MHz, DMSO-d$_6$) δ 7.13-7.18 (m, 1H), 6.69-6.76 (m, 3H), 3.70 (d, J=6.8 Hz, 2H), 2.52-2.59 (m, 4H), 1.90-2.06 (m, 6H), 1.64-1.74 (m, 6H), 1.42-1.60 (m, 4H), 1.30-1.40 (m, 1H). $^{13}$C NMR (100 MHz, DMSO-d$_6$) δ 158.8, 143.6, 129.2, 120.4, 114.5, 111.6, 72.9, 40.5, 36.9, 33.7, 32.4, 28.7, 26.5, 25.8, 24.9. MS: 276 [M+1]$^+$.

Example 100

Preparation of 2-(3-(4-(benzyloxy)butoxy)phenoxy)ethanamine

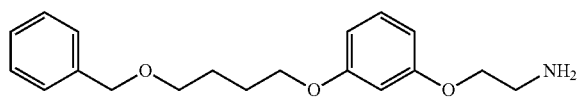

2-(3-(4-(Benzyloxy)butoxy)phenoxy)ethanamine was prepared following the method described in Example 94.
Step 1:
Alkylation reaction of phenol 24 with methanesulfonic acid 4-benzyloxy-butyl ester gave 2-(2-(3-(4-benzyloxybutoxy)phenoxy)ethyl)isoindole-1,3-dione as yellow oil. Yield (1.0 g, 63%): $^1$H NMR (400 MHz, CDCl$_3$) δ 7.81-7.84 (m, 2H), 7.69-7.72 (m, 2H), 7.11-7.16 (m, 1H), 6.73-6.78 (m, 2H), 6.67 (dd, J=8.0, 2.4 Hz, 1H), 6.73 (s, 1H), 6.65 (dd, J=7.6, 2.4 Hz, 1H), 4.52 (s, 2H), 3.94 (t, J=6.0 Hz, 2H), 3.72-3.78 (m, 4H), 2.65 (t, J=7.6 Hz, 2H), 1.98-2.07 (m, 2H), 1.24-1.28 (m, 1H), 0.62-0.66 (m, 2H), 0.32-0.36 (m, 2H).
Step 2:
Phthalimide cleavage of 2-(2-(3-(4-Benzyloxybutoxy) phenoxyethyl)-isoindole-1,3-dione gave Example 100 as yellow oil. Yield (0.48 g, 67%): $^1$H NMR (400 MHz, DMSO-d$_6$) δ 7.25-7.32 (m, 5H), 7.12-7.16 (m, 1H), 6.45-6.50 (m, 3H), 4.46 (s, 2H), 3.95 (t, J=6.0 Hz, 2H), 3.48 (t, J=6.4 Hz, 2H), 2.84 (t, J=5.6 Hz, 2H), 1.71-1.80 (m, 2H), 1.64-1.70 (m, 2H). $^{13}$C NMR (100 MHz, DMSO-d$_6$) δ 159.9, 159.8, 138.7, 129.9, 128.2, 127.4, 127.3, 106.7, 106.6, 101.1, 71.8, 70.2, 69.3, 67.2, 41.0, 25.8, 25.6. MS: 316 [M+1]$^+$.

Example 101

Preparation of 2-(3-(2-methoxybenzyloxy)phenoxy)ethanamine

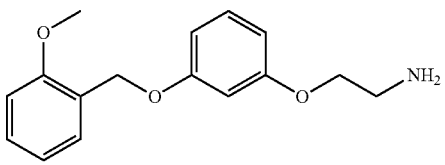 [SMILES: COc1ccccc1COc1cccc(OCCN)c1]

2-(3-(2-Methoxybenzyloxy)phenoxy)ethanamine was prepared following the method described in Example 94.

Step 1:

Alkylation reaction of phenol 24 with methanesulfonic acid 2-methoxy-benzyl ester gave 2-(2-(3-(2-methoxybenzyloxy)phenoxy)ethyl)isoindoline-1,3-dione as yellow oil. Yield (0.320 g, 52%): $^1$H NMR (400 MHz, CDCl$_3$) δ 7.84-7.87 (m, 2H), 7.70-7.74 (m, 2H), 7.43 (d, J=7.2 Hz, 1H), 7.27 (d, J=7.2 Hz, 1H), 7.11-7.16 (m, 1H), 6.94-6.98 (m, 1H), 6.89 (d, J=8.0, 1H), 6.54-6.59 (m, 2H), 6.47 (dd, J=8.4, 2.0 Hz, 1H), 5.06 (s, 2H), 4.21 (t, J=5.6 Hz, 2H), 4.10 (t, J=5.6 Hz, 2H), 3.83 (s, 3H).

Step 2:

Phthalimide cleavage of 2-(2-(3-(2-methoxy benzyloxy)phenoxy)ethyl)isoindoline-1,3-dione gave Example 101 as yellow oil. Yield (0.119 g, 48%): $^1$H NMR (400 MHz, DMSO-d$_6$) δ 7.31-7.38 (m, 2H), 7.14-7.18 (m, 1H), 7.04 (d, J=8.4 Hz, 1H), 6.94-6.98 (m, 1H), 6.50-6.57 (m, 3H), 5.02 (s, 2H), 3.88 (t, J=5.6 Hz, 2H), 3.82 (s, 3H), 2.84 (t, J=5.6 Hz, 2H). $^{13}$C NMR (100 MHz, DMSO-d$_6$) δ 160.4, 160.2, 157.3, 130.4, 129.8, 129.6, 125.1, 120.8, 111.4, 107.4, 107.3, 101.8, 70.6, 64.9, 55.9, 41.4. MS: 274 [M+1]$^+$.

Example 102

Preparation of 3-(3-(2-(benzyloxy)ethoxy)phenyl)propan-1-amine

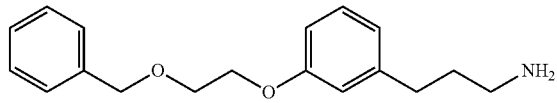 [SMILES: NCCCc1cccc(OCCOCc2ccccc2)c1]

3-(3-(2-(Benzyloxy)ethoxy)phenyl)propan-1-amine was prepared following the method described in Example 59.

Step 1:

Alkylation reaction of phenol 58 with methane sulfonic acid 2-benzyloxyethyl ester gave 2-(3-(3-(2-(benzyloxy)ethoxy)phenyl)propyl)isoindoline-1,3-dione as yellow oil. Yield (0.580 g, 40%): $^1$H NMR (400 MHz, CDCl$_3$) δ 7.81-7.83 (m, 2H), 7.68-7.70 (m, 2H), 7.32-7.39 (m, 5H), 7.12-7.16 (m, 1H), 6.76-6.79 (m, 2H), 6.69 (d, J=6.4 Hz, 1H), 4.64 (s, 2H), 4.13 (t, J=5.2 Hz, 2H), 3.82 (t, J=5.2 Hz, 2H), 3.74 (t, J=7.2 Hz, 2H), 2.65 (t, J=7.8 Hz, 2H), 2.0-2.06 (m, 2H).

Step 2:

Phthalimide cleavage of 2-(3-(3-(2-(benzyloxy)ethoxy)phenyl) propyl)isoindoline-1,3-dione gave Example 102 as pale yellow oil. Yield (0.28 g, 40%): $^1$H NMR (400 MHz, DMSO-d$_6$) δ 7.33-7.37 (m, 4H), 7.26-7.31 (m, 1H), 7.14-7.18 (m, 1H), 6.73-6.77 (m, 3H), 4.55 (s, 2H), 4.11 (t, J=4.6 Hz, 2H), 3.76 (t, J=4.6 Hz, 2H), 2.50-2.58 (m, 4H), 1.59-1.63 (m, 2H). $^{13}$C NMR (100 MHz, DMSO-d$_6$) δ 158.5, 144.0, 138.3, 129.2, 128.2, 127.5, 127.4, 120.6, 114.6, 111.5, 72.1, 68.3, 66.9, 41.1, 35.0, 32.6. MS: 286 [M+1]$^+$.

Example 103

Preparation of 3-(3-(cyclopentylmethoxy)phenyl)propan-1-amine

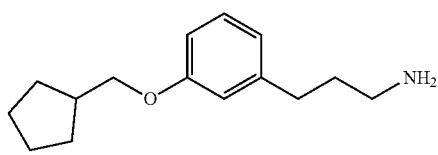 [SMILES: NCCCc1cccc(OCC2CCCC2)c1]

3-(3-(Cyclopentylmethoxy)phenyl)propan-1-amine was prepared following the method described in Examples 2 and 18.

Step 1:

Coupling of cyclopentylmethanol (0.22 g, 2.4 mmol) with compound 58 (0.56 g, 2 mmol) following the method used in Example 2 gave 2-(3-(3-(cyclopentylmethoxy)phenyl)propyl)isoindoline-1,3-dione as a colorless oil. Yield (0.29 g, 40%): $^1$H NMR (400 MHz, CDCl$_3$) δ 7.78-7.83 (m, 2H), 7.66-7.72 (m, 2H), 7.13 (t, J=7.8 Hz, 1H), 6.71-6.77 (m, 2H), 6.66 (ddd, J=0.6, 2.5, 8.0 Hz), 3.78 (d, J=7.0 Hz, 2H), 3.74 (t, J=7.0 Hz, 2H), 2.65 (t, J=7.6 Hz, 2H), 2.28-2.38 (m, 1H), 1.98-2.07 (m, 2H), 1.77-1.87 (m, 2H), 1.52-1.66 (m, 4H), 1.30-1.40 (m, 2H).

Step 2:

Deprotection of 2-(3-(3-(cyclopentylmethoxy)phenyl)propyl)isoindoline-1,3-dione following the method used in Example 18 gave Example 103 as a colorless oil. Yield (0.15 g, 83%): $^1$H NMR (400 MHz, CD$_3$OD) δ 7.13 (t, J=8.2 Hz, 1H), 6.72-6.76 (m, 2H), 6.67-6.71 (m, 1H), 3.81 (d, J=6.9 Hz, 2H), 2.56-2.66 (m, 4H), 2.26-2.39 (m, 1H), 1.70-1.87 (m, 4H), 1.54-1.70 (m, 4H), 1.32-1.42 (m, 2H).

Example 104

Preparation of 2-(3-(cyclopentylmethoxy)phenoxy)ethanamine

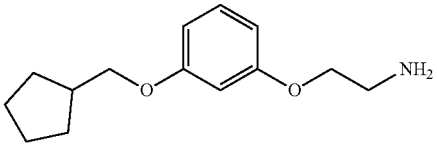

2-(3-(Cyclopentylmethoxy)phenoxy)ethanamine was prepared following the method described in Example 2 and 18.

Step 1:

Coupling of cyclopentylmethyl methanesulfonate (0.2 g, 1.1 mmol) with compound 24 (0.28 g, 1.1 mmol) following the method used in Example 2 gave 2-(2-(3-(cyclopentylmethoxy)phenoxy)ethyl)isoindoline-1,3-dione as a colorless oil. Yield (0.07 g, 19%): $^1$H NMR (400 MHz, CDCl$_3$) δ 7.82-7.87 (m, 2H), 7.68-7.74 (m, 2H), 7.10 (t, J=8.2 Hz, 1H), 6.40-6.48 (m, 3H), 4.20 (d, J=6.3 Hz, 2H), 4.09 (t, J=4.9 Hz, 2H), 3.76 (d, J=7.0 Hz, 2H), 2.26-2.36 (m, 1H), 1.74-1.85 (m, 2H), 1.507-1.66 (m, 4H), 1.27-1.36 (m, 2H).

Step 2:

Deprotection of 2-(2-(2-(3-(cyclopentylmethoxy)phenoxy)ethyl)isoindoline-1,3-dione following the method used in Example 18 gave Example 104 as a colorless oil. Yield (0.04 g, 89%): $^1$H NMR (400 MHz, CD$_3$OD) δ 7.10-7.60 (m, 1H), 6.47-6.53 (m, 3H), 3.99 (t J=5.6 Hz, 2H), 3.81 (d, J=6.0 Hz, 2H), 1.78-1.88 (m, 2H), 1.54-1.72 (m, 4H), 1.34-1.44 (m, 3H).

Example 105

Preparation of 3-amino-1-(3-(2,6-dichlorobenzyloxy)phenyl)propan-1-ol

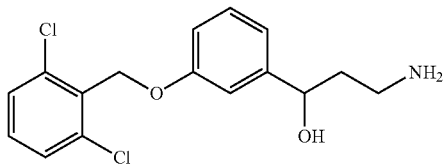 [SMILES: NCCC(O)c1cccc(OCc2c(Cl)cccc2Cl)c1]

3-Amino-1-(3-(2,6-dichlorobenzyloxy)phenyl)propan-1-ol was prepared following the method described in Example 34.

Step 1:

Alkylation of 3-bromobenzaldehyde (11) with 2,6-dichlorobenzyl bromide gave 3-(2,6-dichlorobenzyloxy)benzaldehyde as a clear oil. Yield (2.18 g, 81%): $^1$H NMR (400 MHz, CDCl$_3$) δ 10.0 (s, 1H), 7.45-7.57 (m, 3H), 7.36-7.40 (m, 2H), 7.27-7.30 (m, 2H), 5.34 (s, 2H).

Step 2:

Addition of acetonitrile to 3-(2,6-Dichlorobenzyloxy)benzaldehyde gave 3-[3-(2,6-dichlorobenzyloxy)phenyl]-3-hydroxypropionitrile as a yellow oil. Yield (1.65 g, 68%): $^1$H NMR (400 MHz, CDCl$_3$) δ 7.34-7.39 (m, 3H), 7.24-7.28 (m, 1H), 7.07 (s, 1H), 7.00-7.05 (m, 2H), 5.29 (s, 2H), 5.04 (t, J=6.4 Hz, 1H), 2.78 (d, J=6.4 Hz, 2H).

Step 3:

To an ice-cold stirred solution of 3-[3-(2,6-Dichlorobenzyloxy)phenyl]-3-hydroxypropionitrile (1.6 g, 4.9 mmol) in THF (25 ml), was added BH$_3$.DMS (1.42 mL, 14.9 mmol). The mixture was allowed to warm to room temperature and then gradually warmed to reflux and maintained overnight. The mixture was cooled in an ice-bath and the reaction quenched by the slow addition of large excess of MeOH. After stirring at RT for about 2 h, the excess solvent was removed under reduced pressure. The residue was diluted with MeOH and the solvent removed under reduced pressure four times. Purification by flash chromatography (silica, eluent (0 to 15% (9:1 MeOH—NH$_3$)-DCM gradient) gave Example 105 as a brown solid. Yield (0.820 g, 50%): $^1$H NMR (400 MHz, DMSO-d$_6$) δ 7.55-7.59 (m, 2H), 7.44-7.50 (m, 1H), 7.22-7.27 (m, 1H), 7.00 (s, 1H), 6.88-6.96 (m, 2H), 5.21 (s, 2H), 4.65 (t, J=6.4 Hz, 1H), 2.61-2.68 (m, 2H), 1.63-1.69 (m, 2H). $^{13}$C NMR (100 MHz, DMSO-d$_6$) δ 158.3, 148.4, 136.0, 131.8, 131.5, 129.1, 128.8, 118.6, 112.6, 111.9, 71.1, 64.8, 42.0, 38.8. MS: 326 [M+1]$^+$.

Example 106

Preparation of 3-amino-1-(3-(cyclooctylmethoxy)phenyl)propan-1-ol

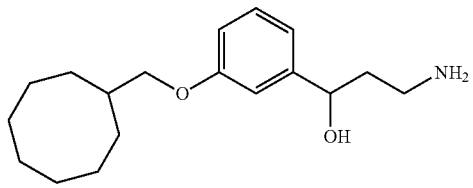 [SMILES: NCCC(O)c1cccc(OCC2CCCCCCC2)c1]

3-Amino-1-(3-(cyclooctylmethoxy)phenyl)propan-1-ol was prepared following the method described in Example 105.

Step 1:

Alkylation of 3-hydroxybenzaldehyde (11) with methanesulfonic acid cyclooctylmethyl ester gave 3-(cyclooctylmethoxy)benzaldehyde as a clear oil. Yield (1.6 g, 72%): $^1$H NMR (400 MHz, CDCl$_3$) δ 9.97 (s, 1H), 7.39-7.44 (m, 2H), 7.36-7.39 (m, 1H), 7.14-7.19 (m, 1H), 3.77 (d, J=6.8 Hz, 2H), 2.0-2.06 (m, 1H), 1.42-1.81 (m, 14H).

Step 2:

Addition of acetonitrile to 3-(cyclooctylmethoxy)benzaldehyde gave 3-(3-(cyclooctylmethoxy)phenyl)-3-hydroxypropanenitrile as a yellow oil. Yield (0.90 g, 48%): $^1$H NMR (400 MHz, CDCl$_3$) δ 7.25-7.31 (m, 1H), 6.91-6.95 (m, 2H), 6.84-6.89 (m, 1H), 5.01 (t, J=6.2 Hz, 1H), 3.72 (d, J=6.8 Hz, 2H), 2.74 (d, J=2.0 Hz, 2H), 1.97-2.04 (m, 1H), 1.33-1.79 (m, 14H).

Step 3:

Reduction of 3-(3-(cyclooctylmethoxy)phenyl)-3-hydroxypropanenitrile with BH$_3$.DMS gave Example 106 as a colorless oil. Yield (0.48 g, 52%): $^1$H NMR (400 MHz, DMSO-d$_6$) δ 7.15-7.21 (m, 1H), 6.83-6.87 (m, 2H), 6.72-6.77 (m, 1H), 4.61 (t, J=6.4 Hz, 1H), 3.71 (d, J=6.8 Hz, 2H), 2.61-2.64 (m, 2H), 1.93 (bs, 1H), 1.30-1.73 (m, 16H). $^{13}$C NMR (100 MHz, DMSO-d$_6$) δ 158.7, 148.2, 128.9, 117.8, 112.5, 111.8, 73.0, 71.2, 42.1, 40.1, 36.9, 28.8, 26.6, 25.9, 24.9. MS: 292 [M+1]$^+$.

Example 107

Preparation of 3-amino-1-(3-(isopentyloxy)phenyl)propan-1-ol

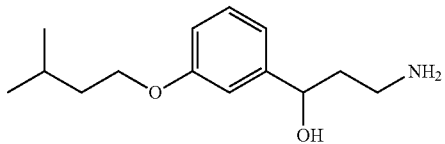 [SMILES: CC(C)CCOc1cccc(C(O)CCN)c1]

3-Amino-1-(3-(isopentyloxy)phenyl)propan-1-ol was prepared following the method described in Example 108.

Step 1:

Alkylation of 3-hydroxybenzaldehyde (11) with methanesulfonic acid 3-methylbutyl ester gave 3-(isopentyloxy)benzaldehyde as a clear oil. Yield (1.26 g, 53%): $^1$H NMR (400 MHz, CDCl$_3$) δ 9.97 (s, 1H), 7.39-7.45 (m, 3H), 7.17-7.19 (m, 1H), 4.03 (t, J=6.8 Hz, 2H), 1.82-1.89 (m, 1H), 1.68-1.73 (m, 2H), 0.97 (d, J=6.8 Hz, 6H).

Step 2:

Addition of acetonitrile to 3-(isopentyloxy)benzaldehyde gave 3-hydroxy-3-(3-(isopentyloxy)phenyl)propanenitrile as a yellow oil. Yield (0.82 g, 54%): $^1$H NMR (400 MHz, CDCl$_3$) δ 7.27-7.32 (m, 1H), 6.94-6.96 (m, 2H), 6.85-6.90 (m, 1H), 5.00-5.03 (m, 1H), 3.99 (t, J=6.4 Hz, 2H), 2.77 (d, J=6.0 Hz, 2H), 1.81-1.88 (m, 1H), 1.64-1.71 (m, 2H), 0.96 (d, J=6.4 Hz, 6H).

Step 3 Reduction of 3-hydroxy-3-(3-(isopentyloxy)phenyl)propanenitrile with BH$_3$.DMS gave Example 107 as a colorless oil. Yield (0.52 g, 63%): $^1$H NMR (400 MHz, DMSO-d$_6$) δ 7.17-7.21 (m, 1H), 6.83-6.87 (m, 2H), 6.73-6.77 (m, 1H), 4.62 (t, J=6.2 Hz, 1H), 3.96 (t, J=6.6 Hz, 2H), 2.57-2.67 (m, 2H), 1.73-1.82 (m, 1H), 1.56-1.65 (m, 4H), 0.96 (d, J=6.8 Hz, 6H). $^{13}$C NMR (100 MHz, DMSO-d$_6$) δ 158.8, 144.4, 137.7, 129.7, 128.9, 128.2, 128.1, 121.3, 115.3, 112.3, 69.5, 41.4, 35.1, 33.0. MS: 242 [M+1]+.

Example 108

Preparation of 3-amino-1-(3-(3-methoxypropoxy)phenyl)propan-1-ol

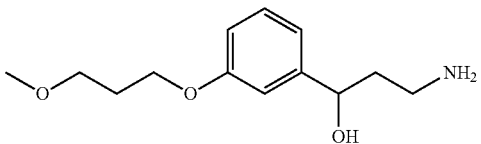 [SMILES: COCCCOc1cccc(C(O)CCN)c1]

3-Amino-1-(3-(3-methoxypropoxy)phenyl)propan-1-ol was prepared following the method described in Example 34.

Step 1:

Alkylation of 3-hydroxybenzaldehyde (11) with methanesulfonic acid 3-methoxypropyl ester following the method used in Example 34 except that the reaction solvent was DMF gave 3-(3-methoxypropoxy)benzaldehyde as a clear oil. Yield (1.32 g, 55%): $^1$H NMR (400 MHz, CDCl$_3$) δ 9.97 (s, 1H), 7.40-7.47 (m, 3H), 7.15-7.20 (m, 1H), 4.12 (t, J=6.4 Hz, 2H), 3.56 (t, J=6.2 Hz, 2H), 3.35 (s, 3H), 2.05-2.11 (m, 2H).

Step 2:

Addition of acetonitrile to 3-(3-methoxypropoxy)benzaldehyde gave 3-hydroxy-3-(3-(3-methoxypropoxy)phenyl)propanenitrile as a yellow oil. Yield (0.86 g, 52%): $^1$H NMR (400 MHz, CDCl$_3$) δ 7.26-7.32 (m, 1H), 6.86-6.97 (m, 3H), 5.02-5.03 (m, 1H), 4.06 (t, J=6.2 Hz, 2H), 3.55 (t, J=6.0 Hz, 2H), 3.35 (s, 3H), 2.75 (d, J=6.0 Hz, 2H), 2.03-2.09 (m, 2H).

Step 3:

Reduction of 3-hydroxy-3-(3-(3-methoxypropoxy)phenyl)propanenitrile with BH$_3$.DMS gave Example 108. Yield (0.57 g, 65%): $^1$H NMR (400 MHz, DMSO-d$_6$) δ 7.18-7.22 (m, 1H), 6.86-6.91 (m, 2H), 6.73-6.77 (m, 1H), 4.62 (t, J=6.4 Hz, 1H), 3.98 (t, J=6.4 Hz, 2H), 3.46 (t, J=6.4 Hz, 2H), 3.24 (s, 3H), 2.89-2.68 (m, 2H), 1.91-1.97 (m, 2H), 1.60-1.65 (m, 2H). $^{13}$C NMR (100 MHz, DMSO-d$_6$) δ 158.4, 148.3, 128.9, 117.8, 112.4, 111.6, 71.2, 68.5, 64.3, 57.9, 42.4, 40.1, 29.0. MS: 240 [M+1]+.

Example 109

Preparation of 3-amino-1-(3-(2-hydroxyethoxy)phenyl)propan-1-ol

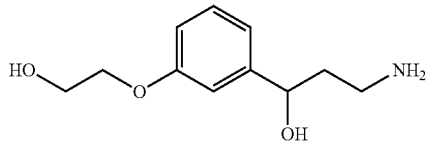 [SMILES: NCCC(O)c1cccc(OCCO)c1]

3-Amino-1-(3-(2-hydroxyethoxy)phenyl)propan-1-ol was prepared following the method described in Example 34.

Step 1:

Alkylation of 3-bromobenzaldehyde 1 with bromoethanol gave 3-(3-hydroxyethoxy)benzaldehyde as a clear oil. Yield (1.81 g, 33%): $^1$H NMR (400 MHz, CDCl$_3$) δ 9.98 (s, 1H), 7.41-7.51 (m, 3H), 7.21-7.25 (m, 1H), 4.16 (t, J=4.4 Hz, 2H), 4.01 (t, J=4.4 Hz, 2H).

Step 2:

Addition of acetonitrile to 3-(3-hydroxyethoxy)benzaldehyde gave 3-hydroxy-3-[3-(3-hydroxyethoxy)phenyl]propionitrile as yellow oil. Yield (1.13 g, 50%): $^1$H NMR (400 MHz, CDCl$_3$) δ 7.29-7.34 (m, 1H), 6.95-7.01 (m, 2H), 6.91 (dd, J=8.4, 2.4 Hz, 1H), 5.00-5.07 (m, 1H), 4.10-4.14 (m, 2H), 3.94-4.0 (m, 2H), 2.77 (d, J=6.0 Hz, 2H).

Step 3:

Reduction of 3-hydroxy-3-[3-(3-hydroxyethoxy)phenyl]propionitrile with Raney-Ni gave Example 109 as colorless oil. Yield (0.365 g, 32%): $^1$H NMR (400 MHz, DMSO-d$_6$) δ 717-7.22 (m, 1H), 6.83-6.87 (m, 2H), 6.76 (d, J=7.2 Hz, 1H), 4.58 (t, J=6.4 Hz, 1H), 3.94 (t, J=4.8 Hz, 2H), 3.68 (t, J=4.8 Hz, 2H), 2.58 (t, J=6.8 Hz, 2H). $^{13}$C NMR (100 MHz, DMSO-d$_6$) δ 159.0, 148.6, 129.4, 118.3, 112.9, 112.2, 71.5, 69.7, 60.0, 42.2, 39.1. MS: 212 [M+1]+.

Example 110

Preparation of 3-amino-1-(3-(3-hydroxypropoxy)phenyl)propan-1-ol

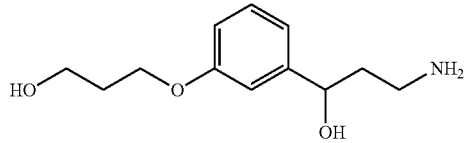 [SMILES: NCCC(O)c1cccc(OCCCO)c1]

3-Amino-1-(3-(3-hydroxypropoxy)phenyl)propan-1-ol was prepared following the method described in Example 34.

Step 1:

Alkylation of 3-hydroxybenzaldehyde 11 with 3-bromo-1-propanol gave 3-(3-hydroxypropoxy) benzaldehyde as a clear oil. Yield (3.3 g, 55%): $^1$H NMR (400 MHz, CDCl$_3$) δ 9.97 (s, 1H), 7.40-7.48 (m, 3H), 7.16-7.20 (m, 1H), 4.19 (t, J=6.4 Hz, 2H), 3.88 (t, J=6.0 Hz, 2H), 2.04-2.12 (m, 2H).

Step 2:

Addition of acetonitrile to 3-(3-hydroxypropoxy)benzaldehyde gave 3-hydroxy-3-[3-(3-hydroxypropoxy)phenyl]propionitrile as yellow oil. Yield (1.80 g, 45%): $^1$H NMR (400 MHz, CDCl$_3$) δ 7.28-7.33 (m, 1H), 6.94-6.99 (m, 2H), 6.89 (dd, J=8.2, 2.0 Hz, 1H), 4.15 (t, J=6.0 Hz, 2H), 3.87 (t, J=6.0 Hz, 2H), 2.77 (d, J=6.0 Hz, 2H), 2.02-2.09 (m, 3H).

Step 3:

Reduction of 3-hydroxy-3-(3-(3-hydroxypropoxy)phenyl) propanenitrile with Raney-Ni gave Example 110 as a colorless oil. Yield (0.595 g, 32%): $^1$H NMR (400 MHz, DMSO-d$_6$) δ 7.16-7.22 (m, 1H), 6.84-6.88 (m, 2H), 6.73-6.77 (m, 1H), 4.58 (t, J=6.0 Hz, 1H), 3.99 (t, J=6.4 Hz, 2H), 3.54 (t, J=6.4 Hz, 2H), 2.58 (t, J=6.8 Hz, 2H), 1.80-1.87 (m, 2H), 1.60-1.66 (m, 2H). $^{13}$C NMR (100 MHz, DMSO-d$_6$) δ 158.5, 148.2, 128.9, 117.8, 112.4, 111.6, 71.2, 64.4, 57.3, 42.3, 32.2. MS: 226 [M+1]+.

Example 111

Preparation of 2-(3-((tetrahydro-2H-pyran-2-yl)methoxy)phenoxy)ethanamine

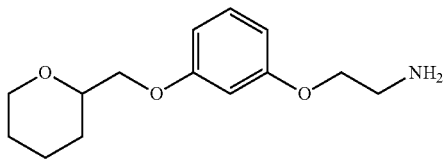 [SMILES: NCCOc1cccc(OCC2CCCCO2)c1]

2-(3-((tetrahydro-2H-pyran-2-yl)methoxy)phenoxy)ethanamine was prepared following the method described in Example 94.

Step 1:

Alkylation reaction of phenol 24 with methanesulfonic acid tetrahydropyran-2-ylmethyl ester gave 2-(2-(3-((tetrahydro-2H-pyran-2-yl)methoxy) phenoxy)ethyl)isoindoline-1,3-dione as yellow oil. Yield (0.70 g, 52%): $^1$H NMR (400 MHz, CDCl$_3$) δ 7.84-7.87 (m, 2H), 7.71-7.75 (m, 2H), 7.08-7.14 (m, 1H), 6.45-6.51 (m, 3H), 3.40-4.20 (m, 7H), 1.40-1.90 (m, 8H).

Step 2:

Phthalimide cleavage of 2-(2-(3-((tetrahydro-2H-pyran-2-yl)methoxy)phenoxy)ethyl)isoindoline-1,3-dione gave Example 111 as yellow oil. Yield (0.12 g, 26%): $^1$H NMR (400 MHz, DMSO-d$_6$) δ 7.12-7.17 (m, 1H), 6.48-6.51 (m, 3H), 3.84-3.91 (m, 5H), 3.60-3.63 (m, 1H), 3.39-3.41 (41 (m, 1H), 2.87 (t, J=5.6 Hz, 2H), 1.80-1.86 (m, 1H), 1.60-1.66 (m, 1H), 2.50-2.60 (m, 4H), 1.60-1.69 (m, 2H). $^{13}$C NMR (100 MHz, DMSO-d$_6$) δ 160.3, 160.2, 130.4, 107.3, 107.2, 101.6, 75.8, 71.4, 70.1, 67.7, 40.6, 28.1, 26.0, 23.0. MS: 252 [M+1]$^+$.

Example 112

Preparation of 2-(3-(2-(benzyloxy)ethoxy)phenoxy)ethanamine

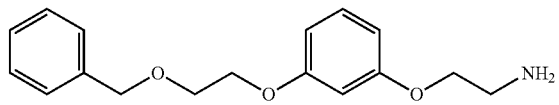 [SMILES: NCCOc1cccc(OCCOCc2ccccc2)c1]

2-(3-(2-(Benzyloxy)ethoxy)phenoxy)ethanamine was prepared following the method described in Example 94.

Step 1:

Alkylation reaction of phenol 24 with methanesulfonic acid 2-benzyloxy-ethyl ester gave 2-(2-(3-(2-(benzyloxy)ethoxy)phenoxy)ethyl)isoindoline-1,3-dione as yellow oil. Yield (0.950 g, 64%): $^1$H NMR (400 MHz, CDCl$_3$) δ 7.84-7.87 (m, 1H), 7.70-7.74 (m, 1H), 7.28-7.38 (m, 8H), 7.10-7.15 (m, 1H), 6.46-6.52 (m, 2H), 4.57 (s, 2H), 4.19 (t, J=6.0 Hz, 1H), 4.09 (t, J=7.2 Hz, 2H), 3.73-3.82 (m, 3H), 3.60-3.63 (m, 2H), 1.99 (t, J=6.4 Hz, 1H).

Step 2:

Phthalimide cleavage of 2-(2-(3-(2-(benzyloxy)ethoxy)phenoxy)ethyl)isoindoline-1,3-dione gave Example 112 as yellow oil. Yield (0.225 g, 32%): $^1$H NMR (400 MHz, DMSO-d$_6$) δ 7.32-7.37 (m, 4H), 7.26-7.31 (m, 1H), 7.13-7.18 (m, 1H), 6.48-6.53 (m, 3H), 4.55 (s, 2H), 4.11 (t, J=4.4 Hz, 2H), 3.88 (t, J=5.6 Hz, 2H), 3.75 (t, J=4.4 Hz, 2H), 2.84 (t, J=5.6 Hz, 2H). $^{13}$C NMR (100 MHz, DMSO-d$_6$) δ 159.9, 159.7, 138.3, 129.9, 128.3, 127.6, 127.5, 106.8, 106.7, 101.2, 72.1, 70.2, 68.2, 67.1, 40.9. MS: 288 [M+1]$^+$.

Example 113

Preparation of 2-(3-(2-methoxyethoxy)phenoxy)ethanamine

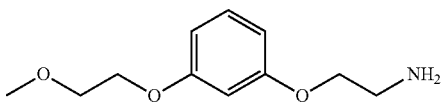

2-(3-(2-Methoxyethoxy)phenoxy)ethanamine was prepared following the method described in Example 46.

Step 1:

Mitsunobu reaction of phenol 24 with 2-methoxyethanol gave 2-(2-(3-(2-methoxyethoxy)phenoxy)ethyl)isoindoline-1,3-dione as a clear oil. Yield (0.5 g, 41%): $^1$H NMR (400 MHz, CDCl$_3$) δ 7.83-7.89 (m, 2H), 7.67-7.75 (m, 2H), 7.10-7.16 (t, J=6.4 Hz, 1H), 6.45-6.52 (m, 3H), 4.19 (t, J=5.8 Hz, 2H), 4.05-4.12 (m, 4H), 3.71-3.74 (m, 2H), 3.45 (s, 3H).

Step 2:

Phthalimide cleavage of 2-(2-(3-(2-methoxyethoxy)phenoxy) ethyl)isoindoline-1,3-dione gave Example 113 as a white foam. Yield (0.27 g, 87%). $^1$H NMR (400 MHz, DMSO-d$_6$) δ 7.15 (t, J=8.2 Hz, 1H), 6.47-6.52 (m, 3H), 4.03-4.06 (m, 2H), 3.87 (t, J=6 Hz, 2H), 3.62-3.65 (m, 2H), 3.3 (s, 3H), 2.85 (t, J=6 Hz, 2H), 1.6 (bs, 2H). $^{13}$C NMR (100 MHz, DMSO-d$_6$) 160.4, 160.1, 130.4, 107.2, 107.1, 101.5, 70.8, 70.6, 67.3, 58.6, 41.4. MS: 212 [M+1]$^+$.

Example 114

Preparation of 3-amino-1-(3-(4-(benzyloxy)butoxy)phenyl)propan-1-ol

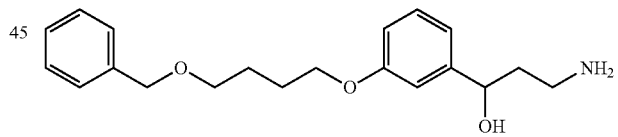

3-Amino-1-(3-(4-(benzyloxy)butoxy)phenyl)propan-1-ol was prepared following the method described in Example 54.

Step 1:

Alkylation of 3-hydroxybenzaldehyde with methanesulfonic acid 4-benzyloxy-butyl ester gave 3-(4-benzyloxybutoxy)benzaldehyde as a clear oil. Yield (1.1 g, 61%): $^1$H NMR (400 MHz, CDCl$_3$) δ 9.97 (s, 1H), 7.41-7.46 (m, 2H), 7.33-7.38 (m, 5H), 7.28-7.31 (m, 1H), 7.14-7.18 (m, 1H), 4.53 (s, 2H), 4.04 (t, J=6.2 Hz, 2H), 3.56 (t, J=6.2 Hz, 2H), 1.88-1.96 (m, 2H), 1.78-1.85 (m, 2H).

Step 2:

Addition of acetonitrile to 3-(4-benzyloxybutoxy)benzaldehyde gave 3-[3-(4-benzyloxy-butoxy)-phenyl]-3-hydroxypropionitrile as yellow oil. Yield (0.3 g, 52%): $^1$H NMR (400 MHz, CDCl$_3$) δ 7.33-7.37 (m, 4H), 7.27-7.32 (m, 2H), 6.93-6.96 (m, 2H), 6.86 (d, J=8.0 Hz, 1H), 5.0 (t, J=6.4

Hz, 2H), 4.52 (s, 2H), 4.01 (t, J=6.2 Hz, 2H), 3.55 (t, J=6.0 Hz, 2H), 2.75 (d, J=6.4 Hz, 2H), 1.87-1.94 (m, 2H), 1.77-1.85 (m, 2H).

Step 3:

Reduction of 3-(3-(4-benzyloxy-butoxy)-phenyl)-3-hydroxy-propionitrile with BH$_3$-DMS gave Example 114 as a colorless oil. Yield (0.18 g, 60%): $^1$H NMR (400 MHz, DMSO-d$_6$) δ 7.25-7.38 (m, 5H), 7.16-7.22 (m, 1H), 6.84-6.88 (m, 2H), 6.74 (d, J=8.0 Hz, 1H), 4.62 (t, J=6.4 Hz, 1H), 4.47 (s, 2H), 3.95 (t, J=6.2 Hz, 2H), 3.49 (t, J=6.2 Hz, 2H), 2.58-2.68 (m, 2H), 1.73-1.79 (m, 2H), 1.68-1.74 (m, 2H), 1.60-1.67 (m, 2H). $^{13}$C NMR (100 MHz, DMSO-d$_6$) δ 159.0, 148.7, 139.1, 129.4, 128.7, 127.9, 127.8, 118.3, 112.9, 112.2, 72.3, 71.7, 69.8, 67.5, 42.7, 26.3, 26.2. MS: 330 [M+1]$^+$.

Example 115

Preparation of 3-amino-1-(3-(5-(benzyloxy)pentyloxy)phenyl)propan-1-ol

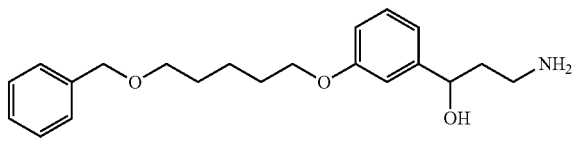 [SMILES: NCCC(O)c1cccc(OCCCCCOCc2ccccc2)c1]

3-Amino-1-(3-(5-(benzyloxy)pentyloxy)phenyl)propan-1-ol was prepared following the method described in Example 54.

Step 1:

Alkylation of 3-hydroxybenzaldehyde with methanesulfonic acid 4-benzyloxypentyl ester gave 3-(5-benzyloxypentoxy)benzaldehyde as a clear oil. Yield (1.3 g, 66%): $^1$H NMR (400 MHz, CDCl$_3$) δ 9.97 (s, 1H), 7.40-7.50 (m, 3H), 7.32-7.38 (m, 5H), 7.16-7.20 (m, 1H), 4.52 (s, 2H), 4.02 (t, J=6.4 Hz, 2H), 3.51 (t, J=6.4 Hz, 2H), 1.81-1.88 (m, 2H), 1.68-1.74 (m, 2H), 1.54-1.62 (m, 2H).

Step 2:

Addition of acetonitrile to 3-(5-benzyloxypentoxy)-benzaldehyde gave 3-[3-(5-benzyloxypentoxy)-phenyl]-3-hydroxypropionitrile as yellow oil. Yield (0.74 g, 51%): $^1$H NMR (400 MHz, CDCl$_3$) δ 7.23-7.41 (m, 6H), 6.90-6.98 (m, 2H), 6.86 (d, J=8.0 Hz, 1H), 5.0 (t, J=6.0 Hz, 1H), 4.51 (s, 2H), 3.98 (t, J=7.0 Hz, 2H), 3.51 (t, J=6.4 Hz, 2H), 2.75 (d, J=6.0 Hz, 2H), 1.75-1.84 (m, 2H), 1.67-1.73 (m, 2H), 1.53-1.62 (m, 2H).

Step 3:

Reduction of 3-(3-(5-benzyloxypentoxy)phenyl)-3-hydroxypropionitrile with BH$_3$.DMS gave Example 115 as colorless oil. Yield (0.51 g, 69%): $^1$H NMR (400 MHz, DMSO-d$_6$) δ 7.28-7.36 (m, 5H), 7.16-7.21 (m, 1H), 6.85-6.87 (m, 2H), 6.74 (d, J=8.0 Hz, 1H), 4.62 (t, J=6.4 Hz, 1H), 4.45 (s, 2H), 3.93 (t, J=6.4 Hz, 2H), 3.45 (t, J=6.4 Hz, 2H), 2.58-2.70 (m, 2H), 1.70-1.76 (m, 2H), 1.59-1.68 (m, 4H), 1.44-1.52 (m, 2H). $^{13}$C NMR (100 MHz, DMSO-d$_6$) δ 158.5, 148.2, 138.7, 128.8, 128.1, 127.3, 127.2, 117.7, 112.3, 111.7, 71.8, 71.2, 69.5, 67.1, 42.2, 38.8, 28.9, 28.5, 22.3. MS: 344 [M+1]$^+$.

Example 116

Preparation of 4-(3-(3-aminopropyl)phenoxy)-N-methylbutanamide

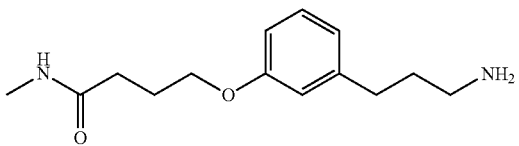 [SMILES: CNC(=O)CCCOc1cccc(CCCN)c1]

4-(3-(3-Aminopropyl)phenoxy)-N-methylbutanamide was prepared following the method described in Example 39.

Step 1:

The acid-amine coupling of acid 65 with methylamine gave tert-butyl 3-(3-(4-(methylamino)-4-oxobutoxy)phenyl)propylcarbamate as yellow oil. Yield (0.66 g, 66%): $^1$H NMR (400 MHz, CDCl$_3$) δ 7.16-7.20 (m, 1H), 6.76 (d, J=7.6 Hz, 1H), 6.70-6.71 (m, 2H), 3.99 (t, J=5.8 Hz, 2H), 3.13-3.15 (m, 2H), 2.80 (s, 3H), 2.61 (t, J=7.6 Hz, 2H), 2.38 (t, J=7.2 Hz, 2H), 2.08-2.15 (m, 2H), 1.76-1.83 (m, 2H), 1.44 (s, 9H).

Step 2:

Boc deprotection of tert-butyl 3-(3-(4-(methylamino)-4-oxobutoxy)phenyl)propylcarbamate gave Example 116 hydrochloride as white solid. Yield (0.360 g, 66%): $^1$H NMR (400 MHz, DMSO-d$_6$) δ 7.16-7.20 (m, 1H), 6.72-6.77 (m, 3H), 3.90 (t, J=5.2 Hz, 2H), 2.74 (t, J=6.8 Hz, 2H), 2.57-2.59 (m, 5H), 2.21 (t, J=6.8 Hz, 2H), 1.86-1.92 (m, 2H), 1.78-1.84 (m, 2H). $^{13}$C NMR (100 MHz, DMSO-d$_6$) δ 171.6, 158.3, 142.1, 129.1, 120.2, 114.2, 111.6, 66.5, 38.0, 31.6, 31.3, 28.3, 25.2, 24.6. MS: 251 [M+1]$^+$.

Example 117

Preparation of 4-(3-(3-aminopropyl)phenoxy)-N,N-dimethylbutanamide

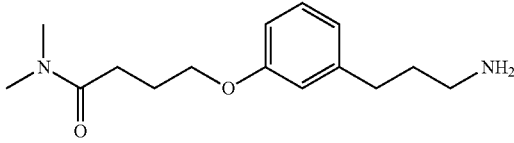 [SMILES: CN(C)C(=O)CCCOc1cccc(CCCN)c1]

4-(3-(3-Aminopropyl)phenoxy)-N,N-dimethylbutanamide was prepared following the method described in Example 39.

Step 9:

The acid-amine coupling of acid 65 with dimethylamine gave tert-butyl 3-(3-(4-(dimethylamino)-4-oxobutoxy)phenyl)propylcarbamate as yellow oil. Yield (0.625 g, 57%): $^1$H NMR (400 MHz, CDCl$_3$) δ 7.15-7.20 (m, 1H), 6.71-6.76 (m, 3H), 4.02 (t, J=5.6 Hz, 2H), 3.02 (s, 3H), 2.96 (s, 3H), 2.58 (t, J=7.6 Hz, 2H), 2.52 (t, J=7.2 Hz, 2H), 2.09-2.15 (m, 2H), 1.76-1.83 (m, 2H), 1.44 (s, 9H).

Step 10:

Boc deprotection of tert-butyl 3-(3-(4-(dimethylamino)-4-oxobutoxy)phenyl)propylcarbamate gave Example 117 hydrochloride as white solid. Yield (0.427 g, 83%): $^1$H NMR (400 MHz, DMSO-d$_6$) δ 7.17-7.22 (m, 1H), 6.75-6.77 (m, 3H), 3.95 (t, J=6.4 Hz, 2H), 2.94 (s, 2H), 2.81 (s, 3H), 2.77 (t, J=7.2 Hz, 2H), 2.60 (t, J=7.6 Hz, 2H), 2.43 (t, J=7.2 Hz, 2H), 1.88-1.93 (m, 2H), 1.79-1.84 (m, 2H). $^{13}$C NMR (100 MHz, DMSO-$d_6$) δ 171.1, 158.4, 142.2, 129.2, 120.2, 114.3, 111.7, 66.5, 38.0, 36.5, 34.7, 31.6, 28.4, 28.3, 24.2. MS: 265 [M+1]$^+$.

Example 118

Preparation of 2-(3-(3-aminopropyl)phenoxy)ethanol

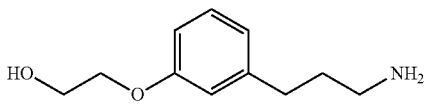 [SMILES: NCCCc1cccc(OCCO)c1]

2-(3-(3-aminopropyl)phenoxy)ethanol was prepared following the method described in Scheme 30.

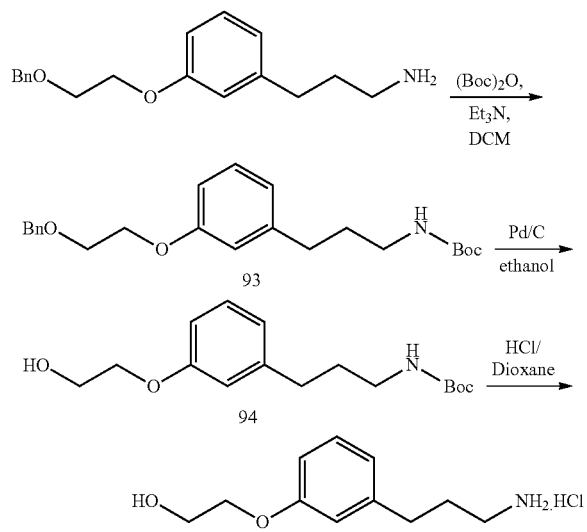

Step 1:
Boc protection of Example 102 gave tert-butyl 3-(3-(2-(benzyloxy)ethoxy)phenyl)propylcarbamate (93) as yellow oil. Yield (0.570 g, 90%): $^1$H NMR (400 MHz, CDCl$_3$) δ 7.33-7.37 (m, 4H), 7.27-7.31 (m, 1H), 7.18 (dd, J=7.2, 2.0 Hz, 1H), 6.73-6.78 (m, 3H), 4.64 (s, 2H), 4.14 (t, J=5.2 Hz, 2H), 3.83 (t, J=5.2 Hz, 2H), 3.10-3.16 (m, 2H), 2.60 (t, J=7.6 Hz, 2H), 1.75-1.81 (m, 2H), 1.44 (s, 9H).
Step 2:
Debenzylation of tert-butyl 3-(3-(2-(benzyloxy)ethoxy) phenyl) propylcarbamate (93) using Pd/C gave tert-butyl 3-(3-(2-hydroxyethoxy)phenyl)propyl carbamate (94) as yellow oil. Yield (0.370 g, 87%): $^1$H NMR (400 MHz, DMSO-$d_6$) δ 7.14-7.19 (m, 1H), 6.71-6.76 (m, 3H), 3.95 (t, J=5.2 Hz, 2H), 3.67-3.71 (m, 2H), 3.32-3.36 (m, 2H), 2.88-2.93 (m, 2H), 1.61-1.69 (m, 2H), 1.37 (s, 9H).
Step 3:
Boc deprotection of tert-butyl 3-(3-(2-hydroxyethoxy) phenyl) propylcarbamate (94) using HCl in dioxane gave Example 118 as yellow oil. Yield (0.232 g, 85%): $^1$H NMR (400 MHz, DMSO-$d_6$) δ 7.16-7.21 (m, 1H), 6.72-6.78 (m, 3H), 3.93 (t, J=4.0 Hz, 2H), 3.69 (t, J=4.0 Hz, 2H), 2.75 (t, J=7.2 Hz, 2H), 2.57 (t, J=7.2 Hz, 2H), 1.76-1.84 (m, 2H). $^{13}$C NMR (100 MHz, DMSO-$d_6$) δ 159.2, 142.8, 129.9, 121.0, 115.0, 112.4, 69.8, 60.1, 38.8, 32.3, 29.0. MS: 232 [M+1]$^+$.

Example 119

Preparation of 3-(3-(4-methylbenzyloxy)phenyl)propan-1-amine

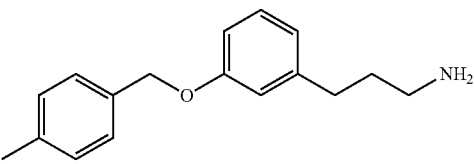 [SMILES: Cc1ccc(COc2cccc(CCCN)c2)cc1]

3-(3-(4-Methylbenzyloxy)phenyl)propan-1-amine was prepared following the method described in Example 33.
Step 1:
Mitsunobu coupling of phenol 58 with 4-methylbenzylalcohol followed by flash chromatography (5 to 30% EtOAc-hexanes gradient) gave 2-(3-(3-(4-methylbenzyloxy)phenyl)propyl)isoindoline-1,3-dione as a white waxy solid. Yield (2.6 g, 69%): $^1$H NMR (400 MHz, CDCl$_3$) δ 7.80 (dd, J=3.2 Hz, 2H), 7.67 (d, J=3.2 Hz, 2H), 7.32 (d, J=8.0 Hz, 2H), 7.16 (dd, J=8.0 Hz, 3H), 6.75-6.85 (m, 3H), 4.98 (s, 2H), 3.74 (t, J=8.0 Hz, 2H), 2.67 (t, J=8.0 Hz, 2H), 2.35 (s, 3H), 2.04 (dddd, J=8.0, 2H).
Step 2:
Hydrazine deprotection of 2-(3-(3-(4-methylbenzyloxy) phenyl)propyl)isoindoline-1,3-dione, followed by flash chromatography (5% 7 M NH$_3$ in MeOH/CH$_2$Cl$_2$) gave Example 119 as a white semisolid. Yield (0.22 g, 65%): $^1$H NMR (400 MHz, CDCl$_3$) δ 7.31 (d, J=8.0 Hz, 2H), 7.17-7.19 (m, 3H), 6.77-6.81 (m, 3H), 4.99 (s, 2H), 2.71 (t, J=8.0 Hz, 2H), 2.62 (t, J=8.0, 2H), 2.35 (s, 3H), 1.76 (dddd, J=6.4, 2H), 1.25 (br s, 2H).

Example 120

Preparation of 3-(3-(4-chlorobenzyloxy)phenyl)propan-1-amine

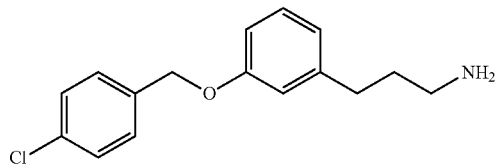 [SMILES: NCCCc1cccc(OCc2ccc(Cl)cc2)c1]

3-(3-(4-Chlorobenzyloxy)phenyl)propan-1-amine was prepared following the method described in Example 33.
Step 1:
Mitsunobu coupling of phenol 58 with 4-chlorobenzylalcohol followed by flash chromatography (5 to 30% EtOAc-hexanes gradient) gave 2-(3-(3-(4-chlorobenzyloxy)phenyl) propyl)isoindoline-1,3-dione as a colorless oil. Yield (2.82 g, 71%). $^1$H NMR (400 MHz, CDCl$_3$) δ 7.79-7.82 (m, 2H), 7.67-7.69 (m, 2H), 7.31-7.38 (m, 4H), 7.15 (t, J 8.0 Hz, 1H), 6.79-6.81 (m, 2H), 6.70-6.73 (m, 1H), 4.99 (s, 2H), 3.72 (t, J=7.2 Hz, 2H), 2.65 (t, J=8.0 Hz, 2H), 2.02 (dddd, J=7.2 Hz, 2H).

Step 2:
Hydrazine deprotection of 2-(3-(3-(4-chlorobenzyloxy)phenyl)propyl)isoindoline-1,3-dione followed by flash chromatography (5% 7 M NH$_3$ in MeOH/CH$_2$Cl$_2$) gave Example 120 as a white solid. Yield (0.213 g, 60%). $^1$H NMR (400 MHz, CDCl$_3$) δ 7.32-7.38 (m, 4H), 7.19 (t, J 8.0 Hz, 1H), 6.74-6.82 (m, 3H), 5.00 (s, 2H), 2.71 (t, J=7.2 Hz, 2H), 2.62 (t, J=8.0 Hz, 2H), 1.75 (dddd, J=7.2, 2H), 1.19 (br s, 2H).

Example 121

Preparation of 3-(3-(4-methoxybenzyloxy)phenyl)propan-1-amine

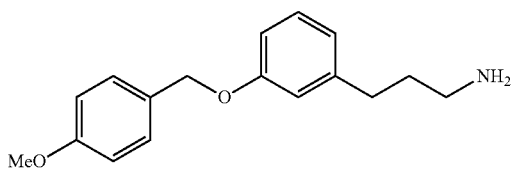 [SMILES: COc1ccc(COc2cccc(CCCN)c2)cc1]

3-(3-(4-Methoxybenzyloxy)phenyl)propan-1-amine was prepared following the method described in Example 33.
Step 1:
Mitsunobu Coupling of 4-methoxybenzylalcohol with phenol 58 gave 2-(3-(3-(4-methoxybenzyloxy)phenyl)propyl)isoindoline-1,3-dione as a white waxy solid. Yield (1.9 g, 48%). $^1$H NMR (400 MHz, CDCl$_3$) δ 7.81 (dd, J=2.4 Hz, 2H), 7.69 (dd, J=3.2 Hz, 2H), 7.34 (d, J=8.8 Hz, 2H), 7.14 (t, J=7.2 Hz, 1H), 6.88-6.92 (m, 2H), 6.77-6.81 (m, 2H), 6.72 (dd, J=2.0, 8.0 Hz, 1H), 4.95 (s, 2H), 3.80 (s, 3H), 3.73 (q, J=7.2 Hz, 2H), 2.65 (t, J=8.0 Hz, 2H), 2.01 (dd, J=7.2 Hz, 2H).
Step 2:
Hydrazine deprotection of 2-(3-(3-(4-methoxybenzyloxy)phenyl)propyl)isoindoline-1,3-dione gave Example 121 as a white solid. Yield (161 mg, 48%). $^1$H NMR (400 MHz, CDCl$_3$) δ 7.34 (d, J=8.0 Hz, 2H), 7.18 (t, J=8.0 Hz, 1H), 7.89-6.92 (m, 2H), 6.77-6.80 (m, 3H), 4.96 (s, 2H), 3.80 (s, 3H), 2.71 (t, J=7.2 Hz, 2H), 2.62 (t, J=8.0 Hz, 2H), 1.76 (dddd, J=8.0 Hz, 2H), 1.26 (bs, 2H).

Example 122

Preparation of 3-(3-(thiazol-2-ylmethoxy)phenyl)propan-1-amine

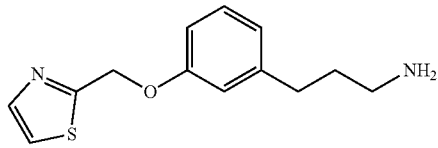 [SMILES: NCCCc1cccc(OCc2nccs2)c1]

3-(3-(Thiazol-2-ylmethoxy)phenyl)propan-1-amine was prepared following the method described in Example 33.
Step 1:
Mitsunobu coupling of 2-hydroxymethylthiazole with phenol 58 gave 2-(3-(3-(thiazol-2-ylmethoxy)phenyl)propyl)isoindoline-1,3-dione as a pale yellow solid with an unknown impurity. Yield (2.27 g, 69%). $^1$H NMR (400 MHz, CDCl$_3$) δ 7.68-7.72 (m, 3H), 7.55-7.60 (m, 2H), 7.27 (d, J=3.2 Hz, 1H), 7.06 (t, J=8.0 Hz, 1H), 6.72-6.78 (m, 2H), 6.67 (dd, J=3.2, 8.0 Hz, 1H), 5.25 (s, 2H), 3.64 (t, J=3.2 Hz, 2H), 2.57 (t, J=4.0 Hz, 2H), 2.01 (dddd, J=3.2 Hz, 2H).
Step 2:
Hydrazine deprotection of 2-(3-(3-(thiazol-2-ylmethoxy)phenyl)propyl)isoindoline-1,3-dione gave Example 122 as a colorless oil. Yield (264 mg, 74%). %). $^1$H NMR (400 MHz, CDCl$_3$) δ 7.77 (d, J=3.2 Hz, 1H), 7.33 (d, J=3.2 Hz, 1H), 7.18 (t, J=8.0 Hz, 1H), 7.79-7.83 (m, 3H), 5.35 (s, 2H), 2.69 (t, J=7.2 Hz, 2H), 2.62 (t, J=7.2 Hz, 2H), 1.74 (dddd, J=7.2, 2H), 1.41 (bs, 2H).

Example 123

Preparation of 2-(3-(cyclohexylmethoxy)phenylthio)ethanamine

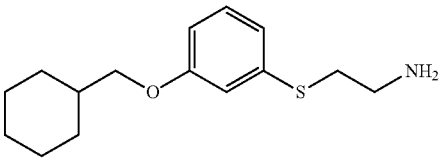

2-(3-(Cyclohexylmethoxy)phenylthio)ethanamine was prepared following the method shown in Scheme 31.

SCHEME 31

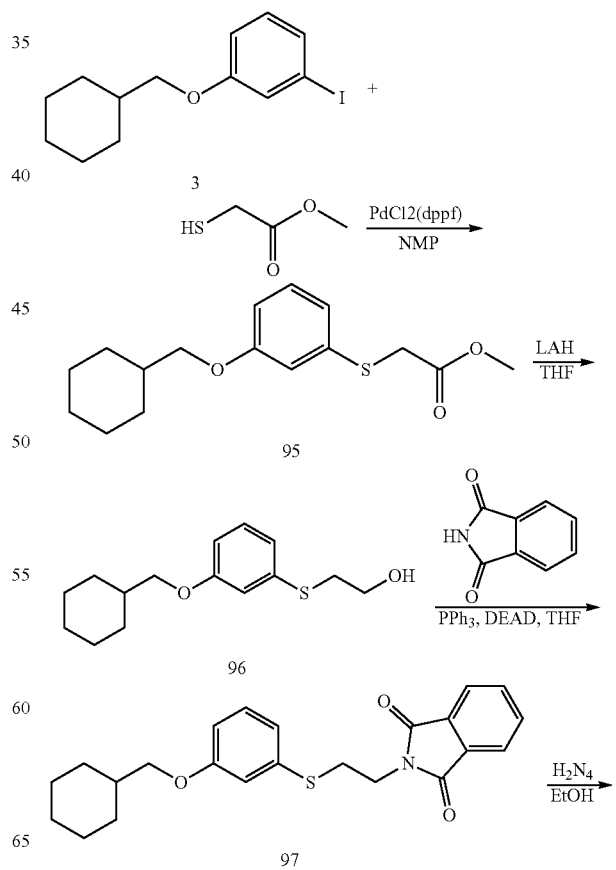

343

-continued

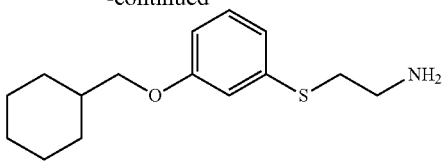

Step 1:

To a degassed solution under argon of 1-(cyclohexyl-methoxy)-3-iodobenzene (3) (3.15 g, 9.96 mmol), triethylamine (4.0 mL, 28.7 mmol), and methylthioglycolate (2.5 mL, 28.0 mmol) in NMP (60 mL) was added dichlorobis (triphenylphosphine)-palladium (II) (0.39 g, 0.48 mmol). The reaction was heated at 80° C. for 24 h. The reaction mixture was extracted from water with EtOAc and the combined organics were washed with water and brine, dried over Na$_2$SO$_4$, filtered, and concentrated under reduced pressure. Purification of the residue by flash chromatography gave the methyl ester 95 as a colorless oil. Yield (0.95 g, 32%): NMR (400 MHz, CDCl$_3$) δ 7.15-7.22 (m, 1H), 6.92-6.95 (m, 2H), 6.72-6.77 (m, 1H), 3.70-3.80 (m, 5H), 3.65 (s, 2H), 1.64-1.90 (m, 6H), 1.14-1.36 (m, 3H), 0.98-1.02 (m, 2H).

Step 2:

Reduction of the methyl ester 95 according to the method used in Example 4 gave the alcohol 96 as a colorless oil. Yield (0.79 g, 92%): NMR (400 MHz, CDCl$_3$) δ 7.18 (t, J=8.0 Hz, 1H), 6.89-6.95 (m, 2H), 6.71-6.76 (m, 1H), 3.70-3.78 (m, 4H), 3.11 (t, J=5.6, 2H), 1.80-1.90 (m, 3H), 1.64-1.80 (m, 4H), 1.14-1.38 (m 3H), 0.98-1.10 (m, 2H).

Step 3:

Mitsunobu coupling of phthalimide with alcohol 96 was carried out according to the procedure used in Example 2. Flash chromatography (0-50% EtOAc/Hex gradient) gave the thioether 97 as off-white solids. Yield (1.4 g, 84%): NMR (400 MHz, CDCl$_3$) δ 7.76-7.81 (m, 2H), 7.66-7.72 (m, 2H), 7.10 (t, J=8.0 Hz, 1H), 6.90-6.96 (m, 2H), 6.58-6.62 (m, 1H), 3.94 (t, J=6.8 Hz, 2H), 3.70-3.72 (d, J=6.4 Hz, 2H), 3.23 (t, J=7.2 Hz, 2H), 1.85-1.90 (m, 2H), 1.65-1.85 (m, 3H), 1.15-1.40 (m, 4H), 1.00-1.15 (m, 2H).

Step 4:

Deprotection of thioether 97 according to the method used in Example 1, followed by flash chromatography (0-10% (7N NH$_3$/MeOH)/dichloromethane gradient), gave Example 123 as a colorless oil. Yield (0.074 g, 50%): $^1$H NMR (400 MHz, DMSO-d$_6$) δ 7.16 (t, J=8.0 Hz, 1H), 6.79-6.85 (m, 2H), 6.67-6.71 (m, 1H), 3.73 (d, J=6.8 Hz, 2H), 2.92 (t, J=6.0 Hz, 2H), 2.67 (t, J=6.0 Hz, 2H), 1.52-1.80 (m, 8H), 1.10-1.30 (m, 3H), 0.94-1.10 (m, 2H).

Example 124

Preparation of 2-(3-(cyclohexylmethoxy)phenylsulfinyl)ethanamine

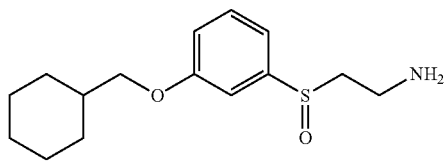 [SMILES: NCCS(=O)c1cccc(OCC2CCCCC2)c1]

344

2-(3-(Cyclohexylmethoxy)phenylsulfinyl)ethanamine was prepared following the method shown in Scheme 32.

SCHEME 32

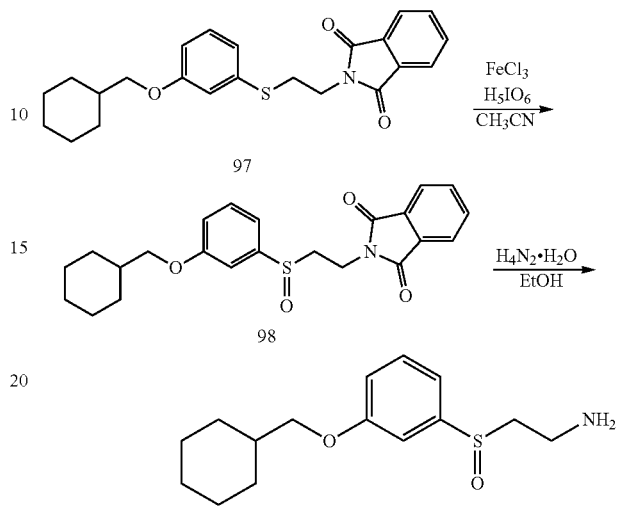

Step 1:

To a mixture of thioether 97 (0.336 g, 0.85 mmol) in acetonitrile was added iron(III) chloride (0.005 g, 0.031 mmol) and the reaction stirred 5 min, followed by addition of periodic acid (0.214 g, 0.94 mmol). The reaction was stirred for 30 min, then quenched by slow addition of 1M Na$_2$S$_2$O$_3$. The reaction was extracted from water with EtOAc and the combined organics washed with water and brine, dried over Na$_2$SO$_4$, filtered and concentrated under reduced pressure. Purification by flash chromatography (20-100% EtOAc/hexanes) gave the sulfoxide 98 as a colorless oil. Yield (0.299 g, 85%): NMR (400 MHz, CDCl$_3$) δ 7.72-7.78 (m, 2H), 7.64-7.70 (m, 2H), 2.26 (t, J=8.0 Hz, 1H), 7.16-7.20 (m, 1H), 7.05-7.19 (m, 1H), 6.75-6.84 (m, 1H), 3.90-4.15 (m, 2H), 3.73 (d, J=6.0 Hz, 2H), 3.19 (t, J=6.4 Hz, 2H), 1.60-1.95 (m, 6H), 0.95-1.35 (m, 5H).

Step 2:

Deprotection of sulfoxide 98 according to the method used in Example 1, followed by Prep TLC (10% (7N NH$_3$/MeOH)/dichloromethane), gave Example 124 as a colorless oil. Yield (0.046 g, 27%): NMR (400 MHz, CD$_3$OD) δ 7.46 (t, J=8.0 Hz, 1H), 7.16-7.26 (m, 2H), 7.06-7.10 (m, 1H), 3.82 (d, J=6.4 Hz, 2H), 2.90-3.10 (m, 4H), 1.84-1.94 (m, 2H), 1.64-1.84 (m, 4H), 1.16-1.40 (m, 3H), 1.04-1.16 (m, 2H).

Example 125

Preparation of 2-(3-(cyclohexylmethoxy)phenylsulfonyl)ethanamine

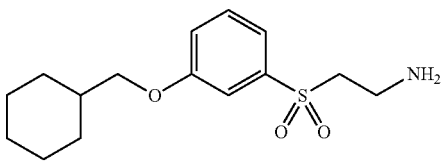 [SMILES: NCCS(=O)(=O)c1cccc(OCC2CCCCC2)c1]

2-(3-(Cyclohexylmethoxy)phenylsulfonyl)ethanamine was prepared following the method shown in Example in Scheme 33.

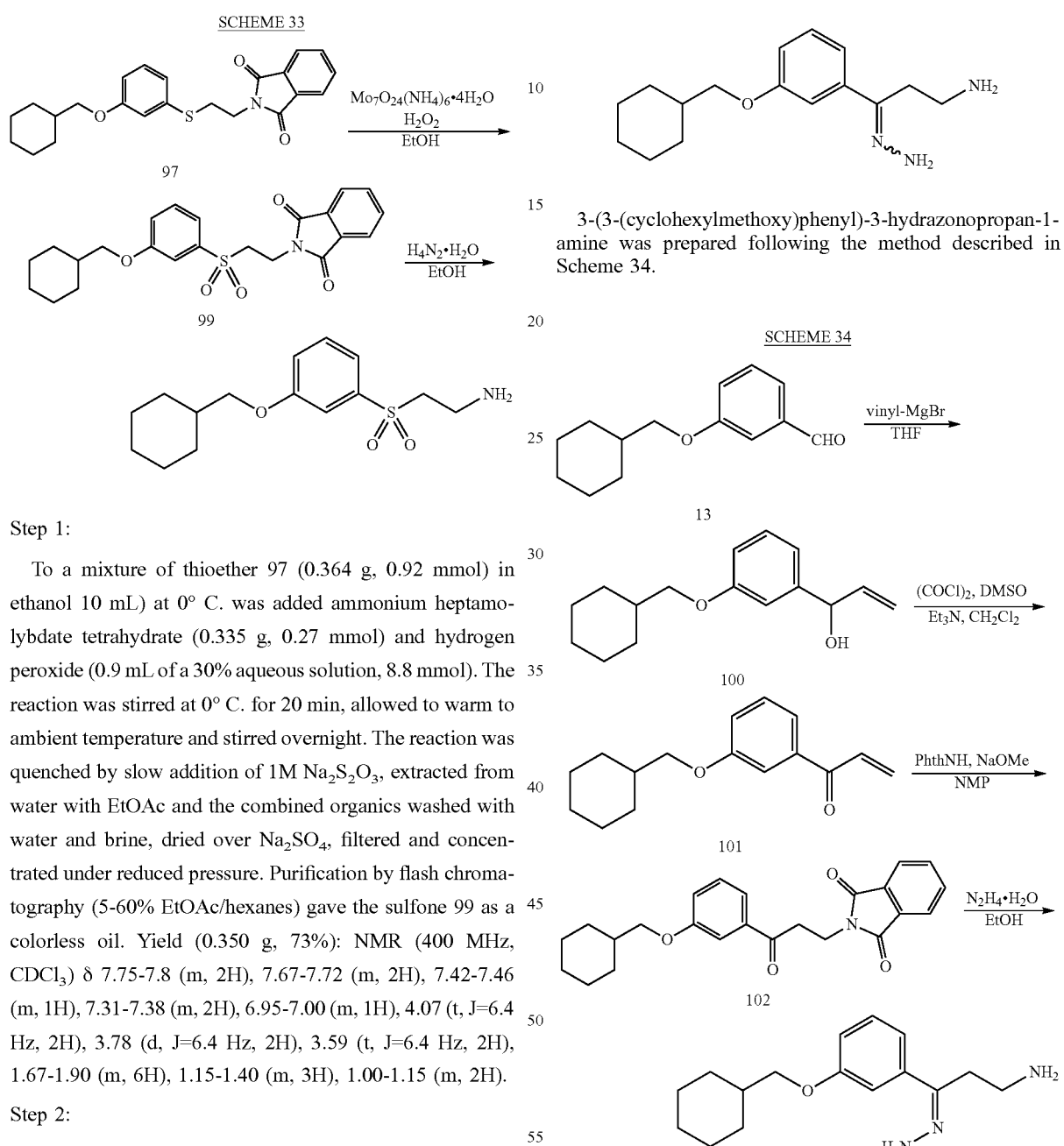

Step 1:

To a mixture of thioether 97 (0.364 g, 0.92 mmol) in ethanol 10 mL at 0° C. was added ammonium heptamolybdate tetrahydrate (0.335 g, 0.27 mmol) and hydrogen peroxide (0.9 mL of a 30% aqueous solution, 8.8 mmol). The reaction was stirred at 0° C. for 20 min, allowed to warm to ambient temperature and stirred overnight. The reaction was quenched by slow addition of 1M Na$_2$S$_2$O$_3$, extracted from water with EtOAc and the combined organics washed with water and brine, dried over Na$_2$SO$_4$, filtered and concentrated under reduced pressure. Purification by flash chromatography (5-60% EtOAc/hexanes) gave the sulfone 99 as a colorless oil. Yield (0.350 g, 73%): NMR (400 MHz, CDCl$_3$) δ 7.75-7.8 (m, 2H), 7.67-7.72 (m, 2H), 7.42-7.46 (m, 1H), 7.31-7.38 (m, 2H), 6.95-7.00 (m, 1H), 4.07 (t, J=6.4 Hz, 2H), 3.78 (d, J=6.4 Hz, 2H), 3.59 (t, J=6.4 Hz, 2H), 1.67-1.90 (m, 6H), 1.15-1.40 (m, 3H), 1.00-1.15 (m, 2H).

Step 2:

Deprotection of sulfone 99 according to the method used in Example 1, followed by flash chromatography (0-10% (7N NH$_3$/MeOH)/dichloromethane gradient), gave Example 125 as a colorless oil. Yield (0.131 g, 90%): $^1$H NMR (400 MHz, DMSO-d$_6$) δ 7.53 (t, J=8.0 Hz, 1H), 7.38-7.42 (m, 1H), 7.30-7.33 (m, 1H) 7.24-7.29 (m, 1H), 3.84 (d, J=6.4 Hz, 2H), 3.32 (t, J=6.8 Hz, 2H), 2.73 (t, J=7.2 Hz, 2H), 1.58-1.84 (m, 6H), 1.51 (brs, 2H), 1.12-1.30 (m, 3H), 0.98-1.12 (m, 2H).

Example 126

Preparation of 3-(3-(cyclohexylmethoxy)phenyl)-3-hydrazonopropan-1-amine

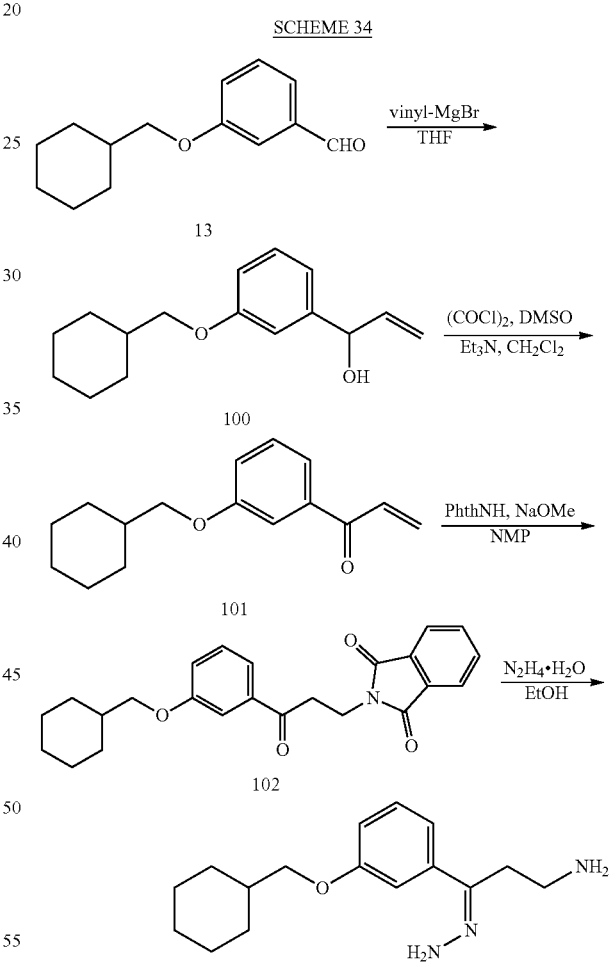

3-(3-(cyclohexylmethoxy)phenyl)-3-hydrazonopropan-1-amine was prepared following the method described in Scheme 34.

Step 1.

Synthesis of aldehyde 13: A mixture of 3-hydroxybenzaldehyde (4.50 kg, 36.8 mol), bromomethylcyclohexane (5.90 kg, 33.3 mol), anhydrous potassium carbonate (5.50 kg, 39.8 mol), and anhydrous N-methyl-2-pyrrolidinone (NMP, 5.9 L) was stirred while heating at 75° C. under nitrogen atmosphere for 18-26 h. The reaction was monitored by GC. Once the reaction is complete the reactor contents are allowed to cool to ambient temperature and are diluted with 17 L of 1 N aq. sodium hydroxide, 6 L of water, and 22 L of heptane. After stirring and separating the layers, the organic phase was washed with 8 L of 1 N aq. sodium hydroxide followed by 6 L of 25% aq. sodium chloride. The heptane solution was dried over 3 kg of anhydrous sodium sulfate, filtered to remove the drying agent, and concentrated under reduced pressure, 40-50° C., to yield 5.55 kg (76.0%) of aldehyde 13 as an amber oil.

To a cold (0° C.) solution of vinyl magnesium bromide in THF (1M, 120 mL) was added a solution of aldehyde 13 (20.04 g, 91.8 mmol) in anhydrous THF (60 mL) under argon atmosphere over 15 mins. The reaction mixture was stirred at 0° C. for 2 hours 40 mins and then allowed to warm to room temperature. Aqueous solution of $NH_4Cl$ (25%, 200 mL) was carefully added, layers were separated and aqueous layer was extracted with EtOAc (100 mL). Combined organic layers were washed with brine, dried with anhydrous $MgSO_4$, and filtered. Concentration of the filtrate under reduced pressure afforded allyl alcohol 100 which was used in the next step without additional purification. Yield (23.34 g, quant.). $^1$H NMR (400 MHz, DMSO-$d_6$) δ 7.17 (t, J=8.2 Hz, 1H), 6.81-6.85 (m, 2H), 6.74 (ddd, J=1.2, 2.2, 7.8 Hz, 1H), 5.89 (ddd, J=5.9, 10.2, 17.0 Hz, 1H), 5.42 (d, J=4.7 Hz, 1H), 5.21 (dt, J=1.8, 17.0 Hz, 1H), 4.95-5.02 (m, 2H), 3.72 (d, J=6.3 Hz, 2H), 1.60-1.80 (m, 6H), 1.10-1.30 (m, 3H), 0.90-1.10 (m, 2H).

Step 2.

To a cold (−78° C.) solution of oxalyl chloride (10 mL, 114.6 mmol) in anhydrous $CH_2Cl_2$ (60 mL) under argon atmosphere was added first half of a solution of DMSO (16 mL, 225.3 mmol) in anhydrous $CH_2Cl_2$ (16 mL) dropwise over 15 mins, second half was added at once. After that a solution of allyl alcohol 100 (23.34 g, 91.8 mmol) in anhydrous $CH_2Cl_2$ (30 mL) was added dropwise over 40 mins followed by $CH_2Cl_2$ (10 mL) and the reaction mixture was stirred for 30 mins at −78° C. Triethylamine (40 mL, 287.0 mmol) was added dropwise over 15 mins and the reaction mixture was allowed to warm to room temperature over 1 hour and transferred into a separating funnel. Water (500 mL) was added, the mixture was shaken, layers were separated and aqueous layer was extracted with $CH_2Cl_2$ (100 mL). Combined organic layers were consequently washed with aqueous HCl (1%, 200 mL), aq. $NaHCO_3$ (5%, 200 mL), brine (30%, 200 mL). Organic layer was treated with activated charcoal, dried over anhydrous $MgSO_4$, and filtered. Filtrated was concentrated under reduced pressure to give vinyl ketone 101 as an orange oil which was used in the next step without additional purification. Yield (23.1 g, quant, 80% pure by NMR). $^1$H NMR (400 MHz, DMSO-$d_6$) δ 7.55 (dt, J=1.2, 8.0 Hz, 1H), 7.39-7.45 (m, 2H), 7.37 (dd, J=10.6, 17.0 Hz, 1H), 6.31 (dd, J=2.0, 17.0 Hz, 1H), 5.94 (dd, J=2.0, 10.4 Hz, 1H), 3.82 (d, J=6.3 Hz, 2H), 1.60-1.80 (m, 6H), 1.10-1.30 (m, 3H), 0.90-1.10 (m, 2H).

Step 3.

To a solution of phthalimide (0.715 g, 4.86 mmol), NaOMe (30% in MeOH, 0.03 mL, 0.16 mmol) in anhydrous N-methylpyrrolidone (NMP, 5 mL) was added neat vinyl ketone 101 (1.024 g, 4.19 mmol) and the reaction mixture was stirred at room temperature for 3.5 hrs. Water (50 mL) was added, the precipitate was filtered off, washed with water, hexanes and dried on air to give phthalimidoketone 102 as a yellowish solid. Yield (1.235 g, 75%). $^1$H NMR (400 MHz, DMSO-$d_6$) δ 7.79-7.87 (m, 4H), 7.45-7.49 (m, 1H), 7.35-7.41 (m, 2H), 7.16 (ddd, J=0.6, 2.0, 8.2 Hz, 1H), 3.90 (t, J=7.2 Hz, 2H), 3.79 (d, J=6.3 Hz, 2H), 3.39 (t, J=7.0 Hz, 2H), 1.58-1.80 (m, 6H), 1.07-1.28 (m, 3H), 0.95-1.07 (m, 2H).

Step 4.

Deprotection of phthalimide 102 was done following the procedure described in Example 7 except that the reaction was stirred at 75° C. for 6 hrs, and then at room temperature for 15 hrs. Purification by flash chromatography (4% 7N $NH_3$/MeOH in $CH_2Cl_2$) gave Example 126 as yellowish oil. Yield (0.119 g, 30%). $^1$H NMR (400 MHz, DMSO-$d_6$) δ 7.12-7.19 (m, 3H), 6.73-6.78 (m, 1H), 6.57 (br. s, 2H), 3.72 (d, J=6.5 Hz, 2H), 1.58-1.81 (m, 6H), 1.55 (br. s, 2H), 1.07-1.28 (m, 3H), 0.95-1.07 (m, 2H); $^{13}$C NMR (400 MHz, DMSO-$d_6$+5% $D_2O$) δ 159.5, 144.7, 141.1, 129.8, 117.9, 114.0, 111.1, 73.3, 38.7, 37.8, 30.0, 26.7, 26.0.

Example 127

Preparation of 2-amino-1-(3-(cyclohexylmethoxy)phenyl)ethanol

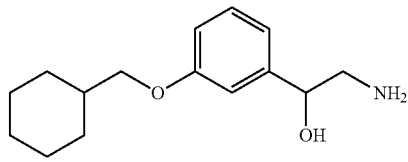 [SMILES: NCC(O)c1cccc(OCC2CCCCC2)c1]

2-Amino-1-(3-(cyclohexylmethoxy)phenyl)ethanol was prepared following the method described in Scheme 35.

SCHEME 35

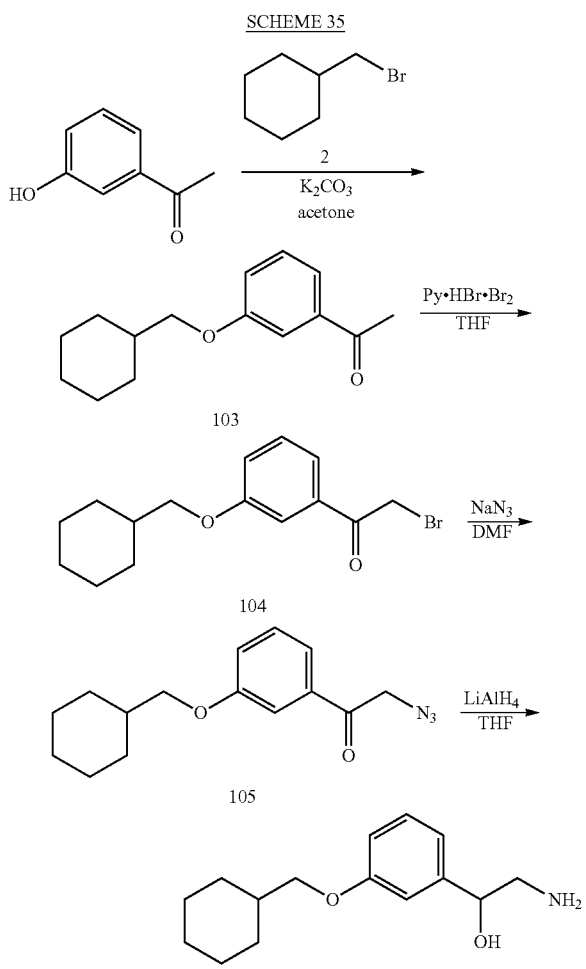

Step 1.

Alkylation of 3'-hydroxy-acetophenone by bromomethyl-cyclohexane (2) was performed following the method given in Example 1. The product was purified by flash chromatography (5 to 30% EtOAc/hexane gradient) to give 1-(3-(cyclohexylmethoxy)phenyl)ethanone (103) as a colorless oil. Yield (3.17 g, 45%). $^1$H NMR (400 MHz, DMSO-d$_6$) δ 7.50 (dt, J=1.4, 6.3 Hz, 1H), 7.36-7.42 (m, 2H), 7.16 (ddd, J=1.0, 2.7, 8.2 Hz, 1H), 3.80 (d, J=6.3 Hz, 2H), 2.54 (s, 3H), 1.60-1.80 (m, 6H), 1.10-1.30 (m, 3H), 0.90-1.10 (m, 2H).

Step 2.

To a solution of ketone 103 (3.17 g, 13.6 mmol) in THF (30 mL) was added pyridinium tribromide (5.47 g, 15.4 mmol) and the reaction mixture was stirred at room temperature for 40 mins. The precipitate was filtered off, filter cake was washed with MTBE, the filtrate was washed with brine, dried over anhydrous MgSO$_4$, treated with activated charcoal, filtered and the filtrate was concentrated under reduced pressure. The residue was purified by flash chromatography (5% to 30% EtOAc/hexane gradient) to give bromide 104 as a white solid. Yield (3.32 g, 78%). $^1$H NMR (400 MHz, DMSO-d$_6$) δ 7.54 (dt, J=1.0, 7.6 Hz, 1H), 7.45 (t, J=2.3 Hz, 1H), 7.42 (t, J=8.0 Hz, 1H), 7.21 (ddd, J=0.8, 2.5, 8.2 Hz, 1H), 4.91 (s, 2H), 3.82 (d, J=6.3 Hz, 2H), 1.55-1.81 (m, 6H), 1.09-1.29 (m, 3H), 0.97-1.09 (m, 2H).

Step 3.

Azidation of bromide 104 by NaN$_3$ was performed following the method given in Example 6 except that no NaI was used and the reaction mixture was heated at 50° C. for 30 mins. Purification by flash chromatography (5% to 30% EtOAc in hexanes gradient) afforded azidoketone 107 as a yellow oil. Yield (0.170 g, 57%). $^1$H NMR (400 MHz, CDCl$_3$) δ 7.27-7.37 (m, 3H), 7.07 (ddd, J=1.2, 2.5, 8.0 Hz, 1H), 4.47 (s, 2H), 3.73 (d, J=6.3 Hz, 2H), 1.60-1.82 (m, 6H), 1.08-1.29 (m, 3H), 0.93-1.05 (m, 2H).

Step 4.

Reduction of azidoketone 107 with LiAlH$_4$ following the method described for Example 4 gave Example 128 as a colorless oil. Yield (0.023 g, 15%). $^1$H NMR (400 MHz, DMSO-d$_6$) δ 7.16 (t, J=7.6 Hz, 1H), 6.80-6.84 (m 2H), 6.71-6.75 (m, 1H), 4.36 (dd, J=4.3, 7.6 Hz, 1H), 3.72 (d, J=6.3 Hz, 2H), 2.62 (ABd, J=4.3, 12.9 Hz, 1H), 2.52 (ABd, J=7.6, 5.1 Hz, 1H), 1.58-1.82 (m, 6H), 1.09-1.29 (m, 3H), 0.97-1.09 (m, 2H). RP-HPLC: 96.4%, t$_R$=7.13 min (Method 2).

Example 128

Preparation of N$^1$-(3-(cyclohexylmethoxy)phenyl)-N$^1$-methylethane-1,2-diamine

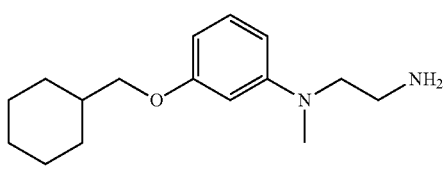 [SMILES: CN(CCN)c1cccc(OCC2CCCCC2)c1]

N$^1$-(3-(Cyclohexylmethoxy)phenyl)-N$^1$-methylethane-1,2-diamine was prepared following the method described in Scheme 36.

SCHEME 36

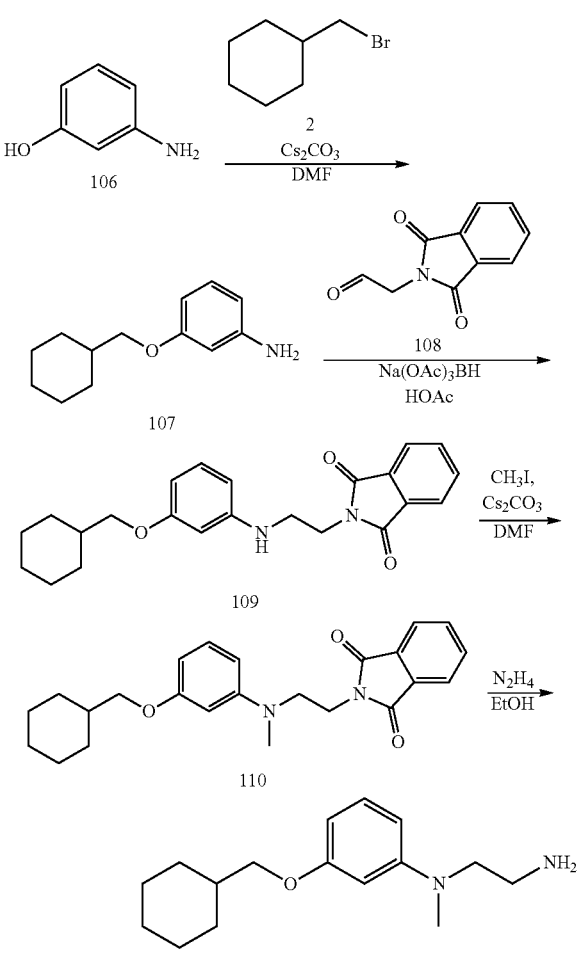

Step 1:

A mixture of bromomethylcyclohexane (2) (18 g, 100 mmol), phenol 106 (13 g, 12 mmol), and cesium carbonate (65 g, 20 mmol) in DMF (200 mL) was heated at 50° C. for 5 h, then diluted with EtOAc and washed with 1N NaOH, water, and brine. The combined organics were dried over Na$_2$SO$_4$, filtered, and concentrated under reduced pressure. Purification by flash chromatography (20-100% EtOAc-hexanes gradient) gave aniline 107 as a brown oil, which solidified upon standing. Yield (12.4 g, 60%): $^1$H NMR (400 MHz, CDCl$_3$) δ 7.04 (t, J=8, 1H), 6.25-6.34 (m, 3H), 3.71 (d, J=5.8, 2H), 3.67 (br s, 2H), 1.82-1.90 (m, 2H), 1.65-1.82 (m, 4H), 1.14-1.36 (m, 3H), 0.97-1.10 (m, 2H).

Step 2:

A mixture of aniline 107 (1.37 g, 6.7 mmol), 2-(1,3-dioxoisoindolin-2-yl)acetaldehyde (108) (1.26 g, 6.7 mmol), sodium triacetoxyborohydride (2.1 g, 10.05 mmol), and acetic acid (0.04 g, 6.7 mmol) in dry dichloromethane under argon was stirred at room temperature for 2 h. The reaction mixture was washed with saturated aqueous NaHCO$_3$, water, and brine. The combined organics were dried over Na$_2$SO$_4$, filtered, and concentrated under reduced vacuum. Flash chromatography (0-60% EtOAc-hexanes gradient), gave the secondary aniline 109 as a yellow oil. Yield (1.6 g, 64%): $^1$H NMR (400 MHz, CDCl$_3$) δ 7.80-7.85 (m, 2H), 7.66-6.72 (m, 2H), 7.01 (t, J=6 Hz, 1H), 6.18-6.22 (m, 2H), 6.14-6.18 (m, 1H), 4.05 (br s, 1H), 3.95 (t, J=6.0 Hz, 2H), 3.68 (d, J=6.4 Hz, 2H), 3.41 (t, J=6.4 Hz, 2H), 1.80-1.88 (m, 2H), 1.64-1.78 (m, 4H), 1.12-1.34 (m, 3H), 0.96-1.08 (m, 2H).

Step 3:

A mixture of secondary aniline 109 (1.35 g, 3.6 mmol), methyl iodide (0.27 mL, 4.3 mmol), and cesium carbonate (2.3 g, 7.2 mmol) in dry DMF (20 mL) under argon was stirred at room temperature for 4 d. A large excess of methyl iodide (1 mL) was added and the reaction heated to 50° C. for 3 h. The reaction mixture was diluted with dichloromethane and washed with water and brine. The organic layers were combined, dried over Na$_2$SO$_4$, filtered, and concentrated under reduced pressure. Purification by flash chromatography (0-30% EtOAc-hexanes gradient) gave the tertiary aniline 110 as a yellow solid. Yield (0.84 g, 60%): $^1$H NMR (400 MHz, CDCl$_3$) δ 7.74-7.80 (m, 2H), 7.63-6.69 (m, 2H), 7.00 (t, J=8 Hz, 1H), 6.35 (dd, J=8, 2 Hz, 1H), 6.27 (t, J=2.4 Hz, 1H), 6.14 (dd, J=8.0, 2.0 Hz, 1H), 3.87 (t, J=6.4 Hz, 2H), 3.68 (d, J=6.8 Hz, 2H), 3.60 (t, J=7.2 Hz, 2H), 2.96 (s, 3H), 1.82-1.90 (m, 2H), 1.64-1.82 (m, 4H), 1.14-1.36 (m, 3H), 0.97-1.10 (m, 2H).

Step 4:

Deprotection of the tertiary aniline 110 was carried out according to the method and purification used in Example 31, giving Example 129 as a colorless oil. Yield (0.42 g, 76%). $^1$H NMR (400 MHz, CDCl$_3$) 7.10 (t, J=8 Hz, 1H), 6.33-6.37 (m, 1H), 6.23-6.29 (m, 2H), 3.73 (d, J=6.4 Hz, 2H), 3.54 (t, J=6.4 Hz, 2H), 2.94 (s, 3H), 2.90 (t, J=6.4 Hz, 2H), 1.82-1.90 (m, 2H), 1.64-1.82 (m, 4H), 1.16-1.36 (m, 3H), 1.13 (s, 2H), 0.97-1.10 (m, 2H).

Example 129

Preparation of N$^1$-(3-(cyclohexylmethoxy)phenyl) ethane-1,2-diamine

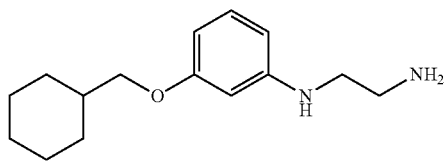 [SMILES: NCCNc1cccc(OCC2CCCCC2)c1]

N$^1$-(3-(Cyclohexylmethoxy)phenyl)ethane-1,2-diamine was prepared following the method described in Example 31:

Step 1:

Deprotection of secondary aniline 109 gave Example 129 as an orange oil. Yield (0.116 g, 66%). $^1$H NMR (400 MHz, CDCl$_3$) 7.04 (t, J=8 Hz, 1H), 6.24 (ddd, J=10, 8.4, 2 Hz, 2H), 6.18 (t, J=2 Hz, 1H), 3.70 (d, J=5.8 Hz, 2H), 3.16 (t, J=5.6 Hz, 2H), 2.93 (t, J=5.6, Hz, 2H), 1.80-1.90 (m, 2H), 1.64-1.80 (m, 4H), 1.10-1.38 (m, 5H), 0.96-1.08 (m, 2H).

Example 130

Preparation of 3-(3-(cyclohexylmethoxy)phenyl)-3-hydroxypropanimidamide

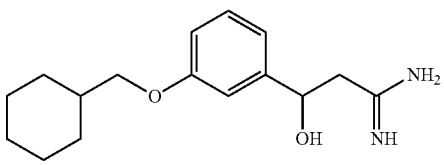 [SMILES: N=C(N)CC(O)c1cccc(OCC2CCCCC2)c1]

3-(3-(Cyclohexylmethoxy)phenyl)-3-hydroxypropanimidamide was prepared following the method shown in Scheme 37.

SCHEME 37

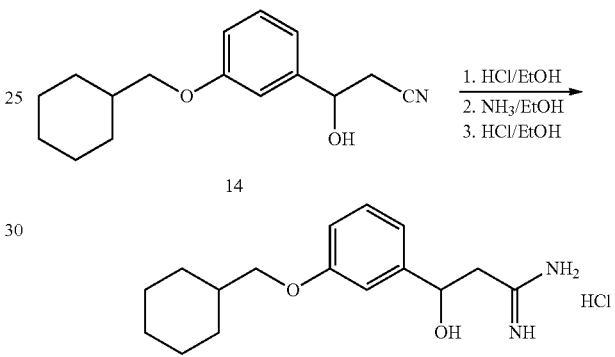

Synthesis of compound 14: Acetonitrile (0.750 L, 14.4 mol) was charged to a solution of 1.0 N potassium t-butoxide in tetrahydrofuran (THF, 15.2 L, 15.2 mol) keeping the temperature between −52 and −34° C. under a nitrogen atmosphere. The mixture was allowed to stir while cold for 30 min to 1 h and then a solution of 3-(cyclohexylmethoxy) benzaldehyde (2.75 kg, 12.6 mol) in THF (1.4 L) was added still maintaining the temperature between −50 and −34° C. The reaction mixture was left to stir until the reaction was found to be complete by HPLC (~30 min). The reaction mixture was then warmed to −20 to −15° C. and the reaction was quenched by the addition of 5.5 L of 25% aq. ammonium chloride. The mixture was warmed to ambient temperature over at least 30 min and the layers were separated. The THF was stripped by evaporation under reduced pressure (40-50° C.) and the residue re-dissolved in 27 L of methyl t-butyl ether (MTBE). The solution was washed with 6 L of 25% aq. sodium chloride, dried over 5 kg of anhydrous sodium sulfate, filtered to remove the drying agent, and concentrated under reduced pressure, 40-50° C., to yield 3.13 kg (96.2%) of compound 14 as a dark amber oil.

Into an ice cold solution of the nitrile 14 (2.50 g, 9.64 mmol) in absolute EtOH (50 ml) was bubbled HCl gas for 4 to 5 min. This mixture was allowed to warm to room temperature and stirred. The solvent was removed under reduced pressure. To the residue was added absolute EtOH (50 ml) with cooling in an ice bath. NH$_3$ gas was bubbled into the solution for 2-3 min. The mixture was allowed to warm to room temperature and stirred for 4 h. The mixture was concentrated under reduced pressure. To the residue was added absolute EtOH (50 ml) with cooling in an ice bath. HCl gas was bubbled into the solution for 1 min. and the mixture was concentrated under reduced pressure. The residue was dissolved in H₂O (50 ml) and extracted with EtOAc (50 ml). The aqueous layer was evaporated to dryness and dried under high vacuum overnight to give Example 130 as a fluffy white solid. Yield (2.73 g, 90%): ¹H NMR (400 MHz, DMSO-d₆) δ 8.99 (s, 2H), 8.65 (s, 2H), 7.22 (t, J=7.8 Hz, 1H), 6.95-6.92 (m, 2H), 6.79 (dd, J=8.0, 2.2 Hz, 1H), 5.83 (d, J=4.4 Hz, 1H), 4.99-4.94 (m, 1H), 3.73 (d, J=6.0 Hz, 2H), 2.71 (dd, J=13.6, 4.0 Hz, 1H), 2.57 (dd, J=13.2, 10.2 Hz, 1H), 1.79-1.61 (m, 6H), 1.28-0.96 (m, 5H).

Example 131

Preparation of 3-amino-1-(3-(3-(benzyloxy)propoxy)phenyl)propan-1-ol

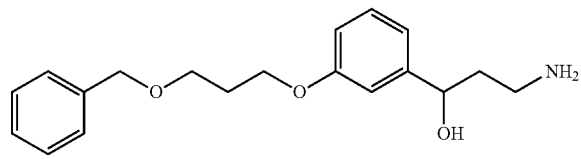 [SMILES: NCCC(O)c1cccc(OCCCOCc2ccccc2)c1]

3-Amino-1-(3-(3-(benzyloxy)propoxy)phenyl)propan-1-ol was prepared following the method use for Example 108.

Step 1:

Alkylation of 3-hydroxybenzaldehyde (11) with methanesulfonic acid 3-benzyloxy-propyl ester gave 3-(3-benzyloxy-propoxy)-benzaldehyde as a clear oil. Yield (1.5 g, 55%): ¹H NMR (400 MHz, CDCl₃) δ 9.97 (s, 1H), 7.38-7.46 (m, 3H), 7.28-7.33 (m, 5H), 7.16 (d, J=6.8 Hz, 1H), 4.53 (s, 2H), 4.15 (t, J=6.0 Hz, 2H), 3.67 (t, J=6.0 Hz, 2H), 2.08-2.14 (m, 2H).

Step 2:

Addition of acetonitrile to 3-(3-benzyloxy-propoxy)-benzaldehyde gave 3-(3-(3-benzyloxy-propoxy)-phenyl)-3-hydroxy-propionitrile as yellow oil. Yield (0.94 g, 54%): ¹H NMR (400 MHz, CDCl₃) δ 7.23-7.38 (m, 6H), 6.90-6.96 (m, 2H), 6.81-6.86 (m, 1H), 5.00 (m, 1H), 4.53 (s, 2H), 4.10 (t, J=6.2 Hz, 2H), 3.67 (t, J=6.0 Hz, 2H), 2.75 (t, J=6.4 Hz, 2H), 2.04-2.13 (m, 2H).

Step 3 Reduction of 3-(3-(3-benzyloxy-propoxy)-phenyl)-3-hydroxy-propionitrile with BH₃-DMS gave Example 12 as a colorless oil. Yield (0.48 g, 51%): ¹H NMR (400 MHz, DMSO-d₆) δ 7.30-7.34 (m, 4H), 7.26-7.29 (m, 1H), 7.18-7.21 (m, 1H), 6.86-6.88 (m, 2H), 6.75 (dd, J=7.2, 2.4 Hz, 1H), 4.62 (t, J=6.4 Hz, 1H), 4.48 (s, 2H), 4.03 (t, J=6.4 Hz, 2H), 3.59 (t, J=6.2 Hz, 2H), 2.60-2.66 (m, 2H), 1.97-2.01 (m, 2H), 1.59-1.65 (m, 2H). ¹³C NMR (100 MHz, DMSO-d₆) δ 158.9, 148.8, 139.0, 129.4, 128.7, 127.9, 127.8, 118.4, 112.9, 112.2, 72.4, 71.7, 66.8, 64.9, 42.9, 39.4, 29.7. MS: 316 [M+1]⁺.

Example 132

Preparation of 3-amino-1-(3-(2-(benzyloxy)ethoxy)phenyl)propan-1-ol

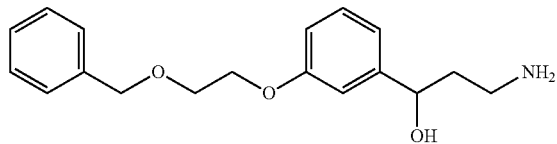 [SMILES: NCCC(O)c1cccc(OCCOCc2ccccc2)c1]

3-Amino-1-(3-(2-(benzyloxy)ethoxy)phenyl)propan-1-ol was prepared following the method used for Example 54.

Step 1:

Alkylation of 3-hydroxybenzaldehyde with methanesulfonic acid 2-benzyloxyethyl ester gave 3-(2-benzyloxyethoxy)benzaldehyde as a clear oil. Yield (0.96 g, 66%): ¹H NMR (400 MHz, CDCl₃) δ 9.97 (s, 1H), 7.43-7.47 (m, 2H), 7.40-7.43 (m, 1H), 7.34-7.39 (m, 4H), 7.30-7.33 (m, 1H), 7.20-7.24 (m, 1H), 4.65 (s, 2H), 4.22 (t, J=4.6 Hz, 2H), 3.86 (t, J=4.6 Hz, 2H).

Step 2:

Addition of acetonitrile to 3-(2-benzyloxyethoxy)benzaldehyde gave 3-(3-(2-benzyloxy-thoxy)-phenyl)-3-hydroxy-propionitrile as yellow oil. Yield (0.45 g, 41%): ¹H NMR (400 MHz, CDCl₃) δ 7.33-7.38 (m, 4H), 7.28-7.32 (m, 2H), 6.95-7.0 (m, 2H), 6.89-6.93 (m, 1H), 4.99-5.03 (m, 1H), 4.64 (s, 2H), 4.17 (t, J=4.8 Hz, 2H), 3.84 (t, J=4.8 Hz, 2H), 2.75 (d, J=5.6 Hz, 2H).

Step 3:

Reduction of 3-(2-benzyloxyethoxy)benzaldehyde gave 3-(3-(2-benzyloxyethoxy)phenyl)-3-hydroxy-propionitrile with BH₃-DMS gave Example 132 as colorless oil. Yield (0.57 g, 65%): ¹H NMR (400 MHz, DMSO-d₆) δ 7.33-7.37 (m, 4H), 7.26-7.32 (m, 1H), 7.18-7.23 (m, 1H), 6.87-6.91 (m, 2H), 6.80 (dd, J=8.0, 1.8 Hz, 1H), 4.63 (t, J=6.4 Hz, 1H), 4.56 (s, 2H), 4.12 (t, J=4.6 Hz, 2H), 3.76 (t, J=4.6 Hz, 2H), 2.60-2.67 (m, 2H), 1.61-1.66 (m, 2H). ¹³C NMR (100 MHz, DMSO-d₆) δ 158.3, 148.2, 138.3, 129.0, 128.3, 127.5, 127.4, 118.0, 112.4, 111.8, 72.1, 71.1, 68.3, 66.9, 41.9, 38.7. MS: 302 [M+1]⁺.

Example 133

Preparation of 4-(3-(2-aminoethoxy)phenoxy)-N-methylbutanamide

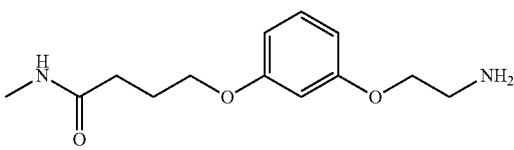 [SMILES: CNC(=O)CCCOc1cccc(OCCN)c1]

4-(3-(2-Aminoethoxy)phenoxy)-N-methylbutanamide was prepared following the method shown in Scheme 38.

SCHEME 38

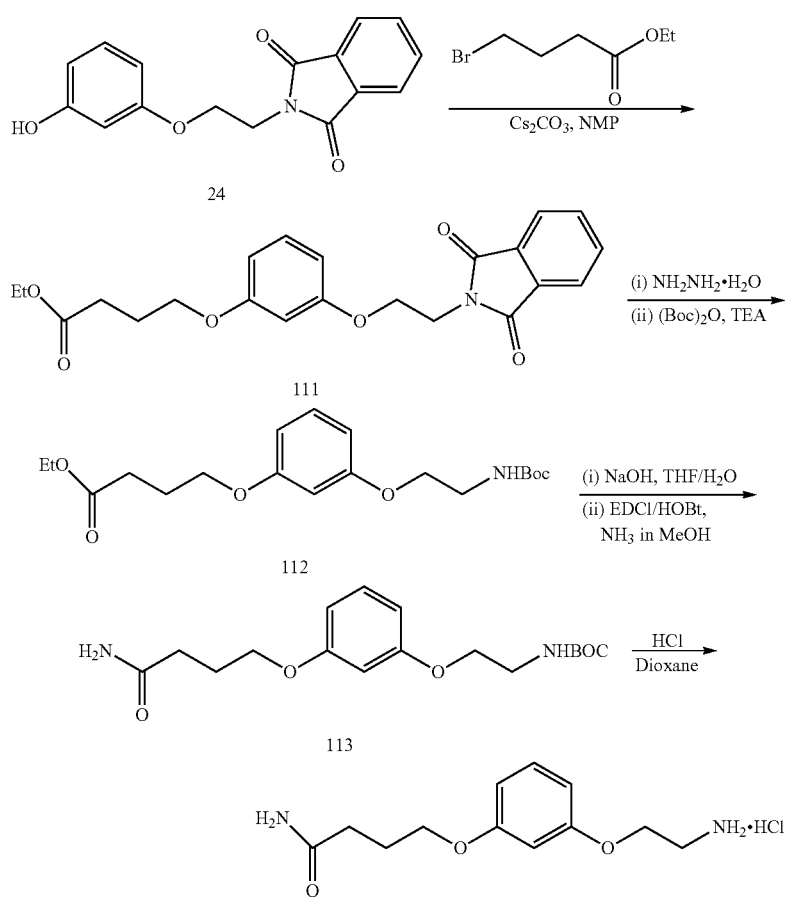

Step 1:

A mixture of 2-[2-(3-hydroxy-phenoxy)-ethyl]-isoindole-1,3-dione (24) (5 g, 17.6 mmol), 4-bromoethyl butyrate (3.0 mL, 21.28 mmol) and cesium carbonate (6.2 g, 35.38 mmol) in NMP (30 mL) was warmed at 70° C. for 12 h. The mixture was cooled to room temperature and poured into crushed ice. This mixture was extracted with EtOAc and the organic layer was washed with water, then brine, dried over Na₂SO₄ and concentrated under reduced pressure. Purification by flash chromatography (0 to 10% EtOAc-hexanes gradient) gave ether 5 as clear oil. Yield (3.33 g, 47%): ¹H NMR (400 MHz, CDCl₃) δ 7.85-7.87 (m, 2H), 7.71-7.74 (m, 2H), 7.10-7.14 (m, 1H), 6.42-6.47 (m, 3H), 4.08-4.22 (m, 6H), 3.95 (t, J=6.0 Hz, 2H), 2.49 (t, J=7.4 Hz, 2H), 2.04-2.11 (m, 2H), 1.26 (t, J=7.2 Hz, 3H).

Step 2:

To a solution of phthalimide 111 (3.33 g, 8.3 mmol) in EtOH (70 mL) was added hydrazine monohydrate (1.3 mL) and the mixture was stirred at 55° C. for 6 h. The mixture was cooled to room temperature and filtered. The filtrate was concentrated under reduced pressure and the residue suspended in water and extracted with DCM. The organic layer was dried over anhydrous Na₂SO₄, filtered and concentrated under reduced pressure to give the amine as yellow oil. Yield (2.0 g, crude): ¹H NMR (400 MHz, CDCl₃) δ 7.14-7.18 (m, 1H), 6.46-6.51 (m, 3H), 4.14 (q, J=7.2 Hz, 2H), 3.95-4.0 (m, 4H), 3.07 (t, J=5.2 Hz, 2H), 2.51 (t, J=7.2 Hz, 2H), 2.07-2.13 (m, 2H), 1.26 (t, J=7.2 Hz, 3H).

To a solution of amine (2.0 g, 7.48 mmol) in DCM (100 mL) was added triethylamine (3 mL, 22.4 mmol) followed by (Boc)₂O (2.0 g, 8.9 mmol). The mixture was stirred at room temperature overnight. The mixture was quenched by the addition of water and extracted with DCM. The organic layer was washed with bicarbonate solution, dried over anhydrous Na₂SO₄, filtered and concentrated under reduced pressure. Purification by flash chromatography (0 to 20% EtOAc-hexanes gradient) afforded Boc protected amine 112 as yellow oil. Yield (2.6 g, 94%): ¹H NMR (400 MHz, CDCl₃) δ 7.14-7.18 (m, 1H), 6.47-6.51 (m, 2H), 6.44 (s, 1H), 4.14 (q, J=7.2 Hz, 2H), 3.97-4.0 (m, 4H), 3.51-3.52 (m, 2H), 2.51 (t, J=7.6 Hz, 2H), 2.07-2.13 (m, 2H), 1.45 (s, 9H), 1.25 (t, J=7.2 Hz, 3H).

Step 3:

To the ester 112 (2.6 g, 7.0 mmol) in THF (28 mL) and MeOH (7 mL) was added 1N NaOH (2.5 mL, 25.7 mmol) and stirred at room temperature overnight. After evaporating the solvent, the mixture was carefully neutralized to pH 6 by the addition of cold dilute HCl. It was extracted with DCM. The organic layer was washed with water, dried over anhydrous Na₂SO₄, filtered and concentrated under reduced pressure. The crude was directly utilized for the next step. Yield (2.3 g, crude): ¹H NMR (400 MHz, CDCl₃) δ 7.13-7.18 (m, 1H), 6.45-6.50 (m, 3H), 5.02 (bs, 1H), 3.98-4.01 (m, 4H), 3.51-3.52 (m, 2H), 2.57 (t, J=7.0 Hz, 2H), 2.07-2.14 (m, 2H), 1.45 (s, 9H).

A mixture of the acid (0.5 g, 1.47 mmol), HOBt (0.27 g, 1.7 mmol) and EDC-HCl (0.338 g, 1.7 mmol) in DCM (30 mL) was stirred at room temperature for 2 h. To this was added ammonia in methanol (5 mL, 2M) and the mixture allowed to stir for another 3 h. This was quenched by the addition of water and extracted with DCM. The organic layer was washed water, dried over anhydrous $Na_2SO_4$, filtered and concentrated under reduced pressure. Purification by flash chromatography (0 to 2% DCM-Methanol gradient) afforded amide 113 as yellow oil. Yield (0.407 g, 78%): $^1$H NMR (400 MHz, $CDCl_3$) δ 7.14-7.18 (m, 1H), 6.43-6.51 (m, 3H), 3.97-4.01 (m, 4H), 3.51-3.54 (m, 2H), 2.81 (d, J=4.8, 3H), 2.37 (t, J=7.2 Hz, 2H), 2.08-2.15 (m, 2H), 1.45 (s, 9H).

Step 4:

To a stirred solution of amide 113 (0.4 g, 1.7 mmol) in THF (10 mL) was added HCl in dioxane (1.7 mL, 4 M) and the resulting mixture was stirred at room temperature overnight. The solvent was removed under reduced pressure and thus obtained solid was triturated with diethyl ether and dried to give Example 113 hydrochloride. Yield (0.230 g, 70%): $^1$H NMR (400 MHz, DMSO-$d_6$ and $D_2O$) δ 7.17-7.21 (m, 1H), 6.50-6.55 (m, 3H), 4.11 (t, J=5.2 Hz, 2H), 3.90-3.95 (m, 2H), 3.17 (t, J=4.8 Hz, 2H), 2.54 (s, 3H), 2.20 (t, J=7.2 Hz, 2H), 1.87-1.91 (m, 2H). $^{13}$C NMR (100 MHz, DMSO-$d_6$) δ 172.4, 160.2, 159.5, 130.5, 107.8, 107.4, 101.9, 67.5, 64.8, 38.7, 32.0, 26.0, 25.3. MS: 253 $[M+1]^+$.

Example 134

Preparation of 2-(3-(5-(benzyloxy)pentyloxy)phenoxy)ethanamine

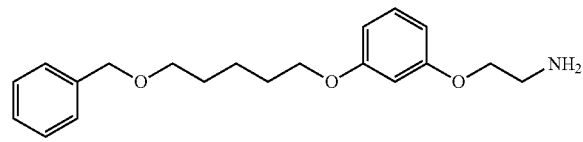 [SMILES: NCCOc1cccc(OCCCCCOCc2ccccc2)c1]

2-(3-(5-(Benzyloxy)pentyloxy)phenoxy)ethanamine was prepared following the method used for Example 57.

Step 1:

Alkylation reaction of phenol 24 with methanesulfonic acid 5-benzyloxypentyl ester gave 2-(2-(3-(5-benzyloxy-pentoxy)phenoxy)ethyl)isoindoline-1,3-dione as yellow oil. Yield (1.0 g, 62%): $^1$H NMR (400 MHz, $CDCl_3$) δ 7.84-7.87 (m, 2H), 7.70-7.73 (m, 2H), 7.25-7.40 (m, 5H), 7.09-7.14 (m, 1H), 6.42-6.48 (m, 3H), 4.50 (s, 2H), 4.20 (t, J=5.8 Hz, 2H), 4.10 (t, J=5.6 Hz, 2H), 3.90 (t, J=6.4 Hz, 2H), 3.64 (t, J=6.0 Hz, 2H), 3.48 (t, J=6.0 Hz, 2H), 1.40-1.80 (m, 6H).

Step 2:

Phthalimide cleavage of 2-(2-(3-(5-benzyloxypentoxy)phenoxy)ethyl)isoindoline-1,3-dione gave Example 134 as yellow oil. Yield (0.44 g, 61%): $^1$H NMR (400 MHz, DMSO-$d_6$) δ 7.27-7.36 (m, 5H), 7.12-7.16 (m, 1H), 6.45-6.50 (m, 3H), 4.45 (s, 2H), 3.93 (t, J=6.4 Hz, 2H), 3.88 (t, J=5.8 Hz, 2H), 3.44 (t, J=6.2 Hz, 2H), 2.85 (t, J=6.4 Hz, 2H), 1.67-1.73 (m, 2H), 1.58-1.64 (m, 2H), 1.42-1.50 (m, 2H). $^{13}$C NMR (100 MHz, DMSO-$d_6$) δ 159.9, 138.7, 129.9, 128.2, 127.4, 127.3, 106.7, 106.6, 101.2, 101.1, 71.8, 70.1, 69.5, 67.3, 40.9, 28.9, 28.5, 22.4. MS: 330 $[M+1]^+$.

Example 135

Preparation of 1-((3-(3-aminopropyl)phenoxy)methyl)cyclooctanol

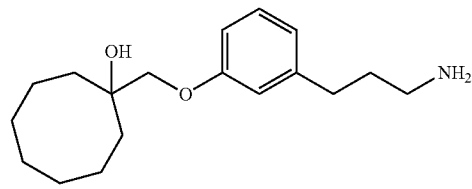 [SMILES: NCCCc1cccc(OCC2(O)CCCCCCC2)c1]

1-((3-(3-Aminopropyl)phenoxy)methyl)cyclooctanol was prepared following the method shown in Scheme 16 and used for Example 18.

Step 1:

A suspension of the phenol 58 (1.0 g, 3.5 mmol), 1-oxa-spiro[2.7]decane (0.5 g, 3.2 mmol) and $Cs_2CO_3$ (1.14 g, 3.5 mmol) in DMSO (4 mL) was heated at 120° C. for 16 h. After completion of reaction, the mixture was quenched by the addition of 1N HCl and extracted with DCM. The organic layer was dried over anhydrous $Na_2SO_4$, filtered and concentrated under reduced pressure. Purification by flash chromatography (0 to 10% 7N $NH_3$/methanol-$CH_2Cl_2$) afforded 2-(3-(3-((1-hydroxycyclooctyl)methoxy)phenyl)propyl)isoindoline-1,3-dione as yellow oil. Yield (1.057 g, 72%): $^1$H NMR (400 MHz, $CDCl_3$) δ 7.10-7.36 (m, 2H), 6.40-6.80 (m, 6H), 3.69 (s, 2H), 2.10-2.45 (m, 2H), 1.30-2.0 (m, 18H).

Step 2:

Phthalimide cleavage of 2-(3-(3-((1-hydroxycyclooctyl)methoxy)phenyl)propyl)isoindoline-1,3-dione gave Example 135 as brown oil. Yield (0.42 g, 59%): $^1$H NMR (400 MHz, DMSO-$d_6$) δ 7.13-7.17 (m, 1H), 6.71-6.75 (m, 3H), 3.69 (s, 2H), 2.50-2.57 (m, 2H), 1.52-1.70 (m, 12H), 1.40-1.50 (m, 6H). $^{13}$C NMR (100 MHz, DMSO-$d_6$) δ 160.3, 145.1, 130.4, 121.7, 115.9, 113.0, 76.6, 73.8, 42.4, 36.1, 34.2, 33.9, 29.2, 25.6, 22.7. MS: 292 $[M+1]^+$.

Example 136

Preparation of 3-(3-(5-(benzyloxy)pentyloxy)phenyl)propan-1-amine

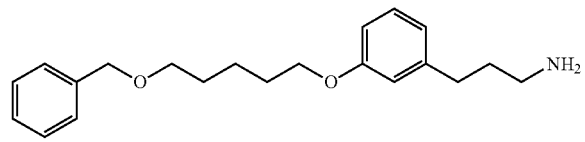 [SMILES: NCCCc1cccc(OCCCCCOCc2ccccc2)c1]

3-(3-(5-(Benzyloxy)pentyloxy)phenyl)propan-1-amine was prepared following the method used for Example 59.

Step 1:

Alkylation of phenol 58 with methane sulfonic acid 5-benzyloxy-pentyl ester gave 2-(3-(3-(5-(benzyloxy)pentoxy)phenyl)propyl)isoindoline-1,3-dione as yellow oil. Yield (0.760 g, 51%): $^1$H NMR (400 MHz, $CDCl_3$) δ 7.80-7.83 (m, 2H), 7.68-7.72 (m, 2H), 7.32-7.36 (m, 4H), 7.27-7.30 (m, 1H), 7.11-7.15 (m, 1H), 6.76 (d, J=7.6 Hz, 1H), 6.72 (s, 1H), 6.64 (dd, J=8.0, 2.0 Hz, 1H), 4.51 (s, 2H), 3.92 (t, J=6.4 Hz, 2H), 3.74 (t, J=7.2 Hz, 2H), 3.50 (t, J=6.4

Hz, 2H), 2.65 (t, J=7.6 Hz, 2H), 2.0-2.06 (m, 2H), 1.77-1.83 (m, 2H), 1.68-1.73 (m, 2H), 1.52-1.58 (m, 2H).
Step 2:
Phthalimide cleavage of 2-(3-(3-(2-(benzyloxy)pentoxy)phenyl) propyl)isoindoline-1,3-dione gave Example 136 as pale yellow oil. Yield (0.26 g, 65%): $^1$H NMR (400 MHz, DMSO-d$_6$) δ 7.24-7.36 (m, 5H), 7.12-7.17 (m, 1H), 6.68-6.76 (m, 3H), 4.45 (s, 2H), 3.92 (t, J=6.4 Hz, 2H), 3.44 (t, J=6.4 Hz, 2H), 2.50-2.56 (m, 4H), 1.68-1.73 (m, 2H), 1.56-1.64 (m, 4H), 1.42-1.50 (m, 2H). $^{13}$C NMR (100 MHz, DMSO-d$_6$) δ 158.7, 143.9, 138.7, 129.2, 128.2, 127.4, 127.3, 120.4, 114.5, 111.5, 71.8, 69.5, 67.1, 41.2, 35.1, 32.6, 28.9, 28.6, 22.4. MS: 328 [M+1]$^+$.

Example 137

Preparation of 3-(3-(2,6-dimethylbenzyloxy)phenyl)propan-1-amine

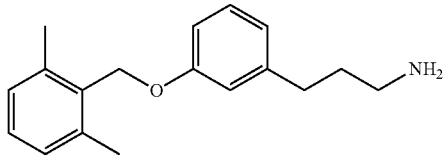 [SMILES: Cc1cccc(C)c1COc1cccc(CCCN)c1]

3-(3-(2,6-Dimethylbenzyloxy)phenyl)propan-1-amine was prepared following the method used for Example 59.
Step 1:
Alkylation of phenol 58 with methanesulfonic acid 2,6-dimethyl-benzyl ester gave 2-(3-(3-(2,6-dimethylbenzyloxy)phenyl)propyl)isoindoline-1,3-dione as yellow oil. Yield (1.1 g, 79%): $^1$H NMR (400 MHz, CDCl$_3$) δ 7.82-7.85 (m, 2H), 7.69-7.72 (m, 2H), 7.13-7.21 (m, 2H), 7.06-7.10 (m, 2H), 6.79-6.88 (m, 3H), 5.02 (s, 2H), 3.76 (t, J=7.2 Hz, 2H), 2.69 (t, J=8.0 Hz, 2H), 2.35 (s, 6H), 2.02-2.07 (m, 2H).
Step 2:
Phthalimide cleavage of 2-(3-(3-(2,6-dimethylbenzyloxy)phenyl)propyl)isoindoline-1,3-dione gave Example 137 as pale yellow oil. Yield (0.470 g, 70%): $^1$H NMR (400 MHz, DMSO-d$_6$) δ 7.13-7.22 (m, 2H), 7.05-7.08 (m, 2H), 6.84-6.86 (m, 2H), 6.79 (d, J=7.6 Hz, 1H), 5.01 (s, 2H), 2.50-2.59 (m, 4H), 2.32 (s, 6H), 1.60-1.67 (m, 2H). $^{13}$C NMR (100 MHz, DMSO-d$_6$) δ 159.5, 144.4, 138.2, 133.5, 129.7, 128.7, 128.5, 121.3, 115.1, 112.2, 64.7, 41.6, 35.3, 33.1, 19.6. MS: 270 [M+1]$^+$.

Example 138

Preparation of 4-(3-(2-aminoethoxy)phenoxy)-N,N-dimethylbutanamide

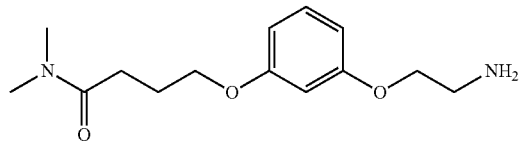 [SMILES: CN(C)C(=O)CCCOc1cccc(OCCN)c1]

4-(3-(2-Aminoethoxy)phenoxy)-N,N-dimethylbutanamide was prepared following the method used for Example 133.

Step 1:
The acid-amine coupling with dimethylamine gave (2-(3-(3-dimethylcarbamoylpropoxy)phenoxy)ethyl)-carbamic acid tert-butyl ester as yellow oil. Yield (0.305 g, 94%): $^1$H NMR (400 MHz, CDCl$_3$) δ 7.14-7.18 (m, 1H), 6.46-6.52 (m, 3H), 5.0 (bs, 1H), 3.98-4.02 (m, 4H), 3.50-3.52 (m, 2H), 3.01 (s, 3H), 2.95 (s, 3H), 2.51 (t, J=7.2 Hz, 2H), 2.09-2.15 (m, 2H), 1.45 (s, 9H).
Step 2:
BOC deprotection of (2-(3-(3-dimethylcarbamoylpropoxy)phenoxy)ethyl)carbamic acid tert-butyl ester gave Example 138 hydrochloride as a white solid. Yield (0.213 g, 86%): $^1$H NMR (400 MHz, DMSO-d$_6$) δ 7.13-7.17 (m, 1H), 6.48-6.51 (m, 3H), 3.95 (t, J=6.6 Hz, 2H), 3.88 (t, J=5.8 Hz, 2H), 2.95 (s, 3H), 2.82-2.85 (m, 5H), 2.43 (t, J=7.2 Hz, 2H), 1.88-1.92 (m, 2H). $^{13}$C NMR (100 MHz, DMSO-d$_6$) δ 171.4, 159.9, 159.8, 129.9, 106.7, 106.6, 101.1, 70.1, 68.8, 40.9, 36.6, 34.8, 28.6, 24.4. MS: 267 [M+1]$^+$.

Example 139

Preparation of 1-((3-(2-aminoethoxy)phenoxy)methyl)cyclooctanol

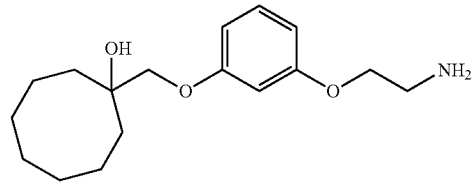 [SMILES: NCCOc1cccc(OCC2(O)CCCCCCC2)c1]

1-((3-(2-Aminoethoxy)phenoxy)methyl)cyclooctanol was prepared following the method used in Example 18.
Step 1:
The suspension of phenol 24 (1.0 g, 3.5 mmol), 1-oxa-spiro[2.7]decane (0.5 g, 3.2 mmol) and Cs$_2$CO$_3$ (1.14 g, 3.5 mmol) in DMSO (4 mL) was heated at 120° C. for 16 h. After completion of reaction, the mixture was quenched by the addition of 1N HCl and extracted with DCM. The organic layer was dried over anhydrous Na$_2$SO$_4$, filtered and concentrated under reduced pressure. Purification by flash chromatography (0 to 10% 7N NH$_3$/methanol-CH$_2$Cl$_2$) afforded 2-(2-(3-(1-hydroxy-cyclooctylmethoxy)-phenoxy)-ethyl)-isoindole-1,3-dione as yellow oil. Yield (0.53 g, 35%): $^1$H NMR (400 MHz, CDCl$_3$) δ 7.92-7.98 (m, 1H), 7.40-7.51 (m, 3H), 7.08-7.14 (m, 1H), 6.45-6.54 (m, 3H), 4.03 (s, 2H), 3.68-3.76 (m, 2H), 1.35-1.92 (m, 16H).
Step 2:
Phthalimide cleavage of 2-(2-(3-(1-hydroxy-cyclooctylmethoxy)-phenoxy)-ethyl)-isoindole-1,3-dione gave Example 139 as yellow oil. Yield (0.160 g, 43%): $^1$H NMR (400 MHz, DMSO-d$_6$) δ 7.12-7.16 (m, 1H), 6.48-6.51 (m, 3H), 3.89 (t, J=5.8 Hz, 2H), 3.69 (s, 2H), 2.85 (t, J=5.8 Hz, 2H), 1.39-1.68 (m, 14H). $^{13}$C NMR (100 MHz, DMSO-d$_6$) δ 160.3, 159.9, 129.8, 106.9, 106.7, 101.3, 75.5, 72.5, 69.9, 40.9, 32.8, 27.9, 24.4, 21.5. MS: 294 [M+1]$^+$.

Example 140

Preparation of 2-(3-(2,6-dimethylbenzyloxy)phenoxy)ethanamine

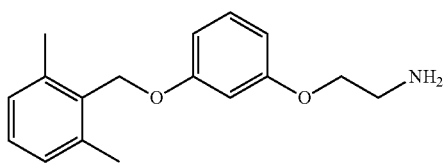 [SMILES: Cc1cccc(C)c1COc1cccc(OCCN)c1]

2-(3-(2,6-Dimethylbenzyloxy)phenoxy)ethanamine was prepared following the method used for Example 7.

Step 1:

Mitsunobu reaction of phenol 24 with 2,6-dimethylbenzyl alcohol gave 2-(2-(3-(2,6-dimethylbenzyloxy)phenoxy)ethyl)isoindoline-1,3-dione as yellow oil. Yield (1.2 g, 85%): $^1$H NMR (400 MHz, CDCl$_3$) δ 7.85-7.88 (m, 2H), 7.71-7.74 (m, 2H), 7.12-7.18 (m, 1H), 7.01-7.10 (m, 3H), 6.60 (dd, J=8.0, 1.8 Hz, 1H), 6.57 (s, 1H), 6.51 (dd, J=8.0, 1.8 Hz, 1H), 4.99 (s, 2H), 4.09-4.24 (m, 4H), 2.38 (s, 6H).

Step 2:

Phthalimide cleavage of 2-(2-(3-(2,6-dimethylbenzyloxy)phenoxy)ethyl)isoindoline-1,3-dione gave Example 140 as yellow oil. Yield (0.33 g, 40%): $^1$H NMR (400 MHz, DMSO-d$_6$) δ 7.14-7.22 (m, 2H), 7.05-7.08 (m, 2H), 6.61-6.63 (m, 2H), 6.54 (d, J=8.0 Hz, 1H), 5.01 (s, 2H), 3.90 (t, J=5.8 Hz, 2H), 2.85 (t, J=5.8 Hz, 2H), 2.32 (s, 6H). $^{13}$C NMR (100 MHz, DMSO-d$_6$) δ 160.7, 160.4, 138.2, 133.4, 130.4, 128.8, 128.5, 107.4, 107.3, 101.8, 70.7, 64.9, 41.4, 19.6. MS: 272 [M+1]$^+$.

Example 141

Preparation of 2-(3-(2-aminoethoxy)phenoxy)ethanol

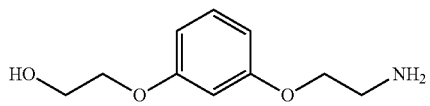 [SMILES: NCCOc1cccc(OCCO)c1]

2-(3-(2-Aminoethoxy)phenoxy)ethanol was prepared following the method shown in Scheme 39.

SCHEME 39

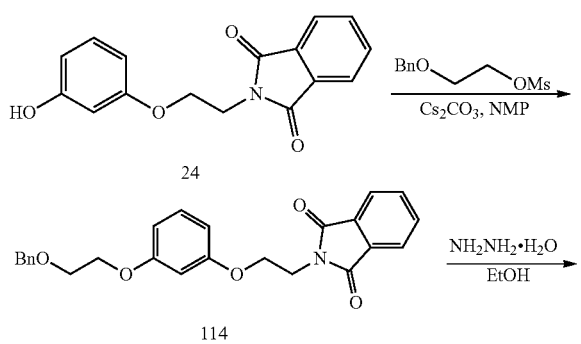

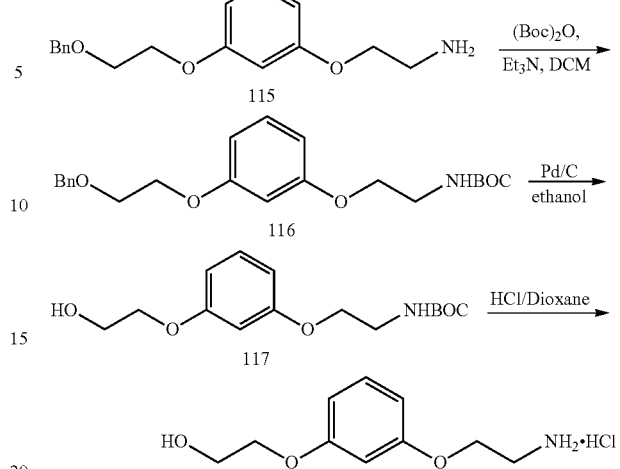

Step 1:

Alkylation reaction of phenol 24 with methanesulfonic acid 2-benzyloxy-ethyl ester following the method used for Example 57 gave 114 as yellow oil. Yield (0.950 g, 64%): $^1$H NMR (400 MHz, CDCl$_3$) δ 7.84-7.87 (m, 1H), 7.70-7.74 (m, 1H), 7.28-7.38 (m, 8H), 7.10-7.15 (m, 1H), 6.46-6.52 (m, 2H), 4.57 (s, 2H), 4.19 (t, J=6.0 Hz, 1H), 4.09 (t, J=7.2 Hz, 2H), 3.73-3.82 (m, 3H), 3.60-3.63 (m, 2H), 1.99 (t, J=6.4 Hz, 1H).

Step 2:

Phthalimide cleavage of 2-(2-(3-(2-(benzyloxy)ethoxy)phenoxy)ethyl)isoindoline-1,3-dione following the method used for Example 57 gave 115 as yellow oil. Yield (0.225 g, 32%): $^1$H NMR (400 MHz, DMSO-d$_6$) δ 7.32-7.37 (m, 4H), 7.26-7.31 (m, 1H), 7.13-7.18 (m, 1H), 6.48-6.53 (m, 3H), 4.55 (s, 2H), 4.11 (t, J=4.4 Hz, 2H), 3.88 (t, J=5.6 Hz, 2H), 3.75 (t, J=4.4 Hz, 2H), 2.84 (t, J=5.6 Hz, 2H). $^{13}$C NMR (100 MHz, DMSO-d$_6$) δ 159.9, 159.7, 138.3, 129.9, 128.3, 127.6, 127.5, 106.8, 106.7, 101.2, 72.1, 70.2, 68.2, 67.1, 40.9. MS: 288 [M+1]$^+$.

Step 3:

To a stirred solution of amine 115 (1.3 g, 4.5 mmol) in DCM (40 mL) was added triethylamine (2 mL, 13.6 mmol). The reaction mixture was cooled to 0° C. To this was added (Boc)$_2$O (1.2 g, 5.4 mmol) and the resulting mixture was stirred for 2 hours during which the conversion was found to be complete. After removal of DCM under reduced pressure, the reaction mixture was extracted with ethyl acetate. After washing with water and brine, the organic phase was dried over anhydrous Na$_2$SO$_4$. This was concentrated to afford crude yellow oil. Purification by flash chromatography (15-30% ethyl acetate:hexane gradient) afforded tert-butylcarbamate 116 as pale yellow oil. Yield (1.2 g, 68%): $^1$H NMR (400 MHz, CDCl$_3$) δ 7.27-7.38 (m, 5H), 7.14-7.19 (m, 1H), 6.49-6.55 (m, 3H), 4.64 (s, 2H), 4.13 (t, J=6.4 Hz, 2H), 3.99 (t, J=5.0 Hz, 2H), 3.82 (t, J=6.4 Hz, 2H), 3.51-3.53 (m, 2H), 1.45 (s, 9H).

Step 4:

A stirred solution of carbamate 116 (1.2 g, 3.1 mmol) in ethanol (50 mL) was degassed and purged with nitrogen. To this was added Pd on C (150 mg, 10%) and the flask was evacuated and purged with hydrogen. This mixture was stirred at room temperature under hydrogen balloon for overnight. The suspension was then filtered through a pad of Celite. The filter cake was washed with ethanol. The filtrate was concentrated to give alcohol 117 as yellow oil. Yield (0.69 g, 75%): $^1$H NMR (400 MHz, DMSO-$d_6$) δ 7.13-7.17 (m, 1H), 6.46-6.52 (m, 3H), 3.91-3.96 (m, 4H), 3.67-3.71 (m, 2H), 3.26 (t, J=6.0 Hz, 2H), 1.38 (s, 9H).

Step 5:

To a solution of alcohol 117 (0.135 g, 0.39 mmol) in THF (10 mL) was added HCl in dioxane (10 mL) and the reaction mixture was stirred at room temperature overnight. After the solvent was removed under reduced pressure, the residue was basified to pH 10 using conc. ammonia followed by extraction with DCM. Purification by flash chromatography (0-(9.5-0.5) MeOH—NH$_3$)-DCM gradient) afforded Example 141 as yellow oil. Yield (0.446 g, 82%): $^1$H NMR (400 MHz, DMSO-$d_6$) δ 7.17-7.22 (m, 1H), 6.51-6.57 (m, 3H), 4.12 (t, J=5.2 Hz, 2H), 3.94 (t, J=5.0 Hz, 2H), 3.68 (t, J=5.2 Hz, 2H), 3.18 (t, J=5.0 Hz, 2H). $^{13}$C NMR (100 MHz, DMSO-$d_6$) δ 160.4, 159.5, 130.5, 107.8, 107.3, 102.0, 70.6, 64.7, 60.0, 38.7. MS: 198 [M+1]$^+$.

Example 142

Preparation of (3-(3-aminopropyl)-5-(cyclohexylmethoxy)phenyl)methanol

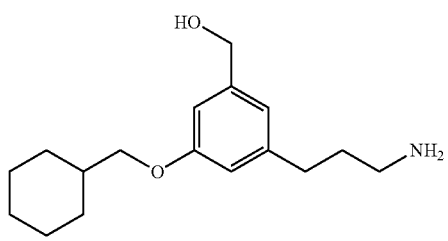 [SMILES: NCCCc1cc(CO)cc(OCC2CCCCC2)c1]

(3-(3-Aminopropyl)-5-(cyclohexylmethoxy)phenyl)methanol was prepared following the method shown in Scheme 40.

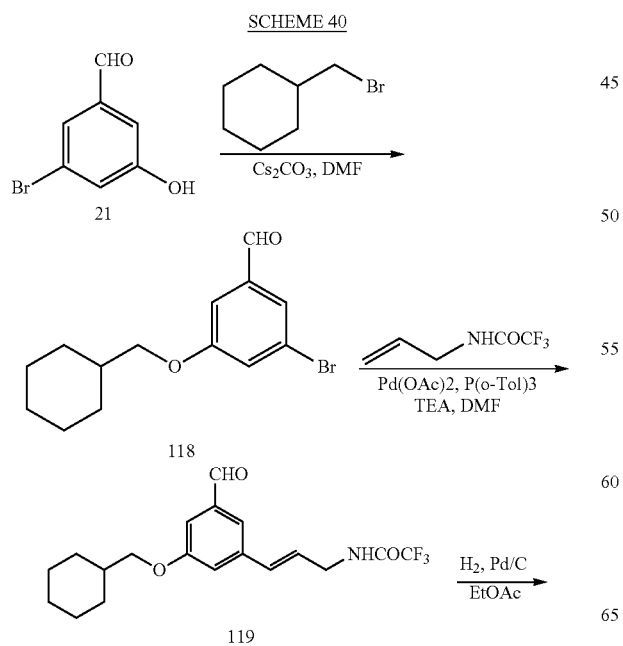

SCHEME 40

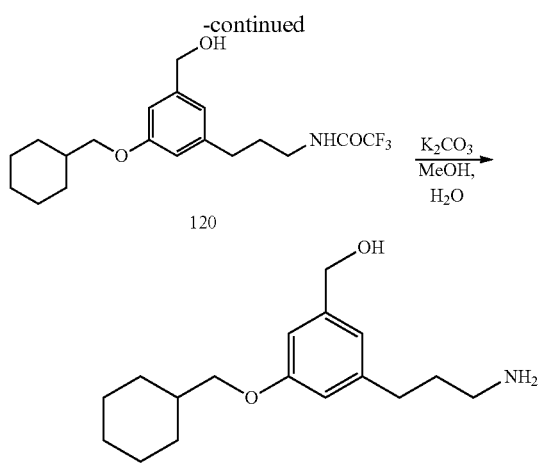

Step 1:

Alkylation of 3-bromo-5-hydroxybenzaldehyde using (bromomethyl)cyclohexane following the method used in Example 154 gave benzaldehyde 118. Yield (2.4 g, 81%): $^1$H NMR (400 MHz, CDCl$_3$) δ 9.88 (s, 1H), 7.54 (t, J=1.6 Hz, 1H), 7.29 (d, J=1.6 Hz, 2H), 3.78 (d, J=6.0 Hz, 2H), 1.66-1.88 (m, 6H), 1.14-1.36 (m, 3H), 1.00-1.11 (m, 2H).

Step 2:

Coupling of benzaldehyde 118 with N-allyl-2,2,2-trifluoroacetamide following the method used in Example 10 except DMF was used as solvent gave akene 119 as a white solid. Yield (1.1 g, 77%): $^1$H NMR (400 MHz, DMSO-$d_6$) δ 9.93 (s, 1H), 9.72 (t, J=4.2 Hz, 1H), 7.55 (s, 1H), 7.31 (t, J=2.4 Hz, 1H), 7.27 (t, J=1.2 Hz, 1H), 6.57 (d, J=15.6 Hz, 2H), 6.40 (dt, J=16.0, 6.0 Hz, 1H), 3.98 (t, J=5.6 Hz, 2H), 3.84 (d, J=6.4 Hz, 2H), 1.58-1.82 (m, 6H), 0.98-1.28 (m, 5H).

Step 3:

Hydrogenation of akene 119 following the method used in Example 10 gave compound 120 as a white solid. Yield (0.095 g, 47%): $^1$H NMR (400 MHz, CD$_3$OD) δ 6.72-6.74 (m, 2H), 6.64 (t, J=1.6 Hz, 1H), 4.51 (s, 2H), 3.74 (d, J=7.2 Hz, 2H), 3.27 (t, J=7.2 Hz, 2H), 2.60 (t, J=8.0 Hz, 2H), 1.66-1.88 (m, 8H), 1.20-1.38 (m, 3H), 1.02-1.11 (m, 2H).

Step 4:

Deprotection of compound 120 following the method used in Example 10 gave Example 142 as a light yellow oil. Yield (0.22 g, 95%): $^1$H NMR (400 MHz, CDCl$_3$) δ 6.72-6.74 (m, 2H), 6.54 (s, 1H), 4.61 (s, 2H), 3.73 (d, J=6.4 Hz, 2H), 2.71 (t, J=7.2 Hz, 2H), 2.60 (t, J=7.2 Hz, 2H), 1.64-1.88 (m, 8H), 1.14-1.34 (m, 3H), 0.98-1.08 (m, 2H).

Example 143

Preparation of 5-(3-(2-aminoethoxy)phenoxy)pentan-1-ol

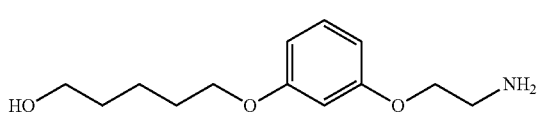 [SMILES: NCCOc1cccc(OCCCCCO)c1]

5-(3-(2-Aminoethoxy)phenoxy)pentan-1-ol was prepared following the method used for Example 7 followed by deprotection as described below.

Step 1:

Mitsunobu reaction of phenol 24 with 5-(tert-butyldimethyl-ilanyloxy)pentan-1-ol gave 2-(2-(3-(5-(tert-butyldimethylsilanyloxy)pentyloxy)phenoxy)ethyl)isoindoline-1,3-dione as yellow oil. Yield (1.4 g, 82%): $^1$H NMR (400 MHz, CDCl$_3$) δ 7.85-7.87 (m, 2H), 7.71-7.73 (m, 2H), 7.09-7.14 (m, 1H), 6.42-6.48 (m, 3H), 4.20 (t, J=5.6 Hz, 2H), 4.10 (t, J=5.6 Hz, 2H), 3.90 (t, J=6.6 Hz, 2H), 3.60-3.68 (m, 4H), 1.73-1.80 (m, 2H), 1.58-1.62 (m, 2H), 0.89 (s, 9H), 0.10 (s, 6H).

Step 2:

Phthalimide cleavage of 2-(2-(3-(5-(tert-butyl-dimethylsilanyloxy)-pentyloxy)phenoxy)ethyl)isoindoline-1,3-dione gave 2-(3-(5-(tert-butyl dimethylsilyloxy)pentyloxy)phenoxy)ethanamine as yellow oil. Yield (0.65 g, 64%): $^1$H NMR (400 MHz, DMSO-d$_6$) δ 7.12-7.16 (m, 1H), 6.45-6.50 (m, 3H), 3.92 (t, J=6.4 Hz, 2H), 3.88 (t, J=5.8 Hz, 2H), 3.58 (t, J=6.0 Hz, 2H), 2.85 (t, J=5.8 Hz, 2H), 1.68-1.74 (m, 2H), 1.40-1.53 (m, 4H), 0.84 (s, 9H), 0.05 (s, 6H).

Step 3:

The TBS-ether was cleaved by the following procedure: To a stirred solution of 2-(3-(5-(tert-butyldimethylsilyloxy)pentyloxy)phenoxy)ethanamine (0.64 g, 1.8 mmol) in THF (10 mL) was added 6N HCl (1 mL) and the resulting mixture was stirred at room temperature for 24 h. The solvent was evaporated under reduced pressure and the reaction mixture was brought up to pH 10 using conc. NH$_4$OH and extracted with DCM. The organic layer was dried over anhydrous Na$_2$SO$_4$, filtered and concentrated under reduced pressure. Purification by flash chromatography (0-(9.5-0.5) MeOH—NH$_3$)-DCM gradient) afforded Example 26 as pale yellow semi-solid. Yield (0.34 g, 77%): $^1$H NMR (400 MHz, DMSO-d$_6$) δ 7.12-7.16 (m, 1H), 6.46-6.49 (m, 3H), 3.92 (t, J=6.4 Hz, 2H), 3.87 (t, J=5.8 Hz, 2H), 3.38 (t, J=6.0 Hz, 2H), 2.84 (t, J=5.8 Hz, 2H), 1.66-1.72 (m, 2H), 1.40-1.48 (m, 4H). $^{13}$C NMR (100 MHz, DMSO-d$_6$) δ 160.4, 130.3, 107.1, 107.0, 101.6, 70.6, 67.9, 61.1, 41.4, 32.7, 29.0, 22.6. MS: 240 [M+1]$^+$.

Example 144

Preparation of 4-(3-(2-aminoethoxy)phenoxy)butanamide

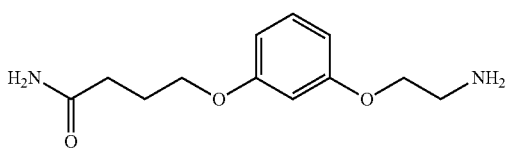 [SMILES: NCCOc1cccc(OCCCC(N)=O)c1]

4-(3-(2-Aminoethoxy)phenoxy)butanamide was prepared following the method used for Example 133.

Step 1:

Amide coupling with methanolic ammonia (2M solution) gave tert-butyl 2-(3-(4-amino-4-oxobutoxy)phenoxy)ethylcarbamate as a yellow semi solid. Yield (0.700 g, 70%): $^1$H NMR (400 MHz, CDCl$_3$) δ 7.14-7.18 (m, 1H), 6.44-6.52 (m, 3H), 5.35-5.55 (m, 2H), 4.99 (bs, 1H), 3.98-4.02 (m, 4H), 3.51-3.54 (m, 2H), 2.44 (t, J=7.2 Hz, 2H), 2.09-2.16 (m, 2H), 1.45 (s, 9H).

Step 2:

BOC deprotection of tert-butyl 2-(3-(4-amino-4-oxobutoxy) phenoxy)ethylcarbamate gave Example 144 hydrochloride as white solid. Yield (0.200 g, 35%): $^1$H NMR (400 MHz, DMSO-d$_6$) δ 7.17-7.21 (m, 1H), 6.51-6.56 (m, 3H), 4.12 (t, J=4.6 Hz, 2H), 3.92 (t, J=6.2 Hz, 2H), 3.18 (t, J=4.6 Hz, 2H), 2.21 (t, J=7.2 Hz, 2H), 1.85-1.93 (m, 2H). $^{13}$C NMR (100 MHz, DMSO-d$_6$) δ 173.6, 159.7, 159.0, 130.0, 107.4, 106.8, 101.4, 67.0, 64.2, 38.2, 31.2, 24.6. MS: 239 [M+1]$^+$.

Example 145

Preparation of 2-(3-(2-aminoethoxy)phenoxy)-1-phenylethanol

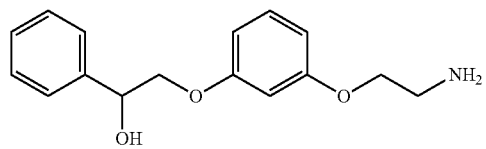 [SMILES: NCCOc1cccc(OCC(O)c2ccccc2)c1]

2-(3-(2-Aminoethoxy)phenoxy)-1-phenylethanol was prepared following the method used for Example 18.

Step 1:

Alkylation reaction of phenol 24 with styrene oxide gave 2-(2-(3-(2-hydroxy-2-phenylethoxy)phenoxy)ethyl)isoindoline-1,3-dione as yellow oil. Yield (0.85 g, 50%): $^1$H NMR (400 MHz, CDCl$_3$) δ 7.99 (d, J=7.2 Hz, 1H), 7.41-7.53 (m, 3H), 7.28-7.38 (m, 5H), 7.12-7.16 (m, 1H), 6.60-6.65 (m, 1H), 6.52 (s, 1H), 6.48 (dd, J=8.0, 2.0 Hz, 1H), 4.79-4.82 (m, 1H), 4.19 (t, J=5.4 Hz, 2H), 3.72-3.84 (m, 4H).

Step 2:

Phthalimide cleavage of 2-(2-(3-(2-hydroxy-2-phenylethoxy) phenoxy)ethyl)isoindoline-1,3-dione gave Example 145 as off-white solid. Yield (0.10 g, 36%): $^1$H NMR (400 MHz, DMSO-d$_6$) δ 7.43-7.45 (m, 2H), 7.33-7.37 (m, 2H), 7.25-7.29 (m, 1H), 7.12-7.16 (m, 1H), 6.46-6.51 (m, 3H), 4.88-4.90 (m, 1H), 3.99 (d, J=6.0 Hz, 2H), 3.87 (t, J=5.8 Hz, 2H), 2.83 (t, J=5.8 Hz, 2H). $^{13}$C NMR (100 MHz, DMSO-d$_6$) δ 160.4, 160.2, 142.9, 130.4, 128.5, 127.7, 126.9, 107.4, 107.3, 101.7, 73.5, 71.3, 70.7, 41.4. MS: 274 [M+1]$^+$.

Example 146

Preparation of 3-amino-1-(2-bromo-5-(cyclohexylmethoxy)phenyl)propan-1-ol

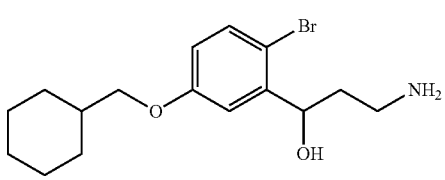 [SMILES: NCCC(O)c1cc(OCC2CCCCC2)ccc1Br]

3-Amino-1-(2-bromo-5-(cyclohexylmethoxy)phenyl)propan-1-ol was prepared following the methods used for Examples 1 and 4.

Step 1:

Alkylation of 2-bromo-5-hydroxybenzaldehyde using (bromomethyl)cyclohexane following the method used in Example 1 gave 2-bromo-5-(cyclohexylmethoxy)benzaldehyde. The crude aldehyde was used in the subsequent reaction.

Step 2:

Reaction of 2-bromo-5-(cyclohexylmethoxy)benzaldehyde with acetonitrile in the presence of LDA was conducted following the procedure given for Example 4 to give 3-(2-bromo-5-(cyclohexylmethoxy)phenyl)-3-hydroxypropanenitrile. Yield (0.49 g, 79%): $^1$H NMR (400 MHz, MeOD) δ 7.40 (d, J=8.8 Hz, 1H), 7.23 (d, J=2.8 Hz, 1H), 6.77 (dd, J=8.8, 2.4 Hz, 1H), 5.20 (dd, J=6.8, 4.4 Hz, 1H), 3.77 (d, J=6.8 Hz, 2H), 2.91 (dd, J=16.8, 4.0 Hz, 1H), 2.74 (dd, J=16.8, 6.8 Hz, 1H), 1.66-1.88 (m, 6H), 1.18-1.36 (m, 3H), 1.02-1.16 (m, 2H).

Step 3:

Reduction of 3-(2-bromo-5-(cyclohexylmethoxy)phenyl)-3-hydroxypropanenitrile using borane-THF following the procedure given for Example 4 gave Example 146 as colorless oil. Yield (0.22 g, 97%): $^1$H NMR (400 MHz, MeOD) δ 7.36 (d, J=8.8 Hz, 1H), 7.13 (d, J=3.2 Hz, 1H), 6.71 (dd, J=8.8, 2.8 Hz, 1H), 5.01 (dd, J=8.8, 4.0 Hz, 1H), 3.75 (d, J=6.4 Hz, 2H), 2.74-2.86 (m, 2H), 1.66-1.92 (m, 6H), 1.16-1.38 (m, 3H), 1.02-1.14 (m, 2H).

Example 147

Preparation of (1,2-cis)-2-((3-(3-aminopropyl)phenoxy)methyl)cyclohexanol

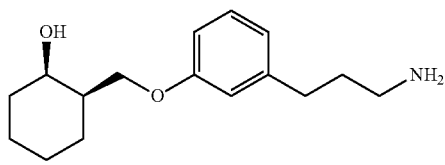 [SMILES: NCCCc1cccc(OC[C@H]2CCCC[C@H]2O)c1]

(1,2-cis)-2-((3-(3-Aminopropyl)phenoxy)methyl)cyclohexanol was prepared following the method shown in Scheme 41.

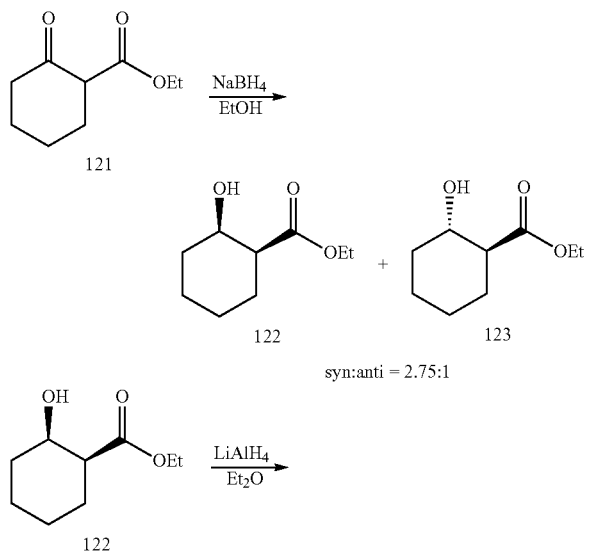

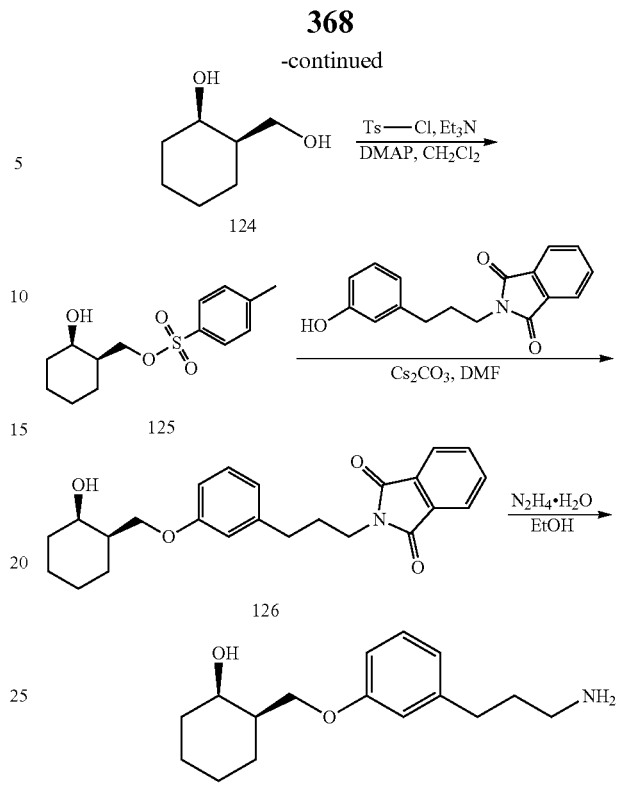

Step 1.

To a cold (0° C.) solution of ethyl 2-oxocyclohexanecarboxylate (121) (5.09 g, 29.9 mmol) in EtOH (abs, 30 mL) was added sodium borohydride (1.25 g, 33.0 mmol). The reaction mixture was stirred at room temperature for 15 min, then water (25 mL) and saturated NaHCO$_3$ (50 mL) were added. The mixture was stirred for 15 min, and then extracted with hexanes (3×40 mL), EtOAc:hexanes (1:1, 50 mL), EtOAc (50 mL). Combined organic layers were washed with brine, concentrated under reduced pressure and purified by flash chromatography (5% to 40% EtOAc/hexanes gradient) to afford of syn-alcohol 122 and anti-alcohol 123 as colorless oils. Yield (syn—1.73 g, 34%; anti—0.63 g, 12%); $^1$H NMR (400 MHz, DMSO-d$_6$) δ syn: 4.44 (dd, J=0.4, 4.5 Hz, 1H), 4.07-4.12 (m, 1H), 3.94-4.06 (m, 2H), 2.33 (dt, J=3.5, 11.7 Hz, 1H), 1.55-1.72 (m, 3H), 1.44-1.55 (m, 2H), 1.34-1.42 (m, 1H), 1.24-1.32 (m, 1H), 0.8-1.2 (m, 1H), 1.14 (t, J=7.0 Hz, 3H); anti: 4.71 (d, J=5.7 Hz, 1H), 4.01 (q, J=7.0 Hz, 2H), 3.42-3.52 (m, 1H), 2.08 (ddd, J=3.7, 9.8, 13.5 Hz, 1H), 1.70-1.82 (m, 2H), 1.50-1.65 (m, 2H), 1.02-1.33 (m, 4H), 1.14 (t, J=7.0 Hz, 3H).

Step 2.

To a cold (0° C.) solution of syn-ester 122 (1.05 g, 6.10 mmol) in anhydrous diethyl ether (20 mL) was added a solution of LiAlH$_4$ (2M, 2.5 mL) under argon. The reaction mixture was stirred for 30 mins at 0° C. after which a saturated solution of Na$_2$SO$_4$ (1 mL total) was added slowly while stirred for 40 mins. White precipitate had formed, and anhydrous MgSO$_4$ was added. The mixture was stirred for 5 min at room temperature, filtered and filtrate was concentrated under reduced pressure. Purification by flash chromatography (30% to 70% EtOAc/hexanes gradient) afforded syn-diol 124 as a colorless oil. Yield (0.44 g, 63%); $^1$H NMR (400 MHz, DMSO-d$_6$) δ 4.18 (t, J=5.3 Hz, 1H), 4.10 (d, J=4.1 Hz, 1H), 3.77-3.82 (m, 1H), 3.39 (ddd, J=5.5, 6.5, 11.9 Hz, 1H), 3.20 (ddd, J=5.3, 6.1, 11.4 Hz, 1H), 1.43-1.64 (m, 3H), 1.24-1.42 (m, 5H), 1.10-1.20 (m, 1H).

Step 3.

To a solution of syn-diol 124 (0.44 g, 3.85 mmol) and N,N-dimethylaminopyridine (DMAP) (0.485 g, 3.97 mmol) in anhydrous $CH_2Cl_2$ (10 mL) was added a solution of p-toluenesulfonyl chloride (0.767 g, 4.02 mmol) in anhydrous $CH_2Cl_2$ (5 mL) under argon at room temperature. The reaction mixture was stirred at room temperature for 22 hrs and triethylamine (0.5 mL) was added. The mixture was stirred for additional 100 min, concentrated under reduced pressure, water was added and the product was extracted with EtOAc twice. Combined organic layers were washed with brine, concentrated under reduced pressure and purified by flash chromatography (20% to 70% EtOAc/hexanes gradient) to give mono-tosylated syn-diol 125 as a colorless oil. Yield (0.732 g, 71%). $^1$H NMR (400 MHz, DMSO-$d_6$) δ 7.72-7.77 (m, 2H), 7.43-7.47 (m, 2H), 4.39 (d, J=4.1 Hz, 1H), 3.97 (dd, J=6.9, 9.4 Hz, 1H), 3.77 (dd, J=7.8, 9.4 Hz, 1H), 3.67-3.72 (m, 1H), 2.40 (s, 3H), 1.60-1.70 (m, 1H), 1.42-1.59 (m, 3H), 1.05-1.32 (m, 5H).

Step 4.

A mixture of syn-tosylate 125 (0.334 g, 1.24 mmol), phthalimide 58 (0.432 g, 1.54 mmol), cesium carbonate (0.562 g, 1.73 mmol) in anhydrous DMF (8 mL) was stirred at 60° C. under argon for 18 hrs, and then concentrated under reduced pressure. Water was added and the product was extracted with EtOAc three times. Combined fractions were washed with sat. $NH_4Cl$, brine, and concentrated under reduced pressure. The residue was purified by flash chromatography (20% to 70% EtOAc/hexanes gradient) to afford syn-ether 126 as a colorless oil. Yield (0.191 g, 41%). $^1$H NMR (400 MHz, DMSO-$d_6$) δ 7.76-7.85 (m, 4H), 7.09 (t, 7.6 Hz, 1H), 6.69-6.74 (m, 2H), 6.61-6.65 (m, 1H), 4.34 (d, J=4.1 Hz, 1H), 3.91 (dd, J=7.0, 9.2 Hz, 1H), 3.86-3.89 (m, 1H), 3.67 (dd, J=6.9, 9.2 Hz, 1H), 3.53-3.60 (m, 2H), 2.55 (t, J=7.6 Hz, 2H), 1.80-1.91 (m, 2H), 1.73-1.80 (m, 1H), 1.51-1.66 (m, 3H), 1.28-1.44 (m, 4H), 1.17-1.25 (m, 1H).

Step 5.

Deprotection of phthalimide 126 was done following the procedure described in Example 7 except that the reaction was stirred at 50° C. for 18 hrs. Purification by flash chromatography (75% to 100% of 5% 7N $NH_3$/MeOH in $CH_2Cl_2$-hexanes gradient) gave Example 147 as a white solid. Yield (0.063 g, 72%). $^1$H NMR (400 MHz, $CD_3OD$) δ 7.13 (t, J=7.8 Hz, 1H), 6.69-6.77 (m, 3H), 4.05-4.10 (m, 1H), 3.99 (dd, J=7.4, 9.4 Hz, 1H), 3.78 (dd, J=6.85, 9.2 Hz, 1H), 2.62 (t, J=7.0 Hz, 2H), 2.60 (t, J=8.0 Hz, 2H), 1.85-1.94 (m, 1H), 1.62-1.83 (m, 5H), 1.26-1.57 (m, 4H); $^{13}$C NMR (100 MHz, $CD_3OD$) δ 159.7, 143.7, 129.1, 120.5, 114.5, 111.6, 70.7, 69.4, 45.4, 40.9, 35.45, 34.4, 33.1, 28.45, 25.3, 24.8; RP-HPLC 97.0% (AUC) ESI MS m/z=264.5 [M+H]$^+$.

Example 148

Preparation of (1,2-trans)-2-((3-(3-aminopropyl)phenoxy)methyl)cyclohexanol

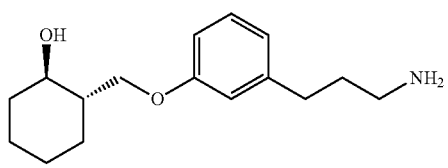 [SMILES: NCCCc1cccc(OC[C@@H]2CCCC[C@H]2O)c1]

(1,2-trans)-2-((3-(3-Aminopropyl)phenoxy)methyl)cyclohexanol was prepared following the method used for Example 147.

Step 1.

To a cold (0° C.) solution of anti-ester 123 (1.05 g, 6.10 mmol) in anhydrous diethyl ether (20 mL) was added a solution of $LiAlH_4$ (2M, 2.5 mL) under argon. The reaction mixture was stirred for 30 mins at 0° C. after which a saturated solution of $Na_2SO_4$ (1 mL total) was added slowly while stirred for 40 mins. White precipitate had formed, and anhydrous $MgSO_4$ was added. The mixture was stirred for 5 min at room temperature, filtered and filtrate was concentrated under reduced pressure. Purification by flash chromatography (30% to 70% EtOAc/hexanes gradient) afforded (1S,2R)-2-(hydroxymethyl)cyclohexanol as a colorless oil. Yield (0.44 g, 63%); $^1$H NMR (400 MHz, DMSO-$d_6$) δ 4.44 (d, J=4.9 Hz, 1H), 4.30 (dd, J=4.7, 5.7 Hz, 1H), 3.55 (dt, J=4.7, 10.4 Hz, 1H), 3.29 (dt, J=6.1, 12.3 Hz, 1H), 3.12 (septet, J=4.9 Hz, 1H), 1.64-1.78 (m, 2H), 1.50-1.63 9m, 2H), 0.99-1.25 (m, 4H), 0.84-0.95 (m, 1H).

Step 3.

To a solution of (1S,2R)-2-(hydroxymethyl)cyclohexanol (0.44 g, 3.85 mmol) and N,N-dimethylaminopyridine (DMAP) (0.485 g, 3.97 mmol) in anhydrous $CH_2Cl_2$ (10 mL) was added a solution of p-toluenesulfonyl chloride (0.767 g, 4.02 mmol) in anhydrous $CH_2Cl_2$ (5 mL) under argon at room temperature. The reaction mixture was stirred at room temperature for 22 hrs and triethylamine (0.5 mL) was added. The mixture was stirred for additional 100 min, concentrated under reduced pressure, water was added and the product was extracted with EtOAc twice. Combined organic layers were washed with brine, concentrated under reduced pressure and purified by flash chromatography (20% to 70% EtOAc/hexanes gradient) to give ((1R,2S)-2-hydroxycyclohexyl)methyl 4-methylbenzenesulfonate as a colorless oil. Yield (0.732 g, 71%). $^1$H NMR (400 MHz, DMSO-$d_6$) δ 7.72-7.76 (m, 2H), 7.42-7.47 (m, 2H), 4.60 (d, J=5.5 Hz, 1H), 4.12 (dd, J=3.1, 9.2 Hz, 1H), 3.90 (dd, J=7.2, 9.2 Hz, 1H), 3.00-3.10 (m, 1H), 2.40 (s, 3H), 1.73-1.80 (m, 1H), 1.46-1.65 (m, 3H), 1.34-1.42 (m, 1H), 0.85-1.16 (m, 4H).

Step 4.

A mixture of ((1R,2S)-2-hydroxycyclohexyl)methyl 4-methylbenzenesulfonate (0.334 g, 1.24 mmol), compound 58 (0.432 g, 1.54 mmol), cesium carbonate (0.562 g, 1.73 mmol) in anhydrous DMF (8 mL) was stirred at 60° C. under argon for 18 hrs, and then concentrated under reduced pressure. Water was added and the product was extracted with EtOAc three times. Combined fractions were washed with sat. $NH_4Cl$, brine, and concentrated under reduced pressure. The residue was purified by flash chromatography (20% to 70% EtOAc/hexanes gradient) to afford 2-(3-(3-(((1R,2S)-2-hydroxycyclohexyl)methoxy)phenyl)propyl)isoindoline-1,3-dione as a colorless oil. Yield (0.191 g, 41%). $^1$H NMR (400 MHz, DMSO-$d_6$) δ 7.76-7.85 (m, 4H), 7.09 (t, 7.6 Hz, 1H), 6.69-6.74 (m, 2H), 6.61-6.65 (m, 1H), 4.34 (d, J=4.1 Hz, 1H), 3.91 (dd, J=7.0, 9.2 Hz, 1H), 3.86-3.89 (m, 1H), 3.67 (dd, J=6.9, 9.2 Hz, 1H), 3.53-3.60 (m, 2H), 2.50 (t, J=7.6 Hz, 2H), 1.80-1.91 (m, 2H), 1.73-1.80 (m, 1H), 1.51-1.66 (m, 3H), 1.28-1.44 (m, 4H), 1.17-1.25 (m, 1H).

Step 5.

Deprotection of 2-(3-(3-(((1R,2S)-2-hydroxycyclohexyl)methoxy)phenyl)propyl)isoindoline-1,3-dione was done following the procedure described in Example 7 except that the reaction was stirred at 50° C. for 18 hrs. Purification by flash chromatography (75% to 100% of 5% 7N $NH_3$/MeOH in CH$_2$Cl$_2$-hexanes gradient) gave Example 148 as a white solid. Yield (0.063 g, 72%). $^1$H NMR (400 MHz, CD$_3$OD) δ 7.13 (t, J=7.8 Hz, 1H), 6.69-6.77 (m, 3H), 4.12 (dd, J=3.3, 9.2 Hz, 1H), 3.92 (dd, J=6.7, 9.2 Hz, 1H), 3.69 (td, J=10.0, 4.5 Hz, 1H), 2.62 (t, J=7.2 Hz, 2H), 2.60 (t, J=8.0 Hz, 2H), 1.91-2.0 (m, 2H), 1.72-1.80 (m, 2H), 1.59-1.71 (m, 3H), 1.19-1.38 (m, 4H); $^{13}$C NMR (100 MHz, CD$_3$OD) δ 159.7, 143.7, 129.1, 120.5, 114.5, 111.6, 70.7, 69.4, 45.4, 40.9, 35.45, 34.4, 33.1, 28.45, 25.3, 24.8; RP-HPLC 98.2% (AUC), ESI MS m/z=264.5 [M+H]$^+$.

Example 149

Preparation of 4-(3-(3-amino-1-hydroxypropyl)phenoxy)butanamide

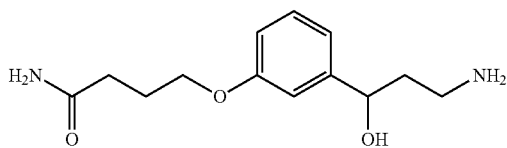 [SMILES: NCCC(O)c1cccc(OCCCC(N)=O)c1]

4-(3-(3-Amino-1-hydroxypropyl)phenoxy)butanamide was prepared following the method shown in Scheme 42.

SCHEME 42

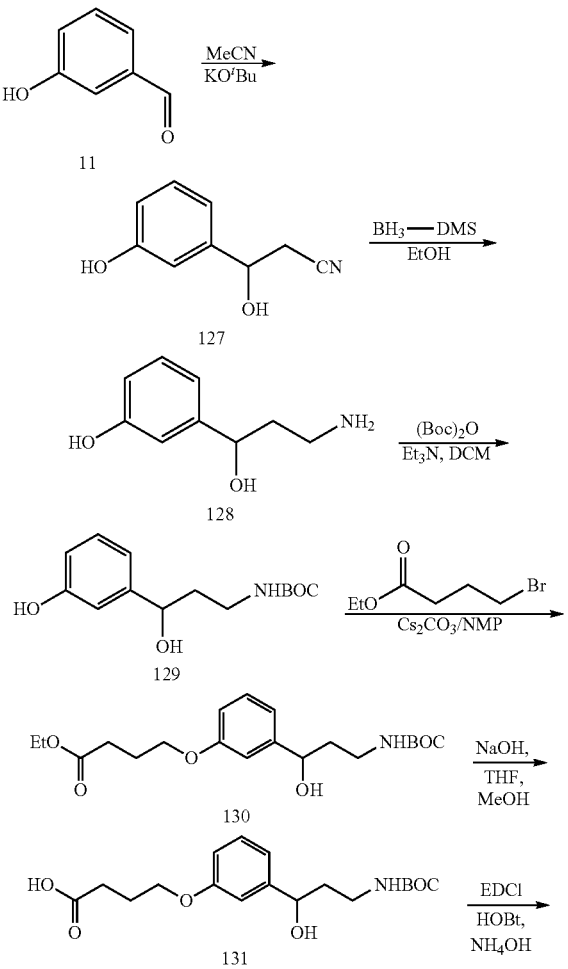

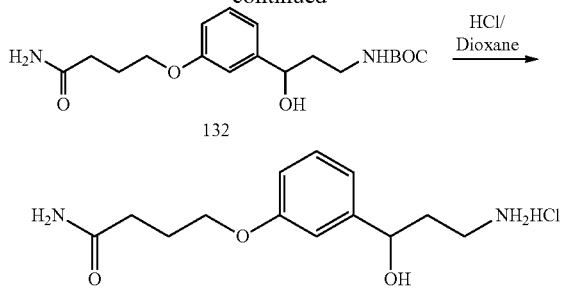

Step 1:

To a stirred suspension of KO$^t$Bu (4.5 g, 40 mmol) in THF (20 mL), cooled to −50° C., was added acetonitrile (1.88 mL, 36 mmol) dropwise over a period of 5 min. The resulting mixture was stirred at −50° C. for 30 min following which a solution of 3-hydroxybenzaldehyde (11) (2.0 g, 16.3 mmol) in THF (10 mL) was added slowly, over a period of 10 min. This was then allowed to warm to 0° C. and stirred for another 3 h during which the reaction was found to be complete. The reaction was quenched by slow addition of ice-water followed by extraction with EtOAc. The combined organics were washed with water, brine and dried over Na$_2$SO$_4$. The filtered solution was concentrated under reduced pressure to give yellow oil which was purified by flash column chromatography (0 to 20% EtOAc-hexanes gradient) to give nitrile 127 Yield (2.1 g, 80%): $^1$H NMR (400 MHz, CDCl$_3$) δ 7.27 (s, 1H), 6.95 (d, J=7.6 Hz, 1H), 6.90-6.93 (m, 1H), 6.82 (dd, J=8.0, 2.4 Hz, 1H), 4.91-5.03 (m, 1H), 2.76 (d, J=6.4 Hz, 2H).

Step 2:

To a stirred solution of nitrile 127 (2.1 g, 12.8 mmol) in THF (20 ml) was added BH$_3$-DMS (3.67 mL, 38.6 mmol) at 0° C. After the addition was complete, the cooling bath was removed and the resulting mixture was gradually warmed to reflux and maintained overnight. This was then cooled in an ice-bath and quenched by the slow addition of large excess of MeOH. After stirring at RT for about 2 h, the excess solvent was removed under reduced pressure. The residue was again treated with MeOH and evaporated. The process was repeated thrice. The brown oil was then applied onto a flash silica gel column and eluted (0 to 15% (9:1 MeOH—NH$_3$)-DCM gradient) to give 3-(3-amino-1-hydroxypropyl)phenol (128) as a brown solid. Yield (1.7 g, 81%): $^1$H NMR (400 MHz, DMSO-d$_6$) δ 7.04-7.09 (m, 1H), 6.74 (s, 1H), 6.70 (d, J=7.6 Hz, 1H), 6.58 (dd, J=8.0, 2.0 Hz, 1H), 4.55 (dd, J=7.2, 5.6 Hz, 1H), 2.57-2.66 (m, 2H), 1.56-1.62 (m, 2H).

Step 3:

To a solution of amine 128 (1.7 g, 10.1 mmol) in 1,4-dioxane (20 mL) was added K$_2$CO$_3$ (1.7 mL, 12.2 mmol) followed by a slow addition of (Boc)$_2$O (2.5 mL, 11.1 mmol). The mixture was stirred at room temperature for 2 h and then quenched by the addition of water followed by extraction with ethyl acetate. The organic layer was washed with water and brine solution, dried over anhydrous Na$_2$SO$_4$, filtered and concentrated under reduced pressure. Purification by flash chromatography (0 to 20% EtOAc-hexanes gradient) afforded tert-butyl 3-hydroxy-3-(3-hydroxyphenyl)propyl carbamate (129) as off-white solid. Yield (2.1 g, 78%): $^1$H NMR (400 MHz, CDCl$_3$) δ 7.05-7.10 (m, 1H), 6.70-6.76 (m, 2H), 6.59 (dd, J=8.0, 1.6 Hz, 1H), 5.11 (d, J=4.4 Hz, 1H), 4.42-4.47 (m, 1H), 3.57 (s, 1H), 2.92-2.98 (m, 2H), 1.61-1.67 (m, 2H), 1.37 (s, 9H).

Step 4:

The suspension of carbamate 129 (2.1 g, 7.9 mmol), ethylbromobutyrate (1.24 mL, 8.7 mmol) and cesium carbonate (3.84 g, 11.7 mmol) in DMF (20 mL) was heated at 70° C. for 24 h. The reaction mixture was cooled and quenched by the addition of water and extracted with ethyl acetate. The organic extract was washed with water, dried over anhy. $Na_2SO_4$. Filtration and concentration under reduced pressure gave the crude product, which was purified by flash chromatography (hexane-ethyl acetate (0-30%) gradient) to give ethyl 4-(3-(3-(tert-butoxycarbonyl amino)-1-hydroxypropyl)phenoxy)butanoate (130) as a yellow solid. Yield (2.3 g, 79%): $^1$H NMR (400 MHz, $CDCl_3$) δ 7.22 (d, J=8.4 Hz, 1H), 6.90-6.93 (m, 2H), 6.78 (d, J=7.2 Hz, 1H), 4.22 (t, J=6.4 Hz, 1H), 4.14 (q, J=7.2 Hz, 2H), 4.01 (t, J=6.0 Hz, 2H), 3.47 (t, J=6.4 Hz, 2H), 2.40-2.54 (m, 3H), 1.98-2.20 (m, 3H), 1.45 (s, 9H), 1.26 (t, J=7.2 Hz, 2H).

Step 5:

To the ester 130 (2.3 g, 6.0 mmol) in THF (80 mL) and MeOH (20 mL) was added NaOH solution (8 mL, 2N). The resulting mixture was stirred at room temperature for overnight following which the solvent was removed under reduced pressure and pH adjusted to 6 by the addition of cold dilute HCl. This was then extracted with DCM. The organic layer was washed with water, dried over anhydrous $Na_2SO_4$, filtered and concentrated under reduced pressure to give 4-(3-(3-(tert-butoxycarbonylamino)-1-hydroxypropyl) phenoxy) butanoic acid (131). The product was directly utilized for the next transformation. Yield (1.94 g, 91%): $^1$H NMR (400 MHz, $CDCl_3$) δ 7.18-7.22 (m, 1H), 6.84-6.90 (m, 2H), 6.77 (dd, J=7.6, 1.6 Hz, 1H), 5.18 (bs, 1H), 4.48-4.53 (m, 1H), 3.96 (t, J=6.4 Hz, 2H), 2.93-2.99 (m, 2H), 2.38 (t, J=7.4 Hz, 2H), 1.90-1.96 (m, 2H), 1.64-1.71 (m, 2H), 1.45 (s, 9H).

Step 6:

A mixture of acid 131 (0.5 g, 1.4 mmol), HOBt (0.260 g, 2.8 mmol) and EDCl (0.325 g, 1.7 mmol) in DCM (20 mL) was stirred at room temperature for 2 h. To this was added ammonia in methanol (1 mL, 2M) and the mixture was stirred for further 3 h. The reaction was quenched by the addition of water and extracted with DCM. The organic layer was washed water, dried over anhydrous $Na_2SO_4$, filtered and concentrated under reduced pressure. Purification by flash chromatography (0 to 2% DCM-Methanol gradient) afforded amide 132 as yellow oil. Yield (0.31 g, 63%): $^1$H NMR (400 MHz, $CDCl_3$) δ 7.31 (bs, 1H), 7.18-7.22 (m, 1H), 6.85-6.87 (m, 2H), 6.75-6.77 (m, 3H), 5.18 (d, J=4.8 Hz, 1H), 4.48-4.53 (m, 1H), 3.93 (t, J=6.4 Hz, 2H), 2.93-3.0 (m, 2H), 2.22 (t, J=7.4 Hz, 2H), 1.88-1.96 (m, 2H), 1.64-1.70 (m, 2H), 1.37 (s, 9H).

Step 7:

To a solution of amide 132 (0.31 g, 0.9 mmol) in EtOAc (10 mL) was added HCl in dioxane (3 mL, 4M). The resulting mixture was stirred at room temperature overnight. This was then concentrated under reduced pressure to give Example 149 hydrochloride as yellow oil. Yield (0.072 g, 33%): $^1$H NMR (400 MHz, DMSO-$d_6$) δ 7.21-7.26 (m, 1H), 6.86-6.88 (m, 2H), 6.80 (dd, J=7.2, 2.0 Hz, 1H), 4.62 (dd, J=7.6, 4.8 Hz, 1H), 3.92 (t, J=6.4 Hz, 2H), 2.80-2.88 (m, 2H), 2.22 (t, J=7.4 Hz, 2H), 1.88-1.94 (m, 4H). $^{13}$C NMR (100 MHz, DMSO-$d_6$) δ 174.2, 159.0, 147.4, 129.7, 118.2, 113.3, 112.1, 70.0, 67.3, 37.0, 36.7, 31.8, 25.2. MS: 253 [M+1]$^+$.

Example 150

Preparation of 2-(3-(3-aminopropyl)phenoxy)-1-phenylethanol

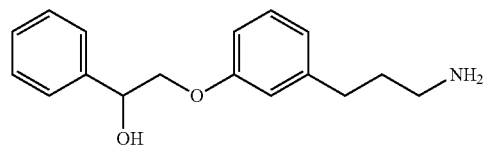 [SMILES: NCCCc1cccc(OCC(O)c2ccccc2)c1]

2-(3-(3-Aminopropyl)phenoxy)-1-phenylethanol was prepared following the method used for Example 32.

Step 1:

Alkylation reaction of phenol 58 with styrene oxide gave 2-(3-(3-(2-hydroxy-2-phenylethoxy)phenyl)propyl)isoindoline-1,3-dione as yellow oil. Yield (0.78 g, 58%): $^1$H NMR (400 MHz, $CDCl_3$) δ 7.50-7.54 (m, 2H), 7.42-7.47 (m, 2H), 7.31-7.41 (m, 5H), 7.16-7.20 (m, 1H), 6.80-6.84 (m, 2H), 6.71 (dd, J=8.4, 2.2 Hz, 1H), 5.10 (dd, J=8.4, 3.2 Hz, 1H), 4.08 (d, J=6.4 Hz, 2H), 3.44-3.49 (m, 2H), 2.68 (t, J=7.4 Hz, 2H), 1.90-1.98 (m, 2H).

Step 2:

Phthalimide cleavage of 2-(3-(3-(2-hydroxy-2-phenylethoxy) phenyl)propyl)isoindoline-1,3-dione gave Example 25 as off white powder. Yield (0.31 g, 60%): $^1$H NMR (400 MHz, DMSO-$d_6$) δ 7.43-7.46 (m, 2H), 7.33-7.37 (m, 2H), 7.25-7.28 (m, 1H), 7.12-7.17 (m, 1H), 6.71-6.75 (m, 3H), 4.90 (t, J=5.4 Hz, 1H), 3.98 (d, J=6.0 Hz, 2H), 2.48-2.56 (m, 4H), 1.56-1.63 (m, 2H). $^{13}$C NMR (100 MHz, DMSO-$d_6$) δ 158.5, 144.0, 142.5, 129.2, 128.0, 127.2, 126.4, 120.6, 114.5, 111.7, 72.9, 70.9, 41.2, 35.1, 32.6. MS: 272 [M+1]$^+$.

Example 151

Preparation of 5-(3-(3-aminopropyl)phenoxy)pentan-1-ol

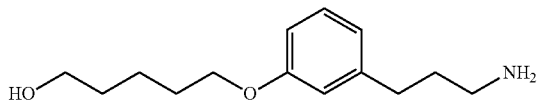 [SMILES: NCCCc1cccc(OCCCCCO)c1]

5-(3-(3-Aminopropyl)phenoxy)pentan-1-ol was prepared following the methods used for Examples 59 and 143.

Step 1:

Mitsunobu reaction of phenol 58 with 5-(tert-butyldimethylsilanyloxy)pentan-1-ol gave 2-(3-(3-(5-(tert-butyldimethylsilanyloxy)pentyloxy)phenyl)propyl)isoindoline-1,3-dione as yellow oil. Yield (0.725 g, 44%): $^1$H NMR (400 MHz, $CDCl_3$) δ 7.80-7.83 (m, 2H), 7.68-7.72 (m, 2H), 7.11-7.16 (m, 1H), 6.75 (d, J=7.6 Hz, 1H), 6.73 (s, 1H), 6.65 (dd, J=8.4, 2.0 Hz, 1H), 3.92 (t, J=6.6 Hz, 2H), 3.74 (t, J=7.2 Hz, 2H), 3.64 (t, J=6.2 Hz, 2H), 2.65 (t, J=7.8 Hz, 2H), 1.99-2.07 (m, 2H), 1.75-1.82 (m, 2H), 1.56-1.62 (m, 2H), 1.47-1.53 (m, 2H), 0.89 (s, 9H), 0.10 (s, 6H).

Step 2:

Phthalimide cleavage of 2-(3-(3-(5-(tert-butyl-dimethylsilanyloxy)pentyloxy)phenyl)propyl)isoindoline-1,3-dione gave 3-(3-(5-(tert-butyldimethylsilanyloxy)pentyloxy)phenyl)propylamine as yellow oil. Yield (0.52 g, 95%): $^1$H NMR (400 MHz, DMSO-$d_6$) 7.14-7.19 (m, 1H), 6.70-6.77

(m, 3H), 3.94 (t, J=6.5 Hz, 2H), 3.64 (t, J=6.2 Hz, 2H), 2.73 (t, J=7.0 Hz, 2H), 2.60-2.67 (m, 2H), 1.76-1.86 (m, 4H), 1.57-1.64 (m, 2H), 1.47-1.54 (m, 2H), 0.90 (s, 9H), 0.05 (s, 6H).

Step 3:

The TBS ether was cleaved according to the following procedure: To 3-(3-(5-(tert-butyl-dimethyl-silanyloxy)pentyloxy)phenyl)propylamine (0.51 g, 1.4 mmol) in THF (10 mL) was added 6N HCl (1 mL) and the reaction mixture was stirred at room temperature for 24 h. The solvent was evaporated under reduced pressure and the reaction mixture was brought up to pH 10 using conc. ammonia and extracted with DCM. The organic layer was dried over anhydrous Na$_2$SO$_4$, filtered and concentrated under reduced pressure. Purification by flash chromatography (0-(9.5-0.5) MeOH—NH$_3$)-DCM gradient) afforded Example 151 as pale yellow oil. Yield (0.23 g, 70%): $^1$H NMR (400 MHz, CDCl$_3$) δ 7.13-7.17 (m, 1H), 6.70-6.74 (m, 3H), 3.92 (t, J=6.4 Hz, 2H), 3.40 (t, J=6.0 Hz, 2H), 2.51-2.57 (m, 4H), 1.68-1.74 (m, 2H), 1.59-1.65 (m, 2H), 1.40-1.50 (m, 4H). $^{13}$C NMR (100 MHz, DMSO-d$_6$) δ 158.7, 143.9, 129.2, 120.4, 114.5, 111.5, 67.2, 60.6, 41.2, 35.1, 32.6, 32.2, 28.7, 22.2. MS: 238 [M+1]$^+$.

Example 152

Preparation of 1-(3-(3-aminopropyl)phenoxy)-3-methylbutan-2-ol

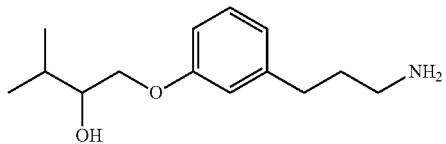 [SMILES: CC(C)C(O)COc1cccc(CCCN)c1]

1-(3-(3-Aminopropyl)phenoxy)-3-methylbutan-2-ol was prepared following the method used for Example 32.

Step 1:

Alkylation reaction of phenol 58 with 1,2-epoxy-3-methylbutane gave 2-(3-(3-(2-hydroxy-3-methylbutoxy)phenyl)propyl)isoindoline-1,3-dione as yellow oil. Yield (1.105 g, 76%): $^1$H NMR (400 MHz, CDCl$_3$) δ 8.11-8.14 (m, 1H), 7.52-7.57 (m, 2H), 7.33-7.36 (m, 1H), 7.17-7.21 (m, 1H), 6.85 (s, 1H), 6.74 (dd, J=8.4, 2.0 Hz, 1H), 3.75 (d, J=5.6 Hz, 2H), 2.70 (t, J=7.2 Hz, 2H), 1.84-2.03 (m, 5H), 1.03 (d, J=6.8 Hz, 3H), 0.99 (d, J=6.8 Hz, 3H).

Step 2:

Phthalimide cleavage of 2-(3-(3-(2-hydroxy-3-methylbutoxy)phenyl)propyl)isoindoline-1,3-dione gave Example 152 as a yellow oil. Yield (0.48 g, 75%): $^1$H NMR (400 MHz, DMSO-d$_6$) δ 7.14-7.17 (m, 1H), 6.71-6.75 (m, 3H), 4.76-4.77 (m, 1H), 3.87-3.91 (m, 1H), 3.79-3.83 (m, 1H), 3.52-3.55 (m, 1H), 2.55 (t, J=7.6 Hz, 2H), 1.73-1.81 (m, 1H), 1.57-1.65 (m, 2H), 1.46-1.52 (m, 1H), 0.88-0.92 (m, 6H). $^{13}$C NMR (100 MHz, DMSO-d$_6$) δ 159.2, 144.4, 129.6, 120.9, 115.0, 112.0, 73.3, 70.8, 41.6, 35.6, 33.1, 31.0, 19.6, 17.7. MS: 238 [M+1]$^+$.

Example 153

Preparation of 1-(3-(2-aminoethoxy)phenoxy)-3-methylbutan-2-ol

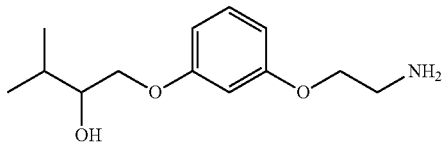

1-(3-(2-Aminoethoxy)phenoxy)-3-methylbutan-2-ol was prepared following the method used for Example 18.

Step 1:

Alkylation reaction of phenol 24 with 1,2-epoxy-3-methylbutane gave 2-(2-(3-(2-hydroxy-3-methylbutoxy)phenoxy)ethyl)isoindoline-1,3-dione as yellow oil. Yield (1.0 g, 76%): $^1$H NMR (400 MHz, CDCl$_3$) δ 8.01-8.03 (m, 1H), 7.47-7.55 (m, 3H), 7.13-7.17 (m, 1H), 6.49-6.54 (m, 3H), 4.12 (t, J=5.6 Hz, 2H), 3.98-4.02 (m, 1H), 3.82-3.88 (m, 3H), 3.68-3.73 (m, 1H), 1.82-1.88 (m, 1H), 1.01 (d, J=6.8 Hz, 3H), 0.91 (d, J=6.8 Hz, 3H).

Step 2:

Phthalimide cleavage of 2-(2-(3-(2-hydroxy-3-methylbutoxy) phenoxy)ethyl)isoindoline-1,3-dione gave Example 153 as yellow oil. Yield (0.45 g, 69%): $^1$H NMR (400 MHz, DMSO-d$_6$) δ 7.12-7.17 (m, 1H), 6.45-6.51 (m, 3H), 3.86-3.90 (m, 3H), 3.78-3.82 (m, 1H), 3.50-3.54 (m, 1H), 2.81 (t, J=5.8 Hz, 2H), 1.72-1.78 (m, 1H), 0.89 (d, J=5.2 Hz, 3H), 0.87 (d, J=5.2 Hz, 3H). $^{13}$C NMR (100 MHz, DMSO-d$_6$) δ 160.5, 160.4, 130.3, 107.2, 107.1, 101.7, 73.3, 71.0, 70.6, 41.4, 31.0, 19.6, 17.7. MS: 240 [M+1]$^+$.

Example 154

Preparation of 2-(3-(cyclohexylmethoxy)-5-methylphenoxy)ethanamine

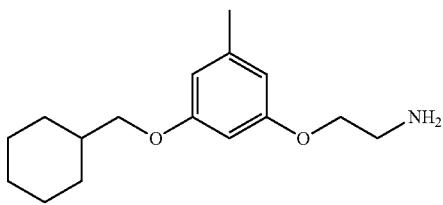 [SMILES: Cc1cc(OCCN)cc(OCC2CCCCC2)c1]

2-(3-(Cyclohexylmethoxy)-5-methylphenoxy)ethanamine was prepared following the method shown in Scheme 43.

SCHEME 43

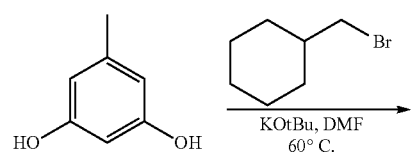

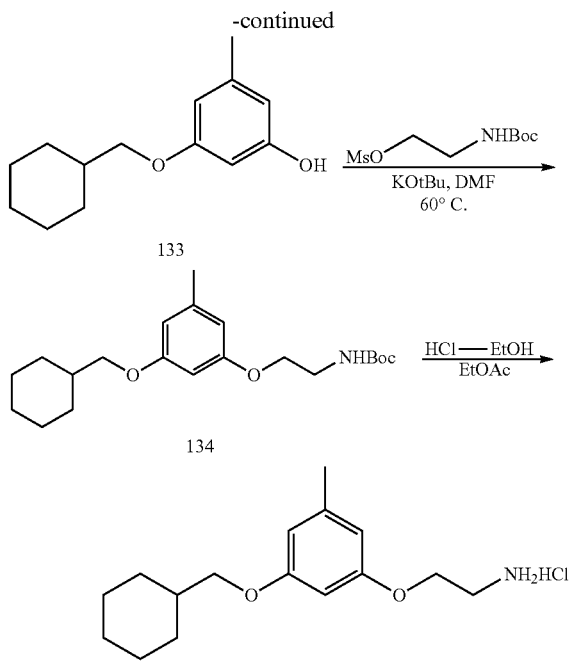
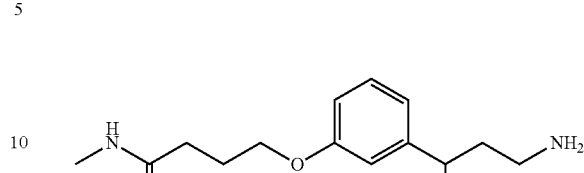

Step 1:

To a solution of 5-methylbenzene-1,3-diol H₂O (1.0 g, 7.0 mmol) in DMF (15 ml) was added potassium tert-butoxide (0.86 g, 77 mmol). The mixture was stirred at 60° C. for 1 h. To the mixture was added (bromomethyl)cyclohexane (1.2 g, 7.0 mmol). The reaction mixture was stirred at 60° C. for 18 h, concentrated under vacuum, partitioned between water (40 ml) and ethyl acetate (60 ml). Ethyl acetate portion was dried over Na₂SO₄. Purification by chromatography (10 to 30% EtOAc-hexanes gradient) gave 3-(cyclohexylmethoxy)-5-methylphenol (133) as a light yellow solid. Yield (0.40 g, 26%): $^1$H NMR (400 MHz, CDCl₃) δ 6.31 (s, 1H), 6.20-6.22 (m, 2H), 4.62 (bs, 1H), 3.69 (d, J=6.4 Hz, 2H), 2.50 (s, 3H), 1.64-1.88 (m, 6H), 1.16-1.34 (m, 3H), 0.98-1.08 (m, 2H).

Step 2:

A mixture of phenol 133 (0.41 g, 1.85 mmol), 2-(tert-butoxycarbonylamino)ethyl methanesulfonate (0.42 g, 2.22 mmol) and cesium carbonate (0.72 g, 2.22 mmol) in DMF (10 ml) was heated at 60° C. for 18 h, concentrated under vacuum, partitioned between water (40 ml) and ethyl acetate (60 ml). Ethyl acetate portion was dried over Na₂SO₄. Purification by chromatography (10 to 30% EtOAc-hexanes gradient) gave carbamate 134 as a light yellow oil. Yield (0.40 g, 60%): $^1$H NMR (400 MHz, CDCl₃) δ 7.21 (s, 1H), 6.17-6.33 (m, 3H), 4.96 (bs, 1H), 3.97 (t, J=4.8 Hz, 2H), 3.69 (d, J=6.4 Hz, 2H), 3.50 (q, J=5.2 Hz, 2H), 2.27 (s, 3H), 1.67-1.86 (m, 6H), 1.44 (s, 9H), 1.15-1.33 (m, 3H), 0.98-1.08 (m, 2H).

Step 3:

Deprotection of carbamate 134 was done following the method used in Example 5 to give Example 154 hydrochloride as a white solid. Yield (0.25 g, 76%): $^1$H NMR (400 MHz, CD₃OD) δ 6.37-6.39 (m, 2H), 6.32-6.34 (m, 1H), 4.16 (t, J=5.2 Hz, 2H), 3.71 (d, J=6.4 Hz, 2H), 3.29 (t, J=5.2 Hz, 2H), 2.26 (s, 3H), 1.65-1.88 (m, 6H), 1.16-1.36 (m, 3H), 1.01-1.10 (m, 2H).

Example 155

Preparation of (4-(3-(3-amino-1-hydroxypropyl)phenoxy)-N-methylbutanamide

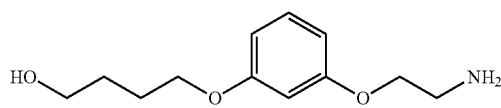 [SMILES: NCCOc1cccc(OCCCCO)c1]

(4-(3-(3-Amino-1-hydroxypropyl)phenoxy)-N-methylbutanamide was prepared following the method used for Example 149.

Step 1:

The acid-amine coupling of compound 131 with methylamine gave tert-butyl 3-hydroxy-3-(3-(4-(methylamino)-4-oxobutoxy)phenyl)propylcarbamate as a yellow oil. Yield (0.24 g, 47%): $^1$H NMR (400 MHz, CDCl₃) δ 7.77 (bs, 1H), 7.18-7.22 (m, 1H), 6.85-6.87 (m, 2H), 6.75-6.77 (m, 2H), 5.18 (d, J=4.4 Hz, 1H), 4.48-4.53 (m, 1H), 3.93 (t, J=6.4 Hz, 2H), 2.93-2.97 (m, 2H), 2.56 (d, J=4.8 Hz, 3H), 2.22 (t, J=7.4 Hz, 2H), 1.90-1.96 (m, 2H), 1.64-1.70 (m, 2H), 1.37 (s, 9H).

Step 2:

BOC-deprotection of tert-butyl 3-hydroxy-3-(3-(4-(methylamino)-4-oxobutoxy)phenyl)propylcarbamate gave Example 155 hydrochloride as a white solid. Yield (0.1 g, 62%): $^1$H NMR (400 MHz, DMSO-d₆) δ 7.21-7.26 (m, 1H), 6.86-6.88 (m, 2H), 6.78 (d, J=8.0 Hz, 1H), 4.62 (dd, J=7.8, 4.6 Hz, 1H), 3.91 (t, J=6.4 Hz, 2H), 2.80-2.86 (m, 2H), 2.55 (s, 3H), 2.21 (t, J=7.4 Hz, 2H), 1.86-1.94 (m, 4H). $^{13}$C NMR (100 MHz, DMSO-d₆) δ 171.9, 158.5, 146.9, 129.2, 117.7, 112.8, 111.7, 69.6, 66.8, 36.5, 36.3, 31.6, 25.4, 24.9. MS: 267 [M+1]$^+$.

Example 156

Preparation of 4-(3-(2-aminoethoxy)phenoxy)butan-1-ol 4-(3-(2-Aminoethoxy)phenoxy)butan-1-ol was prepared following the method used for Example 143.

Step 1:

Mitsunobu reaction of phenol 24 with 4-(tert-butyldimethylsilanyloxy)butan-1-ol gave 2-(2-(3-(4-(tert-butyldimethylsilyloxy)butoxy)phenoxy)ethyl)isoindoline-1,3-dione as yellow oil. Yield (1.3 g, 78%): $^1$H NMR (400 MHz, CDCl₃) δ 7.84-7.87 (m, 2H), 7.70-7.74 (m, 2H), 7.10-7.14 (m, 1H), 6.42-6.49 (m, 3H), 4.20 (t, J=5.6 Hz, 2H), 4.10 (t, J=5.6 Hz, 2H), 3.92 (t, J=6.6 Hz, 2H), 3.66 (t, J=5.6 Hz, 2H), 1.78-1.86 (m, 2H), 1.61-1.69 (m, 2H), 0.89 (s, 9H), 0.06 (s, 6H).

Step 2:

Phthalimide cleavage of 2-(2-(3-(4-(tert-butyldimethylsilyloxy)butoxy)phenoxy)ethyl)isoindoline-1,3-dione gave 2-(3-(4-(tert-butyldimethylsilyloxy)butoxy)phenoxy)ethanamine as yellow oil. Yield (0.70 g, 74%): $^1$H NMR (400 MHz, DMSO-$d_6$) δ 7.13-7.18 (m, 1H), 6.46-6.52 (m, 3H), 3.94-3.99 (m, 4H), 3.68 (t, J=6.2 Hz, 2H), 3.07 (t, J=5.2 Hz, 2H), 1.81-1.87 (m, 2H), 1.63-1.71 (m, 2H), 0.90 (s, 9H), 0.05 (s, 6H).

Step 3:

TBDMS deprotection of 2-(3-(4-(tert-butyldimethylsilyloxy)butoxy)phenoxy)ethanamine gave Example 156 as off white solid. Yield (0.135 g, 29%): $^1$H NMR (400 MHz, CDCl$_3$) δ 7.12-7.16 (m, 1H), 6.45-6.50 (m, 3H), 3.94 (t, J=6.6 Hz, 2H), 3.88 (t, J=5.8 Hz, 2H), 3.44 (t, J=6.2 Hz, 2H), 2.84 (t, J=5.8 Hz, 2H), 1.70-1.76 (m, 2H), 1.51-1.59 (m, 2H). $^{13}$C NMR (100 MHz, DMSO-$d_6$) δ 159.9, 159.8, 129.9, 106.7, 106.6, 101.2, 69.9, 67.4, 60.4, 40.8, 29.0, 25.4. MS: 226 [M+1]$^+$.

Example 157

Preparation of 4-(3-(3-amino-1-hydroxypropyl)phenoxy)-N,N-dimethylbutanamide

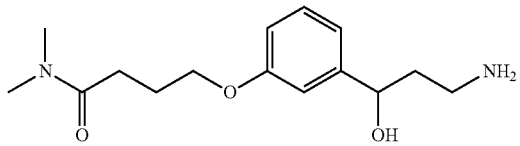 [SMILES: CN(C)C(=O)CCCOc1cccc(C(O)CCN)c1]

4-(3-(3-Amino-1-hydroxypropyl)phenoxy)-N,N-dimethylbutanamide was prepared following the method used in Example 149.

Step 1:

The acid-amine coupling of compound 131 with dimethylamine gave tert-butyl 3-(3-(4-(dimethylamino)-4-oxobutoxy)phenyl)-3-hydroxypropylcarbamate as a yellow oil. Yield (0.3 g, 57%): $^1$H NMR (400 MHz, CDCl$_3$) δ 7.77 (bs, 1H), 7.18-7.22 (m, 1H), 6.85-6.88 (m, 2H), 6.76 (d, J=7.6 Hz, 1H), 5.18 (d, J=4.4 Hz, 1H), 4.48-4.53 (m, 1H), 3.96 (t, J=6.4 Hz, 2H), 2.92-2.98 (m, 5H), 2.82 (s, 3H), 2.44 (t, J=7.2 Hz, 2H), 1.90-1.96 (m, 2H), 1.64-1.70 (m, 2H), 1.37 (s, 9H).

Step 2:

BOC deprotection of tert-butyl 3-(3-(4-(dimethylamino)-4-oxobutoxy)phenyl)-3-hydroxypropylcarbamate gave Example 157 hydrochloride as a white solid. Yield (0.09 g, 45%): $^1$H NMR (400 MHz, DMSO-$d_6$) δ 7.21-7.25 (m, 1H), 6.85-6.88 (m, 2H), 6.79 (d, J=8.8 Hz, 1H), 4.60-4.63 (m, 1H), 3.94 (t, J=6.4, 2H), 2.93 (s, 3H), 2.83 (t, J=7.2 Hz, 2H), 2.79 (s, 3H), 2.42 (t, J=7.0 Hz, 2H), 1.79-1.93 (m, 4H). $^{13}$C NMR (100 MHz, DMSO-$d_6$) δ 171.8, 159.0, 147.4, 129.7, 118.5, 113.3, 112.1, 70.0, 67.2, 37.1, 37.0, 36.8, 35.3, 29.1, 24.9. MS: 281 [M+1]$^+$.

Example 158

Preparation of 1-(3-(3-amino-1-hydroxypropyl)phenoxy)-3-methylbutan-2-ol

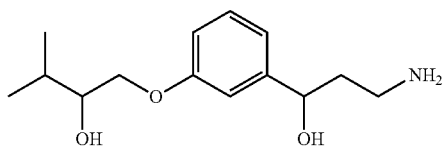 [SMILES: CC(C)C(O)COc1cccc(C(O)CCN)c1]

1-(3-(3-Amino-1-hydroxypropyl)phenoxy)-3-methylbutan-2-ol was prepared following the method shown in Scheme 44.

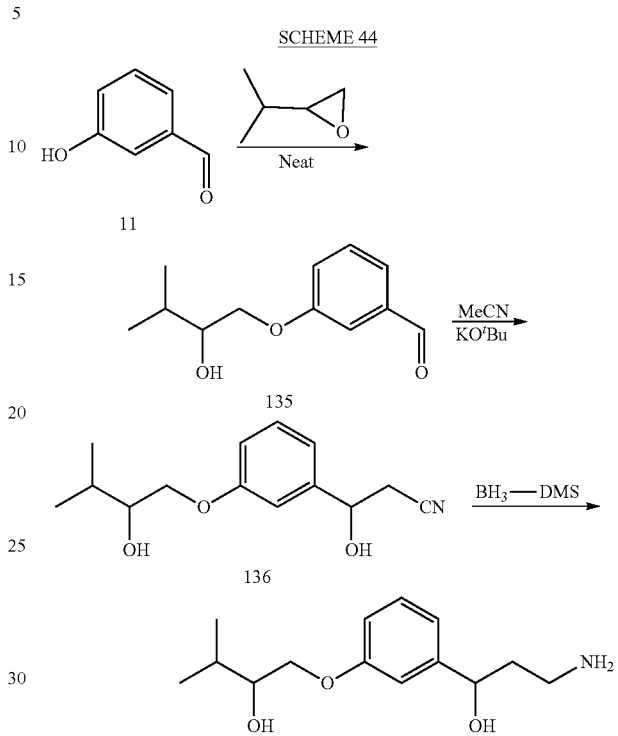

Step 1:

A mixture of 3-hydroxybenzaldehyde (11) (1 g, 8.2 mmol) and 1,2-epoxy-3-methylbutane (1.3 mL, 12.3 mmol) was microwaved at 140° C. and 120 psi pressure for 2 h (CEM, Discover). Purification by flash chromatography (0 to 15% Acetone-hexanes gradient) gave 3-(2-hydroxy-3-methylbutoxy)benzaldehyde (135) as a yellow oil. Yield (1.1 g, 65%): $^1$H NMR (400 MHz, CDCl$_3$) δ 9.98 (s, 1H), 7.41-7.50 (m, 3H), 7.19-7.24 (m, 1H), 4.10 (dd, J=9.4, 3.0 Hz, 1H), 3.97 (dd like t, J=8.4 Hz, 1H), 3.75-3.80 (m, 1H), 2.23 (t, J=4.0 Hz, 1H), 1.86-1.95 (m, 1H), 1.05 (d, J=6.8 Hz, 3H), 1.01 (d, J=6.8 Hz, 3H).

Step 2:

Addition of acetonitrile to benzaldehyde 135 following the method used in Example 34 gave 3-hydroxy-3-(3-(2-hydroxy-3-methylbutoxy)phenyl)propanenitrile (136) as a yellow oil. Yield (0.72 g, 55%): $^1$H NMR (400 MHz, CDCl$_3$) δ 7.29-7.34 (m, 1H), 6.96-7.0 (m, 2H), 6.89 (dd, J=8.2, 2.0 Hz, 1H), 5.0-5.05 (m, 1H), 4.05 (dd, J=9.2, 2.8 Hz, 1H), 3.92 (dd like t, J=8.4 Hz, 1H), 3.72-3.76 (m, 1H), 2.77 (d, J=6.0 Hz, 2H), 2.44 (d, J=3.6 Hz, 1H), 2.25 (d, J=3.6 Hz, 1H), 1.84-1.93 (m, 1H), 1.04 (d, J=6.8 Hz, 3H), 1.0 (d, J=6.8 Hz, 3H).

Step 3:

Reduction of nitrile 136 with BH$_3$-DMS following the method used in Example 48 gave Example 158 as a colorless oil. Yield (0.49 g, 54%): $^1$H NMR (400 MHz, DMSO-$d_6$) δ 7.16-7.21 (m, 1H), 6.83-6.88 (m, 2H), 6.75 (dd, J=8.2, 1.8 Hz, 1H), 4.58 (t, J=6.4 Hz, 1H), 3.87-3.90 (m, 1H), 3.78-3.83 (m, 1H), 3.51-3.55 (m, 1H), 2.56 (d, J=6.8 Hz, 2H), 1.72-1.81 (m, 1H), 1.60-1.66 (m, 2H), 0.89 (d, J=6.2 Hz, 3H), 0.87 (d, J=6.2 Hz, 3H). $^{13}$C NMR (100 MHz, DMSO-d$_6$) δ 158.6, 148.2, 128.8, 117.8, 112.4, 111.7, 72.8, 71.2, 70.3, 42.3, 30.4, 19.1, 17.1. MS: 254 [M+1]$^+$

Example 159

Preparation of 1-(3-(2-aminoethoxy)phenoxy)pentan-2-ol

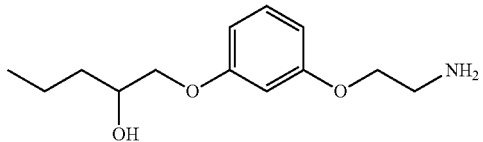 [SMILES: CCCC(O)COc1cccc(OCCN)c1]

1-(3-(2-Aminoethoxy)phenoxy)pentan-2-ol was prepared following the method used for Example 18.

Step 1:
Alkylation reaction of phenol 24 with 1,2-epoxypentane gave 2-(2-(3-(2-hydroxypentyloxy)phenoxy)ethyl)isoindoline-1,3-dione as yellow oil. Yield (1.1 g, 84%): $^1$H NMR (400 MHz, CDCl$_3$) δ 7.98 (d, J=6.8 Hz, 1H), 7.44-7.56 (m, 2H), 7.12-7.16 (m, 1H), 6.68-6.73 (m, 1H), 6.46-6.52 (m, 3H), 4.10 (t, J=5.2 Hz, 2H), 3.90-4.0 (m, 2H), 3.77-3.82 (m, 3H), 1.32-1.56 (m, 4H), 0.94 (t, J=6.8 Hz, 3H).

Step 2:
Phthalimide cleavage of 2-(2-(3-(2-hydroxypentyloxy)phenoxy)ethyl)isoindoline-1,3-dione gave Example 159 as yellow oil. Yield (0.27 g, 42%): $^1$H NMR (400 MHz, DMSO-d$_6$) δ 7.12-7.17 (m, 1H), 6.45-6.51 (m, 3H), 4.78 (d, J=4.4 Hz, 1H), 3.87 (t, J=5.8 Hz, 2H), 3.79 (d, J=5.8 Hz, 2H), 3.75-3.77 (m, 1H), 2.86 (t, J=5.8 Hz, 2H), 1.42-1.50 (m, 2H), 1.30-1.40 (m, 2H), 0.89 (t, J=6.8 Hz, 3H). $^{13}$C NMR (100 MHz, DMSO-d$_6$) δ 160.0, 159.9, 129.9, 106.8, 106.7, 101.2, 72.3, 70.0, 68.0, 40.9, 35.8, 18.2, 14.1. MS: 240 [M+1]$^+$.

Example 160

Preparation of 2-(5-(cyclohexylmethoxy)-2-methylphenoxy)ethanamine

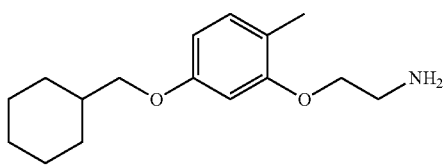 [SMILES: Cc1ccc(OCC2CCCCC2)cc1OCCN]

2-(5-(Cyclohexylmethoxy)-2-methylphenoxy)ethanamine was prepared following the method used in Examples 5 and 154.

Step 1:
Alkylation of 4-methylbenzene-1,3-diol using (bromomethyl)cyclohexane following the method used in Example 154 gave 5-(cyclohexylmethoxy)-2-methylphenol as a light yellow oil. Yield (0.15 g, 8.5%): $^1$H NMR (400 MHz, CDCl$_3$) δ 6.96 (d, J=8.4 Hz, 1H), 6.36-6.41 (m, 2H), 3.68 (d, J=6.4 Hz, 2H), 2.16 (s, 3H), 1.64-1.89 (m, 6H), 1.14-1.34 (m, 3H), 0.96-1.08 (m, 2H).

Step 2:
Alkylation of 5-(cyclohexylmethoxy)-2-methylphenol following the method used in Example 154 gave a mixture of tert-butyl 2-(5-(cyclohexylmethoxy)-2-methylphenoxy)ethylcarbamate and 5-(cyclohexylmethoxy)-2-methylphenol as a light yellow oil. The mixture was directly used in next step reaction.

Step 3:
Deprotection of tert-butyl 2-(5-(cyclohexylmethoxy)-2-methylphenoxy)ethylcarbamate following the method used in Example 5 gave Example 160 hydrochloride as a white solid. Yield (0.05 g, 81%): $^1$H NMR (400 MHz, CD$_3$OD) δ 7.00 (dd, J=8.0, 0.8 Hz, 1H), 6.49 (d, J=2.4 Hz, 1H), 6.44 (dd, J=8.4, 2.4 Hz, 1H), 4.18 (t, J=4.8 Hz, 2H), 3.72 (d, J=6.4 Hz, 2H), 3.37 (t, J=5.2 Hz, 2H), 2.16 (s, 3H), 1.68-1.88 (m, 6H), 1.20-1.36 (m, 3H), 1.01-1.11 (m, 2H).

Example 161

Preparation of 3-amino-1-(3-(2-hydroxy-2-phenylethoxy)phenyl)propan-1-ol

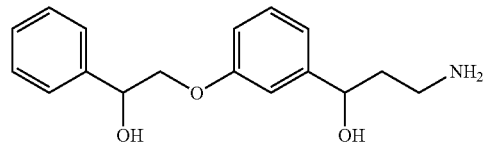 [SMILES: NCCC(O)c1cccc(OCC(O)c2ccccc2)c1]

3-Amino-1-(3-(2-hydroxy-2-phenylethoxy)phenyl)propan-1-ol was prepared following the method used for Example 158.

Step 1:
Alkylation reaction of 3-hydroxybenzaldehyde with styrene oxide gave 3-(2-hydroxy-2-phenylethoxy)benzaldehyde as a clear oil. Yield (0.9 g, 48%): $^1$H NMR (400 MHz, CDCl3) δ 9.89 (s, 1H), 7.23-7.41 (m, 8H), 7.16 (d, J=8.0 Hz, 1H), 5.35 (dd, J=8.2, 3.4 Hz, 1H), 3.93-4.0 (m, 1H), 3.82-3.89 m, 1H).

Step 2:
Addition of acetonitrile to 3-(2-hydroxy-2-phenylethoxy)benzaldehyde gave 3-hydroxy-3-(3-(2-hydroxy-2-phenylethoxy)phenyl)propanenitrile as a yellow oil. Yield (0.97 g, crude): MS: 284 [M+1]+.

Step 3:
Reduction of 3-hydroxy-3-(3-(2-hydroxy-2-phenylethoxy)phenyl)propanenitrile with BH$_3$-DMS gave Example 161 as a colorless oil. Yield (0.08 g, 10%): $^1$H NMR (400 MHz, DMSO-d6) δ 7.29-7.38 (m, 4H), 7.21-7.26 (m, 1H), 7.06-7.11 (m, 1H), 6.87 (s, 1H), 6.76-6.80 (m, 1H), 6.68 (dd, J=8.4, 2.4 Hz, 1H), 5.24 (dd, J=7.6, 4.6 Hz, 1H), 4.47-4.52 (m, 1H), 3.70 (dd, J=11.2, 8.0 Hz, 1H), 3.57 (dd, J=11.2, 8.0 Hz, 1H), 2.49-2.51 (m, 2H), 1.55-1.62 (m, 2H). $^{13}$C NMR (100 MHz, DMSO-d6) δ 158.2, 148.5, 139.7, 129.2, 128.8, 128.0, 127.0, 118.5, 113.9, 113.8, 81.0, 71.5, 66.3, 42.5, 39.2. MS: 288 [M+1]+.

Example 162

Preparation of 3-(3-((tetrahydro-2H-pyran-2-yl)methoxy)phenyl)propan-1-amine

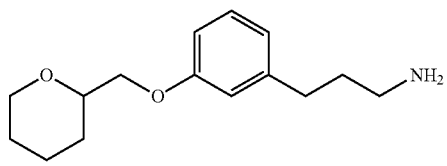 [SMILES: NCCCc1cccc(OCC2CCCCO2)c1]

3-(3-((Tetrahydro-2H-pyran-2-yl)methoxy)phenyl)propan-1-amine was prepared following the method used for Example 33.

Step 1:

Mitsunobu reaction of phenol 58 with (tetrahydro-2H-pyran-2-yl)methanol gave 2-(3-(3-((tetrahydro-2H-pyran-2-yl)methoxy)phenyl)propyl)isoindoline-1,3-dione as yellow oil. Yield (0.2 g, 18%): ¹H NMR (400 MHz, CDCl₃) δ 7.81-7.84 (m, 2H), 7.69-7.72 (m, 2H), 7.12-7.16 (m, 1H), 6.76-6.79 (m, 2H), 6.81 (s, 1H), 6.69 (d, J=8.8 Hz, 1H), 4.17 (d, J=6.2 Hz, 2H), 3.76 (t, J=7.2 Hz, 2H), 3.60-3.66 (m, 1H), 3.44-3.52 (m, 2H), 2.69 (t, J=8.0 Hz, 2H), 1.98-2.06 (m, 2H), 1.86-1.92 (m, 2H), 1.60-1.72 (m, 2H), 1.24-1.40 (m, 2H).

Step 2:

Phthalimide cleavage of 2-(3-(3-((tetrahydro-2H-pyran-2-yl)methoxy)phenyl)propyl)isoindoline-1,3-dione gave Example 162 as a pale yellow oil. Yield (0.112 g, 90%): ¹H NMR (400 MHz, DMSO-d₆) δ 7.13-7.18 (m, 1H), 6.70-6.75 (m, 3H), 3.83-3.87 (m, 2H), 3.57-3.62 (m, 1H), 3.32-3.40 (m, 4H), 2.50-2.59 (m, 4H), 1.80-1.84 (m, 1H), 1.60-1.68 (m, 3H), 1.48-1.54 (m, 2H). ¹³C NMR (100 MHz, DMSO-d₆) δ 159.0, 144.2, 129.7, 121.0, 114.9, 112.0, 75.9, 71.2, 67.7, 41.2, 34.7, 32.9, 28.2, 26.0, 23.0. MS: 250 [M+1]⁺.

Example 163

Preparation of 1-(3-(3-amino-1-hydroxypropyl)phenoxy)pentan-2-ol

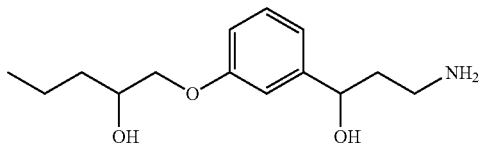 [SMILES: CCCC(O)COc1cccc(C(O)CCN)c1]

3-(1-(3-(3-Amino-1-hydroxypropyl)phenoxy)pentan-2-ol was prepared following the method used for Example 158.

Step 1:

Alkylation reaction of 3-hydroxybenzaldehyde with 1,2-epoxypentane gave 3-(2-hydroxypentyloxy)benzaldehyde as a clear oil. Yield (0.6 g, 24%): ¹H NMR (400 MHz, CDCl₃) δ 9.97 (s, 1H), 7.42-7.49 (m, 2H), 7.40 (s, 1H), 7.21 (d, J=7.2 Hz, 1H), 4.04 (d, J=7.2 Hz, 2H), 3.87-3.93 (m, 1H), 2.28 (d, J=3.6 Hz, 1H), 1.42-1.62 (m, 4H), 0.98 (t, J=6.8 Hz, 3H).

Step 2:

Addition of acetonitrile to 3-(2-hydroxypentyloxy)benzaldehyde gave 3-hydroxy-3-(3-(2-hydroxypentyloxy)phenyl)propanenitrile as a yellow oil. Yield (0.25 g, 12%): 1H NMR (400 MHz, CDCl₃) δ 7.27-7.34 (m, 1H), 6.94-7.00 (m, 2H), 6.88 (dd, J=8.0, 2.0 Hz, 1H), 5.01 (t, J=5.6 Hz, 1H), 3.96-4.06 (m, 2H), 3.83 (dd, J=8.8, 7.6 Hz, 1H), 2.76 (d, J=6.0 Hz, 2H), 1.52-1.60 (m, 2H), 1.40-1.49 (m, 2H), 0.97 (t, J=6.8 Hz, 3H).

Step 3:

Reduction of 3-hydroxy-3-(3-(2-hydroxypentyloxy)phenyl)propanenitrile with BH₃.DMS gave Example 163 as a colorless oil. Yield (0.19 g, 76%): ¹H NMR (400 MHz, DMSO-d₆) δ 7.16-7.21 (m, 1H), 6.83-6.88 (m, 2H), 6.75 (d, J=8.2 Hz, 1H), 4.59 (t, J=6.4 Hz, 1H), 3.72-3.80 (m, 3H), 2.58 (t, J=8.2 Hz, 2H), 1.61-1.67 (m, 2H), 1.32-1.50 (m, 4H), 0.88 (t, J=6.8 Hz, 3H). ¹³C NMR (100 MHz, DMSO-d₆) δ 158.5, 145.8, 130.0, 118.9, 114.0, 112.3, 72.0, 69.5, 40.0, 37.4, 34.6, 18.1, 18.0, 13.3. MS: 254 [M+1]⁺.

Example 164

Preparation of 2-(3-(cyclohexylmethoxy)-2-methylphenoxy)ethanamine

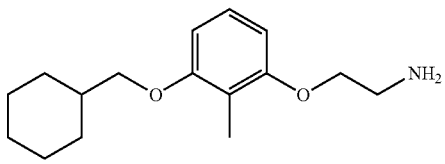 [SMILES: Cc1c(OCCN)cccc1OCC1CCCCC1]

2-(3-(Cyclohexylmethoxy)-2-methylphenoxy)ethanamine was prepared following the method used in Examples 5 and 154.

Step 1:

Alkylation of 2-methylbenzene-1,3-diol using (bromomethyl)cyclohexane following the method used in Example 154 gave 3-(cyclohexylmethoxy)-2-methylphenol. Yield (0.58 g, 37%): ¹H NMR (400 MHz, CDCl₃) δ 6.98 (t, J=8.0 Hz, 1H), 6.42 (t, J=7.6 Hz, 2H), 4.60 (bs, 1H), 3.72 (d, J=6.4 Hz, 2H), 2.12 (s, 3H), 1.68-1.89 (m, 6H), 1.16-1.35 (m, 3H), 1.01-1.11 (m, 2H).

Step 2:

Alkylation of 3-(cyclohexylmethoxy)-2-methylphenol following the method used in Example 154 gave a mixture of tert-butyl 2-(3-(cyclohexylmethoxy)-2-methylphenoxy)ethylcarbamate and 3-(cyclohexylmethoxy)-2-methylphenol as a light yellow oil. The mixture was directly used in next step reaction.

Step 3:

Deprotection of tert-butyl 2-(3-(cyclohexylmethoxy)-2-methylphenoxy)ethylcarbamate following the method used in Example 5 gave Example 164 hydrochloride as a white solid. Yield (0.20 g, 61%): ¹H NMR (400 MHz, DMSO-d₆) δ 8.09 (bs, 3H), 7.06 (t, J=8.4 Hz, 1H), 6.57 (t, J=8.8 Hz, 2H), 4.10 (t, J=4.8 Hz, 2H), 3.73 (d, J=6.0 Hz, 2H), 3.18 (t, J=5.2 Hz, 2H), 2.04 (s, 3H), 1.61-1.81 (m, 6H), 0.98-1.28 (m, 5H).

Example 165

Preparation of 4-(3-(3-amino-1-hydroxypropyl)phenoxy)butan-1-ol

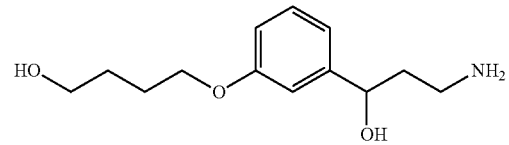 [SMILES: NCCC(O)c1cccc(OCCCCO)c1]

4-(3-(3-Amino-1-hydroxypropyl)phenoxy)butan-1-ol was prepared following the method shown in Scheme 45.

SCHEME 45

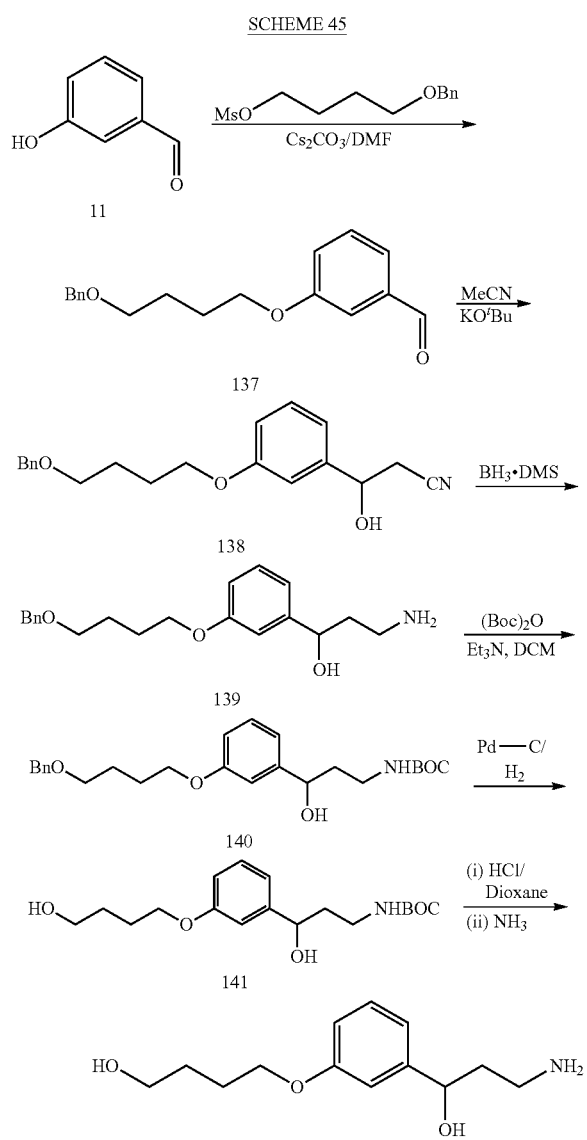

Step 1:

Alkylation reaction of 3-hydroxybenzaldehyde (11) with 4-(benzyloxy)butyl methanesulfonate following the method used in Example 149 gave 3-(4-(benzyloxy)butoxy)benzaldehyde (137) as a clear oil. Yield (1.5 g, 80%): $^1$H NMR (400 MHz, CDCl$_3$) δ 9.97 (s, 1H), 7.42-7.46 (m, 2H), 7.33-7.38 (m, 5H), 7.28-7.31 (m, 1H), 7.14-7.18 (m, 1H), 4.53 (s, 2H), 4.04 (t, J=6.4 Hz, 2H), 3.56 (t, J=6.4 Hz, 2H), 1.88-1.98 (m, 2H), 1.80-1.87 (m, 2H).

Step 2:

Addition of acetonitrile to benzaldehyde 137 following the method used in Example 149 gave nitrile 138 as a yellow oil. Yield (0.82 g, 48%): $^1$H NMR (400 MHz, CDCl$_3$) δ 7.32-7.35 (m, 4H), 7.27-7.30 (m, 2H), 6.92-6.97 (m, 2H), 6.86 (d, J=7.2 Hz, 1H), 5.0 (t, J=6.2 Hz, 1H), 4.52 (s, 2H), 3.99 (t, J=6.4 Hz, 2H), 3.55 (t, J=6.0 Hz, 2H), 2.75 (d, J=6.2 Hz, 2H), 1.87-1.94 (m, 2H), 1.78-1.84 (m, 2H).

Step 3:

Nitrile reduction of nitrile 138 using BH$_3$-DMS following the method used in Example 149 gave amine 139 as a yellow oil. Yield (0.65 g, 81%): $^1$H NMR (400 MHz, DMSO-d$_6$) δ 7.26-7.38 (m, 5H), 7.16-7.21 (m, 1H), 6.85-6.88 (m, 2H), 6.74 (d, J=8.0 Hz, 1H), 4.62 (t, J=6.2 Hz, 1H), 4.47 (s, 2H), 3.96 (t, J=6.2 Hz, 2H), 3.49 (t, J=6.2 Hz, 2H), 2.58-2.68 (m, 2H), 1.74-1.80 (m, 2H), 1.68-1.74 (m, 2H), 1.60-1.66 (m, 2H).

Step 4:

To a solution of amine 139 (0.65 g, 1.9 mmol) in DCM (20 mL) was added triethylamine (0.4 mL, 4 mmol) followed by (Boc)$_2$O (0.5 mL, 2.5 mmol). The mixture was stirred at room temperature overnight during which the conversion was found to be complete. This mixture was quenched by the addition of water and extracted with DCM. The organic layer was washed with satd. NaHCO$_3$ solution, dried over anhydrous Na$_2$SO$_4$, filtered and concentrated under reduced pressure. Purification by flash chromatography (0 to 20% EtOAc-hexanes gradient) afforded tert-butyl 3-(3-(4-(benzyloxy)butoxy)phenyl)-3-hydroxypropylcarbamate (140) as yellow oil. Yield (0.69 g, 82%): $^1$H NMR (400 MHz, CDCl$_3$) δ 7.33-7.37 (m, 4H), 7.27-7.30 (m, 1H), 7.22 (d, J=8.0 Hz, 1H), 6.89-6.92 (m, 2H), 6.78 (d, J=8.0 Hz, 1H), 4.68-4.74 (m, 1H), 4.52 (s, 2H), 3.98 (t, J=6.2 Hz, 2H), 3.55 (t, J=6.0 Hz, 2H), 3.10-3.20 (m, 2H), 1.79-1.90 (m, 6H), 1.45 (s, 9H).

Step 5:

A solution of carbamate 140 (0.69 g, 1.6 mmol) in ethanol was degassed and purged with nitrogen. To this was added Pd on C (0.1 g, 10%). The flask was evacuated and filled with hydrogen. The process was repeated thrice. The resulting reaction mixture was then stirred under hydrogen balloon at room temperature for overnight. Upon completion of the conversion, the suspension was filtered through a pad of Celite. The filter cake was washed with ethanol and the filtrate was concentrated to afford compound 141 as a yellow oil. Yield (0.16 g, 30%): $^1$H NMR (400 MHz, CDCl$_3$) δ 7.18-7.22 (m, 1H), 6.84-6.87 (m, 2H), 6.74-6.77 (m, 2H), 5.16 (d, J=4.8 Hz, 1H), 4.84-4.93 (m, 1H), 4.43 (t, J=5.2 Hz, 1H), 3.95 (t, J=6.6 Hz, 2H), 3.42-3.48 (m, 2H), 2.94-3.0 (m, 2H), 1.64-1.76 (m, 4H), 1.52-1.59 (m, 2H), 1.37 (s, 9H).

Step 6:

To a solution of compound 141 (0.15 g, 0.4 mmol) in DCM (5 mL) was added HCl in dioxane (1 mL, 4 M). The resulting mixture was stirred at room temperature overnight. The reaction mixture was brought up to pH 10 by conc. ammonia and extracted with DCM. The organic layer was washed with water, dried over anhydrous Na$_2$SO$_4$, filtered and concentrated under reduced pressure. Purification by flash chromatography (0 to 15% (9:1 MeOH—NH$_3$)-DCM gradient) gave Example 165 as a colorless oil. Yield (0.1 g, 95%): $^1$H NMR (400 MHz, DMSO-d$_6$) δ 7.21-7.26 (m, 1H), 6.85-6.88 (m, 2H), 6.79 (dd, J=8.0, 2.0 Hz, 1H), 4.60-4.65 (m, 1H), 3.93 (t, J=6.4 Hz, 2H), 3.43 (t, J=6.4 Hz, 2H), 2.76-2.88 (m, 2H), 1.78-1.86 (m, 2H), 1.68-1.73 (m, 2H), 1.50-1.58 (m, 2H). $^{13}$C NMR (100 MHz, DMSO-d$_6$) δ 159.1, 147.4, 129.6, 118.1, 113.2, 112.2, 70.0, 67.7, 60.8, 37.0, 36.7, 29.5, 26.0. MS: 240 [M+1]$^+$.

Example 166

Preparation of 5-(3-(3-amino-1-hydroxypropyl)phenoxy)pentan-1-ol

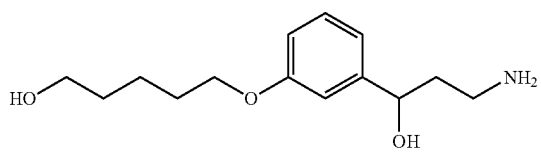 [SMILES: NCCC(O)c1cccc(OCCCCCO)c1]

5-(3-(3-Amino-1-hydroxypropyl)phenoxy)pentan-1-ol was prepared following the method used for Example 165.

Step 1:

Alkylation reaction of 3-hydroxybenzaldehyde with 5-(benzyloxy)pentyl methanesulfonate gave 3-(5-(benzyloxy)pentyloxy)benzaldehyde as a clear oil. Yield (1.3 g, 66%): $^1$H NMR (400 MHz, CDCl$_3$) δ 9.97 (s, 1H), 7.42-7.46 (m, 2H), 7.25-7.39 (m, 6H), 7.15-7.18 (m, 1H), 4.51 (s, 2H), 4.02 (t, J=6.4 Hz, 2H), 3.51 (t, J=6.4 Hz, 2H), 1.82-1.89 (m, 2H), 1.68-1.76 (m, 2H), 1.54-1.62 (m, 2H).

Step 2:

Addition of acetonitrile to 3-(5-(benzyloxy)pentyloxy)benzaldehyde gave 3-(3-(5-(benzyloxy)pentyloxy)phenyl)-3-hydroxypropanenitrile as a yellow oil. Yield (0.74 g, 51%): $^1$H NMR (400 MHz, CDCl$_3$) δ 7.27-7.37 (m, 6H), 6.93-6.96 (m, 2H), 6.86 (d, J=8.0 Hz, 1H), 5.0-5.05 (m, 1H), 4.51 (s, 2H), 3.97 (t, J=6.4 Hz, 2H), 3.51 (t, J=6.4 Hz, 2H), 2.76 (d, J=6.0 Hz, 2H), 2.30 (s, 1H), 1.78-1.85 (m, 2H), 1.58-1.64 (m, 2H), 1.52-1.58 (m, 2H).

Step 3:

Reduction of 3-(3-(5-(benzyloxy)pentyloxy)phenyl)-3-hydroxypropanenitrile with BH$_3$.DMS gave 3-amino-1-(3-(5-(benzyloxy)pentyloxy)phenyl)propan-1-ol as a colorless oil. Yield (0.51 g, 69%): $^1$H NMR (400 MHz, DMSO-d$_6$) δ 7.25-7.38 (m, 5H), 7.16-7.22 (m, 1H), 6.84-6.89 (m, 2H), 6.74 (d, J=7.2 Hz, 1H), 4.62 (t, J=6.2 Hz, 1H), 4.45 (s, 2H), 3.94 (t, J=6.4 Hz, 2H), 3.45 (t, J=6.4 Hz, 2H), 2.60-2.67 (m, 2H), 1.70-1.76 (m, 2H), 1.59-1.67 (m, 4H), 1.46-1.52 (m, 2H).

Step 4:

BOC protection of 3-amino-1-(3-(5-(benzyloxy)pentyloxy)phenyl)propan-1-ol gave tert-butyl 3-(3-(5-(benzyloxy)pentyloxy)phenyl)-3-hydroxypropylcarbamate as yellow oil. Yield (0.23 g, 54%): $^1$H NMR (400 MHz, CDCl$_3$) δ 7.20-7.36 (m, 6H), 6.90-6.94 (m, 2H), 6.78 (d, J=7.2 Hz, 1H), 4.70-4.72 (m, 1H), 4.51 (s, 2H), 3.08-3.20 (m, 2H), 1.77-1.85 (m, 4H), 1.66-1.74 (m, 2H), 1.52-1.60 (m, 2H), 1.53 (s, 9H).

Step 5:

Benzyl deprotection of tert-butyl 3-(3-(5-(benzyloxy)pentyloxy) phenyl)-3-hydroxypropylcarbamate gave tert-butyl 3-hydroxy-3-(3-(5-hydroxypentyloxy) phenyl)propylcarbamate as a yellow oil. Yield (0.24 g, 80%): $^1$H NMR (400 MHz, CDCl$_3$) δ 7.17-7.22 (m, 1H), 6.84-6.88 (m, 2H), 6.73-6.78 (m, 2H), 5.17 (d, J=4.4 Hz, 1H), 4.48-4.53 (m, 1H), 4.38 (t, J=4.4 Hz, 1H), 3.93 (t, J=6.4 Hz, 2H), 3.38-3.43 (m, 2H), 2.93-2.97 (m, 2H), 1.63-1.73 (m, 4H), 1.40-1.50 (m, 4H), 1.37 (s, 9H).

Step 6:

BOC deprotection of tert-butyl 3-hydroxy-3-(3-(5-hydroxypentyloxy)phenyl)propylcarbamate gave Example 166 as a colorless oil. Yield (0.145 g, 90%): $^1$H NMR (400 MHz, DMSO-d$_6$) δ 7.21-7.26 (m, 1H), 6.86-6.88 (m, 2H), 6.79 (dd, J=8.0, 2.0 Hz, 1H), 4.61-4.65 (m, 1H), 3.92 (t, J=6.0 Hz, 2H), 3.39 (t, J=6.0 Hz, 2H), 2.77-2.89 (m, 2H), 1.78-1.88 (m, 2H), 1.65-1.72 (m, 2H), 1.39-1.49 (m, 4H). $^{13}$C NMR (100 MHz, DMSO-d$_6$) δ 159.1, 147.4, 129.6, 118.1, 113.2, 112.2, 70.0, 67.8, 61.1, 37.0, 36.8, 32.7, 29.1, 22.6. MS: 254 [M+1]$^+$.

Example 167

Preparation of 1-(3-(3-aminopropyl)phenoxy)pentan-2-ol

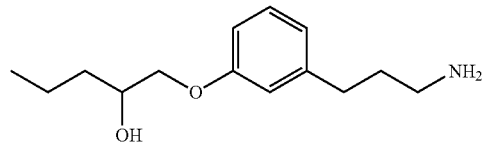 [SMILES: CCCC(O)COc1cccc(CCCN)c1]

1-(3-(3-Aminopropyl)phenoxy)pentan-2-ol was prepared following the method used in Example 32.

Step 1:

Alkylation reaction of phenol 58 with 1,2-epoxypentane gave 2-(3-(3-(2-hydroxypentyloxy)phenyl)propyl)isoindoline-1,3-dione as yellow oil. Yield (0.93 g, 73%): $^1$H NMR (400 MHz, CDCl$_3$) δ 7.74 (d, J=6.0 Hz, 1H), 7.53-7.60 (m, 1H), 7.47-7.52 (m, 1H), 7.40 (d, J=7.6 Hz, 1H), 7.14-7.19 (m, 1H), 6.78-6.83 (m, 2H), 6.73 (d, J=8.2 Hz, 1H), 3.81 (d, J=4.8 Hz, 2H), 3.73-3.79 (m, 1H), 3.18-3.24 (m, 2H), 2.60 (t, J=7.6 Hz, 2H), 1.73-1.81 (m, 2H), 1.30-1.52 (m, 4H), 0.89 (t, J=6.8 Hz, 3H).

Step 2:

Phthalimide cleavage of 2-(3-(3-(2-hydroxypentyloxy) phenyl)propyl)isoindoline-1,3-dione gave Example 167 as yellow oil. Yield (0.13 g, 22%): $^1$H NMR (400 MHz, DMSO-d$_6$) δ 7.13-7.18 (m, 1H), 6.70-6.77 (m, 3H), 3.79 (d, J=4.8 Hz, 2H), 3.73-3.78 (m, 1H), 2.50-2.57 (m, 4H), 1.59-1.65 (m, 2H), 1.42-1.51 (m, 2H), 1.32-1.40 (m, 2H), 0.89 (t, J=6.6 Hz, 3H). $^{13}$C NMR (100 MHz, DMSO-d$_6$) δ 159.2, 144.3, 129.6, 121.0, 115.0, 112.0, 72.6, 68.5, 41.4, 36.3, 35.1, 33.0, 18.7, 14.5. MS: 238 [M+1]$^+$.

Example 168

Preparation of 3-(3-(cyclohexylmethoxy)-5-fluorophenyl)propan-1-amine

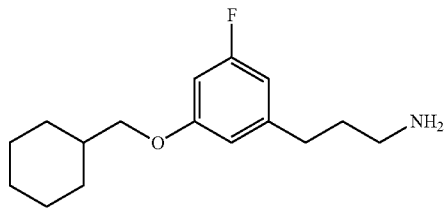 [SMILES: NCCCc1cc(F)cc(OCC2CCCCC2)c1]

3-(3-(Cyclohexylmethoxy)-5-fluorophenyl)propan-1-amine was prepared following the method described in Example 142.

Step 1:

Alkylation of 3-bromo-5-fluorophenol using (bromomethyl)cyclohexane following the method used in Example 1 gave 1-bromo-3-(cyclohexylmethoxy)-5-fluorobenzene. Yield (1.1 g, 73%): $^1$H NMR (400 MHz, CDCl$_3$) δ 6.79-6.83 (m, 2H), 6.52 (dt, J=10.4, 2.0 Hz, 1H), 3.70 (d, J=6.0 Hz, 2H), 1.65-1.86 (m, 6H), 1.16-1.34 (m, 3H), 0.97-1.08 (m, 2H).

Step 2:

Coupling of 1-bromo-3-(cyclohexylmethoxy)-5-fluorobenzene with N-allyl-2,2,2-trifluoroacetamide following the method used in Example 10 except DMF was used as solvent gave (E)-N-(3-(3-(cyclohexylmethoxy)-5-fluorophenyl)allyl)-2,2,2-trifluoroacetamide as a white solid. Yield (0.44 g, 64%): $^1$H NMR (400 MHz, DMSO-d$_6$)$^1$H NMR (400 MHz, CDCl$_3$) δ 9.68 (t, J=4.0 Hz, 1H), 6.79-6.86 (m, 2H), 6.65 (dt, J=10.8, 2.0 Hz, 1H), 6.45 (d, J=15.6 Hz, 1H), 6.31 (dt, J=16.0, 5.6 Hz, 1H), 3.95 (t, J=4.8 Hz, 2H), 3.77 (d, J=5.6 Hz, 2H), 1.58-1.80 (m, 6H), 1.10-1.28 (m, 3H), 0.90-1.06 (m, 2H).

Step 3:

Hydrogenation of (E)-N-(3-(3-(cyclohexylmethoxy)-5-fluorophenyl)allyl)-2,2,2-trifluoroacetamide following the method used in Example 10 gave N-(3-(3-(cyclohexylmethoxy)-5-fluorophenyl)propyl)-2,2,2-trifluoroacetamide as a white solid. Yield (0.22 g, 97%): $^1$H NMR (400 MHz, CD$_3$OD) δ 6.55-6.57 (m, 1H), 6.43-6.52 (m, 2H), 3.73 (d, J=6.4 Hz, 2H), 3.28 (t, J=7.2 Hz, 2H), 2.59 (t, J=8.0 Hz, 2H), 1.63-1.84 (m, 8H), 1.20-1.38 (m, 3H), 1.02-1.13 (m, 2H).

Step 4:

Deprotection of N-(3-(3-(cyclohexylmethoxy)-5-fluorophenyl)propyl)-2,2,2-trifluoroacetamide following the method used in Example 10 gave Example 168 as a light yellow oil. Yield (0.14 g, 86%): $^1$H NMR (400 MHz, CD$_3$OD) δ 6.55-6.57 (m, 1H), 6.42-6.51 (m, 2H), 3.73 (d, J=6.4 Hz, 2H), 2.63 (t, J=7.2 Hz, 2H), 2.59 (t, J=8.0 Hz, 2H), 1.68-1.88 (m, 8H), 1.16-1.38 (m, 3H), 1.02-1.13 (m, 2H).

Example 169

Preparation of 3-amino-1-(3-((4,4-difluorocyclohexyl)methoxy)phenyl)propan-1-ol

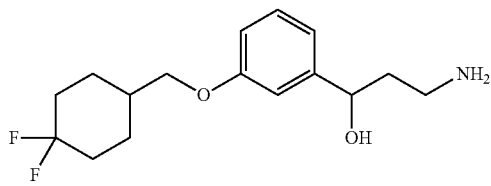 [SMILES: NCCC(O)c1cccc(OCC2CCC(F)(F)CC2)c1]

3-Amino-1-(3-((4,4-difluorocyclohexyl)methoxy)phenyl)propan-1-ol was prepared following the method shown in Scheme 46.

SCHEME 46

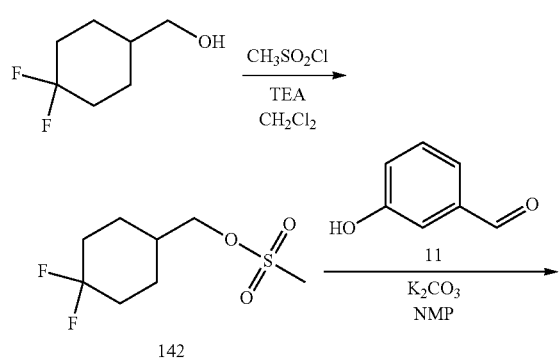

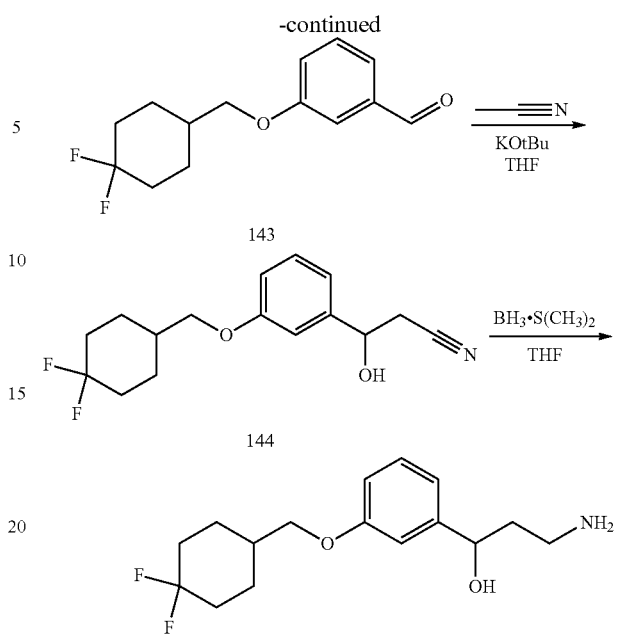

Step 1:

(4,4-Difluorocyclohexyl)methanol (0.7 g, 4.11 mmole) was stirred in CH$_2$Cl$_2$ (5 ml) and cooled in an ice bath. TEA (0.499 g, 4.93 mmoles) was added followed by methanesulfonyl chloride (0.518 g, 4.52 mmoles). Stirring was continued overnight while allowing to warm to room temp. 1.0 N HCl (30 ml) and CH$_2$Cl$_2$ (30 ml) was added and stirred for 5 min. The organic layer was dried over Na$_2$SO$_4$ and evaporated giving (4,4-difluorocyclohexyl)methyl methanesulfonate (142) as an oil. Yield (0.92 g, 98%): $^1$H NMR (400 MHz, DMSO-d$_6$) δ 4.06 (d, J=6.4 Hz, 2H), 3.14 (s, 3H), 2.04-1.95 (m, 2H), 1.88-1.70 (m, 5H), 1.29-1.19 (m, 2H).

Step 2:

Mesylate 142 (0.9 g, 3.94 mmole), 3-hydroxybenzaldehyde (0.577 g, 4.73 mmole), K$_2$CO$_3$ (0.817 g, 5.91 mmole) and NMP (5 ml) were heated at 70° C. overnight. H$_2$O (30 ml) and hexanes (50 ml) was added and stirred for 1 hr. The organic layer was dried over Na$_2$SO$_4$ and evaporated. Purification by flash chromatography (20% ether/hexanes gradient) gave 3-((4,4-difluorocyclohexyl)methoxy)benzaldehyde (143) as an oil. Yield (0.559 g, 56%): $^1$H NMR (400 MHz, DMSO-d$_6$) δ 9.95 (s, 1H), 7.51-7.46 (m, 2H), 7.41-7.40 (m, 1H), 7.25 (dt, J=6.8, 2.8 Hz, 1H), 3.91 (d, J=6.0 Hz, 2H), 2.06-1.98 (m, 5H), 1.89-1.73 (m, 5H), 1.37-1.27 (m, 2H).

Step 3:

Potassium t-butoxide (2.59 mmole, 2.6 ml of a 1.0M solution in THF) was cooled to −50° C. Acetonitrile (0.106 g, 2.59 mmole) was slowly added and stirred for 15 min. Benzaldehyde 143 (0.55 g, 2.16 mmole) in THF (1.0 ml) was added and the reaction was allowed to warm to 0° C. over 30 min. Sat. NH$_4$Cl (20 ml) and EtOAc (30 ml) was added and stirred for 10 min. The organic layer was dried over Na$_2$SO$_4$ and evaporated giving 3-(3-((4,4-difluorocyclohexyl)methoxy)phenyl)-3-hydroxypropanenitrile (144) as an oil. Yield (0.622 g, 97%): $^1$H NMR (400 MHz, DMSO-d$_6$) δ 7.22 (t, J=7.8 Hz, 1H), 6.96-6.93 (m, 2H), 6.82 (ddd, J=8.2, 2.6, 0.8 Hz, 1H), 5.89 (d, J=4.8 Hz, 2H), 4.85-4.81 (m, 1H), 2.86 (ABd, J=16.4, 5.0 Hz, 1H), 2.77 (ABd, J=16.8, 6.8 Hz, 1H), 2.04-1.96 (m, 2H), 1.88-1.73 (m, 5H), 1.35-1.25 (m, 2H).

Step 4:

To nitrile 144 (0.61 g, 2.07 mmole) in THF (5 ml) was slowly added BH$_3$—S(CH$_3$)$_2$ (4.14 mmole, 0.41 ml of a 10.0M solution). This mixture was refluxed for 2.5 hr. and then cooled to room temp. MeOHHCl (25 ml of a 1.25M solution) was slowly added and stirred for 2.0 hr. Evaporation to dryness was followed by basification with 1.0N NaOH (30 ml) and extraction with EtOAc (50 ml). The organic layer was dried over Na$_2$SO$_4$ and evaporated. Purification by flash chromatography (10% MeOH/CH$_2$Cl$_2$ followed by 10% 7N MeOH NH$_3$/CH$_2$Cl$_2$ gradient) gave Example 169 as a white solid. Yield (0.51 g, 82%): $^1$H NMR (400 MHz, DMSO-d$_6$) δ 7.16 (t, J=7.8 Hz, 1H), 6.86-6.83 (m, 2H), 6.73 (ddd, J=8.2, 2.6, 0.8 Hz, 1H), 4.60 (t, J=6.4 Hz, 1H), 3.80 (d, J=6.4 Hz, 1H), 2.66-2.55 (m, 2H), 2.05-1.97 (m, 2H), 1.88-1.72 (m, 5H), 1.60 (q, J=6.6 Hz, 2H), 1.34-1.25 (m, 2H).

Example 170

Preparation of methyl 3-(3-aminopropyl)-5-(cyclohexylmethoxy)benzoate

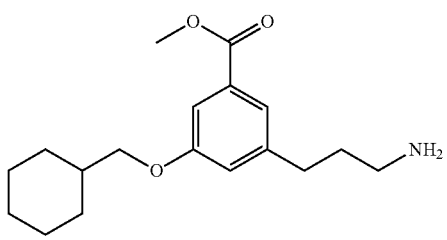 [SMILES: COC(=O)c1cc(CCCN)cc(OCC2CCCCC2)c1]

Methyl 3-(3-aminopropyl)-5-(cyclohexylmethoxy)benzoate was prepared following the method used in Example 142.

Step 1:

Alkylation of ethyl 3-bromo-5-hydroxybenzoate using (bromomethyl)cyclohexane gave ethyl 3-bromo-5-(cyclohexylmethoxy)benzoate. Yield (1.36 g, 100%): $^1$H NMR (400 MHz, CDCl$_3$) δ 7.72 (t, J=1.6 Hz, 1H), 7.46 (dd, J=2.4, 1.2 Hz, 1H), 7.20 (dd, J=2.4, 1.6 Hz, 1H), 4.35 (q, J=7.2 Hz, 2H), 3.76 (d, J=6.4 Hz, 2H), 1.67-1.88 (m, 6H), 1.38 (t, J=7.2 Hz, 3H), 1.16-1.32 (m, 3H), 1.01-1.11 (m, 2H).

Step 2:

Coupling of ethyl 3-bromo-5-(cyclohexylmethoxy)benzoate with N-allyl-2,2,2-trifluoroacetamide gave (E)-ethyl 3-(cyclohexylmethoxy)-5-(3-(2,2,2-trifluoroacetamido)prop-1-enyl)benzoate as a light yellow solid. Yield (0.94 g, 54%): $^1$H NMR (400 MHz, CDCl$_3$) δ 7.61 (t, J=1.2 Hz, 1H), 7.44 (dd, J=2.4, 1.2 Hz, 1H), 7.05 (t, J=2.4 Hz, 1H), 6.57 (d, J=15.6 Hz, 2H), 6.42 (bs, 1H), 6.22 (dt, J=16.0, 6.4 Hz, 1H), 4.36 (q, J=7.2 Hz, 2H), 4.15 (t, J=6.0 Hz, 2H), 3.78 (d, J=6.4 Hz, 2H), 1.68-1.88 (m, 6H), 1.39 (t, J=7.2 Hz, 3H), 1.18-1.34 (m, 3H), 1.01-1.11 (m, 2H).

Step 3:

Hydrogenation of (E)-ethyl 3-(cyclohexylmethoxy)-5-(3-(2,2,2-trifluoroacetamido)prop-1-enyl)benzoate gave ethyl 3-(cyclohexylmethoxy)-5-(3-(2,2,2-trifluoroacetamido)propyl)benzoate as a white solid. Yield (0.50 g, 70%): $^1$H NMR (400 MHz, CD$_3$OD) δ 7.43 (t, J=1.2 Hz, 1H), 7.32 (dd, J=2.4, 1.2 Hz, 1H), 6.99 (t, J=2.4 Hz, 1H), 4.33 (q, J=7.2 Hz, 2H), 3.78 (d, J=6.0 Hz, 2H), 3.20-3.27 (m, 2H), 2.66 (t, J=7.6 Hz, 2H), 1.67-1.92 (m, 8H), 1.04-1.39 (m, 8H).

Step 4:

Deprotection ethyl 3-(cyclohexylmethoxy)-5-(3-(2,2,2-trifluoroacetamido)propyl)benzoate and subsequently treating the crude product with hydrochloride-methanol solution gave Example 170 hydrochloride as a white solid. Yield (0.30 g, 78%): $^1$H NMR (400 MHz, CD$_3$OD) δ 7.46 (t, J=1.2 Hz, 1H), 7.36 (dd, J=2.4, 1.6 Hz, 1H), 7.03 (t, J=2.4 Hz, 1H), 3.87 (s, 3H), 3.79 (d, J=6.4 Hz, 2H), 2.93 (t, J=7.6 Hz, 2H), 2.73 (t, J=8.0 Hz, 2H), 1.68-2.02 (m, 8H), 1.20-1.39 (m, 3H), 1.04-1.16 (m, 2H).

Example 171

Preparation of (1,4-cis)-4-((3-((R)-3-amino-1-hydroxypropyl)phenoxy)methyl)cyclohexanol

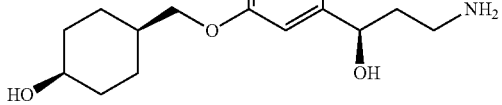

(1,4-cis)-4-((3-((R)-3-Amino-1-hydroxypropyl)phenoxy)methyl)cyclohexanol was prepared following the method shown in Scheme 47.

SCHEME 47

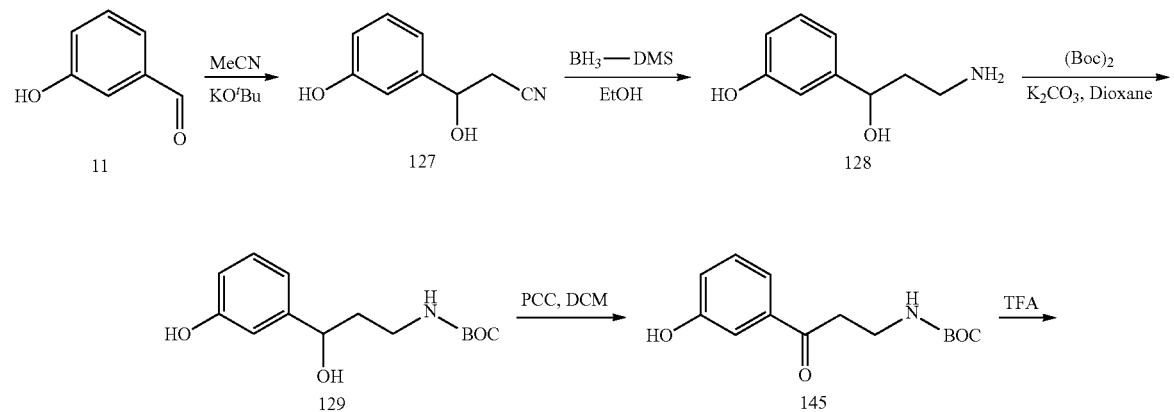

-continued

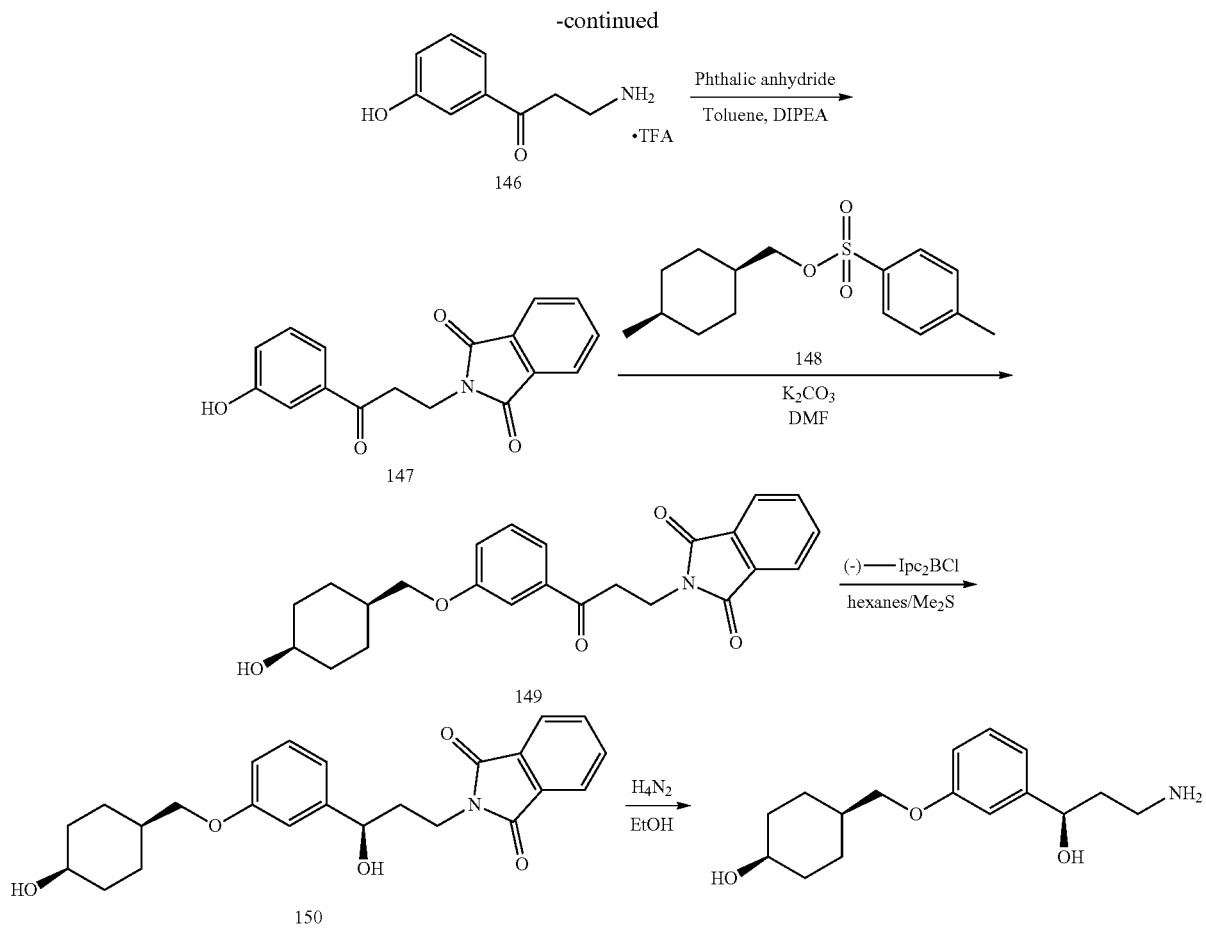

Step 1:

To a stirred suspension of KO'Bu (68.5 g, 614 mmol) in THF (350 mL), cooled to −50° C., was added acetonitrile (30.3 mL, 540 mmol), dropwise over a period of 5 min. The resulting mixture was stirred at −50° C. for 30 min following which a solution of 3-hydroxybenzaldehyde (30.0 g, 244 mmol) in THF (150 mL) was added slowly, over a period of 10 min. This was then allowed to warm to 0° C. and stirred for another 3 h during which the reaction was found to be complete. The reaction was quenched by slow addition of ice-water followed by extraction with EtOAc. The combined organics were washed with water, brine and dried over $Na_2SO_4$. The solution was concentrated under reduced pressure to give 3-hydroxy-3-(3-hydroxyphenyl) propanenitrile (127) as yellow oil which was purified by flash column chromatography (0 to 20% EtOAc-hexanes gradient). Yield (25.0 g, 62%): $^1$H NMR (400 MHz, $CDCl_3$) δ 7.27 (s, 1H), 6.95 (d, J=7.6 Hz, 1H), 6.90-6.93 (m, 1H), 6.82 (dd, J=8.0, 2.4 Hz, 1H), 4.91-5.03 (m, 1H), 2.76 (d, J=6.4 Hz, 2H).

Step 2:

To a stirred solution of the nitrile 127 (25.0 g, 153 mmol) in THF (400 mL), cooled to 0° C., was added $BH_3$.DMS (49.5 mL, 460 mmol), following which the cooling bath was removed. The resulting mixture was gradually warmed to reflux and maintained overnight. This was then cooled in an ice-bath and quenched by the slow addition of large excess of MeOH. After stirring at RT for about 2 h, the excess solvent was removed under reduced pressure. The residue was again treated with MeOH and evaporated. The process was repeated thrice. The brown oil was then applied onto a flash silica gel column and eluted (0 to 15% (9:1 MeOH—$NH_3$)-DCM gradient) to give 3-(3-amino-1-hydroxypropyl)phenol (128) as a brown solid. Yield (25.0 g, 97%): $^1$H NMR (400 MHz, DMSO-$d_6$) δ 7.04-7.09 (m, 1H), 6.74 (s, 1H), 6.70 (d, J=7.6 Hz, 1H), 6.58 (dd, J=8.0, 2.0 Hz, 1H), 4.55 (dd, J=7.2, 5.6 Hz, 1H), 2.57-2.66 (m, 2H), 1.56-1.62 (m, 2H).

Step 3:

To a solution of amine 128 (25.0 g, 0.149 mol) in 1,4-dioxane (100 mL) was added $K_2CO_3$ (20.6 g, 150 mmol) followed by the slow addition of $(Boc)_2O$ (36 mL, 150 mmol). The mixture was stirred at room temperature for 2 h during which the reaction was found to be complete. This mixture was then quenched by the addition of water and extracted with ethyl acetate. The organic layer was washed with water and brine. This was dried over anhydrous $Na_2SO_4$, filtered and concentrated under reduced pressure. Purification by flash chromatography (0 to 20% EtOAc-hexanes gradient) afforded tert-butyl 3-hydroxy-3-(3-hydroxyphenyl)propylcarbamate (129) as off white solid. Yield (35.0 g, crude): $^1$H NMR (400 MHz, $CDCl_3$) δ 7.05-7.10 (m, 1H), 6.70-6.76 (m, 2H), 6.59 (dd, J=8.0, 1.6 Hz, 1H), 5.11 (d, J=4.4 Hz, 1H), 4.42-4.47 (m, 1H), 3.57 (s, 1H), 2.92-2.98 (m, 2H), 1.61-1.67 (m, 2H), 1.37 (s, 9H).

Step 4:

A stirred suspension of PCC (42.3 g, 196 mmol) and Celite (43 g) in DCM (300 mL) was cooled to 0° C. To this was added carbamate 129 (35.0 g, 131 mmol), slowly over a period of 15 min. The reaction mixture was allowed to stir at room temperature for 2 h during which the transformation was found to be complete. The reaction mass was then filtered through a pad of Celite and the filter bed was washed with DCM. Concentration of the filtrate gave a black tarry mass which was purified by flash chromatography (30-50% Ethyl acetate-Hexanes gradient) to give tert-butyl 3-(3-hydroxyphenyl)-3-oxopropylcarbamate (145) as pale yellow solid. Yield (20.3 g, 58%): $^1$H NMR (400 MHz, CDCl$_3$) δ 9.78 (s, 1H), 7.27-7.40 (m, 2H), 7.01 (dd, J=8.0, 1.6 Hz, 1H), 6.80-6.83 (m, 1H), 3.22-3.27 (m, 2H), 3.08 (t, J=6.8 Hz, 2H), 1.36 (s, 9H).

Step 5:

To a stirred solution of TFA (80 mL) and DCM (200 mL) was added ketone 145 (20 g, 75 mmol) slowly at 0° C. The resulting reaction mixture was allowed to stir at RT for 2 h. After the reaction was complete, the solvent was removed under reduced pressure and resulting residue was triturated with toluene. The complete removal of the solvent gave the TFA salt of amine 146. The crude mass was directly utilized for the next transformation. Yield (21.0 g, crude). MS: 166 [M+1]$^+$.

Step 6:

A solution of 146 (21.0 g, 72 mmol) in a mixture of acetonitrile (100 mL) and toluene (300 mL) was cooled to 0° C. To this was added DIPEA (23 mL, 179 mmol). The resulting reaction mixture was stirred at RT for 10 min. This was followed by the addition of phthalic anhydride (10.6 g, 72 mmol). The reaction mixture was then refluxed for 2 h using a Dean-Stark assembly. After completion of the reaction the solvent was distilled off under reduced pressure and the reaction mass extracted with DCM. The organic layer was washed with water and satd. NH$_4$Cl, followed by satd. NaHCO$_3$. This was dried over anhydrous Na$_2$SO$_4$, filtered and concentrated under reduced pressure to give phenol 147 as off-white solid. Yield (14 g, 62%): $^1$H NMR (400 MHz, CDCl$_3$) δ 9.79 (s, 1H), 7.82-7.88 (m, 4H), 7.38 (d, J=8.0 Hz, 1H), 7.31 (d, J=7.6 Hz, 1H), 7.28 (s, 1H), 7.01 (dd, J=8.0, 2.0 Hz, 1H), 3.91 (t, J=7.2 Hz, 2H), 3.37 (t, J=7.2 Hz, 2H). MS: 296 [M+1]$^+$.

Step 7:

Alkylation of phenol 147 with cis-tosylate 148 according to the method used in Example 72, except that K$_2$CO$_3$ was used instead of Cs$_2$CO$_3$, gave ketone 149 as a white solid. Yield (0.863 g, 32%). $^1$H NMR (400 MHz, DMSO) δ 7.78-7.86 (m, 4H), 7.46-7.50 (m, 1H), 7.35-7.41 (m, 2H), 7.15-7.19 (m, 1H), 4.26 (d, J=2.8 Hz, 1H), 3.89 (t, J=7.2 Hz, 2H), 3.81 (d, J=6.4 Hz, 2H), 3.75 (brs, 1H), 3.39 (t, J=7.2 Hz, 2H), 1.68-1.82 (m, 1H), 1.54-1.62 (m, 2H), 1.36-1.51 (m, 6H).

Step 8:

Reduction of the ketone 149 according to the method used in Example 28 gave the R-alcohol 150 as a colorless, glassy oil. Yield (0.566 g, 66%). $^1$H NMR (400 MHz, DMSO) δ 7.76-7.81 (m, 4H), 7.13 (t, J=8.0 Hz, 1H), 6.82-6.88 (m, 2H), 6.66-6.70 (m, 1H), 5.25 (d, J=4.4 Hz, 1H), 4.52-4.58 (m, 1H), 4.26 (d, J=3.2 Hz, 1H), 3.75 (brs, 2H), 3.73 (d, J=6.8 Hz, 1H), 3.66-3.70 (m, 2H), 1.86-1.94 (m, 2H), 1.66-1.78 (m, 1H), 1.54-1.62 (m, 2H), 1.36-1.52 (m, 6H).

Step 9:

Deprotection of 150 according to the method used in Example 7 gave Example 171 as a colorless oil. Yield (0.109 g, 80%). $^1$H NMR (400 MHz, DMSO) δ 7.157 (t, J=8.0 Hz, 1H), 6.81-6.87 (m, 2H), 6.70-6.75 (m, 1H), 4.59 (t, J=6.4 Hz, 1H), 3.72-3.78 (m, 3H), 3.26 (brs, 4H), 2.55-2.68 (m, 2H), 1.66-1.78 (m, 1H), 1.54-1.64 (m, 4H), 1.37-1.52 (m, 6H). ESI MS m/z 280.19 [m+H]$^+$.

Example 172

Preparation of (1,4-trans)-4-((3-((R)-3-amino-1-hydroxypropyl)phenoxy)methyl)cyclohexanol

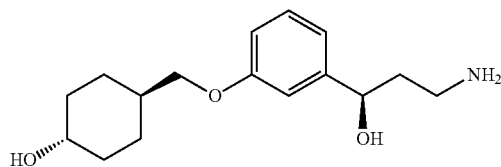 [SMILES: NCC[C@@H](O)c1cccc(OC[C@H]2CC[C@H](O)CC2)c1]

(1,4-trans)-4-((3-((R)-3-Amino-1-hydroxypropyl)phenoxy)methyl)cyclohexanol was prepared following the method used for Example 171.

Step 1:

Alkylation of phenol 147 with trans-tosylate gave 2-(3-(3-(((trans)-4-hydroxycyclohexyl)methoxy)phenyl)-3-oxopropyl)isoindoline-1,3-dione as a white solid. Yield (0.863 g, 32%). $^1$H NMR (400 MHz, DMSO) δ 7.78-7.86 (m, 4H), 7.46-7.50 (m, 1H), 7.35-7.41 (m, 2H), 7.13-7.17 (m, 1H), 4.48 (d, J=4.0 Hz, 1H), 3.89 (t, J=7.2 Hz, 2H), 3.77 (d, J=6.4 Hz, 2H), 3.38 (t, J=7.2 Hz, 2H), 3.26-3.35 (m, 1H), 1.72-1.86 (m, 2H), 1.52-1.68 (m, 1H), 0.88-1.18 (m, 6H).

Step 2:

Reduction of the 2-(3-(3-(((trans)-4-hydroxycyclohexyl)methoxy)phenyl)-3-oxopropyl)isoindoline-1,3-dione gave 2-((R)-3-hydroxy-3-(3-(((trans)-4-hydroxycyclohexyl)methoxy)phenyl)propyl)isoindoline-1,3-dione as a colorless, glassy oil. Yield (0.566 g, 66%). $^1$H NMR (400 MHz, DMSO) δ 7.76-7.81 (m, 4H), 7.13 (t, J=8.0 Hz, 1H), 6.82-6.88 (m, 2H), 6.65-6.69 (m, 1H), 5.25 (d, J=4.4 Hz, 1H), 4.52-4.58 (m, 1H), 4.48 (d, J=4.4 Hz, 1H), 3.69 (d, J=6.4 Hz, 2H), 3.55-3.68 (m, 2H), 3.26-3.40 (m, 1H), 1.86-1.93 (m, 2H), 1.73-1.86 (m, 4H), 1.60 (brs, 1H), 0.96-1.21 (m, 5H).

Step 3:

Deprotection of 2-((R)-3-hydroxy-3-(3-(((trans)-4-hydroxycyclohexyl)methoxy)phenyl)propyl)isoindoline-1,3-dione gave Example 172 as a colorless oil. Yield (0.109 g, 80%). $^1$H NMR (400 MHz, DMSO) δ 7.15 (t, J=8.0 Hz, 1H), 6.81-6.87 (m, 2H), 6.69-6.73 (m, 1H), 4.59 (t, J=6.4 Hz, 1H), 3.71 (d, J=6.4 Hz, 2H), 3.20 (brs, 4H), 3.28-3.37 (m, 1H), 2.55-2.68 (m, 2H), 1.74-1.86 (m, 4H), 1.54-1.66 (m, 3H), 0.98-1.19 (m, 4H). ESI MS m/z 280.19 [m+H]$^+$.

Example 173

Preparation of (1,2-trans)-2-((3-((R)-3-amino-1-hydroxypropyl)phenoxy)methyl)cyclohexyl acetate

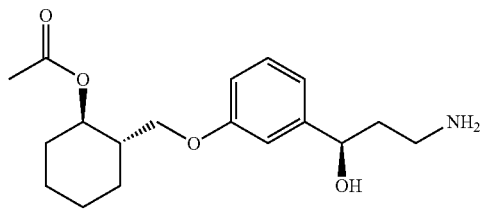 [SMILES: CC(=O)O[C@@H]1CCCC[C@H]1COc1cccc([C@H](O)CCN)c1]

(1,2-trans)-2-((3-((R)-3-Amino-1-hydroxypropyl)phenoxy)methyl)cyclohexyl acetate was prepared following the method shown in Scheme 48.

SCHEME 48

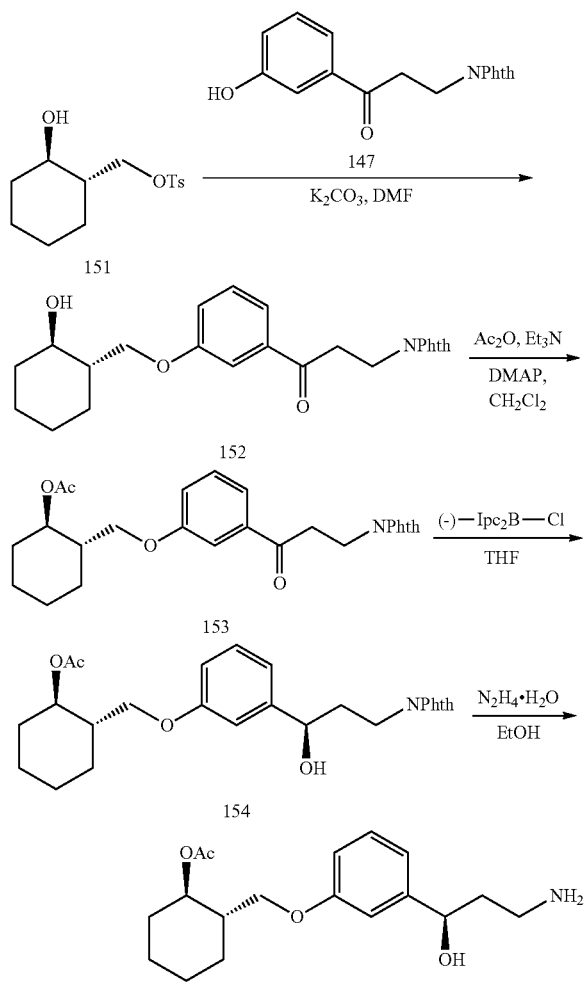

Step 1:
Alkylation of phenol 147 with (±)-trans-tosylate 151 following the method used in Example 171, after flash chromatography purification (30% to 50% EtOAc-hexanes gradient) gave crude (±)-trans-ether 152 as a white solid which was used in the next step without further purification. Yield (0.409 g, 29%).

Step 2:
Acetylation of alcohol 152 by AcCl following the method used in Example 19, except that a catalytic amount of DMAP was added, after flash chromatography purification (20% to 50% EtOAc-hexanes gradient) gave (±)-trans-acetate 153 as a colorless oil. (Yield (0.174 g, 39%): $^1$H NMR (400 MHz, CD$_3$OD) δ 7.21-7.82 (m, 4H), 7.47-7.51 (m, 1H), 7.40 (dd, J=1.8, 2.5 Hz, 1H), 7.31 (t, J=7.8 Hz, 1H), 7.07 (ddd, J=0.8, 2.5, 8.2 Hz, 1H), 4.73 (ddd, J=4.5, 10, 10 Hz, 1H), 4.01 (t, J=7.0 Hz, 2H), 3.97 (dd, J=3.5, 9.2 Hz, 1H), 3.87 (dd, J=5.7, 9.4 Hz, 1H), 3.37 (t, J=7.2 Hz, 2H), 1.86-2.05 (m, 3H), 1.97 (s, 3H), 1.66-1.80 (m, 2H), 1.26-1.42 (m, 4H).

Step 3:
Reduction of (±)-trans-ketone 153 with (−)-Ipc$_2$BCl following the method used in Example 171, after flash chromatography purification (30% to 60% EtOAc-hexanes gradient) gave (±)-trans-alcohol 154 as a colorless oil. Yield (0.163 g, 90%); $^1$H NMR (400 MHz, CD$_3$OD) δ 7.70-7.77 (m, 4H), 7.08 (t, J=7.8 Hz, 1H), 6.83-6.88 (m, 2H), 6.58-6.62 (m, 1H), 4.74 (ddd, J=4.3, 10.0, 10.0 Hz, 1H), 4.63 (t, J=6.7 Hz, 1H), 3.91 (dd, J=3.7, 9.4 Hz, 1H), 3.81 (dd, J=5.9, 9.2 Hz, 1H), 3.68-3.78 (m, 2H), 1.83-2.20 (m, 6H), 1.99 (s, 3H), 1.67-1.80 (m, 2H), 1.25-1.41 (m, 4H).

Step 4:
Deprotection of (±)-trans-alcohol 154 following the method used in Example 171 after flash chromatography purification (30% to 100% of 20% 7N NH$_3$/MeOH/CH$_2$Cl$_2$—CH$_2$Cl$_2$ gradient) gave Example 173 as a colorless oil. Yield (0.034 g, 30%); $^1$H NMR (400 MHz, DMSO-d6) δ 7.20 (t, J=8.2 Hz, 1H), 6.88-6.92 (m, 2H), 6.76 (ddd, J=1.0, 2.5, 8.2 Hz, 1H), 4.77 (ddd, J=4.7, 10.0, 10.0 Hz, 1H), 4.68 (dd, J=5.5, 8.0 Hz, 1H), 3.95 (dd, J=3.5, 9.6 Hz, 1H), 3.86 (dd, J=5.7, 9.4 Hz, 1H), 2.66-2.79 (m, 2H), 1.70-2.06 (m, 7H), 1.89 (s, 3H), 1.24-1.44 (m, 4H); LC-MS (ESI+) 322.58 [M+H]+; RP-HPLC (Method 10): 94.1%, tR=6.17 min.

Example 174

Preparation of (1,2-cis)-2-((3-((R)-3-amino-1-hydroxypropyl)phenoxy)methyl)cyclohexyl acetate

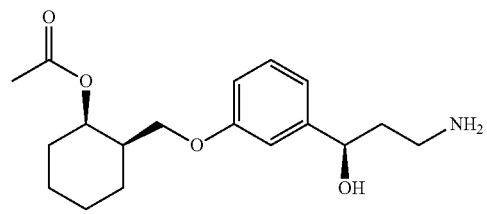 [SMILES: CC(=O)O[C@@H]1CCCC[C@@H]1COc1cccc([C@H](O)CCN)c1]

(1,2-cis)-2-((3-((R)-3-Amino-1-hydroxypropyl)phenoxy)methyl)cyclohexyl acetate was prepared following the method used in Example 173.

Step 1:
Alkylation of phenol 147 with (±)-cis-tosylate after flash chromatography purification (20% acetone-hexanes) gave crude 2-(3-(3-(((±)-cis-2-hydroxycyclohexyl)methoxy)phenyl)-3-oxopropyl)isoindoline-1,3-dione as a white solid which was used in the next step without further purification. Yield (0.43 g, 27%).

Step 2:
Acetylation of 2-(3-(3-(((±)-cis-2-hydroxycyclohexyl)methoxy)phenyl)-3-oxopropyl)isoindoline-1,3-dione with AcCl gave (±)-cis-2-((3-(3-(1,3-dioxoisoindolin-2-yl)propanoyl)phenoxy)methyl)cyclohexyl acetate as a colorless oil. Yield (0.182 g, 38%): $^1$H NMR (400 MHz, CD$_3$OD) δ 7.37-7.84 (m, 4H), 7.49-7.52 (m, 1H), 7.41 (dd, J=1.8, 2.5 Hz, 1H), 7.33 (t, J=8.2 Hz, 1H), 7.09 (ddd, J=0.8, 2.5, 8.2 Hz, 1H), 5.19-5.21 (m, 1H), 4.02 (t, J=6.9 Hz, 2H), 3.80-3.91 (m, 2H), 3.38 (t, J=7.4 Hz, 2H), 2.02-2.11 (m, 1H), 1.99 (s, 3H), 1.88-1.96 (m, 1H), 1.73-1.82 (m, 1H), 1.60-1.70 (m, 1H), 1.45-1.58 (m, 4H), 1.34-1.44 (m, 1H).

Step 3:
Reduction of (±)-cis-2-((3-(3-(1,3-dioxoisoindolin-2-yl)propanoyl)phenoxy)methyl)cyclohexyl acetate with (−)-Ipc$_2$BCl gave (±)-cis-2-((3-(3-((R)-3-(1,3-dioxoisoindolin-2-yl)-1-hydroxypropyl)phenoxy)methyl)cyclohexyl acetate as a colorless oil. Yield (0.161 g, 92%); $^1$H NMR (400 MHz, CD$_3$OD) δ 7.71-7.79 (m, 4H), 7.09 (t, J=7.8 Hz, 1H), 6.83-6.88 (m, 2H), 6.59-6.63 (m, 1H), 5.18-5.23 (m, 1H), 4.64 (t, J=6.7 Hz, 1H), 3.68-3.87 (m, 4H), 1.90-2.18 (m, 4H), 2.01 (d, J=3.1 Hz, 3H), 1.74-1.82 (m, 1H), 1.62-1.70 (m, 1H), 1.35-1.58 (m, 5H).

Step 4:

Deprotection of (±)-cis-2-((3-(3-(1,3-dioxoisoindolin-2-yl)propanoyl)phenoxy)methyl)cyclohexyl acetate gave Example 174 as a colorless oil. Yield (0.082 g, 73%): $^1$H NMR (400 MHz, DMSO-d6) δ 7.20 (t, J=8.2 Hz, 1H), 6.88-6.92 (m, 2H), 6.76 (ddd, J=1.0, 2.5, 8.2 Hz, 1H), 5.20-5.24 (m, 1H), 4.68 (dd, J=5.3, 7.8 Hz, 1H), 3.79-3.89 (m, 2H), 2.67-2.79 (m, 2H), 2.03-2.12 (m, 1H), 2.00 (d, J=1.6 Hz, 3H), 1.74-1.98 (m, 4H), 1.63-1.70 (m, 1H), 1.35-1.58 (m, 4H); LC-MS (ESI+) 322.55 [M+H]+; RP-HPLC (Method 10): 94.7%, tR=6.22 min.

Example 175

Preparation of (1,2-trans)-2-((3-((R)-3-amino-1-hydroxypropyl)phenoxy)methyl)cyclohexanol

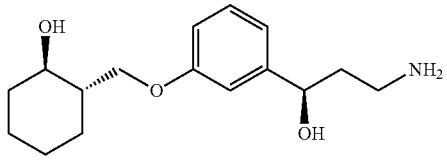 [SMILES: NCC[C@@H](O)c1cccc(OC[C@@H]2CCCC[C@H]2O)c1]

(1,2-trans)-2-((3-((R)-3-Amino-1-hydroxypropyl)phenoxy)methyl)cyclohexanol was prepared from Example 173 following the method below.

LiAlH$_4$ reduction of Example 173 following the method used in Example 4 gave Example 175 as a colorless oil. Yield (0.024 g, 53%); $^1$H NMR (400 MHz, CD$_3$OD) δ 7.20 (t, J=7.8 Hz, 1H), 6.92-6.95 (m, 1H), 6.87-6.90 (m, 1H), 6.79 (ddd, J=0.8, 2.5, 8.2 Hz, 1H), 4.68 (dd, J=5.5, 7.8 Hz, 1H), 4.15 (dd, J=3.5, 9.2 Hz, 1H), 3.95 (dd, J=6.8, 9.2 Hz, 1H), 3.45 (ddd, J=4.3, 10, 10 Hz, 1H), 2.65-2.78 (m, 2H), 1.92-2.2 (m, 2H), 1.72-1.92 (m, 3H), 1.60-1.70 (m, 2H), 1.20-1.35 (m, 4H); LC-MS (ESI+) 280.44 [M+H]+; RP-HPLC (Method 10): 94.5%, tR=5.33 min.

Example 176

Preparation of (1,2-cis)-2-((3-((R)-3-amino-1-hydroxypropyl)phenoxy)methyl)cyclohexanol

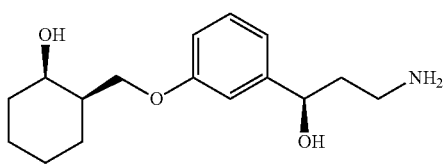 [SMILES: NCC[C@@H](O)c1cccc(OC[C@H]2CCCC[C@H]2O)c1]

(1,2-cis)-2-((3-((R)-3-Amino-1-hydroxypropyl)phenoxy)methyl)cyclohexanol was prepared following the method used for Example 175.

Step 1.

LiAlH$_4$ reduction of Example 174 gave Example 176 as a colorless oil. Yield (0.036 g, 55%); $^1$H NMR (400 MHz, CD$_3$OD) δ 7.20 (t, J=7.8 Hz, 1H), 6.92-6.94 (m, 1H), 6.87-6.90 (m, 1H), 6.79 (ddd, J=0.8, 2.5, 8.2 Hz, 1H), 4.68 (dd, J=5.3, 7.8 Hz, 1H), 4.05-4.09 (m, 1H), 4.02 (dd, J=7.4, 9.4 Hz, 1H), 3.81 (dd, J=6.8, 9.4 Hz, 1H), 1.75-1.97 (m, 4H), 1.62-1.75 (m, 2H), 1.26-1.57 (m, 5H); LC-MS (ESI+) 280.45 [M+H]+; RP-HPLC (Method 10): 92.5%, tR=5.33 min.

Example 177

Preparation of (1R,2R)-3-amino-1-(3-(cyclohexylmethoxy)phenyl)propane-1,2-diol

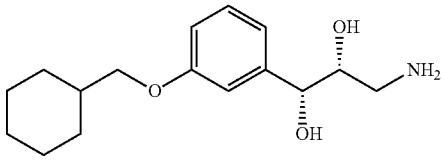 [SMILES: NC[C@@H](O)[C@H](O)c1cccc(OCC2CCCCC2)c1]

(1R,2R)-3-Amino-1-(3-(cyclohexylmethoxy)phenyl)propane-1,2-diol was prepared following the method shown in Scheme 49.

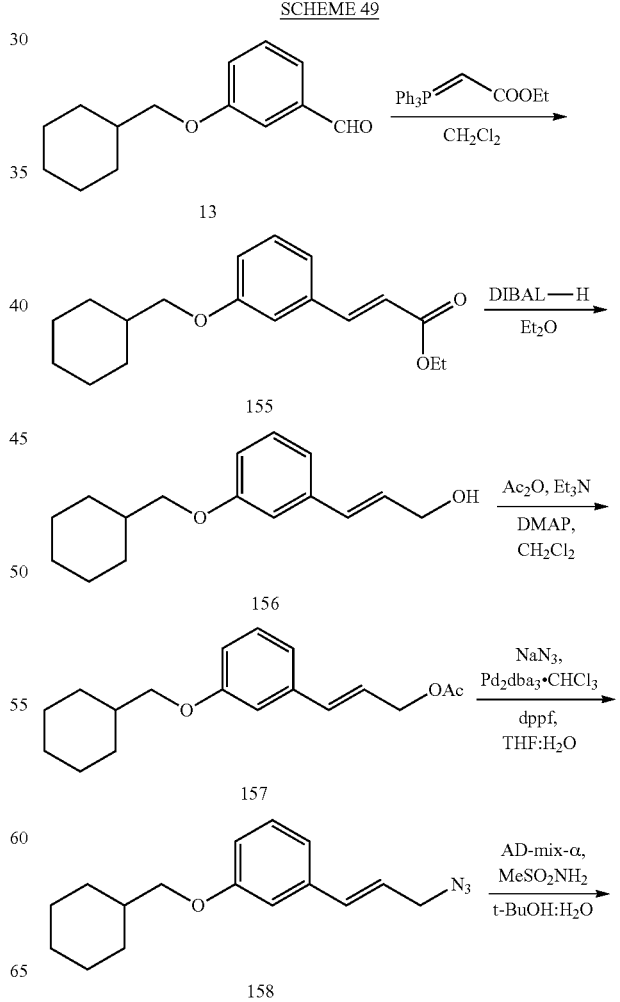

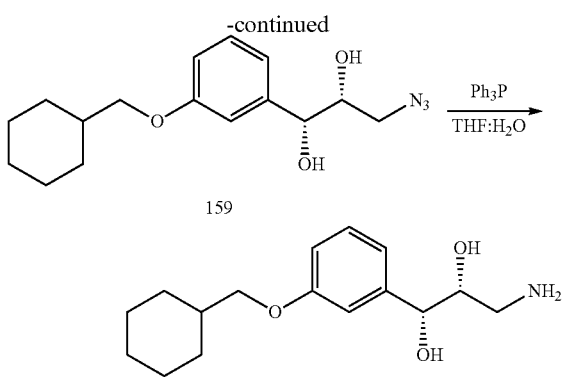

Step 1.

(Carbethoxymethylene)triphenylphosphorane (6.95 g, 20.0 mmol) was added under argon to an ice-cold solution of aldehyde 13 (3.88 g, 17.78 mmol) in anhydrous dichloromethane (100 mL). The reaction mixture was stirred at 0° C. for 5 min, then allowed to warm to room temperature over 2.5 hrs and concentrated under reduced pressure. The residue was resuspended in 10% EtOAc/hexanes, stirred for 10 min and the formed precipitate was filtered. Concentration of the filtrate was under reduced pressure followed by flash column chromatography purification (silica gel, 2% to 10% EtOAc/hexanes gradient) gave allyl ester 155 as a white solid. Yield (4.56 g, 89%); $^1$H NMR (400 MHz, DMSO-$d_6$) δ 7.58 (d, J=16.0 Hz, 1H), 7.20-7.30 (m, 3H), 6.94 (ddd, J=1.0, 2.5, 9.0 Hz, 1H), 6.63 (d, J=15.8 Hz, 1H), 4.16 (q, J=7.0 Hz, 2H), 3.78 (d, J=6.3 Hz, 2H), 1.58-1.82 (m, 6H), 1.08-1.30 (m, 3H), 1.29 (t, J=7.0 Hz, 3H), 0.95-1.07 (m, 2H).

Step 2.

A solution of diisobutyl aluminum hydride (1.0 M/CH$_2$Cl$_2$, 35 mL) was added to an ice-cold solution of ester 155 (4.52 g, 15.67 mmol) in diethyl ether (100 mL). The reaction mixture was stirred at 0° C. for 30 min and then the reaction mixture was partitioned between aqueous HCl (1M, 80 mL) and ether. Organic layer was washed with brine and dried over anhydrous MgSO$_4$. Concentration of the filtrate under reduced pressure gave alcohol 156 as a white solid. Yield (3.84 g, 99.5%); $^1$H NMR (400 MHz, DMSO-$d_6$) δ 7.17 (t, J=8.2 Hz, 1H), 6.91-6.95 (m, 2H), 6.75 (ddd, J=1.2, 2.2, 7.8 Hz, 1H), 6.45-6.51 (m, 1H), 6.35 (dt, J=4.9, 16.0 Hz, 1H), 4.82 (t, J=2.5 Hz, 1H), 4.08 (td, J=1.8, 5.3 Hz, 2H), 3.75 (d, J=6.3 Hz, 2H), 1.58-1.81 (m, 6H), 1.08-1.28 (m, 3H), 0.95-1.08 (m, 2H).

Step 3.

Acetylation of alcohol 156 following the method used in Example 19 except that the reaction was conducted in anhydrous CH$_2$Cl$_2$ in the presence of catalytical amount of DMAP, after flash column chromatography (2% to 20% EtOAc/hexanes gradient) gave allyl acetate 157 as a colorless oil. Yield (1.947 g, 99%). $^1$H NMR (400 MHz, DMSO-$d_6$) δ 7.20 (t, J=8.2 Hz, 1H), 6.96-6.99 (m, 2H), 6.80 (ddd, J=1.2, 2.2, 8.4 Hz, 1H), 6.57-6.63 (m, 1H), 6.34 (dt, J=6.1, 16.0 Hz, 1H), 4.65 (dd, J=1.4, 6.3 Hz, 2H), 3.75 (d, J=6.4 Hz, 2H), 2.03 (s, 3H), 1.58-1.81 (m, 6H), 1.08-1.28 (m, 3H), 0.95-1.08 (m, 2H).

Step 4.

A solution of allyl acetate 157 (1.928 g, 6.69 mmol) in THF:H$_2$O (4:1, 50 mL) was degassed by bubbling argon for 2 min. Sodium azide (0.503 g, 7.74 mmol), dppf (0.1634 g, 0.295 mmol), Pd$_2$dba$_3$·CHCl$_3$ (0.152 g, 0.147 mmol) were added to the reaction mixture which was degassed by bubbling argon for 1 min and then by applying vacuum/argon 3×. The reaction mixture was stirred under argon at +60° C. for 6 hrs and then at room temperature for 14 hrs. The reaction mixture was partitioned between EtOAc and brine and aqueous layer was extracted with EtOAc. Combined organic layers were washed with brine. Concentration in vacuo followed by flash chromatography purification (2% to 10% EtOAc/hexanes gradient) gave allyl azide 158 as a colorless oil. Yield (1.39 g, 77%). $^1$H NMR (400 MHz, DMSO-$d_6$) δ 7.21 (t, J=7.6 Hz, 1H), 6.98-7.02 (m, 2H), 6.81 (ddd, J=0.8, 2.5, 8.4 Hz, 1H), 6.60-6.66 (m, 1H), 6.37 (dt, J=6.7, 15.7 Hz, 1H), 4.00 (dd, J=1.2, 6.7 Hz, 2H), 3.76 (d, J=6.5 Hz, 2H), 1.58-1.81 (m, 6H), 1.08-1.28 (m, 3H), 0.95-1.08 (m, 2H).

Step 5.

A mixture of AD-mix-α (2.313 g), t-BuOH (8 mL) and water (8 mL) was stirred at room temperature for 5 min after which MeSO$_2$NH$_2$ (0.156 g, 1.64 mmol) was added. The reaction mixture was cooled to 0° C., allyl azide 158 (0.44 g, 1.47 mmol) was added and the reaction mixture was stirred at 0° C. for 21 hrs. Na$_2$S$_2$O$_3$ (2.6 g) was added and the mixture was stirred for another hour while warming to room temperature. The mixture was partitioned between EtOAc and brine and aqueous layer was extracted with EtOAc 2×. The combined organic layers were washed with brine and dried over anhydrous MgSO$_4$. Concentration under reduced pressure gave azido diol 159 as a colorless oil. Yield (0.52 g, quant.); $^1$H NMR (400 MHz, DMSO-$d_6$) δ 7.17 (t, J=7.8 Hz, 1H), 6.84-6.87 (m, 2H), 6.74-6.77 (m, 1H), 5.34 (d, J=5.3 Hz, 1H), 5.20 (d, J=5.7 Hz, 1H), 4.43 (t, J=4.9 Hz, 1H), 3.72 (d, J=6.1 Hz, 2H), 3.64-3.71 (m, 1H), 3.08 (ABd, J=3.3, 12.7 Hz, 1H), 2.98 (ABd, J=7.8, 12.5 Hz, 1H), 1.58-1.81 (m, 6H), 1.10-1.28 (m, 3H), 0.95-1.07 (m, 2H).

Step 6.

A mixture of azido diol 159 (0.52 g), triphenylphosphine (0.508 g, 1.94 mmol), THF (10 mL) and water (0.5 mL) was heated at 60° C. for 3.5 hrs, at 40° C. for 16 hrs and concentrated under reduced pressure. The residue was dissolved in CH$_2$Cl$_2$ and treated with hexane while sonicating to form a suspension of a white precipitate. The suspension was cooled to 0° C. and the precipitate was collected by filtration to give Example 177 as a white solid. Yield (0.248 g, 60% after 2 steps); $^1$H NMR (400 MHz, CD$_3$OD) δ 7.20 (t, J=7.8 Hz, 1H), 6.92-6.95 (m, 1H), 6.88-6.92 (m, 1H), 6.79 (ddd, J=1.0, 2.5, 8.2 Hz, 1H), 4.44 (d, J=6.3 Hz, 1H), 3.76 (d, J=6.3 Hz, 2H), 3.58-3.64 (m, 1H), 2.46-2.54 (m, 2H), 1.81-1.90 (m, 2H), 1.64-1.81 (m, 4H), 1.13-1.38 (m, 3H), 1.02-1.13 (m, 2H); RP-HPLC (Method 10) $t_R$=6.28 min, 98.2% (AUC); ESI MS m/z 280.26 [M+H]$^+$.

Example 178

Preparation of (1S,2S)-3-amino-1-(3-(cyclohexylmethoxy)phenyl)propane-1,2-diol

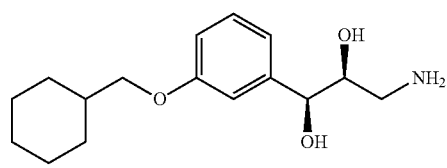 [SMILES: NC[C@H](O)[C@@H](O)c1cccc(OCC2CCCCC2)c1]

(1S,2S)-3-Amino-1-(3-(cyclohexylmethoxy)phenyl)propane-1,2-diol was prepared following the method used for Example 177.

Step 1.

Allyl azide 158 was dihydroxylated using AD-mix-β to give (1S,2S)-3-azido-1-(3-(cyclohexylmethoxy)phenyl)propane-1,2-diol as a colorless oil. Yield (0.58 g, quant); $^1$H NMR (400 MHz, DMSO-$d_6$) δ 7.17 (t, J=7.8 Hz, 1H), 6.84-6.87 (m, 2H), 6.74-6.77 (m, 1H), 5.34 (d, J=5.3 Hz, 1H), 5.20 (d, J=5.7 Hz, 1H), 4.43 (t, J=4.9 Hz, 1H), 3.72 (d, J=6.1 Hz, 2H), 3.64-3.71 (m, 1H), 3.08 (ABd, J=3.3, 12.7 Hz, 1H), 2.98 (ABd, J=7.8, 12.5 Hz, 1H), 1.58-1.81 (m, 6H), 1.10-1.28 (m, 3H), 0.95-1.07 (m, 2H).

Step 2.

Consecutive reduction and hydrolysis of (1S,2S)-3-azido-1-(3-(cyclohexylmethoxy)phenyl)propane-1,2-diol with Ph$_3$P gave Example 178 as a white solid. Yield (0.261 g, 63% after 2 steps); $^1$H NMR (400 MHz, CD$_3$OD) δ 7.20 (t, J=7.8 Hz, 1H), 6.92-6.95 (m, 1H), 6.88-6.92 (m, 1H), 6.79 (ddd, J=1.0, 2.5, 8.2 Hz, 1H), 4.44 (d, J=6.3 Hz, 1H), 3.76 (d, J=6.3 Hz, 2H), 3.58-3.64 (m, 1H), 2.46-2.54 (m, 2H), 1.81-1.90 (m, 2H), 1.64-1.81 (m, 4H), 1.13-1.38 (m, 3H), 1.02-1.13 (m, 2H); $^{13}$C NMR (100 MHz, CD$_3$OD) δ 159.6, 143.6, 129.0, 118.9, 113.6, 112.8, 76.5, 75.8, 73.3, 43.7, 38.0, 29.8, 26.5, 25.8; RP-HPLC (Method 10) $t_R$=6.27 min, 98.7% (AUC); ESI MS m/z 280.26 [M+H]$^+$.

Example 179

Preparation of (R)-3-(3-amino-1-hydroxypropyl)-5-(cyclohexylmethoxy)phenol (R)-3-(3-Amino-1-hydroxypropyl)-5-(cyclohexylmethoxy)phenol was prepared following the method shown in Scheme 50.

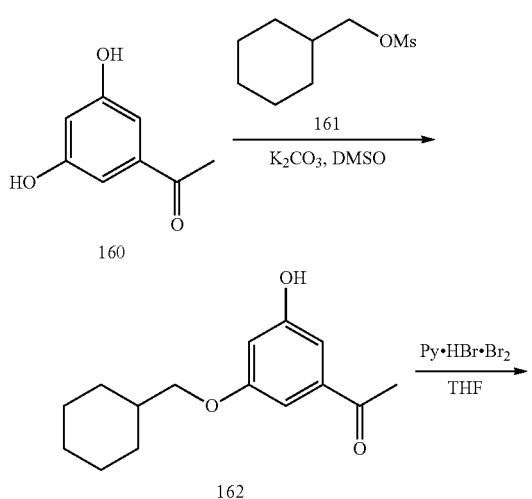

SCHEME 50

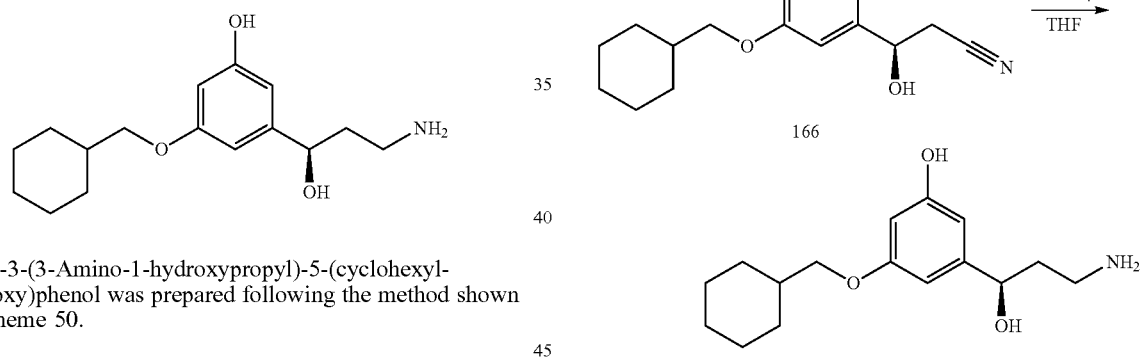

Step 1:

A mixture of phenol 160 (3.03 g, 19.9 mmol), mesylate 161 (1.91 g, 9.93 mmol) and K$_2$CO$_3$ (2.80 g, 20.3 mmol) in anhydrous DMSO was heated 2.5 hrs at +90° C. and cooled to room temperature. The reaction mixture was partitioned between water and EtOAc:hexanes (1:1) and aqueous layer was extracted with EtOAc. The combined organic layers were washed with brine, dried over anhydrous MgSO$_4$, and concentrated under reduced pressure. Purification by flash chromatography (10% to 30% EtOAc-hexanes gradient) followed by crystallization from hexanes gave monoalkyl phenol 162 as white prizms. Yield (1.10 g, 45%); $^1$H NMR (400 MHz, DMSO-$d_6$) δ 9.72 (s, 1H), 6.88 (d, J=2.15 Hz, 2H), 6.53 (t, J=2.35 Hz, 1H), 3.74 (d, J=6.3 Hz, 2H), 2.47 (s, 3H), 1.58-1.80 (m, 6H), 1.06-1.28 (m, 3H), 0.96-1.06 (m, 2H).

Step 2:

Bromination of ketone 162 with pyridinium tribromide following the method described in Example 127 followed by flash chromatography purification (10% to 20% EtOAc-hexanes gradient) gave bromide 163 as a yellow oil. Yield (0.805 g, 56%); $^1$H NMR (400 MHz, CDCl$_3$) δ 7.05-7.07 (m, 1H), 6.99-7.01 (m, 1H), 6.63 (t, J=2.3 Hz, 1H), 5.12 (s, 1H), 4.40 (s, 2H), 3.76 (d, J=6.3 Hz, 2H), 1.65-1.88 (m, 6H), 1.12-1.34 (m, 3H), 0.98-1.10 (m, 2H).

Step 3:

(−)-DIP-Cl (ca. 1.6 M, 5 mL, 8 mmol) was added under argon to a stirred solution of bromoketone 163 (0.80 g, 2.45 mmol) in anhydrous THF. The reaction mixture was stirred at room temperature for 2.5 hrs and partitioned between aqueous NH$_4$Cl (25%) and THF. Aqueous layer was extracted with EtOAc, the combined organic layers were washed with brine, dried over anhydrous MgSO$_4$ and concentrated under reduced pressure. Purification by flash chromatography (10% to 30% EtOAc-hexanes gradient) gave alcohol 164 as a colorless oil. Yield (0.605 g, 75%); $^1$H NMR (400 MHz, DMSO-d$_6$) δ 9.30 (s, 1H), 6.35 (t, J=2.35 Hz, 2H), 6.17 (t, J=2.35 Hz, 1H), 5.65 (d, J=4.7 Hz, 1H), 4.60 (dt, J=4.5, 7.4 Hz, 1H), 3.66 (d, J=6.5 Hz, 2H), 3.58 (dd, J=4.1, 10.2 Hz, 1H), 3.46 (dd, J=7.4, 10.2 Hz, 1H), 1.58-1.80 (m, 6H), 1.07-1.27 (m, 3H), 0.92-1.04 (m, 2H).

Step 4: t-BuO-K+ solution (1M/THF, 2.3 mL) was added under argon to a cooled (0° C.) stirred solution of bromoalcohol 164 (0.60 g, 1.82 mmol) in anhydrous THF. The reaction mixture was stirred at 0° C. for 15 min followed by addition of aqueous NH$_4$Cl (25%). Layers were separated, aqueous layer extracted with EtOAc and combined organic layers were washed with brine. Concentration under reduced pressure followed by flash chromatography (10% to 30% EtOAc-hexanes gradient) gave epoxide 165 as a colorless oil. Yield (0.354 g, 78%); $^1$H NMR (400 MHz, DMSO-d$_6$) δ 9.40 (s, 1H), 6.25-6.27 (m, 1H), 6.22-6.23 (m, 1H), 6.19-6.21 (m, 1H), 3.75 (dd, J=2.5, 4.1 Hz, 1H), 3.66 (d, J=6.3 Hz, 2H), 3.00 (dd, J=4.3, 5.7 Hz, 1H), 2.70 (dd, J=2.5, 5.5 Hz, 1H), 1.58-1.80 (m, 6H), 1.07-1.27 (m, 3H), 0.92-1.04 (m, 2H).

Step 5:

A mixture of epoxide 165 (0.352 g, 1.42 mmol), NaCN (0.1075 g, 2.19 mmol) in EtOH:H$_2$O (5:3, 8 mL) was stirred at room temperature for 18 hrs. The reaction mixture was concentrated under reduced pressure, and partitioned between brine and EtOAc. Aqueous layer was extracted with EtOAc, the combined organic layers were washed with brine, dried over anhydrous MgSO$_4$ and concentrated under reduced pressure. Flash chromatography purification (10% to 50% EtOAc-hexanes gradient) gave hydroxynitrile 166 as a colorless oil. Yield (0.123 g, 31%); $^1$H NMR (400 MHz, DMSO-d$_6$) δ 9.34 (br. s, 1H), 6.35-6.39 (m, 2H), 6.17 (t, J=2.15 Hz, 1H), 5.79 (br. s, 1H), 4.70 (t, J=5.9 Hz, 1H), 3.66 (d, J=6.3 Hz, 2H), 2.80 (ABd, J=4.9, 16.6 Hz, 1H), 2.71 (ABd, J=6.8, 16.8 Hz, 1H), 1.56-1.78 (m, 6H), 1.04-1.27 (m, 3H), 0.92-1.04 (m, 2H).

Step 6:

LiAlH$_4$ reduction of hydroxynitrile 166 following the method described in Example 4, followed by flash chromatography purification (40% to 100% 20% 7N NH$_3$/MeOH/CH$_2$Cl$_2$—CH$_2$Cl$_2$ gradient) gave Example 179 as a white solid. Yield (0.052 g, 42%); $^1$H NMR (400 MHz, CD$_3$OD) δ 6.39 (t, J=1.6 Hz, 1H), 6.37 (t, J=1.76 Hz, 1H), 6.21 (t, J=2.3 Hz, 1H), 4.60 (dd, J=5.5, 7.6 Hz, 1H), 3.71 (d, J=6.5 Hz, 2H), 2.68-2.81 (m, 2H), 1.65-1.90 (m, 8H), 1.15-1.36 (m, 3H), 1.00-1.11 (m, 2H); $^{13}$C NMR (100 MHz, CD$_3$OD) δ 160.8, 158.6, 147.4, 105.1, 103.1, 100.5, 73.3, 72.3, 38.2, 37.9, 29.8, 26.5, 25.8; LC-MS (ESI+) 280.38 [M+H]+; RP-HPLC (Method 10): 96.0%, tR=6.20 min.

Example 180

Preparation of (1S,2R)-3-amino-1-(3-(cyclohexylmethoxy)phenyl)propane-1,2-diol

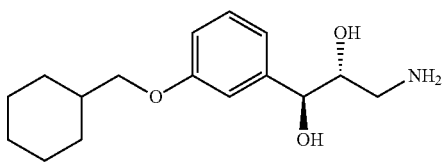 [SMILES: NC[C@@H](O)[C@@H](O)c1cccc(OCC2CCCCC2)c1]

(1S,2R)-3-Amino-1-(3-(cyclohexylmethoxy)phenyl)propane-1,2-diol was prepared following the method described below.

Step 1:

To a cold (−20° C.) mixture of powdered 4 Å molecular sieves (2.81 g) and titanium tetraisopropoxide (2.4 mL, 8.2 mmol) in anhydrous CH$_2$Cl$_2$ was added L-(+)-diisopropyl tartrate (DIPT, 2.1 mL, 10.05 mmol) under inert atmosphere. The reaction mixture was stirred at −20° C. for 10 min and a solution of allyl alcohol 156 (1.99 g, 8.08 mmol) in anhydrous CH$_2$Cl$_2$ was added over 5 mins. After the reaction mixture was stirred at −20° C. for 20 min, tert-butyl hydroperoxide solution (5.0-6.0 M in nonane, 0.9 mL, ca 4.95 mmol) was added. The reaction mixture was stirred at −20° C. for 7.5 hrs, kept at −20° C. overnight, and then stirred at room temperature for 3 days. An aqueous solution of L-tartaric acid (10%, 100 mL) was added to the reaction mixture, the mixture was vigorously stirred for 2 hrs at room temperature and layers were separated. Aqueous layer was extracted with EtOAc. The combined organic layers were washed with dilute brine, dried over anhydrous MgSO$_4$, and concentrated under reduced pressure. Purification by flash column chromatography (silica gel, 5% to 30% EtOAc/hexanes gradient) gave a mixture of (S)-(3-(cyclohexylmethoxy)phenyl)((R)-oxiran-2-yl)methanol and DIPT (1:1.38 molar ratio) as a colorless oil, which was used in the next step without additional purification. Yield (1.34 g); $^1$H NMR (400 MHz, DMSO-d$_6$) δ 7.20 (t, J=8.0 Hz, 1H), 6.88-6.93 (m, 2H), 6.79 (ddd, J=1.0, 2.5, 8.2 Hz, 1H), 5.47 (d, J=4.7 Hz, 1H), 4.35 (t, J=4.9 Hz, 1H), 3.73 (d, J=6.3 Hz, 2H), 2.99 (ddd, J=2.7, 3.9.6.65 Hz, 1H), 2.63-2.70 (m, 2H), 1.58-1.81 (m, 6H), 0.98-1.28 (m, 3H), 0.95-0.98 (m, 2H).

Step 2:

A solution of crude (S)-(3-(cyclohexylmethoxy)phenyl)((R)-oxiran-2-yl)methanol (0.255 g, 0.972 mmol), ammonium hydroxide (aq, 25%, 3 mL) and NH$_3$/MeOH (7N, 3 mL) was stirred in a pressure bottle at room temperature for 21 hrs, and then concentrated under reduced pressure. Purification by flash column chromatography (silica gel, 20% to 100% of 7N NH$_3$/MeOH/CH$_2$Cl$_2$—CH$_2$Cl$_2$ gradient) gave Example 180 as a colorless oil. Yield (0.0836 g, 67%); $^1$H NMR (400 MHz, CD$_3$OD) δ 7.20 (t, J=7.8 Hz, 1H), 6.90-6.95 (m, 2H), 6.78 (ddd, J=0.8, 2.5, 7.2 Hz, 1H), 4.51 (d, J=6.1 Hz, 1H), 3.76 (d, J=6.3 Hz, 2H), 3.61-3.66 (m, 1H), 2.81 (ABd, J=3.3, 13.1 Hz, 1H), 2.65 (ABd, J=7.8, 13.1 Hz, 1H), 1.81-1.91 (m, 2H), 1.66-1.80 (m, 4H), 1.15-1.38 (m, 3H), 1.01-1.14 (m, 2H); RP-HPLC (Method 10): 97.3%, tR=6.25 min.

Example 181

Preparation of 1-(3-(cyclohexylmethoxy)phenyl)-3-(methylamino)propan-1-one

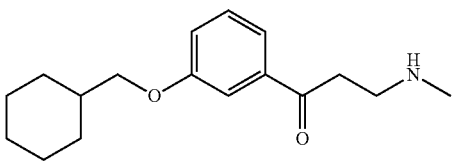 [SMILES: CNCCC(=O)c1cccc(OCC2CCCCC2)c1]

1-(3-(Cyclohexylmethoxy)phenyl)-3-(methylamino)propan-1-one was prepared following the method described below.

A mixture of vinyl ketone 101 (0.341 g, 1.40 mmol) and methylamine (2.0 M in THF, 1.0 mL) in absolute EtOH was stirred in a pressure bottle at room temperature for 3 hrs and concentrated under reduced pressure. Purification by flash chromatography (20% to 100% of 20% 7N NH$_3$/MeOH/CH$_2$Cl$_2$—CH$_2$Cl$_2$ gradient) gave Example 181 as an orange oil. Yield (0.144 g, 38%). Example 181 was dissolved in EtOAc and HCl/EtOH (7.4 M) was added. The precipitate formed was triturated with hexanes and collected by filtration to give Example 181 hydrochloride as a white solid. $^1$H NMR (400 MHz, CD$_3$OD) δ 7.59 (ddd, J=1.2, 1.6, 7.8 Hz, 1H), 7.50 (dd, J=1.8, 2.5 Hz, 1H), 7.42 (t, J=8.0 Hz, 1H), 7.20 (ddd, J=0.8, 2.5, 8.2 Hz, 1H), 3.82 (d, J=6.3 Hz, 2H), 3.48 (t, J=5.5 Hz, 2H), 3.39 (t, J=6.1 Hz, 2H), 2.75 (s, 3H), 1.67-1.90 (m, 6H), 1.15-1.39 (m, 3H), 1.05-1.15 (m, 2H); RP-HPLC (Method 10): 91.5%, tR=7.07 min.

Example 182

Preparation of 1-(3-(cyclohexylmethoxy)phenyl)-3-(dimethylamino)propan-1-one

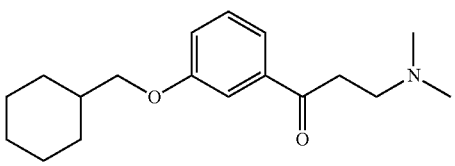 [SMILES: CN(C)CCC(=O)c1cccc(OCC2CCCCC2)c1]

1-(3-(Cyclohexylmethoxy)phenyl)-3-(dimethylamino)propan-1-one was prepared following the method described below.

A mixture of vinyl ketone 101 (0.4321 g, 1.77 mmol), dimethylamine hydrochloride (0.242 g, 2.97 mmol) and triethylamine (0.5 mL, 3.59 mmol) in absolute EtOH was stirred at room temperature for 3 hrs and concentrated under reduced pressure. Purification by flash chromatography (5% to 500% of 20% 7N NH$_3$/MeOH/CH$_2$Cl$_2$—CH$_2$Cl$_2$ gradient) gave Example 182 as a light orange oil. Yield (0.227 g, 44%). Example 182 was dissolved in EtOAc and HCl/EtOH (7.4 M) was added. The precipitate formed was triturated with hexanes and collected by filtration to give Example 182 hydrochloride as a white solid. $^1$H NMR (400 MHz, CD$_3$OD) δ 7.61 (ddd, J=1.0, 1.6, 7.6 Hz, 1H), 7.52 (dd, J=1.8, 2.5 Hz, 1H), 7.43 (t, J=8.0 Hz, 1H), 7.20 (ddd, J=0.8, 2.5, 8.2 Hz, 1H), 3.83 (d, J=6.3 Hz, 2H), 2.5-3.61 (m, 4H), 2.94 (s, 6H), 1.67-1.91 (m, 6H), 1.17-1.39 (m, 3H), 1.05-1.15 (m, 2H); $^{13}$C NMR (100 MHz, CD$_3$OD) δ 197.1, 159.9, 137.3, 129.8, 120.4, 120.3, 113.3, 73.6, 53.3, 42.7, 37.9, 33.0, 29.7, 26.4, 25.8; RP-HPLC (Method 10): 92.4%, t$_R$=7.18 min.

Example 183

Preparation of (3-(2-propylpentyloxy)phenyl)methanamine

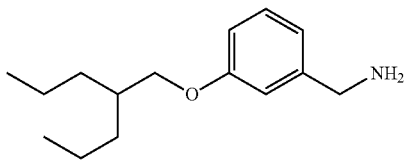 [SMILES: CCCC(CCC)COc1cccc(CN)c1]

(3-(2-Propylpentyloxy)phenyl)methanamine is prepared following the method shown in Scheme 51.

SCHEME 51

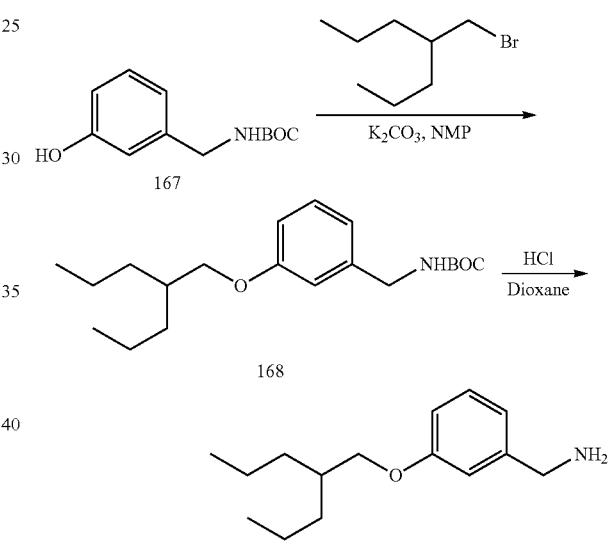

Step 1:
Phenol 167 is alkylated with 4-bromoheptane by the method used for Example 165 to give ether 168.

Step 2:
Ether 168 is deprotected by the method used for Example 165 to give Example 183.

Example 184

Preparation of 4-(3-(cyclohexylmethoxy)phenyl)butan-1-amine

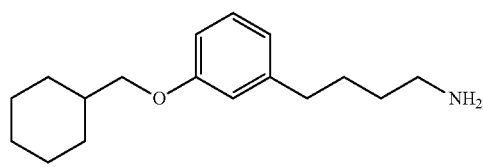 [SMILES: NCCCCc1cccc(OCC2CCCCC2)c1]

4-(3-(Cyclohexylmethoxy)phenyl)butan-1-amine was prepared following the method shown in Scheme 52.

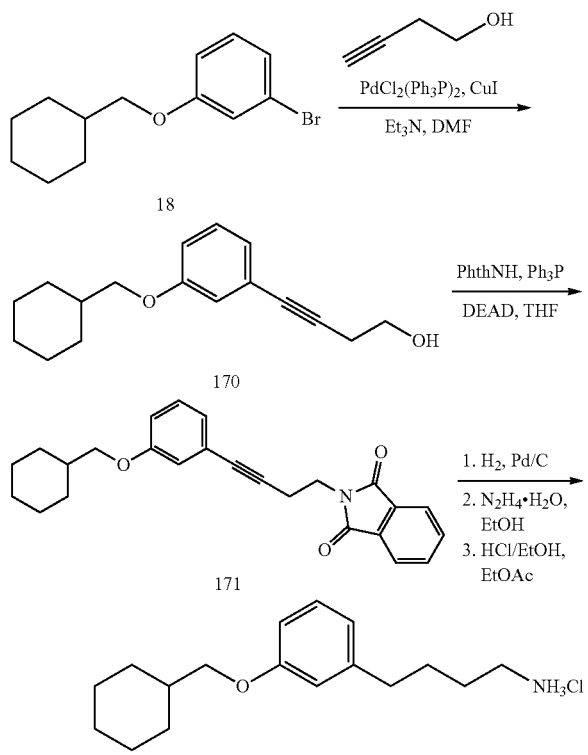

Step 1:

To a degassed solution of bromide 18 (0.677 g, 2.52 mmol) and 3-butyn-1-ol (0.270 g, 3.85 mmol) in triethylamine (5 mL) and DMF (10 mL) was added PdCl$_2$(PPh$_3$)$_2$ (0.0702 g, 0.100 mmol), and CuI (0.0196 g, 0.103 mmol). The resulting mixture was degassed and stirred under argon at 90° C. for 3.5 hrs. The mixture was cooled to room temperature and concentrated under reduced pressure. Purification by flash column chromatography (5 to 30% EtOAc-hexanes gradient) gave 4-(3-(cyclohexylmethoxy)phenyl)but-3-yn-1-ol (170) as a yellow oil. Yield (0.494 g, 76%); $^1$H NMR (400 MHz, DMSO-d$_6$) δ 7.16-7.22 (m, 1H), 6.84-6.92 (m, 3H), 4.85 (t, J=5.5 Hz, 1H), 3.73 (d, J=6.3 Hz, 2H), 3.51-3.58 (m, 2H), 2.51 (t, J=6.8 Hz, 2H), 1.59-1.80 (m, 6H), 1.07-1.27 (m, 3H), 0.92-1.05 (m, 2H).

Step 2:

Mitsunobu condensation of alcohol 170 with phthalimide following the method used in Example 2 followed by purification by flash chromatography (5% to 30% EtOAc-hexanes gradient) gave phthalimide 171 as a colorless oil. Yield (0.492 g, 67%); $^1$H NMR (400 MHz, DMSO-d$_6$) δ 7.80-7.91 (m, 4H), 7.16 (t, J=7.8 Hz, 1H), 6.84 (ddd, J=0.8, 2.5, 8.4 Hz, 1H), 6.78 (dt, J=1.0, 7.6 Hz, 1H), 6.71 (dd, J=1.6, 2.5 Hz, 1H), 3.80 (t, J=6.9 Hz, 2H), 3.67 (d, J=6.5 Hz, 2H), 2.76 (t, J=6.9 Hz, 2H), 1.57-1.78 (m, 6H), 1.07-1.27 (m, 3H), 0.93-1.04 (m, 2H).

Step 3:

Hydrogenation of alkyne 171 following the method used in Example 1 followed by filtration through Celite and concentration under reduced pressure gave 2-(4-(3-(cyclohexylmethoxy)phenyl)butyl)isoindoline-1,3-dione as a colorless oil. Yield (0.236 g, 97%); $^1$H NMR (400 MHz, DMSO-d$_6$) δ 7.77-7.86 (m, 4H), 7.10 (t, J=8.0 Hz, 1H), 6.64-6.72 (m, 3H), 3.69 (d, J=6.3 Hz, 2H), 3.56 (t, J=7.4 Hz, 2H), 2.52 (t, J=7.0 Hz, 2H), 1.50-1.79 (m, 10H), 1.07-1.28 (m, 3H), 0.91-1.04 (m, 2H).

Step 4:

Deprotection of 2-(4-(3-(cyclohexylmethoxy)phenyl)butyl)isoindoline-1,3-dione following the method used in Example 196 gave Example 184 hydrochloride as a white solid. Yield (0.0896 g, 50%); $^1$H NMR (400 MHz, CD$_3$OD) δ 7.14 (t, J=7.8 Hz, 1H), 6.67-6.78 (m, 3H), 3.72 (d, J=6.3 Hz, 2H), 2.91 (t, J=7.4 Hz, 2H), 2.63 (t, J=6.9 Hz, 2H), 1.59-1.90 (m, 10H), 1.15-1.37 (m, 3H), 1.01-1.13 (m, 2H); $^{13}$C NMR (100 MHz, CD$_3$OD) δ 159.7, 143.2, 129.2, 120.5, 114.7, 111.7, 73.2, 39.5, 38.0, 35.0, 29.8, 27.9, 26.9, 26.5, 25.8; RP-HPLC (Method 2), t$_R$=7.40 min, 97.4% (AUC).

Example 185

Preparation of 2-(3-(cyclohexylmethoxy)benzyloxy)ethanamine

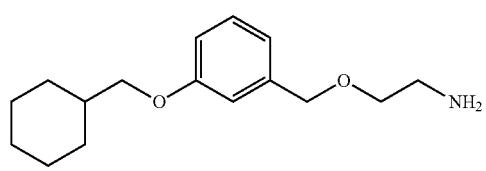 [SMILES: NCCOCc1cccc(OCC2CCCCC2)c1]

2-(3-(Cyclohexylmethoxy)benzyloxy)ethanamine is prepared following the method shown in Scheme 53.

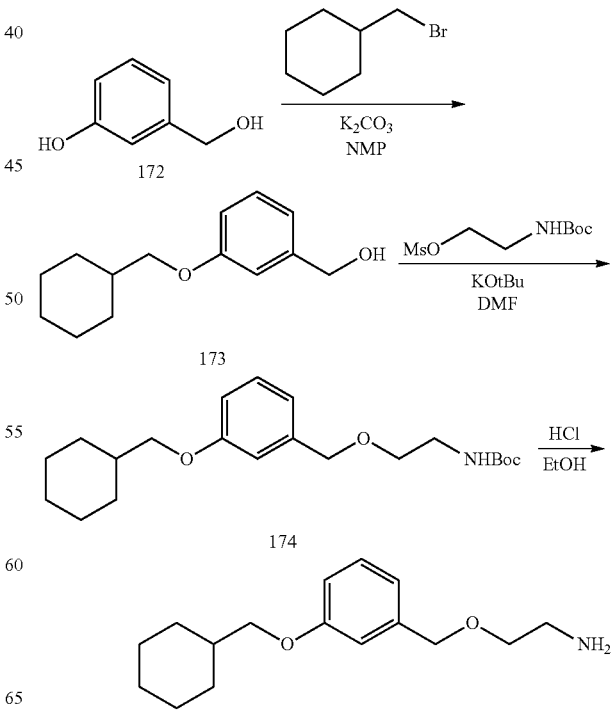

Step 1:
Alkylation of 3-hydroxybenzyl alcohol (172) with bromomethylcyclohexane following the method used in Example 165 gives alcohol 173.
Step 2:
Alkylation of alcohol 173 following the method used in Example 154 gives ether 174.
Step 3:
Deprotection of ether 174 following the method used in Example 5 gives Example 185.

Example 186

Preparation of 3-(3-(cyclohexylmethoxy)phenyl)-N-methylpropan-1-amine

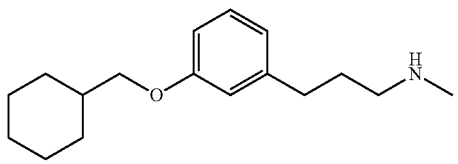 [SMILES: CNCCCc1cccc(OCC2CCCCC2)c1]

3-(3-(Cyclohexylmethoxy)phenyl)-N-methylpropan-1-amine is prepared following the method shown in Scheme 54.

SCHEME 54

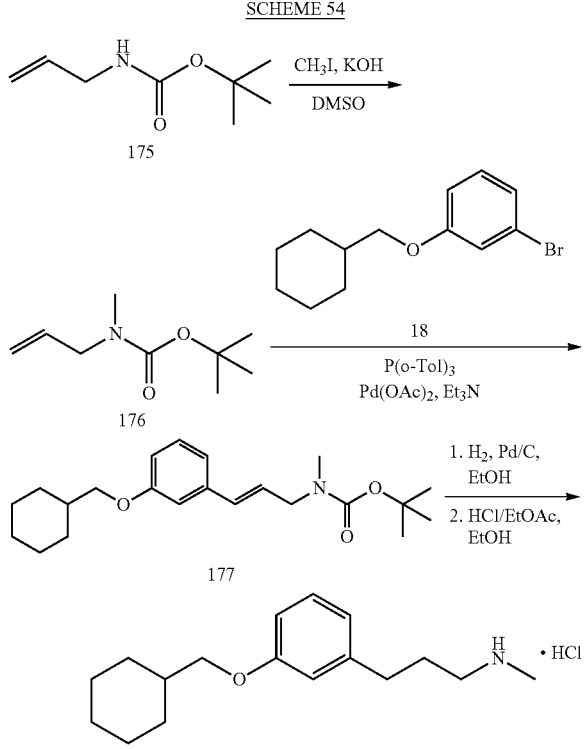

Step 1:
A mixture of allylamine carbamate 175 (1.926 g, 12.2 mmol), powdered KOH (0.734 g, 13.1 mmol) in anhydrous DMSO (10 mL) was stirred at room temperature for 5 min. Then a solution of methyl iodide (2.276 g, 16.03 mmol) in DMSO (2 mL) was added and the reaction mixture was stirred at room temperature for 66 hr. Aqueous NH$_4$Cl (25%, 100 mL) was added and the product was extracted with EtOAc (3×70 mL). Combined organic layers were washed with brine, dried over anhydrous MgSO$_4$, filtered and the filtrate was concentrated under reduced pressure to give N-methylcarbamate 176 as a light yellowish liquid with a low boiling point. Yield (1.595 g, 76%); $^1$H NMR (400 MHz, CDCl$_3$) δ 5.74 (ddt, J=16.8, 10.6, 5.7 Hz, 1H), 5.06-5.13 (m, 2H), 3.79 (d, J=5.5 Hz, 2H), 2.80 (s, 3H), 1.43 (s, 9H).
Step 2:
The Heck coupling of carbamate 176 and bromide 18 is conducted by the method described in Example 10 to give alkene 177.
Step 3:
Hydrogenation of alkene 177 is conducted by the method used for Example 1 followed by Boc deprotection by the method described in Example 5 to give Example 186 hydrochloride.

Example 187

Preparation of 1-(3-(cyclohexylmethoxy)phenyl)-3-(methylamino)propan-1-ol

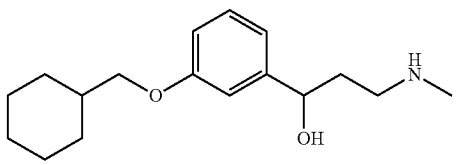 [SMILES: CNCCC(O)c1cccc(OCC2CCCCC2)c1]

1-(3-(Cyclohexylmethoxy)phenyl)-3-(methylamino)propan-1-ol was prepared following the method used in Example 173.
Chiral reduction of Example 181 followed by flash chromatography purification (20% to 100% 20% 7N NH$_3$/MeOH/CH$_2$Cl$_2$—CH$_2$Cl$_2$ gradient) gave Example 187 as a colorless oil. Yield (0.0335 g, 29%). $^1$H NMR (400 MHz, CD$_3$OD) δ 7.20 (t, J=7.8 Hz, 1H), 6.84-6.92 (m, 2H), 6.76 (ddd, J=0.8, 2.5, 8.2 Hz, 1H), 4.67 (dd, J=5.5, 7.6 Hz, 1H), 3.75 (d, J=6.3 Hz, 2H), 2.56-2.70 (m, 2H), 2.35 (s, 3H), 1.81-1.94 (m, 4H), 1.65-1.80 (m, 4H), 1.16-1.38 (m, 3H), 1.01-1.14 (m, 2H); RP-HPLC (Method 10): 98.9%, tR=6.68 min.

Example 188

Preparation of 1-(3-(cyclohexylmethoxy)phenyl)-3-(dimethylamino)propan-1-ol

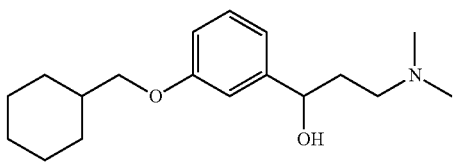 [SMILES: CN(C)CCC(O)c1cccc(OCC2CCCCC2)c1]

1-(3-(Cyclohexylmethoxy)phenyl)-3-(dimethylamino)propan-1-ol is prepared following the method used in Example 187.

Chiral reduction of Example 182 followed by flash chromatography purification (20% to 100% 20% 7N NH₃/MeOH/CH₂Cl₂—CH₂Cl₂ gradient) gives Example 188.

Example 189

Preparation of (R)—N-(3-(3-(cyclohexylmethoxy)phenyl)-3-hydroxypropyl)-2,2,2-trifluoroacetamide

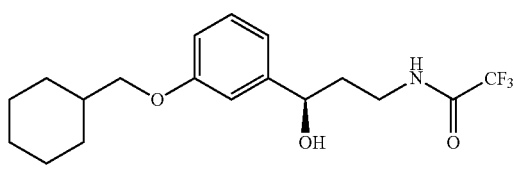 [SMILES: O=C(NCC[C@@H](O)c1cccc(OCC2CCCCC2)c1)C(F)(F)F]

(R)—N-(3-(3-(Cyclohexylmethoxy)phenyl)-3-hydroxypropyl)-2,2,2-trifluoroacetamide was prepared following the method shown in Scheme 55.

SCHEME 55

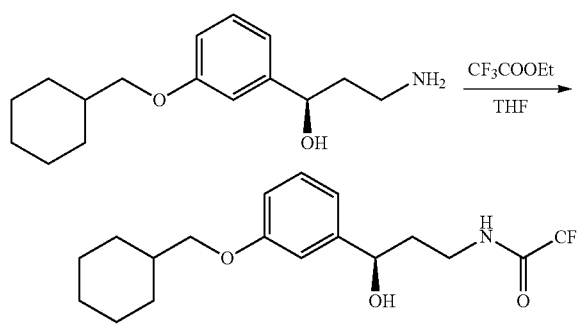

Ethyl trifluoroacetate (0.3 mL, 2.52 mmol) was added to a solution of Example 28 (0.3016 g, 1.145 mmol) in CH₂Cl₂. The reaction mixture was stirred at room temperature for 1 h and then concentrated under reduced pressure to give Example 189 as a colorless oil. Yield (0.346 g, 84%): ¹H NMR (DMSO-d₆) δ 9.31 (t, J=4.7 Hz, 1H), 7.18 (t, J=7.6 Hz, 1H), 6.82-6.87 (m, 2H), 6.74 (ddd, J=1.2, 2.3, 8.2 Hz, 1H), 5.27 (d, J=5.4 Hz, 1H), 4.494.55 (m, 1H), 3.72 (d, J=6.3 Hz, 2H), 3.22 (q, J=6.3 Hz, 2H), 1.59-1.81 (m, 8H), 1.09-1.28 (m, 3H), 0.95-1.07 (m, 2H).

Example 190

Preparation of 1-(3-(cyclohexylmethoxy)benzyl)guanidine

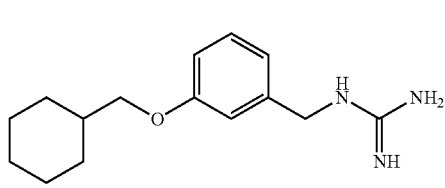 [SMILES: N=C(N)NCc1cccc(OCC2CCCCC2)c1]

1-(3-(Cyclohexylmethoxy)benzyl)guanidine was prepared from following the method shown in Scheme 56.

SCHEME 56

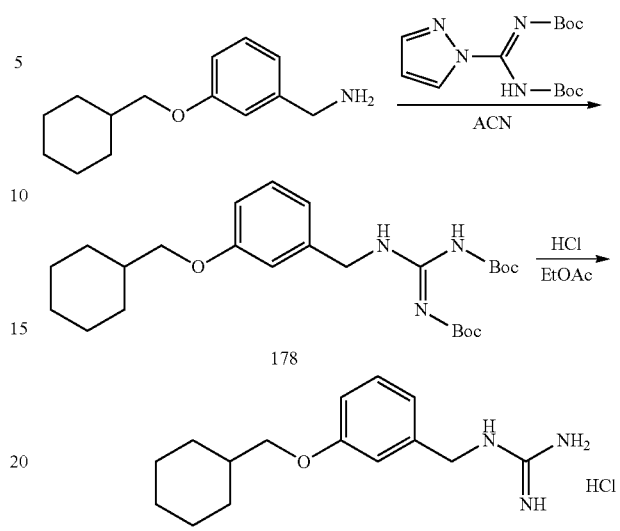

Step 1:

A solution of N,N'-bis(tert-butoxycarbonyl)-1H-pyrazole-1-carboxamidine (0.71 g, 2.28 mmol) and (3-(cyclohexylmethoxy)phenyl)methanamine (0.50 g, 2.28 mmol) in acetonitrile (15 ml) was stirred at 50° C. for 18 h under argon. After cooling to room temperature, a white solid was formed, collected via filtration, and dried under vacuum to give (Z)-tert-butyl (tert-butoxycarbonylamino)(3-(cyclohexylmethoxy)benzylamino)methylenecarbamate. Yield (400 mg, 38%). ¹H NMR (400 MHz, DMSO-d₆) δ 11.47 (s, 1H), 8.61 (t, J=6.0 Hz, 1H), 7.20 (t, J=8.0 Hz, 1H), 6.77-6.86 (m, 3H), 4.44 (d, J=5.6 Hz, 2H), 3.72 (d, J=6.4 Hz, 2H), 1.60-1.80 (m, 6H), 1.45 (s, 9H), 1.36 (s, 9H), 0.95-1.25 (m, 5H).

Step 2:

Boc deprotection of (Z)-tert-butyl (tert-butoxycarbonylamino)(3-(cyclohexylmethoxy)benzylamino)methylenecarbamate was performed by the method described in Example 5 to give Example 190 hydrochloride. Yield (140 mg, 95%). ¹H NMR (400 MHz, DMSO-d₆) δ 7.99 (t, J=6.4 Hz, 1H), 6.90-7.50 (m, 4H), 6.80-6.84 (m, 3H), 4.30 (d, J=6.4 Hz, 2H), 3.74 (d, J=6.0 Hz, 2H), 1.60-1.80 (m, 6H), 0.95-1.30 (m, 5H).

Example 191

Preparation of (R)-1-(3-(3-(cyclohexylmethoxy)phenyl)-3-hydroxypropyl)guanidine

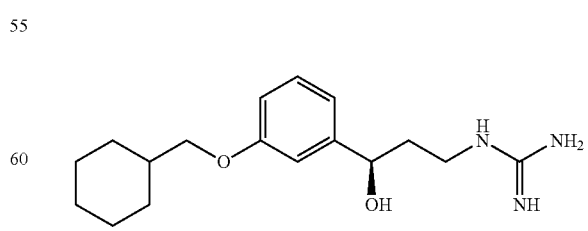

(R)-1-(3-(3-(Cyclohexylmethoxy)phenyl)-3-hydroxypropyl)guanidine is prepared following the method used in Example 190.

Step 1:

A solution of N,N'-bis(tert-butoxycarbonyl)-1H-pyrazole-1-carboxamidine and Example 28 in acetonitrile is mixed until no Example 28 is observed by TLC. The mixture is concentrated under reduced pressure and partitioned between EtOAc and water. The organic layer is dried over MgSO$_4$, filtered, and concentrated under reduced pressure. Purification by flash chromatography (EtOAc-hexanes gradient) gives (R,E)-tert-butyl (tert-butoxycarbonylamino)(3-(3-(cyclohexylmethoxy)phenyl)-3-hydroxypropylamino)methylenecarbamate.

Step 2:

Boc deprotection of (R,E)-tert-butyl (tert-butoxycarbonylamino)(3-(3-(cyclohexylmethoxy)phenyl)-3-hydroxypropylamino)methylenecarbamate is done by the method described in Example 5 to give Example 191 hydrochloride.

Example 192

Preparation of 3-(3-(cyclohexylmethoxy)phenyl)-3-methoxypropan-1-amine

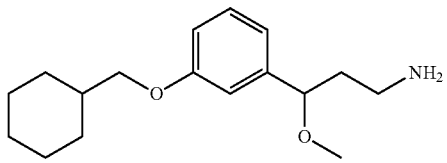 [SMILES: COC(CCN)c1cccc(OCC2CCCCC2)c1]

3-(3-(Cyclohexylmethoxy)phenyl)-3-methoxypropan-1-amine is prepared following the method shown in Scheme 57.

SCHEME 57

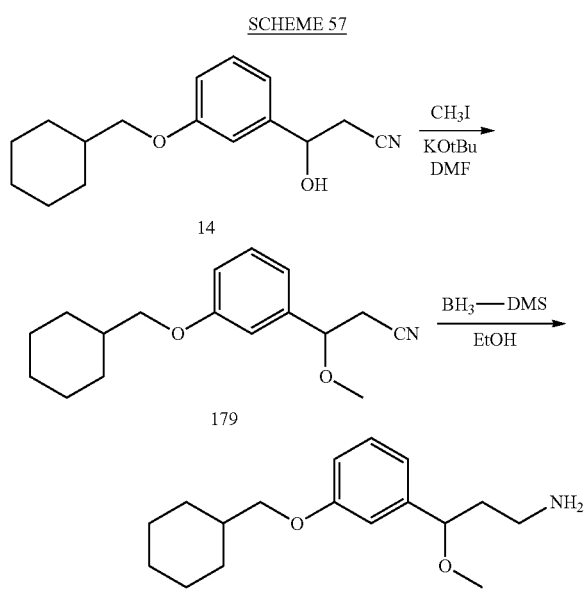

Step 1:

The alkylation of alcohol 14 is conducted by the method used for Example 154 to give nitrile 179.

Step 2:

The reduction of nitrile 179 is done by the method used for Example 171 to give Example 192.

Example 193

Preparation of 3-(3-(cyclohexylmethoxy)phenyl)-3-fluoropropan-1-amine

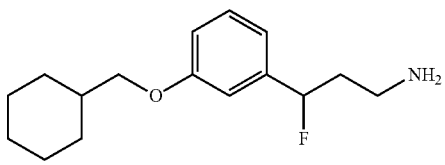 [SMILES: NCCC(F)c1cccc(OCC2CCCCC2)c1]

3-(3-(Cyclohexylmethoxy)phenyl)-3-fluoropropan-1-amine was prepared following the method shown in Scheme 58.

SCHEME 58

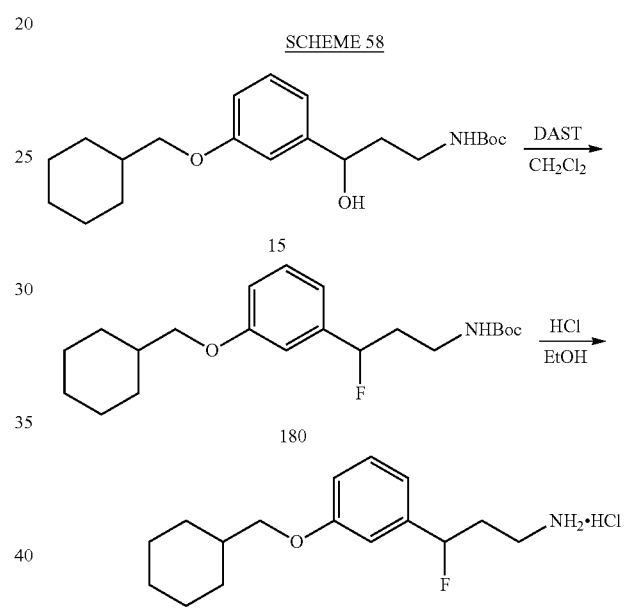

Step 1.

Dimethylaminosulfur trifluoride (DAST, 0.15 mL, 1.145 mmol) was added under argon atmosphere to a cooled (−78° C.) solution of alcohol 15 (0.4086 g, 1.124 mmol) in anhydrous CH$_2$Cl$_2$. The reaction mixture was stirred at −78° C. for 10 min and concentrated under reduced pressure. The residue was treated with hexanes/EtOAc and the precipitate formed was filtered off. The filtrate was concentrated under reduced pressure to give fluoride 180 which was used without purification.

Step 2.

An EtOAc solution of fluoride 180 was treated with HCl/EtOH and the reaction mixture was stirred at room temperature for 30 min, followed by concentration under reduced pressure. Purification by flash chromatography (10% to 50% EtOAc-hexanes gradient) gave Example 193 as a colorless oil. Yield (0.0784 g, 23%): $^1$H NMR (CD$_3$OD, 400 MHz) δ 7.22-7.27 (m, 1H), 6.80-6.90 (m, 3H), 5.50 (ddd, J=4.3, 8.6, 47.9 Hz, 1H), 3.76 (d, J=6.3 Hz, 2H), 2.70-2.82 (m, 2H), 1.66-2.14 (m, 8H), 1.16-1.38 (m, 3H), 1.02-1.14 (m, 2H); $^{19}$F NMR (CD$_3$OD, 376 MHz) δ −178.7 (ddd, J=16.7, 31.0, 47.7 Hz); RP-HPLC (Method 2) t$_R$=6.94 min, 96.5% (AUC).

Example 194

Preparation of 1-amino-3-(3-(cyclohexylmethoxy)phenyl)propan-2-one

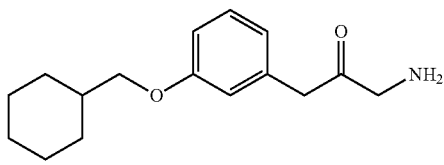 [SMILES: NCC(=O)Cc1cccc(OCC2CCCCC2)c1]

1-Amino-3-(3-(cyclohexylmethoxy)phenyl)propan-2-one is prepared following the method shown in Scheme 59.

SCHEME 59

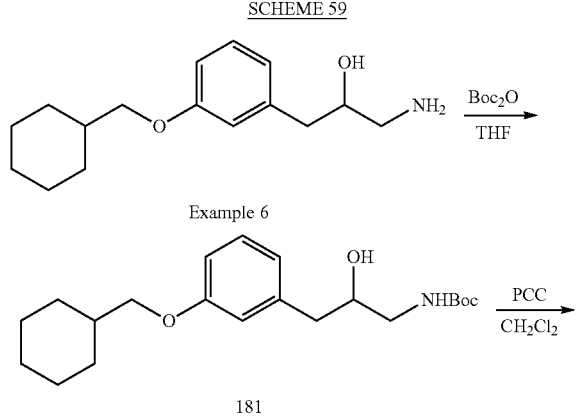

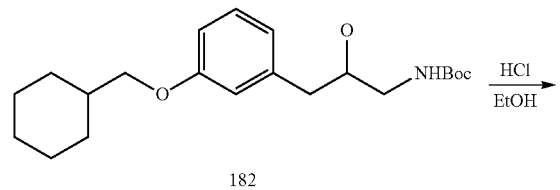

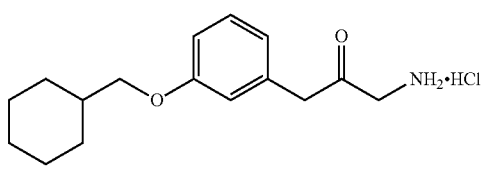

Step 1:

Example 6 is protected with Boc₂O following the method used in Example 5 to give carbamate 181.

Step 2:

PCC oxidation of alcohol 181 following the method used in Example 5 gives ketone 182.

Step 3:

Deprotection of ketone 182 following the method used in Example 5 gives Example 194 hydrochloride.

Example 195

Preparation of 3-(3-(cyclohexylmethoxy)phenyl)-2-fluoropropan-1-amine

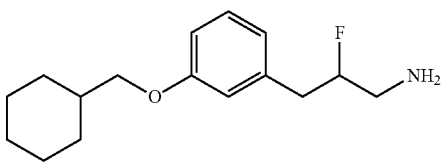 [SMILES: NCC(F)Cc1cccc(OCC2CCCCC2)c1]

3-(3-(Cyclohexylmethoxy)phenyl)-2-fluoropropan-1-amine is prepared following the method used for Example 193.

Step 1.

tert-Butyl 3-(3-(cyclohexylmethoxy)phenyl)-2-hydroxypropylcarbamate and DAST are reacted together to give tert-butyl 3-(3-(cyclohexylmethoxy)phenyl)-2-fluoropropylcarbamate.

Step 2.

Deprotection of tert-butyl 3-(3-(cyclohexylmethoxy)phenyl)-2-fluoropropylcarbamate gives Example 193 hydrochloride.

Example 196

Preparation of 4-(3-(cyclohexylmethoxy)phenyl)but-3-yn-1-amine

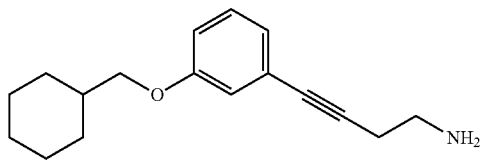 [SMILES: NCCC#Cc1cccc(OCC2CCCCC2)c1]

4-(3-(Cyclohexylmethoxy)phenyl)but-3-yn-1-amine was prepared following the method used in Example 1.

Deprotection of phthalimide 171 was performed following the method used in Example 1 except that the reaction mixture was heated at 50° C. for 24 hrs. After flash chromatography purification (10% to 50% of 10% 7N NH₃/MeOH/CH₂Cl₂—CH₂Cl₂ gradient) gave Example 196 as a colorless oil. The oil was dissolved in a small amount of EtOAc, and HCl/EtOH (7.4M, 0.1 mL) was added. The precipitate formed was collected by filtration, washed with EtOAc and hexanes, and dried in vacuo overnight to give Example 196 hydrochloride as a white solid. Yield (0.100 g, 55%); $^1$H NMR (400 MHz, CD₃OD) δ 7.19 (t, J=8.0 Hz, 1H), 6.94-6.99 (m, 2H), 6.88 (ddd, J=0.98, 2.5, 8.4 Hz, 1H), 3.74 (d, J=6.3 Hz, 2H), 3.16 (t, J=6.9 Hz, 2H), 2.82 (t, J=6.9 Hz, 2H), 1.65-1.88 (m, 6H), 1.15-1.37 (m, 3H), 1.01-1.13 (m, 2H); $^{13}$C NMR (100 MHz, CD₃OD) δ 159.4, 129.3, 123.9, 123.75, 117.4, 114.9, 83.2, 83.1, 73.4, 38.4, 37.9, 29.7, 26.4, 25.8, 17.8; RP-HPLC (Method 2), $t_R$=7.25 min, 98.8% (AUC).

Example 197

Preparation of 3-(3-(cyclohexylmethoxy)phenyl)prop-2-yn-1-amine

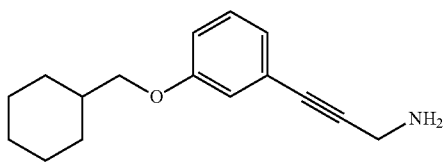 [SMILES: NCC#Cc1cccc(OCC2CCCCC2)c1]

3-(3-(Cyclohexylmethoxy)phenyl)prop-2-yn-1-amine was prepared as shown in Scheme 57

SCHEME 57

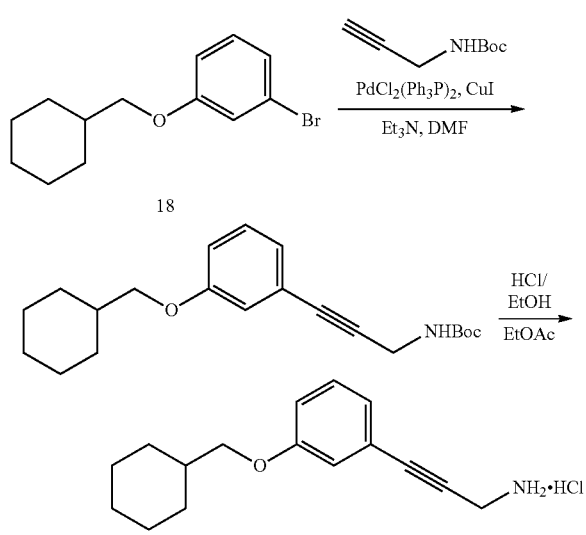

Step 1:

Sonogashira coupling between bromide 18 and tert-butyl prop-2-ynylcarbamate following the method used in Example 196 followed by purification by flash chromatography (5% to 30% EtOAc-hexanes gradient) gave tert-butyl 3-(3-(cyclohexylmethoxy)phenyl)prop-2-ynylcarbamate as a yellow oil. Yield (0.325 g, 49%); $^1$H NMR (400 MHz, DMSO-$d_6$) δ 7.31 (br.t, 1H), 7.22 (t, J=7.8 Hz, 1H), 6.86-6.94 (m, 3H), 3.94 (d, J=5.5 Hz, 2H), 3.74 (d, J=6.5 Hz, 2H), 1.58-1.80 (m, 6H), 1.37 (s, 9H), 1.10-1.28 (m, 3H), 0.94-1.06 (m, 2H).

Step 2:

Deprotection of tert-butyl 3-(3-(cyclohexylmethoxy)phenyl)prop-2-ynylcarbamate following the method used in Example 5 gave Example 197 hydrochloride as a white solid. Yield (0.1655 g, 63%); $^1$H NMR (400 MHz, CD$_3$OD) δ 7.25 (dt, J=0.6, 8.2 Hz, 1H), 7.01 (dt, J=1.0, 7.4 Hz, 1H), 6.92-6.98 (m, 2H), 4.01 (s, 2H), 3.75 (d, J=6.3 Hz, 2H), 1.68-1.89 (m, 6H), 1.15-1.38 (m, 3H), 1.10-1.14 (m, 2H); $^{13}$C NMR (100 MHz, CD$_3$OD) δ 159.5, 129.6, 123.8, 122.5, 117.4, 115.8, 86.6, 79.8, 73.4, 37.8, 29.7, 29.6, 26.4, 25.7; RP-HPLC (Method 2), $t_R$=7.25 min, 98.8% (AUC), LC-MS m/z 244.31 [M+H]$^+$.

Example 198

Preparation of (E)-3-(3-(cyclohexylmethoxy)-5-fluorophenyl)prop-2-en-1-amine

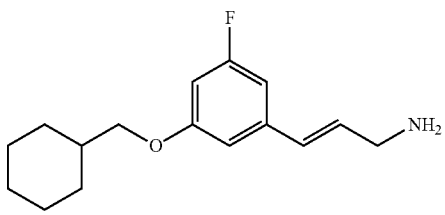 [SMILES: NC/C=C/c1cc(F)cc(OCC2CCCCC2)c1]

(E)-3-(3-(cyclohexylmethoxy)-5-fluorophenyl)prop-2-en-1-amine was prepared following the method described in Example 10.

Step 1:

Deprotection of (E)-N-(3-(3-(cyclohexylmethoxy)-5-fluorophenyl)allyl)-2,2,2-trifluoroacetamide following the method used in Example 10 gave Example 198 as a light yellow oil. Yield (0.10 g, 95%): $^1$H NMR (400 MHz, CD$_3$OD) δ 6.68-6.74 (m, 2H), 6.44-6.52 (m, 2H), 6.34 (dt, J=16.0, 6.0 Hz, 1H), 3.75 (d, J=6.4 Hz, 2H), 3.38 (d, J=5.6 Hz, 2H), 1.66-1.80 (m, 6H), 1.16-1.38 (m, 3H), 1.02-1.14 (m, 2H).

Biological Examples

Example 199

In Vitro Isomerase Inhibition Assay

The capability of compounds disclosed herein to inhibit the activity of a visual cycle isomerase was determined.

Isomerase inhibition reactions were performed essentially as described (Stecher et al., *J Biol. Chem.* 274:8577-85 (1999); see also Golczak et al., *Proc. Natl. Acad. Sci.* USA 102:8162-67 (2005)). Bovine Retinal Pigment Epithelium (RPE) microsome membranes were the source of a visual cycle isomerase.

RPE Microsome Membrane Preparation

Bovine RPE microsome membrane extracts were prepared according to methods described (Golczak et al., *Proc. Natl. Acad. Sci.* USA 102:8162-67 (2005)) and stored at −80° C. Crude RPE microsome extracts were thawed in a 37° C. water bath, and then immediately placed on ice. 50 ml crude RPE microsomes were placed into a 50 ml Teflon-glass homogenizer (Fisher Scientific, catalog no. 0841416M) on ice, powered by a hand-held DeWalt drill, and homogenized ten times up and down on ice under maximum speed. This process was repeated until the crude RPE microsome solution was homogenized. The homogenate was then subjected to centrifugation (50.2 Ti rotor (Beckman, Fullerton, Calif.), 13,000 RPM; 15360 Rcf) for 15 minutes at 4° C. The supernatant was collected and subjected to centrifugation at 42,000 RPM (160,000 Rcf, 50.2 Ti rotor) for 1 hour at 4° C. The supernatant was removed, and the pellets were suspended in 12 ml (final volume) cold 10 mM MOPS buffer, pH 7.0. The resuspended RPE membranes in 5 ml aliquots were homogenized in a glass-to-glass homogenizer (Fisher Scientific, catalog no. K885500-0021) to high homogeneity. Protein concentration was quantified using the BCA protein assay according to the manufacturer's protocol (Pierce, Rockford, Ill.). The homogenized RPE preparations were stored at −80° C.

Isolation of Human Apo Cellular Retinaldehyde-Binding Protein (CRALBP)

Recombinant human apo cellular retinaldehyde-binding protein (CRALBP) was cloned and expressed according to standard molecular biology methods (see Crabb et al., *Protein Science* 7:746-57 (1998); Crabb et al., *J. Biol. Chem.* 263:18688-92 (1988)). Briefly, total RNA was prepared from confluent ARPE19 cells (American Type Culture Collection, Manassas, Va.), cDNA was synthesized using an oligo(dT)$_{12-18}$ primer, and then DNA encoding CRALBP was amplified by two sequential polymerase chain reactions (see Crabb et al., *J. Biol. Chem.* 263:18688-92 (1988); Intres, et al., *J. Biol. Chem.* 269:25411-18 (1994); GenBank Accession No. L34219.1). The PCR product was sub-cloned into pTrcHis2-TOPO TA vector according to the manufacturer's protocol (Invitrogen Inc., Carlsbad, Calif.; catalog no. K4400-01), and then the sequence was confirmed according to standard nucleotide sequencing techniques. Recombinant 6xHis-tagged human CRALBP was expressed in One Shot TOP 10 chemically competent *E. coli* cells (Invitrogen), and the recombinant polypeptide was isolated from *E. coli* cell lysates by nickel affinity chromatography using nickel (Ni) Sepharose XK16-20 columns for HPLC (Amersham Bioscience, Pittsburgh, Pa.; catalog no. 17-5268-02). The purified 6xHis-tagged human CRALBP was dialyzed against 10 mM bis-tris-Propane (BTP) and analyzed by SDS-PAGE. The molecular weight of the recombinant human CRALBP was approximately 39 kDal.

Isomerase Assay

Compounds disclosed herein and control compounds were reconstituted in ethanol to 0.1 M. Ten-fold serial dilutions ($10^{-2}$, $10^{-3}$, $10^{-4}$, $10^{-5}$, $10^{-6}$ M) in ethanol of each compound were prepared for analysis in the isomerase assay.

The isomerase assay was performed in 10 mM bis-tris-propane (BTP) buffer, pH 7.5, 0.5% BSA (diluted in BTP buffer), 1 mM sodium pyrophosphate, 20 µM all-trans retinol (in ethanol), and 6 µM apo-CRALBP. The test compounds (2 µl) (final 1/15 dilution of serial dilution stocks) were added to the above reaction mixture to which RPE microsomes were added. The same volume of ethanol was added to the control reaction (absence of test compound). Bovine RPE microsomes (9 µl) (see above) were then added, and the mixtures transferred to 37° C. to initiate the reaction (total volume=150 µl). The reactions were stopped after 30 minutes by adding methanol (300 µl). Heptane was added (300 µl) and mixed into the reaction mixture by pipetting. Retinoid was extracted by agitating the reaction mixtures, followed by centrifugation in a microcentrifuge. The upper organic phase was transferred to HPLC vials and then analyzed by HPLC using an Agilent 1100 HPLC system with normal phase column: SILICA (Agilent Technologies, dp 5µ, 4.6 mmX, 25 CM; running method had flow rate of 1.5 ml/min; injection volume 100 µl). The solvent components were 20% of 2% isopropanol in EtOAc and 80% of 100% hexane.

Figure 4:
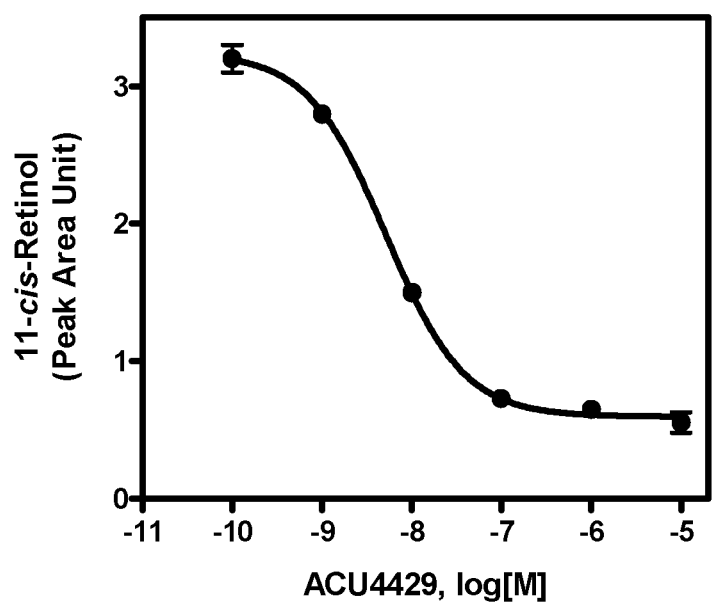
FIG. 4 illustrates concentration-dependent inhibition of isomerase activity by the compound of Example 28 (Compound 28) in an isomerase assay.

The area under the $A_{318}$ nm curve represented the 11-cis retinol peak, which was calculated by Agilent Chemstation software and recorded manually. The IC$_{50}$ values (concentration of compound that gives 50% inhibition of 11-cis retinol formation in vitro) were calculated using GraphPad Prism® 4 Software (Irvine, Calif.). All tests were performed in duplicate. The IC$_{50}$ value for Compound 28 is shown in FIG. 4.

The concentration dependent effect of the compounds disclosed herein on the retinol isomerization reaction was also evaluated with a recombinant human enzyme system. In particular, the human in vitro isomerase assay was performed essentially as in Golczak et al. 2005, PNAS 102: 8162-8167, ref. 3). A homogenate of HEK293 cell clone expressing recombinant human RPE65 and LRAT were the source of the visual enzymes, and exogenous all-trans-retinol (about 20 µM) was used as the substrate. Recombinant human CRALBP (about 80 ug/mL) was added to enhance the formation of 11 cis-retinal. The 200 µL Bis-Tris Phosphate buffer (10 mM, pH 7.2) based reaction mixture also contains 0.5% BSA, and 1 mM NaPPi. In this assay, the reaction was carried out at 37° C. in duplicates for one hour and was terminated by addition of 300 µL methanol. The amount of reaction product, 11-cis-retinol, was measured by HPLC analysis following Heptane extraction of the reaction mixture. The Peak Area Units (PAUs) corresponding to 11 cis-retinol in the HPLC chromatograms were recorded and concentration dependent curves analyzed by GraphPad Prism for IC$_{50}$ values. The ability of the numerous compounds disclosed herein to inhibit isomerization reaction is quantified and the respective IC50 value is determined. Tables 9A and 9B below summarize the IC50 values of various compounds disclosed herein determined by either of the above two methods.

TABLE 9A

Human in vitro Inhibition data

| IC$_{50}$ (µM) | Compound/Example Number |
|---|---|
| ≤0.01 µM | 4, 13, 15, 17, 28, 30, 34, 35, 45, 48, 55, 56, 72, 74, 87, 88, 169, 171, 172, 175, 176 |
| >0.01 µM-≤0.1 µM | 1, 2, 3, 5, 6, 7, 9, 10, 12, 16, 20, 25, 29, 32, 36, 37, 46, 47, 49, 54, 66, 67, 68, 69, 71, 73, 75, 81, 83, 90, 92, 93, 103, 104, 105, 106, 107, 108, 114, 115, 123, 130, 131,147, 148, 154, 158, 161, 163, 166, 170, 173, 174, 178, 179, 180, 187, 193, 197 |
| >0.1 µM-≤1 µM | 8, 11, 14, 18, 26, 31, 33, 38, 41, 44, 50, 51, 52, 53, 57, 58, 59, 60, 61, 62, 63, 64, 65, 70, 78, 80, 82, 84, 85, 86, 89, 91, 94, 96, 99, 101, 102, 122, 124, 125, 126, 127, 129, 135, 139, 140, 143, 150, 151, 152, 153, 156, 157, 162, 164, 165, 167, 168, 177, 181, 198 |
| >1 µM-≤10 µM | 40, 42, 76, 77, 79, 95, 98, 100, 109, 113, 128, 133, 134, 136, 137, 138, 142, 144, 145, 146, 149, 159, 160, 184, 190, 196 |
| >10 µM | 170, 182 |
| No detectable activity | 119, 120, 121, 141 |

TABLE 9B

Bovine in vitro Inhibition data

| IC$_{50}$ (µM) | Compound/Example Number |
|---|---|
| ≤1 µM | 1, 2, 3, 4, 5, 6, 7, 9, 10, 11, 12, 13, 14, 15, 16, 17, 20, 28, 29 |
| >1 µM-≤10 µM | 8, 18, 19 |

Example 200

In Vivo Murine Isomerase Assay

The capability of compounds described herein to inhibit isomerase was determined by an in vivo murine isomerase assay. Brief exposure of the eye to intense light ("photobleaching" of the visual pigment or simply "bleaching") is known to photo-isomerize almost all 11-cis-retinal in the retina. The recovery of 11-cis-retinal after bleaching can be used to estimate the activity of isomerase in vivo. Delayed recovery, as represented by lower 11-cis-retinal oxime levels, indicates inhibition of isomerization reaction. Procedures were performed essentially as described by Golczak et al., *Proc. Natl. Acad. Sci. USA* 102:8162-67 (2005). See also Deigner et al., *Science*, 244: 968-71 (1989); Gollapalli et al., *Biochim Biophys Acta.* 1651: 93-101 (2003); Parish, et al., *Proc. Natl. Acad. Sci. USA*, 14609-13 (1998); Radu, et al., *Proc Natl Acad Sci USA* 101: 5928-33 (2004).

Six-week old dark-adapted CD-1 (albino) male mice were orally gavaged with compound (0.03-3 mg/kg) dissolved in 100 µl corn oil containing 10% ethanol (five animals per group). Mice were gavaged with the compound of Example 4 (3-amino-1-(3-(cyclohexylmethoxy)phenyl)propan-1-ol) (referred to Compound 4). After 2-24 hours in the dark, the mice were exposed to photobleaching of 5,000 lux of white light for 10 minutes. The mice were allowed to recover 2 hours in the dark. The animals were then sacrificed by carbon dioxide inhalation. Retinoids were extracted from the eye and the regeneration of 11-cis-retinal was assessed at various time intervals.

Eye Retinoid Extraction

All steps were performed in darkness with minimal redlight illumination (low light darkroom lights and redfiltered flashlights for spot illumination as needed) (see, e.g., Maeda et al., *J. Neurochem* 85:944-956, 2003; Van Hooser et al., *J Biol Chem* 277:19173-82, 2002). After the mice were sacrificed, the eyes were immediately removed and placed in liquid nitrogen for storage.

The eyes were placed in 500 µL of bis-tris propane buffer (10 mM, pH~7.3) and 20 µL of 0.8M hydroxile amine (pH~7.3). The eyes were cut up into small pieces with small iris scissors and then thoroughly homogenized at 30000 rpm with a mechanical homogenizer (Polytron PT 1300 D) in the tube until no visible tissue remained. 500 µL of methanol and 500 µL of heptane were added to each tube. The tubes were attached to a vortexer so that the contents were mixed thoroughly for 15 minutes in room temperature. The organic phase was separated from the aqueous phase by centrifugation for 10 min at 13K rpm, 4° C. 240 µL of the solution from the top layer (organic phase) was removed and transferred to clean 300 µl glass inserts in HPLC vials using glass pipette and the vials were crimped shut tightly.

The samples were analyzed on an Agilent 1100 HPLC system with normal phase column: SILICA (Beckman Coutlier, dp 5 µm, 4.6 mM×250 mM). The running method has a flow rate of 1.5 ml/min; solvent components are 15% solvent 1 (1% isopropanol in ethyl acetate), and 85% solvent 2 (100% hexanes). Loading volume for each sample is 100 µl; detection wavelength is 360 nm. The area under the curve for 11-cis retinal oxime was calculated by Agilent Chemstation software and was recorded manually. Data processing was performed using Prizm software.

Positive control mice (no compound administered) were sacrificed fully dark-adapted and the eye retinoids analyzed. Light (bleached) control mice (no compound administered) were sacrificed and retinoids isolated and analyzed immediately after light treatment.

Figure 2:
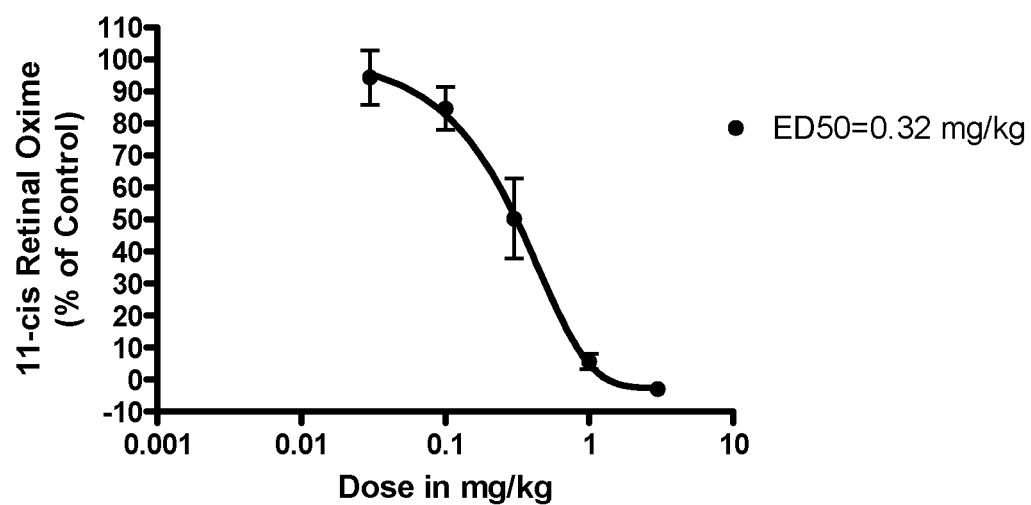
FIG. 2 illustrates concentration-dependent inhibition of isomerase activity by Compound 4 in an in vivo mouse model.

The time-dependent isomerase inhibitory activity of Compound 4 is presented in FIG. 1 The concentration-dependent isomerase inhibitory activity of Compound 4 is presented in FIG. 2. The estimated $ED_{50}$ (dose of compound that gives 50% inhibition of 11-cis retinal (oxime) recovery) calculated was 0.32 mg/kg for Compound 4.

Figure 3:
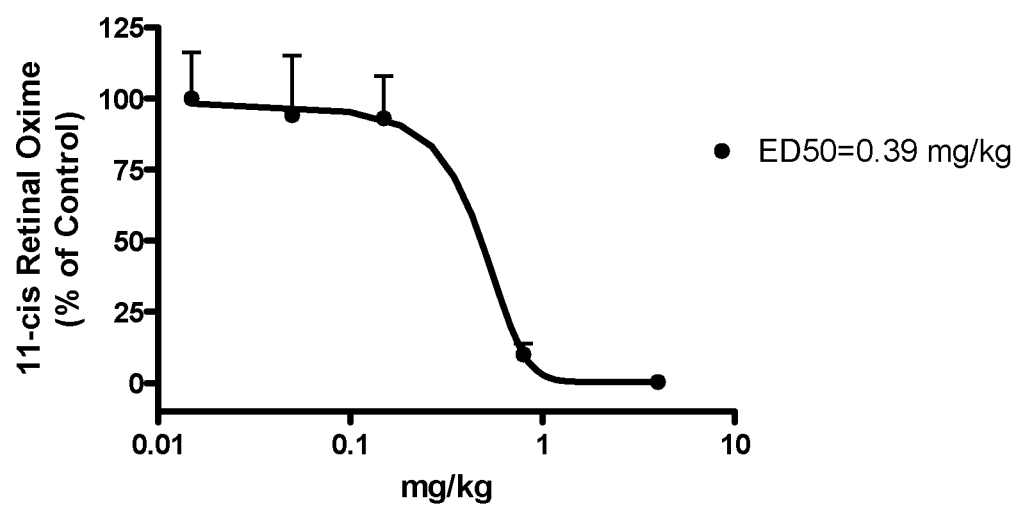
FIG. 3 illustrates concentration-dependent inhibition of isomerase activity by Compound 4 when the compound was administered daily for a week.

An additional experiment was performed to determine the $ED_{50}$ of Compound 4 when administered to animals daily for one week. Compound 4 was administered to five groups of mice at doses between 0.015 to 4 mg/kg by oral gavage once daily. After the last dose on day 7 the mice were housed 4 hours in the dark and then photobleached by exposing the animals to 5,000 lux of white light for 10 minutes. The mice were allowed to recover 2 hours in the dark. The animals were then sacrificed by carbon dioxide inhalation. Retinoids were extracted from the eye and the regeneration of 11-cis-retinal was assessed. The data are presented in FIG. 3.

A time course study was performed to determine the isomerase inhibitory activity of the compound of Example 28 (Compound 28). Male Balb/c mice (4/group) received 0.3 mg Compound 28-HCl (in water) per kg bodyweight orally, by gavage. The animals were then "photo-bleached" (5000 Lux white light for 10 minutes) at 2, 4, 8, 16 and 24 hours after dosing, and returned to darkness to allow recovery of the 11-cis-retinal content of the eyes. Mice were sacrificed 2 hours after bleaching, eyes were enucleated, and retinoid content was analyzed by HPLC.

Figure 5:
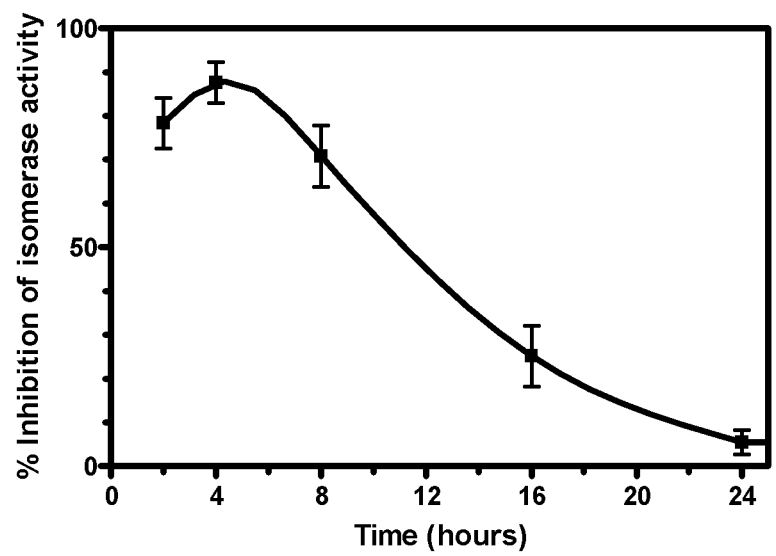
FIG. 5 illustrates time-dependent inhibition of isomerase activity by Compound 28 in a mouse model. Four animals were included in each treatment group. The error bars correspond to standard error.

Full effect was seen at 4 hours after administration of Compound 28. Recovery control mice (vehicle-only treated) were light-treated and left to recover for 2 hours in the dark before sacrifice and analysis. Light control mice (vehicle only treated) were sacrificed for analysis immediately after photo-bleaching. Results are presented in FIG. 5. Maximum effect was achieved at about 4 hours after oral gavage with Compound 28. Recovery was substantially inhibited at all subsequent time points, returning to normal at 24 hours. The 4 hour time point was selected for assessments in subsequent studies.

Figure 6:
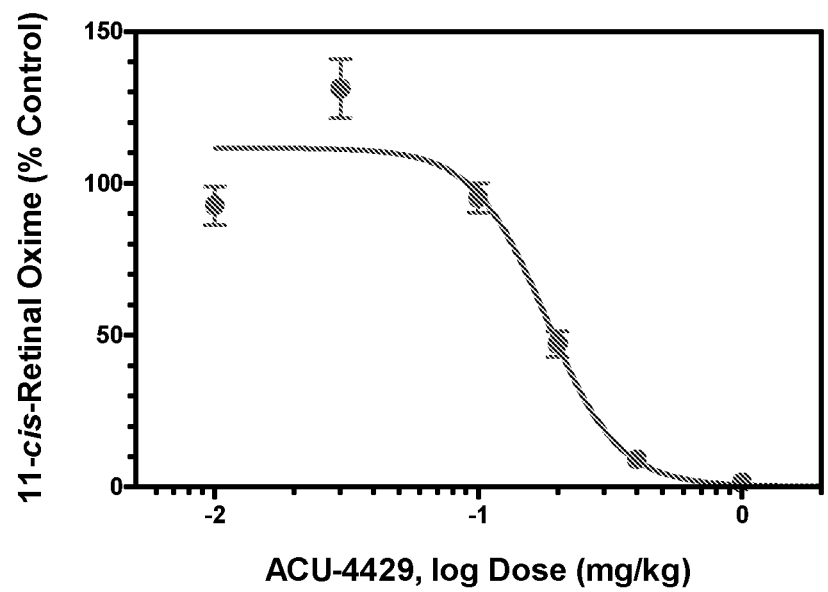
FIG. 6 illustrates concentration-dependent inhibition of isomerase activity by Compound 28 in an in vivo mouse model. Eight animals were included in a treatment group. The error bars correspond to standard error.

An in vivo dose response isomerase inhibition study was performed with Compound 28. Male Balb/c mice (8/group) were dosed orally with 0.03, 0.1, 0.3, 1 and 3 mg/kg Compound 28-HCl in sterile water as solution, and photo-bleached 4 hours after dosing. Recovery and retinoid analysis were performed as described above. Dark control mice were vehicle-only treated, sacrificed fully dark adapted without light treatment, and analyzed. Recovery control mice and light control mice were as per the initial phase. Results are presented in FIG. 6. Inhibition of recovery was dose related, with the $ED_{50}$ estimated at 0.18 mg/kg (n=8). A similar experiment was performed with the compound of Example 29 (Compound 29). The $ED_{50}$ estimated from the data was 0.83 mg/kg.

In another experiment, male Balb/c mice were dosed with Compound 28-HCl as above but the dosing was repeated twice daily for 7 consecutive days. The animals were photobleached 4 hours after the last dose. Recovery and retinoid analysis was as per the initial phase and the $ED_{50}$ was estimated at 0.16 mg/kg in this repeat dose study (n=8). Compound 28 effectively inhibited isomerization in a dose-related manner in mice. Maximum inhibition was achieved 4 hours after dosing.

In similar experiments, female Sprague-Dawley rats (n=4) were dosed with a single dose of Compound 28-HCl in sterile water by oral gavage. The time course and dose response after a single dose was very similar in rats ($ED_{50}$=0.12 mg/kg) as observed in mice.

Table 10 presents in vivo inhibition of isomerase data.

TABLE 10

In Vivo Inhibition Data

| Example No. | % Inhibition 1 mg/kg, 4 h | $ED_{50}$ (mg/Kg) |
|---|---|---|
| 1 | 68 | |
| 2 | 1 | |
| 3 | 12 | |
| 4 | 94 | 0.32 |

TABLE 10-continued

In Vivo Inhibition Data

| Example No. | % Inhibition 1 mg/kg, 4 h | $ED_{50}$ (mg/Kg) |
|---|---|---|
| 5 | | 1 |
| 7 | 17 | 4.2 |
| 9 | 6 | |
| 12 | 59 | |
| 13 | 41 | |
| 14 | 89 | |
| 15 | 91 | |
| 16 | 60 | |
| 17 | 96 | |
| 20 | 98 | |
| 28 | 98 | 0.18 |
| 29 | | 0.83 |
| 30 | 57 | |
| 35 | 95 | |
| 45 | 98 | |
| 47 | 6 | |
| 48 | 47 | |
| 55 | 82 | |
| 56 | 10 | |
| 72 | 13 | |
| 73 | 23 | |
| 74 | 6 | |
| 77 | 22 | |
| 88 | 78 | |
| 107 | 62 | |
| 125 | 4 | |
| 130 | 3 | |

*The compounds of Example 6, 8, 10-11, 18, 49 and 75 have no detectable activity in this particular assay.

Example 201

Preparation of Retinal Neuronal Cell Culture System

This example describes methods for preparing a long-term culture of retinal neuronal cells. All compounds and reagents can be obtained from Sigma Aldrich Chemical Corporation (St. Louis, Mo.) or other suitable vendors.

Retinal Neuronal Cell Culture

Porcine eyes are obtained from Kapowsin Meats, Inc. (Graham, Wash.). Eyes are enucleated, and muscle and tissue are cleaned away from the orbit. Eyes are cut in half along their equator and the neural retina is dissected from the anterior part of the eye in buffered saline solution, according to standard methods known in the art. Briefly, the retina, ciliary body, and vitreous are dissected away from the anterior half of the eye in one piece, and the retina is gently detached from the clear vitreous. Each retina is dissociated with papain (Worthington Biochemical Corporation, Lakewood, N.J.), followed by inactivation with fetal bovine serum (FBS) and addition of 134 Kunitz units/ml of DNaseI. The enzymatically dissociated cells are triturated and collected by centrifugation, resuspended in Dulbecco's modified Eagle's medium (DMEM)/F12 medium (Gibco BRL, Invitrogen Life Technologies, Carlsbad, Calif.) containing about 25 μg/ml of insulin, about 100 μg/ml of transferrin, about 60 μM putrescine, about 30 nM selenium, about 20 nM progesterone, about 100 U/ml of penicillin, about 100 μg/ml of streptomycin, about 0.05 M Hepes, and about 10% FBS. Dissociated primary retinal cells are plated onto Poly-D-lysine- and Matrigel- (BD, Franklin Lakes, N.J.) coated glass coverslips that are placed in 24-well tissue culture plates (Falcon Tissue Culture Plates, Fisher Scientific, Pittsburgh, Pa.). Cells are maintained in culture for 5 days to one month in 0.5 ml of media (as above, except with only 1% FBS) at 37° C. and 5% $CO_2$.

Immunocytochemistry Analysis

The retinal neuronal cells are cultured for about 1, 3, 6, and 8 weeks, and the cells are analyzed by immunohistochemistry at each time point. Immunocytochemistry analysis is performed according to standard techniques known in the art. Rod photoreceptors are identified by labeling with a rhodopsin-specific antibody (mouse monoclonal, diluted about 1:500; Chemicon, Temecula, Calif.). An antibody to mid-weight neurofilament (NFM rabbit polyclonal, diluted about 1:10,000, Chemicon) is used to identify ganglion cells; an antibody to 33-tubulin (G7121 mouse monoclonal, diluted about 1:1000, Promega, Madison, Wis.) is used to generally identify interneurons and ganglion cells, and antibodies to calbindin (AB 1778 rabbit polyclonal, diluted about 1:250, Chemicon) and calretinin (AB5054 rabbit polyclonal, diluted about 1:5000, Chemicon) are used to identify subpopulations of calbindin- and calretinin-expressing interneurons in the inner nuclear layer. Briefly, the retinal cell cultures are fixed with 4% paraformaldehyde (Polysciences, Inc, Warrington, Pa.) and/or ethanol, rinsed in Dulbecco's phosphate buffered saline (DPBS), and incubated with primary antibody for about 1 hour at 37° C. The cells are then rinsed with DPBS, incubated with a secondary antibody (Alexa 488- or Alexa 568-conjugated secondary antibodies (Molecular Probes, Eugene, Oreg.)), and rinsed with DPBS. Nuclei are stained with 4', 6-diamidino-2-phenylindole (DAPI, Molecular Probes), and the cultures are rinsed with DPBS before removing the glass coverslips and mounting them with Fluoromount-G (Southern Biotech, Birmingham, Ala.) on glass slides for viewing and analysis.

Survival of mature retinal neurons after varying times in culture is indicated by the histochemical analyses. Photoreceptor cells are identified using a rhodopsin antibody; ganglion cells are identified using an NFM antibody; and amacrine and horizontal cells are identified by staining with an antibody specific for calretinin.

Cultures are analyzed by counting rhodopsin-labeled photoreceptors and NFM-labeled ganglion cells using an Olympus IX81 or CZX41 microscope (Olympus, Tokyo, Japan). Twenty fields of view are counted per coverslip with a 20× objective lens. Six coverslips are analyzed by this method for each condition in each experiment. Cells that are not exposed to any stressor are counted, and cells exposed to a stressor are normalized to the number of cells in the control. It is expected that compounds presented in this disclosure promote dose-dependent and time-dependent survival of mature retinal neurons.

Example 202

Effect of Compounds on Retinal Cell Survival

This Example describes the use of the mature retinal cell culture system that comprises a cell stressor for determining the effects of any compound disclosed herein on the viability of the retinal cells.

Retinal cell cultures are prepared as described in Example 201. A2E is added as a retinal cell stressor. After culturing the cells for about 1 week, a chemical stress, A2E, is applied. A2E is diluted in ethanol and added to the retinal cell cultures at concentration of about 0, 10 μM, 20 μM, and 40 μM. Cultures are treated for about 24 and 48 hours. A2E is obtained from Dr. Koji Nakanishi (Columbia University, New York City, N.Y.) or is synthesized according to the method of Parish et al. (*Proc. Natl. Acad. Sci. USA* 95:14602-13 (1998)). Any compound disclosed herein is then added to the culture. To other retinal cell cultures, any compound disclosed herein is added before application of the stressor or is added at the same time that A2E is added to the retinal cell culture. The cultures are maintained in tissue culture incubators for the duration of the stress at 37° C. and 5% $CO_2$. The cells are then analyzed by immunocytochemistry as described in Example 201.

Apoptosis Analysis

Retinal cell cultures are prepared as described in Example 201 and cultured for about 2 weeks and then exposed to white light stress at about 6000 lux for about 24 hours followed by a 13-hour rest period. A device was built to uniformly deliver light of specified wavelengths to specified wells of the 24-well plates. The device contains a fluorescent cool white bulb (GE P/N FC12T9/CW) wired to an AC power supply. The bulb is mounted inside a standard tissue culture incubator. White light stress is applied by placing plates of cells directly underneath the fluorescent bulb. The $CO_2$ levels are maintained at about 5%, and the temperature at the cell plate is maintained at 37° C. The temperature is monitored by using thin thermocouples. The light intensities for all devices is measured and adjusted using a light meter from Extech Instruments Corporation (P/N 401025; Waltham, Mass.). Any compound disclosed herein is added to wells of the culture plates prior to exposure of the cells to white light and is added to other wells of the cultures after exposure to white light. To assess apoptosis, TUNEL is performed as described herein.

Apoptosis analysis is also performed after exposing retinal cells to blue light. Retinal cell cultures are cultured as described in Example 201. After culturing the cells for about 1 week, a blue light stress is applied. Blue light is delivered by a custom-built light-source, which consists of two arrays of 24 (4×6) blue light-emitting diodes (Sunbrite LED P/N SSP-01TWB7UWB12), designed such that each LED is registered to a single well of a 24 well disposable plate. The first array is placed on top of a 24 well plate full of cells, while the second one is placed underneath the plate of cells, allowing both arrays to provide a light stress to the plate of cells simultaneously. The entire apparatus is placed inside a standard tissue culture incubator. The $CO_2$ levels are maintained at about 5%, and the temperature at the cell plate is maintained at about 37° C. The temperature is monitored with thin thermocouples. Current to each LED is controlled individually by a separate potentiometer, allowing a uniform light output for all LEDs. Cell plates are exposed to about 2000 lux of blue light stress for either about 2 hours or 48 hours, followed by a about 14-hour rest period. One or more compounds disclosed herein are added to wells of the culture plates prior to exposure of the cells to blue light and added to other wells of the cultures after exposure to blue light. To assess apoptosis, TUNEL is performed as described herein.

To assess apoptosis, TUNEL is performed according to standard techniques practiced in the art and according to the manufacturer's instructions. Briefly, the retinal cell cultures are first fixed with 4% paraformaldehyde and then ethanol, and then rinsed in DPBS. The fixed cells are incubated with TdT enzyme (0.2 units/µl final concentration) in reaction buffer (Fermentas, Hanover, Md.) combined with Chroma-Tide Alexa568-5-dUTP (0.1 µM final concentration) (Molecular Probes) for about 1 hour at 37° C. Cultures are rinsed with DPBS and incubated with primary antibody either overnight at 4° C. or for about 1 hour at 37° C. The cells are then rinsed with DPBS, incubated with Alexa 488-conjugated secondary antibodies, and rinsed with DPBS. Nuclei are stained with DAPI, and the cultures are rinsed with DPBS before removing the glass coverslips and mounting them with Fluoromount-G on glass slides for viewing and analysis.

Cultures are analyzed by counting TUNEL-labeled nuclei using an Olympus IX81 or CZX41 microscope (Olympus, Tokyo, Japan). Twenty fields of view are counted per coverslip with a 20× objective lens. Six coverslips are analyzed by this method for each condition. Cells that are not exposed to a test compound are counted, and cells exposed to the antibody are normalized to the number of cells in the control. Data are analyzed using the unpaired Student's t-test. It is expected that compounds of this disclosure reduce A2E-induced apoptosis and cell death in retinal cell cultures in a dose-dependent and time-dependent manner.

Example 203

In Vivo Light Mouse Model

This Example describes the effect of a compound disclosed herein in an in vivo light damage mouse model.

Exposure of the eye to intense white light can cause photo-damage to the retina. The extent of damage after light treatment can be evaluated by measuring cytoplasmic histone-associated-DNA-fragment (mono- and oligonucleosomes) content in the eye (see, e.g., Wenzel et al., *Prog. Retin. Eye Res.* 24:275-306 (2005)).

Figure 7:
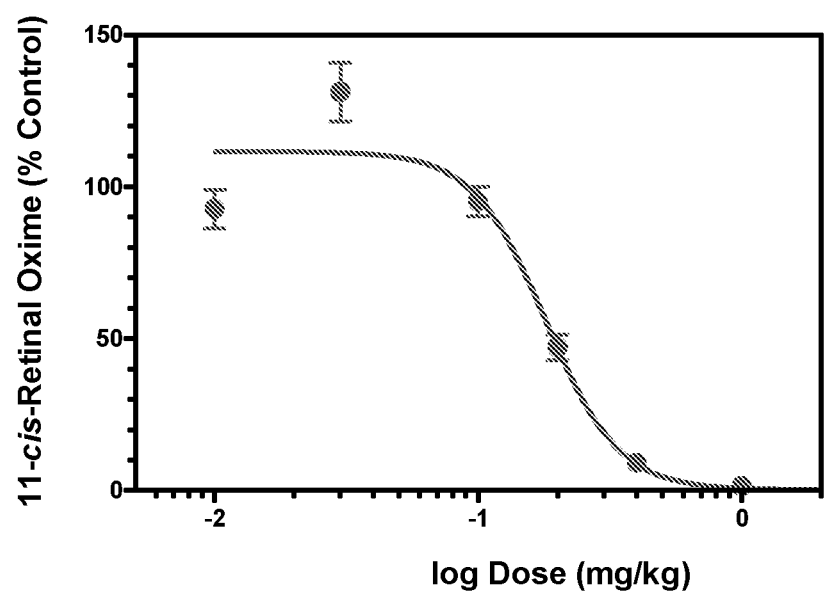
FIG. 7 illustrates concentration-dependent inhibition of light damage to the retina of mice (10 animals per group) treated with Compound 4 prior to exposure to light treatment (8,000 lux of white light for one hour). The error bars correspond to standard error.

Dark adapted male Balb/c (albino, 10/group) mice were gavaged with the Compound of Example 4 (Compound 4) at various doses (0.03, 0.1, 0.3, 1, and 3 mg/kg) or vehicle only was administered. Six hours after dosing, the animals were subjected to light treatment (8,000 lux of white light for 1 hour). Mice were sacrificed after 40 hours of recovery in dark, and retinas were dissected. A cell death detection ELISA assay was performed according to the manufacturer's instructions (ROCHE APPLIED SCIENCE, Cell Death Detection ELISA plus Kit). Contents of fragmented DNA in the retinas were measured to estimate the retinal-protective activity of Compound 4; the results are presented in FIG. 7. Compound 4 had an $ED_{50}$ of 0.3 mg/kg.

Example 204

Electroretinographic (ERG) Study

ERG experiments were performed using 11-16 week old BALB/c mice of both genders (n=5). All studies involved the pharmacodynamic assessment of dark-adapted (scotopic, rod-dominated) and light-adapted (photopic, cone-dominated) ERG responses. Experiments were performed using the Compound of Example 4 (Compound 4). All recording procedures were performed according to the same protocol and with the same equipment. Data were aggregated across individual studies to generate summary graphs.

Figure 8:
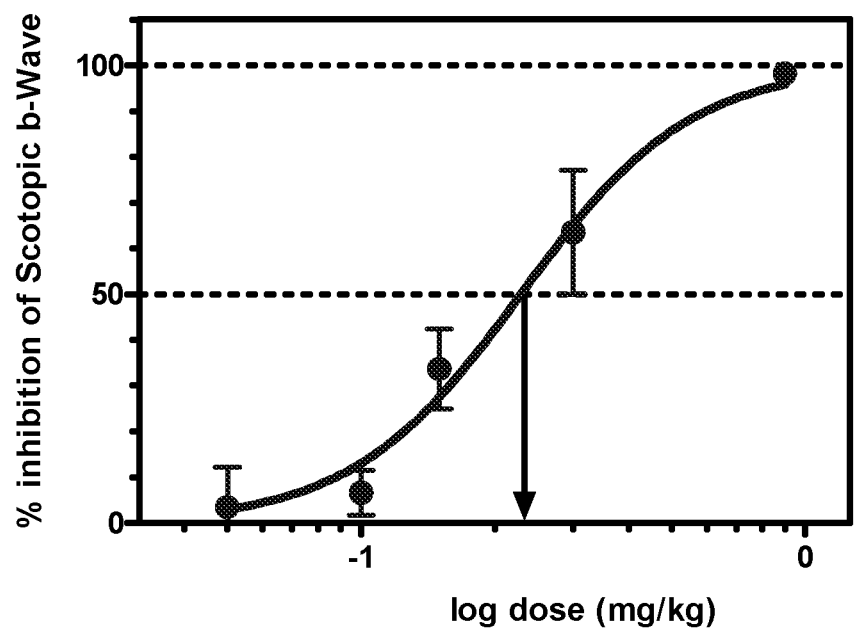
FIG. 8 illustrates the concentration-dependent inhibition of scotopic b-wave amplitude in adult BALB/c mice (4 mice/group) that received Compound 4.

Results from four independent studies were combined to build the dose-response function between administration of Compound 4 and changes in the amplitude of the scotopic b-wave (0.01 cd·s/m²), 4 hours after single oral administration of the drug (base form, dissolved in corn oil). The resulting relationship is presented in FIG. 8. As shown in FIG. 8, a typical sigmoidal dose-response function fitted the data relatively well ($R^2$=0.62). Based on the fit, an $ED_{50}$ value of 0.23 mg/kg was determined.

The effect on the cone system was estimated based on recording and measurement of the ERG b-wave intensity-response function under photopic conditions. In such studies, two parameters are typically evaluated: maximal response ($V_{max}$), measured in microvolts, and semi-saturation constant (k), measured in cd·s/m².

Figure 9:
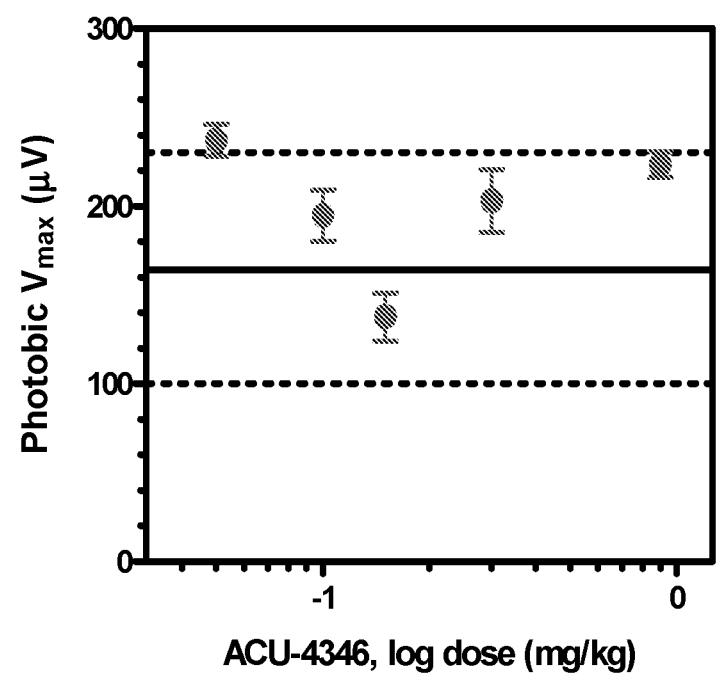
FIG. 9 illustrates the effect of Compound 4 on photobic $V_{max}$. The solid line represents the average and the dotted line represents the upper and lower limits for the parameter (3 mice/group). The error bars correspond to standard error.

Results from three independent studies were combined to estimate the effect of single dosing of Compound 4 on the photopic ERG (11-16 week old BALB/c mice of both genders, n=5). As shown in FIG. 9, Compound 4 had no effect on the maximal photopic response ($V_{max}$). However, the semi-saturation constant (photopic k) was increased with an estimated $ED_{50}$ of 0.36 mg/kg.

Example 205

Effect of Compounds on Reduction of Lipofuscin Fluorophores

This Example describes the capability of compound described herein to reduce the level of existing A2E in the retina of mice as well as prevention of the formation of A2E.

The eyes of abca4-null (abca4–/–) mutant mice (see, e.g., Weng et al., Cell 98:13-23 (1999) have an increased accumulation of lipofuscin flourophores, such as A2E (see, e.g., Karan et al., Proc. Natl. Acad. Sci. USA 102:4164-69 (2005)). The Compound of Example 4 (Compound 4) (1 mg/kg) or vehicle was administered daily for three months by oral gavage to abca4$^{-/-}$ mice that were about 2 months old. Mice were sacrificed after three months of treatment. Retinas and RPE were extracted for A2E analysis.

Figure 10:
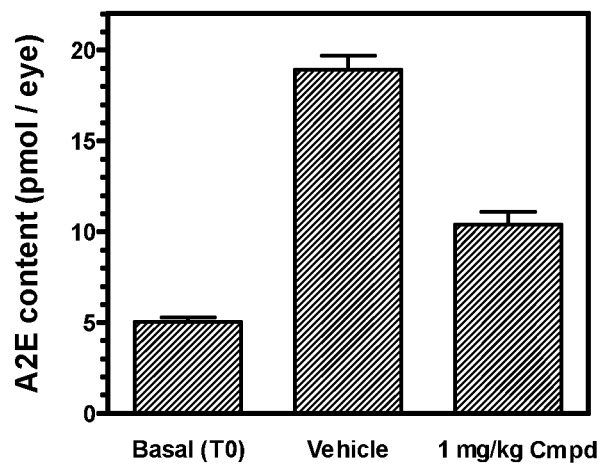
FIG. 10 illustrates the A2E content in the eyes of mice treated with Compound 4 for three months (n=10; five males and five females).

Compound 4-HCl significantly reduced the levels of A2E (10.4 picomoles/eye) in retina of abca4$^{-/-}$ mice treated with 1 mg/kg/day for three months compared to abca4$^{-/-}$ mice treated with vehicle (18.9 picomole/eye, p<0.001). The data are presented in FIG. 10.

Figure 11:
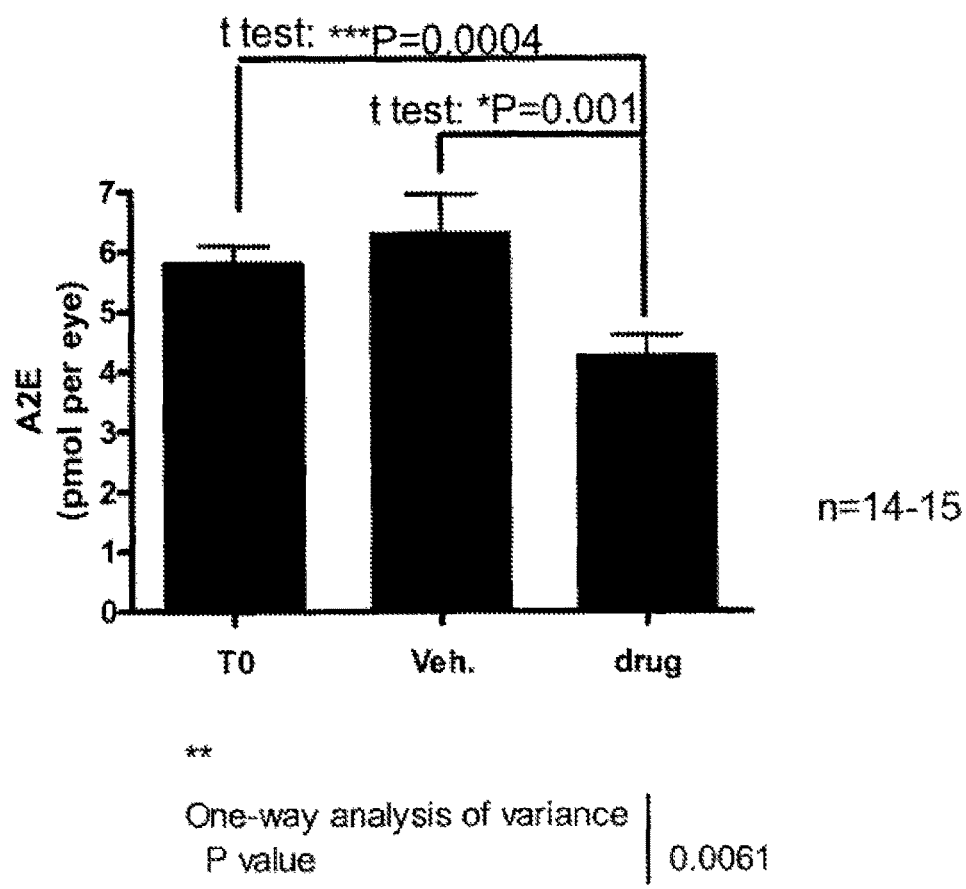
FIG. 11 illustrates the effect of Compound 4 on reducing A2E level in aged BALB/c mice (10 months old).

A similar experiment was performed with aged balb/c mice (10 months old). The test mice were treated with 1 mg/kg/day of Compound 4 for three months and the control mice was treated with vehicle. The results are presented in FIG. 11. This experiment demonstrates that a subject compound exhibits the capability to reduce the level of existing A2E.

Example 206

Effect of Compounds on Retinoid Nuclear Receptor Activity

Retinoid nuclear receptor activity is associated with transduction of the non-visual physiologic, pharmacologic, and toxicologic retinoid signals that affect tissue and organ growth, development, differentiation, and homeostasis.

The effect of the Compounds of Examples 4, 28, and 29 (Compound 4, Compound 28, and Compound 29) and the effect of a retinoic acid receptor (RAR) agonist (E-4-[2-(5, 6,7,8-tetrahydro-5,5,8,8-tetramethyl-2-naphthylenyl)-1-propenyl] benzoic acid) (TTNPB), and of all-trans-retinoic acid (at-RA), which is an RAR and retinoid X receptor (RXR) agonist, were studied on RAR and RXR receptors essentially as described by Achkar et al. (Proc. Natl. Acad. Sci. USA 93:4879-84 (1996)). Results of these assays are presented in Table 11. Amounts as great as 10 µM of each of Compound 4-HCl, Compound 28-HCl, and Compound 29-HCl did not show any significant effects on retinoid nuclear receptors (RAR and RXR). By comparison, TTNPB and at-RA activated the RXR$_\alpha$, RAR$_\alpha$, RAR$_\beta$ and RAR$_\gamma$ receptors as expected (Table 11).

TABLE 11

| Compound | RARα $EC_{50}$ (nM) | RARβ $EC_{50}$ (nM) | RARγ $EC_{50}$ (nM) | RXRα $EC_{50}$ (nM) |
|---|---|---|---|---|
| TTNPB | 5.5 +/– 4.5 | 0.3 +/– 0.1 | 0.065 +/– 0.005 | N/A |
| at-RA | N/A | N/A | N/A | 316 +/– 57 |
| Cmpd 4 | N/D | N/D | N/D | N/D |
| Cmpd 28 | N/D | N/D | N/D | N/D |
| Cmpd 29 | N/D | N/D | N/D | N/D |

N/D = No activity detected;
N/A = Not applicable

When ranges are used herein for physical properties, such as molecular weight, or chemical properties, such as chemical formulae, all combinations and subcombinations of ranges and specific embodiments therein are intended to be included.

The various embodiments described herein can be combined to provide further embodiments. All U.S. patents, U.S. patent application publications, U.S. patent applications, foreign patents, foreign patent applications, and non-patent publications referred to in this specification and/or listed in the Application Data Sheet, are incorporated herein by reference in their entireties.

From the foregoing it will be appreciated that, although specific embodiments have been described herein for purposes of illustration, various modifications may be made. Those skilled in the art will recognize, or be able to ascertain, using no more than routine experimentation, many equivalents to the specific embodiments described herein. Such equivalents are intended to be encompassed by the following claims. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method of modulating chromophore flux in a retinoid cycle comprising introducing into a subject a non-retinoid aromatic compound that inhibits 11-cis-retinol production with an $IC_{50}$ of about 0.1 micromolar or less when assayed in vitro, the assay consisting of a homogenate of HEK293 cell clone expressing recombinant human RPE65 and LRAT as the source of visual enzyme, exogenous all-trans-retinol in the amount of about 20 µM, recombinant human CRALBP in the amount of about 80 µg/mL, about 10 mM pH 7.2 phosphate buffer, about 0.5% BSA and about 1 mM NaPPi, and wherein the amount of assay reaction product 11-cis-retinol being determined by HPLC analysis following heptane extraction of the assay reaction mixture and wherein the non-retinoid aromatic compound consists of a benzene core that is substituted with a first substituent, a second substituent, and an optional third substituent, wherein the first and second substituents are attached to the benzene core in a meta-substitution configuration, wherein the first substituent is an optionally substituted 3-aminoprop-1-yl group, the second substituent is a (c-$C_6H_{11}$)$CH_2$—O— group, and the optional third substituent is a halogen or —OH; wherein the optionally substituted 3-aminoprop-1-yl group has the formula —C($R^9$)($R^{10}$)C($R^1$)($R^2$)$CH_2NH_2$, wherein $R^1$ and $R^2$ are each independently selected from hydrogen, halogen, C1-C5 unsubstituted alkyl, or —$OR^6$;

$R^9$ and $R^{19}$ are each independently selected from hydrogen, halogen, C1-C5 alkyl optionally substituted with hydroxy or halogen, or —$OR^{19}$, and $R^6$, and $R^{19}$ are each independently hydrogen or $CH_3$.

2. The method of claim 1, wherein $R^6$ and $R^{19}$ are hydrogen.

3. The method of claim 1, wherein $R^9$ is hydrogen.

4. The method of claim 2, wherein $R^9$ is hydrogen.

5. The method of claim 1, wherein $R^{10}$ is —$OR^{19}$.

6. The method of claim 2, wherein $R^{10}$ is —$OR^{19}$.

7. The method of claim 3, wherein $R^{10}$ is —$OR^{19}$.

8. The method of claim 4, wherein $R^{10}$ is —$OR^{19}$.

9. The method of claim 1, wherein $R^{10}$ is halogen.

10. The method of claim 2, wherein $R^{10}$ is halogen.

11. The method of claim 3, wherein $R^{10}$ is halogen.

12. The method of claim 4, wherein $R^{10}$ is halogen.

13. The method of claim 1, wherein $R^1$ is hydrogen.

14. The method of claim 4, wherein $R^1$ is hydrogen.

15. The method of claim 8, wherein $R^1$ is hydrogen.

* * * * *